(12) United States Patent
Diener et al.

(10) Patent No.: US 11,066,469 B2
(45) Date of Patent: Jul. 20, 2021

(54) NATRIURETIC PEPTIDE RECEPTOR 1 ANTIBODIES AND METHODS OF USE

(71) Applicant: NOVARTIS AG, Basel (CH)

(72) Inventors: John Louis Diener, Cambridge, MA (US); Lars Gadtke, Munich (DE); Felix Hartlepp, Munich (DE); Kathrin Ladetzki-Baehs, Planegg (DE); Michael Romanowski, Lexington, MA (US); Cesare Russo, Bachlettenstrasse (CH); Xenia Wezler, Munich (DE)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/897,935

(22) Filed: Jun. 10, 2020

(65) Prior Publication Data
US 2020/0392225 A1    Dec. 17, 2020

Related U.S. Application Data

(60) Provisional application No. 62/860,508, filed on Jun. 12, 2019.

(51) Int. Cl.
| | | |
|---|---|---|
| *C07K 16/28* | (2006.01) | |
| *A61K 39/395* | (2006.01) | |
| *A61P 9/00* | (2006.01) | |
| *A61P 13/12* | (2006.01) | |
| *C07K 14/72* | (2006.01) | |
| *A61K 45/06* | (2006.01) | |
| *A61K 39/00* | (2006.01) | |
| *C07K 14/58* | (2006.01) | |

(52) U.S. Cl.
CPC .......... *C07K 16/28* (2013.01); *A61K 39/3955* (2013.01); *A61P 9/00* (2018.01); *A61P 13/12* (2018.01); *C07K 16/2869* (2013.01); *A61K 45/06* (2013.01); *A61K 2039/505* (2013.01); *C07K 14/58* (2013.01); *C07K 14/72* (2013.01); *C07K 2317/50* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/75* (2013.01)

(58) Field of Classification Search
CPC .. C07K 16/28; C07K 16/2869; A61K 39/395; A61K 39/3955; A61P 9/10
See application file for complete search history.

(56) References Cited

U.S. PATENT DOCUMENTS

| | | |
|---|---|---|
| 9,090,695 B2 | 7/2015 | Waterman et al. |
| 9,987,330 B2 | 6/2018 | Hoon et al. |
| 10,184,942 B2 | 1/2019 | Mohapatra et al. |
| 2004/0253242 A1 | 12/2004 | Bowdish et al. |
| 2008/0181903 A1 | 7/2008 | Bhaskar et al. |
| 2008/0214437 A1 | 9/2008 | Mohapatra et al. |
| 2012/0270923 A1 | 10/2012 | Mohapatra et al. |
| 2014/0343120 A1 | 11/2014 | Mohapatra et al. |
| 2016/0168251 A1 | 6/2016 | Waterman et al. |

FOREIGN PATENT DOCUMENTS

| | | |
|---|---|---|
| CN | 104059154 A | 9/2014 |
| WO | 91/00292 A1 | 1/1991 |
| WO | 01/79231 A2 | 10/2001 |
| WO | 2002/036688 A2 | 5/2002 |
| WO | 02/46238 A2 | 6/2002 |
| WO | 02/078683 A1 | 10/2002 |
| WO | 2004/050017 A2 | 6/2004 |
| WO | 2004/108078 A2 | 12/2004 |
| WO | 2005/060642 A2 | 7/2005 |
| WO | 2007/070175 A2 | 6/2007 |
| WO | 2007/115164 A2 | 10/2007 |
| WO | 2007/115175 A2 | 10/2007 |
| WO | 2007/115182 A2 | 10/2007 |
| WO | 2008151257 A2 | 12/2008 |
| WO | 2009/006732 A1 | 1/2009 |
| WO | 2009/015011 A1 | 1/2009 |
| WO | 2009/073527 A2 | 6/2009 |
| WO | 2009/142307 A1 | 11/2009 |
| WO | 2009/149278 A1 | 12/2009 |
| WO | 2009/149279 A2 | 12/2009 |
| WO | 2010/009319 A2 | 1/2010 |
| WO | 2010/065293 A1 | 6/2010 |
| WO | 2010/135541 A1 | 11/2010 |
| WO | 2011/069038 A2 | 6/2011 |
| WO | 2012/019237 A1 | 2/2012 |
| WO | 2012/088608 A1 | 7/2012 |
| WO | 2012/118042 A1 | 9/2012 |
| WO | 2013/027680 A1 | 2/2013 |
| WO | 2014/115797 A1 | 7/2014 |
| WO | 2015/085055 A2 | 6/2015 |
| WO | 2016/033699 A1 | 3/2016 |
| WO | 2016/131943 A1 | 8/2016 |
| WO | 2017/082186 A1 | 5/2017 |
| WO | 2017/156310 A1 | 9/2017 |
| WO | 2018/034622 A1 | 2/2018 |
| WO | 2020/086406 A2 | 4/2020 |
| WO | 2020/236690 A1 | 11/2020 |

OTHER PUBLICATIONS

Saito et al, 2010. Journal of Cardiology. 56: 262-270.*
Ma et al, 2011. Medical Hypotheses. 77: 832-33.*
Blech, M. et al.: "Structure of a Therapeutic Full-Length Anti-NPRA IgG4 Antibody: Dissecting Conformational Diversity", Biophysical Journal, vol. 116, No. 9, May 1, 2019, pp. 1637-1649.
Ellmers L. J. et al.: "Npr1-regulated gene pathways contributing to cardiac hypertrophy and fibrosis",. Journal of Molecular Endocrinology, Feb. 2007;38(1-2):245-57.
Notification of Transmittal of the International Search Report and the Written Opinion of the International Searching Authority, or the Declaration, dated Sep. 16, 2020, issued in International Patent Application No. PCT/IB2020/055468, filed Jun. 10, 2020.

(Continued)

*Primary Examiner* — Zachary C Howard
(74) *Attorney, Agent, or Firm* — Meghan S. Adams

(57) ABSTRACT

This disclosure relates to anti-Natriuretic Peptide Receptor 1 (NPR1) antibodies including agonist antibodies which are able to activate the NPR1 receptor, pharmaceutical compositions comprising the same, and methods of treatment comprising the same.

17 Claims, 40 Drawing Sheets

Specification includes a Sequence Listing.

(56) References Cited

OTHER PUBLICATIONS

Kitano K. et al.:"Production and characterization of monoclonal antibodies against human natriuretic peptide receptor-A or -B", Immunol Lett.,Sep. 1995;47(3):215-22.
Lowe D. G. et al.: "Human atrial natriuretic peptide receptor defines a new paradigm for second messenger signal transduction", The EMBO Journal, (1989), 8(5):1377-1384.
Lowe D. G. et al.: "Human natriuretic peptide receptor-A guanylyl cyclase. Hormone cross-linking and antibody reactivity distinguish receptor glycoforms", Journal Biol. Chem., Oct. 25, 1992, 267(30):21691-7.
Mezo, Adam R. et al.: "Atrial Natriuretic Peptide-Fc, ANP-Fc, Fusion Proteins: Semisynthesis, In Vitro Activity and Pharmacokinetics in Rats", Bioconjugate Chemistry, (2012), 23(3): 518-526.
Oliver P. M. et al.: "Hypertension, cardiac hypertrophy, and sudden death in mice lacking natriuretic peptide receptor A", Proc. Natl. Acad. Sci. U S A., Dec. 23, 1997,94(26)14730-5.
Potter, L. et al.: "Natriuretic Peptides: Their Structures, Receptors, Physiologic Functions and Therapeutic Applications", Handbook of Experimental Pharmacology 2009, (191):341-66.
Rondeau, Jean Jacques et al: "Production of polyclonal antibody to the bovine adrenal atrial natriuretic factor-R1 receptor", Journal of Receptor Research, (1992), 12(4):485-505.
Vellaichamy, E. et al.: "Genetically Altered Mutant Mouse Models of Guanylyl Cyclase/Natriuretic Peptide Receptor-A Exhibit the Cardiac Expression of Proinflammatory Mediators in a Gene-Dose-Dependent Manner", Endocrinology, Mar. 2014 (Published online Jan. 3, 2014), 155(3):1045-1056.

List, K et al.: "Different mechanisms are involved in the antibody mediated inhibition of ligand binding to the urokinase receptor: a study based on biosensor technology", Journal of Immunological Methods, (1999), vol. 222, pp. 125-133.
Mumey, Brendan M. et al.: "A New Method for Mapping Discontinuous Antibody Epitopes to Reveal Structural Features of Proteins", Journal of Computational Biology, (2003), vol. 10, No. 3-4, pp. 555-567.
Arora, P et al.: "Atrial natriuretic peptide is negatively regulated by microRNA-425", The Journal of Clinical Investigation, (2013), vol. 123, No. 8, pp. 3378-3382.
Cui, Y. et al.: "Role of corin in trophoblast invasion and uterine spiral artery remodelling in pregnancy", Nature, (2012), vol. 484, pp. 246-252.
Dries, D. L. et al.: "Corin Gene Minor Allele Defined by 2 Missense Mutations Is Common in Blacks and Associated With High Blood Pressure and Hypertension", Circulation, (2005), vol. 112, pp. 2403-2410.
Hodgson-Zingman, D. M. et al.: "Atrial Natriuretic Peptide Frameshift Mutation in Familial Atrial Fibrillation", The New England Journal of Medicine, (2008), vol. 359, No. 2, pp. 158-165.
Liu, C. et al.: "Meta-analysis identifies common and rare variants influencing blood pressure and overlapping with metabolic trait loci", Nature Genetics, Oct. 2016, vol. 48, No. 10, pp. 1162-1170.
Rame, J. E., et al.: "Dysfunctional Corin I555(P568) Allele Is Associated With Impaired Brain Natriuretic Peptide Processing and Adverse Outcomes in Blacks With Systolic Heart Failure (Results From the Genetic Risk Assessment in Heart Failure Substudy)", Cir. Heart Fail., (2009), vol. 2, pp. 541-548.

\* cited by examiner

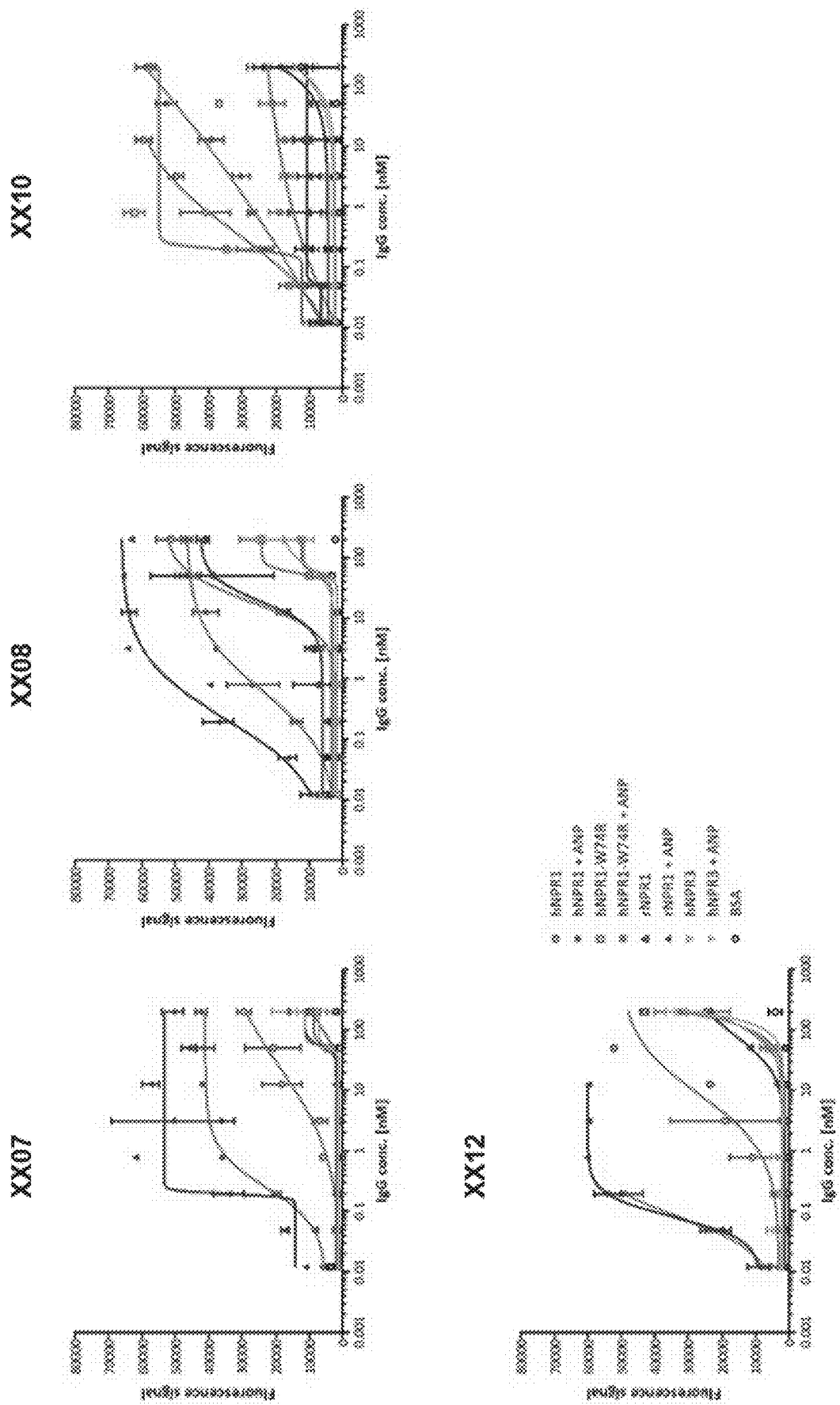

SEQUENCE LISTING

<160> NUMBER OF SEQ ID NOS: 473

<210> SEQ ID NO 1
<211> LENGTH: 1061
<212> TYPE: PRT
<213> ORGANISM: Homo sapiens

<400> SEQUENCE: 1

Met Pro Gly Pro Arg Arg Pro Ala Gly Ser Arg Leu Arg Leu Leu Leu
1               5                   10                  15

Leu Leu Leu Leu Pro Pro Leu Leu Leu Leu Arg Gly Ser His Ala
                20                  25                  30

Gly Asn Leu Thr Val Ala Val Val Leu Pro Leu Ala Asn Thr Ser Tyr
                35                  40                  45

Pro Trp Ser Trp Ala Arg Val Gly Pro Ala Val Glu Leu Ala Leu Ala
            50                  55                  60

Gln Val Lys Ala Arg Pro Asp Leu Leu Pro Gly Trp Thr Val Arg Thr
65              70                  75                  80

Val Leu Gly Ser Ser Glu Asn Ala Leu Gly Val Cys Ser Asp Thr Ala
                85                  90                  95

Ala Pro Leu Ala Ala Val Asp Leu Lys Trp Glu His Asn Pro Ala Val
                100                 105                 110

Phe Leu Gly Pro Gly Cys Val Tyr Ala Ala Pro Val Gly Arg Phe
                115                 120                 125

Thr Ala His Trp Arg Val Pro Leu Leu Thr Ala Gly Ala Pro Ala Leu
                130                 135                 140

Gly Phe Gly Val Lys Asp Glu Tyr Ala Leu Thr Thr Arg Ala Gly Pro
145                 150                 155                 160

Ser Tyr Ala Lys Leu Gly Asp Phe Val Ala Ala Leu His Arg Arg Leu
                165                 170                 175

Gly Trp Glu Arg Gln Ala Leu Met Leu Tyr Ala Tyr Arg Pro Gly Asp
                180                 185                 190

Glu Glu His Cys Phe Phe Leu Val Gly Leu Phe Met Arg Val Arg
                195                 200                 205

Asp Arg Leu Asn Ile Thr Val Asp His Leu Glu Phe Ala Glu Asp Asp
                210                 215                 220

Leu Ser His Tyr Thr Arg Leu Leu Arg Thr Met Pro Arg Lys Gly Arg
225                 230                 235                 240

Val Ile Tyr Ile Cys Ser Ser Pro Asp Ala Phe Arg Thr Leu Met Leu
                245                 250                 255

Leu Ala Leu Glu Ala Gly Leu Cys Gly Glu Asp Tyr Val Phe Phe His
                260                 265                 270

Leu Asp Ile Phe Gly Gln Ser Leu Gln Gly Gln Gly Pro Ala Pro
                275                 280                 285

Arg Arg Pro Trp Glu Arg Gly Asp Gly Gln Asp Val Ser Ala Arg Gln
                290                 295                 300

Ala Phe Gln Ala Ala Lys Ile Ile Thr Tyr Lys Asp Pro Asp Asn Pro
305                 310                 315                 320

Glu Tyr Leu Glu Phe Leu Lys Gln Leu Lys His Leu Ala Tyr Glu Gln
                325                 330                 335

Phe Asn Phe Thr Met Glu Asp Gly Leu Val Asn Thr Ile Pro Ala Ser
                340                 345                 350

Phe His Asp Gly Leu Leu Leu Tyr Ile Gln Ala Val Thr Glu Thr Leu
                355                 360                 365

```
Ala His Gly Gly Thr Val Thr Asp Gly Glu Asn Ile Thr Gln Arg Met
    370             375                 380
Trp Asn Arg Ser Phe Gln Gly Val Thr Gly Tyr Leu Lys Ile Asp Ser
385                 390                 395                 400
Ser Gly Asp Arg Glu Thr Asp Phe Ser Leu Trp Asp Met Asp Pro Glu
                405                 410                 415
Asn Gly Ala Phe Arg Val Val Leu Asn Tyr Asn Gly Thr Ser Gln Glu
                420                 425                 430
Leu Val Ala Val Ser Gly Arg Lys Leu Asn Trp Pro Leu Gly Tyr Pro
            435                 440                 445
Pro Pro Asp Ile Pro Lys Cys Gly Phe Asp Asn Glu Asp Pro Ala Cys
450                 455                 460
Asn Gln Asp His Leu Ser Thr Leu Glu Val Leu Ala Leu Val Gly Ser
465                 470                 475                 480
Leu Ser Leu Leu Gly Ile Leu Ile Val Ser Phe Phe Ile Tyr Arg Lys
                485                 490                 495
Met Gln Leu Glu Lys Glu Leu Ala Ser Glu Leu Trp Arg Val Arg Trp
                500                 505                 510
Glu Asp Val Glu Pro Ser Ser Leu Glu Arg His Leu Arg Ser Ala Gly
                515                 520                 525
Ser Arg Leu Thr Leu Ser Gly Arg Gly Ser Asn Tyr Gly Ser Leu Leu
530                 535                 540
Thr Thr Glu Gly Gln Phe Gln Val Phe Ala Lys Thr Ala Tyr Tyr Lys
545                 550                 555                 560
Gly Asn Leu Val Ala Val Lys Arg Val Asn Arg Lys Arg Ile Glu Leu
                565                 570                 575
Thr Arg Lys Val Leu Phe Glu Leu Lys His Met Arg Asp Val Gln Asn
                580                 585                 590
Glu His Leu Thr Arg Phe Val Gly Ala Cys Thr Asp Pro Pro Asn Ile
                595                 600                 605
Cys Ile Leu Thr Glu Tyr Cys Pro Arg Gly Ser Leu Gln Asp Ile Leu
610                 615                 620
Glu Asn Glu Ser Ile Thr Leu Asp Trp Met Phe Arg Tyr Ser Leu Thr
625                 630                 635                 640
Asn Asp Ile Val Lys Gly Met Leu Phe Leu His Asn Gly Ala Ile Cys
                645                 650                 655
Ser His Gly Asn Leu Lys Ser Ser Asn Cys Val Val Asp Gly Arg Phe
                660                 665                 670
Val Leu Lys Ile Thr Asp Tyr Gly Leu Glu Ser Phe Arg Asp Leu Asp
                675                 680                 685
Pro Glu Gln Gly His Thr Val Tyr Ala Lys Lys Leu Trp Thr Ala Pro
690                 695                 700
Glu Leu Leu Arg Met Ala Ser Pro Pro Val Arg Gly Ser Gln Ala Gly
705                 710                 715                 720
Asp Val Tyr Ser Phe Gly Ile Ile Leu Gln Glu Ile Ala Leu Arg Ser
                725                 730                 735
Gly Val Phe His Val Glu Gly Leu Asp Leu Ser Pro Lys Glu Ile Ile
                740                 745                 750
Glu Arg Val Thr Arg Gly Glu Gln Pro Pro Phe Arg Pro Ser Leu Ala
                755                 760                 765
Leu Gln Ser His Leu Glu Glu Leu Gly Leu Leu Met Gln Arg Cys Trp
770                 775                 780
Ala Glu Asp Pro Gln Glu Arg Pro Pro Phe Gln Gln Ile Arg Leu Thr
```

```
            785                 790                 795                 800
Leu Arg Lys Phe Asn Arg Glu Asn Ser Ser Asn Ile Leu Asp Asn Leu
                    805                 810                 815

Leu Ser Arg Met Glu Gln Tyr Ala Asn Asn Leu Glu Glu Leu Val Glu
                820                 825                 830

Glu Arg Thr Gln Ala Tyr Leu Glu Glu Lys Arg Lys Ala Glu Ala Leu
            835                 840                 845

Leu Tyr Gln Ile Leu Pro His Ser Val Ala Glu Gln Leu Lys Arg Gly
        850                 855                 860

Glu Thr Val Gln Ala Glu Ala Phe Asp Ser Val Thr Ile Tyr Phe Ser
865                 870                 875                 880

Asp Ile Val Gly Phe Thr Ala Leu Ser Ala Glu Ser Thr Pro Met Gln
                885                 890                 895

Val Val Thr Leu Leu Asn Asp Leu Tyr Thr Cys Phe Asp Ala Val Ile
                900                 905                 910

Asp Asn Phe Asp Val Tyr Lys Val Glu Thr Ile Gly Asp Ala Tyr Met
            915                 920                 925

Val Val Ser Gly Leu Pro Val Arg Asn Gly Arg Leu His Ala Cys Glu
        930                 935                 940

Val Ala Arg Met Ala Leu Ala Leu Leu Asp Ala Val Arg Ser Phe Arg
945                 950                 955                 960

Ile Arg His Arg Pro Gln Glu Gln Leu Arg Leu Arg Ile Gly Ile His
                965                 970                 975

Thr Gly Pro Val Cys Ala Gly Val Val Gly Leu Lys Met Pro Arg Tyr
            980                 985                 990

Cys Leu Phe Gly Asp Thr Val Asn Thr Ala Ser Arg Met Glu Ser Asn
        995                 1000                1005

Gly Glu Ala Leu Lys Ile His Leu Ser Ser Glu Thr Lys Ala Val
    1010                1015                1020

Leu Glu Glu Phe Gly Gly Phe Glu Leu Glu Leu Arg Gly Asp Val
    1025                1030                1035

Glu Met Lys Gly Lys Gly Lys Val Arg Thr Tyr Trp Leu Leu Gly
    1040                1045                1050

Glu Arg Gly Ser Ser Thr Arg Gly
    1055                1060
```

<210> SEQ ID NO 2
<211> LENGTH: 1057
<212> TYPE: PRT
<213> ORGANISM: Mus musculus

<400> SEQUENCE: 2

```
Met Pro Gly Ser Arg Arg Val Arg Pro Arg Leu Arg Ala Leu Leu Leu
1               5                   10                  15

Leu Pro Pro Leu Leu Leu Arg Ser Gly His Ala Ser Asp Leu Thr
                20                  25                  30

Val Ala Val Val Leu Pro Leu Thr Asn Thr Ser Tyr Pro Trp Ser Trp
            35                  40                  45

Ala Arg Val Gly Pro Ala Val Glu Leu Ala Leu Gly Arg Val Lys Ala
        50                  55                  60

Arg Pro Asp Leu Leu Pro Gly Trp Thr Val Arg Met Val Leu Gly Ser
65                  70                  75                  80

Ser Glu Asn Ala Ala Gly Val Cys Ser Asp Thr Ala Ala Pro Leu Ala
                85                  90                  95
```

-continued

Ala Val Asp Leu Lys Trp Glu His Ser Pro Ala Val Phe Leu Gly Pro
            100                 105                 110

Gly Cys Val Tyr Ser Ala Ala Pro Val Gly Arg Phe Thr Ala His Trp
            115                 120                 125

Arg Val Pro Leu Leu Thr Ala Gly Ala Pro Ala Leu Gly Ile Gly Val
            130                 135                 140

Lys Asp Glu Tyr Ala Leu Thr Thr Arg Thr Gly Pro Ser His Val Lys
145                 150                 155                 160

Leu Gly Asp Phe Val Thr Ala Leu His Arg Arg Leu Gly Trp Glu His
                    165                 170                 175

Gln Ala Leu Val Leu Tyr Ala Asp Arg Leu Gly Asp Arg Pro Cys
            180                 185                 190

Phe Phe Ile Val Glu Gly Leu Tyr Met Arg Val Arg Glu Arg Leu Asn
            195                 200                 205

Ile Thr Val Asn His Gln Glu Phe Val Glu Gly Asp Pro Asp His Tyr
            210                 215                 220

Thr Lys Leu Leu Arg Thr Val Gln Arg Lys Gly Arg Val Ile Tyr Ile
225                 230                 235                 240

Cys Ser Ser Pro Asp Ala Phe Arg Asn Leu Met Leu Ala Leu Asp
                    245                 250                 255

Ala Gly Leu Thr Gly Glu Asp Tyr Val Phe Phe His Leu Asp Val Phe
            260                 265                 270

Gly Gln Ser Leu Gln Gly Ala Gln Gly Pro Val Pro Arg Lys Pro Trp
            275                 280                 285

Glu Arg Asp Asp Gly Gln Asp Arg Arg Ala Arg Gln Ala Phe Gln Ala
            290                 295                 300

Ala Lys Ile Ile Thr Tyr Lys Glu Pro Asp Asn Pro Glu Tyr Leu Glu
305                 310                 315                 320

Phe Leu Lys Gln Leu Lys Leu Ala Asp Lys Lys Phe Asn Phe Thr
                    325                 330                 335

Met Glu Asp Gly Leu Lys Asn Ile Ile Pro Ala Ser Phe His Asp Gly
            340                 345                 350

Leu Leu Leu Tyr Val Gln Ala Val Thr Glu Thr Leu Ala Gln Gly Gly
            355                 360                 365

Thr Val Thr Asp Gly Glu Asn Ile Thr Gln Arg Met Trp Asn Arg Ser
370                 375                 380

Phe Gln Gly Val Thr Gly Tyr Leu Lys Ile Asp Arg Asn Gly Asp Arg
385                 390                 395                 400

Asp Thr Asp Phe Ser Leu Trp Asp Met Asp Pro Glu Thr Gly Ala Phe
                    405                 410                 415

Arg Val Val Leu Asn Phe Asn Gly Thr Ser Gln Glu Leu Met Ala Val
            420                 425                 430

Ser Glu His Arg Leu Tyr Trp Pro Leu Gly Tyr Pro Pro Asp Ile
            435                 440                 445

Pro Lys Cys Gly Phe Asp Asn Glu Asp Pro Ala Cys Asn Gln Asp His
            450                 455                 460

Phe Ser Thr Leu Glu Val Leu Ala Leu Val Gly Ser Leu Ser Leu Val
465                 470                 475                 480

Ser Phe Leu Ile Val Ser Phe Phe Ile Tyr Arg Lys Met Gln Leu Glu
                    485                 490                 495

Lys Glu Leu Val Ser Glu Leu Trp Arg Val Arg Trp Glu Asp Leu Gln
            500                 505                 510

Pro Ser Ser Leu Glu Arg His Leu Arg Ser Ala Gly Ser Arg Leu Thr

```
            515                 520                 525
Leu Ser Gly Arg Gly Ser Asn Tyr Gly Ser Leu Leu Thr Thr Glu Gly
    530                 535                 540

Gln Phe Gln Val Phe Ala Lys Thr Ala Tyr Tyr Lys Gly Asn Leu Val
545                 550                 555                 560

Ala Val Lys Arg Val Asn Arg Lys Arg Ile Glu Leu Thr Arg Lys Val
                565                 570                 575

Leu Phe Glu Leu Lys His Met Arg Asp Val Gln Asn Glu His Leu Thr
            580                 585                 590

Arg Phe Val Gly Ala Cys Thr Asp Pro Pro Asn Ile Cys Ile Leu Thr
        595                 600                 605

Glu Tyr Cys Pro Arg Gly Ser Leu Gln Asp Ile Leu Glu Asn Glu Ser
    610                 615                 620

Ile Thr Leu Asp Trp Met Phe Arg Tyr Ser Leu Thr Asn Asp Ile Val
625                 630                 635                 640

Lys Gly Met Leu Phe Leu His Asn Gly Ala Ile Gly Ser His Gly Asn
                645                 650                 655

Leu Lys Ser Ser Asn Cys Val Val Asp Gly Arg Phe Val Leu Lys Ile
            660                 665                 670

Thr Asp Tyr Gly Leu Glu Ser Phe Arg Asp Pro Glu Pro Glu Gln Gly
        675                 680                 685

His Thr Leu Phe Ala Lys Lys Leu Trp Thr Ala Pro Glu Leu Leu Arg
    690                 695                 700

Met Ala Ser Pro Pro Ala Arg Gly Ser Gln Ala Gly Asp Val Tyr Ser
705                 710                 715                 720

Phe Gly Ile Ile Leu Gln Glu Ile Ala Leu Arg Ser Gly Val Phe Tyr
                725                 730                 735

Val Glu Gly Leu Asp Leu Ser Pro Lys Glu Ile Ile Glu Arg Val Thr
            740                 745                 750

Arg Gly Glu Gln Pro Pro Phe Arg Pro Ser Met Asp Leu Gln Ser His
        755                 760                 765

Leu Glu Glu Leu Gly Gln Leu Met Gln Arg Cys Trp Ala Glu Asp Pro
    770                 775                 780

Gln Glu Arg Pro Pro Phe Gln Gln Ile Arg Leu Ala Leu Arg Lys Phe
785                 790                 795                 800

Asn Lys Glu Asn Ser Ser Asn Ile Leu Asp Asn Leu Leu Ser Arg Met
                805                 810                 815

Glu Gln Tyr Ala Asn Asn Leu Glu Glu Leu Val Glu Glu Arg Thr Gln
            820                 825                 830

Ala Tyr Leu Glu Glu Lys Arg Lys Ala Glu Ala Leu Leu Tyr Gln Ile
        835                 840                 845

Leu Pro His Ser Val Ala Glu Gln Leu Lys Arg Gly Glu Thr Val Gln
    850                 855                 860

Ala Glu Ala Phe Asp Ser Val Thr Ile Tyr Phe Ser Asp Ile Val Gly
865                 870                 875                 880

Phe Thr Ala Leu Ser Ala Glu Ser Thr Pro Met Gln Val Val Thr Leu
                885                 890                 895

Leu Asn Asp Leu Tyr Thr Cys Phe Asp Ala Val Ile Asp Asn Phe Asp
            900                 905                 910

Val Tyr Lys Val Glu Thr Ile Gly Asp Ala Tyr Met Val Val Ser Gly
        915                 920                 925

Leu Pro Val Arg Asn Gly Gln Leu His Ala Arg Glu Val Ala Arg Met
    930                 935                 940
```

```
Ala Leu Ala Leu Leu Asp Ala Val Arg Ser Phe Arg Ile Arg His Arg
945                 950                 955                 960

Pro Gln Glu Gln Leu Arg Leu Arg Ile Gly Ile His Thr Gly Pro Val
                965                 970                 975

Cys Ala Gly Val Val Gly Leu Lys Met Pro Arg Tyr Cys Leu Phe Gly
            980                 985                 990

Asp Thr Val Asn Thr Ala Ser Arg Met Glu Ser Asn Gly Glu Ala Leu
        995                 1000                1005

Arg Ile His Leu Ser Ser Glu Thr Lys Ala Val Leu Glu Glu Phe
    1010                1015                1020

Asp Gly Phe Glu Leu Glu Leu Arg Gly Asp Val Glu Met Lys Gly
    1025                1030                1035

Lys Gly Lys Val Arg Thr Tyr Trp Leu Leu Gly Glu Arg Gly Cys
    1040                1045                1050

Ser Thr Arg Gly
    1055

<210> SEQ ID NO 3
<211> LENGTH: 1057
<212> TYPE: PRT
<213> ORGANISM: Rattus norvegicus

<400> SEQUENCE: 3

Met Pro Gly Ser Arg Arg Val Arg Pro Arg Leu Arg Ala Leu Leu Leu
1               5                   10                  15

Leu Pro Pro Leu Leu Leu Arg Gly Gly His Ala Ser Asp Leu Thr
            20                  25                  30

Val Ala Val Val Leu Pro Leu Thr Asn Thr Ser Tyr Pro Trp Ser Trp
            35                  40                  45

Ala Arg Val Gly Pro Ala Val Glu Leu Ala Leu Ala Arg Val Lys Ala
        50                  55                  60

Arg Pro Asp Leu Leu Pro Gly Trp Thr Val Arg Met Val Leu Gly Ser
65                  70                  75                  80

Ser Glu Asn Ala Ala Gly Val Cys Ser Asp Thr Ala Ala Pro Leu Ala
                85                  90                  95

Ala Val Asp Leu Lys Trp Glu His Ser Pro Ala Val Phe Leu Gly Pro
            100                 105                 110

Gly Cys Val Tyr Ser Ala Ala Pro Val Gly Arg Phe Thr Ala His Trp
        115                 120                 125

Arg Val Pro Leu Leu Thr Ala Gly Ala Pro Ala Leu Gly Ile Gly Val
130                 135                 140

Lys Asp Glu Tyr Ala Leu Thr Thr Arg Thr Gly Pro Ser His Val Lys
145                 150                 155                 160

Leu Gly Asp Phe Val Thr Ala Leu His Arg Arg Leu Gly Trp Glu His
                165                 170                 175

Gln Ala Leu Val Leu Tyr Ala Asp Arg Leu Gly Asp Asp Arg Pro Cys
            180                 185                 190

Phe Phe Ile Val Glu Gly Leu Tyr Met Arg Val Arg Glu Arg Leu Asn
        195                 200                 205

Ile Thr Val Asn His Gln Glu Phe Val Glu Gly Asp Pro Asp His Tyr
    210                 215                 220

Pro Lys Leu Leu Arg Ala Val Arg Arg Lys Gly Arg Val Ile Tyr Ile
225                 230                 235                 240

Cys Ser Ser Pro Asp Ala Phe Arg Asn Leu Met Leu Leu Ala Leu Asn
```

-continued

```
                245                 250                 255
Ala Gly Leu Thr Gly Glu Asp Tyr Val Phe Phe His Leu Asp Val Phe
                260                 265                 270
Gly Gln Ser Leu Lys Ser Ala Gln Gly Leu Val Pro Gln Lys Pro Trp
                275                 280                 285
Glu Arg Gly Asp Gly Gln Asp Arg Ser Ala Arg Gln Ala Phe Gln Ala
            290                 295                 300
Ala Lys Ile Ile Thr Tyr Lys Glu Pro Asp Asn Pro Glu Tyr Leu Glu
305                 310                 315                 320
Phe Leu Lys Gln Leu Lys Leu Leu Ala Asp Lys Lys Phe Asn Phe Thr
                325                 330                 335
Val Glu Asp Gly Leu Lys Asn Ile Ile Pro Ala Ser Phe His Asp Gly
                340                 345                 350
Leu Leu Leu Tyr Val Gln Ala Val Thr Glu Thr Leu Ala Gln Gly Gly
                355                 360                 365
Thr Val Thr Asp Gly Glu Asn Ile Thr Gln Arg Met Trp Asn Arg Ser
            370                 375                 380
Phe Gln Gly Val Thr Gly Tyr Leu Lys Ile Asp Arg Asn Gly Asp Arg
385                 390                 395                 400
Asp Thr Asp Phe Ser Leu Trp Asp Met Asp Pro Glu Thr Gly Ala Phe
                405                 410                 415
Arg Val Val Leu Asn Tyr Asn Gly Thr Ser Gln Glu Leu Met Ala Val
                420                 425                 430
Ser Glu His Lys Leu Tyr Trp Pro Leu Gly Tyr Pro Pro Pro Asp Val
                435                 440                 445
Pro Lys Cys Gly Phe Asp Asn Glu Asp Pro Ala Cys Asn Gln Asp His
            450                 455                 460
Phe Ser Thr Leu Glu Val Leu Ala Leu Val Gly Ser Leu Ser Leu Ile
465                 470                 475                 480
Ser Phe Leu Ile Val Ser Phe Phe Ile Tyr Arg Lys Met Gln Leu Glu
                485                 490                 495
Lys Glu Leu Val Ser Glu Leu Trp Arg Val Arg Trp Glu Asp Leu Gln
                500                 505                 510
Pro Ser Ser Leu Glu Arg His Leu Arg Ser Ala Gly Ser Arg Leu Thr
            515                 520                 525
Leu Ser Gly Arg Gly Ser Asn Tyr Gly Ser Leu Leu Thr Thr Glu Gly
            530                 535                 540
Gln Phe Gln Val Phe Ala Lys Thr Ala Tyr Tyr Lys Gly Asn Leu Val
545                 550                 555                 560
Ala Val Lys Arg Val Asn Arg Lys Arg Ile Glu Leu Thr Arg Lys Val
                565                 570                 575
Leu Phe Glu Leu Lys His Met Arg Asp Val Gln Asn Glu His Leu Thr
                580                 585                 590
Arg Phe Val Gly Ala Cys Thr Asp Pro Pro Asn Ile Cys Ile Leu Thr
            595                 600                 605
Glu Tyr Cys Pro Arg Gly Ser Leu Gln Asp Ile Leu Glu Asn Glu Ser
            610                 615                 620
Ile Thr Leu Asp Trp Met Phe Arg Tyr Ser Leu Thr Asn Asp Ile Val
625                 630                 635                 640
Lys Gly Met Leu Phe Leu His Asn Gly Ala Ile Cys Ser His Gly Asn
                645                 650                 655
Leu Lys Ser Ser Asn Cys Val Val Asp Gly Arg Phe Val Leu Lys Ile
                660                 665                 670
```

```
Thr Asp Tyr Gly Leu Glu Ser Phe Arg Asp Pro Glu Pro Glu Gln Gly
            675                 680                 685

His Thr Leu Phe Ala Lys Lys Leu Trp Thr Ala Pro Glu Leu Leu Arg
        690                 695                 700

Met Ala Ser Pro Pro Ala Arg Gly Ser Gln Ala Gly Asp Val Tyr Ser
705                 710                 715                 720

Phe Gly Ile Ile Leu Gln Glu Ile Ala Leu Arg Ser Gly Val Phe Tyr
                725                 730                 735

Val Glu Gly Leu Asp Leu Ser Pro Lys Glu Ile Ile Glu Arg Val Thr
            740                 745                 750

Arg Gly Glu Gln Pro Pro Phe Arg Pro Ser Met Asp Leu Gln Ser His
        755                 760                 765

Leu Glu Glu Leu Gly Gln Leu Met Gln Arg Cys Trp Ala Glu Asp Pro
    770                 775                 780

Gln Glu Arg Pro Pro Phe Gln Gln Ile Arg Leu Ala Leu Arg Lys Phe
785                 790                 795                 800

Asn Lys Glu Asn Ser Ser Asn Ile Leu Asp Asn Leu Leu Ser Arg Met
                805                 810                 815

Glu Gln Tyr Ala Asn Asn Leu Glu Glu Leu Val Glu Glu Arg Thr Gln
            820                 825                 830

Ala Tyr Leu Glu Glu Lys Arg Lys Ala Glu Ala Leu Leu Tyr Gln Ile
        835                 840                 845

Leu Pro His Ser Val Ala Glu Gln Leu Lys Arg Gly Glu Thr Val Gln
850                 855                 860

Ala Glu Ala Phe Asp Ser Val Thr Ile Tyr Phe Ser Asp Ile Val Gly
865                 870                 875                 880

Phe Thr Ala Leu Ser Ala Glu Ser Thr Pro Met Gln Val Val Thr Leu
                885                 890                 895

Leu Asn Asp Leu Tyr Thr Cys Phe Asp Ala Val Ile Asp Asn Phe Asp
            900                 905                 910

Val Tyr Lys Val Glu Thr Ile Gly Asp Ala Tyr Met Val Val Ser Gly
        915                 920                 925

Leu Pro Val Arg Asn Gly Gln Leu His Ala Arg Glu Val Ala Arg Met
    930                 935                 940

Ala Leu Ala Leu Leu Asp Ala Val Arg Ser Phe Arg Ile Arg His Arg
945                 950                 955                 960

Pro Gln Glu Gln Leu Arg Leu Arg Ile Gly Ile His Thr Gly Pro Val
                965                 970                 975

Cys Ala Gly Val Val Gly Leu Lys Met Pro Arg Tyr Cys Leu Phe Gly
            980                 985                 990

Asp Thr Val Asn Thr Ala Ser Arg Met Glu Ser Asn Gly Glu Ala Leu
        995                1000                1005

Lys Ile His Leu Ser Ser Glu Thr Lys Ala Val Leu Glu Glu Phe
   1010                1015                1020

Asp Gly Phe Glu Leu Glu Leu Arg Gly Asp Val Glu Met Lys Gly
   1025                1030                1035

Lys Gly Lys Val Arg Thr Tyr Trp Leu Leu Gly Glu Arg Gly Cys
   1040                1045                1050

Ser Thr Arg Gly
   1055

<210> SEQ ID NO 4
<211> LENGTH: 10
```

```
-continued

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Phe Thr Phe Asn Thr His Tyr Ile His
1               5                   10

<210> SEQ ID NO 5
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Ser Ile Ser Gly Ser Gly Ser Asn Thr Tyr Tyr Ala Asp Ser Val Lys
1               5                   10                  15

Gly

<210> SEQ ID NO 6
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Glu Arg Gly Tyr Val Tyr Tyr His Met Phe Asp Pro
1               5                   10

<210> SEQ ID NO 7
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Thr His Tyr Ile His
1               5

<210> SEQ ID NO 8
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gly Phe Thr Phe Asn Thr His
1               5

<210> SEQ ID NO 9
<211> LENGTH: 6
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 9

Ser Gly Ser Gly Ser Asn
1               5

<210> SEQ ID NO 10
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Gly Phe Thr Phe Asn Thr His Tyr
1               5

<210> SEQ ID NO 11
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ile Ser Gly Ser Gly Ser Asn Thr
1               5

<210> SEQ ID NO 12
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Ala Arg Glu Arg Gly Tyr Val Tyr Tyr His Met Phe Asp Pro
1               5                   10

<210> SEQ ID NO 13
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr His
            20                  25                  30

Tyr Ile His Trp Val Arg Gln Ala Pro Gly Lys Gly Leu Glu Trp Val
        35                  40                  45

Ser Ser Ile Ser Gly Ser Gly Ser Asn Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Gly Tyr Val Tyr Tyr His Met Phe Asp Pro Trp Gly
            100                 105                 110

Gln Gly Thr Leu Val Thr Val Ser Ser
        115                 120
```

<210> SEQ ID NO 14
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 14

```
caggtgcaat tgctggaaag cggcggtggc ctggtgcagc cgggtggcag cctgcgtctg      60
agctgcgcgg cgtccggatt cacctttaac actcattaca tccattgggt gcgccaggcc     120
cccggcaaag gtctcgagtg gtttcctct atctctggtt ctggttctaa cacctactat     180
gcggatagcg tgaaaggccg cttaccatc agccgcgata ttcgaaaaa caccctgtat     240 ctgcaaatga acagcctgcg tgcggaagat acggccgtgt attattgcgc gcgtgaacgt     300
ggttacgttt actaccatat gttcgatccg tggggccaag gcaccctggt gactgttagc     360
tca                                                                   363
```

<210> SEQ ID NO 15
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

```
Gln Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Asn Thr His
             20                  25                  30

Tyr Ile His Trp Val Arg Gln Ala Pro Gly Lys Gly Leu Glu Trp Val
         35                  40                  45

Ser Ser Ile Ser Gly Ser Gly Ser Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Gly Tyr Val Tyr Tyr His Met Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160
```

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
            210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 16
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 16
caggtgcaat tgctggaaag cggcggtggc ctggtgcagc cgggtggcag cctgcgtctg      60
agctgcgcgg cgtccggatt cacctttaac actcattaca tccattgggt gcgccaggcc     120
cccggcaaag gtctcgagtg gtttcctctc atctctggtt ctggttctaa cacctactat     180
gcggatagcg tgaaaggccg ctttaccatc agccgcgata ttcgaaaaa caccctgtat     240 ctgcaaatga acagcctgcg tgcggaagat acggccgtgt attattgcgc gcgtgaacgt     300

```
ggttacgttt actaccatat gttcgatccg tggggccaag gcaccctggt gactgttagc    360
tcagcctcca ccaagggtcc atcggtcttc ccctggcac cctcctccaa gagcacctct     420
ggggcacag cggccctggg ctgcctggtc aaggactact ccccgaacc ggtgacggtg      480
tcgtggaact caggcgccct gaccagcggc gtgcacacct cccggctgt cctacagtcc     540
tcaggactct actccctcag cagcgtggtg accgtgccct ccagcagctt gggcacccag    600
acctacatct gcaacgtgaa tcacaagccc agcaacacca aggtggacaa gagagttgag    660
cccaaatctt gtgacaaaac tcacacatgc ccaccgtgcc cagcacctga agcagcgggg    720
ggaccgtcag tcttcctctt cccccccaaaa cccaaggaca ccctcatgat ctcccggacc   780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgggtggt cagcgtcctc accgtcctgc accaggactg gctgaatggc    960
aaggagtaca agtgcaaggt ctccaacaaa gccctcccag cccccatcga gaaaaccatc    1020
tccaaagcca agggcagcc cgagaaccca caggtgtaca ccctgccccc atcccgggag    1080
gagatgacca agaaccaggt cagcctgacc tgcctggtca aaggcttcta tcccagcgac    1140
atcgccgtgg agtgggagag caatgggcag ccggagaaca actacaagac cacgcctccc    1200
gtgctggact ccgacggctc cttcttcctc tacagcaagc tcaccgtgga caagagcagg    1260
tggcagcagg ggaacgtctt ctcatgctcc gtgatgcatg aggctctgca caaccactac    1320
acgcagaaga gcctctccct gtctccgggt aaa                                 1353

<210> SEQ ID NO 17
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Arg Ala Ser Gln Ser Ile Thr Arg Asn Tyr Leu Ala
1               5                   10

<210> SEQ ID NO 18
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Gly Ala Ser Ser Arg Ala Thr
1               5

<210> SEQ ID NO 19
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19
```

```
Gln Gln His Ser Met Tyr Pro Arg Thr
1               5
```

<210> SEQ ID NO 20
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

```
Ser Gln Ser Ile Thr Arg Asn Tyr
1               5
```

<210> SEQ ID NO 21
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

```
Gly Ala Ser
1
```

<210> SEQ ID NO 22
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

```
His Ser Met Tyr Pro Arg
1               5
```

<210> SEQ ID NO 23
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

```
Gln Ser Ile Thr Arg Asn Tyr
1               5
```

<210> SEQ ID NO 24
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Thr Arg Asn
```

```
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Ala Arg Phe Ser
        50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln His Ser Met Tyr Pro
                85                  90                  95

Arg Thr Phe Gly Gln Gly Thr Lys Val Glu Ile Lys
            100                 105

<210> SEQ ID NO 25
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 25
gatatcgtgc tgacccagag cccggcgacc ctgagcctga gcccgggtga acgtgccacc      60
ctgagctgca gcgagcca gtctatcact cgtaactacc tggcttggta ccagcagaaa      120
ccgggccagg ccccgcgtct attaatctac ggtgcttctt ctcgtgcgac cggcattccg     180
gcgcgtttta gcggcagcgg atccggcacc gatttcaccc tgaccattag cagcctggaa    240
ccggaagact ttgcggtgta ttattgccag cagcattcta tgtacccgcg taccttggc    300 cagggcacga aagttgaaat taaa                                            324

<210> SEQ ID NO 26
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Thr Arg Asn
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Ala Arg Phe Ser
        50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln His Ser Met Tyr Pro
                85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140
```

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 27
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 27
gatatcgtgc tgacccagag cccggcgacc ctgagcctga gcccgggtga acgtgccacc      60
ctgagctgca gcgagcca gtctatcact cgtaactacc tggcttggta ccagcagaaa     120
ccgggccagg ccccgcgtct attaatctac ggtgcttctt ctcgtgcgac cggcattccg     180
gcgcgtttta gcggcagcgg atccggcacc gatttcaccc tgaccattag cagcctggaa     240
ccggaagact ttgcggtgta ttattgccag cagcattcta tgtacccgcg tacctttggc     300
cagggcacga aagttgaaat taaacgtacg gtggccgctc ccagcgtgtt catcttcccc     360
cccagcgacg agcagctgaa gagcggcacc gccagcgtgg tgtgcctgct gaacaacttc     420
tacccccggg aggccaaggt gcagtggaag gtggacaacg ccctgcagag cggcaacagc     480
caggaaagcg tcaccgagca ggacagcaag gactccacct acagcctgag cagcaccctg     540
accctgagca aggccgacta cgagaagcac aaggtgtacg cctgcgaggt gacccaccag     600
ggcctgtcca gccccgtgac caagagcttc aaccggggcg agtgt                    645

<210> SEQ ID NO 28
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Gly Phe Thr Phe Ser Ser Tyr Trp Met Asn
1               5                   10

<210> SEQ ID NO 29
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Ala Ile Ser Ser Asp Gly Ser Tyr Thr Tyr Tyr Ala Asp Ser Val Lys
1               5                   10                  15

Gly

```
<210> SEQ ID NO 30
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Asp Arg Tyr Ser Met Ile Tyr Ser Tyr Gly Ala Gly Ala Phe Asp Tyr
1               5                   10                  15

<210> SEQ ID NO 31
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Ser Tyr Trp Met Asn
1               5

<210> SEQ ID NO 32
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gly Phe Thr Phe Ser Ser Tyr
1               5

<210> SEQ ID NO 33
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Ser Ser Asp Gly Ser Tyr
1               5

<210> SEQ ID NO 34
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Gly Phe Thr Phe Ser Ser Tyr Trp
1               5
```

<210> SEQ ID NO 35
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Ile Ser Ser Asp Gly Ser Tyr Thr
1               5

<210> SEQ ID NO 36
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Ala Arg Asp Arg Tyr Ser Met Ile Tyr Ser Tyr Gly Ala Gly Ala Phe
1               5                   10                  15

Asp Tyr

<210> SEQ ID NO 37
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ser Ala Ile Ser Ser Asp Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Tyr Ser Met Ile Tyr Ser Tyr Gly Ala Gly Ala Phe
            100                 105                 110

Asp Tyr Trp Gly Gln Gly Thr Leu Val Thr Val Ser Ser
        115                 120                 125

<210> SEQ ID NO 38
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 38

```
caggtgcaat tgctggaaag cggcggtggc ctggtgcagc cgggtggcag cctgcgtctg    60
agctgcgcgg cgtccggatt caccttttct tcttactgga tgaactgggt gcgccaggcc   120
ccgggcaaag gtctcgagtg ggtttccgct atctcttctg acggttctta cacctactat   180
gcggatagcg tgaaaggccg ctttaccatc agccgcgata attcgaaaaa caccctgtat   240
ctgcaaatga acagcctgcg tgcggaagat acggccgtgt attattgcgc gcgtgaccgt   300
tactctatga tctactctta cggtgctggt gctttcgatt actggggcca aggcaccctg   360
gtgactgtta gctca                                                    375
```

<210> SEQ ID NO 39
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ser Ala Ile Ser Ser Asp Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Tyr Ser Met Ile Tyr Ser Tyr Gly Ala Gly Ala Phe
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285
```

```
Gly Val Glu Val His Asn Ala Lys Thr Lys Pro Arg Glu Glu Gln Tyr
    290                 295                 300
Asn Ser Thr Tyr Arg Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Glu Glu Met Thr Lys
        355                 360                 365
Asn Gln Val Ser Leu Thr Cys Leu Val Lys Gly Phe Tyr Pro Ser Asp
    370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
Leu Ser Leu Ser Pro Gly Lys
    450                 455

<210> SEQ ID NO 40
<211> LENGTH: 1365
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 40
caggtgcaat tgctggaaag cggcggtggc ctggtgcagc cgggtggcag cctgcgtctg      60
agctgcgcgg cgtccggatt cacctttttct tcttactgga tgaactgggt gcgccaggcc     120
ccgggcaaag gtctcgagtg ggtttccgct atctcttctg acggttctta cacctactat     180
gcggatagcg tgaaaggccg ctttaccatc agccgcgata ttcgaaaaaa cacccctgtat    240
ctgcaaatga acagcctgcg tgcggaagat acggccgtgt attattgcgc gcgtgaccgt     300
tactctatga tctactctta cggtgctggt gctttcgatt actggggcca aggcaccctg     360
gtgactgtta gctcagcctc caccaagggt ccatcggtct tccccctggc acctcctcc      420
aagagcacct ctgggggcac agcggccctg ggctgcctgg tcaaggacta cttccccgaa     480
ccggtgacgg tgtcgtggaa ctcaggcgcc ctgaccagcg gcgtgcacac cttcccggct     540
gtcctacagt cctcaggact ctactccctc agcagcgtgg tgaccgtgcc ctccagcagc     600
ttgggcaccc agacctacat ctgcaacgtg aatcacaagc ccagcaacac caaggtggac     660
aagagagttg agcccaaatc ttgtgacaaa actcacacat gcccaccgtg cccagcacct     720
gaagcagcgg ggggaccgtc agtcttcctc ttccccccaa aacccaagga caccctcatg     780
atctcccgga cccctgaggt cacatgcgtg gtggtggacg tgagccacga agaccctgag     840
gtcaagttca actggtacgt ggacggcgtg gaggtgcata atgccaagac aaagccgcgg     900
gaggagcagt acaacagcac gtaccgggtg gtcagcgtcc tcaccgtcct gcaccaggac     960
tggctgaatg gcaaggagta caagtgcaag gtctccaaca aagccctccc agcccccatc    1020
```

```
gagaaaacca tctccaaagc caaagggcag ccccgagaac cacaggtgta caccctgccc    1080
ccatcccggg aggagatgac caagaaccag gtcagcctga cctgcctggt caaaggcttc    1140
tatcccagcg acatcgccgt ggagtgggag agcaatgggc agccggagaa caactacaag    1200
accacgcctc ccgtgctgga ctccgacggc tccttcttcc tctacagcaa gctcaccgtg    1260
gacaagagca ggtggcagca ggggaacgtc ttctcatgct ccgtgatgca tgaggctctg    1320
cacaaccact acacgcagaa gagcctctcc ctgtctccgg gtaaa                   1365
```

<210> SEQ ID NO 41
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

```
Arg Ala Ser Gln Gly Ile Ser Ser Tyr Leu Ala
1               5                   10
```

<210> SEQ ID NO 42
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

```
Thr Ala Ser Thr Leu Gln Ser
1               5
```

<210> SEQ ID NO 43
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

```
Met Gln Ser Tyr Glu Lys Pro Arg Thr
1               5
```

<210> SEQ ID NO 44
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

```
Ser Gln Gly Ile Ser Ser Tyr
1               5
```

<210> SEQ ID NO 45
<211> LENGTH: 3
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 45

Thr Ala Ser
1

<210> SEQ ID NO 46
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Ser Tyr Glu Lys Pro Arg
1               5

<210> SEQ ID NO 47
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Gln Gly Ile Ser Ser Tyr
1               5

<210> SEQ ID NO 48
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Lys Pro Gly Lys Ala Pro Lys Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Met Gln Ser Tyr Glu Lys Pro Arg
                85                  90                  95

Thr Phe Gly Gln Gly Thr Lys Val Glu Ile Lys
            100                 105

<210> SEQ ID NO 49
<211> LENGTH: 321
<212> TYPE: DNA
<213> ORGANISM: Artificial Sequence
<220> FEATURE:
<221> NAME/KEY: source
```

<223> OTHER INFORMATION: /note="Description of Artificial Sequence:
Synthetic polynucleotide"

<400> SEQUENCE: 49

```
gatatccaga tgacccagag cccgagcagc ctgagcgcca gcgtgggcga tcgcgtgacc    60
attacctgca gagccagcca gggtatttct tcttacctgg cttggtacca gcagaaaccg   120
ggcaaagcgc cgaaactatt aatctacact gcttctactc tgcaaagcgg cgtgccgagc   180
cgctttagcg gcagcggatc cggcaccgat tcaccctga ccattagctc tctgcaaccg    240
gaagactttg cgacctatta ttgcatgcag tcttacgaaa aaccgcgtac ctttggccag   300
ggcacgaaag ttgaaattaa a                                              321
```

<210> SEQ ID NO 50
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 50

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Met Gln Ser Tyr Glu Lys Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 51
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 51

```
gatatccaga tgacccagag cccgagcagc ctgagcgcca gcgtgggcga tcgcgtgacc      60
attacctgca gagccagcca gggtatttct tcttacctgg cttggtacca gcagaaaccg     120
ggcaaagcgc cgaaactatt aatctacact gcttctactc tgcaaagcgg cgtgccgagc     180
cgctttagcg gcagcggatc cggcaccgat tcacccctga ccattagctc tctgcaaccg     240
gaagactttg cgacctatta ttgcatgcag tcttacgaaa aaccgcgtac ctttggccag     300
ggcacgaaag ttgaaattaa acgtacggtg gccgctccca gcgtgttcat cttcccccc      360
agcgacgagc agctgaagag cggcaccgcc agcgtggtgt gcctgctgaa caacttctac     420
ccccggagg ccaaggtgca gtggaaggtg acaacgccc tgcagagcgg caacagccag       480
gaaagcgtca ccgagcagga cagcaaggac tccacctaca gcctgagcag caccctgacc     540
ctgagcaagg ccgactacga gaagcacaag gtgtacgcct gcgaggtgac ccaccagggc     600
ctgtccagcc ccgtgaccaa gagcttcaac cggggcgagt gt                        642
```

<210> SEQ ID NO 52
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Gly Tyr Ser Phe Ser Asn Tyr Trp Ile Gly
1               5                   10

<210> SEQ ID NO 53
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Ile Ile Tyr Pro Asp Val Ser Tyr Thr Arg Tyr Ser Pro Ser Phe Gln
1               5                   10                  15

Gly

<210> SEQ ID NO 54
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Tyr Trp Ser Glu Ala Tyr Thr Phe Asp Tyr
1               5                   10

<210> SEQ ID NO 55
<211> LENGTH: 5
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 55

Asn Tyr Trp Ile Gly
1               5

<210> SEQ ID NO 56
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Gly Tyr Ser Phe Ser Asn Tyr
1               5

<210> SEQ ID NO 57
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Tyr Pro Asp Val Ser Tyr
1               5

<210> SEQ ID NO 58
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Gly Tyr Ser Phe Ser Asn Tyr Trp
1               5

<210> SEQ ID NO 59
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Ile Tyr Pro Asp Val Ser Tyr Thr
1               5

<210> SEQ ID NO 60
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

-continued

```
<400> SEQUENCE: 60

Ala Arg Tyr Trp Ser Glu Ala Tyr Thr Phe Asp Tyr
1               5                   10

<210> SEQ ID NO 61
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Tyr Pro Asp Val Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Trp Ser Glu Ala Tyr Thr Phe Asp Tyr Trp Gly Gln Gly
            100                 105                 110

Thr Leu Val Thr Val Ser Ser
        115

<210> SEQ ID NO 62
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 62
caggtgcaat tggtgcagag cggtgcggaa gtgaaaaaac cgggcgaaag cctgaaaatt      60
agctgcaaag gctccggata tagcttctct aactactgga tcggttgggt gcgccagatg     120
ccgggcaaag gtctcgagtg gatgggcatc atctacccgg acgttagcta cacccgttat     180
agcccgagct ttcagggcca ggtgaccatt agcgcggata aaagcatcag caccgcgtat     240
ctgcaatgga gcagcctgaa agcgagcgat accgcgatgt attattgcgc gcgttactgg     300
tctgaagctt acactttcga ttactggggc caaggcaccc tggtgactgt tagctca        357

<210> SEQ ID NO 63
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Gln Val Gln Leu Val Gln Ser Gly Ala Glu Val Lys Lys Pro Gly Glu
1               5                   10                  15
```

```
Ser Leu Lys Ile Ser Cys Lys Gly Ser Gly Tyr Ser Phe Ser Asn Tyr
             20                  25                  30

Trp Ile Gly Trp Val Arg Gln Met Pro Gly Lys Gly Leu Glu Trp Met
         35                  40                  45

Gly Ile Ile Tyr Pro Asp Val Ser Tyr Thr Arg Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Tyr Trp Ser Glu Ala Tyr Thr Phe Asp Tyr Trp Gly Gln Gly
             100                 105                 110

Thr Leu Val Thr Val Ser Ser Ala Ser Thr Lys Gly Pro Ser Val Phe
         115                 120                 125

Pro Leu Ala Pro Ser Ser Lys Ser Thr Ser Gly Gly Thr Ala Ala Leu
     130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                 165                 170                 175

Gln Ser Ser Gly Leu Tyr Ser Leu Ser Ser Val Val Thr Val Pro Ser
             180                 185                 190

Ser Ser Leu Gly Thr Gln Thr Tyr Ile Cys Asn Val Asn His Lys Pro
         195                 200                 205

Ser Asn Thr Lys Val Asp Lys Arg Val Glu Pro Lys Ser Cys Asp Lys
     210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                 245                 250                 255

Arg Thr Pro Glu Val Thr Cys Val Val Val Asp Val Ser His Glu Asp
             260                 265                 270

Pro Glu Val Lys Phe Asn Trp Tyr Val Asp Gly Val Glu Val His Asn
         275                 280                 285

Ala Lys Thr Lys Pro Arg Glu Glu Gln Tyr Asn Ser Thr Tyr Arg Val
     290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                 325                 330                 335

Thr Ile Ser Lys Ala Lys Gly Gln Pro Arg Glu Pro Gln Val Tyr Thr
             340                 345                 350

Leu Pro Pro Ser Arg Glu Glu Met Thr Lys Asn Gln Val Ser Leu Thr
         355                 360                 365

Cys Leu Val Lys Gly Phe Tyr Pro Ser Asp Ile Ala Val Glu Trp Glu
     370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                 405                 410                 415

Ser Arg Trp Gln Gln Gly Asn Val Phe Ser Cys Ser Val Met His Glu
             420                 425                 430
```

Ala Leu His Asn His Tyr Thr Gln Lys Ser Leu Ser Leu Ser Pro Gly
    435                 440                 445

Lys

<210> SEQ ID NO 64
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 64
caggtgcaat tggtgcagag cggtgcggaa gtgaaaaaac cgggcgaaag cctgaaaatt      60
agctgcaaag ctccggata tagcttctct aactactgga tcggttgggt gcgccagatg     120
ccgggcaaag gtctcgagtg gatgggcatc atctacccgg acgttagcta cacccgttat     180
agcccgagct ttcagggcca ggtgaccatt agcgcggata aaagcatcag caccgcgtat     240
ctgcaatgga gcagcctgaa agcgagcgat accgcgatgt attattgcgc gcgttactgg     300
tctgaagctt acactttcga ttactggggc caaggcaccc tggtgactgt tagctcagcc     360
tccaccaagg gtccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagagagt tgagcccaaa     660
tcttgtgaca aaactcacac atgcccaccg tgcccagcac ctgaagcagc gggggggaccg     720 tcagtcttcc tcttccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccggg tggtcagcgt cctcaccgtc ctgcaccagg actggctgaa tggcaaggag     960
tacaagtgca aggtctccaa caaagccctc ccagccccca tcgagaaaac catctccaaa    1020
gccaaagggc agccccgaga accacaggtg tacaccctgc ccccatcccg ggaggagatg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaa                                        1347

<210> SEQ ID NO 65
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Ser Gly Asp Asn Ile Arg Lys Lys Tyr Val Phe
1               5                   10

```
<210> SEQ ID NO 66
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Gly Asp Asn Asp Arg Pro Ser
1               5

<210> SEQ ID NO 67
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Gly Thr Tyr Thr Leu Leu Phe Thr Ser Lys Val
1               5                   10

<210> SEQ ID NO 68
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Asp Asn Ile Arg Lys Lys Tyr
1               5

<210> SEQ ID NO 69
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Gly Asp Asn
1

<210> SEQ ID NO 70
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Tyr Thr Leu Leu Phe Thr Ser Lys
1               5

<210> SEQ ID NO 71
<211> LENGTH: 6
<212> TYPE: PRT
<213> ORGANISM: Artificial Sequence
```

<220> FEATURE:
<221> NAME/KEY: source
<223> OTHER INFORMATION: /note="Description of Artificial Sequence:
      Synthetic peptide"

<400> SEQUENCE: 71

Asn Ile Arg Lys Lys Tyr
1               5

<210> SEQ ID NO 72
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Asp Ile Glu Leu Thr Gln Pro Pro Ser Val Ser Val Ser Pro Gly Gln
1               5                   10                  15

Thr Ala Ser Ile Thr Cys Ser Gly Asp Asn Ile Arg Lys Lys Tyr Val
            20                  25                  30

Phe Trp Tyr Gln Gln Lys Pro Gly Gln Ala Pro Val Leu Val Ile Tyr
        35                  40                  45

Gly Asp Asn Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gly Thr Tyr Thr Leu Leu Phe Thr Ser
                85                  90                  95

Lys Val Phe Gly Gly Gly Thr Lys Leu Thr Val Leu
            100                 105

<210> SEQ ID NO 73
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 73
gatatcgaac tgacccagcc gccgagcgtg agcgtgagtc cgggccagac cgcgagcatt      60
acctgtagcg gcgataacat ccgtaaaaaa tacgttttct ggtaccagca gaaaccgggc     120
caggcgccgg tgctggtgat ctacggtgac aacgaccgtc cgagcggcat cccggaacgt     180
tttagcggat ccaacagcgg caacaccgcg accctgacca ttagcggcac ccaggcggaa     240
gacgaagcgg attattactg cggtacttac actctgctgt tcacttctaa agtgtttggc     300
ggcggcacga gttaaccgt ccta                                              324

<210> SEQ ID NO 74
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

```
Asp Ile Glu Leu Thr Gln Pro Pro Ser Val Ser Val Ser Pro Gly Gln
1               5                   10                  15

Thr Ala Ser Ile Thr Cys Ser Gly Asp Asn Ile Arg Lys Lys Tyr Val
            20                  25                  30

Phe Trp Tyr Gln Gln Lys Pro Gly Gln Ala Pro Val Leu Val Ile Tyr
        35                  40                  45

Gly Asp Asn Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gly Thr Tyr Thr Leu Leu Phe Thr Ser
                85                  90                  95

Lys Val Phe Gly Gly Gly Thr Lys Leu Thr Val Leu Gly Gln Pro Lys
                100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 75
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 75
gatatcgaac tgacccagcc gccgagcgtg agcgtgagtc cgggccagac cgcgagcatt      60
acctgtagcg gcgataacat ccgtaaaaaa tacgttttct ggtaccagca gaaaccgggc     120
caggcgccgg tgctggtgat ctacggtgac aacgaccgtc cgagcggcat cccggaacgt     180
tttagcggat ccaacagcgg caacaccgcg accctgacca ttagcggcac ccaggcggaa     240
gacgaagcgg attattactg cggtacttac actctgctgt tcacttctaa agtgtttggc     300
ggcggcacga agttaaccgt cctaggtcag cccaaggctg cccccctcgg tcactctgttc    360 ccgcccctcct ctgaggagct tcaagccaac aaggccacac tggtgtgtct cataagtgac    420
ttctacccgg gagccgtgac agtggcctgg aaggcagata gcagccccgt caaggcggga    480
gtggagacca ccacccctc caaacaaagc aacaacaagt acgcggccag cagctatctg      540
agcctgacgc ctgagcagtg gaagtcccac agaagctaca gctgccaggt cacgcatgaa     600
gggagcaccg tggagaagac agtggcccct acagaatgtt ca                        642

<210> SEQ ID NO 76
<211> LENGTH: 10
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Gly Tyr Ser Phe Thr Ser Tyr Trp Ile Ala
1               5                   10

<210> SEQ ID NO 77
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Arg Ile Asp Pro Asp Asn Ser Tyr Thr Arg Tyr Ser Pro Ser Phe Gln
1               5                   10                  15
Gly

<210> SEQ ID NO 78
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Trp Leu Ser Pro Gly Tyr Ala Leu Gly Glu Gln Pro Ala Gly Met Asp
1               5                   10                  15
His

<210> SEQ ID NO 79
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Ser Tyr Trp Ile Ala
1               5

<210> SEQ ID NO 80
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Gly Tyr Ser Phe Thr Ser Tyr
1               5

<210> SEQ ID NO 81
<211> LENGTH: 6
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Asp Pro Asp Asn Ser Tyr
1               5

<210> SEQ ID NO 82
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Gly Tyr Ser Phe Thr Ser Tyr Trp
1               5

<210> SEQ ID NO 83
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Ile Asp Pro Asp Asn Ser Tyr Thr
1               5

<210> SEQ ID NO 84
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Ala Arg Trp Leu Ser Pro Gly Tyr Ala Leu Gly Glu Gln Pro Ala Gly
1               5                   10                  15

Met Asp His

<210> SEQ ID NO 85
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Ala Trp Val Arg Gln Met Pro Gly Lys Gly Leu Glu Trp Met
            35                  40                  45
```

Gly Arg Ile Asp Pro Asp Asn Ser Tyr Thr Arg Tyr Ser Pro Ser Phe
            50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Leu Ser Pro Gly Tyr Ala Leu Gly Glu Gln Pro Ala Gly
            100                 105                 110

Met Asp His Trp Gly Gln Gly Thr Leu Val Thr Val Ser Ser
            115                 120                 125

<210> SEQ ID NO 86
<211> LENGTH: 378
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 86
caggtgcaat tggtgcagag cggtgcggaa gtgaaaaaac cgggcgaaag cctgaaaatt    60
agctgcaaag ctccggata tagcttcact tcttactgga tcgcttgggt gcgccagatg   120
ccgggcaaag gtctcgagtg gatgggccgt atcgacccgg acaacagcta cacccgttat   180
agcccgagct ttcagggcca ggtgaccatt agcgcggata aaagcatcag caccgcgtat   240
ctgcaatgga gcagcctgaa agcgagcgat accgcgatgt attattgcgc gcgttggctg   300
tctccgggtt acgctctggg tgaacagccg gctggtatgg atcattgggg ccaaggcacc   360
ctggtgactg ttagctca                                                 378

<210> SEQ ID NO 87
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Trp Met
        35                  40                  45

Gly Arg Ile Asp Pro Asp Asn Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Leu Ser Pro Gly Tyr Ala Leu Gly Glu Gln Pro Ala Gly
            100                 105                 110

Met Asp His Trp Gly Gln Gly Thr Leu Val Thr Val Ser Ser Ala Ser
            115                 120                 125

Thr Lys Gly Pro Ser Val Phe Pro Leu Ala Pro Ser Ser Lys Ser Thr

```
            130                 135                 140
Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
                180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Arg Val
        210                 215                 220

Glu Pro Lys Ser Cys Asp Lys Thr His Thr Cys Pro Pro Cys Pro Ala
225                 230                 235                 240

Pro Glu Ala Ala Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Glu Glu Met Thr
            355                 360                 365

Lys Asn Gln Val Ser Leu Thr Cys Leu Val Lys Gly Phe Tyr Pro Ser
        370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
            435                 440                 445

Ser Leu Ser Leu Ser Pro Gly Lys
        450                 455
```

<210> SEQ ID NO 88
<211> LENGTH: 1368
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 88

```
caggtgcaat tggtgcagag cggtgcggaa gtgaaaaaac cgggcgaaag cctgaaaatt      60
agctgcaaag ctccggata tagcttcact tcttactgga tcgcttgggt gcgccagatg     120
ccgggcaaag gtctcgagtg gatgggccgt atcgacccgg acaacagcta caccccgttat     180
```

-continued

```
agcccgagct tcagggcca ggtgaccatt agcgcggata aaagcatcag caccgcgtat      240
ctgcaatgga gcagcctgaa agcgagcgat accgcgatgt attattgcgc gcgttggctg      300
tctccgggtt acgctctggg tgaacagccg gctggtatgg atcattgggg ccaaggcacc      360
ctggtgactg ttagctcagc ctccaccaag ggtccatcgg tcttcccct ggcaccctcc       420 tccaagagca cctctggggg cacagcggcc ctgggctgcc tggtcaagga ctacttcccc      480
gaaccggtga cggtgtcgtg gaactcaggc gccctgacca gcggcgtgca caccttcccg      540
gctgtcctac agtcctcagg actctactcc ctcagcagcg tggtgaccgt gccctccagc      600
agcttgggca cccagaccta catctgcaac gtgaatcaca agcccagcaa caccaaggtg      660
gacaagagag ttgagcccaa atcttgtgac aaaactcaca catgcccacc gtgcccagca      720
cctgaagcag cggggggacc gtcagtcttc ctcttcccc caaaacccaa ggacaccctc       780
atgatctccc ggacccctga ggtcacatgc gtggtggtgg acgtgagcca cgaagaccct      840
gaggtcaagt tcaactggta cgtggacggc gtggaggtgc ataatgccaa gacaaagccg      900
cgggaggagc agtacaacag cacgtaccgg gtggtcagcg tcctcaccgt cctgcaccag      960
gactggctga atggcaagga gtacaagtgc aaggtctcca acaaagccct cccagccccc     1020
atcgagaaaa ccatctccaa agccaaaggg cagccccgag aaccacaggt gtacaccctg     1080
cccccatccc gggaggagat gaccaagaac caggtcagcc tgacctgcct ggtcaaaggc     1140
ttctatccca gcgacatcgc cgtggagtgg gagagcaatg ggcagccgga gaacaactac     1200
aagaccacgc ctcccgtgct ggactccgac ggctccttct tcctctacag caagctcacc     1260
gtggacaaga gcaggtggca gcaggggaac gtcttctcat gctccgtgat gcatgaggct     1320
ctgcacaacc actacacgca gaagagcctc tccctgtctc cgggtaaa                  1368
```

<210> SEQ ID NO 89
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Thr Gly Ser Ser Ser Asn Ile Gly Ala Gly Tyr Ala Val His
1               5                   10

<210> SEQ ID NO 90
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Ser Asn Asn Lys Arg Pro Ser
1               5

<210> SEQ ID NO 91
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:

-continued

Synthetic peptide"

<400> SEQUENCE: 91

Gln Ser Tyr Asp Leu Gln Lys Ser Ser Arg Val
1               5                   10

<210> SEQ ID NO 92
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Ser Ser Ser Asn Ile Gly Ala Gly Tyr Ala
1               5                   10

<210> SEQ ID NO 93
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Ser Asn Asn
1

<210> SEQ ID NO 94
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Tyr Asp Leu Gln Lys Ser Ser Arg
1               5

<210> SEQ ID NO 95
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Ser Ser Asn Ile Gly Ala Gly Tyr Ala
1               5

<210> SEQ ID NO 96
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

Asp Ile Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Ala Val His Trp Tyr Gln Gln Leu Pro Gly Thr Ala Pro Lys Leu
        35                  40                  45

Leu Ile Tyr Ser Asn Asn Lys Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Leu Gln
                85                  90                  95

Lys Ser Ser Arg Val Phe Gly Gly Gly Thr Lys Leu Thr Val Leu
            100                 105                 110

<210> SEQ ID NO 97
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 97
gatatcgtgc tgacccagcc gccgagcgtg agcggtgcac cgggccagcg cgtgaccatt      60
agctgtaccg gcagcagcag caacattggt gctggttacg ctgtgcattg gtaccagcag     120
ctgccgggca cggcgccgaa actgctgatc tactctaaca caaacgccc gagcggcgtg      180 ccggatcgct ttagcggatc caaaagcggc accagcgcca gcctggcgat taccggcctg     240
caagcagaag acgaagcgga ttattactgc cagtcttacg acctgcagaa atcttctcgt     300
gtgtttggcg gcggcacgaa gttaaccgtc cta                                  333

<210> SEQ ID NO 98
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

Asp Ile Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Ala Val His Trp Tyr Gln Gln Leu Pro Gly Thr Ala Pro Lys Leu
        35                  40                  45

Leu Ile Tyr Ser Asn Asn Lys Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Leu Gln
                85                  90                  95

Lys Ser Ser Arg Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu

```
            115                 120                 125
Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
                195                 200                 205

Lys Thr Val Ala Pro Thr Glu Cys Ser
    210                 215

<210> SEQ ID NO 99
<211> LENGTH: 651
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 99
gatatcgtgc tgacccagcc gccgagcgtg agcggtgcac cgggccagcg cgtgaccatt      60
agctgtaccg gcagcagcag caacattggt gctggttacg ctgtgcattg gtaccagcag     120
ctgccgggca cggcgccgaa actgctgatc tactctaaca caaacgccc gagcggcgtg     180 ccggatcgct ttagcggatc caaaagcggc accagcgcca gcctggcgat taccggcctg     240
caagcagaag acgaagcgga ttattactgc cagtcttacg acctgcagaa atcttctcgt     300
gtgtttggcg gcggcacgaa gttaaccgtc ctaggtcagc ccaaggctgc ccctcggtc      360 actctgttcc cgcccctcctc tgaggagctt caagccaaca ggccacact ggtgtgtctc     420 ataagtgact tctacccggg agccgtgaca gtggcctgga aggcagatag cagccccgtc     480
aaggcgggag tggagaccac cacacccctcc aaacaaagca caacaagta cgcggccagc     540 agctatctga gcctgacgcc tgagcagtgg aagtcccaca gaagctacag ctgccaggtc     600
acgcatgaag ggagcaccgt ggagaagaca gtggccccta cagaatgttc a             651

<210> SEQ ID NO 100
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Ser Ile Ser Ser Ser Gly Gln Ser Thr Tyr Tyr Ala Asp Ser Val Lys
1               5                   10                  15

Gly

<210> SEQ ID NO 101
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 101

Ser Ser Ser Gly Gln Ser
1               5

<210> SEQ ID NO 102
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Ile Ser Ser Ser Gly Gln Ser Thr
1               5

<210> SEQ ID NO 103
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr His
            20                  25                  30

Tyr Ile His Trp Val Arg Gln Ala Pro Gly Lys Gly Leu Glu Trp Val
        35                  40                  45

Ser Ser Ile Ser Ser Ser Gly Gln Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Gly Tyr Val Tyr Tyr His Met Phe Asp Pro Trp Gly
            100                 105                 110

Gln Gly Thr Leu Val Thr Val Ser Ser
        115                 120

<210> SEQ ID NO 104
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 104
gaggtgcaat tgctggaaag cggcggtggc ctggtgcagc cgggtggcag cctgcgtctg      60
agctgcgcgg cgtccggatt cacctttaac actcattaca tccattgggt gcgccaggcc     120
cccggcaaag gtctcgagtg gtttcctct atctcttctt ctggccagtc tacttactat     180
gcggatagcg tgaaaggccg ctttaccatc agccgcgata attcgaaaaa cacccctgtat    240 ctgcaaatga acagcctgcg tgcggaagat acggccgtgt attattgcgc gcgtgaacgt     300

-continued

```
ggttacgttt actaccatat gttcgatccg tggggccaag gcaccctggt gactgttagc    360
tca                                                                  363
```

<210> SEQ ID NO 105
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 105

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr His
            20                  25                  30

Tyr Ile His Trp Val Arg Gln Ala Pro Gly Lys Gly Leu Glu Trp Val
        35                  40                  45

Ser Ser Ile Ser Ser Ser Gly Gln Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Gly Tyr Val Tyr Tyr His Met Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

```
Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 106
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 106
gaggtgcaat tgctggaaag cggcggtggc ctggtgcagc cgggtggcag cctgcgtctg      60
agctgcgcgg cgtccggatt cacctttaac actcattaca tccattgggt gcgccaggcc     120
cccggcaaag gtctcgagtg gtttcctct atctcttctt ctggccagtc tacttactat     180
gcggatagcg tgaaaggccg ctttaccatc agccgcgata attcgaaaaa cacccctgtat    240 ctgcaaatga acagcctgcg tgcggaagat acggccgtgt attattgcgc gcgtgaacgt     300
ggttacgttt actaccatat gttcgatccg tggggccaag caccctggt gactgttagc      360 tcagcctcca ccaagggtcc atcggtcttc cccctgcac cctcctccaa gagcacctct      420
gggggcacag cggccctggg ctgcctggtc aaggactact ccccgaacc ggtgacggtg      480 tcgtggaact caggcgccct gaccagcggc gtgcacacct cccggctgt cctacagtcc     540 tcaggactct actccctcag cagcgtggtg accgtgccct ccagcagctt gggcacccag    600
acctacatct gcaacgtgaa tcacaagccc agcaacacca aggtggacaa gagagttgag    660
cccaaatctt gtgacaaaac tcacacatgc ccaccgtgcc cagcacctga gcagcgggg    720 ggaccgtcag tcttcctctt cccccccaaaa cccaaggaca cctcatgat ctcccggacc    780 cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgggtggt cagcgtcctc accgtcctgc accaggactg gctgaatggc    960
aaggagtaca agtgcaaggt ctccaacaaa gccctcccag cccccatcga gaaaaccatc   1020
tccaaagcca aagggcagcc ccgagaacca caggtgtaca ccctgccccc atccgggag   1080 gagatgacca gaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
```

```
tggcagcagg ggaacgtctt ctcatgctcc gtgatgcatg aggctctgca caaccactac   1320
acgcagaaga gcctctccct gtctccgggt aaa                                1353
```

<210> SEQ ID NO 107
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 107

```
gaagtgcagc tgcttgagtc cggggtgga ctggtgcagc ccggaggatc cctgcgcctg    60
agctgcgctg catccggctt caccttcaac acgcactaca tccattgggt cagacaggcc  120
ccaggaaaag gcctggaatg ggtgtcctcc atctcctcgt cggggcagtc aacctactac  180
gcggactccg tcaagggccg gtttaccatt agccgggaca acagcaagaa taccctgtac  240
ctccaaatga actcgctgag ggccgaagat accgccgtgt attactgtgc ccgcgagaga  300
ggctacgtgt actaccacat gttcgacccg tggggacagg gtactctcgt gactgtgtct  360
tct                                                                363
```

<210> SEQ ID NO 108
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 108

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr His
            20                  25                  30

Tyr Ile His Trp Val Arg Gln Ala Pro Gly Lys Gly Leu Glu Trp Val
        35                  40                  45

Ser Ser Ile Ser Ser Ser Gly Gln Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Gly Tyr Val Tyr Tyr His Met Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His

```
            195                 200                 205
Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ala Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Ala Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 109
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 109
gaagtgcagc tgcttgagtc cggggtgga ctggtgcagc cggaggatc cctgcgcctg      60 agctgcgctg catccggctt caccttcaac acgcactaca tccattgggt cagacaggcc    120
ccaggaaaag gcctggaatg ggtgtcctcc atctcctcgt cggggcagtc aacctactac    180
gcggactccg tcaagggccg gtttaccatt agccgggaca cagcaagaa taccctgtac    240 ctccaaatga actcgctgag gccgaagat accgccgtgt attactgtgc ccgcgagaga    300
ggctacgtgt actaccacat gttcgacccg tggggacagg gtactctcgt gactgtgtct    360
tctgcgagca ctaagggccc gtcagtgttc ccgctggctc catcgtcgaa gtccacctcc    420
ggaggaaccg cagcactcgg ttgcctggtc aaggactact ccctgagcc agtgaccgtg    480 tcgtggaaca gcggagccct gacttccggc gtgcacactt ttcccgcggt gctgcagtcc    540
```

```
tccggtctgt actccctttc gtccgtggtc accgtgccgt cgtctagcct gggcacccag    600
acctacatct gcaacgtgaa ccacaagccg tccaacacca aagtggataa gcgggtggag    660
ccgaagtcct gcgataagac acacgtgc ccgccatgtc cagcgcctga attgcttggc      720
ggaccttccg tgttcctgtt cccgcctaag cccaaggaca ccttgatgat tagccggact    780
cccgaagtca cctgtgtggt ggtggcagtg tcccacgagg accccgaggt caagtttaat    840
tggtacgtgg acggcgtcga agtgcacaac gccaagacta gccccggga ggaacagtac     900 aacagcacct accgggtcgt gtccgtgctg accgtgctgc accaggactg gctgaatggg    960
aaagagtaca agtgcaaagt gtccaacaag gccttggccg ctcctatcga aaaaactatc   1020
agcaaggcta agggacagcc gagggaaccc caagtctaca ccctgccccc ttcacgcgaa   1080
gagatgacca agaatcaagt gtcgctgacc tgcctcgtca agggattcta cccctccgac   1140
attgcggtgg agtgggagtc caacggccag cccgagaaca actacaagac tactccgccc   1200
gtgctggact ccgacggcag cttcttcctg tattccaagc tgaccgtgga caagtcccgg   1260
tggcagcaag gaaacgtgtt ctcctgctcg gtcatgcacg aagccctgca caaccactat   1320
acgcagaagt ccctgtcctt gagcccgggg aaa                                1353

<210> SEQ ID NO 110
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 110
gacatcgtgc tgactcagtc ccctgcgact ctgagcctgt caccgggaga acgggccacc     60
ctctcttgcc gcgcctccca atccattact cggaactacc tggcctggta tcagcagaag    120
ccaggacagg cccctaggct tctgatctac ggggccagct caagagcaac tggcatcccg    180
gctcgcttct ccggtcgggg aagcggcacc gacttcaccc tgacaatttc gtccctcgaa    240
cccgaggatt tcgccgtgta ctactgccaa cagcactcca tgtaccccg gacctttggg     300 cagggaacca agtcgagat caag                                            324

<210> SEQ ID NO 111
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 111
gacatcgtgc tgactcagtc ccctgcgact ctgagcctgt caccgggaga acgggccacc     60
ctctcttgcc gcgcctccca atccattact cggaactacc tggcctggta tcagcagaag    120
ccaggacagg cccctaggct tctgatctac ggggccagct caagagcaac tggcatcccg    180
gctcgcttct ccggttcggg aagcggcacc gacttcaccc tgacaatttc gtccctcgaa    240
cccgaggatt tcgccgtgta ctactgccaa cagcactcca tgtaccccg gacctttggg     300 cagggaacca agtcgagat caagcgtacg gtggccgctc ccagcgtgtt catcttcccc    360
cccagcgacg agcagctgaa gagcggcacc gccagcgtgg tgtgcctgct gaacaacttc    420
```

-continued

```
tacccccggg aggccaaggt gcagtggaag gtggacaacg ccctgcagag cggcaacagc    480
caggagagcg tcaccgagca ggacagcaag gactccacct acagcctgag cagcaccctg    540
accctgagca aggccgacta cgagaagcat aaggtgtacg cctgcgaggt gacccaccag    600
ggcctgtcca gccccgtgac caagagcttc aacaggggcg agtgc                    645
```

<210> SEQ ID NO 112
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

```
Gly Phe Thr Phe Ser Thr His Tyr Ile His
1               5                   10
```

<210> SEQ ID NO 113
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

```
Gly Phe Thr Phe Ser Thr His
1               5
```

<210> SEQ ID NO 114
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 114

```
Gly Phe Thr Phe Ser Thr His Tyr
1               5
```

<210> SEQ ID NO 115
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 115

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr His
            20                  25                  30

Tyr Ile His Trp Val Arg Gln Ala Pro Gly Lys Gly Leu Glu Trp Val
        35                  40                  45

Ser Ser Ile Ser Ser Ser Gly Gln Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                    85                  90                  95

Ala Arg Glu Arg Gly Tyr Val Tyr Tyr His Met Phe Asp Pro Trp Gly
                100                 105                 110

Gln Gly Thr Leu Val Thr Val Ser Ser
            115                 120

<210> SEQ ID NO 116
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 116

```
gaagtgcagc tgcttgagtc cggggggtgga ctggtgcagc ccggaggatc cctgcgcctg      60
agctgcgctg catccggctt caccttcagc acgcactaca tccattgggt cagacaggcc     120
ccaggaaaag gcctggaatg ggtgtcctcc atctcctcgt cggggcagtc aacctactac     180
gcggactccg tcaagggccg gtttaccatt agccgggaca cagcaagaa taccctgtac     240 ctccaaatga actcgctgag ggccgaagat accgccgtgt attactgtgc ccgcgagaga     300
ggctacgtgt actaccacat gttcgacccg tggggacagg gtactctcgt gactgtgtct     360
tct                                                                    363
```

<210> SEQ ID NO 117
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 117

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr His
                20                  25                  30

Tyr Ile His Trp Val Arg Gln Ala Pro Gly Lys Gly Leu Glu Trp Val
            35                  40                  45

Ser Ser Ile Ser Ser Ser Gly Gln Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Gly Tyr Val Tyr Tyr His Met Phe Asp Pro Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala

```
                165                 170                 175
Val Leu Gln Ser Ser Gly Leu Tyr Ser Leu Ser Ser Val Val Thr Val
            180                 185                 190

Pro Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ala Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Ala Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 118
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 118
gaagtgcagc tgcttgagtc cggggggtgga ctggtgcagc cggaggatc cctgcgcctg    60 agctgcgctg catccggctt caccttcagc acgcactaca tccattgggt cagacaggcc   120
ccaggaaaag gcctggaatg ggtgtcctcc atctcctcgt cggggcagtc aacctactac   180
gcggactccg tcaagggccg gtttaccatt agccgggaca acagcaagaa taccctgtac   240
ctccaaatga actcgctgag ggccgaagat accgccgtgt attactgtgc ccgcagagaga   300 ggctacgtgt actaccacat gttcgacccg tggggacagg gtactctcgt gactgtgtct   360
```

```
tctgcgagca ctaagggccc gtcagtgttc ccgctggctc catcgtcgaa gtccacctcc   420
ggaggaaccg cagcactcgg ttgcctggtc aaggactact ccctgagcc agtgaccgtg   480 tcgtggaaca gcggagccct gacttccggc gtgcacactt ttcccgcggt gctgcagtcc   540
tccggtctgt actcccttc gtccgtggtc accgtgccgt cgtctagcct gggcacccag   600
acctacatct gcaacgtgaa ccacaagccg tccaacacca agtggataa gcgggtggag   660 ccgaagtcct gcgataagac acacgcgtgc cgccatgtc cagcgcctga attgcttggc   720
ggaccttccg tgttcctgtt cccgcctaag cccaaggaca ccttgatgat tagccggact   780
cccgaagtca cctgtgtggt ggtggcagtg tcccacgagg accccgaggt caagtttaat   840
tggtacgtgg acggcgtcga agtgcacaac gccaagacta gccccggga ggaacagtac   900 aacagcacct accgggtcgt gtccgtgctg accgtgctgc accaggactg gctgaatggg   960
aaagagtaca agtgcaaagt gtccaacaag gccttggccg ctcctatcga aaaaactatc  1020
agcaaggcta agggacagcc gagggaaccc caagtctaca ccctgccccc ttcacgcgaa  1080
gagatgacca agaatcaagt gtcgctgacc tgcctcgtca agggattcta ccctccgac  1140 attgcggtgg agtgggagtc caacggccag cccgagaaca actacaagac tactccgccc  1200
gtgctggact ccgacggcag cttcttcctg tattccaagc tgaccgtgga caagtcccgg  1260
tggcagcaag gaacgtgtt ctcctgctcg gtcatgcacg aagccctgca caaccactat  1320
acgcagaagt ccctgtcctt gagcccgggg aaa                              1353
```

<210> SEQ ID NO 119
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Val Ile Glu Ser Lys Gly Asn Tyr Ile Phe Tyr Ala Asp Ser Val Lys
1               5                   10                  15

Gly

<210> SEQ ID NO 120
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

Glu Ser Lys Gly Asn Tyr
1               5

<210> SEQ ID NO 121
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Ile Glu Ser Lys Gly Asn Tyr Ile
1               5

<210> SEQ ID NO 122
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ser Val Ile Glu Ser Lys Gly Asn Tyr Ile Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Tyr Ser Met Ile Tyr Ser Tyr Gly Ala Gly Ala Phe
            100                 105                 110

Asp Tyr Trp Gly Gln Gly Thr Leu Val Thr Val Ser Ser
        115                 120                 125

<210> SEQ ID NO 123
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 123
gaggtgcaat tgctggaaag cggcggtggc ctggtgcagc cgggtggcag cctgcgtctg      60
agctgcgcgg cgtccggatt caccttttct tcttactgga tgaactgggt gcgccaggcc     120
ccgggcaaag gtctcgagtg ggtttccgtt atcgaatcta aaggcaacta catcttctat     180
gcggatagcg tgaaaggccg ctttaccatc agccgcgata ttcgaaaaa cacccctgtat    240 ctgcaaatga acagcctgcg tgcggaagat acggccgtgt attattgcgc gcgtgaccgt     300
tactctatga tctactctta cggtgctggt gctttcgatt actggggcca aggcaccctg     360
gtgactgtta gctca                                                     375

<210> SEQ ID NO 124
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 124

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
         20                  25                  30

Trp Met Asn Trp Val Arg Gln Ala Pro Gly Lys Gly Leu Glu Trp Val
         35                  40                  45

Ser Val Ile Glu Ser Lys Gly Asn Tyr Ile Phe Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Tyr Ser Met Ile Tyr Ser Tyr Gly Ala Gly Ala Phe
                100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
        210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430
```

Cys Ser Val Met His Glu Ala Leu His Asn His Tyr Thr Gln Lys Ser
            435                 440                 445

Leu Ser Leu Ser Pro Gly Lys
    450                 455

<210> SEQ ID NO 125
<211> LENGTH: 1365
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 125
gaggtgcaat tgctggaaag cggcggtggc ctggtgcagc cgggtggcag cctgcgtctg      60
agctgcgcgg cgtccggatt caccttttct tcttactgga tgaactgggt gcgccaggcc     120
ccgggcaaag gtctcgagtg gtttccgtt atcgaatcta aaggcaacta catcttctat      180
gcggatagcg tgaaaggccg ctttaccatc agccgcgata attcgaaaaa caccctgtat     240
ctgcaaatga acagcctgcg tgcggaagat acggccgtgt attattgcgc gcgtgaccgt     300
tactctatga tctactctta cggtgctggt gctttcgatt actggggcca aggcaccctg     360
gtgactgtta gctcagcctc caccaagggt ccatcggtct tccccctggc accctcctcc     420
aagagcacct ctgggggcac agcggccctg ggctgcctgg tcaaggacta cttccccgaa     480
ccggtgacgg tgtcgtggaa ctcaggcgcc ctgaccagcg gcgtgcacac cttcccggct     540
gtcctacagt cctcaggact ctactccctc agcagcgtgg tgaccgtgcc ctccagcagc     600
ttgggcaccc agacctacat ctgcaacgtg aatcacaagc ccagcaacac caaggtggac     660
aagagagttg agcccaaatc ttgtgacaaa actcacacat gcccaccgtg cccagcacct     720
gaagcagcgg ggggaccgtc agtcttcctc ttccccccaa aacccaagga caccctcatg     780
atctcccgga cccctgaggt cacatgcgtg gtggtggacg tgagccacga agaccctgag     840
gtcaagttca actggtacgt ggacggcgtg gaggtgcata atgccaagac aaagccgcgg     900
gaggagcagt acaacagcac gtaccgggtg gtcagcgtcc tcaccgtcct gcaccaggac     960
tggctgaatg gcaaggagta caagtgcaag gtctccaaca aagccctccc agcccccatc    1020
gagaaaacca tctccaaagc caaagggcag ccccgagaac cacaggtgta caccctgccc    1080
ccatcccggg aggagatgac caagaaccag gtcagcctga cctgcctggt caaaggcttc    1140
tatcccagcg acatcgccgt ggagtgggag agcaatgggc agccggagaa caactacaag    1200
accacgcctc ccgtgctgga ctccgacggc tccttcttcc tctacagcaa gctcaccgtg    1260
gacaagagca ggtggcagca ggggaacgtc ttctcatgct ccgtgatgca tgaggctctg    1320
cacaaccact acacgcagaa gagcctctcc ctgtctccgg gtaaa                    1365

<210> SEQ ID NO 126
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Gln Gln Glu Trp Val Lys Pro Arg Thr
1               5

```
<210> SEQ ID NO 127
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 127

Glu Trp Val Lys Pro Arg
1               5

<210> SEQ ID NO 128
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Trp Val Lys Pro Arg
                85                  90                  95

Thr Phe Gly Gln Gly Thr Lys Val Glu Ile Lys
            100                 105

<210> SEQ ID NO 129
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 129
gatatccaga tgacccagag cccgagcagc ctgagcgcca gcgtgggcga tcgcgtgacc      60
attacctgca gagccagcca gggtatttct tcttacctgg cttggtacca gcagaaaccg     120
ggcaaagcgc cgaaactatt aatctacact gcttctactc tgcaaagcgg cgtgccgagc     180
cgctttagcg gcagcggatc cggcaccgat ttcaccctga ccattagctc tctgcaaccg     240
gaagactttg cgacctatta ttgccagcag gaatgggtta aaccgcgtac ctttggccag     300
ggcacgaaag ttgaaattaa a                                               321

<210> SEQ ID NO 130
<211> LENGTH: 214
<212> TYPE: PRT
<213> ORGANISM: Artificial Sequence
<220> FEATURE:
<221> NAME/KEY: source
```

<223> OTHER INFORMATION: /note="Description of Artificial Sequence:
Synthetic polypeptide"

<400> SEQUENCE: 130

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Val Lys Pro Arg
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 131
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 131
gatatccaga tgacccagag cccgagcagc ctgagcgcca gcgtgggcga tcgcgtgacc      60
attacctgca gagccagcca gggtatttct tcttacctgg cttggtacca gcagaaaccg     120
ggcaaagcgc cgaaactatt aatctacact gcttctactc tgcaaagcgg cgtgccgagc     180
cgctttagcg gcagcggatc cggcaccgat ttcaccctga ccattagctc tctgcaaccg     240
gaagactttg cgacctatta ttgccagcag gaatgggtta aaccgcgtac ctttggccag     300
ggcacgaaag ttgaaattaa acgtacggtg gccgctccca gcgtgttcat cttccccccc     360
agcgacgagc agctgaagag cggcaccgcc agcgtggtgt gcctgctgaa caacttctac     420
ccccgggagg ccaaggtgca gtggaaggtg gacaacgccc tgcagagcgg caacagccag     480
gaaagcgtca ccgagcagga cagcaaggac tccacctaca gcctgagcag cacactgacc     540
ctgagcaagg ccgactacga aagcacaag gtgtacgcct gcgaggtgac ccaccagggc     600

```
ctgtccagcc ccgtgaccaa gagcttcaac cggggcgagt gt                  642
```

<210> SEQ ID NO 132
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 132

```
caggtgcaat tgctggaaag cggcggtggc ctggtgcagc cgggtggcag cctgcgtctg    60
agctgcgcgg cgtccggatt cacctttttct tcttactgga tgaactgggt gcgccaggcc  120
ccaggcaaag gtctcgagtg gtttccgct atctcttctg acggttctta cacctactat   180
gcggatagcg tgaaaggccg ctttaccatc agccgcgata attcgaaaaa cacccctgtat 240
ctgcaaatga acagcctgcg tgcggaagat acggccgtgt attattgcgc gcgtgaccgt  300
tactctatga tctactctta cggtgctggt gctttcgatt actggggcca aggcaccctg  360
gtgactgtta gctca                                                   375
```

<210> SEQ ID NO 133
<211> LENGTH: 1365
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 133

```
caggtgcaat tgctggaaag cggcggtggc ctggtgcagc cgggtggcag cctgcgtctg    60
agctgcgcgg cgtccggatt cacctttttct tcttactgga tgaactgggt gcgccaggcc  120
ccaggcaaag gtctcgagtg gtttccgct atctcttctg acggttctta cacctactat   180
gcggatagcg tgaaaggccg ctttaccatc agccgcgata attcgaaaaa cacccctgtat 240
ctgcaaatga acagcctgcg tgcggaagat acggccgtgt attattgcgc gcgtgaccgt  300
tactctatga tctactctta cggtgctggt gctttcgatt actggggcca aggcaccctg  360
gtgactgtta gctcagcctc caccaagggt ccatcggtct tccccctggc acctcctcc   420
aagagcacct ctgggggcac agcggccctg ggctgcctgg tcaaggacta cttccccgaa  480
ccggtgacgg tgtcgtggaa ctcaggcgcc ctgaccagcg gcgtgcacac cttcccggct  540
gtcctacagt cctcaggact ctactccctc agcagcgtgg tgaccgtgcc ctccagcagc  600
ttgggcaccc agacctacat ctgcaacgtg aatcacaagc ccagcaacac caaggtggac  660
aagagagttg agcccaaatc ttgtgacaaa actcacacat gcccaccgtg cccagcacct  720
gaagcagcgg ggggaccgtc agtcttcctc ttccccccaa aacccaagga caccctcatg  780
atctcccgga cccctgaggt cacatgcgtg gtggtggacg tgagccacga agaccctgag  840
gtcaagttca actggtacgt ggacggcgtg gaggtgcata atgccaagac aaagccgcgg  900
gaggagcagt acaacagcac gtaccgggtg gtcagcgtcc tcaccgtcct gcaccaggac  960
tggctgaatg gcaaggagta caagtgcaag gtctccaaca aagccctccc agcccccatc 1020
gagaaaacca tctccaaagc caagggcag cccgagaac cacaggtgta cacccctgccc 1080
ccatccccgg aggagatgac caagaaccag gtcagcctga cctgcctggt caaaggcttc 1140
tatcccagcg acatcgccgt ggagtgggag agcaatgggc agccggagaa caactacaag 1200
```

```
accacgcctc ccgtgctgga ctccgacggc tccttcttcc tctacagcaa gctcaccgtg    1260
gacaagagca ggtggcagca ggggaacgtc ttctcatgct ccgtgatgca tgaggctctg    1320
cacaaccact acacgcagaa gagcctctcc ctgtctccgg gtaaa                    1365
```

<210> SEQ ID NO 134
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 134

Gln Gln Thr Trp Arg Lys Pro Arg Thr
1               5

<210> SEQ ID NO 135
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 135

Thr Trp Arg Lys Pro Arg
1               5

<210> SEQ ID NO 136
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Trp Arg Lys Pro Arg
                85                  90                  95

Thr Phe Gly Gln Gly Thr Lys Val Glu Ile Lys
            100                 105

<210> SEQ ID NO 137
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 137

```
gatatccaga tgacccagag cccgagcagc ctgagcgcca gcgtgggcga tcgcgtgacc    60
attacctgca gagccagcca gggtatttct tcttacctgg cttggtacca gcagaaaccg   120
ggcaaagcgc cgaaactatt aatctacact gcttctactc tgcaaagcgg cgtgccgagc   180
cgctttagcg gcagcggatc cggcaccgat ttcaccctga ccattagctc tctgcaaccg   240
gaagactttg cgacctatta ttgccagcag acttggcgta aaccgcgtac ctttggccag   300
ggcacgaaag ttgaaattaa a                                             321
```

<210> SEQ ID NO 138
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 138

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Trp Arg Lys Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 139
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 139

```
gatatccaga tgacccagag cccgagcagc ctgagcgcca gcgtgggcga tcgcgtgacc     60
attacctgca gagccagcca gggtatttct tcttacctgg cttggtacca gcagaaaccg    120
ggcaaagcgc cgaaactatt aatctacact gcttctactc tgcaaagcgg cgtgccgagc    180
cgctttagcg gcagcggatc cggcaccgat ttcaccctga ccattagctc tctgcaaccg    240
gaagactttg cgacctatta ttgccagcag acttggcgta aaccgcgtac ctttggccag    300
ggcacgaaag ttgaaattaa acgtacggtg gccgctccca gcgtgttcat cttccccccc    360
agcgacgagc agctgaagag cggcaccgcc agcgtggtgt gcctgctgaa caacttctac    420
ccccggggagg ccaaggtgca gtggaaggtg acaacgccc tgcagagcgg caacagccag     480
gaaagcgtca ccgagcagga cagcaaggac tccacctaca gcctgagcag caccctgacc    540
ctgagcaagg ccgactacga aagcacaag gtgtacgcct gcgaggtgac caccagggc      600
ctgtccagcc ccgtgaccaa gagcttcaac cggggcgagt gt                       642
```

<210> SEQ ID NO 140
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 140

```
caagtgcagc tgcttgagag cggtggcgga ctggtgcagc caggggggatc cttgcgcctg     60
tcatgcgctg cgtcgggggtt caccttctcg tcctactgga tgaactgggt cagacaggct    120
ccggggaagg gactcgaatg ggtgtccgcc atttcctccg acggctccta cacttactac    180
gccgatagcg tcaagggccg gttcaccatc tcccgggaca attcgaagaa caccctgtac    240
ctccaaatga actcactgcg cgccgaggac actgcggtgt attactgtgc ccgggatagg    300
tacagcatga tctactccta cggtgccgga gcctttgact actggggaca gggaacccct    360
gtgaccgtgt ctagc                                                    375
```

<210> SEQ ID NO 141
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 141

```
Gln Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ser Ala Ile Ser Ser Asp Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Asp Arg Tyr Ser Met Ile Tyr Ser Tyr Gly Ala Gly Ala Phe
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Ala Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Ala Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 142
<211> LENGTH: 1365
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 142

```
caagtgcagc tgcttgagag cggtggcgga ctggtgcagc caggggatc cttgcgcctg      60
tcatgcgctg cgtcggggtt caccttctcg tcctactgga tgaactgggt cagacaggct    120
ccggggaagg gactcgaatg ggtgtccgcc atttcctccg acggctccta cacttactac    180
gccgatagcg tcaagggccg gttcaccatc tcccgggaca attcgaagaa caccctgtac    240
ctccaaatga actcactgcg cgccgaggac actgcggtgt attactgtgc ccgggatagg    300
tacagcatga tctactccta cggtgccgga gcctttgact actggggaca gggaaccctt    360
gtgaccgtgt ctagcgcgtc cactaagggc ccgtcagtgt tcccgctggc tccatcgtcg    420
aagtccacct ccggaggaac cgcagcactc ggttgcctgg tcaaggacta cttccctgag    480
ccagtgaccg tgtcgtggaa cagcggagcc ctgacttccg gcgtgcacac tttcccgcg    540
gtgctgcagt cctccggtct gtactccctt cgtccgtgg tcaccgtgcc gtcgtctagc    600
ctgggcaccc agacctacat ctgcaacgtg aaccacaagc cgtccaacac caaagtggat    660
aagcgggtgg agccgaagtc ctgcgataag acacacacgt gcccgccatg tccagcgcct    720
gaattgcttg gcggaccttc cgtgttcctg ttcccgccta gcccaagga cccttgatg     780
attagccgga ctcccgaagt cacctgtgtg gtggtggcag tgtcccacga ggaccccgag    840
gtcaagttta ttggtacgt ggacggcgtg gaagtgcaca acgccaagac taagcccgg     900
gaggaacagt acaacagcac ctaccgggtc gtgtccgtgc tgaccgtgct gcaccaggac    960
tggctgaatg ggaaagagta caagtgcaaa gtgtccaaca aggccttggc cgctcctatc   1020
gaaaaaacta tcagcaaggc taagggacag ccgagggaac cccaagtcta caccctgccc   1080
ccttcacgcg aagagatgac caagaatcaa gtgtcgctga cctgcctcgt caagggattc   1140
taccccctccg acattgcggt ggagtgggag tccaacggcc agcccgagaa caactacaag   1200
actactccgc ccgtgctgga ctccgacggc agcttcttcc tgtattccaa gctgaccgtg   1260
gacaagtccc ggtggcagca aggaaacgtg ttctcctgct cggtcatgca cgaagccctg   1320
cacaaccact atacgcagaa gtccctgtcc ttgagcccgg ggaaa              1365
```

<210> SEQ ID NO 143
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 143

```
gacatccaga tgacccagtc tccgtcctcc ctgtccgcat cagtggggga cagagtgacc     60
atcacttgtc gggcctccca aggcatctcg tcatacctgg cctggtatca gcagaaaccc   120
ggaaaggctc caaagctgct catctacacc gcctcgactc tgcaatccgg agtgccttcc   180
cgcttctccg gatccggttc gggaaccgac ttcaccctca ccattagcag ccttcagccg   240
gaagatttcg cgacctacta ctgccagcaa acctggcgga agcccaggac atttggccag   300
ggcactaagg tcgagattaa g                                          321
```

<210> SEQ ID NO 144
<211> LENGTH: 642
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic polynucleotide"

<400> SEQUENCE: 144

```
gacatccaga tgacccagtc tccgtcctcc ctgtccgcat cagtgggggga cagagtgacc    60
atcacttgtc gggcctccca aggcatctcg tcatacctgg cctggtatca gcagaaaccc   120
ggaaaggctc caaagctgct catctacacc gcctcgactc tgcaatccgg agtgccttcc   180
cgcttctccg gatccggttc gggaaccgac ttcaccctca ccattagcag ccttcagccg   240
gaagatttcg cgacctacta ctgccagcaa acctggcgga agcccaggac atttggccag   300
ggcactaagg tcgagattaa gcgtacggtg gccgctccca gcgtgttcat cttcccccc    360
agcgacgagc agctgaagag cggcaccgcc agcgtggtgt gcctgctgaa caacttctac   420
ccccgggagg ccaaggtgca gtggaaggtg acaacgccc tgcagagcgg caacagccag   480
gagagcgtca ccgagcagga cagcaaggac tccacctaca gcctgagcag cacccctgacc   540
ctgagcaagg ccgactacga gaagcataag gtgtacgcct gcgaggtgac ccaccagggc   600
ctgtccagcc ccgtgaccaa gagcttcaac aggggcgagt gc                      642
```

<210> SEQ ID NO 145
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 145

Gln Gln Ile Trp Thr Val Pro Arg Thr
1               5

<210> SEQ ID NO 146
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 146

Ile Trp Thr Val Pro Arg
1               5

<210> SEQ ID NO 147
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 147

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

```
Tyr Thr Ala Ser Thr Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ile Trp Thr Val Pro Arg
                 85                  90                  95

Thr Phe Gly Gln Gly Thr Lys Val Glu Ile Lys
            100                 105
```

<210> SEQ ID NO 148
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 148

```
gatatccaga tgacccagag cccgagcagc ctgagcgcca gcgtgggcga tcgcgtgacc    60
attacctgca gagccagcca gggtatttct tcttacctgg cttggtacca gcagaaaccg   120
ggcaaagcgc cgaaactatt aatctacact gcttctactc tgcaaagcgg cgtgccgagc   180
cgctttagcg gcagcggatc cggcaccgat ttcaccctga ccattagctc tctgcaaccg   240
gaagactttg cgacctatta ttgccagcag atctggactg ttccgcgtac ctttggccag   300
ggcacgaaag ttgaaattaa a                                              321
```

<210> SEQ ID NO 149
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 149

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Tyr
             20                  25                  30

Leu Ala Trp Tyr Gln Gln Lys Pro Gly Lys Ala Pro Lys Leu Leu Ile
         35                  40                  45

Tyr Thr Ala Ser Thr Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ile Trp Thr Val Pro Arg
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 150
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 150
gatatccaga tgacccagag cccgagcagc ctgagcgcca gcgtgggcga tcgcgtgacc        60
attacctgca gagccagcca gggtatttct tcttacctgg cttggtacca gcagaaaccg       120
ggcaaagcgc cgaaactatt aatctacact gcttctactc tgcaaagcgg cgtgccgagc       180
cgctttagcg gcagcggatc cggcaccgat ttcaccctga ccattagctc tctgcaaccg       240
gaagactttg cgacctatta ttgccagcag atctggactg ttccgcgtac ctttggccag       300
ggcacgaaag ttgaaattaa acgtacggtg gccgctccca gcgtgttcat cttcccccc        360 agcgacgagc agctgaagag cggcaccgcc agcgtggtgt gcctgctgaa caacttctac       420
ccccgggagg ccaaggtgca gtggaaggtg gacaacgccc tgcagagcgg caacagccag       480
gaaagcgtca ccgagcagga cagcaaggac tccacctaca gcctgagcag caccctgacc       540
ctgagcaagg ccgactacga aagcacaag gtgtacgcct gcgaggtgac ccaccagggc        600
ctgtccagcc ccgtgaccaa gagcttcaac cggggcgagt gt                         642

<210> SEQ ID NO 151
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 151

Ser Ile Gly Gly Gln Gly Gly Met Thr Leu Tyr Ala Asp Ser Val Lys
1               5                   10                  15
Gly

<210> SEQ ID NO 152
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 152

Gly Gly Gln Gly Gly Met
1               5

<210> SEQ ID NO 153

```
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 153

Ile Gly Gly Gln Gly Gly Met Thr
1               5

<210> SEQ ID NO 154
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 154

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr His
            20                  25                  30

Tyr Ile His Trp Val Arg Gln Ala Pro Gly Lys Gly Leu Glu Trp Val
        35                  40                  45

Ser Ser Ile Gly Gly Gln Gly Gly Met Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Gly Tyr Val Tyr Tyr His Met Phe Asp Pro Trp Gly
            100                 105                 110

Gln Gly Thr Leu Val Thr Val Ser Ser
        115                 120

<210> SEQ ID NO 155
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 155
gaggtgcaat tgctggaaag cggcggtggc ctggtgcagc cgggtggcag cctgcgtctg      60
agctgcgcgg cgtccggatt caccttaac actcattaca tccattgggt gcgccaggcc     120
cccggcaaag gtctcgagtg gtttcctct atcggtggtc agggcggtat gactctgtat      180
gcggatagcg tgaaaggccg ctttaccatc agccgcgata ttcgaaaaa caccctgtat     240 ctgcaaatga acagcctgcg tgcggaagat acggccgtgt attattgcgc gcgtgaacgt     300
ggttacgttt actaccatat gttcgatccg tggggccaag gcacccctggt gactgttagc     360 tca                                                                  363

<210> SEQ ID NO 156
<211> LENGTH: 451
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 156

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr His
            20                  25                  30

Tyr Ile His Trp Val Arg Gln Ala Pro Gly Lys Gly Leu Glu Trp Val
        35                  40                  45

Ser Ser Ile Gly Gly Gln Gly Gly Met Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Gly Tyr Val Tyr Tyr His Met Phe Asp Pro Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380
```

```
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
        435                 440                 445

Pro Gly Lys
    450
```

<210> SEQ ID NO 157
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 157

| | | | | | |
|---|---|---|---|---|---|
| gaggtgcaat | tgctggaaag | cggcggtggc | ctggtgcagc | cgggtggcag | cctgcgtctg | 60 |
| agctgcgcgg | cgtccggatt | cacctttaac | actcattaca | tccattgggt | gcgccaggcc | 120 |
| cccggcaaag | gtctcgagtg | ggtttcctct | atcggtggtc | agggcggtat | gactctgtat | 180 |
| gcggatagcg | tgaaaggccg | ctttaccatc | agccgcgata | attcgaaaaa | caccctgtat | 240 |
| ctgcaaatga | acagcctgcg | tgcggaagat | acggccgtgt | attattgcgc | gcgtgaacgt | 300 |
| ggttacgttt | actaccatat | gttcgatccg | tggggccaag | gcaccctggt | gactgttagc | 360 |
| tcagcctcca | ccaagggtcc | atcggtcttc | cccctggcac | cctcctccaa | gagcacctct | 420 |
| gggggcacag | cggccctggg | ctgcctggtc | aaggactact | tccccgaacc | ggtgacggtg | 480 |
| tcgtggaact | caggcgccct | gaccagcggc | gtgcacacct | tcccggctgt | cctacagtcc | 540 |
| tcaggactct | actccctcag | cagcgtggtg | accgtgccct | ccagcagctt | gggcacccag | 600 |
| acctacatct | gcaacgtgaa | tcacaagccc | agcaacacca | aggtggacaa | gagagttgag | 660 |
| cccaaatctt | gtgacaaaac | tcacacatgc | ccaccgtgcc | cagcacctga | agcagcgggg | 720 |
| ggaccgtcag | tcttcctctt | cccccaaaa | cccaaggaca | ccctcatgat | ctcccggacc | 780 |
| cctgaggtca | catgcgtggt | ggtggacgtg | agccacgaag | accctgaggt | caagttcaac | 840 |
| tggtacgtgg | acggcgtgga | ggtgcataat | gccaagacaa | agccgcggga | ggagcagtac | 900 |
| aacagcacgt | accgggtggt | cagcgtcctc | accgtcctgc | accaggactg | gctgaatggc | 960 |
| aaggagtaca | agtgcaaggt | ctccaacaaa | gccctcccag | cccccatcga | gaaaaccatc | 1020 |
| tccaaagcca | aagggcagcc | ccgagaacca | caggtgtaca | ccctgccccc | atcccgggag | 1080 |
| gagatgacca | agaaccaggt | cagcctgacc | tgcctggtca | aaggcttcta | tcccagcgac | 1140 |
| atcgccgtgg | agtgggagag | caatgggcag | ccggagaaca | actacaagac | cacgcctccc | 1200 |
| gtgctggact | ccgacggctc | cttcttcctc | tacagcaagc | tcaccgtgga | caagagcagg | 1260 |
| tggcagcagg | ggaacgtctt | ctcatgctcc | gtgatgcatg | aggctctgca | caaccactac | 1320 |
| acgcagaaga | gcctctccct | gtctccgggt | aaa | | | 1353 |

<210> SEQ ID NO 158
<211> LENGTH: 363
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic polynucleotide"

<400> SEQUENCE: 158
gaagtgcagc tcctggagtc gggtggcgga ctggtgcagc ctggcggatc actgcggctg      60
tcatgtgccg cgagcgggtt tactttcaac acccactaca tccactgggt ccgccaagct    120
cccggaaagg gactcgaatg ggtgtcctcc attggtggac agggcggcat gacccttttac   180 gcggatagcg tgaaggggag gttcaccatc tcccgcgaca acagcaagaa caccctgtac    240
ctccaaatga actcgcttcg ggccgaggac actgccgtgt actattgcgc aagagagcgg    300
ggctacgtgt actaccacat gttcgaccca tggggacagg gaacgctggt caccgtgtcc    360
tcc                                                                   363

<210> SEQ ID NO 159
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 159
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr His
            20                  25                  30

Tyr Ile His Trp Val Arg Gln Ala Pro Gly Lys Gly Leu Glu Trp Val
        35                  40                  45

Ser Ser Ile Gly Gly Gln Gly Gly Met Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Gly Tyr Val Tyr Tyr His Met Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met

```
                        245                 250                 255
Ile Ser Arg Thr Pro Glu Val Thr Cys Val Val Ala Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Ala Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 160
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 160
gaagtgcagc tcctggagtc gggtggcgga ctggtgcagc ctggcggatc actgcggctg      60
tcatgtgccg cgagcgggtt tactttcaac acccactaca tccactgggt ccgccaagct     120
cccggaaagg gactcgaatg ggtgtcctcc attggtggac agggcggcat gacccttttac    180 gcggatagcg tgaaggggag gttcaccatc tcccgcgaca acagcaagaa caccctgtac     240
ctccaaatga actcgcttcg ggccgaggac actgccgtgt actattgcgc aagagagcgg     300
ggctacgtgt actaccacat gttcgaccca tggggacagg gaacgctggt caccgtgtcc     360
tccgcctcca ctaagggccc gtcagtgttc cgctggctc atcgtcgaa gtccacctcc       420 ggaggaaccg cagcactcgg ttgcctggtc aaggactact cccctgagcc agtgaccgtg     480
tcgtggaaca gcggagccct gacttccggc gtgcacactt ttcccgcggt gctgcagtcc    540
tccggtctgt actccctttc gtccgtggtc accgtgccgt cgtctagcct gggcacccag     600
acctacatct gcaacgtgaa ccacaagccg tccaacacca agtggataa gcgggtggag      660 ccgaagtcct gcgataagac acacgtgc ccgccatgtc cagcgcctga attgcttggc       720
ggaccttccg tgttcctgtt cccgcctaag cccaaggaca ccttgatgat tagccggact     780
```

```
cccgaagtca cctgtgtggt ggtggcagtg tcccacgagg accccgaggt caagtttaat    840
tggtacgtgg acggcgtcga agtgcacaac gccaagacta agccccggga ggaacagtac    900
aacagcacct accgggtcgt gtccgtgctg accgtgctgc accaggactg gctgaatggg    960
aaagagtaca agtgcaaagt gtccaacaag gccttggccg ctcctatcga aaaaactatc   1020
agcaaggcta agggacagcc gagggaaccc caagtctaca ccctgccccc ttcacgcgaa   1080
gagatgacca agaatcaagt gtcgctgacc tgcctcgtca agggattcta cccctccgac   1140
attgcggtgg agtgggagtc caacggccag cccgagaaca actacaagac tactccgccc   1200
gtgctggact ccgacggcag cttcttcctg tattccaagc tgaccgtgga caagtcccgg   1260
tggcagcaag gaaacgtgtt ctcctgctcg gtcatgcacg aagccctgca caaccactat   1320
acgcagaagt ccctgtcctt gagcccgggg aaa                                1353
```

<210> SEQ ID NO 161
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 161

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr His
            20                  25                  30

Tyr Ile His Trp Val Arg Gln Ala Pro Gly Lys Gly Leu Glu Trp Val
        35                  40                  45

Ser Ser Ile Gly Gly Gln Gly Gly Met Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Gly Tyr Val Tyr Tyr His Met Phe Asp Pro Trp Gly
            100                 105                 110

Gln Gly Thr Leu Val Thr Val Ser Ser
        115                 120
```

<210> SEQ ID NO 162
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 162

```
gaagtgcagc tcctggagtc gggtggcgga ctggtgcagc ctggcggatc actgcggctg     60
tcatgtgccg cgagcgggtt tactttctcc acccactaca tccactgggt ccgccaagct    120
cccggaaagg gactcgaatg ggtgtcctcc attggtggac agggcggcat gaccctttac    180
gcggatagcg tgaaggggag gttcaccatc tcccgcgaca acagcaagaa caccctgtac    240
ctccaaatga actcgcttcg ggccgaggac actgccgtgt actattgcgc aagagagcgg    300
ggctacgtgt actaccacat gttcgaccca tggggacagg gaacgctggt caccgtgtcc    360
```

```
tcc                                                                         363
```

<210> SEQ ID NO 163
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 163

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr His
            20                  25                  30

Tyr Ile His Trp Val Arg Gln Ala Pro Gly Lys Gly Leu Glu Trp Val
        35                  40                  45

Ser Ser Ile Gly Gly Gln Gly Gly Met Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Gly Tyr Val Tyr Tyr His Met Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ala Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Ala Ala Pro Ile
                325                 330                 335

Glu Lys Thr Ile Ser Lys Ala Lys Gly Gln Pro Arg Glu Pro Gln Val

```
                340                 345                 350
Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 164
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 164
gaagtgcagc tcctggagtc gggtggcgga ctggtgcagc ctggcggatc actgcggctg      60
tcatgtgccg cgagcgggtt tactttctcc acccactaca tccactgggt ccgccaagct     120
cccggaaagg gactcgaatg ggtgtcctcc attggtggac agggcggcat gacccttac      180 gcggatagcg tgaaggggag gttcaccatc tcccgcgaca cagcaagaa caccctgtac      240 ctccaaatga actcgcttcg ggccgaggac actgccgtgt actattgcgc aagagagcgg      300
ggctacgtgt actaccacat gttcgaccca tggggacagg gaacgctggt caccgtgtcc      360
tccgcctcca ctaagggccc gtcagtgttc ccgctggctc catcgtcgaa gtccacctcc      420
ggaggaaccg cagcactcgg ttgcctggtc aaggactact ccctgagcc agtgaccgtg      480 tcgtggaaca gcggagccct gacttccggc gtgcacactt tcccgcggt gctgcagtcc      540 tccggtctgt actccctttc gtccgtggtc accgtgccgt cgtctagcct gggcacccag      600
acctacatct gcaacgtgaa ccacaagccg tccaacacca agtggataa gcgggtggag      660 ccgaagtcct gcgataagac acacgcgtgc cgccatgtc cagcgcctga attgcttggc      720
ggaccttccg tgttcctgtt cccgcctaag cccaaggaca ccttgatgat tagccggact      780
cccgaagtca cctgtgtggt ggtggcagtg tcccacgagg accccgaggt caagtttaat      840
tggtacgtgg acggcgtcga agtgcacaac gccaagacta gccccggga ggaacagtac      900 aacagcacct accgggtcgt gtccgtgctg accgtgctgc accaggactg gctgaatggg      960
aaagagtaca agtgcaaagt gtccaacaag gccttggccg ctcctatcga aaaactatc     1020 agcaaggcta agggacagcc gagggaaccc caagtctaca ccctgcccc ttcacgcgaa     1080 gagatgacca gaatcaagt gtcgctgacc tgcctcgtca aggattcta cccctccgac     1140 attgcggtgg agtgggagtc caacggccag cccgagaaca actacaagac tactccgccc     1200
gtgctggact ccgacggcag cttcttcctg tattccaagc tgaccgtgga caagtccgg     1260 tggcagcaag gaaacgtgtt ctcctgctcg gtcatgcacg aagccctgca caaccactat     1320
```
acgcagaagt ccctgtcctt gagcccgggg aaa    1353

```
<210> SEQ ID NO 165
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 165
```

Gly Phe Thr Phe Gln Thr His Tyr Ile His
1               5                   10

```
<210> SEQ ID NO 166
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 166
```

Gly Phe Thr Phe Gln Thr His
1               5

```
<210> SEQ ID NO 167
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 167
```

Gly Phe Thr Phe Gln Thr His Tyr
1               5

```
<210> SEQ ID NO 168
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 168
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gln Thr His
            20                  25                  30

Tyr Ile His Trp Val Arg Gln Ala Pro Gly Lys Gly Leu Glu Trp Val
        35                  40                  45

Ser Ser Ile Gly Gly Gln Gly Gly Met Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Gly Tyr Val Tyr His Met Phe Asp Pro Trp Gly
            100                 105                 110

```
Gln Gly Thr Leu Val Thr Val Ser Ser
        115                 120
```

<210> SEQ ID NO 169
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 169

```
gaagtgcagc tcctggagtc gggtggcgga ctggtgcagc ctggcggatc actgcggctg      60
tcatgtgccg cgagcgggtt tactttccag acccactaca tccactgggt ccgccaagct     120
cccggaaagg gactcgaatg ggtgtcctcc attggtggac agggcggcat gaccctttac     180
gcggatagcg tgaaggggag gttcaccatc tcccgcgaca acagcaagaa cacccctgtac   240 ctccaaatga actcgcttcg ggccgaggac actgccgtgt actattgcgc aagagagcgg     300
ggctacgtgt actaccacat gttcgaccca tggggacagg gaacgctggt caccgtgtcc     360
tcc                                                                   363
```

<210> SEQ ID NO 170
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 170

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gln Thr His
            20                  25                  30

Tyr Ile His Trp Val Arg Gln Ala Pro Gly Lys Gly Leu Glu Trp Val
        35                  40                  45

Ser Ser Ile Gly Gly Gln Gly Gly Met Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Gly Tyr Val Tyr Tyr His Met Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
```

```
               195                 200                 205
Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ala Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Ala Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 171
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 171
gaagtgcagc tcctggagtc gggtggcgga ctggtgcagc ctggcggatc actgcggctg      60
tcatgtgccg cgagcgggtt tactttccag acccactaca tccactgggt ccgccaagct     120
cccggaaagg gactcgaatg ggtgtcctcc attggtggac agggcggcat gacccttttac     180 gcggatagcg tgaaggggag gttcaccatc tcccgcgaca acagcaagaa caccctgtac     240
ctccaaatga actcgcttcg ggccgaggac actgccgtgt actattgcgc aagagagcgg     300
ggctacgtgt actaccacat gttcgaccca tggggacagg gaacgctggt caccgtgtcc     360
tccgcctcca ctaagggccc gtcagtgttc ccgctggctc catcgtcgaa gtccacctcc     420
ggaggaaccg cagcactcgg ttgcctggtc aaggactact ccctgagcc agtgaccgtg     480 tcgtggaaca gcggagccct gacttccggc gtgcacactt ttcccgcggt gctgcagtcc     540
```

-continued

```
tccggtctgt actcccttc gtccgtggtc accgtgccgt cgtctagcct gggcacccag      600
acctacatct gcaacgtgaa ccacaagccg tccaacacca aagtggataa gcgggtggag      660
ccgaagtcct gcgataagac acacgtgc ccgccatgtc cagcgcctga attgcttggc       720
ggaccttccg tgttcctgtt cccgcctaag cccaaggaca ccttgatgat tagccggact      780
cccgaagtca cctgtgtggt ggtggcagtg tcccacgagg accccgaggt caagtttaat      840
tggtacgtgg acggcgtcga agtgcacaac gccaagacta gccccggga ggaacagtac       900 aacagcacct accgggtcgt gtccgtgctg accgtgctgc accaggactg gctgaatggg      960
aaagagtaca agtgcaaagt gtccaacaag gccttggccg ctcctatcga aaaaactatc      1020
agcaaggcta agggacagcc gagggaaccc caagtctaca ccctgccccc ttcacgcgaa      1080
gagatgacca gaatcaagt gtcgctgacc tgcctcgtca agggattcta ccctccgac       1140 attgcggtgg agtgggagtc caacggccag cccgagaaca actacaagac tactccgccc      1200
gtgctggact ccgacggcag cttcttcctg tattccaagc tgaccgtgga caagtcccgg      1260
tggcagcaag gaaacgtgtt ctcctgctcg gtcatgcacg aagccctgca caaccactat      1320
acgcagaagt ccctgtcctt gagcccgggg aaa                                   1353
```

```
<210> SEQ ID NO 172
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 172

Gln Gln Glu Trp Ala Lys Pro Arg Thr
1               5

<210> SEQ ID NO 173
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 173

Glu Trp Ala Lys Pro Arg
1               5

<210> SEQ ID NO 174
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 174

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45
```

```
Tyr Thr Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Glu Trp Ala Lys Pro Arg
                 85                  90                  95

Thr Phe Gly Gln Gly Thr Lys Val Glu Ile Lys
                100                 105

<210> SEQ ID NO 175
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 175
gatatccaga tgacccagag cccgagcagc ctgagcgcca gcgtgggcga tcgcgtgacc      60
attacctgca gagccagcca gggtatttct tcttacctgg cttggtacca gcagaaaccg     120
ggcaaagcgc cgaaactatt aatctacact gcttctactc tgcaaagcgg cgtgccgagc     180
cgctttagcg gcagcggatc cggcaccgat ttcaccctga ccattagctc tctgcaaccg     240
gaagactttg cgacctatta ttgccagcag gaatgggcta aaccgcgtac ctttggccag     300
ggcacgaaag ttgaaattaa a                                               321

<210> SEQ ID NO 176
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 176

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Tyr
                 20                  25                  30

Leu Ala Trp Tyr Gln Gln Lys Pro Gly Lys Ala Pro Lys Leu Leu Ile
             35                  40                  45

Tyr Thr Ala Ser Thr Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Glu Trp Ala Lys Pro Arg
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 177
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 177
gatatccaga tgacccagag cccgagcagc ctgagcgcca gcgtgggcga tcgcgtgacc       60
attacctgca gagccagcca gggtatttct tcttacctgg cttggtacca gcagaaaccg     120
ggcaaagcgc cgaaactatt aatctacact gcttctactc tgcaaagcgg cgtgccgagc     180
cgctttagcg gcagcggatc cggcaccgat ttcaccctga ccattagctc tctgcaaccg     240
gaagactttg cgacctatta ttgccagcag gaatgggcta aaccgcgtac ctttggccag     300
ggcacgaaag ttgaaattaa acgtacggtg gccgctccca gcgtgttcat cttccccccc     360
agcgacgagc agctgaagag cggcaccgcc agcgtggtgt gcctgctgaa caacttctac     420
ccccgggagg ccaaggtgca gtggaaggtg gacaacgccc tgcagagcgg caacagccag     480
gaaagcgtca ccgagcagga cagcaaggac tccacctaca gcctgagcag cacccctgacc     540 ctgagcaagg ccgactacga aagcacaag gtgtacgcct gcgaggtgac ccaccagggc     600
ctgtccagcc ccgtgaccaa gagcttcaac cggggcgagt gt                        642

<210> SEQ ID NO 178
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 178

Gln Gln Ser Trp Thr Arg Pro Arg Thr
1               5

<210> SEQ ID NO 179
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 179

Ser Trp Thr Arg Pro Arg
1               5

<210> SEQ ID NO 180
<211> LENGTH: 107

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 180

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Thr Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Thr Arg Pro Arg
                85                  90                  95

Thr Phe Gly Gln Gly Thr Lys Val Glu Ile Lys
            100                 105

<210> SEQ ID NO 181
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 181
gatatccaga tgacccagag cccgagcagc ctgagcgcca gcgtgggcga tcgcgtgacc      60
attacctgca gagccagcca gggtatttct tcttacctgg cttggtacca gcagaaaccg     120
ggcaaagcgc cgaaactatt aatctacact gcttctactc tgcaaagcgg cgtgccgagc     180
cgctttagcg gcagcggatc cggcaccgat ttcaccctga ccattagctc tctgcaaccg     240
gaagactttg cgacctatta ttgccagcag tcttggactc gtccgcgtac ctttggccag     300
ggcacgaaag ttgaaattaa a                                                321

<210> SEQ ID NO 182
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 182

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Thr Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Ser Trp Thr Arg Pro Arg
                    85                  90                  95

Thr Phe Gly Gln Gly Thr Lys Val Glu Ile Lys Arg Thr Val Ala Ala
                    100                 105                 110

Pro Ser Val Phe Ile Phe Pro Pro Ser Asp Glu Gln Leu Lys Ser Gly
                    115                 120                 125

Thr Ala Ser Val Val Cys Leu Leu Asn Asn Phe Tyr Pro Arg Glu Ala
                    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                    180                 185                 190

Ala Cys Glu Val Thr His Gln Gly Leu Ser Ser Pro Val Thr Lys Ser
                    195                 200                 205

Phe Asn Arg Gly Glu Cys
    210

<210> SEQ ID NO 183
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 183
gatatccaga tgacccagag cccgagcagc ctgagcgcca gcgtgggcga tcgcgtgacc      60
attacctgca gagccagcca gggtatttct tcttacctgg cttggtacca gcagaaaccg     120
ggcaaagcgc cgaaactatt aatctacact gcttctactc tgcaaagcgg cgtgccgagc     180
cgctttagcg gcagcggatc cggcaccgat ttcaccctga ccattagctc tctgcaaccg     240
gaagactttg cgacctatta ttgccagcag tcttggactg tccgcgtac  ctttggccag     300 ggcacgaaag ttgaaattaa acgtacggtg gccgctccca gcgtgttcat cttccccccc     360
agcgacgagc agctgaagag cggcaccgcc agcgtggtgt gcctgctgaa caacttctac     420
ccccgggagg ccaaggtgca gtggaaggtg gacaacgccc tgcagagcgg caacagccag     480
gaaagcgtca ccgagcagga cagcaaggac tccacctaca gcctgagcag caccctgacc     540
ctgagcaagg ccgactacga gaagcacaag gtgtacgcct gcgaggtgac ccaccagggc     600
ctgtccagcc ccgtgaccaa gagcttcaac cggggcgagt gt                       642

<210> SEQ ID NO 184
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 184

Gln Gln Ile Trp Met Ala Pro Arg Thr
1               5
```

<210> SEQ ID NO 185
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 185

Ile Trp Met Ala Pro Arg
1               5

<210> SEQ ID NO 186
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 186

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Lys Pro Gly Lys Ala Pro Lys Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ile Trp Met Ala Pro Arg
                85                  90                  95

Thr Phe Gly Gln Gly Thr Lys Val Glu Ile Lys
            100                 105

<210> SEQ ID NO 187
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 187
gatatccaga tgacccagag cccgagcagc ctgagcgcca gcgtgggcga tcgcgtgacc    60
attacctgca gagccagcca gggtatttct tcttacctgg cttggtacca gcagaaaccg   120
ggcaaagcgc cgaaactatt aatctacact gcttctactc tgcaaagcgg cgtgccgagc   180
cgctttagcg gcagcggatc cggcaccgat ttcaccctga ccattagctc tctgcaaccg   240
gaagactttg cgacctatta ttgccagcag atctggatgg ctccgcgtac ctttggccag   300
ggcacgaaag ttgaaattaa a                                             321

<210> SEQ ID NO 188
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 188

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ile Trp Met Ala Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 189
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 189
gatatccaga tgacccagag cccgagcagc ctgagcgcca gcgtgggcga tcgcgtgacc      60
attacctgca gagccagcca gggtatttct tcttacctgg cttggtacca gcagaaaccg     120
ggcaaagcgc cgaaactatt aatctacact gcttctactc tgcaaagcgg cgtgccgagc     180
cgctttagcg gcagcggatc cggcaccgat ttcaccctga ccattagctc tctgcaaccg     240
gaagactttg cgacctatta ttgccagcag atctggatgg ctccgcgtac ctttggccag     300
ggcacgaaag ttgaaattaa acgtacggtg gccgctccca gcgtgttcat cttccccccc     360
agcgacgagc agctgaagag cggcaccgcc agcgtggtgt gcctgctgaa caacttctac     420
ccccgggagg ccaaggtgca gtggaaggtg gacaacgccc tgcagagcgg caacagccag     480
gaaagcgtca ccgagcagga cagcaaggac tccacctaca gcctgagcag cacccctgacc     540 ctgagcaagg ccgactacga gaagcacaag gtgtacgcct gcgaggtgac ccaccagggc     600
ctgtccagcc ccgtgaccaa gagcttcaac cggggcgagt gt                        642

<210> SEQ ID NO 190
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 190

Ala Ile Ser Ser Lys Gly Ser Tyr Thr Tyr Tyr Ala Asp Ser Val Lys
1               5                   10                  15

Gly

<210> SEQ ID NO 191
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 191

Ser Ser Lys Gly Ser Tyr
1               5

<210> SEQ ID NO 192
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 192

Ile Ser Ser Lys Gly Ser Tyr Thr
1               5

<210> SEQ ID NO 193
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 193

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ser Ala Ile Ser Ser Lys Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Tyr Ser Met Ile Tyr Ser Tyr Gly Ala Gly Ala Phe

```
                 100                 105                 110
Asp Tyr Trp Gly Gln Gly Thr Leu Val Thr Val Ser Ser
            115                 120                 125

<210> SEQ ID NO 194
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 194
caagttcagc tccttgagtc tgggggggc  ctggtgcaac ctgggggctc tctgcggctt      60
tcatgtgcgg cctcagggtt cactttcagc tcatactgga tgaattgggt acgccaagct     120
ccaggcaaag gactcgaatg ggtaagcgct atatccagca aagggagcta tacctattac     180
gcggattccg ttaagggcag gttcactata tcccgcgaca actccaaaaa tactttgtat     240
ctgcaaatga attccctccg agccgaagat accgcagtat attactgtgc gagggacagg     300
tactccatga tttacagcta cggtgccggt gctttcgatt attggggaca ggggacactt     360
gtgaccgtca gttct                                                      375

<210> SEQ ID NO 195
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 195

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ser Ala Ile Ser Ser Lys Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Tyr Ser Met Ile Tyr Ser Tyr Gly Ala Gly Ala Phe
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190
```

```
Val Val Thr Val Pro Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 196
<211> LENGTH: 1365
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 196
caagttcagc tccttgagtc tggggggggc ctggtgcaac ctgggggctc tctgcggctt     60
tcatgtgcgg cctcagggtt cactttcagc tcatactgga tgaattgggt acgccaagct    120
ccaggcaaag gactcgaatg ggtaagcgct atatccagca aagggagcta taccattac    180 gcggattccg ttaagggcag gttcactata tcccgcgaca actccaaaaa tactttgtat    240
ctgcaaatga attccctccg agccgaagat accgcagtat attactgtgc gagggacagg    300
tactccatga tttacagcta cggtgccggt gctttcgatt attggggaca ggggacactt    360
gtgaccgtca gttctgcaag taccaaaggg ccgtctgttt tcccattggc ccctcatcc    420 aagagcacga gtggaggcac cgccgcgctg ggatgccttg tgaaagacta tttcccggag    480
```

```
cccgtgaccg ttagctggaa cagcggcgct cttaccagtg gcgttcacac attcccagct    540
gttttgcagt catccgggct ctactctctc tcatccgtgg tcaccgtgcc gtctagttct    600
ttgggcaccc agacctacat ctgtaacgta aatcacaaac ctagtaatac taaggtggac    660
aagcgagttg aaccgaagag ctgtgataag acacatactt gtccaccatg tccggcaccc    720
gaggcagcgg gggggcccag tgttttctc ttcccaccca agcccaaaga cacattgatg    780
atctcacgaa ccccagaggt aacttgtgtc gtggtagatg taagccatga ggaccccgaa    840
gttaagttca attggtatgt tgacggtgta gaggtgcaca atgccaaaac taaaccccgg    900
gaggagcaat acaactcaac ttacagagtc gtatccgtgc tgaccgtttt gcaccaggat    960
tggttgaatg gtaaggaata caaatgtaaa gtgagcaata aagctctccc agcgcccatc   1020
gagaagacca ttagcaaagc caagggtcaa cccaggaac cccaggtata tacgctgcca   1080
ccctcaaggg aagagatgac aaagaatcaa gtgtcactga cgtgtcttgt caagggtttc   1140
tatcctagcg acattgcggt ggaatgggag tcaaatgggc aacccgagaa caactacaag   1200
actactcctc ccgtcctgga cagcgacggc tccttcttcc tgtatagtaa actgaccgtc   1260
gataaaagta ggtggcagca ggggaatgtc tttagttgct ctgtcatgca tgaggcgctc   1320
cataaccact acacccaaaa atctttgagc ttgagccctg ggaaa                  1365
```

<210> SEQ ID NO 197
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 197

```
gacattcaaa tgacacaaag tccgtccagt cttagtgctt ctgtgggcga tagggtcacc     60
atcacttgtc gggcgtctca ggggatcagc tcttacttgg catggtatca acaaaagcca    120
ggaaaagcac ctaaattgct tatttataca gcgtccaccc tccagtcagg agtgcctagt    180
aggttctcag gctctgggtc cggtactgac ttcacgctga ctatatcaag cttgcaaccc    240
gaagattttg caacatacta ctgccaacag acatggagga agccaagaac tttcggtcag    300
ggaacgaaag ttgagataaa g                                             321
```

<210> SEQ ID NO 198
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 198

```
gacattcaaa tgacacaaag tccgtccagt cttagtgctt ctgtgggcga tagggtcacc     60
atcacttgtc gggcgtctca ggggatcagc tcttacttgg catggtatca acaaaagcca    120
ggaaaagcac ctaaattgct tatttataca gcgtccaccc tccagtcagg agtgcctagt    180
aggttctcag gctctgggtc cggtactgac ttcacgctga ctatatcaag cttgcaaccc    240
gaagattttg caacatacta ctgccaacag acatggagga agccaagaac tttcggtcag    300
ggaacgaaag ttgagataaa gcgcactgtc gcagcacctt ccgtgttcat tttccccgcct   360
tccgacgagc agcttaaatc agggaccgcg agtgttgttt gcttgcttaa taactttttac   420
```

```
ccacgggaag ccaaagttca gtggaaggtg acaatgcac tccaaagcgg aatagtcag      480 gagtcagtta ctgagcaaga tagtaaagac tctacttact ctttgagttc aaccttgacc   540
ctctcaaaag cggactacga gaagcataaa gtgtacgcct gcgaggtgac gcatcaaggt   600
ttgtcttccc cggttacgaa gtcctttaat agggggaat gt                        642
```

<210> SEQ ID NO 199
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 199

```
gatatacaga tgacgcaaag tccctctagt ctttctgcaa gtgtcgggga cagagttacc   60
attacctgca gagcgtcaca aggcatctct agttatctcg cgtggtacca acagaagcca   120
ggtaaagcac ctaaactgtt gatttacacg gcatcaacat tgcagtcagg tgtcccctcc   180
cgatttagtg gcagtggtag cggtacagat tttactctta ccatttcatc tcttcagcca   240
gaagattttg ctacgtacta ctgtcaacaa gaatgggcta aaccacgaac ctttggacag   300
ggtacgaagg tcgaaataaa a                                              321
```

<210> SEQ ID NO 200
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 200

```
gatatacaga tgacgcaaag tccctctagt ctttctgcaa gtgtcgggga cagagttacc   60
attacctgca gagcgtcaca aggcatctct agttatctcg cgtggtacca acagaagcca   120
ggtaaagcac ctaaactgtt gatttacacg gcatcaacat tgcagtcagg tgtcccctcc   180
cgatttagtg gcagtggtag cggtacagat tttactctta ccatttcatc tcttcagcca   240
gaagattttg ctacgtacta ctgtcaacaa gaatgggcta aaccacgaac ctttggacag   300
ggtacgaagg tcgaaataaa acggaccgtt gccgccccct ccgtcttcat cttcccccg    360 tctgacgagc agctcaaatc cggcacagct tctgtagtct gcttgctgaa taacttctac   420
ccaagagaag ccaaagttca gtggaaggtc gataatgcat gcaatctgg taatagtcag    480 gaatctgtga ctgagcagga tagcaaagac tcaacttaca gcctctcttc aaccttgacg   540
ttgtccaaag cggattatga gaaacacaag gtgtacgctt gcgaggtgac gcatcaaggg   600
cttagttccc cggtaaccaa atctttcaac cgaggtgaat gc                      642
```

<210> SEQ ID NO 201
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 201

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ser Val Ile Glu Ser Lys Gly Asn Tyr Ile Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Tyr Ser Met Ile Tyr Ser Tyr Gly Ala Gly Ala Phe
            100                 105                 110

Asp Tyr Trp Gly Gln Gly Thr Leu Val Thr Val Ser Ser
        115                 120                 125

<210> SEQ ID NO 202
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 202
caagttcaat tgctggaaag cggaggtgga cttgtccaac ctggagggtc actccgactg      60
tcttgcgctg catcaggatt cacctttagt agctattgga tgaactgggt ccggcaggct     120
cctgggaaag gccttgagtg gtaagtgtc attgaatcaa agggcaacta catctttat      180 gctgattctg taaagggtag gttcaccatc tccagggaca attcaaaaaa tactttgtat     240
ctgcagatga actctctcag gcagaagac acggccgttt attactgcgc ccgcgatcga     300
tacagcatga tatactccta cggcgcagga gcttttgact actggggtca aggcacactt     360
gttactgtca gtagc                                                     375

<210> SEQ ID NO 203
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 203

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ser Val Ile Glu Ser Lys Gly Asn Tyr Ile Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Tyr Ser Met Ile Tyr Ser Tyr Gly Ala Gly Ala Phe
            100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Arg Val Glu
            210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
            245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
            450                 455

<210> SEQ ID NO 204
<211> LENGTH: 1365
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 204

```
caagttcaat tgctggaaag cggaggtgga cttgtccaac ctggagggtc actccgactg      60
tcttgcgctg catcaggatt cacctttagt agctattgga tgaactgggt ccggcaggct     120
cctgggaaag ggcttgagtg ggtaagtgtc attgaatcaa agggcaacta catcttttat     180
gctgattctg taaagggtag gttcaccatc tccagggaca attcaaaaaa tactttgtat     240
ctgcagatga actctctcag ggcagaagac acggccgttt attactgcgc cgcgatcga      300
tacagcatga tatactccta cggcgcagga gcttttgact actggggtca aggcacactt     360
gttactgtca gtagcgcctc aacgaaagga ccgtccgtgt tcctcttgc tcctagctcc      420
aaatccacct caggtggaac ggccgccctg ggtgcctgg taaaggacta tttcccagag      480
ccagttactg tgtcttggaa ttctggtgca ttgacaagtg gcgtacacac ttttcccgcg     540
gtcctccaat ctagtggtct gtactcactg tcctccgttg tgactgtccc aagtagctca     600
cttggcacac agacttacat ctgtaatgtt aatcataagc cgtcaaacac gaaggtggat     660
aagagggtag aacctaagtc atgtgacaaa acgcatactt gccccccctg ccctgcgccg     720
gaagccgctg gcggaccctc cgtattcttg ttccctccaa agccaaagga cactctgatg     780
attagccgga caccggaggt cacttgtgtt gtagttgacg tcagccatga ggatcctgag     840
gtgaaattta attggtacgt ggacggggt gaagtccaca atgctaaaac taaacctagg      900
gaagagcaat ataatagtac atacagggtt gtcagtgtgc tgaccgttct ccatcaggac     960
tggctgaacg gcaaggaata caagtgcaag gtcagcaaca aggccttgcc ggcccccatc    1020
gagaagacga tctccaaagc caaggggcaa ccccgagaac cgcaggtata cacgctcccc    1080
cctagtagag aagagatgac aaagaatcaa gtttccttga cgtgccttgt gaaaggcttc    1140
taccctagtg acatcgcagt cgaatgggag agcaacgggc agccggagaa taactataaa    1200
acaacccccc ccgtgcttga ctcagacggg tcattttttc tgtatagcaa attgactgtt    1260
gataaatcac ggtggcaaca aggaaacgtg tttagttgca gcgtaatgca cgaagctctc    1320
cacaatcact atactcaaaa gtcactgtca ctctcccctg gcaag                    1365
```

<210> SEQ ID NO 205
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 205

```
gacatacaaa tgacgcaatc tccgagtagc ttgtcagcgt ccgtaggcga ccgagtaacg      60
attacgtgta gagcgagcca gggaatttca tcttatttgg cttggtatca gcaaaagccg     120
ggaaaagcac ccaaactcct catttatact gccagcacgt tgcaaagcgg cgttccgagt     180
cggttctctg gatcagggtc cggacggac ttcaccttga cgatttcatc tttgcaacct      240
gaagattttg caacatacta ctgtcaacag gagtgggtga agccaaggac cttcggacaa     300
ggcacgaagg tcgaaatcaa g                                              321
```

<210> SEQ ID NO 206
<211> LENGTH: 642
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic polynucleotide"

<400> SEQUENCE: 206

```
gacatacaaa tgacgcaatc tccgagtagc ttgtcagcgt ccgtaggcga ccgagtaacg      60
attacgtgta gagcgagcca gggaatttca tcttatttgg cttggtatca gcaaaagccg     120
ggaaaagcac ccaaactcct catttatact gccagcacgt tgcaaagcgg cgttccgagt     180
cggttctctg gatcagggtc cgggacggac ttcaccttga cgatttcatc tttgcaacct     240
gaagattttg caacatacta ctgtcaacag gagtgggtga agccaaggac cttcggacaa     300
ggcacgaagg tcgaaatcaa gcgaaccgtg gcagctccgt ccgtgtttat ttttccgcct     360
tccgacgaac aacttaaaag tggaacagcc tctgtcgtct gtctccttaa caacttctac     420
cccagggaag ctaaagtaca gtggaaggta gataacgctc tgcaaagtgg taattctcag     480
gagagcgtca cggaacagga ctccaaagac tccacctatt ctctgagctc tacactgacg     540
ctcagcaagg cagactacga aaagcacaaa gtatatgcgt gtgaggtgac gcatcaaggc     600
cttagcagtc cagttacaaa aagttttaac aggggagaat gc                        642
```

<210> SEQ ID NO 207
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 207

```
gaagtgcagc tgctggaatc cggcggaggt ctggtccagc ctggaggttc cctgcgcctg      60
tcatgcgcag cctccggatt cacctttcg tcgtactgga tgaactgggt cagacaggct     120
cctggaaagg gcctgaatg gtgtctgtg attgaatcca aggggaacta catcttctac     180
gcggacagcg tgaagggccg gttcactatc agcagagaca acagcaagaa caccctgtac     240
ctccaaatga actcgctgag ggccgaagat actgccgtgt actactgtgc cgcgatcgc     300
tactcgatga tctacagcta tggtgccgga gcgttcgatt actggggaca gggaaccctc     360
gtgaccgtca gctcc                                                      375
```

<210> SEQ ID NO 208
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 208

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ser Val Ile Glu Ser Lys Gly Asn Tyr Ile Phe Tyr Ala Asp Ser Val
    50                  55                  60

Lys Gly Arg Phe Thr Ile Ser Arg Asp Asn Ser Lys Asn Thr Leu Tyr
```

```
            65                  70                  75                  80
Leu Gln Met Asn Ser Leu Arg Ala Glu Asp Thr Ala Val Tyr Tyr Cys
                    85                  90                  95

Ala Arg Asp Arg Tyr Ser Met Ile Tyr Ser Tyr Gly Ala Gly Ala Phe
                100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Ala Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Ala Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 209
<211> LENGTH: 1365
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic polynucleotide"

<400> SEQUENCE: 209
gaagtgcagc tgctggaatc cggcggaggt ctggtccagc ctggaggttc cctgcgcctg      60
tcatgcgcag cctccggatt cacctttcg tcgtactgga tgaactgggt cagacaggct     120
cctggaaagg gcctggaatg ggtgtctgtg attgaatcca aggggaacta catcttctac     180
gcggacagcg tgaagggccg gttcactatc agcagagaca acagcaagaa ccccctgtac     240
ctccaaatga actcgctgag ggccgaagat actgccgtgt actactgtgc ccgcgatcgc     300
tactcgatga tctacagcta tggtgccgga gcgttcgatt actggggaca gggaaccctc     360
gtgaccgtca gctccgcctc aaccaagggc ccgtcagtgt tcccgctggc tccatcgtcg     420
aagtccacct ccggaggaac cgcagcactc ggttgcctgg tcaaggacta cttccctgag     480
ccagtgaccg tgtcgtggaa cagcggagcc ctgacttccg gcgtgcacac ttttcccgcg     540
gtgctgcagt cctccggtct gtactccctt tcgtccgtgg tcaccgtgcc gtcgtctagc     600
ctgggcaccc agacctacat ctgcaacgtg aaccacaagc cgtccaacac caaagtggat     660
aagcgggtgg agccgaagtc ctgcgataag acacacacgt gcccgccatg tccagcgcct     720
gaattgcttg gcggaccttc cgtgttcctg ttcccgccta gcccaaggga cccttgatg      780
attagccgga ctcccgaagt cacctgtgtg gtggtggcag tgtcccacga ggacccgag     840
gtcaagttta ttggtacgt ggacggcgtc gaagtgcaca acgccaagac taagcccgg      900
gaggaacagt acaacagcac ctaccgggtc gtgtccgtgc tgaccgtgct gcaccaggac     960
tggctgaatg gaaagagta caagtgcaaa gtgtccaaca aggccttggc cgctcctatc    1020
gaaaaaacta tcagcaaggc taagggacag ccgagggaac cccaagtcta caccctgccc    1080
ccttcacgcg aagagatgac caagaatcaa gtgtcgctga cctgcctcgt caagggattc    1140
taccctccg acattgcggt ggagtgggag tccaacggcc agcccgagaa caactacaag    1200
actactccgc ccgtgctgga ctccgacggc agcttcttcc tgtattccaa gctgaccgtg    1260
gacaagtccc ggtggcagca aggaaacgtg ttctcctgct cggtcatgca cgaagccctg    1320
cacaaccact atacgcagaa gtccctgtcc ttgagcccgg ggaaa                     1365

<210> SEQ ID NO 210
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 210
gacatccaga tgacccagtc tccgtcctcc ctgtccgcat cagtggggga cagagtgacc      60
atcacttgtc gggcctccca aggcatctcg tcatacctgg cctggtatca gcagaaaccc     120
ggaaaggctc caaagctgct catctacacc gcctcgactc tgcaatccgg agtgccttcc     180
cgcttctccg gatccggttc gggaaccgac ttcaccctca ccattagcag ccttcagccg     240
gaagatttcg cgacctacta ctgccagcaa gaatgggtga agcccaggac atttggccag     300
ggcactaagg tcgagattaa g                                               321

<210> SEQ ID NO 211
```

```
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 211
gacatccaga tgacccagtc tccgtcctcc ctgtccgcat cagtggggga cagagtgacc      60
atcacttgtc gggcctccca aggcatctcg tcatacctgg cctggtatca gcagaaaccc     120
ggaaaggctc caaagctgct catctacacc gcctcgactc tgcaatccgg agtgccttcc     180
cgcttctccg gatccggttc gggaaccgac ttcaccctca ccattagcag ccttcagccg     240
gaagatttcg cgacctacta ctgccagcaa gaatgggtga agcccaggac atttggccag     300
ggcactaagg tcgagattaa gcgtacggtg gccgctccca gcgtgttcat cttccccccc     360
agcgacgagc agctgaagag cggcaccgcc agcgtggtgt gcctgctgaa caacttctac     420
ccccgggagg ccaaggtgca gtggaaggtg gacaacgccc tgcagagcgg caacagccag     480
gagagcgtca ccgagcagga cagcaaggac tccacctaca gcctgagcag caccctgacc     540
ctgagcaagg ccgactacga gaagcataag gtgtacgcct gcgaggtgac ccaccagggc     600
ctgtccagcc ccgtgaccaa gagcttcaac aggggcgagt gc                        642

<210> SEQ ID NO 212
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 212
gacatacaga tgactcagag tccttcctcc ctcagtgctt cagtgggtga tcgcgtgacg      60
atcacgtgca gagcctcaca agggatctcc agttacctgg cctggtatca acaaaaacca     120
ggcaaggcgc ctaagctgtt gatatatacg gcatctacat tgcagtctgg ggtaccaagt     180
cgattcagtg gttctggctc aggcactgac tttacccttta caatatcaag tcttcagccg     240
gaggatttcg caacttacta ttgccagcag atttggacgg tgccgcgcac tttcggtcag     300
ggaacaaagg tggaaataaa a                                               321

<210> SEQ ID NO 213
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 213
gacatacaga tgactcagag tccttcctcc ctcagtgctt cagtgggtga tcgcgtgacg      60
atcacgtgca gagcctcaca agggatctcc agttacctgg cctggtatca acaaaaacca     120
ggcaaggcgc ctaagctgtt gatatatacg gcatctacat tgcagtctgg ggtaccaagt     180
cgattcagtg gttctggctc aggcactgac tttacccttta caatatcaag tcttcagccg     240
gaggatttcg caacttacta ttgccagcag atttggacgg tgccgcgcac tttcggtcag     300
ggaacaaagg tggaaataaa agaacggtc gcagcaccga gtgtttcat cttccctccc       360
```

```
tccgacgagc agcttaaaag cggtacagcc agcgtagtgt gtttgttgaa taattttat     420 ccacgcgaag caaagttca gtggaaggta gacaacgcat tgcaaagcgg aaattcccaa     480
gaaagtgtta cggagcaaga cagtaaggac tctacatatt ccttgtcatc aacactcacc    540
cttagtaaag cagattacga gaaacacaag gtctatgcat gtgaggtaac gcatcagggc    600
ctctccagtc ccgtcaccaa gtccttcaac aggggtgagt gc                       642
```

<210> SEQ ID NO 214
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 214

```
gacatccaga tgacccagtc tccgtcctcc ctgtccgcat cagtggggga cagagtgacc     60
atcacttgtc gggcctccca aggcatctcg tcatacctgg cctggtatca gcagaaaccc    120
ggaaaggctc caaagctgct catctacacc gcctcgactc tgcaatccgg agtgccttcc    180
cgcttctccg gatccggttc gggaaccgac ttcaccctca ccattagcag ccttcagccg    240
gaagatttcg cgacctacta ctgccagcaa atctggaccg tgcccaggac atttggccag    300
ggcactaagg tcgagattaa g                                              321
```

<210> SEQ ID NO 215
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 215

```
gacatccaga tgacccagtc tccgtcctcc ctgtccgcat cagtggggga cagagtgacc     60
atcacttgtc gggcctccca aggcatctcg tcatacctgg cctggtatca gcagaaaccc    120
ggaaaggctc caaagctgct catctacacc gcctcgactc tgcaatccgg agtgccttcc    180
cgcttctccg gatccggttc gggaaccgac ttcaccctca ccattagcag ccttcagccg    240
gaagatttcg cgacctacta ctgccagcaa atctggaccg tgcccaggac atttggccag    300
ggcactaagg tcgagattaa gcgtacggtg gccgctccca gcgtgttcat cttcccccc    360 agcgacgagc agctgaagag cggcaccgcc agcgtggtgt gcctgctgaa caacttctac    420
ccccgggagg ccaaggtgca gtggaaggtg gacaacgccc tgcagagcgg caacagccag    480
gagagcgtca ccgagcagga cagcaaggac tccacctaca gcctgagcag caccctgacc    540
ctgagcaagg ccgactacga gaagcataag gtgtacgcct gcgaggtgac ccaccagggc    600
ctgtccagcc ccgtgaccaa gagcttcaac aggggcgagt gc                       642
```

<210> SEQ ID NO 216
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 216

```
gacatccaga tgacccagtc tccgtcctcc ctgtccgcat cagtgggga cagagtgacc      60
atcacttgtc gggcctccca aggcatctcg tcatacctgg cctggtatca gcagaaaccc    120
ggaaaggctc caaagctgct catctacacc gcctcgactc tgcaatccgg agtgccttcc    180
cgcttctccg gatccggttc gggaaccgac ttcaccctca ccattagcag ccttcagccg    240
gaagatttcg cgacctacta ctgccagcaa gaatgggcca gcccaggac atttggccag     300
ggcactaagg tcgagattaa g                                              321
```

<210> SEQ ID NO 217
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 217

```
gacatccaga tgacccagtc tccgtcctcc ctgtccgcat cagtgggga cagagtgacc      60
atcacttgtc gggcctccca aggcatctcg tcatacctgg cctggtatca gcagaaaccc    120
ggaaaggctc caaagctgct catctacacc gcctcgactc tgcaatccgg agtgccttcc    180
cgcttctccg gatccggttc gggaaccgac ttcaccctca ccattagcag ccttcagccg    240
gaagatttcg cgacctacta ctgccagcaa gaatgggcca gcccaggac atttggccag     300
ggcactaagg tcgagattaa gcgtacggtg gccgctccca gcgtgttcat cttccccccc    360
agcgacgagc agctgaagag cggcaccgcc agcgtggtgt gcctgctgaa caacttctac    420
ccccgggagg ccaaggtgca gtggaaggtg acaacgccc tgcagagcgg caacagccag     480
gagagcgtca ccgagcagga cagcaaggac tccacctaca gcctgagcag caccctgacc    540
ctgagcaagg ccgactacga aagcataag gtgtacgcct gcgaggtgac ccaccagggc     600
ctgtccagcc ccgtgaccaa gagcttcaac aggggcgagt gc                       642
```

<210> SEQ ID NO 218
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 218

```
gatattcaga tgacgcaatc tccgtcttcc ttgtcagcta gtgtaggaga ccgcgtcaca     60
attacctgta gagccagcca ggggattcc tcataccttg catggtacca gcaaaagcca    120
ggcaaagccc ccaaactgct gatctacacc gcgtctacct tgcaatctgg tgtgccgtca    180
cgcttttccg gctctggctc aggtactgat ttcacattga cgatctcaag tctccagccc   240
gaagacttcg caacttacta ctgccaacaa tcctggacga ggccgaggac tttcgggcag   300
ggaacaaagg ttgaaattaa a                                             321
```

<210> SEQ ID NO 219
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 219

| gatattcaga tgacgcaatc tccgtcttcc ttgtcagcta gtgtaggaga ccgcgtcaca | 60 |
| attacctgta gagccagcca ggggatttcc tcataccttg catggtacca gcaaaagcca | 120 |
| ggcaaagccc ccaaactgct gatctacacc gcgtctacct tgcaatctgg tgtgccgtca | 180 |
| cgcttttccg gctctggctc aggtactgat ttcacattga cgatctcaag tctccagccg | 240 |
| gaagacttcg caacttacta ctgccaacaa tcctggacga ggccgaggac tttcgggcag | 300 |
| ggaacaaagg ttgaaattaa agaacagtc gcagcaccaa gtgtttttat ttttccaccc | 360 |
| tcagacgagc agctcaagtc tggcaccgcg agcgtagtat gtttgttgaa taattttac | 420 |
| cctagggaag ctaaggtaca gtggaaagtg gataatgctc tccaaagtgg caactcccag | 480 |
| gaatcagtga ctgagcaaga ttcaaaggac agcacgtatt ctctttcttc tacgcttact | 540 |
| ctctctaagg ccgactacga aaaacacaaa gtttacgctt gcgaggttac ccaccagggg | 600 |
| ctgtcctcac cagtaacgaa aagttttaac cggggcgagt gt | 642 |

<210> SEQ ID NO 220
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 220

| gacatccaga tgacccagtc tccgtcctcc ctgtccgcat cagtggggga cagagtgacc | 60 |
| atcacttgtc gggcctccca aggcatctcg tcatacctgg cctggtatca gcagaaaccc | 120 |
| ggaaaggctc caaagctgct catctacacc gcctcgactc tgcaatccgg agtgccttcc | 180 |
| cgcttctccg gatccggttc gggaaccgac ttcaccctca ccattagcag ccttcagccg | 240 |
| gaagatttcg cgacctacta ctgccagcaa agctggacca ggcccaggac atttggccag | 300 |
| ggcactaagg tcgagattaa g | 321 |

<210> SEQ ID NO 221
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 221

| gacatccaga tgacccagtc tccgtcctcc ctgtccgcat cagtggggga cagagtgacc | 60 |
| atcacttgtc gggcctccca aggcatctcg tcatacctgg cctggtatca gcagaaaccc | 120 |
| ggaaaggctc caaagctgct catctacacc gcctcgactc tgcaatccgg agtgccttcc | 180 |
| cgcttctccg gatccggttc gggaaccgac ttcaccctca ccattagcag ccttcagccg | 240 |
| gaagatttcg cgacctacta ctgccagcaa agctggacca ggcccaggac atttggccag | 300 |
| ggcactaagg tcgagattaa gcgtacggtg gccgctccca gcgtgttcat cttccccccc | 360 |
| agcgacgagc agctgaagag cggcaccgcc agcgtggtgt gcctgctgaa caacttctac | 420 |
| ccccgggagg ccaaggtgca gtggaaggtg gacaacgccc tgcagagcgg caacagccag | 480 |

```
gagagcgtca ccgagcagga cagcaaggac tccacctaca gcctgagcag caccctgacc      540
ctgagcaagg ccgactacga gaagcataag gtgtacgcct gcgaggtgac ccaccagggc      600
ctgtccagcc ccgtgaccaa gagcttcaac aggggcgagt gc                         642

<210> SEQ ID NO 222
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 222
gacattcaaa tgactcagtc tccctcatct ttgtcagcat cagttgggga cagggtgaca      60
atcacatgcc gagcctcaca ggggatttct agctatcttg catggtacca acagaagccc      120
ggcaaagccc ccaagctttt gatatatacg gcatccactc ttcagagcgg agtacccagt      180
aggtttagtg gctccgggag tggtacggac tttactctga cgatttcctc ccttcaacct      240
gaagactttg caacgtatta ctgtcagcaa atatggatgg ctcccagaac gtttggtcaa      300
ggtactaaag ttgaaataaa g                                                321

<210> SEQ ID NO 223
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 223
gacattcaaa tgactcagtc tccctcatct ttgtcagcat cagttgggga cagggtgaca      60
atcacatgcc gagcctcaca ggggatttct agctatcttg catggtacca acagaagccc      120
ggcaaagccc ccaagctttt gatatatacg gcatccactc ttcagagcgg agtacccagt      180
aggtttagtg gctccgggag tggtacggac tttactctga cgatttcctc ccttcaacct      240
gaagactttg caacgtatta ctgtcagcaa atatggatgg ctcccagaac gtttggtcaa      300
ggtactaaag ttgaaataaa gcgaactgta gcagcaccta gtgtatttat cttccccct       360 tctgatgaac agttgaagtc cggacggct tccgtcgtat gtctcctgaa caacttttac      420
ccaagggagg caaaggtgca atggaaggtg gataatgcac tccagagtgg caatagccaa      480
gaatcagtaa ccgaacagga ttccaaggat tctacctaca gcctttcctc tacgcttaca      540
ttgagcaagg cggactatga aaagcataag gtgtatgcgt gcgaagtaac acaccagggt      600
ctcagcagtc cagttacgaa gtctttcaat cggggagaat gt                         642

<210> SEQ ID NO 224
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 224
gacatccaga tgacccagtc tccgtcctcc ctgtccgcat cagtggggga cagagtgacc      60
atcacttgtc gggcctccca aggcatctcg tcataccctgg cctggtatca gcagaaaccc      120
```

```
ggaaaggctc caaagctgct catctacacc gcctcgactc tgcaatccgg agtgccttcc    180
cgcttctccg gatccggttc gggaaccgac ttcaccctca ccattagcag ccttcagccg    240
gaagatttcg cgacctacta ctgccagcaa atctggatgg cccccaggac atttggccag    300
ggcactaagg tcgagattaa g                                              321

<210> SEQ ID NO 225
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 225
gacatccaga tgacccagtc tccgtcctcc ctgtccgcat cagtggggga cagagtgacc     60
atcacttgtc gggcctccca aggcatctcg tcatacctgg cctggtatca gcagaaaccc    120
ggaaaggctc caaagctgct catctacacc gcctcgactc tgcaatccgg agtgccttcc    180
cgcttctccg gatccggttc gggaaccgac ttcaccctca ccattagcag ccttcagccg    240
gaagatttcg cgacctacta ctgccagcaa atctggatgg cccccaggac atttggccag    300
ggcactaagg tcgagattaa gcgtacggtg gccgctccca gcgtgttcat cttccccccc    360
agcgacgagc agctgaagag cggcaccgcc agcgtggtgt gcctgctgaa caacttctac    420
ccccgggagg ccaaggtgca gtggaaggtg acaacgccc tgcagagcgg caacagccag    480
gagagcgtca ccgagcagga cagcaaggac tccacctaca gcctgagcag caccctgacc    540
ctgagcaagg ccgactacga gaagcataag gtgtacgcct gcgaggtgac ccaccagggc    600
ctgtccagcc ccgtgaccaa gagcttcaac aggggcgagt gc                       642

<210> SEQ ID NO 226
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 226

Gly Phe Thr Phe Ser Ser Tyr Trp Ile Ser
1               5                   10

<210> SEQ ID NO 227
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 227

Asn Ile Lys Gln Ser Gly Ser Glu Thr Tyr Tyr Val Glu Ser Val Lys
1               5                   10                  15

Gly

<210> SEQ ID NO 228
<211> LENGTH: 14
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 228

Ser Leu Arg Arg Arg Ser Thr Glu His Ala Gly Phe Asp Val
1               5                   10

<210> SEQ ID NO 229
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 229

Ser Tyr Trp Ile Ser
1               5

<210> SEQ ID NO 230
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 230

Lys Gln Ser Gly Ser Glu
1               5

<210> SEQ ID NO 231
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 231

Ile Lys Gln Ser Gly Ser Glu Thr
1               5

<210> SEQ ID NO 232
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 232

Ala Arg Ser Leu Arg Arg Arg Ser Thr Glu His Ala Gly Phe Asp Val
1               5                   10                  15

<210> SEQ ID NO 233
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 233

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Ile Ser Trp Val Arg Gln Ala Pro Gly Lys Gly Leu Glu Trp Val
        35                  40                  45

Ala Asn Ile Lys Gln Ser Gly Ser Glu Thr Tyr Tyr Val Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Arg Arg Ser Thr Glu His Ala Gly Phe Asp Val
            100                 105                 110

Trp Gly Gln Gly Thr Leu Val Thr Val Ser Ser
        115                 120

<210> SEQ ID NO 234
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 234
gaagtgcagc tggtggaaag cggcggtggc ctggtgcagc caggtggtag cctgcgcctg      60
agctgcgccg ccagcggctt tacctttagc agctattgga ttagctgggt tcgccaggcc     120
ccaggcaaag gcctggaatg ggtggcgaac atcaaacaga gcggcagcga gacctactat     180
gtggagagcg tgaaaggccg ctttaccatt agccgcgata acgccaaaaa cagcctgtat     240
ctgcaaatga acagcctgcg ggccgaagat accgccgtgt attattgcgc gcgtagcctg     300
cgtcgtcgta gcactgagca cgcaggattc gacgtttggg gccagggcac cctggttact     360
gtctcgagc                                                             369

<210> SEQ ID NO 235
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 235

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Ile Ser Trp Val Arg Gln Ala Pro Gly Lys Gly Leu Glu Trp Val
        35                  40                  45

Ala Asn Ile Lys Gln Ser Gly Ser Glu Thr Tyr Tyr Val Glu Ser Val
    50                  55                  60

Lys Gly Arg Phe Thr Ile Ser Arg Asp Asn Ala Lys Asn Ser Leu Tyr

```
            65                  70                  75                  80
Leu Gln Met Asn Ser Leu Arg Ala Glu Asp Thr Ala Val Tyr Tyr Cys
                85                  90                  95

Ala Arg Ser Leu Arg Arg Ser Thr Glu His Ala Gly Phe Asp Val
            100                 105                 110

Trp Gly Gln Gly Thr Leu Val Thr Val Ser Ser Ala Ser Thr Lys Gly
                115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Arg Val Glu Pro Lys
            210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly Lys
        450

<210> SEQ ID NO 236
<211> LENGTH: 1359
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic polynucleotide"

<400> SEQUENCE: 236
gaagtgcagc tggtggaaag cggcggtggc ctggtgcagc caggtggtag cctgcgcctg      60
agctgcgccg ccagcggctt tacctttagc agctattgga ttagctgggt tcgccaggcc     120
ccaggcaaag gcctggaatg gtggcgaaac atcaaacaga gcggcagcga gacctactat     180
gtggagagcg tgaaaggccg ctttaccatt agccgcgata cgccaaaaa cagcctgtat      240 ctgcaaatga acagcctgcg ggccgaagat accgccgtgt attattgcgc gcgtagcctg     300
cgtcgtcgta gcactgagca cgcaggattc gacgtttggg gccagggcac cctggttact     360
gtctcgagcg cgtcgaccaa aggccccagc gtgttccctc tggcccccag cagcaagagc     420
acctctggcg gaacagccgc cctgggctgc ctggtcaagg actacttccc cgagcccgtg     480
accgtgtcct ggaactctgg cgccctgacc agcggcgtgc acacctttcc agccgtgctc     540
cagagcagcg gcctgtacag cctgagcagc gtcgtgaccg tgcccagcag cagcctgggc     600
acccagacct acatctgcaa cgtgaaccac aagcccagca cacaaaggt ggacaagcgg      660 gtggaaccca gagctgcga caagacccac acctgtcccc cctgccctgc ccctgaagcg      720
gcgggaggcc cctccgtgtt cctgttcccc ccaaagccta aggacaccct gatgatcagc     780 cggaccccg aagtgacctg cgtggtggtg gacgtgtccc acgaggaccc tgaagtgaag      840
tttaattggt acgtggacgg cgtggaagtg cacaacgcca agaccaagcc cagagaggaa     900
cagtacaaca gcacctaccg ggtggtgtcc gtgctgaccg tgctgcacca ggactggctg     960
aacggcaaag agtacaagtg caaggtgtcc aacaaggccc tgcctgcccc catcgagaaa    1020
accatcagca aggccaaagg ccagccccgc gagcccagg tgtacacact gcccccctagc    1080 cgggaagaga tgaccaagaa ccaggtgtcc ctgacctgcc tcgtgaaggg cttctacccc    1140
agcgacattg ccgtggaatg ggagagcaac ggccagcccg agaacaacta caagaccacc    1200 cccctgtgc tggacagcga cggctcattc ttcctgtaca gcaagctgac cgtggacaag    1260
agccggtgga gcagggcaa cgtgttcagc tgctccgtga tgcacgaggc cctgcacaac    1320
cactacaccc agaagtccct gagcctgagc cccggcaag                           1359
```

```
<210> SEQ ID NO 237
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 237

Arg Ala Ser Gln Gly Ile Ser Asn Tyr Leu Ala
1               5                   10

<210> SEQ ID NO 238
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 238
```

```
Ala Ala Ser Thr Leu Gln Ser
1               5

<210> SEQ ID NO 239
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 239

Gln Gln Ala Asp Lys Phe Pro Tyr Thr
1               5

<210> SEQ ID NO 240
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 240

Ser Gln Gly Ile Ser Asn Tyr
1               5

<210> SEQ ID NO 241
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 241

Ala Ala Ser
1

<210> SEQ ID NO 242
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 242

Ala Asp Lys Phe Pro Tyr
1               5

<210> SEQ ID NO 243
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 243

Gln Gly Ile Ser Asn Tyr
1               5
```

```
<210> SEQ ID NO 244
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 244

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Ala Asp Lys Phe Pro Tyr
                85                  90                  95

Thr Phe Gly Gln Gly Thr Lys Val Glu Ile Lys
            100                 105

<210> SEQ ID NO 245
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 245
gatattcaga tgacccagag cccgagcagc ctgagcgcaa gcgtgggcga tcgcgtgacc      60
attacctgcc gcgccagcca gggcattagc aactatctgg cctggtatca gcagaaaccg    120
ggcaaagtgc cgaaactgct gatctatgcc gccagcaccc tgcaaagcgg cgtgccaagt    180
cgctttagcg gcagcggtag cggcaccgat ttcaccctga ccattagcag cctgcaaccg    240
gaagacgtgg cgacctatta ttgccagcag gctgacaaat tcccgtacac cttcggccag    300
ggtaccaaag tggaaatcaa g                                              321

<210> SEQ ID NO 246
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 246

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
```

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Ala Asp Lys Phe Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 247
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 247
gatattcaga tgacccagag cccgagcagc ctgagcgcaa gcgtgggcga tcgcgtgacc      60
attacctgcc gcgccagcca gggcattagc aactatctgg cctggtatca gcagaaaccg     120
ggcaaagtgc cgaaactgct gatctatgcc gccagcaccc tgcaaagcgg cgtgccaagt     180
cgctttagcg gcagcggtag cggcaccgat ttcaccctga ccattagcag cctgcaaccg     240
gaagacgtgg cgacctatta ttgccagcag gctgacaaat tcccgtacac cttcggccag     300
ggtaccaaag tggaaatcaa gcggaccgtg gccgctccct ccgtgttcat cttcccaccc     360
agcgacgagc agctgaagtc cggcacagcc agcgtcgtgt gcctgctgaa caacttctac     420
ccccgcgagg ccaaagtgca gtggaaggtg gacaacgccc tccagagcgg caacagccag     480
gaaagcgtca ccgagcagga cagcaaggac tccacctaca gcctgagcag caccctgacc     540
ctgagcaagg ccgactacga aaagcacaag gtgtacgcct gcgaagtgac ccaccagggc     600
ctgtccagcc ccgtgaccaa gagcttcaac cggggcgagt gt                        642

<210> SEQ ID NO 248
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 248

Gly Phe Thr Phe Ser Ser Tyr Ser Met Asn

```
1               5                   10
```

<210> SEQ ID NO 249
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 249

```
Ser Ile Ser Ser Ser Ser Ser Tyr Ile Tyr Tyr Ala Asp Ser Val Lys
1               5                   10                  15

Gly
```

<210> SEQ ID NO 250
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 250

```
Ser Gly Tyr Arg Gly Val Tyr Gly Phe Asp Tyr
1               5                   10
```

<210> SEQ ID NO 251
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 251

```
Ser Tyr Ser Met Asn
1               5
```

<210> SEQ ID NO 252
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 252

```
Ser Ser Ser Ser Ser Tyr
1               5
```

<210> SEQ ID NO 253
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 253

```
Gly Phe Thr Phe Ser Ser Tyr Ser
1               5
```

<210> SEQ ID NO 254
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 254

Ile Ser Ser Ser Ser Ser Tyr Ile
1               5

<210> SEQ ID NO 255
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 255

Ala Arg Ser Gly Tyr Arg Gly Val Tyr Gly Phe Asp Tyr
1               5                   10

<210> SEQ ID NO 256
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 256

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Arg Gly Val Tyr Gly Phe Asp Tyr Trp Gly Gln
            100                 105                 110

Gly Thr Leu Val Thr Val Ser Ser
        115                 120

<210> SEQ ID NO 257
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 257
gaagtgcagc tggtggaaag cggcggtggc ctggtgaaac caggcggtag cctgcgcctg     60

-continued

```
agctgcgccg ccagcggctt tacctttagc agctatagca tgaactgggt tcgccaggcc      120
ccaggcaaag gcctggaatg ggttagcagc atcagcagca gtagcagcta tatctattac      180
gccgatagcg tgaaaggccg ctttaccatt agccgcgata cgccaaaaa cagcctgtat        240 ctgcaaatga acagcctgcg ggccgaagat accgccgtgt attattgcgc gcgaagcgga      300
tatcgtggag tttacggatt tgattattgg ggccaggca ccctggttac tgtctcgagc       360
```

<210> SEQ ID NO 258
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 258

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Arg Gly Val Tyr Gly Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300
```

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 259
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 259
gaagtgcagc tggtggaaag cggcggtggc ctggtgaaac caggcggtag cctgcgcctg      60
agctgcgccg ccagcggctt tacctttagc agctatagca tgaactgggt tcgccaggcc     120
ccaggcaaag gcctggaatg ggttagcagc atcagcagca gtagcagcta tatctattac     180
gccgatagcg tgaaaggccg ctttaccatt agccgcgata cgccaaaaaa cagcctgtat     240
ctgcaaatga acagcctgcg ggccgaagat accgccgtgt attattgcgc gcgaagcgga     300
tatcgtggag tttacggatt tgattattgg ggccagggca ccctggttac tgtctcgagc     360
gcgtcgacca aaggcccag cgtgttccct ctggcccca gcagcaagag cacctctggc     420
ggaacagccg ccctgggctg cctggtcaag gactacttcc ccgagcccgt gaccgtgtcc     480
tggaactctg gcgccctgac cagcggcgtg cacaccttc agccgtgct ccagagcagc     540 ggcctgtaca gcctgagcag cgtcgtgacc gtgcccagca gcctgggg cacccagacc     600 tacatctgca acgtgaacca caagcccagc aacacaaagg tggacaagcg ggtggaaccc     660
aagagctgcg acaagaccca cacctgtccc ccctgccctg ccctgaagc ggcgggaggc     720 cctccgtgt tcctgttccc cccaaagcct aaggacaccc tgatgatcag ccggaccccc     780
gaagtgacct gcgtggtggt ggacgtgtcc cacgaggacc ctgaagtgaa gtttaattgg     840
tacgtggacg gcgtggaagt gcacaacgcc aagaccaagc cagagagga acagtacaac     900 agcacctacc gggtggtgtc cgtgctgacc gtgctgcacc aggactggct gaacggcaaa     960
gagtacaagt gcaaggtgtc caacaaggcc ctgcctgccc ccatcgagaa aaccatcagc    1020
aaggccaaag gccagccccg cgagcccag gtgtacacac tgcccctag ccgggaagag    1080

```
atgaccaaga accaggtgtc cctgacctgc ctcgtgaagg gcttctaccc cagcgacatt    1140
gccgtggaat gggagagcaa cggccagccc gagaacaact acaagaccac ccccctgtg     1200 ctggacagcg acggctcatt cttcctgtac agcaagctga ccgtggacaa gagccggtgg    1260
cagcagggca acgtgttcag ctgctccgtg atgcacgagg ccctgcacaa ccactacacc    1320
cagaagtccc tgagcctgag ccccggcaag                                     1350
```

<210> SEQ ID NO 260
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 260

Arg Ala Ser Gln Gly Ile Ser Ser Trp Leu Ala
1               5                   10

<210> SEQ ID NO 261
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 261

Ala Ala Ser Ser Leu Gln Ser
1               5

<210> SEQ ID NO 262
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 262

Gln Gln Tyr Tyr His Ser Pro Leu Thr
1               5

<210> SEQ ID NO 263
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 263

Ser Gln Gly Ile Ser Ser Trp
1               5

<210> SEQ ID NO 264
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 264

Tyr Tyr His Ser Pro Leu
1               5

<210> SEQ ID NO 265
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 265

Gln Gly Ile Ser Ser Trp
1               5

<210> SEQ ID NO 266
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 266

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr His Ser Pro Leu
                85                  90                  95

Thr Phe Gly Gln Gly Thr Lys Val Glu Ile Lys
            100                 105

<210> SEQ ID NO 267
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 267
gatattcaga tgacccagag cccgagcagc gttagcgcca gcgtgggcga tcgcgtgacc    60
attacctgcc gcgccagtca gggcattagc agctggctgg cctggtatca gcagaaaccg   120
ggcaaagccc cgaaactgct gatctatgcc gccagcagcc tgcaaagcgg cgtgccaagt   180
cgctttagcg gcagcggtag cggcaccgat ttcaccctga ccattagcag tctgcaaccg   240
gaagactttg ccacctatta ttgccagcag tactaccatt ctccgctgac cttcggccag   300
ggtaccaaag tggaaatcaa g                                             321

-continued

```
<210> SEQ ID NO 268
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 268
```

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr His Ser Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 269
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 269
gatattcaga tgacccagag cccgagcagc gttagcgcca gcgtgggcga tcgcgtgacc      60
attacctgcc gcgccagtca gggcattagc agctggctgg cctggtatca gcagaaaccg     120
ggcaaagccc cgaaactgct gatctatgcc gccagcagcc tgcaaagcgg cgtgccaagt     180
cgctttagcg gcagcggtag cggcaccgat ttcaccctga ccattagcag tctgcaaccg     240
gaagactttg ccacctatta ttgccagcag tactaccatt ctccgctgac cttcggccag     300
ggtaccaaag tggaaatcaa gcggaccgtg gccgctccct ccgtgttcat cttcccaccc     360
agcgacgagc agctgaagtc cggcacagcc agcgtcgtgt gcctgctgaa caacttctac     420
```

```
ccccgcgagg ccaaagtgca gtggaaggtg acaacgccc tccagagcgg caacagccag    480
gaaagcgtca ccgagcagga cagcaaggac tccacctaca gcctgagcag caccctgacc    540
ctgagcaagg ccgactacga aagcacaag gtgtacgcct gcgaagtgac ccaccagggc     600
ctgtccagcc ccgtgaccaa gagcttcaac cggggcgagt gt                       642
```

<210> SEQ ID NO 270
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 270

Gly Phe Thr Phe Ser Ser Tyr Ala Ile Ser
1               5                   10

<210> SEQ ID NO 271
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 271

Ala Ile Ser Gly Ser Gly Gly Ser Thr Tyr Tyr Ala Glu Ser Val Lys
1               5                   10                  15

Gly

<210> SEQ ID NO 272
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 272

Glu Ser Gly Tyr Val Tyr Tyr Leu Lys Phe Asp Tyr
1               5                   10

<210> SEQ ID NO 273
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 273

Ser Tyr Ala Ile Ser
1               5

<210> SEQ ID NO 274
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

-continued

<400> SEQUENCE: 274

Ser Gly Ser Gly Gly Ser
1               5

<210> SEQ ID NO 275
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 275

Gly Phe Thr Phe Ser Ser Tyr Ala
1               5

<210> SEQ ID NO 276
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 276

Ile Ser Gly Ser Gly Gly Ser Thr
1               5

<210> SEQ ID NO 277
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 277

Ala Arg Glu Ser Gly Tyr Val Tyr Tyr Leu Lys Phe Asp Tyr
1               5                   10

<210> SEQ ID NO 278
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 278

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Ile Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                        85                  90                  95

Ala Arg Glu Ser Gly Tyr Val Tyr Tyr Leu Lys Phe Asp Tyr Trp Gly
            100                 105                 110

Gln Gly Thr Leu Val Thr Val Ser Ser
            115                 120
```

<210> SEQ ID NO 279
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 279

```
gaagtgcagc tgctggaaag cggtggcggt ctggtgcagc caggtggtag cctgcgcctg      60
agctgtgccg caagcggctt tacctttagc agctatgcca ttagctgggt gcgccaagca     120
ccaggcaaag cctggaatgg gtgagcgcc attagcggga gcggtggcag cacctattat     180
gccgagagcg tgaaaggtcg ctttaccatt agtcgcgata acagcaaaaa cacccctgtat    240 ctgcaaatga acagcctgcg ggcagaagat accgcagttt attattgcgc gcgtgagagc     300
ggatacgttt actatctgaa attcgattat tggggccagg caccctggt tactgtctcg     360 agc                                                                   363
```

<210> SEQ ID NO 280
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 280

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Ile Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Gly Tyr Val Tyr Tyr Leu Lys Phe Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

-continued

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Glu Glu Met Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Lys
    450

<210> SEQ ID NO 281
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 281
gaagtgcagc tgctggaaag cggtggcggt ctggtgcagc caggtggtag cctgcgcctg      60
agctgtgccg caagcggctt tacctttagc agctatgcca ttagctgggt gcgccaagca     120
ccaggcaaag gcctggaatg ggtgagcgcc attagcggca gcggtggcag cacctattat     180
gccgagagcg tgaaaggtcg ctttaccatt agtcgcgata cagcaaaaa caccctgtat     240 ctgcaaatga acagcctgcg cggcagaagat accgcagttt attattgcgc gcgtgagagc     300
ggatacgttt actatctgaa attcgattat tgggccagg gcaccctggt tactgtctcg     360
agcgcgtcga ccaaaggccc cagcgtgttc cctctggccc ccagcagcaa gagcacctct     420

```
ggcggaacag ccgccctggg ctgcctggtc aaggactact tccccgagcc cgtgaccgtg    480
tcctggaact ctggcgccct gaccagcggc gtgcacacct tccagccgt gctccagagc     540 agcggcctgt acagcctgag cagcgtcgtg accgtgccca gcagcagcct gggcacccag    600
acctacatct gcaacgtgaa ccacaagccc agcaacacaa aggtggacaa gcgggtggaa    660
cccaagagct gcgacaagac ccacacctgt cccccctgcc ctgccccctga gcggcggga   720 ggcccctccg tgttcctgtt ccccccaaag cctaaggaca ccctgatgat cagccggacc    780
cccgaagtga cctgcgtggt ggtggacgtg tcccacgagg accctgaagt gaagtttaat    840
tggtacgtgg acggcgtgga agtgcacaac gccaagacca gcccagaga ggaacagtac    900 aacagcacct accgggtggt gtccgtgctg accgtgctgc accaggactg gctgaacggc    960
aaagagtaca gtgcaaggt gtccaacaag gccctgcctg ccccatcga aaaaccatc    1020 agcaaggcca aggccagcc ccgcgagccc caggtgtaca cactgccccc tagccgggaa   1080
gagatgacca gaaccaggt gtccctgacc tgcctcgtga agggcttcta ccccagcgac   1140
attgccgtgg aatgggagag caacggccag cccgagaaca actacaagac caccccccct  1200
gtgctggaca cgacggctc attcttcctg tacagcaagc tgaccgtgga caagagccgg   1260
tggcagcagg gcaacgtgtt cagctgctcc gtgatgcacg aggccctgca caaccactac   1320
acccagaagt ccctgagcct gagccccggc aag                                 1353

<210> SEQ ID NO 282
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 282

Arg Ala Ser Gln Ser Ile Ser Ser Tyr Leu Asn
1               5                   10

<210> SEQ ID NO 283
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 283

Gln Gln His Val Arg Val Pro Ile Thr
1               5

<210> SEQ ID NO 284
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 284

Ser Gln Ser Ile Ser Ser Tyr
1               5
```

<210> SEQ ID NO 285
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 285

His Val Arg Val Pro Ile
1               5

<210> SEQ ID NO 286
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 286

Gln Ser Ile Ser Ser Tyr
1               5

<210> SEQ ID NO 287
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 287

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Val Arg Val Pro Ile
                85                  90                  95

Thr Phe Gly Gln Gly Thr Lys Val Glu Ile Lys
            100                 105

<210> SEQ ID NO 288
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 288
gatattcaga tgacccagag cccgagcagc ctgagcgcca gcgtgggtga tcgcgtgacc      60
attacctgtc gcgcaagcca gagcattagc agctatctga actggtatca gcagaaacca     120
ggcaaagccc caaaactgct gatttatgcc gcaagcagcc tgcaaagcgg tgtgccgagc     180

```
cgctttagcg gcagcggtag cggcaccgat tttaccctga ccattagtag cctgcaaccg    240
gaagactttg ccacctatta ttgccagcag catgttcgtg ttccgatcac cttcggccag    300
ggtaccaaag tggaaatcaa g                                              321
```

<210> SEQ ID NO 289
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 289

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Val Arg Val Pro Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 290
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 290

```
gatattcaga tgacccagag cccgagcagc ctgagcgcca gcgtgggtga tcgcgtgacc    60
attacctgtc gcgcaagcca gagcattagc agctatctga actggtatca gcagaaacca    120
ggcaaagccc caaaactgct gatttatgcc gcaagcagcc tgcaaagcgg tgtgccgagc    180
```

```
cgctttagcg gcagcggtag cggcaccgat tttaccctga ccattagtag cctgcaaccg    240
gaagactttg ccacctatta ttgccagcag catgttcgtg ttccgatcac cttcggccag    300
ggtaccaaag tggaaatcaa gcggaccgtg gccgctccct ccgtgttcat cttcccaccc    360
agcgacgagc agctgaagtc cggcacagcc agcgtcgtgt gcctgctgaa caacttctac    420
ccccgcgagg ccaaagtgca gtggaaggtg gacaacgccc tccagagcgg caacagccag    480
gaaagcgtca ccgagcagga cagcaaggac tccacctaca gcctgagcag caccctgacc    540
ctgagcaagg ccgactacga aagcacaag gtgtacgcct gcgaagtgac ccaccagggc    600
ctgtccagcc ccgtgaccaa gagcttcaac cggggcgagt gt                      642
```

```
<210> SEQ ID NO 291
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 291

Gly Phe Thr Phe Ser Asn Tyr Trp Ile Ser
1               5                   10

<210> SEQ ID NO 292
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 292

Arg Ile Lys Ser Lys Thr Tyr Gly Gly Thr Thr Asp Tyr Ala Glu Pro
1               5                   10                  15

Val Lys Gly

<210> SEQ ID NO 293
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 293

Glu Lys Tyr Ser Ile Arg Ala Arg Gly His Gly Asp Tyr Gly Phe Asp
1               5                   10                  15

Val

<210> SEQ ID NO 294
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 294

Asn Tyr Trp Ile Ser
1               5
```

```
<210> SEQ ID NO 295
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 295

Gly Phe Thr Phe Ser Asn Tyr
1               5

<210> SEQ ID NO 296
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 296

Lys Ser Lys Thr Tyr Gly Gly Thr
1               5

<210> SEQ ID NO 297
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 297

Gly Phe Thr Phe Ser Asn Tyr Trp
1               5

<210> SEQ ID NO 298
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 298

Ile Lys Ser Lys Thr Tyr Gly Gly Thr Thr
1               5                   10

<210> SEQ ID NO 299
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 299

Ala Arg Glu Lys Tyr Ser Ile Arg Ala Arg Gly His Gly Asp Tyr Gly
1               5                   10                  15

Phe Asp Val
```

-continued

<210> SEQ ID NO 300
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 300

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Trp Ile Ser Trp Val Arg Gln Ala Pro Gly Lys Gly Leu Glu Trp Val
        35                  40                  45

Gly Arg Ile Lys Ser Lys Thr Tyr Gly Gly Thr Thr Asp Tyr Ala Glu
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Glu Lys Tyr Ser Ile Arg Ala Arg Gly His Gly Asp
            100                 105                 110

Tyr Gly Phe Asp Val Trp Gly Gln Gly Thr Leu Val Thr Val Ser Ser
        115                 120                 125

<210> SEQ ID NO 301
<211> LENGTH: 384
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 301
gaagtgcagc tggtggaaag cggcggtggc ctggtgaaac caggcggtag cctgcgcctg      60
agctgcgccg ccagcggctt tacctttagc aactattgga ttagctgggt tcgccaggcc     120
ccaggcaaag cctggaatg ggttggccgc atcaaaagca aaacctatgg cggcaccacc      180
gattatgccg agccagtgaa aggccgcttt accattagcc gcgacgatag caaaaacacc     240
ctgtacctgc aaatgaacag cctgaaaacc gaagataccg ccgtgtatta ttgcgcgcgt     300
gagaaatatt ccatccgtgc acgtggtcac ggagactacg gatttgatgt gtggggccag     360
ggcaccctgg ttactgtctc gagc                                            384

<210> SEQ ID NO 302
<211> LENGTH: 458
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 302

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

```
Trp Ile Ser Trp Val Arg Gln Ala Pro Gly Lys Gly Leu Glu Trp Val
         35                  40                  45
Gly Arg Ile Lys Ser Lys Thr Tyr Gly Gly Thr Thr Asp Tyr Ala Glu
 50                  55                  60
Pro Val Lys Gly Arg Phe Thr Ile Ser Arg Asp Asp Ser Lys Asn Thr
 65                  70                  75                  80
Leu Tyr Leu Gln Met Asn Ser Leu Lys Thr Glu Asp Thr Ala Val Tyr
                     85                  90                  95
Tyr Cys Ala Arg Glu Lys Tyr Ser Ile Arg Ala Arg Gly His Gly Asp
                100                 105                 110
Tyr Gly Phe Asp Val Trp Gly Gln Gly Thr Leu Val Thr Val Ser Ser
            115                 120                 125
Ala Ser Thr Lys Gly Pro Ser Val Phe Pro Leu Ala Pro Ser Ser Lys
130                 135                 140
Ser Thr Ser Gly Gly Thr Ala Ala Leu Gly Cys Leu Val Lys Asp Tyr
145                 150                 155                 160
Phe Pro Glu Pro Val Thr Val Ser Trp Asn Ser Gly Ala Leu Thr Ser
                165                 170                 175
Gly Val His Thr Phe Pro Ala Val Leu Gln Ser Ser Gly Leu Tyr Ser
            180                 185                 190
Leu Ser Ser Val Val Thr Val Pro Ser Ser Ser Leu Gly Thr Gln Thr
        195                 200                 205
Tyr Ile Cys Asn Val Asn His Lys Pro Ser Asn Thr Lys Val Asp Lys
    210                 215                 220
Arg Val Glu Pro Lys Ser Cys Asp Lys Thr His Thr Cys Pro Pro Cys
225                 230                 235                 240
Pro Ala Pro Glu Ala Ala Gly Gly Pro Ser Val Phe Leu Phe Pro Pro
                245                 250                 255
Lys Pro Lys Asp Thr Leu Met Ile Ser Arg Thr Pro Glu Val Thr Cys
            260                 265                 270
Val Val Val Asp Val Ser His Glu Asp Pro Glu Val Lys Phe Asn Trp
        275                 280                 285
Tyr Val Asp Gly Val Glu Val His Asn Ala Lys Thr Lys Pro Arg Glu
    290                 295                 300
Glu Gln Tyr Asn Ser Thr Tyr Arg Val Val Ser Val Leu Thr Val Leu
305                 310                 315                 320
His Gln Asp Trp Leu Asn Gly Lys Glu Tyr Lys Cys Lys Val Ser Asn
                325                 330                 335
Lys Ala Leu Pro Ala Pro Ile Glu Lys Thr Ile Ser Lys Ala Lys Gly
            340                 345                 350
Gln Pro Arg Glu Pro Gln Val Tyr Thr Leu Pro Pro Ser Arg Glu Glu
        355                 360                 365
Met Thr Lys Asn Gln Val Ser Leu Thr Cys Leu Val Lys Gly Phe Tyr
    370                 375                 380
Pro Ser Asp Ile Ala Val Glu Trp Glu Ser Asn Gly Gln Pro Glu Asn
385                 390                 395                 400
Asn Tyr Lys Thr Thr Pro Pro Val Leu Asp Ser Asp Gly Ser Phe Phe
                405                 410                 415
Leu Tyr Ser Lys Leu Thr Val Asp Lys Ser Arg Trp Gln Gln Gly Asn
            420                 425                 430
Val Phe Ser Cys Ser Val Met His Glu Ala Leu His Asn His Tyr Thr
        435                 440                 445
Gln Lys Ser Leu Ser Leu Ser Pro Gly Lys
```

450                 455

<210> SEQ ID NO 303
<211> LENGTH: 1374
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 303

```
gaagtgcagc tggtggaaag cggcggtggc ctggtgaaac caggcggtag cctgcgcctg      60
agctgcgccg ccagcggctt tacctttagc aactattgga ttagctgggt tcgccaggcc     120
ccaggcaaag gcctggaatg ggttggccgc atcaaaagca aaacctatgg cggcaccacc     180
gattatgccg agccagtgaa aggccgcttt accattagcc gcgacgatag caaaaacacc     240
ctgtacctgc aaatgaacag cctgaaaacc gaagataccg ccgtgtatta ttgcgcgcgt     300
gagaaatatt ccatccgtgc acgtggtcac ggagactacg gatttgatgt gtggggccag     360
ggcaccctgg ttactgtctc gagcgcgtcg accaaaggcc cagcgtgttt ccctctggcc     420
cccagcagca gagcacctc tggcggaaca gccgccctgg gctgcctggt caaggactac     480
ttccccgagc ccgtgaccgt gtcctggaac tctggcgccc tgaccagcgg cgtgcacacc     540
tttccagccg tgctccagag cagcggcctg tacagcctga gcgcgtcgt gaccgtgccc     600 agcagcagcc tgggcaccca gacctacatc tgcaacgtga accacaagcc cagcaacaca     660
aaggtggaca gcgggtgga acccaagagc tgcgacaaga cccacacctg tcccccctgc     720
cctgcccctg aagcggcggg aggcccctcc gtgttcctgt tccccccaaa gcctaaggac     780
accctgatga tcagccggac ccccgaagtg acctgcgtgg tggtggacgt gtcccacgag     840
gaccctgaag tgaagtttaa ttggtacgtg gacggcgtgg aagtgcacaa cgccaagacc     900
aagcccagag aggaacagta caacagcacc taccgggtgg tgtccgtgct gaccgtgctg     960
caccaggact ggctgaacgg caaagagtac aagtgcaagg tgtccaacaa ggccctgcct    1020 gccccccatcg agaaaaccat cagcaaggcc aaaggccagc ccgcgagcc ccaggtgtac    1080 acactgcccc ctagccggga agagatgacc aagaaccagg tgtccctgac ctgcctcgtg    1140
aagggcttct accccagcga cattgccgtg gaatgggaga gcaacggcca gcccgagaac    1200
aactacaaga ccacccccc tgtgctggac agcgacggct cattcttcct gtacagcaag    1260
ctgaccgtgg acaagagccg gtggcagcag ggcaacgtgt tcagctgctc cgtgatgcac    1320
gaggccctgc acaaccacta cacccagaag tccctgagcc tgagccccgg caag          1374
```

<210> SEQ ID NO 304
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 304

Gln Gln Gly Tyr His Ala Pro Phe Thr
1               5

<210> SEQ ID NO 305
<211> LENGTH: 6
<212> TYPE: PRT

<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 305

Gly Tyr His Ala Pro Phe
1               5

<210> SEQ ID NO 306
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 306

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Gly Tyr His Ala Pro Phe
                85                  90                  95

Thr Phe Gly Gln Gly Thr Lys Val Glu Ile Lys
            100                 105

<210> SEQ ID NO 307
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 307
gatattcaga tgacccagag cccgagcagc ctgagcgcaa gcgtgggcga tcgcgtgacc      60
attacctgcc gcgccagcca gggcattagc aactatctgg cctggtatca gcagaaaccg     120
ggcaaagtgc cgaaactgct gatctatgcc gccagcaccc tgcaaagcgg cgtgccaagt     180
cgctttagcg gcagcggtag cggcaccgat ttcaccctga ccattagcag cctgcaaccg     240
gaagacgtgg cgacctatta ttgccagcag ggttaccatg ctccgttcac cttcggccag     300
ggtaccaaag tggaaatcaa g                                                321

<210> SEQ ID NO 308
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 308

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Gly Tyr His Ala Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 309
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 309
gatattcaga tgacccagag cccgagcagc ctgagcgcaa gcgtgggcga tcgcgtgacc      60
attacctgcc gcgccagcca gggcattagc aactatctgg cctggtatca gcagaaaccg     120
ggcaaagtgc cgaaactgct gatctatgcc gccagcaccc tgcaaagcgg cgtgccaagt     180
cgctttagcg gcagcggtag cggcaccgat ttcaccctga ccattagcag cctgcaaccg     240
gaagacgtgg cgacctatta ttgccagcag ggttaccatg ctccgttcac cttcggccag     300
ggtaccaaag tggaaatcaa gcggaccgtg gcggctccct ccgtgttcat cttcccaccc     360
agcgacgagc agctgaagtc cggcacagcc agcgtcgtgt gcctgctgaa caacttctac     420
ccccgcgagg ccaaagtgca gtggaaggtg gacaacgccc tccagagcgg caacagccag     480
gaaagcgtca ccgagcagga cagcaaggac tccacctaca gcctgagcag caccctgacc     540
ctgagcaagg ccgactacga gaagcacaag gtgtacgcct gcgaagtgac ccaccagggc     600
ctgtccagcc ccgtgaccaa gagcttcaac cggggcgagt gt                        642

<210> SEQ ID NO 310
```

```
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 310

Gly Tyr Ser Phe Thr Ser Tyr Trp Ile Ser
1               5                   10

<210> SEQ ID NO 311
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 311

Ile Ile Tyr Pro Gly Thr Ser Tyr Thr Arg Tyr Ser Pro Ser Phe Gln
1               5                   10                  15
Gly

<210> SEQ ID NO 312
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 312

Gly Ala Val Ala Gly Gln Leu Gly Phe Asp His
1               5                   10

<210> SEQ ID NO 313
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 313

Tyr Pro Gly Thr Ser Tyr
1               5

<210> SEQ ID NO 314
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 314

Ile Tyr Pro Gly Thr Ser Tyr Thr
1               5

<210> SEQ ID NO 315
<211> LENGTH: 13
<212> TYPE: PRT
```

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 315

Ala Arg Gly Ala Val Ala Gly Gln Leu Gly Phe Asp His
1               5                   10

<210> SEQ ID NO 316
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 316

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Ile Ile Tyr Pro Gly Thr Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Ala Val Ala Gly Gln Leu Gly Phe Asp His Trp Gly Gln
            100                 105                 110

Gly Thr Leu Val Thr Val Ser Ser
        115                 120

<210> SEQ ID NO 317
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 317
gaagtgcagc tggtgcagag cggtgccgaa gtgaaaaaac cgggcgaaag cctgaaaatc       60
agctgcaaag gcagcggcta tagctttacc agctattgga ttagctgggt cgccagatg      120 ccgggcaaag gcctggaatg gatgggcatt atctatccgg gcaccagcta tacccgctat      180
agcccgagct tcagggcca ggttacaatt agcgccgaca aaagcatcag caccgcctat       240
ctgcaatgga gcagcctgaa agccagcgat accgccatgt attattgcgc gcgtggtgca      300
gttgcaggac aactgggatt tgatcactgg ggccagggca ccctggttac tgtctcgagc      360

<210> SEQ ID NO 318
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 318

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Ile Ile Tyr Pro Gly Thr Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Ala Val Ala Gly Gln Leu Gly Phe Asp His Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 319
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 319
gaagtgcagc tggtgcagag cggtgccgaa gtgaaaaaac cgggcgaaag cctgaaaatc        60
agctgcaaag gcagcggcta tagctttacc agctattgga ttagctgggt cgccagatg       120 ccgggcaaag gcctggaatg gatgggcatt atctatccgg gcaccagcta tacccgctat      180
agcccgagct ttcagggcca ggttacaatt agcgccgaca aaagcatcag caccgcctat      240
ctgcaatgga gcagcctgaa agccagcgat accgccatgt attattgcgc gcgtggtgca      300
gttgcaggac aactgggatt tgatcactgg ggccagggca ccctggttac tgtctcgagc      360
gcgtcgacca aaggccccag cgtgttccct ctggccccca gcagcaagag cacctctggc      420
ggaacagccg ccctgggctg cctggtcaag gactacttcc ccgagcccgt gaccgtgtcc      480
tggaactctg gcgccctgac cagcggcgtg cacacctttc cagccgtgct ccagagcagc      540
ggcctgtaca gcctgagcag cgtcgtgacc gtgcccagca gcagcctggg cacccagacc      600
tacatctgca acgtgaacca caagcccagc aacacaaagg tggacaagcg ggtggaaccc      660
aagagctgcg acaagaccca cacctgtccc cctgccctg cccctgaagc ggcgggaggc       720
ccctccgtgt tcctgttccc cccaaagcct aaggacaccc tgatgatcag ccggaccccc      780
gaagtgacct gcgtggtggt ggacgtgtcc cacgaggacc ctgaagtgaa gtttaattgg      840
tacgtggacg gcgtggaagt gcacaacgcc aagaccaagc cagagagga cagtacaac       900 agcacctacc gggtggtgtc cgtgctgacc gtgctgcacc aggactggct gaacggcaaa      960
gagtacaagt gcaaggtgtc caacaaggcc ctgcctgccc catcgagaa aaccatcagc      1020 aaggccaaag gccagccccg cgagccccag gtgtacacac tgcccccta gccgggaagag     1080 atgaccaaga accaggtgtc cctgacctgc ctcgtgaagg gcttctaccc cagcgacatt     1140
gccgtggaat gggagagcaa cggccagccc gagaacaact acaagaccac ccccctgtg      1200 ctggacagcg acggctcatt cttcctgtac agcaagctga ccgtggacaa gagccggtgg     1260
cagcagggca cgtgttcag ctgctccgtg atgcacgagg ccctgcacaa ccactacacc      1320
cagaagtccc tgagcctgag ccccggcaag                                      1350

<210> SEQ ID NO 320
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 320

Thr Gly Ser Ser Ser Asn Ile Gly Ala Gly Tyr Asp Val His
1               5                   10

<210> SEQ ID NO 321
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 321

Gly Asn Ser Asn Arg Pro Ser
1               5

<210> SEQ ID NO 322
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 322

Gln Ser Tyr Tyr Thr Ser Ser His Gly Pro Val
1               5                   10

<210> SEQ ID NO 323
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 323

Ser Ser Ser Asn Ile Gly Ala Gly Tyr Asp
1               5                   10

<210> SEQ ID NO 324
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 324

Gly Asn Ser
1

<210> SEQ ID NO 325
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 325

Tyr Tyr Thr Ser Ser His Gly Pro
```

<210> SEQ ID NO 326
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 326

Ser Ser Asn Ile Gly Ala Gly Tyr Asp
1               5

<210> SEQ ID NO 327
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 327

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Tyr Thr Ser
                85                  90                  95

Ser His Gly Pro Val Phe Gly Gly Gly Thr Lys Leu Thr Val Leu
            100                 105                 110

<210> SEQ ID NO 328
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 328
cagagcgtgc tgacccagcc accaagcgtg agcggtgcac caggtcagcg cgtgaccatt      60
agctgcaccg gcagcagcag caacattggc gcaggctatg atgtgcattg gtatcagcag     120
ctgccaggca ccgcaccgaa actgctgatt tatggcaaca gcaatcgccc aagcggtgtg     180
ccggatcgct tagcggcag caaaagcggc accagcgcca gcctggcgat taccggtctg     240
caagccgaag acgaagccga ttattactgc cagtcttact acacttcttc tcatggtccg     300
gtgtttggcg gcggtaccaa gctgaccgtg ctg                                  333

<210> SEQ ID NO 329
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 329

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Tyr Thr Ser
                85                  90                  95

Ser His Gly Pro Val Phe Gly Gly Gly Thr Lys Leu Thr Val Leu Gly
                100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 330
<211> LENGTH: 651
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 330

| | | | | | |
|---|---|---|---|---|---|
| cagagcgtgc | tgacccagcc | accaagcgtg | agcggtgcac | caggtcagcg | cgtgaccatt | 60 |
| agctgcaccg | gcagcagcag | caacattggc | gcaggctatg | atgtgcattg | gtatcagcag | 120 |
| ctgccaggca | ccgcaccgaa | actgctgatt | tatggcaaca | gcaatcgccc | aagcggtgtg | 180 |
| ccggatcgct | ttagcggcag | caaaagcggc | accagcgcca | gcctggcgat | taccggtctg | 240 |
| caagccgaag | acgaagccga | ttattactgc | cagtcttact | acacttcttc | tcatggtccg | 300 |
| gtgtttggcg | gcggtaccaa | gctgaccgtg | ctgggccagc | ccaaagccgc | ccctagcgtg | 360 |
| accctgttcc | ccccaagcag | cgaggaactc | caggccaaca | aggccaccct | cgtgtgcctg | 420 |
| atcagcgact | tctaccctgg | cgccgtgacc | gtggcctgga | aggccgatag | cagccctgtg | 480 |
| aaggccggcg | tggaaaccac | cacccccagc | aagcagagca | caacaaata | cgccgccagc | 540 |

```
agctacctga gcctgacccc cgagcagtgg aagtcccaca gatcctacag ctgccaggtc    600
acacacgagg gcagcaccgt ggaaaagacc gtggccccca ccgagtgcag c             651
```

<210> SEQ ID NO 331
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 331

Pro Tyr Leu Gly Asp Arg Arg Ser Tyr Gly Phe Asp His
1               5                   10

<210> SEQ ID NO 332
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 332

Ala Arg Pro Tyr Leu Gly Asp Arg Arg Ser Tyr Gly Phe Asp His
1               5                   10                  15

<210> SEQ ID NO 333
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 333

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Ile Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Tyr Leu Gly Asp Arg Arg Ser Tyr Gly Phe Asp His Trp
            100                 105                 110

Gly Gln Gly Thr Leu Val Thr Val Ser Ser
        115                 120

<210> SEQ ID NO 334
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 334

```
gaagtgcagc tgctggaaag cggtggcggt ctggtgcagc caggtggtag cctgcgcctg    60
agctgtgccg caagcggctt tacctttagc agctatgcca ttagctgggt gcgccaagca   120
ccaggcaaag gcctggaatg ggtgagcgcc attagcggca gcggtggcag cacctattat   180
gccgagagcg tgaaaggtcg ctttaccatt agtcgcgata acagcaaaaa caccctgtat   240
ctgcaaatga acagcctgcg cgcagaagat accgcagttt attattgcgc gcgacctat    300
ctgggtgacc gtcgtagcta tggtttcgac cactggggcc agggcaccct ggttactgtc   360
tcgagc                                                              366
```

<210> SEQ ID NO 335
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 335

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Ile Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Tyr Leu Gly Asp Arg Arg Ser Tyr Gly Phe Asp His Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
             275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
435                 440                 445

Ser Pro Gly Lys
    450

<210> SEQ ID NO 336
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 336
gaagtgcagc tgctggaaag cggtggcggt ctggtgcagc caggtggtag cctgcgcctg     60
agctgtgccg caagcggctt tacctttagc agctatgcca ttagctgggt gcgccaagca    120
ccaggcaaag cctggaatg gtgagcgcc attagcggca gcggtggcag cacctattat    180
gccgagagcg tgaaaggtcg ctttaccatt agtcgcgata cagcaaaaa caccctgtat    240 ctgcaaatga acagcctgcg cgcagaagat accgcagttt attattgcgc gcgacccttat    300 ctgggtgacc gtcgtagcta tggtttcgac cactggggcc agggcaccct ggttactgtc    360
tcgagcgcgt cgaccaaagg ccccagcgtg ttccctctgg ccccagcag caagagcacc    420 tctggcggaa cagccgccct gggctgcctg gtcaaggact acttccccga gccgtgacc    480 gtgtcctgga actctggcgc cctgaccagc ggcgtgcaca cctttccagc cgtgctccag    540
agcagcggcc tgtacagcct gagcagcgtc gtgaccgtgc ccagcagcag cctgggcacc    600
cagacctaca tctgcaacgt gaaccacaag cccagcaaca caaaggtgga caagcgggtg    660
gaacccaaga gctgcgacaa gacccacacc tgtccccct gccctgcccc tgaagcggcg    720
ggaggcccct ccgtgttcct gttccccca aagcctaagg acaccctgat gatcagccgg    780
acccccgaag tgacctgcgt ggtggtggac gtgtcccacg aggaccctga agtgaagttt    840
aattggtacg tggacggcgt ggaagtgcac aacgccaaga ccaagcccag agaggaacag    900

```
tacaacagca cctaccgggt ggtgtccgtg ctgaccgtgc tgcaccagga ctggctgaac    960
ggcaaagagt acaagtgcaa ggtgtccaac aaggccctgc ctgccccat cgagaaaacc   1020 atcagcaagg ccaaaggcca gccccgcgag ccccaggtgt acacactgcc ccctagccgg   1080
gaagagatga ccaagaacca ggtgtccctg acctgcctcg tgaagggctt ctaccccagc   1140
gacattgccg tggaatggga gagcaacggc cagcccgaga caactacaa gaccacccccc  1200 cctgtgctgg acagcgacgg ctcattcttc ctgtacagca agctgaccgt ggacaagagc   1260
cggtggcagc agggcaacgt gttcagctgc tccgtgatgc acgaggccct gcacaaccac   1320
tacacccaga agtccctgag cctgagcccc ggcaag                             1356
```

<210> SEQ ID NO 337
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 337

Thr Gly Thr Ser Ser Asp Val Gly Ser Tyr Asn Leu Val Ser
1               5                   10

<210> SEQ ID NO 338
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 338

Glu Gly Ser Lys Arg Pro Ser
1               5

<210> SEQ ID NO 339
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 339

Ser Ser Tyr Gly Phe His Ile Val Val Val Val
1               5                   10

<210> SEQ ID NO 340
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 340

Thr Ser Ser Asp Val Gly Ser Tyr Asn Leu
1               5                   10

<210> SEQ ID NO 341
<211> LENGTH: 3

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 341

Glu Gly Ser
1

<210> SEQ ID NO 342
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 342

Tyr Gly Phe His Ile Val Val Val
1               5

<210> SEQ ID NO 343
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 343

Ser Ser Asp Val Gly Ser Tyr Asn Leu
1               5

<210> SEQ ID NO 344
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 344

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Gly Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Gly Phe His
                85                  90                  95

Ile Val Val Val Phe Gly Gly Gly Thr Lys Leu Thr Val Leu
                100                 105                 110

<210> SEQ ID NO 345
<211> LENGTH: 333
<212> TYPE: DNA
```

<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 345

```
cagagcgccc tgacccagcc agccagcgtt agcggtagcc caggccagag cattaccatt      60
agctgcaccg gcaccagcag cgacgtgggc agctataacc tggttagctg gtatcagcag     120
catccgggca aagccccgaa actgatgatc tatgaaggca gcaaacgccc gagcggcgtt     180
agcaaccgct ttagtggcag caaaagcggc aacaccgcca gcctgaccat tagcggcctg     240
caagccgaag acgaagccga ttattactgc tcctcttacg gtttccatat cgttgttgtt     300
gtgtttggcg gcggtaccaa gctgaccgtg ctg                                  333
```

<210> SEQ ID NO 346
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 346

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Gly Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Gly Phe His
                85                  90                  95

Ile Val Val Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 347
<211> LENGTH: 651
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic polynucleotide"

<400> SEQUENCE: 347
cagagcgccc tgacccagcc agccagcgtt agcggtagcc caggccagag cattaccatt    60
agctgcaccg gcaccagcag cgacgtgggc agctataacc tggttagctg gtatcagcag   120
catccgggca aagccccgaa actgatgatc tatgaaggca gcaaacgccc gagcggcgtt   180
agcaaccgct ttagtggcag caaaagcggc aacaccgcca gcctgaccat tagcggcctg   240
caagccgaag acgaagccga ttattactgc tcctcttacg gtttccatat cgttgttgtt   300
gtgtttggcg gcggtaccaa gctgaccgtg ctgggccagc ccaaagccgc ccctagcgtg   360
accctgttcc ccccaagcag cgaggaactc caggccaaca aggccaccct cgtgtgcctg   420
atcagcgact tctaccctgg cgccgtgacc gtggcctgga aggccgatag cagccctgtg   480
aaggccggcg tggaaaccac caccccccagc aagcagagca caacaaata cgccgccagc   540 agctacctga gcctgacccc cgagcagtgg aagtcccaca gatcctacag ctgccaggtc   600
acacacgagg cagcaccgt ggaaaagacc gtggccccca ccgagtgcag c            651

<210> SEQ ID NO 348
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 348

Gly Ser Leu Pro Gly Leu Leu Gly Phe Asp His
1               5                   10

<210> SEQ ID NO 349
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 349

Ala Arg Gly Ser Leu Pro Gly Leu Leu Gly Phe Asp His
1               5                   10

<210> SEQ ID NO 350
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 350

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45
```

Gly Ile Ile Tyr Pro Gly Thr Ser Tyr Thr Arg Tyr Ser Pro Ser Phe
        50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Ser Leu Pro Gly Leu Leu Gly Phe Asp His Trp Gly Gln
                100                 105                 110

Gly Thr Leu Val Thr Val Ser Ser
            115                 120

<210> SEQ ID NO 351
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 351
gaagtgcagc tggtgcagag cggtgccgaa gtgaaaaaac cgggcgaaag cctgaaaatc      60
agctgcaaag gcagcggcta tagctttacc agctattgga ttagctgggt tcgccagatg     120
ccgggcaaag gcctggaatg gatgggcatt atctatccgg gcaccagcta tacccgctat     180
agcccgagct ttcagggcca ggttacaatt agcgccgaca aaagcatcag caccgcctat     240
ctgcaatgga gcagcctgaa agccagcgat accgccatgt attattgcgc gcgtggaagc     300
ctgcctggtc tgctgggttt tgatcactgg ggccagggca ccctggttac tgtctcgagc     360

<210> SEQ ID NO 352
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 352

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
                 20                  25                  30

Trp Ile Ser Trp Val Arg Gln Met Pro Gly Lys Gly Leu Glu Trp Met
             35                  40                  45

Gly Ile Ile Tyr Pro Gly Thr Ser Tyr Thr Arg Tyr Ser Pro Ser Phe
        50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Ser Leu Pro Gly Leu Leu Gly Phe Asp His Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 353
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 353
gaagtgcagc tggtgcagag cggtgccgaa gtgaaaaaac cgggcgaaag cctgaaaatc    60
agctgcaaag cagcggcta tagctttacc agctattgga ttagctgggt tcgccagatg    120
ccgggcaaag gcctggaatg gatgggcatt atctatccgg gcaccagcta tacccgctat    180
agcccgagct ttcagggcca ggttacaatt agcgccgaca aaagcatcag caccgcctat    240

```
ctgcaatgga gcagcctgaa agccagcgat accgccatgt attattgcgc gcgtggaagc    300
ctgcctggtc tgctgggttt tgatcactgg ggccagggca ccctggttac tgtctcgagc    360
gcgtcgacca aaggcccag cgtgttccct ctggccccca gcagcaagag cacctctggc     420
ggaacagccg ccctgggctg cctggtcaag gactacttcc ccgagcccgt gaccgtgtcc    480
tggaactctg gcgccctgac cagcggcgtg cacacctttc cagccgtgct ccagagcagc    540
ggcctgtaca gcctgagcag cgtcgtgacc gtgcccagca gcagcctggg cacccagacc    600
tacatctgca acgtgaacca caagcccagc aacacaaagg tggacaagcg ggtggaaccc    660
aagagctgcg acaagaccca cacctgtccc cctgccctg cccctgaagc ggcgggaggc     720
ccctccgtgt tcctgttccc cccaaagcct aaggacaccc tgatgatcag ccggaccccc    780
gaagtgacct gcgtggtggt ggacgtgtcc cacgaggacc ctgaagtgaa gtttaattgg    840
tacgtggacg gcgtggaagt gcacaacgcc aagaccaagc ccagagagga acagtacaac    900
agcacctacc gggtggtgtc cgtgctgacc gtgctgcacc aggactggct gaacggcaaa    960
gagtacaagt gcaaggtgtc caacaaggcc ctgcctgccc ccatcgagaa aaccatcagc   1020
aaggccaaag gccagccccg cgagcccag gtgtacacac tgcccccag ccgggaagag     1080
atgaccaaga accaggtgtc cctgacctgc ctcgtgaagg gcttctaccc cagcgacatt   1140
gccgtggaat gggagagcaa cggccagccc gagaacaact acaagaccac ccccctgtg    1200
ctggacagcg acggctcatt cttcctgtac agcaagctga ccgtggacaa gagccggtgg   1260
cagcagggca acgtgttcag ctgctccgtg atgcacgagg ccctgcacaa ccactacacc   1320
cagaagtccc tgagcctgag ccccggcaag                                    1350
```

<210> SEQ ID NO 354
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 354

Gly Asn Ser Asn Arg Pro Asn
1               5

<210> SEQ ID NO 355
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 355

Gln Ser Tyr Asp Ser Pro Thr Ser Ser Ser Val
1               5                   10

<210> SEQ ID NO 356
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 356

Tyr Asp Ser Pro Thr Ser Ser Ser
1               5

<210> SEQ ID NO 357
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 357

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Asn Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Pro
                85                  90                  95

Thr Ser Ser Ser Val Phe Gly Gly Gly Thr Lys Leu Thr Val Leu
            100                 105                 110

<210> SEQ ID NO 358
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 358
cagagcgtgc tgacccagcc accaagcgtg agcggtgcac caggtcagcg cgtgaccatt      60
agctgcaccg gcagcagcag caacattggc gcaggctatg atgtgcattg gtatcagcag     120
ctgccaggca ccgcaccgaa actgctgatt tatggcaaca gcaatcgccc aaacggtgtg     180
ccggatcgct ttagcggcag caaaagcggc accagcgcca gcctggcgat taccggtctg     240
caagccgaag acgaagccga ttattactgc cagtcttacg actctccgac ttcttcttct     300
gtgtttggcg gcggtaccaa gctgaccgtg ctg                                  333

<210> SEQ ID NO 359
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 359

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Asn Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Pro
                 85                  90                  95

Thr Ser Ser Ser Val Phe Gly Gly Thr Lys Leu Thr Val Leu Gly
                100                 105                 110

Gln Pro Lys Ala Ala Pro Ser Val Thr Leu Phe Pro Pro Ser Ser Glu
                115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
                195                 200                 205

Lys Thr Val Ala Pro Thr Glu Cys Ser
210                 215

<210> SEQ ID NO 360
<211> LENGTH: 651
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 360
cagagcgtgc tgacccagcc accaagcgtg agcggtgcac caggtcagcg cgtgaccatt      60
agctgcaccg gcagcagcag caacattggc gcaggctatg atgtgcattg gtatcagcag     120
ctgccaggca ccgcaccgaa actgctgatt tatggcaaca gcaatcgccc aaacggtgtg     180
ccggatcgct ttagcggcag caaaagcggc accagcgcca gcctggcgat taccggtctg     240
caagccgaag acgaagccga ttattactgc cagtcttacg actctccgac ttcttcttct     300
gtgtttggcg gcggtaccaa gctgaccgtg ctgggccagc ccaaagccgc ccctagcgtg     360
accctgttcc ccccaagcag cgaggaactc caggccaaca aggccaccct cgtgtgcctg     420
atcagcgact tctaccctgg cgccgtgacc gtggcctgga aggccgatag cagccctgtg     480
aaggccggcg tggaaaccac cacccccagc aagcagagca caacaaaata cgccgccagc     540
agctacctga gcctgacccc cgagcagtgg aagtcccaca gatcctacag ctgccaggtc     600
acacacgagg gcagcaccgt ggaaaagacc gtggccccca ccgagtgcag c              651

<210> SEQ ID NO 361
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 361

Gln Ser Tyr Gly Ala Phe Pro Arg Phe Val Val
1               5                   10

<210> SEQ ID NO 362
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 362

Tyr Gly Ala Phe Pro Arg Phe Val
1               5

<210> SEQ ID NO 363
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 363

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Asn Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Gly Ala Phe
                85                  90                  95

Pro Arg Phe Val Val Phe Gly Gly Gly Thr Lys Leu Thr Val Leu
            100                 105                 110

<210> SEQ ID NO 364
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 364
cagagcgtgc tgacccagcc accaagcgtg agcggtgcac caggtcagcg cgtgaccatt      60
agctgcaccg gcagcagcag caacattggc gcaggctatg atgtgcattg gtatcagcag     120
ctgccaggca ccgcaccgaa actgctgatt tatggcaaca gcaatcgccc aaacggtgtg     180
ccggatcgct ttagcggcag caaaagcggc accagcgcca gcctggcgat taccggtctg     240
caagccgaag acgaagccga ttattactgc caatcctatg gtgccttccc tcgtttcgtt     300
gtttttggcg gcggtaccaa gctgaccgtg ctg                                  333

<210> SEQ ID NO 365
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 365

```
Gln Ser Val Leu Thr Gln Pro Pro Ser Val Ser Gly Ala Pro Gly Gln
1               5                   10                  15
Arg Val Thr Ile Ser Cys Thr Gly Ser Ser Ser Asn Ile Gly Ala Gly
            20                  25                  30
Tyr Asp Val His Trp Tyr Gln Gln Leu Pro Gly Thr Ala Pro Lys Leu
        35                  40                  45
Leu Ile Tyr Gly Asn Ser Asn Arg Pro Asn Gly Val Pro Asp Arg Phe
    50                  55                  60
Ser Gly Ser Lys Ser Gly Thr Ser Ala Ser Leu Ala Ile Thr Gly Leu
65                  70                  75                  80
Gln Ala Glu Asp Glu Ala Asp Tyr Tyr Cys Gln Ser Tyr Gly Ala Phe
                85                  90                  95
Pro Arg Phe Val Val Phe Gly Gly Gly Thr Lys Leu Thr Val Leu Gly
            100                 105                 110
Gln Pro Lys Ala Ala Pro Ser Val Thr Leu Phe Pro Pro Ser Ser Glu
        115                 120                 125
Glu Leu Gln Ala Asn Lys Ala Thr Leu Val Cys Leu Ile Ser Asp Phe
130                 135                 140
Tyr Pro Gly Ala Val Thr Val Ala Trp Lys Ala Asp Ser Ser Pro Val
145                 150                 155                 160
Lys Ala Gly Val Glu Thr Thr Thr Pro Ser Lys Gln Ser Asn Asn Lys
                165                 170                 175
Tyr Ala Ala Ser Ser Tyr Leu Ser Leu Thr Pro Glu Gln Trp Lys Ser
            180                 185                 190
His Arg Ser Tyr Ser Cys Gln Val Thr His Glu Gly Ser Thr Val Glu
        195                 200                 205
Lys Thr Val Ala Pro Thr Glu Cys Ser
    210                 215
```

<210> SEQ ID NO 366
<211> LENGTH: 651
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 366

```
cagagcgtgc tgacccagcc accaagcgtg agcggtgcac caggtcagcg cgtgaccatt     60
agctgcaccg gcagcagcag caacattggc gcaggctatg atgtgcattg gtatcagcag    120
ctgccaggca ccgcaccgaa actgctgatt tatggcaaca gcaatcgccc aaacggtgtg    180
ccggatcgct ttagcggcag caaaagcggc accagcgcca gcctggcgat taccggtctg    240
caagccgaag acgaagccga ttattactgc caatcctatg gtgccttccc tcgtttcgtt    300
gttttttggc gcggtaccaa gctgaccgtg ctgggccagc ccaaagccgc ccctagcgtg    360
accctgttcc ccccaagcag cgaggaactc caggccaaca aggccaccct cgtgtgcctg    420
```

```
atcagcgact tctaccctgg cgccgtgacc gtggcctgga aggccgatag cagccctgtg    480
aaggccggcg tggaaaccac cacccccagc aagcagagca caacaaata cgccgccagc    540 agctacctga gcctgacccc cgagcagtgg aagtcccaca gatcctacag ctgccaggtc    600
acacacgagg cagcaccgt ggaaaagacc gtggccccca ccgagtgcag c             651
```

```
<210> SEQ ID NO 367
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 367

Gly Phe Ser Phe Ser Lys Tyr Tyr Leu Asn
1               5                   10

<210> SEQ ID NO 368
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 368

Ser Ile His Gln Gln Ala His Glu Lys Lys Tyr Val Glu Ser Val Lys
1               5                   10                  15

Gly

<210> SEQ ID NO 369
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 369

Lys Tyr Tyr Leu Asn
1               5

<210> SEQ ID NO 370
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 370

Gly Phe Ser Phe Ser Lys Tyr
1               5

<210> SEQ ID NO 371
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
```

```
                          Synthetic peptide"

<400> SEQUENCE: 371

His Gln Gln Ala His Glu
1               5

<210> SEQ ID NO 372
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 372

Gly Phe Ser Phe Ser Lys Tyr Tyr
1               5

<210> SEQ ID NO 373
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 373

Ile His Gln Gln Ala His Glu Lys
1               5

<210> SEQ ID NO 374
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 374

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Lys Tyr
            20                  25                  30

Tyr Leu Asn Trp Val Arg Gln Ala Pro Gly Lys Gly Leu Glu Trp Val
        35                  40                  45

Ala Ser Ile His Gln Gln Ala His Glu Lys Lys Tyr Val Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Arg Arg Arg Ser Thr Glu His Ala Gly Phe Asp Val
            100                 105                 110

Trp Gly Gln Gly Thr Leu Val Thr Val Ser Ser
        115                 120

<210> SEQ ID NO 375
<211> LENGTH: 369
<212> TYPE: DNA
<213> ORGANISM: Artificial Sequence
<220> FEATURE:
```

<220> FEATURE:
<221> NAME/KEY: source
<223> OTHER INFORMATION: /note="Description of Artificial Sequence:
      Synthetic polynucleotide"

<400> SEQUENCE: 375

```
gaagtgcagc tggtggaaag cggcggtggc ctggtgcagc caggtggtag cctgcgcctg      60
agctgcgccg ccagcggctt tagcttcagc aaatattact tgaactgggt tcgccaggcc     120
ccaggcaaag gcctggaatg ggtggccagc attcaccagc aagcacacga gaaaaaatac     180
gtggagtccg tgaaaggccg ctttaccatt agccgcgata acgccaaaaa cagcctgtat     240
ctgcaaatga acagcctgcg ggccgaagat accgccgtgt attattgcgc gcgtagcctg     300
cgtcgtcgta gcactgagca cgcaggattc gacgtttggg gccagggcac cctggttact     360
gtctcgagc                                                             369
```

<210> SEQ ID NO 376
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 376

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Lys Tyr
            20                  25                  30

Tyr Leu Asn Trp Val Arg Gln Ala Pro Gly Lys Gly Leu Glu Trp Val
        35                  40                  45

Ala Ser Ile His Gln Gln Ala His Glu Lys Lys Tyr Val Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Arg Arg Arg Ser Thr Glu His Ala Gly Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255
```

Leu Met Ile Ser Arg Thr Pro Glu Val Thr Cys Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 377
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 377
gaagtgcagc tggtggaaag cggcggtggc ctggtgcagc caggtggtag cctgcgcctg      60
agctgcgccg ccagcggctt tagcttcagc aaatattact tgaactgggt tcgccaggcc     120
ccaggcaaag gcctggaatg ggtggccagc attcaccagc aagcacacga gaaaaaatac     180
gtggagtccg tgaaaggccg ctttaccatt agccgcgata cgccaaaaaa cagcctgtat     240
ctgcaaatga acagcctgcg ggccgaagat accgccgtgt attattgcgc gcgtagcctg     300
cgtcgtcgta gcactgagca cgcaggattc gacgtttggg gccagggcac cctggttact     360
gtctcgagcg cgtcgaccaa ggccccagc gtgttccctc tggccccag cagcaagagc     420 acctctggcg gaacagccgc cctgggctgc ctggtcaagg actacttccc cgagcccgtg     480
accgtgtcct ggaactctgg cgccctgacc agcggcgtgc acacctttcc agccgtgctc     540
cagagcagcg gcctgtacag cctgagcagc gtcgtgaccg tgcccagcag cagcctgggc     600
acccagacct acatctgcaa cgtgaaccac aagcccagca cacaaaaggt ggacaagcgg     660
gtggaaccca gagctgcga caagacccac acctgtcccc cctgccctgc cctgaagcg      720 gcgggaggcc cctccgtgtt cctgttcccc ccaaagccta aggacaccct gatgatcagc     780 cggaccccg aagtgacctg cgtggtggtg gacgtgtccc acgaggaccc tgaagtgaag     840

```
tttaattggt acgtggacgg cgtggaagtg cacaacgcca agaccaagcc cagagaggaa    900
cagtacaaca gcacctaccg ggtggtgtcc gtgctgaccg tgctgcacca ggactggctg    960
aacggcaaag agtacaagtg caaggtgtcc aacaaggccc tgcctgcccc catcgagaaa   1020
accatcagca aggccaaagg ccagccccgc gagccccagg tgtacacact gcccccctagc  1080 cgggaagaga tgaccaagaa ccaggtgtcc ctgacctgcc tcgtgaaggg cttctacccc   1140
agcgacattg ccgtggaatg ggagagcaac ggccagcccg agaacaacta caagaccacc   1200 cccctgtgc tggacagcga cggctcattc ttcctgtaca gcaagctgac cgtggacaag    1260
agccggtggc agcagggcaa cgtgttcagc tgctccgtga tgcacgaggc cctgcacaac   1320
cactacaccc agaagtccct gagcctgagc cccggcaag                          1359
```

<210> SEQ ID NO 378
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 378

Gly Phe Thr Phe Ser Arg Tyr Tyr Ile Asn
1               5                   10

<210> SEQ ID NO 379
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 379

Ser Ile His Gln His Gly Leu Glu Thr Arg Tyr Val Glu Ser Val Lys
1               5                   10                  15
Gly

<210> SEQ ID NO 380
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 380

Arg Tyr Tyr Ile Asn
1               5

<210> SEQ ID NO 381
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 381

Gly Phe Thr Phe Ser Arg Tyr

<210> SEQ ID NO 382
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 382

His Gln His Gly Leu Glu
1               5

<210> SEQ ID NO 383
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 383

Gly Phe Thr Phe Ser Arg Tyr Tyr
1               5

<210> SEQ ID NO 384
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 384

Ile His Gln His Gly Leu Glu Thr
1               5

<210> SEQ ID NO 385
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 385

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Tyr Ile Asn Trp Val Arg Gln Ala Pro Gly Lys Gly Leu Glu Trp Val
        35                  40                  45

Ala Ser Ile His Gln His Gly Leu Glu Thr Arg Tyr Val Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Arg Arg Arg Ser Thr Glu His Ala Gly Phe Asp Val
            100                 105                 110

Trp Gly Gln Gly Thr Leu Val Thr Val Ser Ser
        115                 120

<210> SEQ ID NO 386
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 386
gaagtgcagc tggtggaaag cggcggtggc ctggtgcagc caggtggtag cctgcgcctg      60
agctgcgccg ccagcgggtt tactttttcc agatattaca ttaattgggt tcgccaggcc     120
ccaggcaaag gcctggaatg ggtggcgagc atccaccagc acggcctgga gaccagatat     180
gtggaatctg tcaaagggcg ctttaccatt agccgcgata acgccaaaaa cagcctgtat     240
ctgcaaatga acagcctgcg ggccgaagat accgccgtgt attattgcgc gcgtagcctg     300
cgtcgtcgta gcactgagca cgcaggattc gacgtttggg gccagggcac cctggttact     360
gtctcgagc                                                             369

<210> SEQ ID NO 387
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 387

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Tyr Ile Asn Trp Val Arg Gln Ala Pro Gly Lys Gly Leu Glu Trp Val
        35                  40                  45

Ala Ser Ile His Gln His Gly Leu Glu Thr Arg Tyr Val Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Arg Arg Arg Ser Thr Glu His Ala Gly Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val

```
            195                 200                 205
Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 388
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 388
gaagtgcagc tggtggaaag cggcggtggc ctggtgcagc caggtggtag cctgcgcctg      60
agctgcgccg ccagcgggtt tacttttcc agatattaca ttaattgggt tcgccaggcc     120
ccaggcaaag gcctggaatg ggtggcgagc atccaccagc acggcctgga gaccagatat     180
gtggaatctg tcaaagggcg ctttaccatt agccgcgata cgccaaaaa cagcctgtat     240 ctgcaaatga acagcctgcg ggccgaagat accgccgtgt attattgcgc gcgtagcctg     300
cgtcgtcgta gcactgagca cgcaggattc gacgtttggg gccagggcac cctggttact     360
gtctcgagcg cgtcgaccaa aggcccagc gtgttccctc tggccccag cagcaagagc     420 acctctggcg gaacagccgc cctgggctgc ctggtcaagg actacttccc cgagcccgtg     480
accgtgtcct ggaactctgg cgccctgacc agcggcgtgc acacctttcc agccgtgctc     540
```

```
cagagcagcg gcctgtacag cctgagcagc gtcgtgaccg tgcccagcag cagcctgggc      600
acccagacct acatctgcaa cgtgaaccac aagcccagca acacaaaggt ggacaagcgg      660
gtggaaccca agagctgcga caagacccac acctgtcccc cctgccctgc ccctgaagcg      720 gcggaggc cctccgtgtt cctgttcccc ccaaagccta aggacaccct gatgatcagc        780 cggaccccg aagtgacctg cgtggtggtg gacgtgtccc acgaggaccc tgaagtgaag       840
tttaattggt acgtggacgg cgtggaagtg cacaacgcca agaccaagcc cagagaggaa      900
cagtacaaca gcacctaccg ggtggtgtcc gtgctgaccg tgctgcacca ggactggctg      960
aacggcaaag agtacaagtg caaggtgtcc aacaaggcca tgcctgcccc catcgagaaa     1020
accatcagca aggccaaagg ccagccccgc gagcccagg tgtacacact gcccctagc      1080 cgggaagaga tgaccaagaa ccaggtgtcc ctgacctgcc tcgtgaaggg cttctacccc     1140
agcgacattg ccgtggaatg ggagagcaac ggccagcccg agaacaacta caagaccacc     1200
ccccctgtgc tggacagcga cggctcattc ttcctgtaca gcaagctgac cgtggacaag     1260
agccggtggc agcagggcaa cgtgttcagc tgctccgtga tgcacgaggc cctgcacaac     1320
cactacaccc agaagtccct gagcctgagc cccggcaag                           1359
```

<210> SEQ ID NO 389
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 389

Ser Ile Ser Ser His Gly Tyr Tyr Thr Arg Tyr Ala Glu Ser Val Lys
1               5                   10                  15

Gly

<210> SEQ ID NO 390
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 390

Ser Ser His Gly Tyr Tyr
1               5

<210> SEQ ID NO 391
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 391

Ile Ser Ser His Gly Tyr Tyr Thr
1               5

<210> SEQ ID NO 392
<211> LENGTH: 122

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 392
```

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Ala | Ile | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | | 35 | | | | | 40 | | | | | 45 | | |

| Ser | Ser | Ile | Ser | Ser | His | Gly | Tyr | Tyr | Thr | Arg | Tyr | Ala | Glu | Ser | Val |
|---|---|---|---|---|---|---|---|---|---|---|---|---|---|---|---|
| 50 | | | | | 55 | | | | | 60 | | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Pro | Tyr | Leu | Gly | Asp | Arg | Arg | Ser | Tyr | Gly | Phe | Asp | His | Trp |
|---|---|---|---|---|---|---|---|---|---|---|---|---|---|---|---|
| | | 100 | | | | | 105 | | | | | 110 | | | |

| Gly | Gln | Gly | Thr | Leu | Val | Thr | Val | Ser | Ser |
|---|---|---|---|---|---|---|---|---|---|
| | | 115 | | | | | 120 | | |

```
<210> SEQ ID NO 393
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 393
gaagtgcagc tgctggaaag cggtggcggt ctggtgcagc caggtggtag cctgcgcctg      60
agctgtgccg caagcgggtt tacatttccc agctatgcta tcagctgggt cgcccaagca     120
ccaggcaaag gcctggaatg ggtgagcagc attagctcac atggatatta cacccggtat     180
gccgagtccg tgaaaggtcg ctttaccatt agtcgcgata acagcaaaaa caccctgtat     240
ctgcaaatga acagcctgcg ggcagaagat accgcagttt attattgcgc gcgacccttat    300
ctgggtgacc gtcgtagcta tggtttcgac cactggggcc agggcaccct ggttactgtc     360
tcgagc                                                                366

<210> SEQ ID NO 394
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 394
```

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Ala | Ile | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | | 35 | | | | | 40 | | | | | 45 | | |

```
Ser Ser Ile Ser Ser His Gly Tyr Tyr Thr Arg Tyr Ala Glu Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Pro Tyr Leu Gly Asp Arg Arg Ser Tyr Gly Phe Asp His Trp
            100                 105                 110
Gly Gln Gly Thr Leu Val Thr Val Ser Ser Ala Ser Thr Lys Gly Pro
        115                 120                 125
Ser Val Phe Pro Leu Ala Pro Ser Ser Lys Ser Thr Ser Gly Gly Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Arg Val Glu Pro Lys Ser
    210                 215                 220
Cys Asp Lys Thr His Thr Cys Pro Pro Cys Pro Ala Pro Glu Ala Ala
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Glu Glu Met Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly Lys
    450
```

<210> SEQ ID NO 395
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 395

```
gaagtgcagc tgctggaaag cggtggcggt ctggtgcagc aggtggtag cctgcgcctg       60
agctgtgccg caagcgggtt tacatttttcc agctatgcta tcagctgggt gcgccaagca      120
ccaggcaaag gcctggaatg ggtgagcagc attagctcac atggatatta caccceggtat      180
gccgagtccg tgaaaggtcg ctttaccatt agtcgcgata cagcaaaaa caccetgtat       240
ctgcaaatga acagcctgcg ggcagaagat accgcagttt attattgcgc gcgacctttat      300
ctgggtgacc gtcgtagcta tggtttcgac cactgggggcc agggcaccct ggttactgtc      360
tcgagcgcgt cgaccaaagg ccccagcgtg ttccctctgg ccccagcag caagagcacc      420
tctggcggaa cagccgccct gggctgcctg gtcaaggact acttccccga gccgtgacc      480
gtgtcctgga actctggcgc cctgaccagc ggcgtgcaca ccttttccagc cgtgctccag      540
agcagcggcc tgtacagcct gagcagcgtc gtgaccgtgc ccagcagcag cctgggcacc      600
cagacctaca tctgcaacgt gaaccacaag cccagcaaca caaaggtgga caagcgggtg      660
gaacccaaga gctgcgacaa gacccacacc tgtccccct gcctgcccc tgaagcggcg       720
ggaggccct ccgtgttcct gttccccca aagcctaagg acaccctgat gatcagccgg       780
accccgaag tgacctgcgt ggtggtggac gtgtccacg aggaccctga agtgaagttt       840
aattggtacg tggacggcgt ggaagtgcac aacgccaaga ccaagcccag agaggaacag       900
tacaacagca cctaccgggt ggtgtccgtg ctgaccgtgc tgcaccagga ctggctgaac       960
ggcaaagagt acaagtgcaa ggtgtccaac aaggccctgc ctgcccccat cgagaaaacc      1020
atcagcaagg ccaaaggcca gccccgcgag ccccaggtgt acacactgcc ccctagccgg      1080
gaagagatga ccaagaacca ggtgtccctg acctgcctcg tgaagggctt ctaccccagc      1140
gacattgccg tggaatggga gagcaacggc cagcccgaga caactacaa gaccacccc       1200
cctgtgctgg acagcgacgg ctcattcttc ctgtacagca agctgaccgt ggacaagagc      1260
cggtggcagc agggcaacgt gttcagctgc tccgtgatgc acgaggccct gcacaaccac      1320
tacacccaga gtccctgag cctgagcccc ggcaag                                  1356
```

<210> SEQ ID NO 396
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 396

Gly Phe Thr Phe Ala Ser Tyr Ala Ile Thr
1               5                   10

<210> SEQ ID NO 397
<211> LENGTH: 17
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 397

Thr Ile Ser Gly Ser Gly Val Tyr Thr Tyr Tyr Ala Glu Ser Val Lys
1               5                   10                  15
Gly

<210> SEQ ID NO 398
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 398

Ser Tyr Ala Ile Thr
1               5

<210> SEQ ID NO 399
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 399

Gly Phe Thr Phe Ala Ser Tyr
1               5

<210> SEQ ID NO 400
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 400

Ser Gly Ser Gly Val Tyr
1               5

<210> SEQ ID NO 401
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 401

Gly Phe Thr Phe Ala Ser Tyr Ala
1               5

<210> SEQ ID NO 402
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 402

Ile Ser Gly Ser Gly Val Tyr Thr
1               5

<210> SEQ ID NO 403
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 403

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Ser Tyr
            20                  25                  30

Ala Ile Thr Trp Val Arg Gln Ala Pro Gly Lys Gly Leu Glu Trp Val
        35                  40                  45

Ser Thr Ile Ser Gly Ser Gly Val Tyr Thr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Tyr Leu Gly Asp Arg Arg Ser Tyr Gly Phe Asp His Trp
            100                 105                 110

Gly Gln Gly Thr Leu Val Thr Val Ser Ser
        115                 120

<210> SEQ ID NO 404
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 404
gaagtgcagc tgctggaaag cggtggcggt ctggtgcagc caggtggtag cctgcgcctg      60
agctgtgccg caagcgggtt cacattcgca tcctatgcaa ttacttgggt gcgccaagca     120
ccaggcaaag gcctggaatg ggtgagcacc atttccgggt ccggtgtgta cacctattac     180
gccgagtccg tcaaaggccg ctttaccatt agtcgcgata acagcaaaaa caccctgtat     240
ctgcaaatga acagcctgcg ggcagaagat accgcagttt attattgcgc gcgaccttat     300
ctgggtgacc gtcgtagcta tggtttcgac cactggggcc aggcaccct ggttactgtc     360 tcgagc                                                                366

<210> SEQ ID NO 405
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

```
<400> SEQUENCE: 405

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Ser Tyr
            20                  25                  30

Ala Ile Thr Trp Val Arg Gln Ala Pro Gly Lys Gly Leu Glu Trp Val
        35                  40                  45

Ser Thr Ile Ser Gly Ser Gly Val Tyr Thr Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Tyr Leu Gly Asp Arg Arg Ser Tyr Gly Phe Asp His Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415
```

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 406
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 406

```
gaagtgcagc tgctggaaag cggtggcggt ctggtgcagc caggtggtag cctgcgcctg    60
agctgtgccg caagcgggtt cacattcgca tcctatgcaa ttacttgggt gcgccaagca   120
ccaggcaaag gcctggaatg ggtgagcacc atttccgggt ccggtgtgta cacctattac   180
gccgagtccg tcaaaggccg ctttaccatt agtcgcgata cagcaaaaa caccctgtat   240 ctgcaaatga acagcctgcg ggcagaagat accgcagttt attattgcgc gcgaccttat   300
ctgggtgacc gtcgtagcta tggtttcgac cactggggcc agggcaccct ggttactgtc   360
tcgagcgcgt cgaccaaagg ccccagcgtg ttccctctgg cccccagcag caagagcacc   420 tctgcggaa cagccgccct gggctgcctg gtcaaggact cttcccga gcccgtgacc    480 gtgtcctgga actctggcgc cctgaccagc ggcgtgcaca cctttccagc cgtgctccag   540
agcagcggcc tgtacagcct gagcagcgtc gtgaccgtgc ccagcagcag cctgggcacc   600
cagacctaca tctgcaacgt gaaccacaag cccagcaaca caaaggtgga caagcgggtg   660
gaacccaaga gctgcgacaa gacccacacc tgtccccct gccctgcccc tgaagcggcg   720
ggaggcccct ccgtgttcct gttcccccca aagcctaagg acaccctgat gatcagccgg   780 accccgaag tgacctgcgt ggtggtggac gtgtcccacg aggaccctga agtgaagttt   840
aattggtacg tggacggcgt ggaagtgcac aacgccaaga ccaagcccag agaggaacag   900
tacaacagca cctaccgggt ggtgtccgtg ctgaccgtgc tgcaccagga ctggctgaac   960
ggcaaagagt acaagtgcaa ggtgtccaac aaggccctgc ctgcccccat cgagaaaacc  1020
atcagcaagg ccaaaggcca gccccgcgag ccccaggtgt acacactgcc cctagccgg  1080 gaagagatga ccaagaacca ggtgtccctg acctgcctcg tgaagggctt ctaccccagc  1140
gacattgccg tggaatggga gagcaacggc cagcccgaga caactacaa gaccacccc  1200 cctgtgctgg acagcgacgg ctcattcttc ctgtacagca gctgaccgt ggacaagagc  1260 cggtggcagc agggcaacgt gttcagctgc tccgtgatgc acgaggccct gcacaaccac  1320
tacacccaga gtccctgag cctgagcccc ggcaag                             1356
```

<210> SEQ ID NO 407
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 407

```
Gly Phe Thr Phe Gly Thr Tyr Ala Met Thr
1               5                   10

<210> SEQ ID NO 408
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 408

Ser Ile Ser Ala Ser Gly Tyr Tyr Ala Asn Tyr Ala Gly Ser Val Lys
1               5                   10                  15
Gly

<210> SEQ ID NO 409
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 409

Thr Tyr Ala Met Thr
1               5

<210> SEQ ID NO 410
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 410

Gly Phe Thr Phe Gly Thr Tyr
1               5

<210> SEQ ID NO 411
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 411

Ser Ala Ser Gly Tyr Tyr
1               5

<210> SEQ ID NO 412
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 412

Gly Phe Thr Phe Gly Thr Tyr Ala
```

<210> SEQ ID NO 413
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 413

Ile Ser Ala Ser Gly
1               5

<210> SEQ ID NO 414
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 414

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Gly Thr Tyr
            20                  25                  30
Ala Met Thr Trp Val Arg Gln Ala Pro Gly Lys Gly Leu Glu Trp Val
        35                  40                  45
Ser Ser Ile Ser Ala Ser Gly Tyr Tyr Ala Asn Tyr Ala Gly Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Pro Tyr Leu Gly Asp Arg Arg Ser Tyr Gly Phe Asp His Trp
            100                 105                 110
Gly Gln Gly Thr Leu Val Thr Val Ser Ser
        115                 120

<210> SEQ ID NO 415
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 415
gaagtgcagc tgctggaaag cggtggcggt ctggtgcagc caggtggtag cctgcgcctg      60
agctgtgccg caagcgggtt tacattcggc acctatgcaa tgacttgggt gcgccaagca     120
ccaggcaaag gcctggaatg ggtgagtagc attagcgcat ccggatatta cgctaactac     180
gcaggcagcg tcaaaggccg ctttaccatt agtcgcgata cagcaaaaa cacccctgtat     240 ctgcaaatga acagcctgcg ggcagaagat accgcagttt attattgcgc gcgaccttat     300
ctgggtgacc gtcgtagcta tggtttcgac cactggggcc agggcaccct ggttactgtc     360
tcgagc                                                                366

<210> SEQ ID NO 416
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 416

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Thr Tyr
            20                  25                  30

Ala Met Thr Trp Val Arg Gln Ala Pro Gly Lys Gly Leu Glu Trp Val
        35                  40                  45

Ser Ser Ile Ser Ala Ser Gly Tyr Tyr Ala Asn Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Tyr Leu Gly Asp Arg Arg Ser Tyr Gly Phe Asp His Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
```

```
                355                 360                 365
Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
                435                 440                 445

Ser Pro Gly Lys
    450

<210> SEQ ID NO 417
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 417
gaagtgcagc tgctggaaag cggtggcggt ctggtgcagc caggtggtag cctgcgcctg      60
agctgtgccg caagcgggtt tacattcggc acctatgcaa tgacttgggt gcgccaagca     120
ccaggcaaag gcctggaatg ggtgagtagc attagcgcat ccggatatta cgctaactac     180
gcaggcagcg tcaaaggccg ctttaccatt agtcgcgata cagcaaaaa caccctgtat     240 ctgcaaatga acagcctgcg ggcagaagat accgcagttt attattgcgc gcgaccttat     300
ctgggtgacc gtcgtagcta tggtttcgac cactggggcc agggcaccct ggttactgtc     360
tcgagcgcgt cgaccaaagg ccccagcgtg ttccctctgg cccccagcag caagagcacc     420 tctgcggaa cagccgccct gggctgcctg gtcaaggact acttcccga gcccgtgacc     480 gtgtcctgga actctggcgc cctgaccagc ggcgtgcaca ccttccagc cgtgctccag     540 agcagcggcc tgtacagcct gagcagcgtc gtgaccgtgc ccagcagcag cctgggcacc     600
cagacctaca tctgcaacgt gaaccacaag cccagcaaca caaaggtgga caagcgggtg     660
gaacccaaga gctgcgacaa gacccacacc tgtccccct gccctgcccc tgaagcggcg     720
ggaggcccct ccgtgttcct gttccccca aagcctaagg acaccctgat gatcagccgg     780
acccccgaag tgacctgcgt ggtggtggac gtgtcccacg aggaccctga agtgaagttt     840
aattggtacg tggacggcgt ggaagtgcac aacgccaaga ccaagccag agaggaacag     900 tacaacagca cctaccgggt ggtgtccgtg ctgaccgtgc tgcaccagga ctggctgaac     960
ggcaaagagt acaagtgcaa ggtgtccaac aaggccctgc ctgccccat cgagaaaacc    1020 atcagcaagg ccaaaggcca gccccgcgag ccccaggtgt acacactgcc cctagccgg    1080 gaagagatga ccaagaacca ggtgtccctg acctgcctcg tgaagggctt ctaccccagc    1140
gacattgccg tggaatggga gagcaacggc cagcccgaga caactacaa gaccaccccc    1200 cctgtgctgg acagcgacgg ctcattcttc ctgtacagca agctgaccgt ggacaagagc    1260
cggtggcagc agggcaacgt gttcagctgc tccgtgatgc acgaggccct gcacaaccac    1320
tacacccaga gtccctgag cctgagcccc ggcaag                                1356
```

-continued

```
<210> SEQ ID NO 418
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 418

Gly Phe Thr Phe Ser Asp Tyr Ala Ile Ser
1               5                   10

<210> SEQ ID NO 419
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 419

Ser Ile Ser Gly Gly Gly Tyr His Thr Gln Tyr Ala Gly Ser Val Lys
1               5                   10                  15

Gly

<210> SEQ ID NO 420
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 420

Asp Tyr Ala Ile Ser
1               5

<210> SEQ ID NO 421
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 421

Gly Phe Thr Phe Ser Asp Tyr
1               5

<210> SEQ ID NO 422
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 422

Ser Gly Gly Gly Tyr His
1               5

<210> SEQ ID NO 423
<211> LENGTH: 8
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 423

Gly Phe Thr Phe Ser Asp Tyr Ala
1               5

<210> SEQ ID NO 424
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 424

Ile Ser Gly Gly Gly Tyr His Thr
1               5

<210> SEQ ID NO 425
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 425

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Ile Ser Trp Val Arg Gln Ala Pro Gly Lys Gly Leu Glu Trp Val
        35                  40                  45

Ser Ser Ile Ser Gly Gly Gly Tyr His Thr Gln Tyr Ala Gly Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Tyr Leu Gly Asp Arg Arg Ser Tyr Gly Phe Asp His Trp
            100                 105                 110

Gly Gln Gly Thr Leu Val Thr Val Ser Ser
        115                 120

<210> SEQ ID NO 426
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 426
gaagtgcagc tgctggaaag cggtggcggt ctggtgcagc caggtggtag cctgcgcctg     60
agctgtgccg caagcggctt taccttttcc gactatgcaa tcagctgggt gcgccaagca    120
```

-continued

```
ccaggcaaag gcctggaatg ggtgagcagc atttccgggg gggggtatca tacacaatat    180
gcaggatccg tgaaaggccg ctttaccatt agtcgcgata acagcaaaaa caccctgtat    240
ctgcaaatga acagcctgcg ggcagaagat accgcagttt attattgcgc gcgacccttat  300 ctgggtgacc gtcgtagcta tggtttcgac cactggggcc agggcaccct ggttactgtc    360
tcgagc                                                              366
```

<210> SEQ ID NO 427
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 427

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Ile Ser Trp Val Arg Gln Ala Pro Gly Lys Gly Leu Glu Trp Val
        35                  40                  45

Ser Ser Ile Ser Gly Gly Gly Tyr His Thr Gln Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Tyr Leu Gly Asp Arg Arg Ser Tyr Gly Phe Asp His Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 428
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 428
gaagtgcagc tgctggaaag cggtggcggt ctggtgcagc aggtggtag cctgcgcctg      60 agctgtgccg caagcggctt tacctttttcc gactatgcaa tcagctgggt gcgccaagca    120
ccaggcaaag gcctggaatg ggtgagcagc atttccgggg ggggtatca tacacaatat     180 gcaggatccg tgaaaggccg ctttaccatt agtcgcgata cagcaaaaa caccctgtat    240 ctgcaaatga acagcctgcg ggcagaagat accgcagttt attattgcgc gcgaccttat    300
ctgggtgacc gtcgtagcta tggtttcgac cactgggggcc agggcaccct ggttactgtc   360
tcgagcgcgt cgaccaaagg ccccagcgtg ttccctctgg cccccagcag caagagcacc    420
tctgccggaa cagccgccct gggctgcctg gtcaaggact acttcccga gcccgtgacc    480 gtgtcctgga actctggcgc cctgaccagc ggcgtgcaca ccttttccagc cgtgctccag   540 agcagcggcc tgtacagcct gagcagcgtc gtgaccgtgc cagcagcag cctgggcacc    600 cagacctaca tctgcaacgt gaaccacaag cccagcaaca caaaggtgga caagcgggtg    660
gaacccaaga gctgcgacaa gacccacacc tgtcccccct gccctgcccc tgaagcggcg    720 ggaggccct ccgtgttcct gttcccccca aagcctaagg acaccctgat gatcagccgg    780 accccccgaag tgacctgcgt ggtggtggac gtgtcccacg aggaccctga agtgaagttt    840
aattggtacg tggacggcgt ggaagtgcac aacgccaaga ccaagcccag agaggaacag   900
tacaacagca cctaccgggt ggtgtccgtg ctgaccgtgc tgcaccagga ctggctgaac    960
ggcaaagagt acaagtgcaa ggtctccaac aaggccctgc ctgccccat cgagaaaacc    1020 atcagcaagg ccaaaggcca gccccgcgag ccccaggtgt acacactgcc cctagccgg    1080 gaagagatga ccaagaacca ggtgtccctg acctgcctcg tgaagggctt ctaccccagc    1140

```
gacattgccg tggaatggga gagcaacggc cagcccgaga acaactacaa gaccacccc    1200 cctgtgctgg acagcgacgg ctcattcttc ctgtacagca agctgaccgt ggacaagagc   1260
cggtggcagc agggcaacgt gttcagctgc tccgtgatgc acgaggccct gcacaaccac   1320
tacacccaga agtccctgag cctgagcccc ggcaag                             1356
```

```
<210> SEQ ID NO 429
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="V"
<220> FEATURE:
<221> NAME/KEY: VARIANT
<222> LOCATION: (3)..(3)
<223> OTHER INFORMATION: /replace="E"
<220> FEATURE:
<221> NAME/KEY: VARIANT
<222> LOCATION: (5)..(5)
<223> OTHER INFORMATION: /replace="K"
<220> FEATURE:
<221> NAME/KEY: VARIANT
<222> LOCATION: (7)..(7)
<223> OTHER INFORMATION: /replace="N"
<220> FEATURE:
<221> NAME/KEY: VARIANT
<222> LOCATION: (9)..(9)
<223> OTHER INFORMATION: /replace="T"
<220> FEATURE:
<221> NAME/KEY: VARIANT
<222> LOCATION: (10)..(10)
<223> OTHER INFORMATION: /replace="F"
<220> FEATURE:
<221> NAME/KEY: SITE
<222> LOCATION: (1)..(17)
<223> OTHER INFORMATION: /note="Variant residues given in the sequence
      have no preference with respect to those in the annotations for
      variant positions"

<400> SEQUENCE: 429

Ala Ile Ser Ser Asp Gly Ser Tyr Ile Tyr Tyr Ala Asp Ser Val Lys
1               5                   10                  15

Gly

<210> SEQ ID NO 430
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Q"
<220> FEATURE:
<221> NAME/KEY: VARIANT
<222> LOCATION: (3)..(3)
<223> OTHER INFORMATION: /replace="E" or "T" or "I"
<220> FEATURE:
<221> NAME/KEY: VARIANT
<222> LOCATION: (4)..(4)
<223> OTHER INFORMATION: /replace="W"
<220> FEATURE:
<221> NAME/KEY: VARIANT
```

```
<222> LOCATION: (5)..(5)
<223> OTHER INFORMATION: /replace="V" or "R" or "A" or "T" or "M"
<220> FEATURE:
<221> NAME/KEY: VARIANT
<222> LOCATION: (6)..(6)
<223> OTHER INFORMATION: /replace="V" or "R" or "A"
<220> FEATURE:
<221> NAME/KEY: SITE
<222> LOCATION: (1)..(9)
<223> OTHER INFORMATION: /note="Variant residues given in the sequence
      have no preference with respect to those in the annotations for
      variant positions"

<400> SEQUENCE: 430

Met Gln Ser Tyr Glu Lys Pro Arg Thr
1               5

<210> SEQ ID NO 431
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="E"
<220> FEATURE:
<221> NAME/KEY: VARIANT
<222> LOCATION: (3)..(3)
<223> OTHER INFORMATION: /replace="K"
<220> FEATURE:
<221> NAME/KEY: VARIANT
<222> LOCATION: (5)..(5)
<223> OTHER INFORMATION: /replace="N"
<220> FEATURE:
<221> NAME/KEY: SITE
<222> LOCATION: (1)..(6)
<223> OTHER INFORMATION: /note="Variant residues given in the sequence
      have no preference with respect to those in the annotations for
      variant positions"

<400> SEQUENCE: 431

Ser Ser Asp Gly Ser Tyr
1               5

<210> SEQ ID NO 432
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="E" or "T" or "I"
<220> FEATURE:
<221> NAME/KEY: VARIANT
<222> LOCATION: (2)..(2)
<223> OTHER INFORMATION: /replace="W"
<220> FEATURE:
<221> NAME/KEY: VARIANT
<222> LOCATION: (3)..(3)
<223> OTHER INFORMATION: /replace="V" or "R" or "A" or "T" or "M"
<220> FEATURE:
<221> NAME/KEY: VARIANT
<222> LOCATION: (4)..(4)
<223> OTHER INFORMATION: /replace="V" or "R" or "A"
<220> FEATURE:
<221> NAME/KEY: SITE
<222> LOCATION: (1)..(6)
```

```
<223> OTHER INFORMATION: /note="Variant residues given in the sequence
      have no preference with respect to those in the annotations for
      variant positions"

<400> SEQUENCE: 432

Ser Tyr Glu Lys Pro Arg
1               5

<210> SEQ ID NO 433
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="E"
<220> FEATURE:
<221> NAME/KEY: VARIANT
<222> LOCATION: (4)..(4)
<223> OTHER INFORMATION: /replace="K"
<220> FEATURE:
<221> NAME/KEY: VARIANT
<222> LOCATION: (6)..(6)
<223> OTHER INFORMATION: /replace="N"
<220> FEATURE:
<221> NAME/KEY: VARIANT
<222> LOCATION: (8)..(8)
<223> OTHER INFORMATION: /replace="T"
<220> FEATURE:
<221> NAME/KEY: SITE
<222> LOCATION: (1)..(8)
<223> OTHER INFORMATION: /note="Variant residues given in the sequence
      have no preference with respect to those in the annotations
      for variant positions"

<400> SEQUENCE: 433

Ile Ser Ser Asp Gly Ser Tyr Ile
1               5

<210> SEQ ID NO 434
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="E" or "T" or "I"
<220> FEATURE:
<221> NAME/KEY: VARIANT
<222> LOCATION: (5)..(5)
<223> OTHER INFORMATION: /replace="R" or "A" or "T" or "M"
<220> FEATURE:
<221> NAME/KEY: VARIANT
<222> LOCATION: (6)..(6)
<223> OTHER INFORMATION: /replace="V" or "R" or "A"
<220> FEATURE:
<221> NAME/KEY: SITE
<222> LOCATION: (1)..(9)
<223> OTHER INFORMATION: /note="Variant residues given in the sequence
      have no preference with respect to those in the annotations
      for variant positions"

<400> SEQUENCE: 434

Gln Gln Ser Trp Val Lys Pro Arg Thr
1               5
```

-continued

```
<210> SEQ ID NO 435
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="E" or "T" or "I"
<220> FEATURE:
<221> NAME/KEY: VARIANT
<222> LOCATION: (3)..(3)
<223> OTHER INFORMATION: /replace="R" or "A" or "T" or "M"
<220> FEATURE:
<221> NAME/KEY: VARIANT
<222> LOCATION: (4)..(4)
<223> OTHER INFORMATION: /replace="V" or "R" or "A"
<220> FEATURE:
<221> NAME/KEY: SITE
<222> LOCATION: (1)..(6)
<223> OTHER INFORMATION: /note="Variant residues given in the sequence
      have no preference with respect to those in the annotations
      for variant positions"

<400> SEQUENCE: 435

Ser Trp Val Lys Pro Arg
1               5

<210> SEQ ID NO 436
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (5)..(5)
<223> OTHER INFORMATION: /replace="S" or "Q"
<220> FEATURE:
<221> NAME/KEY: SITE
<222> LOCATION: (1)..(10)
<223> OTHER INFORMATION: /note="Variant residues given in the sequence
      have no preference with respect to those in the annotations
      for variant positions"

<400> SEQUENCE: 436

Gly Phe Thr Phe Asn Thr His Tyr Ile His
1               5                   10

<210> SEQ ID NO 437
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="G"
<220> FEATURE:
<221> NAME/KEY: VARIANT
<222> LOCATION: (4)..(4)
<223> OTHER INFORMATION: /replace="G"
<220> FEATURE:
<221> NAME/KEY: VARIANT
<222> LOCATION: (5)..(5)
<223> OTHER INFORMATION: /replace="Q"
```

```
<220> FEATURE:
<221> NAME/KEY: VARIANT
<222> LOCATION: (7)..(7)
<223> OTHER INFORMATION: /replace="Q" or "G"
<220> FEATURE:
<221> NAME/KEY: VARIANT
<222> LOCATION: (8)..(8)
<223> OTHER INFORMATION: /replace="N" or "M"
<220> FEATURE:
<221> NAME/KEY: VARIANT
<222> LOCATION: (10)..(10)
<223> OTHER INFORMATION: /replace="L"
<220> FEATURE:
<221> NAME/KEY: SITE
<222> LOCATION: (1)..(17)
<223> OTHER INFORMATION: /note="Variant residues given in the sequence
      have no preference with respect to those in the annotations
      for variant positions"

<400> SEQUENCE: 437

Ser Ile Ser Ser Ser Gly Ser Ser Thr Tyr Tyr Ala Asp Ser Val Lys
1               5                   10                  15

Gly

<210> SEQ ID NO 438
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (5)..(5)
<223> OTHER INFORMATION: /replace="S" or "Q"
<220> FEATURE:
<221> NAME/KEY: SITE
<222> LOCATION: (1)..(7)
<223> OTHER INFORMATION: /note="Variant residues given in the sequence
      have no preference with respect to those in the annotations
      for variant positions"

<400> SEQUENCE: 438

Gly Phe Thr Phe Asn Thr His
1               5

<210> SEQ ID NO 439
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="G"
<220> FEATURE:
<221> NAME/KEY: VARIANT
<222> LOCATION: (2)..(2)
<223> OTHER INFORMATION: /replace="G"
<220> FEATURE:
<221> NAME/KEY: VARIANT
<222> LOCATION: (3)..(3)
<223> OTHER INFORMATION: /replace="Q"
<220> FEATURE:
<221> NAME/KEY: VARIANT
<222> LOCATION: (5)..(5)
<223> OTHER INFORMATION: /replace="Q" or "G"
<220> FEATURE:
<221> NAME/KEY: VARIANT
<222> LOCATION: (6)..(6)
```

```
<223> OTHER INFORMATION: /replace="N" or "M"
<220> FEATURE:
<221> NAME/KEY: SITE
<222> LOCATION: (1)..(6)
<223> OTHER INFORMATION: /note="Variant residues given in the sequence
      have no preference with respect to those in the annotations
      for variant positions"

<400> SEQUENCE: 439

Ser Ser Ser Gly Ser Ser
1               5

<210> SEQ ID NO 440
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (5)..(5)
<223> OTHER INFORMATION: /replace="S" or "Q"
<220> FEATURE:
<221> NAME/KEY: SITE
<222> LOCATION: (1)..(8)
<223> OTHER INFORMATION: /note="Variant residues given in the sequence
      have no preference with respect to those in the annotations
      for variant positions"

<400> SEQUENCE: 440

Gly Phe Thr Phe Asn Thr His Tyr
1               5

<210> SEQ ID NO 441
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="G"
<220> FEATURE:
<221> NAME/KEY: VARIANT
<222> LOCATION: (3)..(3)
<223> OTHER INFORMATION: /replace="G"
<220> FEATURE:
<221> NAME/KEY: VARIANT
<222> LOCATION: (4)..(4)
<223> OTHER INFORMATION: /replace="Q"
<220> FEATURE:
<221> NAME/KEY: VARIANT
<222> LOCATION: (6)..(6)
<223> OTHER INFORMATION: /replace="Q" or "G"
<220> FEATURE:
<221> NAME/KEY: VARIANT
<222> LOCATION: (7)..(7)
<223> OTHER INFORMATION: /replace="N" or "M"
<220> FEATURE:
<221> NAME/KEY: SITE
<222> LOCATION: (1)..(8)
<223> OTHER INFORMATION: /note="Variant residues given in the sequence
      have no preference with respect to those in the annotations
      for variant positions"

<400> SEQUENCE: 441

Ile Ser Ser Ser Gly Ser Ser Thr
1               5
```

```
<210> SEQ ID NO 442
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(4)
<223> OTHER INFORMATION: /replace="G"
<220> FEATURE:
<221> NAME/KEY: VARIANT
<222> LOCATION: (7)..(7)
<223> OTHER INFORMATION: /replace="Q"
<220> FEATURE:
<221> NAME/KEY: VARIANT
<222> LOCATION: (8)..(8)
<223> OTHER INFORMATION: /replace="N"
<220> FEATURE:
<221> NAME/KEY: SITE
<222> LOCATION: (1)..(17)
<223> OTHER INFORMATION: /note="Variant residues given in the sequence
      have no preference with respect to those in the annotations
      for variant positions"

<400> SEQUENCE: 442

Ser Ile Ser Ser Ser Gly Ser Ser Thr Tyr Tyr Ala Asp Ser Val Lys
1               5                   10                  15

Gly

<210> SEQ ID NO 443
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="G"
<220> FEATURE:
<221> NAME/KEY: VARIANT
<222> LOCATION: (5)..(5)
<223> OTHER INFORMATION: /replace="Q"
<220> FEATURE:
<221> NAME/KEY: VARIANT
<222> LOCATION: (6)..(6)
<223> OTHER INFORMATION: /replace="N"
<220> FEATURE:
<221> NAME/KEY: SITE
<222> LOCATION: (1)..(6)
<223> OTHER INFORMATION: /note="Variant residues given in the sequence
      have no preference with respect to those in the annotations
      for variant positions"

<400> SEQUENCE: 443

Ser Ser Ser Gly Ser Ser
1               5

<210> SEQ ID NO 444
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
```

```
<222> LOCATION: (3)..(3)
<223> OTHER INFORMATION: /replace="G"
<220> FEATURE:
<221> NAME/KEY: VARIANT
<222> LOCATION: (6)..(6)
<223> OTHER INFORMATION: /replace="Q"
<220> FEATURE:
<221> NAME/KEY: VARIANT
<222> LOCATION: (7)..(7)
<223> OTHER INFORMATION: /replace="N"
<220> FEATURE:
<221> NAME/KEY: SITE
<222> LOCATION: (1)..(8)
<223> OTHER INFORMATION: /note="Variant residues given in the sequence
      have no preference with respect to those in the annotations
      for variant positions"

<400> SEQUENCE: 444

Ile Ser Ser Ser Gly Ser Ser Thr
1               5

<210> SEQ ID NO 445
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="T"
<220> FEATURE:
<221> NAME/KEY: VARIANT
<222> LOCATION: (6)..(6)
<223> OTHER INFORMATION: /replace="K" or "R"
<220> FEATURE:
<221> NAME/KEY: VARIANT
<222> LOCATION: (8)..(8)
<223> OTHER INFORMATION: /replace="Y"
<220> FEATURE:
<221> NAME/KEY: VARIANT
<222> LOCATION: (9)..(9)
<223> OTHER INFORMATION: /replace="L"
<220> FEATURE:
<221> NAME/KEY: VARIANT
<222> LOCATION: (10)..(10)
<223> OTHER INFORMATION: /replace="N"
<220> FEATURE:
<221> NAME/KEY: SITE
<222> LOCATION: (1)..(10)
<223> OTHER INFORMATION: /note="Variant residues given in the sequence
      have no preference with respect to those in the annotations
      for variant positions"

<400> SEQUENCE: 445

Gly Phe Ser Phe Ser Ser Tyr Trp Ile Ser
1               5                   10

<210> SEQ ID NO 446
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="N"
<220> FEATURE:
<221> NAME/KEY: VARIANT
<222> LOCATION: (3)..(3)
```

```
<223> OTHER INFORMATION: /replace="H"
<220> FEATURE:
<221> NAME/KEY: VARIANT
<222> LOCATION: (5)..(5)
<223> OTHER INFORMATION: /replace="Q" or "H"
<220> FEATURE:
<221> NAME/KEY: VARIANT
<222> LOCATION: (6)..(6)
<223> OTHER INFORMATION: /replace="A"
<220> FEATURE:
<221> NAME/KEY: VARIANT
<222> LOCATION: (7)..(7)
<223> OTHER INFORMATION: /replace="H" or "L"
<220> FEATURE:
<221> NAME/KEY: VARIANT
<222> LOCATION: (9)..(9)
<223> OTHER INFORMATION: /replace="K"
<220> FEATURE:
<221> NAME/KEY: VARIANT
<222> LOCATION: (10)..(10)
<223> OTHER INFORMATION: /replace="K" or "R"
<220> FEATURE:
<221> NAME/KEY: SITE
<222> LOCATION: (1)..(17)
<223> OTHER INFORMATION: /note="Variant residues given in the sequence
      have no preference with respect to those in the annotations
      for variant positions"

<400> SEQUENCE: 446

Ser Ile Lys Gln Ser Gly Ser Glu Thr Tyr Tyr Val Glu Ser Val Lys
1               5                   10                  15
Gly

<210> SEQ ID NO 447
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="K" or "R"
<220> FEATURE:
<221> NAME/KEY: VARIANT
<222> LOCATION: (3)..(3)
<223> OTHER INFORMATION: /replace="Y"
<220> FEATURE:
<221> NAME/KEY: VARIANT
<222> LOCATION: (4)..(4)
<223> OTHER INFORMATION: /replace="L"
<220> FEATURE:
<221> NAME/KEY: VARIANT
<222> LOCATION: (5)..(5)
<223> OTHER INFORMATION: /replace="N"
<220> FEATURE:
<221> NAME/KEY: SITE
<222> LOCATION: (1)..(5)
<223> OTHER INFORMATION: /note="Variant residues given in the sequence
      have no preference with respect to those in the annotations
      for variant positions"

<400> SEQUENCE: 447

Ser Tyr Trp Ile Ser
1               5

<210> SEQ ID NO 448
<211> LENGTH: 7
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="T"
<220> FEATURE:
<221> NAME/KEY: VARIANT
<222> LOCATION: (6)..(6)
<223> OTHER INFORMATION: /replace="K" or "R"
<220> FEATURE:
<221> NAME/KEY: SITE
<222> LOCATION: (1)..(7)
<223> OTHER INFORMATION: /note="Variant residues given in the sequence
      have no preference with respect to those in the annotations
      for variant positions"

<400> SEQUENCE: 448

Gly Phe Ser Phe Ser Ser Tyr
1               5

<210> SEQ ID NO 449
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="H"
<220> FEATURE:
<221> NAME/KEY: VARIANT
<222> LOCATION: (3)..(3)
<223> OTHER INFORMATION: /replace="Q" or "H"
<220> FEATURE:
<221> NAME/KEY: VARIANT
<222> LOCATION: (4)..(4)
<223> OTHER INFORMATION: /replace="A"
<220> FEATURE:
<221> NAME/KEY: VARIANT
<222> LOCATION: (5)..(5)
<223> OTHER INFORMATION: /replace="H" or "L"
<220> FEATURE:
<221> NAME/KEY: SITE
<222> LOCATION: (1)..(6)
<223> OTHER INFORMATION: /note="Variant residues given in the sequence
      have no preference with respect to those in the annotations
      for variant positions"

<400> SEQUENCE: 449

Lys Gln Ser Gly Ser Glu
1               5

<210> SEQ ID NO 450
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="T"
<220> FEATURE:
<221> NAME/KEY: VARIANT
<222> LOCATION: (6)..(6)
<223> OTHER INFORMATION: /replace="K" or "R"
<220> FEATURE:
<221> NAME/KEY: VARIANT
<222> LOCATION: (8)..(8)
```

```
<223> OTHER INFORMATION: /replace="Y"
<220> FEATURE:
<221> NAME/KEY: SITE
<222> LOCATION: (1)..(8)
<223> OTHER INFORMATION: /note="Variant residues given in the sequence
      have no preference with respect to those in the annotations
      for variant positions"

<400> SEQUENCE: 450

Gly Phe Ser Phe Ser Ser Tyr Trp
1               5

<210> SEQ ID NO 451
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="H"
<220> FEATURE:
<221> NAME/KEY: VARIANT
<222> LOCATION: (4)..(4)
<223> OTHER INFORMATION: /replace="Q" or "H"
<220> FEATURE:
<221> NAME/KEY: VARIANT
<222> LOCATION: (5)..(5)
<223> OTHER INFORMATION: /replace="A"
<220> FEATURE:
<221> NAME/KEY: VARIANT
<222> LOCATION: (6)..(6)
<223> OTHER INFORMATION: /replace="H" or "L"
<220> FEATURE:
<221> NAME/KEY: VARIANT
<222> LOCATION: (8)..(8)
<223> OTHER INFORMATION: /replace="K"
<220> FEATURE:
<221> NAME/KEY: SITE
<222> LOCATION: (1)..(8)
<223> OTHER INFORMATION: /note="Variant residues given in the sequence
      have no preference with respect to those in the annotations
      for variant positions"

<400> SEQUENCE: 451

Ile Lys Gln Ser Gly Ser Glu Thr
1               5

<210> SEQ ID NO 452
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (6)..(6)
<223> OTHER INFORMATION: /replace="R"
<220> FEATURE:
<221> NAME/KEY: VARIANT
<222> LOCATION: (8)..(8)
<223> OTHER INFORMATION: /replace="Y"
<220> FEATURE:
<221> NAME/KEY: VARIANT
<222> LOCATION: (10)..(10)
<223> OTHER INFORMATION: /replace="N"
<220> FEATURE:
<221> NAME/KEY: SITE
<222> LOCATION: (1)..(10)
<223> OTHER INFORMATION: /note="Variant residues given in the sequence
``` have no preference with respect to those in the annotations
for variant positions"

<400> SEQUENCE: 452

Gly Phe Thr Phe Ser Ser Tyr Trp Ile Ser
1               5                   10

<210> SEQ ID NO 453
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (5)..(5)
<223> OTHER INFORMATION: /replace="H"
<220> FEATURE:
<221> NAME/KEY: VARIANT
<222> LOCATION: (6)..(6)
<223> OTHER INFORMATION: /replace="A"
<220> FEATURE:
<221> NAME/KEY: VARIANT
<222> LOCATION: (7)..(7)
<223> OTHER INFORMATION: /replace="L"
<220> FEATURE:
<221> NAME/KEY: VARIANT
<222> LOCATION: (9)..(9)
<223> OTHER INFORMATION: /replace="K"
<220> FEATURE:
<221> NAME/KEY: VARIANT
<222> LOCATION: (10)..(10)
<223> OTHER INFORMATION: /replace="R"
<220> FEATURE:
<221> NAME/KEY: SITE
<222> LOCATION: (1)..(17)
<223> OTHER INFORMATION: /note="Variant residues given in the sequence
      have no preference with respect to those in the annotations
      for variant positions"

<400> SEQUENCE: 453

Ser Ile His Gln Gln Gly His Glu Thr Lys Tyr Val Glu Ser Val Lys
1               5                   10                  15

Gly

<210> SEQ ID NO 454
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="R"
<220> FEATURE:
<221> NAME/KEY: VARIANT
<222> LOCATION: (3)..(3)
<223> OTHER INFORMATION: /replace="Y"
<220> FEATURE:
<221> NAME/KEY: VARIANT
<222> LOCATION: (5)..(5)
<223> OTHER INFORMATION: /replace="N"
<220> FEATURE:
<221> NAME/KEY: SITE
<222> LOCATION: (1)..(5)
<223> OTHER INFORMATION: /note="Variant residues given in the sequence
      have no preference with respect to those in the annotations
      for variant positions"

```
<400> SEQUENCE: 454

Ser Tyr Trp Ile Ser
1               5

<210> SEQ ID NO 455
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (6)..(6)
<223> OTHER INFORMATION: /replace="R"
<220> FEATURE:
<221> NAME/KEY: SITE
<222> LOCATION: (1)..(7)
<223> OTHER INFORMATION: /note="Variant residues given in the sequence
      have no preference with respect to those in the annotations
      for variant positions"

<400> SEQUENCE: 455

Gly Phe Thr Phe Ser Ser Tyr
1               5

<210> SEQ ID NO 456
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="H"
<220> FEATURE:
<221> NAME/KEY: VARIANT
<222> LOCATION: (4)..(4)
<223> OTHER INFORMATION: /replace="A"
<220> FEATURE:
<221> NAME/KEY: VARIANT
<222> LOCATION: (5)..(5)
<223> OTHER INFORMATION: /replace="L"
<220> FEATURE:
<221> NAME/KEY: SITE
<222> LOCATION: (1)..(6)
<223> OTHER INFORMATION: /note="Variant residues given in the sequence
      have no preference with respect to those in the annotations
      for variant positions"

<400> SEQUENCE: 456

His Gln Gln Gly His Glu
1               5

<210> SEQ ID NO 457
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (6)..(6)
<223> OTHER INFORMATION: /replace="R"
<220> FEATURE:
<221> NAME/KEY: VARIANT
<222> LOCATION: (8)..(8)
```

```
<223> OTHER INFORMATION: /replace="Y"
<220> FEATURE:
<221> NAME/KEY: SITE
<222> LOCATION: (1)..(8)
<223> OTHER INFORMATION: /note="Variant residues given in the sequence
      have no preference with respect to those in the annotations
      for variant positions"

<400> SEQUENCE: 457

Gly Phe Thr Phe Ser Ser Tyr Trp
1               5

<210> SEQ ID NO 458
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(4)
<223> OTHER INFORMATION: /replace="H"
<220> FEATURE:
<221> NAME/KEY: VARIANT
<222> LOCATION: (5)..(5)
<223> OTHER INFORMATION: /replace="A"
<220> FEATURE:
<221> NAME/KEY: VARIANT
<222> LOCATION: (6)..(6)
<223> OTHER INFORMATION: /replace="L"
<220> FEATURE:
<221> NAME/KEY: VARIANT
<222> LOCATION: (8)..(8)
<223> OTHER INFORMATION: /replace="K"
<220> FEATURE:
<221> NAME/KEY: SITE
<222> LOCATION: (1)..(8)
<223> OTHER INFORMATION: /note="Variant residues given in the sequence
      have no preference with respect to those in the annotations
      for variant positions"

<400> SEQUENCE: 458

Ile His Gln Gln Gly His Glu Thr
1               5

<210> SEQ ID NO 459
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="S"
<220> FEATURE:
<221> NAME/KEY: VARIANT
<222> LOCATION: (3)..(3)
<223> OTHER INFORMATION: /replace="L"
<220> FEATURE:
<221> NAME/KEY: VARIANT
<222> LOCATION: (4)..(4)
<223> OTHER INFORMATION: /replace="P"
<220> FEATURE:
<221> NAME/KEY: VARIANT
<222> LOCATION: (6)..(6)
<223> OTHER INFORMATION: /replace="L"
<220> FEATURE:
<221> NAME/KEY: SITE
<222> LOCATION: (1)..(11)
<223> OTHER INFORMATION: /note="Variant residues given in the sequence
``` have no preference with respect to those in the annotations
for variant positions"

<400> SEQUENCE: 459

Gly Ala Val Ala Gly Gln Leu Gly Phe Asp His
1               5                   10

<210> SEQ ID NO 460
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (7)..(7)
<223> OTHER INFORMATION: /replace="N"
<220> FEATURE:
<221> NAME/KEY: SITE
<222> LOCATION: (1)..(7)
<223> OTHER INFORMATION: /note="Variant residues given in the sequence
      have no preference with respect to those in the annotations
      for variant positions"

<400> SEQUENCE: 460

Gly Asn Ser Asn Arg Pro Ser
1               5

<210> SEQ ID NO 461
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(4)
<223> OTHER INFORMATION: /replace="D" or "G"
<220> FEATURE:
<221> NAME/KEY: VARIANT
<222> LOCATION: (5)..(5)
<223> OTHER INFORMATION: /replace="S" or "A"
<220> FEATURE:
<221> NAME/KEY: VARIANT
<222> LOCATION: (6)..(6)
<223> OTHER INFORMATION: /replace="P" or "F"
<220> FEATURE:
<221> NAME/KEY: VARIANT
<222> LOCATION: (7)..(7)
<223> OTHER INFORMATION: /replace="T" or "P"
<220> FEATURE:
<221> NAME/KEY: VARIANT
<222> LOCATION: (8)..(8)
<223> OTHER INFORMATION: /replace="S" or "R"
<220> FEATURE:
<221> NAME/KEY: VARIANT
<222> LOCATION: (9)..(9)
<223> OTHER INFORMATION: /replace="S" or "F"
<220> FEATURE:
<221> NAME/KEY: VARIANT
<222> LOCATION: (10)..(10)
<223> OTHER INFORMATION: /replace="S" or "V"
<220> FEATURE:
<221> NAME/KEY: SITE
<222> LOCATION: (1)..(11)
<223> OTHER INFORMATION: /note="Variant residues given in the sequence
      have no preference with respect to those in the annotations
      for variant positions"

<400> SEQUENCE: 461

```
Gln Ser Tyr Tyr Thr Ser Ser His Gly Pro Val
1               5                   10
```

<210> SEQ ID NO 462
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="D" or "G"
<220> FEATURE:
<221> NAME/KEY: VARIANT
<222> LOCATION: (3)..(3)
<223> OTHER INFORMATION: /replace="S" or "A"
<220> FEATURE:
<221> NAME/KEY: VARIANT
<222> LOCATION: (4)..(4)
<223> OTHER INFORMATION: /replace="P" or "F"
<220> FEATURE:
<221> NAME/KEY: VARIANT
<222> LOCATION: (5)..(5)
<223> OTHER INFORMATION: /replace="T" or "P"
<220> FEATURE:
<221> NAME/KEY: VARIANT
<222> LOCATION: (6)..(6)
<223> OTHER INFORMATION: /replace="S" or "R"
<220> FEATURE:
<221> NAME/KEY: VARIANT
<222> LOCATION: (7)..(7)
<223> OTHER INFORMATION: /replace="S" or "F"
<220> FEATURE:
<221> NAME/KEY: VARIANT
<222> LOCATION: (8)..(8)
<223> OTHER INFORMATION: /replace="S" or "V"
<220> FEATURE:
<221> NAME/KEY: SITE
<222> LOCATION: (1)..(8)
<223> OTHER INFORMATION: /note="Variant residues given in the sequence
      have no preference with respect to those in the annotations
      for variant positions"

<400> SEQUENCE: 462

```
Tyr Tyr Thr Ser Ser His Gly Pro
1               5
```

<210> SEQ ID NO 463
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(4)
<223> OTHER INFORMATION: /replace="S"
<220> FEATURE:
<221> NAME/KEY: VARIANT
<222> LOCATION: (5)..(5)
<223> OTHER INFORMATION: /replace="L"
<220> FEATURE:
<221> NAME/KEY: VARIANT
<222> LOCATION: (6)..(6)
<223> OTHER INFORMATION: /replace="P"
<220> FEATURE:
<221> NAME/KEY: VARIANT
<222> LOCATION: (8)..(8)
<223> OTHER INFORMATION: /replace="L"
<220> FEATURE:
<221> NAME/KEY: SITE

```
<222> LOCATION: (1)..(13)
<223> OTHER INFORMATION: /note="Variant residues given in the sequence
      have no preference with respect to those in the annotations
      for variant positions"

<400> SEQUENCE: 463

Ala Arg Gly Ala Val Ala Gly Gln Leu Gly Phe Asp His
1               5                   10

<210> SEQ ID NO 464
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (5)..(5)
<223> OTHER INFORMATION: /replace="G"
<220> FEATURE:
<221> NAME/KEY: VARIANT
<222> LOCATION: (6)..(6)
<223> OTHER INFORMATION: /replace="T"
<220> FEATURE:
<221> NAME/KEY: VARIANT
<222> LOCATION: (9)..(9)
<223> OTHER INFORMATION: /replace="M"
<220> FEATURE:
<221> NAME/KEY: VARIANT
<222> LOCATION: (10)..(10)
<223> OTHER INFORMATION: /replace="T"
<220> FEATURE:
<221> NAME/KEY: SITE
<222> LOCATION: (1)..(10)
<223> OTHER INFORMATION: /note="Variant residues given in the sequence
      have no preference with respect to those in the annotations
      for variant positions"

<400> SEQUENCE: 464

Gly Phe Thr Phe Ser Ser Tyr Ala Ile Ser
1               5                   10

<210> SEQ ID NO 465
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="S"
<220> FEATURE:
<221> NAME/KEY: VARIANT
<222> LOCATION: (4)..(4)
<223> OTHER INFORMATION: /replace="S" or "G"
<220> FEATURE:
<221> NAME/KEY: VARIANT
<222> LOCATION: (5)..(5)
<223> OTHER INFORMATION: /replace="H"
<220> FEATURE:
<221> NAME/KEY: VARIANT
<222> LOCATION: (7)..(7)
<223> OTHER INFORMATION: /replace="Y"
<220> FEATURE:
<221> NAME/KEY: VARIANT
<222> LOCATION: (8)..(8)
<223> OTHER INFORMATION: /replace="Y"
<220> FEATURE:
<221> NAME/KEY: VARIANT
<222> LOCATION: (9)..(9)
```

```
<223> OTHER INFORMATION: /replace="A"
<220> FEATURE:
<221> NAME/KEY: VARIANT
<222> LOCATION: (10)..(10)
<223> OTHER INFORMATION: /replace="R" or "N"
<220> FEATURE:
<221> NAME/KEY: VARIANT
<222> LOCATION: (13)..(13)
<223> OTHER INFORMATION: /replace="G"
<220> FEATURE:
<221> NAME/KEY: SITE
<222> LOCATION: (1)..(17)
<223> OTHER INFORMATION: /note="Variant residues given in the sequence
      have no preference with respect to those in the annotations
      for variant positions"

<400> SEQUENCE: 465

Ala Ile Ser Ala Ser Gly Gly Ser Thr Tyr Tyr Ala Glu Ser Val Lys
1               5                   10                  15
Gly

<210> SEQ ID NO 466
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="T"
<220> FEATURE:
<221> NAME/KEY: VARIANT
<222> LOCATION: (4)..(4)
<223> OTHER INFORMATION: /replace="M"
<220> FEATURE:
<221> NAME/KEY: VARIANT
<222> LOCATION: (5)..(5)
<223> OTHER INFORMATION: /replace="T"
<220> FEATURE:
<221> NAME/KEY: SITE
<222> LOCATION: (1)..(5)
<223> OTHER INFORMATION: /note="Variant residues given in the sequence
      have no preference with respect to those in the annotations
      for variant positions"

<400> SEQUENCE: 466

Ser Tyr Ala Ile Ser
1               5

<210> SEQ ID NO 467
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (5)..(5)
<223> OTHER INFORMATION: /replace="G"
<220> FEATURE:
<221> NAME/KEY: VARIANT
<222> LOCATION: (6)..(6)
<223> OTHER INFORMATION: /replace="T"
<220> FEATURE:
<221> NAME/KEY: SITE
<222> LOCATION: (1)..(7)
<223> OTHER INFORMATION: /note="Variant residues given in the sequence
      have no preference with respect to those in the annotations
      for variant positions"
```

<400> SEQUENCE: 467

Gly Phe Thr Phe Ser Ser Tyr
1               5

<210> SEQ ID NO 468
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="S" or "G"
<220> FEATURE:
<221> NAME/KEY: VARIANT
<222> LOCATION: (3)..(3)
<223> OTHER INFORMATION: /replace="H"
<220> FEATURE:
<221> NAME/KEY: VARIANT
<222> LOCATION: (5)..(5)
<223> OTHER INFORMATION: /replace="Y"
<220> FEATURE:
<221> NAME/KEY: VARIANT
<222> LOCATION: (6)..(6)
<223> OTHER INFORMATION: /replace="Y"
<220> FEATURE:
<221> NAME/KEY: SITE
<222> LOCATION: (1)..(6)
<223> OTHER INFORMATION: /note="Variant residues given in the sequence
      have no preference with respect to those in the annotations
      for variant positions"

<400> SEQUENCE: 468

Ser Ala Ser Gly Gly Ser
1               5

<210> SEQ ID NO 469
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (5)..(5)
<223> OTHER INFORMATION: /replace="G"
<220> FEATURE:
<221> NAME/KEY: VARIANT
<222> LOCATION: (6)..(6)
<223> OTHER INFORMATION: /replace="T"
<220> FEATURE:
<221> NAME/KEY: SITE
<222> LOCATION: (1)..(8)
<223> OTHER INFORMATION: /note="Variant residues given in the sequence
      have no preference with respect to those in the annotations
      for variant positions"

<400> SEQUENCE: 469

Gly Phe Thr Phe Ser Ser Tyr Ala
1               5

<210> SEQ ID NO 470
<211> LENGTH: 8
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="G"
<220> FEATURE:
<221> NAME/KEY: VARIANT
<222> LOCATION: (4)..(4)
<223> OTHER INFORMATION: /replace="H"
<220> FEATURE:
<221> NAME/KEY: VARIANT
<222> LOCATION: (6)..(6)
<223> OTHER INFORMATION: /replace="Y"
<220> FEATURE:
<221> NAME/KEY: VARIANT
<222> LOCATION: (7)..(7)
<223> OTHER INFORMATION: /replace="Y"
<220> FEATURE:
<221> NAME/KEY: SITE
<222> LOCATION: (1)..(8)
<223> OTHER INFORMATION: /note="Variant residues given in the sequence
      have no preference with respect to those in the annotations
      for variant positions"

<400> SEQUENCE: 470

Ile Ser Ser Ser Gly Gly Ser Thr
1               5

<210> SEQ ID NO 471
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(4)
<223> OTHER INFORMATION: /replace="S"
<220> FEATURE:
<221> NAME/KEY: VARIANT
<222> LOCATION: (5)..(5)
<223> OTHER INFORMATION: /replace="H"
<220> FEATURE:
<221> NAME/KEY: VARIANT
<222> LOCATION: (9)..(9)
<223> OTHER INFORMATION: /replace="A"
<220> FEATURE:
<221> NAME/KEY: VARIANT
<222> LOCATION: (10)..(10)
<223> OTHER INFORMATION: /replace="N"
<220> FEATURE:
<221> NAME/KEY: VARIANT
<222> LOCATION: (13)..(13)
<223> OTHER INFORMATION: /replace="G"
<220> FEATURE:
<221> NAME/KEY: SITE
<222> LOCATION: (1)..(17)
<223> OTHER INFORMATION: /note="Variant residues given in the sequence
      have no preference with respect to those in the annotations
      for variant positions"

<400> SEQUENCE: 471

Ser Ile Ser Ala Ser Gly Tyr Tyr Thr Arg Tyr Ala Glu Ser Val Lys
1               5                   10                  15

Gly

<210> SEQ ID NO 472
<211> LENGTH: 6
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="S"
<220> FEATURE:
<221> NAME/KEY: VARIANT
<222> LOCATION: (3)..(3)
<223> OTHER INFORMATION: /replace="H"
<220> FEATURE:
<221> NAME/KEY: SITE
<222> LOCATION: (1)..(6)
<223> OTHER INFORMATION: /note="Variant residues given in the sequence
      have no preference with respect to those in the annotations
      for variant positions"

<400> SEQUENCE: 472

Ser Ala Ser Gly Tyr Tyr
1               5

<210> SEQ ID NO 473
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="S" or "G"
<220> FEATURE:
<221> NAME/KEY: VARIANT
<222> LOCATION: (4)..(4)
<223> OTHER INFORMATION: /replace="H"
<220> FEATURE:
<221> NAME/KEY: SITE
<222> LOCATION: (1)..(5)
<223> OTHER INFORMATION: /note="Variant residues given in the sequence
      have no preference with respect to those in the annotations
      for variant positions"

<400> SEQUENCE: 473

Ile Ser Ala Ser Gly
1               5
```

NATRIURETIC PEPTIDE RECEPTOR 1 ANTIBODIES AND METHODS OF USE

RELATED APPLICATIONS

This application claims the benefit of and priority to U.S. Provisional Application No. 62/860,508 filed Jun. 12, 2019, the entire contents of each of which are incorporated herein by reference in its entirety.

SEQUENCE LISTING

The instant application contains a Sequence Listing which has been submitted electronically in ASCII format and is hereby incorporated by reference in its entirety. Said ASCII copy, created on Jun. 8, 2020, is named PAT058321-US-NP_SL.txt and is 447,935 bytes in size.

BACKGROUND

Heart failure is a major public health problem concerning more than 20 million patients around the world (Orso et al., 2014, Expert Opin Pharmacother. 15(13):1849-1861) and is associated with high morbidity (Ibebuogu et al., 2011, Circulation. Heart failure 4(2):114-120). Natriuretic Peptide Receptor 1 (NPR1; also known as NPRA) is a receptor guanylate cyclase, which is activated by Atrial Natriuretic Peptide (ANP) resulting in lowering of blood pressure and blood volume (Chen & Burnett, 2006, European Heart Journal Supplements 8(Suppl E):E18-E25; Ibebuogu et al. 2011, supra; Mani et al. 2015, Bioscience Reports 35(5): e00260). ANP binding induces dimerization and twisting of the receptor that induces activation of the guanylate cyclase domain and conversion of GTP into cGMP (Misono et al., 2011, The FEBS journal 278(11):1818-1829). ANP is cleared by NPR3, a natriuretic peptide receptor that lacks the guanylate cyclase domain, and degraded by Neutral Endopeptidase (NEP) (Chen & Burnett 2006, supra; Schmitt et al., 2003, Clin Sci (Lond). 105(2):141-160). Certain antibodies against NPR1 have been described, for example, in WO2010/065293 (including antibody 5591-IgG). However, these antibodies appeared to have no functional activity in the absence of ANP in vitro and no functional activity in vivo.

It has been shown that an increase in ANP may be beneficial for patients with heart failure with reduced ejection fraction (outbound pumping of blood by heart). See McMurray et al., N. Engl. J. Med.; Vol. 371, No. 11, pp 993-1004 (2014); and Nougué et al., Eur J Heart Fail. 2019 May; 21(5):598-605. However, there is a need for further longer acting agents that have an alternative mode of action to supplement or replace existing therapies.

SUMMARY OF THE DISCLOSURE

Herein is demonstrated that it is possible to activate NPR1 by the use of agonistic anti-NPR1 antibodies or antigen binding fragments thereof. Furthermore, the present disclosure demonstrates that there are two types of such antibodies. While one type binds to NPR1 and competes with ANP binding (yet still activates NPR1; hereinafter "ANP competitive" anti-NPR1 antibodies), the second type is able to bind and activate NPR1 while not competing with ANP (hereinafter "ANP non-competitive" anti-NPR1 antibodies). Such antibodies (e.g., ANP non-competitive anti-NPR1 antibodies) may be used to bolster the body's natural system and/or existing treatment rationales. Furthermore, certain NPR1 agonist antibodies that are able to activate NPR1 in the absence of ANP have been found to be functionally equivalent to ANP.

The antibodies of the instant application show in vivo activity in both mouse and rat. Furthermore, the unique epitope binding of the antibodies described herein has been demonstrated using crystal structure data.

Thus the disclosure provides anti-NPR1 antibodies (e.g., human monoclonal antibodies) or antigen-binding fragments thereof that (i) bind to natriuretic peptide receptor 1 (NPR1); and (ii) are capable of activating NPR1 in the absence of ANP. Such antibodies are agonistic anti-NPR1 antibodies. In some embodiments of the invention, the disclosure also provides anti-NPR1 antibodies or antigen binding fragments thereof that (i) bind to natriuretic peptide receptor 1 (NPR1); and (ii) activate NPR1 in the absence of ANP. In some embodiments of the invention, the disclosure also provides antibodies or antigen binding fragments thereof that (i) bind to natriuretic peptide receptor 1 (NPR1); and (ii) activate NPR1 in both the presence and absence of ANP. Also provided are nucleic acids encoding said antibodies, vectors comprising said nucleic acids, host cells comprising said nucleic acids and/or vectors, and methods of manufacture of said antibodies using said nucleic acids, vectors and/or host cells. Also provided are pharmaceutical compositions and combinations comprising said antibodies, nucleic acids, vectors or host cells, as well as methods of treatment using said antibodies, nucleic acids, vectors, host cells or pharmaceutical compositions. The use of said antibodies, nucleic acids, vectors, host cells or pharmaceutical compositions or combinations in treating disease is also disclosed herein.

Thus, in one aspect of the invention, herein is provided an isolated antibody or antigen binding fragment that (i) binds to natriuretic peptide receptor 1 (NPR1); and (ii) is capable of activating NPR1 in the absence of atrial natriuretic peptide (ANP). In some embodiments of the invention, the isolated antibody or antigen binding fragment does not bind to and/or does not activate natriuretic peptide receptor 2 (NPR2) and/or natriuretic peptide receptor 3 (NPR3). In some embodiments of the invention, the isolated antibody or antigen binding fragment binds to (a) human NPR1; and (b) mouse NPR1 and/or rat NPR1.

In some embodiments of the invention, the antibody or antigen binding fragment binds to (a) human NPR1; and (b) cyno NPR1. In some embodiments of the invention, the antibody or antigen binding fragment is ANP non-competitive. In some embodiments of the invention, the antibody or antigen binding fragment is ANP competitive. In some embodiments of the invention, the antibody or antigen binding fragment is capable of stabilizing the ANP-NPR1 complex.

In some embodiments of the invention, the antibody or antigen binding fragment binds to an epitope within amino acids 99-133 of SEQ ID NO: 1, e.g., within a region of human NPR1 encompassed by amino acids 99-133 of SEQ ID NO: 1. In some embodiments of the invention, the antibody or antigen binding fragment binds to an epitope comprising at least two amino acid residues within amino acids 99-133 of SEQ ID NO: 1. In some embodiments of the invention, the antibody or antigen binding fragment binds to an epitope comprising at least 3, 4, 5, 6, 7, or 8 amino acid residues within amino acids 99-133 of SEQ ID NO: 1.

In some embodiments of the invention, the antibody or antigen binding fragment binds to an epitope within amino acids 99-111 of SEQ ID NO: 1. In some embodiments of the invention, the antibody or antigen binding fragment binds to an epitope within amino acids 99-103 of SEQ ID NO: 1. In some embodiments of the invention, the antibody or antigen binding fragment binds to an epitope within amino acids 105-111 of SEQ ID NO: 1. In some embodiments of the invention, the antibody or antigen binding fragment binds to an epitope comprising at least 2, 3, or 4 amino acid residues within amino acids 105-111 of SEQ ID NO: 1. In some embodiments of the invention, the antibody or antigen binding fragment binds to a conformational epitope of human NPR1, and wherein the conformational epitope comprises at least one amino acid residue within each of (i) amino acids 99-103 of SEQ ID NO: 1, (ii) 105-111 of SEQ ID NO: 1, (iii) 131-134 of SEQ ID NO: 1, and additionally binds to amino acid 375 and/or 378 of SEQ ID NO: 1. In some embodiments of the invention, the epitope is a conformational epitope, and the conformational epitope additionally comprises at least one amino acid residue selected from the group consisting of amino acids 33, 34, 76, 82, and 104 of SEQ ID NO: 1. In some embodiments of the invention, the conformational epitope additionally comprises at least one amino acid residue selected from the group consisting of amino acids 33, 34, 76, 82, 104, 374, and 375 of SEQ ID NO: 1.

In some embodiments of the invention, the antibody or antigen binding fragment binds to at least amino acids 82, 102, 103, 105, 106, 109, 132, and 375 of SEQ ID NO: 1. In some embodiments of the invention, the antibody or antigen binding fragment binds to at least amino acids 34, 82, 102, 103, 105, 106, 107, 109, 132, 133, 375, and 378 of SEQ ID NO: 1. In some embodiments of the invention, the antibody or antigen binding fragment binds to at least amino acids 79, 82, 99, 102, 103, 105, 106, 109, 131, 132, and 375 of SEQ ID NO: 1.

In some embodiments of the invention, the antibody or antigen binding fragment binds to an epitope within amino acids 188-219 of SEQ ID NO: 1. In some embodiments of the invention, the antibody or antigen binding fragment binds to an epitope comprising at least 2, 3, 4, 5, 6, or 7 amino acids within amino acids 188-219 of SEQ ID NO: 1. In some embodiments of the invention, the antibody or antigen binding fragment binds to a conformational epitope within NPR1, and the conformational epitope comprises at least one amino acid residue within each of (i) amino acids 188-198 of SEQ ID NO: 1, (ii) 201-208 of SEQ ID NO: 1, (iii) 215-238 of SEQ ID NO: 1, and (iv) 294-297 of SEQ ID NO: 1. In some embodiments of the invention, the antibody or antigen binding fragment binds to at least amino acids 188, 192, 194, 197, 201, 208, and 219 of SEQ ID NO: 1. In some embodiments of the invention, the antibody or antigen binding fragment binds to at least amino acids 188, 192, 194, 197, 201, 208, 219, and 295 of SEQ ID NO: 1.

In some embodiments of the invention, the antibody or antigen binding fragment comprises three heavy chain complementarity determining regions (HCDR1, HCDR2, and HCDR3) and three light chain complementarity determining regions (LCDR1, LCDR2, and LCDR3), wherein: (a) (I) HCDR1 comprises or consists of an amino acid sequence as set forth in SEQ ID NO: 28; HCDR2 comprises or consists of an amino acid sequence as set forth in $X_1IX_2SX_3GX_4YX_5X_6YADSVKG$ (SEQ ID NO: 429), wherein $X_1$ is A or V, $X_2$ is S or E, $X_3$ is D or K, $X_4$ is S or N, $X_5$ is I or T, and $X_6$ is Y or F; HCDR3 comprises or consists of an amino acid sequence as set forth in SEQ ID NO: 30; LCDR1 comprises or consists of an amino acid sequence as set forth in SEQ ID NO: 41; LCDR2 comprises or consists of an amino acid sequence as set forth in SEQ ID NO: 42; and LCDR3 comprises or consists of an amino acid sequence as set forth in $Y_1QY_2Y_3Y_4Y_5PRT$ (SEQ ID NO: 430); wherein $Y_1$ is M or Q, $Y_2$ is S, E, T, or I, $Y_3$ is Y or W, $Y_4$ is E, V, R, A, T, or M, and $Y_5$ is K, V, R, or A; (II) HCDR1 comprises or consists of an amino acid sequence as set forth in SEQ ID NO: 31; HCDR2 comprises or consists of an amino acid sequence as set forth in $X_1IX_2SX_3GX_4YX_5X_6YADSVKG$ (SEQ ID NO: 429), wherein $X_1$ is A or V, $X_2$ is S or E, $X_3$ is D or K, $X_4$ is S or N, $X_5$ is I or T, and $X_6$ is Y or F; HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in $Y_1QY_2Y_3Y_4Y_5PRT$ (SEQ ID NO: 430); wherein $Y_1$ is M or Q, $Y_2$ is S, E, T, or I, $Y_3$ is Y or W, $Y_4$ is E, V, R, A, T, or M, and $Y_5$ is K, V, R, or A; (III) HCDR1 comprises or consists of an amino acid sequence as set forth in SEQ ID NO: 32, HCDR2 comprises or consists of an amino acid sequence as set forth in $X_1SX_2GX_3Y$ (SEQ ID NO: 431), wherein $X_1$ is S or E, $X_2$ is D or K, or $X_3$ is S or N, HCDR3 comprises or consists of an amino acid sequence as set forth in SEQ ID NO: 30, LCDR1 comprises or consists of an amino acid sequence as set forth in SEQ ID NO: 44, LCDR2 comprises or consists of an amino acid sequence as set forth in SEQ ID NO: 45, and LCDR3 comprises or consists of an amino acid sequence as set forth in $Y_1Y_2Y_3Y_4PR$ (SEQ ID NO: 432); wherein $Y_1$ is S, E, T, or I, $Y_2$ is Y or W, $Y_3$ is E, V, R, A, T, or M, and $Y_4$ is K, V, R, or A; or (IV) HCDR1 comprises or consists of an amino acid sequence as set forth in SEQ ID NO: 34, HCDR2 comprises or consists of an amino acid sequence as set forth in $IX_1SX_2GX_3YX_4$ (SEQ ID NO: 433), wherein $X_1$ is S or E, $X_2$ is D or K, $X_3$ is S or N, and $X_4$ is I or T, HCDR3 comprises or consists of an amino acid sequence as set forth in SEQ ID NO: 36, LCDR1 comprises or consists of an amino acid sequence as set forth in SEQ ID NO: 47, LCDR2 comprises or consists of an amino acid sequence as set forth in SEQ ID NO: 45, and LCDR3 comprises or consists of an amino acid sequence as set forth in $Y_1QY_2Y_3Y_4Y_5PRT$ (SEQ ID NO: 430); wherein $Y_1$ is M or Q, $Y_2$ is S, E, T, or I, $Y_3$ is Y or W, $Y_4$ is E, V, R, A, T, or M, and $Y_5$ is K, V, R, or A; (b) (I) HCDR1 comprises or consists of an amino acid sequence as set forth in SEQ ID NO: 28; HCDR2 comprises or consists of an amino acid sequence as set forth in $X_1IX_2SX_3GX_4YX_5X_6YADSVKG$ (SEQ ID NO: 429), wherein $X_1$ is A or V, $X_2$ is S or E, $X_3$ is D or K, $X_4$ is S or N, $X_5$ is I or T, and $X_6$ is Y or F; HCDR3 comprises or consists of an amino acid sequence as set forth in SEQ ID NO: 30; LCDR1 comprises or consists of an amino acid sequence as set forth in SEQ ID NO: 41; LCDR2 comprises or consists of an amino acid sequence as set forth in SEQ ID NO: 42; and LCDR3 comprises or consists of an amino acid sequence as set forth in $QQY_1WY_2Y_3PRT$ (SEQ ID NO: 434); wherein $Y_1$ is S, E, T, or I, $Y_2$ is V, R, A, T, or M, and $Y_3$ is K, V, R, or A; (II) HCDR1 comprises or consists of an amino acid sequence as set forth in SEQ ID NO: 31; HCDR2 comprises or consists of an amino acid sequence as set forth in $X_1IX_2SX_3GX_4YX_5X_6YADSVKG$ (SEQ ID NO: 429), wherein $X_1$ is A or V, $X_2$ is S or E, $X_3$ is D or K, $X_4$ is S or N, $X_5$ is I or T, and $X_6$ is Y or F; HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in $QQY_1WY_2Y_3PRT$ (SEQ ID NO:

434); wherein $Y_1$ is S, E, T, or I, $Y_2$ is V, R, A, T, or M, and $Y_3$ is K, V, R, or A; (III) HCDR1 comprises or consists of an amino acid sequence as set forth in SEQ ID NO: 32, HCDR2 comprises or consists of an amino acid sequence as set forth in $X_1SX_2GX_3Y$ (SEQ ID NO: 431), wherein $X_1$ is S or E, $X_2$ is D or K, or $X_3$ is S or N, HCDR3 comprises or consists of an amino acid sequence as set forth in SEQ ID NO: 30, LCDR1 comprises or consists of an amino acid sequence as set forth in SEQ ID NO: 44, LCDR2 comprises or consists of an amino acid sequence as set forth in SEQ ID NO: 45, and LCDR3 comprises or consists of an amino acid sequence as set forth in $Y_1WY_2Y_3PR$ (SEQ ID NO: 435); wherein $Y_1$ is S, E, T, or I, $Y_2$ is V, R, A, T, or M, and $Y_3$ is K, V, R, or A; or (IV) HCDR1 comprises or consists of an amino acid sequence as set forth in SEQ ID NO: 34, HCDR2 comprises or consists of an amino acid sequence as set forth in $IX_1SX_2GX_3YX_4$ (SEQ ID NO: 433), wherein $X_1$ is S or E, $X_2$ is D or K, $X_3$ is S or N, and $X_4$ is I or T, HCDR3 comprises or consists of an amino acid sequence as set forth in SEQ ID NO: 36, LCDR1 comprises or consists of an amino acid sequence as set forth in SEQ ID NO: 47, LCDR2 comprises or consists of an amino acid sequence as set forth in SEQ ID NO: 45, and LCDR3 comprises or consists of an amino acid sequence as set forth in $QQY_1WY_2Y_3PRT$ (SEQ ID NO: 434); wherein $Y_1$ is S, E, T, or I, $Y_2$ is V, R, A, T, or M, and $Y_3$ is K, V, R, or A; (c) (I) HCDR1 comprises or consists of an amino acid sequence as set forth in SEQ ID NO: 28; HCDR2 comprises or consists of an amino acid sequence as set forth in SEQ ID NO: 119; HCDR3 comprises or consists of an amino acid sequence as set forth in SEQ ID NO: 30; LCDR1 comprises or consists of an amino acid sequence as set forth in SEQ ID NO: 41; LCDR2 comprises or consists of an amino acid sequence as set forth in SEQ ID NO: 42; and LCDR3 comprises or consists of an amino acid sequence as set forth in $QQY_1WY_2Y_3PRT$ (SEQ ID NO: 434); wherein $Y_1$ is S, E, T, or I, $Y_2$ is V, R, A, T, or M, and $Y_3$ is K, V, R, or A; (II) HCDR1 comprises or consists of an amino acid sequence as set forth in SEQ ID NO: 31; HCDR2 comprises or consists of an amino acid sequence as set forth in SEQ ID NO: 119; HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in $QQY_1WY_2Y_3PRT$ (SEQ ID NO: 434); wherein $Y_1$ is S, E, T, or I, $Y_2$ is V, R, A, T, or M, and $Y_3$ is K, V, R, or A; (III) HCDR1 comprises or consists of an amino acid sequence as set forth in SEQ ID NO: 32, HCDR2 comprises or consists of an amino acid sequence as set forth in SEQ ID NO: 120, HCDR3 comprises or consists of an amino acid sequence as set forth in SEQ ID NO: 30, LCDR1 comprises or consists of an amino acid sequence as set forth in SEQ ID NO: 44, LCDR2 comprises or consists of an amino acid sequence as set forth in SEQ ID NO: 45, and LCDR3 comprises or consists of an amino acid sequence as set forth in $Y_1WY_2Y_3PR$ (SEQ ID NO: 435); wherein $Y_1$ is S, E, T, or I, $Y_2$ is V, R, A, T, or M, and $Y_3$ is K, V, R, or A; or (IV) HCDR1 comprises or consists of an amino acid sequence as set forth in SEQ ID NO: 34, HCDR2 comprises or consists of an amino acid sequence as set forth in SEQ ID NO: 121, HCDR3 comprises or consists of an amino acid sequence as set forth in SEQ ID NO: 36, LCDR1 comprises or consists of an amino acid sequence as set forth in SEQ ID NO: 47, LCDR2 comprises or consists of an amino acid sequence as set forth in SEQ ID NO: 45, and LCDR3 comprises or consists of an amino acid sequence as set forth in $QQY_1WY_2Y_3PRT$ (SEQ ID NO: 434); wherein $Y_1$ is S, E, T, or I, $Y_2$ is V, R, A, T, or M, and $Y_3$ is K, V, R, or A; (d) (I) HCDR1 comprises or consists of an amino acid sequence as set forth in GFTFX$_1$THYIH (SEQ ID NO: 436), wherein $X_1$ is N, S, or Q, HCDR2 comprises or consists of an amino acid sequence as set forth in $SIY_1Y_2Y_3GY_4Y_5TY_6YADSVKG$ (SEQ ID NO: 437), wherein $Y_1$ is S or G, $Y_2$ is S or G, $Y_3$ is S or Q, $Y_4$ is S, Q, or G, $Y_5$ is S, N, or M, and $Y_6$ is Y or L, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19; (II) HCDR1 comprises or consists of an amino acid sequence as set forth in SEQ ID NO: 7, HCDR2 comprises or consists of an amino acid sequence as set forth in $SIY_1Y_2Y_3GY_4Y_5TY_6YADSVKG$ (SEQ ID NO: 437), wherein $Y_1$ is S or G, $Y_2$ is S or G, $Y_3$ is S or Q, $Y_4$ is S, Q, or G, $Y_5$ is S, N, or M, and $Y_6$ is Y or L, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19; (III) HCDR1 comprises or consists of an amino acid sequence as set forth in GFTFX$_1$TH (SEQ ID NO: 438), wherein $X_1$ is N, S, or Q, HCDR2 comprises or consists of an amino acid sequence as set forth in $Y_1Y_2Y_3GY_4Y_5$ (SEQ ID NO: 439), wherein $Y_1$ is S or G, $Y_2$ is S or G, $Y_3$ is S or Q, $Y_4$ is S, Q, or G, and $Y_5$ is S, N, or M, HCDR3 comprises or consists of an amino acid sequence as set forth in SEQ ID NO: 6, LCDR1 comprises or consists of an amino acid sequence as set forth in SEQ ID NO: 20, LCDR2 comprises or consists of an amino acid sequence as set forth in SEQ ID NO: 21, and LCDR3 comprises or consists of an amino acid sequence as set forth in SEQ ID NO: 22; or (IV) HCDR1 comprises or consists of an amino acid sequence as set forth in GFTFX$_1$THY (SEQ ID NO: 440), wherein $X_1$ is N, S, or Q, HCDR2 comprises or consists of an amino acid sequence as set forth in $IY_1Y_2Y_3GY_4Y_5T$ (SEQ ID NO: 441), wherein $Y_1$ is S or G, $Y_2$ is S or G, $Y_3$ is S or Q, $Y_4$ is S, Q, or G, and $Y_5$ is S, N, or M, HCDR3 comprises or consists of an amino acid sequence as set forth in SEQ ID NO: 12, LCDR1 comprises or consists of an amino acid sequence as set forth in SEQ ID NO: 23, LCDR2 comprises or consists of an amino acid sequence as set forth in SEQ ID NO: 21, and LCDR3 comprises or consists of an amino acid sequence as set forth in SEQ ID NO: 19; (e) (I) HCDR1 comprises or consists of an amino acid sequence as set forth in GFTFX$_1$THYIH (SEQ ID NO: 436), wherein $X_1$ is N, S, or Q, HCDR2 comprises or consists of an amino acid sequence as set forth in $SISY_1SGY_2Y_3TYYADSVKG$ (SEQ ID NO: 442), wherein $Y_1$ is S or G, $Y_2$ is S or Q, and $Y_3$ is S or N, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19; (II) HCDR1 comprises or consists of an amino acid sequence as set forth in SEQ ID NO: 7, HCDR2 comprises or consists of an amino acid sequence as set forth in $SISY_1SGY_2Y_3TYYADSVKG$ (SEQ ID NO: 442), wherein $Y_1$ is S or G, $Y_2$ is S or Q, and $Y_3$ is S or N, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19; (III) HCDR1 comprises or consists of an amino acid sequence as set forth in GFTFX$_1$TH (SEQ ID NO: 438), wherein X$_1$ is N, S, or Q, HCDR2 comprises or consists of an amino acid sequence as set forth in SY$_1$SGY$_2$Y$_3$ (SEQ ID NO: 443), wherein Y$_1$ is S or G, Y$_2$ is S or Q, and Y$_3$ is S or N, HCDR3 comprises or consists of an amino acid sequence as set forth in SEQ ID NO: 6, LCDR1 comprises or consists of an amino acid sequence as set forth in SEQ ID NO: 20, LCDR2 comprises or consists of an amino acid sequence as set forth in SEQ ID NO: 21, and LCDR3 comprises or consists of an amino acid sequence as set forth in SEQ ID NO: 22; or (IV) HCDR1 comprises or consists of an amino acid sequence as set forth in GFTFX$_1$THY (SEQ ID NO: 440), wherein X$_1$ is N, S, or Q, HCDR2 comprises or consists of an amino acid sequence as set forth in ISY$_1$SGY$_2$Y$_3$T (SEQ ID NO: 444), wherein Y$_1$ is S or G, Y$_2$ is S or Q, and Y$_3$ is S or N, HCDR3 comprises or consists of an amino acid sequence as set forth in SEQ ID NO: 12, LCDR1 comprises or consists of an amino acid sequence as set forth in SEQ ID NO: 23, LCDR2 comprises or consists of an amino acid sequence as set forth in SEQ ID NO: 21, and LCDR3 comprises or consists of an amino acid sequence as set forth in SEQ ID NO: 19; (f) (I) HCDR1 comprises or consists of an amino acid sequence as set forth in GFX$_1$FSX$_2$YX$_3$X$_4$X$_5$ (SEQ ID NO: 445), wherein X$_1$ is S or T, X$_2$ is S, K, or R, X$_3$ is W or Y, X$_4$ is I or L, and X$_5$ is S or N, HCDR2 comprises or consists of an amino acid sequence as set forth in Y$_1$IY$_2$QY$_3$Y$_4$Y$_5$EY$_6$Y$_7$YVESVKG (SEQ ID NO: 446), wherein Y$_1$ is S or N, Y$_2$ is K or H, Y$_3$ is S, Q, or H, Y$_4$ is G or A, Y$_5$ is S, H, or L, Y$_6$ is T or K, and Y$_7$ is Y, K, or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239; (II) HCDR1 comprises or consists of an amino acid sequence as set forth in X$_1$YX$_2$X$_3$X$_4$ (SEQ ID NO: 447), wherein X$_1$ is S, K, or R, X$_2$ is W or Y, X$_3$ is I or L, and X$_4$ is S or N, HCDR2 comprises or consists of an amino acid sequence as set forth in Y$_1$IY$_2$QY$_3$Y$_4$Y$_5$EY$_6$Y$_7$YVESVKG (SEQ ID NO: 446), wherein Y$_1$ is S or N, Y$_2$ is K or H, Y$_3$ is S, Q, or H, Y$_4$ is G or A, Y$_5$ is S, H, or L, Y$_6$ is T or K, and Y$_7$ is Y, K, or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239; (III) HCDR1 comprises or consists of an amino acid sequence as set forth in GFX$_1$FSX$_2$Y (SEQ ID NO: 448), wherein X$_1$ is S or T, and X$_2$ is S, K, or R, HCDR2 comprises or consists of an amino acid sequence as set forth in Y$_1$QY$_2$Y$_3$Y$_4$E (SEQ ID NO: 449), wherein Y$_1$ is K or H, Y$_2$ is S, Q, or H, Y$_3$ is G or A, and Y$_4$ is S, H, or L, HCDR3 comprises or consists of an amino acid sequence as set forth in SEQ ID NO: 228, LCDR1 comprises or consists of an amino acid sequence as set forth in SEQ ID NO: 240, LCDR2 comprises or consists of an amino acid sequence as set forth in SEQ ID NO: 241, and LCDR3 comprises or consists of an amino acid sequence as set forth in SEQ ID NO: 242; or (IV) HCDR1 comprises or consists of an amino acid sequence as set forth in GFX$_1$FSX$_2$YX$_3$ (SEQ ID NO: 450), wherein X$_1$ is S or T, X$_2$ is S, K, or R, and X$_3$ is W or Y, HCDR2 comprises or consists of an amino acid sequence as set forth in IY$_1$QY$_2$Y$_3$Y$_4$EY$_5$ (SEQ ID NO: 451), wherein Y$_1$ is K or H, Y$_2$ is S, Q, or H, Y$_3$ is G or A, Y$_4$ is S, H, or L, and Y$_5$ is T or K, HCDR3 comprises or consists of an amino acid sequence as set forth in SEQ ID NO: 232, LCDR1 comprises or consists of an amino acid sequence as set forth in SEQ ID NO: 243, LCDR2 comprises or consists of an amino acid sequence as set forth in SEQ ID NO: 241, and LCDR3 comprises or consists of an amino acid sequence as set forth in SEQ ID NO: 239; (g) (I) HCDR1 comprises or consists of an amino acid sequence as set forth in GFX$_1$FSX$_2$YX$_3$X$_4$X$_5$ (SEQ ID NO: 445), wherein X$_1$ is S or T, X$_2$ is S, K, or R, X$_3$ is W or Y, X$_4$ is I or L, and X$_5$ is S or N, HCDR2 comprises or consists of an amino acid sequence as set forth in SIHQY$_1$Y$_2$Y$_3$EY$_4$Y$_5$YVESVKG (SEQ ID NO: 453), wherein Y$_1$ is Q or H, Y$_2$ is G or A, Y$_3$ is H or L, Y$_4$ is T or K, and Y$_5$ is K or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239; (II) HCDR1 comprises or consists of an amino acid sequence as set forth in X$_1$YX$_2$X$_3$X$_4$ (SEQ ID NO: 447), wherein X$_1$ is S, K, or R, X$_2$ is W or Y, X$_3$ is I or L, and X$_4$ is S or N, HCDR2 comprises or consists of an amino acid sequence as set forth in SIHQY$_1$Y$_2$Y$_3$EY$_4$Y$_5$YVESVKG (SEQ ID NO: 453), wherein Y$_1$ is Q or H, Y$_2$ is G or A, Y$_3$ is H or L, Y$_4$ is T or K, and Y$_5$ is K or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239; (III) HCDR1 comprises or consists of an amino acid sequence as set forth in GFX$_1$FSX$_2$Y (SEQ ID NO: 448), wherein X$_1$ is S or T, and X$_2$ is S, K, or R, HCDR2 comprises or consists of an amino acid sequence as set forth in HQY$_1$Y$_2$Y$_3$E (SEQ ID NO: 456), wherein Y$_1$ is Q or H, Y$_2$ is G or A, and Y$_3$ is H or L, HCDR3 comprises or consists of an amino acid sequence as set forth in SEQ ID NO: 228, LCDR1 comprises or consists of an amino acid sequence as set forth in SEQ ID NO: 240, LCDR2 comprises or consists of an amino acid sequence as set forth in SEQ ID NO: 241, and LCDR3 comprises or consists of an amino acid sequence as set forth in SEQ ID NO: 242; or (IV) HCDR1 comprises or consists of an amino acid sequence as set forth in GFX$_1$FSX$_2$YX$_3$ (SEQ ID NO: 450), wherein X$_1$ is S or T, X$_2$ is S, K, or R, and X$_3$ is W or Y, HCDR2 comprises or consists of an amino acid sequence as set forth in IHQY$_1$Y$_2$Y$_3$EY$_4$ (SEQ ID NO: 458), wherein Y$_1$ is Q or H, Y$_2$ is G or A, Y$_3$ is H or L, and Y$_4$ is T or K, HCDR3 comprises or consists of an amino acid sequence as set forth in SEQ ID NO: 232, LCDR1 comprises or consists of an amino acid sequence as set forth in SEQ ID NO: 243, LCDR2 comprises or consists of an amino acid sequence as set forth in SEQ ID NO: 241, and LCDR3 comprises or consists of an amino acid sequence as set forth in SEQ ID NO: 239; (h) (I) HCDR1 comprises or consists of an amino acid sequence as set forth in GFTFSX$_1$YX$_2$IX$_3$ (SEQ ID NO: 452), wherein X$_1$ is S or R, X$_2$ is W or Y, and X$_3$ is S or N, HCDR2 comprises or consists of an amino acid sequence as set forth in $Y_1IY_2QY_3Y_4Y_5EY_6Y_7YVESVKG$ (SEQ ID NO: 446), wherein $Y_1$ is S or N, $Y_2$ is K or H, $Y_3$ is S, Q, or H, $Y_4$ is G or A, $Y_5$ is S, H, or L, $Y_6$ is T or K, and $Y_7$ is Y, K, or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239; (II) HCDR1 comprises or consists of an amino acid sequence as set forth in $X_1YX_2IX_3$ (SEQ ID NO: 454), wherein $X_1$ is S or R, $X_2$ is W or Y, and $X_3$ is S or N, HCDR2 comprises or consists of an amino acid sequence as set forth in $Y_1IY_2QY_3Y_4Y_5EY_6Y_7YVESVKG$ (SEQ ID NO: 446), wherein $Y_1$ is S or N, $Y_2$ is K or H, $Y_3$ is S, Q, or H, $Y_4$ is G or A, $Y_5$ is S, H, or L, $Y_6$ is T or K, and $Y_7$ is Y, K, or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239; (III) HCDR1 comprises or consists of an amino acid sequence as set forth in $GFTFSX_1Y$ (SEQ ID NO: 455), wherein $X_1$ is S or R, HCDR2 comprises or consists of an amino acid sequence as set forth in $Y_1QY_2Y_3Y_4E$ (SEQ ID NO: 449), wherein $Y_1$ is K or H, $Y_2$ is S, Q, or H, $Y_3$ is G or A, and $Y_4$ is S, H, or L, HCDR3 comprises or consists of an amino acid sequence as set forth in SEQ ID NO: 228, LCDR1 comprises or consists of an amino acid sequence as set forth in SEQ ID NO: 240, LCDR2 comprises or consists of an amino acid sequence as set forth in SEQ ID NO: 241, and LCDR3 comprises or consists of an amino acid sequence as set forth in SEQ ID NO: 242; or (IV) HCDR1 comprises or consists of an amino acid sequence as set forth in $GFTFSX_1YX_2$ (SEQ ID NO: 457), wherein $X_1$ is S or R, and $X_2$ is W or Y, HCDR2 comprises or consists of an amino acid sequence as set forth in $IY_1QY_2Y_3Y_4EY_5$ (SEQ ID NO: 451), wherein $Y_1$ is K or H, $Y_2$ is S, Q, or H, $Y_3$ is G or A, $Y_4$ is S, H, or L, and $Y_5$ is T or K, HCDR3 comprises or consists of an amino acid sequence as set forth in SEQ ID NO: 232, LCDR1 comprises or consists of an amino acid sequence as set forth in SEQ ID NO: 243, LCDR2 comprises or consists of an amino acid sequence as set forth in SEQ ID NO: 241, and LCDR3 comprises or consists of an amino acid sequence as set forth in SEQ ID NO: 239; or (i) (I) HCDR1 comprises or consists of an amino acid sequence as set forth in $GFTFSX_1YX_2IX_3$ (SEQ ID NO: 452), wherein $X_1$ is S or R, $X_2$ is W or Y, and $X_3$ is S or N, HCDR2 comprises or consists of an amino acid sequence as set forth in $SIHQY_1Y_2Y_3EY_4Y_5YVESVKG$ (SEQ ID NO: 453), wherein $Y_1$ is Q or H, $Y_2$ is G or A, $Y_3$ is H or L, $Y_4$ is T or K, and $Y_5$ is K or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239; (II) HCDR1 comprises or consists of an amino acid sequence as set forth in $X_1YX_2IX_3$ (SEQ ID NO: 454), wherein $X_1$ is S or R, $X_2$ is W or Y, and $X_3$ is S or N, HCDR2 comprises or consists of an amino acid sequence as set forth in $SIHQY_1Y_2Y_3EY_4Y_5YVESVKG$ (SEQ ID NO: 453), wherein $Y_1$ is Q or H, $Y_2$ is G or A, $Y_3$ is H or L, $Y_4$ is T or K, and $Y_5$ is K or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239; (III) HCDR1 comprises or consists of an amino acid sequence as set forth in $GFTFSX_1Y$ (SEQ ID NO: 455), wherein $X_1$ is S or R, HCDR2 comprises or consists of an amino acid sequence as set forth in $HQY_1Y_2Y_3E$ (SEQ ID NO: 456), wherein $Y_1$ is Q or H, $Y_2$ is G or A, and $Y_3$ is H or L, HCDR3 comprises or consists of an amino acid sequence as set forth in SEQ ID NO: 228, LCDR1 comprises or consists of an amino acid sequence as set forth in SEQ ID NO: 240, LCDR2 comprises or consists of an amino acid sequence as set forth in SEQ ID NO: 241, and LCDR3 comprises or consists of an amino acid sequence as set forth in SEQ ID NO: 242; or (IV) HCDR1 comprises or consists of an amino acid sequence as set forth in $GFTFSX_1YX_2$ (SEQ ID NO: 457), wherein $X_1$ is S or R, and $X_2$ is W or Y, HCDR2 comprises or consists of an amino acid sequence as set forth in $IHQY_1Y_2Y_3EY_4$ (SEQ ID NO: 458), wherein $Y_1$ is Q or H, $Y_2$ is G or A, $Y_3$ is H or L, and $Y_4$ is T or K, HCDR3 comprises or consists of an amino acid sequence as set forth in SEQ ID NO: 232, LCDR1 comprises or consists of an amino acid sequence as set forth in SEQ ID NO: 243, LCDR2 comprises or consists of an amino acid sequence as set forth in SEQ ID NO: 241, and LCDR3 comprises or consists of an amino acid sequence as set forth in SEQ ID NO: 239.

In some embodiments of the invention, the antibody or antigen binding fragment comprises three heavy chain complementarity determining regions (HCDR1, HCDR2, and HCDR3) and three light chain complementarity determining regions (LCDR1, LCDR2, and LCDR3), wherein: (a) (I) HCDR1 comprises or consists of an amino acid sequence as set forth in SEQ ID NO: 310, HCDR2 comprises or consists of an amino acid sequence as set forth in SEQ ID NO: 311, HCDR3 comprises or consists of an amino acid sequence as set forth in $GX_1X_2X_3GX_4LGFDH$ (SEQ ID NO: 459), wherein $X_1$ is A or S, $X_2$ is V or L, $X_3$ is A or P, and $X_4$ is Q or L, LCDR1 comprises or consists of an amino acid sequence as set forth in SEQ ID NO: 320, LCDR2 comprises or consists of an amino acid sequence as set forth in $GNSNRPY_1$ (SEQ ID NO: 460), wherein $Y_1$ is S or N, and LCDR3 comprises or consists of an amino acid sequence as set forth in $QSYZ_1Z_2Z_3Z_4Z_5Z_6Z_7V$ (SEQ ID NO: 461), wherein $Z_1$ is Y, D, or G, $Z_2$ is T, S, or A, $Z_3$ is S, P, or F, $Z_4$ is S, T, or P, $Z_5$ is H, S, or R, $Z_6$ is G, S, or F, and $Z_7$ is P, S, or V; (II) HCDR1 comprises or consists of an amino acid sequence as set forth in SEQ ID NO: 229, HCDR2 comprises or consists of an amino acid sequence as set forth in SEQ ID NO: 311, HCDR3 comprises or consists of an amino acid sequence as set forth in $GX_1X_2X_3GX_4LGFDH$ (SEQ ID NO: 459), wherein $X_1$ is A or S, $X_2$ is V or L, $X_3$ is A or P, and $X_4$ is Q or L, LCDR1 comprises or consists of an amino acid sequence as set forth in SEQ ID NO: 320, LCDR2 comprises or consists of an amino acid sequence as set forth in $GNSNRPY_1$ (SEQ ID NO: 460), wherein $Y_1$ is S or N, and LCDR3 comprises or consists of an amino acid sequence as set forth in $QSYZ_1Z_2Z_3Z_4Z_5Z_6Z_7V$ (SEQ ID NO: 461), wherein $Z_1$ is Y, D, or G, $Z_2$ is T, S, or A, $Z_3$ is S, P, or F, $Z_4$ is S, T, or P, $Z_5$ is H, S, or R, $Z_6$ is G, S, or F, and $Z_7$ is P, S, or V; (III) HCDR1 comprises or consists of an amino acid sequence as set forth in SEQ ID NO: 80, HCDR2 comprises or consists of an amino acid sequence as set forth in SEQ ID NO: 313, HCDR3 comprises or consists of an amino acid sequence as set forth in GX$_1$X$_2$X$_3$GX$_4$LGFDH (SEQ ID NO: 459), wherein X$_1$ is A or S, X$_2$ is V or L, X$_3$ is A or P, and X$_4$ is Q or L, LCDR1 comprises or consists of an amino acid sequence as set forth in SEQ ID NO: 323, LCDR2 comprises or consists of an amino acid sequence as set forth in SEQ ID NO: 324, and LCDR3 comprises or consists of an amino acid sequence as set forth in YZ$_1$Z$_2$Z$_3$Z$_4$Z$_5$Z$_6$Z$_7$ (SEQ ID NO: 462), wherein Z$_1$ is Y, D, or G, Z$_2$ is T, S, or A, Z$_3$ is S, P, or F, Z$_4$ is S, T, or P, Z$_5$ is H, S, or R, Z$_6$ is G, S, or F, and Z$_7$ is P, S, or V; or (IV) HCDR1 comprises or consists of an amino acid sequence as set forth in SEQ ID NO: 82, HCDR2 comprises or consists of an amino acid sequence as set forth in SEQ ID NO: 314, HCDR3 comprises or consists of an amino acid sequence as set forth in ARGX$_1$X$_2$X$_3$GX$_4$LGFDH (SEQ ID NO: 463), wherein X$_1$ is A or S, X$_2$ is V or L, X$_3$ is A or P, and X$_4$ is Q or L, LCDR1 comprises or consists of an amino acid sequence as set forth in SEQ ID NO: 326, LCDR2 comprises or consists of an amino acid sequence as set forth in SEQ ID NO: 324, and LCDR3 comprises or consists of an amino acid sequence as set forth in QSYZ$_1$Z$_2$Z$_3$Z$_4$Z$_5$Z$_6$Z$_7$V (SEQ ID NO: 461), wherein Z$_1$ is Y, D, or G, Z$_2$ is T, S, or A, Z$_3$ is S, P, or F, Z$_4$ is S, T, or P, Z$_5$ is H, S, or R, Z$_6$ is G, S, or F, and Z$_7$ is P, S, or V; (b) (I) HCDR1 comprises or consists of an amino acid sequence as set forth in GFTFX$_1$X$_2$YAX$_3$X$_4$ (SEQ ID NO: 464), wherein X$_1$ is S or G, X$_2$ is S or T, X$_3$ is I or M, and X$_4$ is S or T, HCDR2 comprises or consists of an amino acid sequence as set forth in Y$_1$ISY$_2$Y$_3$GY$_4$Y$_5$Y$_6$Y$_7$YAY$_8$SVKG (SEQ ID NO: 465), wherein Y$_1$ is A or S, Y$_2$ is A, S, or G, Y$_3$ is S or H, Y$_4$ is G or Y, Y$_5$ is S or Y, Y$_6$ is T or A, Y$_7$ is Y, R, or N, and Y$_8$ is E or G, HCDR3 comprises or consists of an amino acid sequence as set forth in SEQ ID NO: 331, LCDR1 comprises or consists of an amino acid sequence as set forth in SEQ ID NO: 337, LCDR2 comprises or consists of an amino acid sequence as set forth in SEQ ID NO: 338, and LCDR3 comprises or consists of an amino acid sequence as set forth in SEQ ID NO: 339; (II) HCDR1 comprises or consists of an amino acid sequence as set forth in X$_1$YAX$_2$X$_3$ (SEQ ID NO: 466), wherein X$_1$ is S or T, X$_2$ is I or M, and X$_3$ is S or T, HCDR2 comprises or consists of an amino acid sequence as set forth in Y$_1$ISY$_2$Y$_3$GY$_4$Y$_5$Y$_6$Y$_7$YAY$_8$SVKG (SEQ ID NO: 465), wherein Y$_1$ is A or S, Y$_2$ is A, S, or G, Y$_3$ is S or H, Y$_4$ is G or Y, Y$_5$ is S or Y, Y$_6$ is T or A, Y$_7$ is Y, R, or N, and Y$_8$ is E or G, HCDR3 comprises or consists of an amino acid sequence as set forth in SEQ ID NO: 331, LCDR1 comprises or consists of an amino acid sequence as set forth in SEQ ID NO: 337, LCDR2 comprises or consists of an amino acid sequence as set forth in SEQ ID NO: 338, and LCDR3 comprises or consists of an amino acid sequence as set forth in SEQ ID NO: 339; (III) HCDR1 comprises or consists of an amino acid sequence as set forth in GFTFX$_1$X$_2$Y (SEQ ID NO: 467), wherein X$_1$ is S or G, and X$_2$ is S or T, HCDR2 comprises or consists of an amino acid sequence as set forth in SY$_1$Y$_2$GY$_3$Y$_4$ (SEQ ID NO: 468), wherein Y$_1$ is A, S, or G, Y$_2$ is S or H, Y$_3$ is G or Y, and Y$_4$ is S or Y, HCDR3 comprises or consists of an amino acid sequence as set forth in SEQ ID NO: 331, LCDR1 comprises or consists of an amino acid sequence as set forth in SEQ ID NO: 340, LCDR2 comprises or consists of an amino acid sequence as set forth in SEQ ID NO: 341, and LCDR3 comprises or consists of an amino acid sequence as set forth in SEQ ID NO: 342; or (IV) HCDR1 comprises or consists of an amino acid sequence as set forth in GFTFX$_1$X$_2$YA (SEQ ID NO: 469), wherein X$_1$ is S or G, and X$_2$ is S or T, HCDR2 comprises or consists of an amino acid sequence as set forth in ISY$_1$Y$_2$GY$_3$Y$_4$T (SEQ ID NO: 470), wherein Y$_1$ is S or G, Y$_2$ is S or H, Y$_3$ is G or Y, and Y$_4$ is S or Y, HCDR3 comprises or consists of an amino acid sequence as set forth in SEQ ID NO: 332, LCDR1 comprises or consists of an amino acid sequence as set forth in SEQ ID NO: 343, LCDR2 comprises or consists of an amino acid sequence as set forth in SEQ ID NO: 341, and LCDR3 comprises or consists of an amino acid sequence as set forth in SEQ ID NO: 339; or (c) (I) HCDR1 comprises or consists of an amino acid sequence as set forth in GFTFX$_1$X$_2$YAX$_3$X$_4$ (SEQ ID NO: 464), wherein X$_1$ is S or G, X$_2$ is S or T, X$_3$ is I or M, and X$_4$ is S or T, HCDR2 comprises or consists of an amino acid sequence as set forth in SISY$_1$Y$_2$GYYY$_3$Y$_4$YAY$_5$SVKG (SEQ ID NO: 471), wherein Y$_1$ is A or S, Y$_2$ is S or H, Y$_3$ is T or A, Y$_4$ is R or N, and Y$_5$ is E or G, HCDR3 comprises or consists of an amino acid sequence as set forth in SEQ ID NO: 331, LCDR1 comprises or consists of an amino acid sequence as set forth in SEQ ID NO: 337, LCDR2 comprises or consists of an amino acid sequence as set forth in SEQ ID NO: 338, and LCDR3 comprises or consists of an amino acid sequence as set forth in SEQ ID NO: 339; (II) HCDR1 comprises or consists of an amino acid sequence as set forth in X$_1$YAX$_2$X$_3$ (SEQ ID NO: 466), wherein X$_1$ is S or T, X$_2$ is I or M, and X$_3$ is S or T, HCDR2 comprises or consists of an amino acid sequence as set forth in SISY$_1$Y$_2$GYYY$_3$Y$_4$YAY$_5$SVKG (SEQ ID NO: 471), wherein Y$_1$ is A or S, Y$_2$ is S or H, Y$_3$ is T or A, Y$_4$ is R or N, and Y$_5$ is E or G, HCDR3 comprises or consists of an amino acid sequence as set forth in SEQ ID NO: 331, LCDR1 comprises or consists of an amino acid sequence as set forth in SEQ ID NO: 337, LCDR2 comprises or consists of an amino acid sequence as set forth in SEQ ID NO: 338, and LCDR3 comprises or consists of an amino acid sequence as set forth in SEQ ID NO: 339; (III) HCDR1 comprises or consists of an amino acid sequence as set forth in GFTFX$_1$X$_2$Y (SEQ ID NO: 467), wherein X$_1$ is S or G, and X$_2$ is S or T, HCDR2 comprises or consists of an amino acid sequence as set forth in SY$_1$Y$_2$GYY (SEQ ID NO: 472), wherein Y$_1$ is A or S, and Y$_2$ is S or H, HCDR3 comprises or consists of an amino acid sequence as set forth in SEQ ID NO: 331, LCDR1 comprises or consists of an amino acid sequence as set forth in SEQ ID NO: 340, LCDR2 comprises or consists of an amino acid sequence as set forth in SEQ ID NO: 341, and LCDR3 comprises or consists of an amino acid sequence as set forth in SEQ ID NO: 342; or (IV) HCDR1 comprises or consists of an amino acid sequence as set forth in GFTFX$_1$X$_2$YA (SEQ ID NO: 469), wherein X$_1$ is S or G, and X$_2$ is S or T, HCDR2 comprises or consists of an amino acid sequence as set forth in ISY$_1$Y$_2$G (SEQ ID NO: 473), wherein Y$_1$ is A, S, or G, and Y$_2$ is S or H, HCDR3 comprises or consists of an amino acid sequence as set forth in SEQ ID NO: 332, LCDR1 comprises or consists of an amino acid sequence as set forth in SEQ ID NO: 343, LCDR2 comprises or consists of an amino acid sequence as set forth in SEQ ID NO: 341, and LCDR3 comprises or consists of an amino acid sequence as set forth in SEQ ID NO: 339.

In some embodiments of the invention, the antibody or antigen binding fragment comprises three heavy chain complementarity determining regions (HCDR1, HCDR2, and HCDR3) and three light chain complementarity determining regions (LCDR1, LCDR2, and LCDR3), wherein: (a) (I) HCDR1 comprises or consists of an amino acid sequence as set forth in SEQ ID NO: 28, HCDR2 comprises or consists of an amino acid sequence as set forth in any one of SEQ ID NOs: 29, 119, and 190, HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in any one of SEQ ID NOs: 43, 126, 134, 145, 172, 178, and 184; (II) HCDR1 comprises or consists of an amino acid sequence as set forth in SEQ ID NO: 31, HCDR2 comprises or consists of an amino acid sequence as set forth in any one of SEQ ID NOs: 29, 119, and 190, HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in any one of SEQ ID NOs: 43, 126, 134, 145, 172, 178, and 184; (III) HCDR1 comprises or consists of an amino acid sequence as set forth in SEQ ID NO: 32, HCDR2 comprises or consists of an amino acid sequence as set forth in any one of SEQ ID NOs: 33, 120, and 191, HCDR3 comprises or consists of an amino acid sequence as set forth in SEQ ID NO: 30, LCDR1 comprises or consists of an amino acid sequence as set forth in SEQ ID NO: 44, LCDR2 comprises or consists of an amino acid sequence as set forth in SEQ ID NO: 45, and LCDR3 comprises or consists of an amino acid sequence as set forth in any one of SEQ ID NOs: 46, 127, 135, 146, 173, 179, and 185; or (IV) HCDR1 comprises or consists of an amino acid sequence as set forth in SEQ ID NO: 34, HCDR2 comprises or consists of an amino acid sequence as set forth in any one of SEQ ID NOs: 35, 121, and 192, HCDR3 comprises or consists of an amino acid sequence as set forth in SEQ ID NO: 36, LCDR1 comprises or consists of an amino acid sequence as set forth in SEQ ID NO: 47, LCDR2 comprises or consists of an amino acid sequence as set forth in SEQ ID NO: 45, and LCDR3 comprises or consists of an amino acid sequence as set forth in any one of SEQ ID NOs: 43, 126, 134, 145, 172, 178, and 184; (b) (I) HCDR1 comprises or consists of an amino acid sequence as set forth in any one of SEQ ID NOs: 4, 112, and 165, HCDR2 comprises or consists of an amino acid sequence as set forth in any one of SEQ ID NOs: 5, 100, and 151, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19; (II) HCDR1 comprises or consists of an amino acid sequence as set forth in SEQ ID NO: 7, HCDR2 comprises or consists of an amino acid sequence as set forth in any one of SEQ ID NOs: 5, 100, and 151, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19; (III) HCDR1 comprises or consists of an amino acid sequence as set forth in any one of SEQ ID NOs: 8, 113, and 166, HCDR2 comprises or consists of an amino acid sequence as set forth in any one of SEQ ID NOs: 9, 101, and 152, HCDR3 comprises or consists of an amino acid sequence as set forth in SEQ ID NO: 6, LCDR1 comprises or consists of an amino acid sequence as set forth in SEQ ID NO: 20, LCDR2 comprises or consists of an amino acid sequence as set forth in SEQ ID NO: 21, and LCDR3 comprises or consists of an amino acid sequence as set forth in SEQ ID NO: 22; or (IV) HCDR1 comprises or consists of an amino acid sequence as set forth in any one of SEQ ID NOs: 10, 114, and 167, HCDR2 comprises or consists of an amino acid sequence as set forth in any one of SEQ ID NOs: 11, 102, and 153, HCDR3 comprises or consists of an amino acid sequence as set forth in SEQ ID NO: 12, LCDR1 comprises or consists of an amino acid sequence as set forth in SEQ ID NO: 23, LCDR2 comprises or consists of an amino acid sequence as set forth in SEQ ID NO: 21, and LCDR3 comprises or consists of an amino acid sequence as set forth in SEQ ID NO: 19; or (c) (I) HCDR1 comprises or consists of an amino acid sequence as set forth in any one of SEQ ID NOs: 226, 367, and 378, HCDR2 comprises or consists of an amino acid sequence as set forth in any one of SEQ ID NOs: 227, 368, and 379, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239; (II) HCDR1 comprises or consists of an amino acid sequence as set forth in any one of SEQ ID NOs: 229, 369, and 380, HCDR2 comprises or consists of an amino acid sequence as set forth in any one of SEQ ID NOs: 227, 368, and 379, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239; (III) HCDR1 comprises or consists of an amino acid sequence as set forth in any one of SEQ ID NOs: 32, 370, and 381, HCDR2 comprises or consists of an amino acid sequence as set forth in any one of SEQ ID NOs: 230, 371, and 382, HCDR3 comprises or consists of an amino acid sequence as set forth in SEQ ID NO: 228, LCDR1 comprises or consists of an amino acid sequence as set forth in SEQ ID NO: 240, LCDR2 comprises or consists of an amino acid sequence as set forth in SEQ ID NO: 241, and LCDR3 comprises or consists of an amino acid sequence as set forth in SEQ ID NO: 242; or (IV) HCDR1 comprises or consists of an amino acid sequence as set forth in any one of SEQ ID NOs: 34, 372, and 383, HCDR2 comprises or consists of an amino acid sequence as set forth in any one of SEQ ID NOs: 231, 373, and 384, HCDR3 comprises or consists of an amino acid sequence as set forth in SEQ ID NO: 232, LCDR1 comprises or consists of an amino acid sequence as set forth in SEQ ID NO: 243, LCDR2 comprises or consists of an amino acid sequence as set forth in SEQ ID NO: 241, and LCDR3 comprises or consists of an amino acid sequence as set forth in SEQ ID NO: 239.

In some embodiments of the invention, the antibody or antigen binding fragment comprises three heavy chain complementarity determining regions (HCDR1, HCDR2, and HCDR3) and three light chain complementarity determining regions (LCDR1, LCDR2, and LCDR3), wherein: (a) (I) HCDR1 comprises or consists of an amino acid sequence as set forth in SEQ ID NO: 310, HCDR2 comprises or consists of an amino acid sequence as set forth in SEQ ID NO: 311, HCDR3 comprises or consists of an amino acid sequence as set forth in any one of SEQ ID NOs: 312 and 348, LCDR1 comprises or consists of an amino acid sequence as set forth in SEQ ID NO: 320, LCDR2 comprises or consists of an amino acid sequence as set forth in any one of SEQ ID NOs: 321 and 354, and LCDR3 comprises or consists of an amino acid sequence as set forth in any one of SEQ ID NOs: 322, 355, and 361; (II) HCDR1 comprises or consists of an amino acid sequence as set forth in SEQ ID NO: 229, HCDR2 comprises or consists of an amino acid sequence as set forth in SEQ ID NO: 311, HCDR3 comprises or consists of an amino acid sequence as set forth in any one of SEQ ID NOs: 312 and 348, LCDR1 comprises or consists of an amino acid sequence as set forth in SEQ ID NO: 320, LCDR2 comprises or consists of an amino acid sequence as set forth in any one of SEQ ID NOs: 321 and 354, and LCDR3 comprises or consists of an amino acid sequence as set forth in any one of SEQ ID NOs: 322, 355, and 361; (III) HCDR1 comprises or consists of an amino acid sequence as set forth in SEQ ID NO: 80, HCDR2 comprises or consists of an amino acid sequence as set forth in SEQ ID NO: 313, HCDR3 comprises or consists of an amino acid sequence as set forth in any one of SEQ ID NOs: 312 and 348, LCDR1 comprises or consists of an amino acid sequence as set forth in SEQ ID NO: 323, LCDR2 comprises or consists of an amino acid sequence as set forth in SEQ ID NO: 324, and LCDR3 comprises or consists of an amino acid sequence as set forth in any one of SEQ ID NOs: 325, 356, and 362; or (IV) HCDR1 comprises or consists of an amino acid sequence as set forth in SEQ ID NO: 82, HCDR2 comprises or consists of an amino acid sequence as set forth in SEQ ID NO: 314, HCDR3 comprises or consists of an amino acid sequence as set forth in any one of SEQ ID NOs: 315 and 349, LCDR1 comprises or consists of an amino acid sequence as set forth in SEQ ID NO: 326, LCDR2 comprises or consists of an amino acid sequence as set forth in SEQ ID NO: 324, and LCDR3 comprises or consists of an amino acid sequence as set forth in any one of SEQ ID NOs: 322, 355, and 361; or (b) (I) HCDR1 comprises or consists of an amino acid sequence as set forth in any one of SEQ ID NOs: 270 and 407, HCDR2 comprises or consists of an amino acid sequence as set forth in any one of SEQ ID NOs: 271, 389, and 408, HCDR3 comprises or consists of an amino acid sequence as set forth in SEQ ID NO: 331, LCDR1 comprises or consists of an amino acid sequence as set forth in SEQ ID NO: 337, LCDR2 comprises or consists of an amino acid sequence as set forth in SEQ ID NO: 338, and LCDR3 comprises or consists of an amino acid sequence as set forth in SEQ ID NO: 339; (II) HCDR1 comprises or consists of an amino acid sequence as set forth in any one of SEQ ID NOs: 273 and 409, HCDR2 comprises or consists of an amino acid sequence as set forth in any one of SEQ ID NOs: 271, 389, and 408, HCDR3 comprises or consists of an amino acid sequence as set forth in SEQ ID NO: 331, LCDR1 comprises or consists of an amino acid sequence as set forth in SEQ ID NO: 337, LCDR2 comprises or consists of an amino acid sequence as set forth in SEQ ID NO: 338, and LCDR3 comprises or consists of an amino acid sequence as set forth in SEQ ID NO: 339; (III) HCDR1 comprises or consists of an amino acid sequence as set forth in any one of SEQ ID NOs:32 and 410, HCDR2 comprises or consists of an amino acid sequence as set forth in any one of SEQ ID NOs: 274, 390, and 411, HCDR3 comprises or consists of an amino acid sequence as set forth in SEQ ID NO: 331, LCDR1 comprises or consists of an amino acid sequence as set forth in SEQ ID NO: 340, LCDR2 comprises or consists of an amino acid sequence as set forth in SEQ ID NO: 341, and LCDR3 comprises or consists of an amino acid sequence as set forth in SEQ ID NO: 342; or (IV) HCDR1 comprises or consists of an amino acid sequence as set forth in any one of SEQ ID NOs: 275 and 412, HCDR2 comprises or consists of an amino acid sequence as set forth in any one of SEQ ID NOs: 276, 391, and 413, HCDR3 comprises or consists of an amino acid sequence as set forth in SEQ ID NO: 332, LCDR1 comprises or consists of an amino acid sequence as set forth in SEQ ID NO: 343, LCDR2 comprises or consists of an amino acid sequence as set forth in SEQ ID NO: 341, and LCDR3 comprises or consists of an amino acid sequence as set forth in SEQ ID NO: 339.

In some embodiments of the invention, the antibody or antigen binding fragment comprises three heavy chain complementarity determining regions (HCDR1, HCDR2, and HCDR3) and three light chain complementarity determining regions (LCDR1, LCDR2, and LCDR3) selected from: (a) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 134 (LCDR3); (b) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 126 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 126 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 127 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 126 (LCDR3); (c) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 146 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 145 (LCDR3); (d) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 173 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 172 (LCDR3); (e) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3); (III) SEQ ID NO: 32 (HCDR1), SEQ ID NO: 120 (HCDR2), SEQ ID NO: 30 (HCDR3), SEQ ID NO: 44

(LCDR1), SEQ ID NO: 45 (LCDR2), and SEQ ID NO: 179 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 178 (LCDR3); (f) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 185 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 184 (LCDR3); (g) (I) SEQ ID NO: 4 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 8 (HCDR1), SEQ ID NO: 101 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 10 (HCDR1), SEQ ID NO: 102 (HCDR2), SEQ ID NO: 12 (HCDR3), SEQ ID NO: 23 (LCDR1), SEQ ID NO: 21 (LCDR2), and SEQ ID NO: 19 (LCDR3); (h) (I) SEQ ID NO: 112 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 113 (HCDR1), SEQ ID NO: 101 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 114 (HCDR1), SEQ ID NO: 102 (HCDR2), SEQ ID NO: 12 (HCDR3), SEQ ID NO: 23 (LCDR1), SEQ ID NO: 21 (LCDR2), and SEQ ID NO: 19 (LCDR3); (i) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 43 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 43 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 46 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 43 (LCDR3); (j) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 126 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 126 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 127 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 126 (LCDR3); (k) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 134 (LCDR3); (1) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 145 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 145 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 146 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 145 (LCDR3); (m) (I) SEQ ID NO: 4 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 8 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 10 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3); (n) (I) SEQ ID NO: 112 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 113 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 114 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3); (o) (I) SEQ ID NO: 165 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 166 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 167 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3); (p) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 172 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 172 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 173 (LCDR3); or (IV) SEQ ID NO: 34 (HCDR1), SEQ ID NO:

35 (HCDR2), SEQ ID NO: 36 (HCDR3), SEQ ID NO: 47 (LCDR1), SEQ ID NO: 45 (LCDR2), and SEQ ID NO: 172 (LCDR3); (q) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 178 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 178 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 179 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 178 (LCDR3); (r) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 184 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 184 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 185 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 184 (LCDR3); (s) (I) SEQ ID NO: 28 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 191 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 192 (HCDR2), SEQ ID NO: 36 (HCDR3), SEQ ID NO: 47 (LCDR1), SEQ ID NO: 45 (LCDR2), and SEQ ID NO: 134 (LCDR3); (t) (I) SEQ ID NO: 28 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 172 (LCDR3); (II) SEQ ID NO: 31 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 172 (LCDR3); (III) SEQ ID NO: 32 (HCDR1), SEQ ID NO: 191 (HCDR2), SEQ ID NO: 30 (HCDR3), SEQ ID NO: 44 (LCDR1), SEQ ID NO: 45 (LCDR2), and SEQ ID NO: 173 (LCDR3); or (IV) SEQ ID NO: 34 (HCDR1), SEQ ID NO: 192 (HCDR2), SEQ ID NO: 36 (HCDR3), SEQ ID NO: 47 (LCDR1), SEQ ID NO: 45 (LCDR2), and SEQ ID NO: 172 (LCDR3); (u) (I) SEQ ID NO: 4 (HCDR1), SEQ ID NO: 5 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 5 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 8 (HCDR1), SEQ ID NO: 9 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 10 (HCDR1), SEQ ID NO: 11 (HCDR2), SEQ ID NO: 12 (HCDR3), SEQ ID NO: 23 (LCDR1), SEQ ID NO: 21 (LCDR2), and SEQ ID NO: 19 (LCDR3); (v) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 43 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 43 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 46 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 43 (LCDR3); (w) (I) SEQ ID NO: 367 (HCDR1), SEQ ID NO: 368 (HCDR2), SEQ ID NO: 228 (HCDR3), SEQ ID NO: 237 (LCDR1), SEQ ID NO: 238 (LCDR2), and SEQ ID NO: 239 (LCDR3); (II) SEQ ID NO: 369 (HCDR1), SEQ ID NO: 368 (HCDR2), SEQ ID NO: 228 (HCDR3), SEQ ID NO: 237 (LCDR1), SEQ ID NO: 238 (LCDR2), and SEQ ID NO: 239 (LCDR3); (III) SEQ ID NO: 370 (HCDR1), SEQ ID NO: 371 (HCDR2), SEQ ID NO: 228 (HCDR3), SEQ ID NO: 240 (LCDR1), SEQ ID NO: 241 (LCDR2), and SEQ ID NO: 242 (LCDR3); or (IV) SEQ ID NO: 372 (HCDR1), SEQ ID NO: 373 (HCDR2), SEQ ID NO: 232 (HCDR3), SEQ ID NO: 243 (LCDR1), SEQ ID NO: 241 (LCDR2), and SEQ ID NO: 239 (LCDR3); (x) (I) SEQ ID NO: 378 (HCDR1), SEQ ID NO: 379 (HCDR2), SEQ ID NO: 228 (HCDR3), SEQ ID NO: 237 (LCDR1), SEQ ID NO: 238 (LCDR2), and SEQ ID NO: 239 (LCDR3); (II) SEQ ID NO: 380 (HCDR1), SEQ ID NO: 379 (HCDR2), SEQ ID NO: 228 (HCDR3), SEQ ID NO: 237 (LCDR1), SEQ ID NO: 238 (LCDR2), and SEQ ID NO: 239 (LCDR3); (III) SEQ ID NO: 381 (HCDR1), SEQ ID NO: 382 (HCDR2), SEQ ID NO: 228 (HCDR3), SEQ ID NO: 240 (LCDR1), SEQ ID NO: 241 (LCDR2), and SEQ ID NO: 242 (LCDR3); or (IV) SEQ ID NO: 383 (HCDR1), SEQ ID NO: 384 (HCDR2), SEQ ID NO: 232 (HCDR3), SEQ ID NO: 243 (LCDR1), SEQ ID NO: 241 (LCDR2), and SEQ ID NO: 239 (LCDR3); (y) (I) SEQ ID NO: 226 (HCDR1), SEQ ID NO: 227 (HCDR2), SEQ ID NO: 228 (HCDR3), SEQ ID NO: 237 (LCDR1), SEQ ID NO: 238 (LCDR2), and SEQ ID NO: 239 (LCDR3); (II) SEQ ID NO: 229 (HCDR1), SEQ ID NO: 227 (HCDR2), SEQ ID NO: 228 (HCDR3), SEQ ID NO: 237 (LCDR1), SEQ ID NO: 238 (LCDR2), and SEQ ID NO: 239 (LCDR3); (III) SEQ ID NO: 32 (HCDR1), SEQ ID NO: 230 (HCDR2), SEQ ID NO: 228 (HCDR3), SEQ ID NO: 240 (LCDR1), SEQ ID NO: 241 (LCDR2), and SEQ ID NO: 242 (LCDR3); or (IV) SEQ ID NO: 34 (HCDR1), SEQ ID NO: 231 (HCDR2), SEQ ID NO: 232 (HCDR3), SEQ ID NO: 243 (LCDR1), SEQ ID NO: 241 (LCDR2), and SEQ ID NO: 239 (LCDR3); (z) (I) SEQ ID NO: 270 (HCDR1), SEQ ID NO: 271 (HCDR2), SEQ ID NO: 272 (HCDR3), SEQ ID NO: 282 (LCDR1), SEQ ID NO: 261 (LCDR2), and SEQ ID NO: 283 (LCDR3); (II) SEQ ID NO: 273 (HCDR1), SEQ ID NO: 271 (HCDR2), SEQ ID NO: 272 (HCDR3), SEQ ID NO: 282 (LCDR1), SEQ ID NO: 261 (LCDR2), and SEQ ID NO: 283 (LCDR3); (III) SEQ ID NO: 32 (HCDR1), SEQ ID NO: 274 (HCDR2), SEQ ID NO: 272 (HCDR3), SEQ ID NO: 284 (LCDR1), SEQ ID NO: 241 (LCDR2), and SEQ ID NO: 285 (LCDR3); or (IV) SEQ ID NO: 275 (HCDR1), SEQ ID NO: 276 (HCDR2), SEQ ID NO: 277 (HCDR3), SEQ ID NO: 286 (LCDR1), SEQ ID NO: 241 (LCDR2), and SEQ ID NO: 283 (LCDR3); or (aa) (I) SEQ ID NO: 291 (HCDR1), SEQ ID NO: 292 (HCDR2), SEQ ID NO: 293 (HCDR3), SEQ ID NO: 237 (LCDR1), SEQ ID NO: 238 (LCDR2), and SEQ ID NO: 304 (LCDR3); (II) SEQ ID NO: 294 (HCDR1), SEQ ID NO: 292 (HCDR2), SEQ ID NO: 293 (HCDR3), SEQ ID NO: 237 (LCDR1), SEQ ID NO: 238 (LCDR2), and SEQ ID NO: 304 (LCDR3); (III) SEQ ID NO: 295 (HCDR1), SEQ ID NO: 296 (HCDR2), SEQ ID NO: 293 (HCDR3), SEQ ID NO: 240 (LCDR1), SEQ ID NO: 241 (LCDR2), and SEQ ID NO: 305 (LCDR3); or (IV) SEQ ID NO: 297 (HCDR1), SEQ ID NO: 298 (HCDR2), SEQ ID NO: 299 (HCDR3), SEQ ID NO: 243 (LCDR1), SEQ ID NO: 241 (LCDR2), and SEQ ID NO: 304 (LCDR3).

In some embodiments of the invention, the antibody or antigen binding fragment comprises three heavy chain complementarity determining regions (HCDR1, HCDR2, and HCDR3) and three light chain complementarity determining regions (LCDR1, LCDR2, and LCDR3) selected from: (a) (I) SEQ ID NO: 52 (HCDR1), SEQ ID NO: 53 (HCDR2), SEQ ID NO: 54 (HCDR3), SEQ ID NO: 65 (LCDR1), SEQ ID NO: 66 (LCDR2), and SEQ ID NO: 67 (LCDR3); (II) SEQ ID NO: 55 (HCDR1), SEQ ID NO: 53 (HCDR2), SEQ ID NO: 54 (HCDR3), SEQ ID NO: 65 (LCDR1), SEQ ID NO: 66 (LCDR2), and SEQ ID NO: 67 (LCDR3); (III) SEQ ID NO: 56 (HCDR1), SEQ ID NO: 57 (HCDR2), SEQ ID NO: 54 (HCDR3), SEQ ID NO: 68 (LCDR1), SEQ ID NO: 69 (LCDR2), and SEQ ID NO: 70 (LCDR3); or (IV) SEQ ID NO: 58 (HCDR1), SEQ ID NO: 59 (HCDR2), SEQ ID NO: 60 (HCDR3), SEQ ID NO: 71 (LCDR1), SEQ ID NO: 69 (LCDR2), and SEQ ID NO: 67 (LCDR3); (b) (I) SEQ ID NO: 76 (HCDR1), SEQ ID NO: 77 (HCDR2), SEQ ID NO: 78 (HCDR3), SEQ ID NO: 89 (LCDR1), SEQ ID NO: 90 (LCDR2), and SEQ ID NO: 91 (LCDR3); (II) SEQ ID NO: 79 (HCDR1), SEQ ID NO: 77 (HCDR2), SEQ ID NO: 78 (HCDR3), SEQ ID NO: 89 (LCDR1), SEQ ID NO: 90 (LCDR2), and SEQ ID NO: 91 (LCDR3); (III) SEQ ID NO: 80 (HCDR1), SEQ ID NO: 81 (HCDR2), SEQ ID NO: 78 (HCDR3), SEQ ID NO: 92 (LCDR1), SEQ ID NO: 93 (LCDR2), and SEQ ID NO: 94 (LCDR3); or (IV) SEQ ID NO: 82 (HCDR1), SEQ ID NO: 83 (HCDR2), SEQ ID NO: 84 (HCDR3), SEQ ID NO: 95 (LCDR1), SEQ ID NO: 93 (LCDR2), and SEQ ID NO: 91 (LCDR3); (c) (I) SEQ ID NO: 310 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 361 (LCDR3); (II) SEQ ID NO: 229 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 361 (LCDR3); (III) SEQ ID NO: 80 (HCDR1), SEQ ID NO: 313 (HCDR2), SEQ ID NO: 348 (HCDR3), SEQ ID NO: 323 (LCDR1), SEQ ID NO: 324 (LCDR2), and SEQ ID NO: 362 (LCDR3); or (IV) SEQ ID NO: 82 (HCDR1), SEQ ID NO: 314 (HCDR2), SEQ ID NO: 349 (HCDR3), SEQ ID NO: 326 (LCDR1), SEQ ID NO: 324 (LCDR2), and SEQ ID NO: 361 (LCDR3); (d) (I) SEQ ID NO: 270 (HCDR1), SEQ ID NO: 389 (HCDR2), SEQ ID NO: 331 (HCDR3), SEQ ID NO: 337 (LCDR1), SEQ ID NO: 338 (LCDR2), and SEQ ID NO: 339 (LCDR3); (II) SEQ ID NO: 273 (HCDR1), SEQ ID NO: 389 (HCDR2), SEQ ID NO: 331 (HCDR3), SEQ ID NO: 337 (LCDR1), SEQ ID NO: 338 (LCDR2), and SEQ ID NO: 339 (LCDR3); (III) SEQ ID NO: 32 (HCDR1), SEQ ID NO: 390 (HCDR2), SEQ ID NO: 331 (HCDR3), SEQ ID NO: 340 (LCDR1), SEQ ID NO: 341 (LCDR2), and SEQ ID NO: 342 (LCDR3); or (IV) SEQ ID NO: 275 (HCDR1), SEQ ID NO: 391 (HCDR2), SEQ ID NO: 332 (HCDR3), SEQ ID NO: 343 (LCDR1), SEQ ID NO: 341 (LCDR2), and SEQ ID NO: 339 (LCDR3); (e) (I) SEQ ID NO: 407 (HCDR1), SEQ ID NO: 408 (HCDR2), SEQ ID NO: 331 (HCDR3), SEQ ID NO: 337 (LCDR1), SEQ ID NO: 338 (LCDR2), and SEQ ID NO: 339 (LCDR3); (II) SEQ ID NO: 409 (HCDR1), SEQ ID NO: 408 (HCDR2), SEQ ID NO: 331 (HCDR3), SEQ ID NO: 337 (LCDR1), SEQ ID NO: 338 (LCDR2), and SEQ ID NO: 339 (LCDR3); (III) SEQ ID NO: 410 (HCDR1), SEQ ID NO: 411 (HCDR2), SEQ ID NO: 331 (HCDR3), SEQ ID NO: 340 (LCDR1), SEQ ID NO: 341 (LCDR2), and SEQ ID NO: 342 (LCDR3); or (IV) SEQ ID NO: 412 (HCDR1), SEQ ID NO: 413 (HCDR2), SEQ ID NO: 332 (HCDR3), SEQ ID NO: 343 (LCDR1), SEQ ID NO: 341 (LCDR2), and SEQ ID NO: 339 (LCDR3); (f) (I) SEQ ID NO: 310 (HCDR1), SEQ ID NO: 311 (HCDR2), SEQ ID NO: 312 (HCDR3), SEQ ID NO: 320 (LCDR1), SEQ ID NO: 321 (LCDR2), and SEQ ID NO: 322 (LCDR3); (II) SEQ ID NO: 229 (HCDR1), SEQ ID NO: 311 (HCDR2), SEQ ID NO: 312 (HCDR3), SEQ ID NO: 320 (LCDR1), SEQ ID NO: 321 (LCDR2), and SEQ ID NO: 322 (LCDR3); (III) SEQ ID NO: 80 (HCDR1), SEQ ID NO: 313 (HCDR2), SEQ ID NO: 312 (HCDR3), SEQ ID NO: 323 (LCDR1), SEQ ID NO: 324 (LCDR2), and SEQ ID NO: 325 (LCDR3); or (IV) SEQ ID NO: 82 (HCDR1), SEQ ID NO: 314 (HCDR2), SEQ ID NO: 315 (HCDR3), SEQ ID NO: 326 (LCDR1), SEQ ID NO: 324 (LCDR2), and SEQ ID NO: 322 (LCDR3); (g) (I) SEQ ID NO: 270 (HCDR1), SEQ ID NO: 271 (HCDR2), SEQ ID NO: 331 (HCDR3), SEQ ID NO: 337 (LCDR1), SEQ ID NO: 338 (LCDR2), and SEQ ID NO: 339 (LCDR3); (II) SEQ ID NO: 273 (HCDR1), SEQ ID NO: 271 (HCDR2), SEQ ID NO: 331 (HCDR3), SEQ ID NO: 337 (LCDR1), SEQ ID NO: 338 (LCDR2), and SEQ ID NO: 339 (LCDR3); (III) SEQ ID NO: 32 (HCDR1), SEQ ID NO: 274 (HCDR2), SEQ ID NO: 331 (HCDR3), SEQ ID NO: 340 (LCDR1), SEQ ID NO: 341 (LCDR2), and SEQ ID NO: 342 (LCDR3); or (IV) SEQ ID NO: 275 (HCDR1), SEQ ID NO: 276 (HCDR2), SEQ ID NO: 332 (HCDR3), SEQ ID NO: 343 (LCDR1), SEQ ID NO: 341 (LCDR2), and SEQ ID NO: 339 (LCDR3); or (h) (I) SEQ ID NO: 310 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 355 (LCDR3); (II) SEQ ID NO: 229 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 355 (LCDR3); (III) SEQ ID NO: 80 (HCDR1), SEQ ID NO: 313 (HCDR2), SEQ ID NO: 348 (HCDR3), SEQ ID NO: 323 (LCDR1), SEQ ID NO: 324 (LCDR2), and SEQ ID NO: 356 (LCDR3); or (IV) SEQ ID NO: 82 (HCDR1), SEQ ID NO: 314 (HCDR2), SEQ ID NO: 349 (HCDR3), SEQ ID NO: 326 (LCDR1), SEQ ID NO: 324 (LCDR2), and SEQ ID NO: 355 (LCDR3).

In some embodiments of the invention, the antibody or antigen binding fragment comprises: (a) a heavy chain variable region comprising an amino acid sequence of SEQ ID NO: 201, and a light chain variable region comprising an amino acid sequence of SEQ ID NO: 136; (b) a heavy chain variable region comprising an amino acid sequence of SEQ ID NO: 122, and a light chain variable region comprising an amino acid sequence of SEQ ID NO: 136; (c) a heavy chain variable region comprising an amino acid sequence of SEQ ID NO: 201, and a light chain variable region comprising an amino acid sequence of SEQ ID NO: 128; (d) a heavy chain variable region comprising an amino acid sequence of SEQ ID NO: 122, and a light chain variable region comprising an amino acid sequence of SEQ ID NO: 128; (e) a heavy chain variable region comprising an amino acid sequence of SEQ ID NO: 201, and a light chain variable region comprising an amino acid sequence of SEQ ID NO: 147; (f) a heavy chain variable region comprising an amino acid sequence of SEQ ID NO: 122, and a light chain variable region comprising an amino acid sequence of SEQ ID NO: 147; (g) a heavy chain variable region comprising an amino acid sequence of SEQ ID NO: 201, and a light chain variable region comprising an amino acid sequence of SEQ ID NO: 174; (h) a heavy chain variable region comprising an amino acid sequence of SEQ ID NO: 122, and a light chain variable region comprising an amino acid sequence of SEQ ID NO: 174; (i) a heavy chain variable region comprising an amino acid sequence of SEQ ID NO: 201, and a light chain variable region comprising an amino acid sequence of SEQ ID NO: 180; (j) a heavy chain variable region comprising an amino acid sequence of SEQ ID NO: 122, and a light chain variable region comprising an amino acid sequence of SEQ ID NO: 180; (k) a heavy chain variable region comprising an amino acid sequence of SEQ ID NO: 201, and a light chain variable region comprising an amino acid sequence of SEQ ID NO: 186; (l) a heavy chain variable region comprising an amino acid sequence of SEQ ID NO: 122, and a light chain variable region comprising an amino acid sequence of SEQ ID NO: 186; (m) a heavy chain variable region comprising an amino acid sequence of SEQ ID NO: 103, and a light chain variable region comprising an amino acid sequence of SEQ ID NO: 24; (n) a heavy chain variable region comprising an amino acid sequence of SEQ ID NO: 115, and a light chain variable region comprising an amino acid sequence of SEQ ID NO: 24; (o) a heavy chain variable region comprising an amino acid sequence of SEQ ID NO: 122, and a light chain variable region comprising an amino acid sequence of SEQ ID NO: 48; (p) a heavy chain variable region comprising an amino acid sequence of SEQ ID NO: 37, and a light chain variable region comprising an amino acid sequence of SEQ ID NO: 128; (q) a heavy chain variable region comprising an amino acid sequence of SEQ ID NO: 37, and a light chain variable region comprising an amino acid sequence of SEQ ID NO: 136; (r) a heavy chain variable region comprising an amino acid sequence of SEQ ID NO: 37, and a light chain variable region comprising an amino acid sequence of SEQ ID NO: 147; (s) a heavy chain variable region comprising an amino acid sequence of SEQ ID NO: 154, and a light chain variable region comprising an amino acid sequence of SEQ ID NO: 24; (t) a heavy chain variable region comprising an amino acid sequence of SEQ ID NO: 161, and a light chain variable region comprising an amino acid sequence of SEQ ID NO: 24; (u) a heavy chain variable region comprising an amino acid sequence of SEQ ID NO: 168, and a light chain variable region comprising an amino acid sequence of SEQ ID NO: 24; (v) a heavy chain variable region comprising an amino acid sequence of SEQ ID NO: 37, and a light chain variable region comprising an amino acid sequence of SEQ ID NO: 174; (w) a heavy chain variable region comprising an amino acid sequence of SEQ ID NO: 37, and a light chain variable region comprising an amino acid sequence of SEQ ID NO: 180; (x) a heavy chain variable region comprising an amino acid sequence of SEQ ID NO: 37, and a light chain variable region comprising an amino acid sequence of SEQ ID NO: 186; (y) a heavy chain variable region comprising an amino acid sequence of SEQ ID NO: 193, and a light chain variable region comprising an amino acid sequence of SEQ ID NO: 136; (z) a heavy chain variable region comprising an amino acid sequence of SEQ ID NO: 193, and a light chain variable region comprising an amino acid sequence of SEQ ID NO: 174; (aa) a heavy chain variable region comprising an amino acid sequence of SEQ ID NO: 13, and a light chain variable region comprising an amino acid sequence of SEQ ID NO: 24; (bb) a heavy chain variable region comprising an amino acid sequence of SEQ ID NO: 37, and a light chain variable region comprising an amino acid sequence of SEQ ID NO: 48; (cc) a heavy chain variable region comprising an amino acid sequence of SEQ ID NO: 374, and a light chain variable region comprising an amino acid sequence of SEQ ID NO: 244; (dd) a heavy chain variable region comprising an amino acid sequence of SEQ ID NO: 385, and a light chain variable region comprising an amino acid sequence of SEQ ID NO: 244; (ee) a heavy chain variable region comprising an amino acid sequence of SEQ ID NO: 233, and a light chain variable region comprising an amino acid sequence of SEQ ID NO: 244; (ff) a heavy chain variable region comprising an amino acid sequence of SEQ ID NO: 278, and a light chain variable region comprising an amino acid sequence of SEQ ID NO: 287; or (gg) a heavy chain variable region comprising an amino acid sequence of SEQ ID NO: 300, and a light chain variable region comprising an amino acid sequence of SEQ ID NO: 306.

In some embodiments of the invention, the antibody or antigen binding fragment comprises: (a) a heavy chain variable region comprising an amino acid sequence of SEQ ID NO: 61, and a light chain variable region comprising an amino acid sequence of SEQ ID NO: 72; (b) a heavy chain variable region comprising an amino acid sequence of SEQ ID NO: 85, and a light chain variable region comprising an amino acid sequence of SEQ ID NO: 96; (c) a heavy chain variable region comprising an amino acid sequence of SEQ ID NO: 350, and a light chain variable region comprising an amino acid sequence of SEQ ID NO: 363; (d) a heavy chain variable region comprising an amino acid sequence of SEQ ID NO: 392, and a light chain variable region comprising an amino acid sequence of SEQ ID NO: 344; (e) a heavy chain variable region comprising an amino acid sequence of SEQ ID NO: 414, and a light chain variable region comprising an amino acid sequence of SEQ ID NO: 344; (f) a heavy chain variable region comprising an amino acid sequence of SEQ ID NO: 316, and a light chain variable region comprising an amino acid sequence of SEQ ID NO: 327; (g) a heavy chain variable region comprising an amino acid sequence of SEQ ID NO: 333, and a light chain variable region comprising an amino acid sequence of SEQ ID NO: 344; or (h) a heavy chain variable region comprising an amino acid sequence of SEQ ID NO: 350, and a light chain variable region comprising an amino acid sequence of SEQ ID NO: 357.

In some embodiments of the invention, the antibody or antigen binding fragment comprises: (a) a heavy chain comprising an amino acid sequence of SEQ ID NO: 203, and a light chain comprising an amino acid sequence of SEQ ID NO: 138; (b) a heavy chain comprising an amino acid sequence of SEQ ID NO: 208, and a light chain comprising an amino acid sequence of SEQ ID NO: 138; (c) a heavy chain comprising an amino acid sequence of SEQ ID NO: 203, and a light chain comprising an amino acid sequence of SEQ ID NO: 130; (d) a heavy chain comprising an amino acid sequence of SEQ ID NO: 208, and a light chain comprising an amino acid sequence of SEQ ID NO: 130; (e) a heavy chain comprising an amino acid sequence of SEQ ID NO: 203, and a light chain comprising an amino acid sequence of SEQ ID NO: 149; (f) a heavy chain comprising an amino acid sequence of SEQ ID NO: 208, and a light chain comprising an amino acid sequence of SEQ ID NO: 149; (g) a heavy chain comprising an amino acid sequence of SEQ ID NO: 203, and a light chain comprising an amino acid sequence of SEQ ID NO: 176; (h) a heavy chain comprising an amino acid sequence of SEQ ID NO: 208, and a light chain comprising an amino acid sequence of SEQ ID NO: 176; (i) a heavy chain comprising an amino acid sequence of SEQ ID NO: 203, and a light chain comprising an amino acid sequence of SEQ ID NO: 182; (j) a heavy chain comprising an amino acid sequence of SEQ ID NO: 208, and a light chain comprising an amino acid sequence of SEQ ID NO: 182; (k) a heavy chain comprising an amino acid sequence of SEQ ID NO: 203, and a light chain comprising an amino acid sequence of SEQ ID NO: 188; (l) a heavy chain comprising an amino acid sequence of SEQ ID NO: 208, and a light chain comprising an amino acid sequence of SEQ ID NO: 188; (m) a heavy chain comprising an amino acid sequence of SEQ ID NO: 105, and a light chain comprising an amino acid sequence of SEQ ID NO: 26; (n) a heavy chain comprising an amino acid sequence of SEQ ID NO: 108, and a light chain comprising an amino acid sequence of SEQ ID NO: 26; (o) a heavy chain comprising an amino acid sequence of SEQ ID NO: 117, and a light chain comprising an amino acid sequence of SEQ ID NO: 26; (p) a heavy chain comprising an amino acid sequence of SEQ ID NO: 124, and a light chain comprising an amino acid sequence of SEQ ID NO: 50; (q) a heavy chain comprising an amino acid sequence of SEQ ID NO: 39, and a light chain comprising an amino acid sequence of SEQ ID NO: 130; (r) a heavy chain comprising an amino acid sequence of SEQ ID NO: 39, and a light chain comprising an amino acid sequence of SEQ ID NO: 138; (s) a heavy chain comprising an amino acid sequence of SEQ ID NO: 141, and a light chain comprising an amino acid sequence of SEQ ID NO: 138; (t) a heavy chain comprising an amino acid sequence of SEQ ID NO: 39, and a light chain comprising an amino acid sequence of SEQ ID NO: 149; (u) a heavy chain comprising an amino acid sequence of SEQ ID NO: 156, and a light chain comprising an amino acid sequence of SEQ ID NO: 26; (v) a heavy chain comprising an amino acid sequence of SEQ ID NO: 159, and a light chain comprising an amino acid sequence of SEQ ID NO: 26; (w) a heavy chain comprising an amino acid sequence of SEQ ID NO: 163, and a light chain comprising an amino acid sequence of SEQ ID NO: 26; (x) a heavy chain comprising an amino acid sequence of SEQ ID NO: 170, and a light chain comprising an amino acid sequence of SEQ ID NO: 26; (y) a heavy chain comprising an amino acid sequence of SEQ ID NO: 39, and a light chain comprising an amino acid sequence of SEQ ID NO: 176; (z) a heavy chain comprising an amino acid sequence of SEQ ID NO: 39, and a light chain comprising an amino acid sequence of SEQ ID NO: 182; (aa) a heavy chain comprising an amino acid sequence of SEQ ID NO: 39, and a light chain comprising an amino acid sequence of SEQ ID NO: 188; (bb) a heavy chain comprising an amino acid sequence of SEQ ID NO: 195, and a light chain comprising an amino acid sequence of SEQ ID NO: 138; (cc) a heavy chain comprising an amino acid sequence of SEQ ID NO: 195, and a light chain comprising an amino acid sequence of SEQ ID NO: 176; (dd) a heavy chain comprising an amino acid sequence of SEQ ID NO: 15, and a light chain comprising an amino acid sequence of SEQ ID NO: 26; (ee) a heavy chain comprising an amino acid sequence of SEQ ID NO: 39, and a light chain comprising an amino acid sequence of SEQ ID NO: 50; (ff) a heavy chain comprising an amino acid sequence of SEQ ID NO: 376, and a light chain comprising an amino acid sequence of SEQ ID NO: 246; (gg) a heavy chain comprising an amino acid sequence of SEQ ID NO: 387, and a light chain comprising an amino acid sequence of SEQ ID NO: 246; (hh) a heavy chain comprising an amino acid sequence of SEQ ID NO: 235, and a light chain comprising an amino acid sequence of SEQ ID NO: 246; (ii) a heavy chain comprising an amino acid sequence of SEQ ID NO: 280, and a light chain comprising an amino acid sequence of SEQ ID NO: 289; or (jj) a heavy chain comprising an amino acid sequence of SEQ ID NO: 302, and a light chain comprising an amino acid sequence of SEQ ID NO: 308.

In some embodiments of the invention, the antibody or antigen binding fragment comprises: (a) a heavy chain comprising an amino acid sequence of SEQ ID NO: 63, and a light chain comprising an amino acid sequence of SEQ ID NO: 74; (b) a heavy chain comprising an amino acid sequence of SEQ ID NO: 87, and a light chain comprising an amino acid sequence of SEQ ID NO: 98; (c) a heavy chain comprising an amino acid sequence of SEQ ID NO: 352, and a light chain comprising an amino acid sequence of SEQ ID NO: 365; (d) a heavy chain comprising an amino acid sequence of SEQ ID NO: 394, and a light chain comprising an amino acid sequence of SEQ ID NO: 346; (e) a heavy chain comprising an amino acid sequence of SEQ ID NO: 416, and a light chain comprising an amino acid sequence of SEQ ID NO: 346; (f) a heavy chain comprising an amino acid sequence of SEQ ID NO: 318, and a light chain comprising an amino acid sequence of SEQ ID NO: 329; (g) a heavy chain comprising an amino acid sequence of SEQ ID NO: 335, and a light chain comprising an amino acid sequence of SEQ ID NO: 346; or (h) a heavy chain comprising an amino acid sequence of SEQ ID NO: 352, and a light chain comprising an amino acid sequence of SEQ ID NO: 359.

In some embodiments of the invention, the antibody or antigen binding fragment is an antigen binding fragment selected from the group consisting of a Fab, Fab', F(ab)$_2$, Fv, single domain antibody (dAb), and a single chain variable fragment (scFv). In some embodiments of the invention, the antibody or antigen binding fragment is an antigen binding fragment selected from the group consisting of a Fab, Fab', Fv, single domain antibody (dAb), and a single chain variable fragment (scFv).

In some embodiments of the invention, the antibody or antigen binding fragment is monoclonal. In some embodiments of the invention, the antibody or antigen binding fragment is fully human. In some embodiments of the invention, the antibody or antigen binding fragment is an IgG antibody. In some embodiments of the invention, the antibody or antigen binding fragment is an IgG1 antibody. In some embodiments of the invention, the antibody or antigen binding fragment is an IgG1 antibody having a kappa light chain. In some embodiments of the invention, the antibody or antigen binding fragment is a fully human antibody of the IgG1 isotype and has a kappa light chain.

In some embodiments of the invention, the antibody or antigen binding fragment additionally has mutations in the Fc region according to the EU index of Kabat, wherein the mutations comprise at least D265A and P329A.

In some embodiments of the invention, the antibody or antigen binding fragment additionally has mutations in the Fc region according to the EU index of Kabat, wherein the mutations comprise at least L234A and L235A.

In some embodiments of the invention, the antibody or antigen binding fragment is therapeutic.

In some embodiments of the invention, the antibody or antigen binding fragment binds to the same epitope on human NPR1 as any of the antibodies or antigen binding fragments or groups defined herein (e.g., XX16). In some embodiments of the invention, the antibody or antigen binding fragment competes for binding to human NPR1 with any of the antibodies or antigen binding fragments or groups defined herein (e.g., XX16).

In one aspect of the invention, provided herein is an isolated nucleic acid or nucleic acids encoding the amino acid sequence of any of the antibodies or antigen binding fragments or groups defined herein. In one aspect of the invention, provided herein is a vector comprising the isolated nucleic acid(s). In one aspect of the invention, provided herein is a host cell comprising the isolated nucleic acid(s) or the vector.

In one aspect of the invention, provided herein is a method of producing any of the antibodies or antigen binding fragments described herein, comprising culturing the host cell described herein under conditions suitable to produce the antibody or antigen binding fragment. In some embodiments of the invention, the method additionally comprises purification of the antibody or antigen binding fragment.

In one aspect of the invention, provided herein is pharmaceutical composition comprising a purified antibody or antigen binding fragment produced by the method described herein and a pharmaceutically acceptable carrier.

In one aspect of the invention, provided herein is pharmaceutical composition comprising any of the antibodies or antigen binding fragments described herein and a pharmaceutically acceptable carrier.

In one aspect of the invention, provided herein is pharmaceutical composition comprising: a) means for binding natriuretic peptide receptor 1 (NPR1) and activating NPR1 in the absence of ANP; and b) a pharmaceutically acceptable excipient. In some embodiments of the invention, said means for binding and activating is ANP non-competitive. In some embodiments of the invention, said means for binding and activating is ANP competitive. In some embodiments of the invention, said means for binding and activating is additionally capable of stabilizing the ANP-NPR1 complex. In some embodiments of the invention, the composition further comprises an additional therapeutic agent.

In some embodiments of the invention, the additional therapeutic agent is selected from an ACE (angiotensin-converting-enzyme) inhibitor, an angiotensin receptor blocker (ARB), a neprilysin inhibitor, a beta blocker, a diuretic, a calcium channel blocker, a cardiac glycoside, a sodium-glucose co-transporter 2 inhibitor (SGLT2i), and combinations thereof. In some embodiments of the invention, the additional therapeutic agent is selected from enalapril, benazepril, captopril, fosinopril, lisinopril, moexipril, perindopril, quinapril, ramipril, trandolapril, valsartan, azilsartan, candesartan, eprosartan, irbesartan, losartan, olmesartan, telmisartan, sacubitril, bisoprolol, carvedilol, propanolol, metoprolol, metoprolol tartrate, metoprolol succinate, thiazide diuretics, loop diuretics, potassium-sparing diuretics, amlodipine, clevidipine, diltiazem, felodipine, isradipine, nicardipine, nifedipine, nisoldipine, verapamil, a digitalis glycoside, canagliflozin, dapagliflozin, empagliflozin, ertugliflozin, and combinations thereof. In some embodiments of the invention, the additional therapeutic agent is selected from chlorothiazide, chlorthalidone, hydrochlorothiazide, indapamide, metolazone, bumetanide, ethacrynic acid, furosemide, torsemide, amiloride, eplerenone, spironolactonem, triamterene, digoxin, and combinations thereof. In some embodiments of the invention, the additional therapeutic agent is an angiotensin receptor-neprilysin inhibitor (ARNi).

In some embodiments of the invention, the additional therapeutic agent is selected from a corticosteroid, a leukotriene modifier, a bronchodilator, and combinations thereof. In some embodiments of the invention, the additional therapeutic agent is selected from fluticasone, budesonide, mometasone, beclomethasone, ciclesonide, fluticasone furoate, prednisone, methylprednisolone, montelukast, zafirlukast, zileuton, a long-acting beta agonist, a short-acting beta agonist, theophylline and ipratropium, and combinations thereof. In some embodiments of the invention, the additional therapeutic agent is selected from salmeterol, formoterol, albuterol, and levalbuterol, and combinations thereof.

In some embodiments of the invention, the additional therapeutic agent is selected from a beta-adrenoceptor antagonist, a carbonic anhydrase inhibitor, an alpha 2-adrenoceptor agonist, a parasympathomimetic, a prostaglandin analog, a rho kinase inhibitor, and combinations thereof, and combinations thereof. In some embodiments of the invention, the additional therapeutic agent is selected from timolol, levobunolol, metipranolol, carteolol, betaxolol, acetazolamide, dorzolamide, brinzolamide, methazolamide, brimonidine, apraclonidine, a cholinomimetic, latanoprost, latanoprostene bunod, travoprost, bimatoprost, tafluprost, netarsudil and ripasudil, and combinations thereof.

In one aspect of the invention, provided herein is a method of treating a disorder or a disease associated with natriuretic peptide receptor activity in a subject in need thereof, the method comprising administering to the subject a therapeutically effective amount of any of the antibodies or antigen binding fragments described herein or a pharmaceutical composition or combination as described herein.

In one aspect of the invention, provided herein is a method of treating a cardiovascular disorder in a subject in need thereof, the method comprising administering to the subject a therapeutically effective amount of any one of the antibodies or antigen binding fragments thereof described herein or any one of the pharmaceutical compositions or combinations described herein.

In some embodiments of the invention, the cardiovascular disorder is selected from: hypertension, peripheral vascular disease, heart failure, coronary artery disease (CAD), ischemic heart disease (IHD), mitral stenosis and regurgitation, angina, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, and myocardial infarction (MI).

In one aspect of the invention, provided herein is a method of treating heart failure, hypertrophic cardiomyopathy (HCM), hypertension, preeclampsia, asthma, glaucoma, and/or cytokine release syndrome in a subject in need thereof, comprising administering to the subject a therapeutically effective amount of any one of the antibodies or antigen binding fragments thereof described herein or any one of the pharmaceutical compositions or combinations described herein.

In some embodiments of the invention, the subject has heart failure, wherein the heart failure is selected from a heart failure with reduced ejection fraction (HFrEF), heart failure with preserved ejection fraction (HFpEF), heart failure after acute myocardial infarct, or acute decompensated heart failure. In some embodiments of the invention, the subject has hypertrophic cardiomyopathy, wherein the hypertrophic cardiomyopathy is ventricular hypertrophy. In some embodiments of the invention, the subject has hypertension, wherein the hypertension is selected from resistant hypertension, hypertensive heart disease, pulmonary hypertension, pulmonary arterial hypertension, isolated systolic hypertension, resistant hypertension, and pulmonary arterial hypertension. In some embodiments of the invention, the subject has hypertension, wherein the hypertension is selected from resistant hypertension or hypertensive heart disease.

In one aspect of the invention, provided herein is a method of treating a kidney disorder in a subject in need thereof, the method comprising administering to the subject a therapeutically effective amount of any one of the antibodies or antigen binding fragments thereof described herein or any one of the pharmaceutical compositions or combinations described herein. In some embodiments of the invention, the kidney disorder is selected from: diabetic renal insufficiency, non-diabetic renal insufficiency, renal failure, diabetic nephropathy, non-diabetic nephropathy, acute renal injury, contrast induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, renal fibrosis, and polycystic kidney disease (PKD).

In one aspect of the invention, provided herein is a use of any one of the antibodies or antigen binding fragments thereof described herein or any one of the pharmaceutical compositions or combinations described herein, for the manufacture of a medicament for the treatment of a disorder or disease associated with natriuretic peptide receptor activity in a subject in need of such treatment.

In one aspect of the invention, provided herein is a use of any one of the antibodies or antigen binding fragments thereof described herein or any one of the pharmaceutical compositions or combinations described herein, for the manufacture of a medicament for the treatment of a cardiovascular disorder in a subject in need of such treatment.

In some embodiments of the invention, the cardiovascular disorder is selected from: hypertension, peripheral vascular disease, heart failure, coronary artery disease (CAD), ischemic heart disease (IHD), mitral stenosis and regurgitation, angina, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, and myocardial infarction (MI).

In one aspect of the invention, provided herein is a use of any one of the antibodies or antigen binding fragments thereof described herein or any one of the pharmaceutical compositions or combinations described herein, for the manufacture of a medicament for the treatment of heart failure, hypertrophic cardiomyopathy (HCM), hypertension, preeclampsia, asthma, glaucoma, and/or cytokine release syndrome in a subject in need of such treatment.

In some embodiments of the invention, the subject has heart failure, and the heart failure is selected from a heart failure with reduced ejection fraction (HFrEF), heart failure with preserved ejection fraction (HFpEF), heart failure after acute myocardial infarct, or acute decompensated heart failure. In some embodiments of the invention, the subject has hypertrophic cardiomyopathy, wherein the hypertrophic cardiomyopathy is ventricular hypertrophy. In some embodiments of the invention, the subject has hypertension, wherein the hypertension is selected from resistant hypertension, hypertensive heart disease, pulmonary hypertension, pulmonary arterial hypertension, isolated systolic hypertension, resistant hypertension, and pulmonary arterial hypertension. In some embodiments of the invention, the subject has hypertension, wherein the hypertension is selected from resistant hypertension or hypertensive heart disease.

In one aspect of the invention, provided herein is a use of any one of the antibodies or antigen binding fragments thereof described herein or any one of the pharmaceutical compositions or combinations described herein, for the manufacture of a medicament for the treatment of a kidney disorder in a subject in need of such treatment. In some embodiments of the invention, the kidney disorder is selected from: diabetic renal insufficiency, non-diabetic renal insufficiency, renal failure, diabetic nephropathy, non-diabetic nephropathy, acute renal injury, contrast induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, renal fibrosis, and polycystic kidney disease (PKD).

In one aspect of the invention, provided herein is an antibody or antigen binding fragment thereof described herein or any one of the pharmaceutical compositions or combinations described herein, for use in the treatment of a disorder or disease associated with natriuretic peptide receptor activity in a subject in need of such treatment.

In one aspect of the invention, provided herein is an antibody or antigen binding fragment thereof described herein or any one of the pharmaceutical compositions or combinations described herein, for use in the treatment of a cardiovascular disorder in a subject in need of such treatment.

In some embodiments of the invention, the cardiovascular disorder is selected from: hypertension, peripheral vascular disease, heart failure, coronary artery disease (CAD), ischemic heart disease (IHD), mitral stenosis and regurgitation, angina, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, and myocardial infarction (MI).

In one aspect of the invention, provided herein is an antibody or antigen binding fragment thereof described herein or any one of the pharmaceutical compositions or combinations described herein, for use in the treatment of heart failure, hypertrophic cardiomyopathy (HCM), hypertension, preeclampsia, asthma, glaucoma, and/or cytokine release syndrome in a subject in need of such treatment.

In some embodiments of the invention, the subject has heart failure, and the heart failure is selected from a heart failure with reduced ejection fraction (HFrEF), heart failure with preserved ejection fraction (HFpEF), heart failure after acute myocardial infarct, or acute decompensated heart failure. In some embodiments of the invention, the subject has hypertrophic cardiomyopathy, wherein the hypertrophic cardiomyopathy is ventricular hypertrophy. In some embodiments of the invention, the subject has hypertension, wherein the hypertension is selected from resistant hypertension, hypertensive heart disease, pulmonary hypertension, pulmonary arterial hypertension, isolated systolic hypertension, resistant hypertension, and pulmonary arterial hypertension. In some embodiments of the invention, the subject has hypertension, wherein the hypertension is selected from resistant hypertension or hypertensive heart disease.

In one aspect of the invention, provided herein is an antibody or antigen binding fragment thereof described herein or any one of the pharmaceutical compositions or combinations described herein, for use in the treatment of a kidney disorder in a subject in need of such treatment. In some embodiments of the invention, the kidney disorder is selected from: diabetic renal insufficiency, non-diabetic renal insufficiency, renal failure, diabetic nephropathy, non-diabetic nephropathy, acute renal injury, contrast induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, renal fibrosis, and polycystic kidney disease (PKD).

In one aspect of the invention, provided herein is a method of treating a disorder or a disease associated with natriuretic peptide receptor activity in a subject in need thereof, comprising administering a pharmaceutical composition comprising: means for binding natriuretic peptide receptor 1 (NPR1) and activating NPR1 in the absence of ANP; and a pharmaceutically acceptable excipient.

In one aspect of the invention, provided herein is a method of treating a cardiovascular disorder in a subject in need thereof, comprising administering a pharmaceutical composition comprising: means for binding natriuretic peptide receptor 1 (NPR1) and activating NPR1 in the absence of ANP; and a pharmaceutically acceptable excipient. In some embodiments of the invention, the cardiovascular disorder is selected from: hypertension, peripheral vascular disease, heart failure, coronary artery disease (CAD), ischemic heart disease (IHD), mitral stenosis and regurgitation, angina, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, and myocardial infarction (MI).

In one aspect of the invention, provided herein is a method of treating heart failure, hypertrophic cardiomyopathy (HCM), hypertension, preeclampsia, asthma, glaucoma, and/or cytokine release syndrome in a subject in need thereof, comprising administering a pharmaceutical composition comprising: means for binding natriuretic peptide receptor 1 (NPR1) and activating NPR1 in the absence of ANP; and a pharmaceutically acceptable excipient. In some embodiments of the invention, the subject has heart failure, wherein the heart failure is selected from a heart failure with reduced ejection fraction (HFrEF), heart failure with preserved ejection fraction (HFpEF), heart failure after acute myocardial infarct, or acute decompensated heart failure. In some embodiments of the invention, the subject has hypertrophic cardiomyopathy, wherein the hypertrophic cardiomyopathy is ventricular hypertrophy. In some embodiments of the invention, the subject has hypertension, wherein the hypertension is selected from resistant hypertension, hypertensive heart disease, pulmonary hypertension, pulmonary arterial hypertension, isolated systolic hypertension, resistant hypertension, and pulmonary arterial hypertension. In some embodiments of the invention, the subject has hypertension, wherein the hypertension is selected from resistant hypertension or hypertensive heart disease.

In one aspect of the invention, provided herein is a method of treating a kidney disorder in a subject in need thereof, comprising administering a pharmaceutical composition comprising: means for binding natriuretic peptide receptor 1 (NPR1) and activating NPR1 in the absence of ANP; and a pharmaceutically acceptable excipient. In some embodiments of the invention, the kidney disorder is selected from: diabetic renal insufficiency, non-diabetic renal insufficiency, renal failure, diabetic nephropathy, non-diabetic nephropathy, acute renal injury, contrast induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, renal fibrosis, and polycystic kidney disease (PKD). In some embodiments of the invention, said means for binding and activating is ANP non-competitive. In some embodiments of the invention, said means for binding and activating is ANP competitive. In some embodiments of the invention, said means for binding and activating is additionally capable of stabilizing the ANP-NPR1 complex.

In one aspect of the invention, herein is provided an isolated anti-NPR1 antibody or antigen binding fragment, wherein the antibody or antigen binding fragment thereof binds to a conformational epitope of human NPR1, and wherein the conformational epitope comprises at least one amino acid residue within each of (i) amino acids 99-103 of SEQ ID NO: 1, (ii) 105-111 of SEQ ID NO: 1, (iii) 131-134 of SEQ ID NO: 1, and additionally binds to amino acid 375 and/or 378 of SEQ ID NO: 1.

In one aspect of the invention, herein is provided an isolated anti-NPR1 antibody or antigen binding fragment, wherein the antibody or antigen binding fragment thereof binds to a conformational epitope within NPR1, and wherein the conformational epitope comprises at least one amino acid residue within each of (i) amino acids 188-198 of SEQ ID NO: 1, (ii) 201-208 of SEQ ID NO: 1, (iii) 215-238 of SEQ ID NO: 1, and (iv) 294-297 of SEQ ID NO: 1, optionally wherein the antibody or antigen binding fragment thereof binds to at least amino acids 188, 192, 194, 197, 201, 208, and 219 of SEQ ID NO: 1.

In some embodiments of the invention, the antibody or antigen binding fragment comprises three heavy chain complementarity determining regions (HCDR1, HCDR2, and HCDR3) and three light chain complementarity determining regions (LCDR1, LCDR2, and LCDR3), wherein: (a) (I) HCDR1 comprises or consists of an amino acid sequence as set forth in SEQ ID NO: 28; HCDR2 comprises or consists of an amino acid sequence as set forth in $X_1IX_2SX_3GX_4YX_5X_6YADSVKG$ (SEQ ID NO: 429), wherein $X_1$ is A or V, $X_2$ is S or E, $X_3$ is D or K, $X_4$ is S or N, $X_5$ is I or T, and $X_6$ is Y or F; HCDR3 comprises or consists of an amino acid sequence as set forth in SEQ ID NO: 30; LCDR1 comprises or consists of an amino acid sequence as set forth in SEQ ID NO: 41; LCDR2 comprises or consists of an amino acid sequence as set forth in SEQ ID NO: 42; and LCDR3 comprises or consists of an amino acid sequence as set forth in $Y_1QY_2Y_3Y_4Y_5PRT$ (SEQ ID NO: 430); wherein $Y_1$ is M or Q, $Y_2$ is S, E, T, or I, $Y_3$ is Y or W, $Y_4$ is E, V, R, A, T, or M, and $Y_5$ is K, V, R, or A; (II) HCDR1 comprises or consists of an amino acid sequence as set forth in SEQ ID NO: 31; HCDR2 comprises or consists of an amino acid sequence as set forth in $X_1IX_2SX_3GX_4YX_5X_6YADSVKG$ (SEQ ID NO: 429), wherein $X_1$ is A or V, $X_2$ is S or E, $X_3$ is D or K, $X_4$ is S or N, $X_5$ is I or T, and $X_6$ is Y or F; HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in $Y_1QY_2Y_3Y_4Y_5PRT$ (SEQ ID NO: 430); wherein $Y_1$ is M or Q, $Y_2$ is S, E, T, or I, $Y_3$ is Y or W, $Y_4$ is E, V, R, A, T, or M, and $Y_5$ is K, V, R, or A; (III) HCDR1 comprises or consists of an amino acid sequence as set forth in SEQ ID NO: 32, HCDR2 comprises or consists of an amino acid sequence as set forth in $X_1SX_2GX_3Y$ (SEQ ID NO: 431), wherein $X_1$ is S or E, $X_2$ is D or K, or $X_3$ is S or N, HCDR3 comprises or consists of an amino acid sequence as set forth in SEQ ID NO: 30, LCDR1 comprises or consists of an amino acid sequence as set forth in SEQ ID NO: 44, LCDR2 comprises or consists of an amino acid sequence as set forth in SEQ ID NO: 45, and LCDR3 comprises or consists of an amino acid sequence as set forth in $Y_1Y_2Y_3Y_4PR$ (SEQ ID NO: 432); wherein $Y_1$ is S, E, T, or I, $Y_2$ is Y or W, $Y_3$ is E, V, R, A, T, or M, and $Y_4$ is K, V, R, or A; or (IV) HCDR1 comprises or consists of an amino acid sequence as set forth in SEQ ID NO: 34, HCDR2 comprises or consists of an amino acid sequence as set forth in IX$_1$SX$_2$GX$_3$YX$_4$ (SEQ ID NO: 433), wherein X$_1$ is S or E, X$_2$ is D or K, X$_3$ is S or N, and X$_4$ is I or T, HCDR3 comprises or consists of an amino acid sequence as set forth in SEQ ID NO: 36, LCDR1 comprises or consists of an amino acid sequence as set forth in SEQ ID NO: 47, LCDR2 comprises or consists of an amino acid sequence as set forth in SEQ ID NO: 45, and LCDR3 comprises or consists of an amino acid sequence as set forth in Y$_1$QY$_2$Y$_3$Y$_4$Y$_5$PRT (SEQ ID NO: 430); wherein Y$_1$ is M or Q, Y$_2$ is S, E, T, or I, Y$_3$ is Y or W, Y$_4$ is E, V, R, A, T, or M, and Y$_5$ is K, V, R, or A; (b) (I) HCDR1 comprises or consists of an amino acid sequence as set forth in SEQ ID NO: 28; HCDR2 comprises or consists of an amino acid sequence as set forth in X$_1$IX$_2$SX$_3$GX$_4$YX$_5$X$_6$YADSVKG (SEQ ID NO: 429), wherein X$_1$ is A or V, X$_2$ is S or E, X$_3$ is D or K, X$_4$ is S or N, X$_5$ is I or T, and X$_6$ is Y or F; HCDR3 comprises or consists of an amino acid sequence as set forth in SEQ ID NO: 30; LCDR1 comprises or consists of an amino acid sequence as set forth in SEQ ID NO: 41; LCDR2 comprises or consists of an amino acid sequence as set forth in SEQ ID NO: 42; and LCDR3 comprises or consists of an amino acid sequence as set forth in QQY$_1$WY$_2$Y$_3$PRT (SEQ ID NO: 434); wherein Y$_1$ is S, E, T, or I, Y$_2$ is V, R, A, T, or M, and Y$_3$ is K, V, R, or A; (II) HCDR1 comprises or consists of an amino acid sequence as set forth in SEQ ID NO: 31; HCDR2 comprises or consists of an amino acid sequence as set forth in X$_1$IX$_2$SX$_3$GX$_4$YX$_5$X$_6$YADSVKG (SEQ ID NO: 429), wherein X$_1$ is A or V, X$_2$ is S or E, X$_3$ is D or K, X$_4$ is S or N, X$_5$ is I or T, and X$_6$ is Y or F; HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in QQY$_1$WY$_2$Y$_3$PRT (SEQ ID NO: 434); wherein Y$_1$ is S, E, T, or I, Y$_2$ is V, R, A, T, or M, and Y$_3$ is K, V, R, or A; (III) HCDR1 comprises or consists of an amino acid sequence as set forth in SEQ ID NO: 32, HCDR2 comprises or consists of an amino acid sequence as set forth in X$_1$SX$_2$GX$_3$Y (SEQ ID NO: 431), wherein X$_1$ is S or E, X$_2$ is D or K, or X$_3$ is S or N, HCDR3 comprises or consists of an amino acid sequence as set forth in SEQ ID NO: 30, LCDR1 comprises or consists of an amino acid sequence as set forth in SEQ ID NO: 44, LCDR2 comprises or consists of an amino acid sequence as set forth in SEQ ID NO: 45, and LCDR3 comprises or consists of an amino acid sequence as set forth in Y$_1$WY$_2$Y$_3$PR (SEQ ID NO: 435); wherein Y$_1$ is S, E, T, or I, Y$_2$ is V, R, A, T, or M, and Y$_3$ is K, V, R, or A; or (IV) HCDR1 comprises or consists of an amino acid sequence as set forth in SEQ ID NO: 34, HCDR2 comprises or consists of an amino acid sequence as set forth in IX$_1$SX$_2$GX$_3$YX$_4$ (SEQ ID NO: 433), wherein X$_1$ is S or E, X$_2$ is D or K, X$_3$ is S or N, and X$_4$ is I or T, HCDR3 comprises or consists of an amino acid sequence as set forth in SEQ ID NO: 36, LCDR1 comprises or consists of an amino acid sequence as set forth in SEQ ID NO: 47, LCDR2 comprises or consists of an amino acid sequence as set forth in SEQ ID NO: 45, and LCDR3 comprises or consists of an amino acid sequence as set forth in QQY$_1$WY$_2$Y$_3$PRT (SEQ ID NO: 434); wherein Y$_1$ is S, E, T, or I, Y$_2$ is V, R, A, T, or M, and Y$_3$ is K, V, R, or A; (c) (I) HCDR1 comprises or consists of an amino acid sequence as set forth in SEQ ID NO: 28; HCDR2 comprises or consists of an amino acid sequence as set forth in SEQ ID NO: 119; HCDR3 comprises or consists of an amino acid sequence as set forth in SEQ ID NO: 30; LCDR1 comprises or consists of an amino acid sequence as set forth in SEQ ID NO: 41; LCDR2 comprises or consists of an amino acid sequence as set forth in SEQ ID NO: 42; and LCDR3 comprises or consists of an amino acid sequence as set forth in QQY$_1$WY$_2$Y$_3$PRT (SEQ ID NO: 434); wherein Y$_1$ is S, E, T, or I, Y$_2$ is V, R, A, T, or M, and Y$_3$ is K, V, R, or A; (II) HCDR1 comprises or consists of an amino acid sequence as set forth in SEQ ID NO: 31; HCDR2 comprises or consists of an amino acid sequence as set forth in SEQ ID NO: 119; HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in QQY$_1$WY$_2$Y$_3$PRT (SEQ ID NO: 434); wherein Y$_1$ is S, E, T, or I, Y$_2$ is V, R, A, T, or M, and Y$_3$ is K, V, R, or A; (III) HCDR1 comprises or consists of an amino acid sequence as set forth in SEQ ID NO: 32, HCDR2 comprises or consists of an amino acid sequence as set forth in SEQ ID NO: 120, HCDR3 comprises or consists of an amino acid sequence as set forth in SEQ ID NO: 30, LCDR1 comprises or consists of an amino acid sequence as set forth in SEQ ID NO: 44, LCDR2 comprises or consists of an amino acid sequence as set forth in SEQ ID NO: 45, and LCDR3 comprises or consists of an amino acid sequence as set forth in Y$_1$WY$_2$Y$_3$PR (SEQ ID NO: 435); wherein Y$_1$ is S, E, T, or I, Y$_2$ is V, R, A, T, or M, and Y$_3$ is K, V, R, or A; or (IV) HCDR1 comprises or consists of an amino acid sequence as set forth in SEQ ID NO: 34, HCDR2 comprises or consists of an amino acid sequence as set forth in SEQ ID NO: 121, HCDR3 comprises or consists of an amino acid sequence as set forth in SEQ ID NO: 36, LCDR1 comprises or consists of an amino acid sequence as set forth in SEQ ID NO: 47, LCDR2 comprises or consists of an amino acid sequence as set forth in SEQ ID NO: 45, and LCDR3 comprises or consists of an amino acid sequence as set forth in QQY$_1$WY$_2$Y$_3$PRT (SEQ ID NO: 434); wherein Y$_1$ is S, E, T, or I, Y$_2$ is V, R, A, T, or M, and Y$_3$ is K, V, R, or A; (d) (I) HCDR1 comprises or consists of an amino acid sequence as set forth in GFTFX$_1$THYIH (SEQ ID NO: 436), wherein X$_1$ is N, S, or Q, HCDR2 comprises or consists of an amino acid sequence as set forth in SIY$_1$Y$_2$Y$_3$GY$_4$Y$_5$TY$_6$YADSVKG (SEQ ID NO: 437), wherein Y$_1$ is S or G, Y$_2$ is S or G, Y$_3$ is S or Q, Y$_4$ is S, Q, or G, Y$_5$ is S, N, or M, and Y$_6$ is Y or L, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19; (II) HCDR1 comprises or consists of an amino acid sequence as set forth in SEQ ID NO: 7, HCDR2 comprises or consists of an amino acid sequence as set forth in SIY$_1$Y$_2$Y$_3$GY$_4$Y$_5$TY$_6$YADSVKG (SEQ ID NO: 437), wherein Y$_1$ is S or G, Y$_2$ is S or G, Y$_3$ is S or Q, Y$_4$ is S, Q, or G, Y$_5$ is S, N, or M, and Y$_6$ is Y or L, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19; (III) HCDR1 comprises or consists of an amino acid sequence as set forth in GFTFX$_1$TH (SEQ ID NO: 438), wherein X$_1$ is N, S, or Q, HCDR2 comprises or consists of an amino acid sequence as set forth in Y$_1$Y$_2$Y$_3$GY$_4$Y$_5$ (SEQ ID NO: 439), wherein Y$_1$ is S or G, $Y_2$ is S or G, $Y_3$ is S or Q, $Y_4$ is S, Q, or G, and $Y_5$ is S, N, or M, HCDR3 comprises or consists of an amino acid sequence as set forth in SEQ ID NO: 6, LCDR1 comprises or consists of an amino acid sequence as set forth in SEQ ID NO: 20, LCDR2 comprises or consists of an amino acid sequence as set forth in SEQ ID NO: 21, and LCDR3 comprises or consists of an amino acid sequence as set forth in SEQ ID NO: 22; or (IV) HCDR1 comprises or consists of an amino acid sequence as set forth in GFTFX$_1$THY (SEQ ID NO: 440), wherein $X_1$ is N, S, or Q, HCDR2 comprises or consists of an amino acid sequence as set forth in IY$_1$Y$_2$Y$_3$GY$_4$Y$_5$T (SEQ ID NO: 441), wherein $Y_1$ is S or G, $Y_2$ is S or G, $Y_3$ is S or Q, $Y_4$ is S, Q, or G, and $Y_5$ is S, N, or M, HCDR3 comprises or consists of an amino acid sequence as set forth in SEQ ID NO: 12, LCDR1 comprises or consists of an amino acid sequence as set forth in SEQ ID NO: 23, LCDR2 comprises or consists of an amino acid sequence as set forth in SEQ ID NO: 21, and LCDR3 comprises or consists of an amino acid sequence as set forth in SEQ ID NO: 19; or (e) (I) HCDR1 comprises or consists of an amino acid sequence as set forth in GFTFX$_1$THYIH (SEQ ID NO: 436), wherein $X_1$ is N, S, or Q, HCDR2 comprises or consists of an amino acid sequence as set forth in SISY$_1$SGY$_2$Y$_3$TYYADSVKG (SEQ ID NO: 442), wherein $Y_1$ is S or G, $Y_2$ is S or Q, and $Y_3$ is S or N, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19; (II) HCDR1 comprises or consists of an amino acid sequence as set forth in SEQ ID NO: 7, HCDR2 comprises or consists of an amino acid sequence as set forth in SISY$_1$SGY$_2$Y$_3$TYYADSVKG (SEQ ID NO: 442), wherein $Y_1$ is S or G, $Y_2$ is S or Q, and $Y_3$ is S or N, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19; (III) HCDR1 comprises or consists of an amino acid sequence as set forth in GFTFX$_1$TH (SEQ ID NO: 438), wherein $X_1$ is N, S, or Q, HCDR2 comprises or consists of an amino acid sequence as set forth in SY$_1$SGY$_2$Y$_3$ (SEQ ID NO: 443), wherein $Y_1$ is S or G, $Y_2$ is S or Q, and $Y_3$ is S or N, HCDR3 comprises or consists of an amino acid sequence as set forth in SEQ ID NO: 6, LCDR1 comprises or consists of an amino acid sequence as set forth in SEQ ID NO: 20, LCDR2 comprises or consists of an amino acid sequence as set forth in SEQ ID NO: 21, and LCDR3 comprises or consists of an amino acid sequence as set forth in SEQ ID NO: 22; or (IV) HCDR1 comprises or consists of an amino acid sequence as set forth in GFTFX$_1$THY (SEQ ID NO: 440), wherein $X_1$ is N, S, or Q, HCDR2 comprises or consists of an amino acid sequence as set forth in ISY$_1$SGY$_2$Y$_3$T (SEQ ID NO: 444), wherein $Y_1$ is S or G, $Y_2$ is S or Q, and $Y_3$ is S or N, HCDR3 comprises or consists of an amino acid sequence as set forth in SEQ ID NO: 12, LCDR1 comprises or consists of an amino acid sequence as set forth in SEQ ID NO: 23, LCDR2 comprises or consists of an amino acid sequence as set forth in SEQ ID NO: 21, and LCDR3 comprises or consists of an amino acid sequence as set forth in SEQ ID NO: 19.

In some aspects and embodiments of the invention, herein is provided an isolated anti-NPR1 antibody or antigen binding fragment, wherein the antibody or antigen binding fragment comprises three heavy chain complementarity determining regions (HCDR1, HCDR2, and HCDR3) and three light chain complementarity determining regions (LCDR1, LCDR2, and LCDR3), and wherein: (I) HCDR1 comprises or consists of an amino acid sequence as set forth in SEQ ID NO: 28, HCDR2 comprises or consists of an amino acid sequence as set forth in any one of comprises or consists of an amino acid sequence as set forth in any one of SEQ ID NOs: 29, 119, and 190, HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in any one of SEQ ID NOs: 43, 126, 134, 145, 172, 178, and 184; (II) HCDR1 comprises or consists of an amino acid sequence as set forth in SEQ ID NO: 31, HCDR2 comprises or consists of an amino acid sequence as set forth in any one of SEQ ID NOs: 29, 119, and 190, HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in any one of SEQ ID NOs: 43, 126, 134, 145, 172, 178, and 184; (III) HCDR1 comprises or consists of an amino acid sequence as set forth in SEQ ID NO: 32, HCDR2 comprises or consists of an amino acid sequence as set forth in any one of SEQ ID NOs: 33, 120, and 191, HCDR3 comprises or consists of an amino acid sequence as set forth in SEQ ID NO: 30, LCDR1 comprises or consists of an amino acid sequence as set forth in SEQ ID NO: 44, LCDR2 comprises or consists of an amino acid sequence as set forth in SEQ ID NO: 45, and LCDR3 comprises or consists of an amino acid sequence as set forth in any one of SEQ ID NOs: 46, 127, 135, 146, 173, 179, and 185; or (IV) HCDR1 comprises or consists of an amino acid sequence as set forth in SEQ ID NO: 34, HCDR2 comprises or consists of an amino acid sequence as set forth in any one of SEQ ID NOs: 35, 121, and 192, HCDR3 comprises or consists of an amino acid sequence as set forth in SEQ ID NO: 36, LCDR1 comprises or consists of an amino acid sequence as set forth in SEQ ID NO: 47, LCDR2 comprises or consists of an amino acid sequence as set forth in SEQ ID NO: 45, and LCDR3 comprises or consists of an amino acid sequence as set forth in any one of SEQ ID NOs: 43, 126, 134, 145, 172, 178, and 184.

In some embodiments of the invention, the antibody or antigen binding fragment comprises three heavy chain complementarity determining regions (HCDR1, HCDR2, and HCDR3) and three light chain complementarity determining regions (LCDR1, LCDR2, and LCDR3) selected from: (a) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 134 (LCDR3); (b) (I) SEQ ID NO: 28 (HCDR1), SEQ ID NO: 119 (HCDR2), SEQ ID NO: 30 (HCDR3), SEQ ID NO: 41

(LCDR1), SEQ ID NO: 42 (LCDR2), and SEQ ID NO: 126 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 126 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 127 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 126 (LCDR3); (c) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 146 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 145 (LCDR3); (d) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 173 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 172 (LCDR3); (e) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 179 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 178 (LCDR3); (f) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 185 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 184 (LCDR3); (g) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 43 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 43 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 46 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 43 (LCDR3); (h) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 126 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 126 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 127 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 126 (LCDR3); (i) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 134 (LCDR3); (j) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 145 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 145 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 146 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 145 (LCDR3); (k) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 172 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 172 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 173 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 172 (LCDR3); (1) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 178 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 178 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 179 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 178 (LCDR3); (m) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 184 (LCDR3); (II) SEQ ID NO: 31 (HCDR1), SEQ ID NO: 29

(HCDR2), SEQ ID NO: 30 (HCDR3), SEQ ID NO: 41 (LCDR1), SEQ ID NO: 42 (LCDR2), and SEQ ID NO: 184 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 185 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 184 (LCDR3); (n) (I) SEQ ID NO: 28 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 191 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 192 (HCDR2), SEQ ID NO: 36 (HCDR3), SEQ ID NO: 47 (LCDR1), SEQ ID NO: 45 (LCDR2), and SEQ ID NO: 134 (LCDR3); (o) (I) SEQ ID NO: 28 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 172 (LCDR3); (II) SEQ ID NO: 31 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 172 (LCDR3); (III) SEQ ID NO: 32 (HCDR1), SEQ ID NO: 191 (HCDR2), SEQ ID NO: 30 (HCDR3), SEQ ID NO: 44 (LCDR1), SEQ ID NO: 45 (LCDR2), and SEQ ID NO: 173 (LCDR3); or (IV) SEQ ID NO: 34 (HCDR1), SEQ ID NO: 192 (HCDR2), SEQ ID NO: 36 (HCDR3), SEQ ID NO: 47 (LCDR1), SEQ ID NO: 45 (LCDR2), and SEQ ID NO: 172 (LCDR3); (p) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 43 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 43 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 46 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 43 (LCDR3).

In some embodiments of the invention, the antibody or antigen binding fragment comprises three heavy chain complementarity determining regions (HCDR1, HCDR2, and HCDR3) and three light chain complementarity determining regions (LCDR1, LCDR2, and LCDR3) selected from: (I) SEQ ID NO: 76 (HCDR1), SEQ ID NO: 77 (HCDR2), SEQ ID NO: 78 (HCDR3), SEQ ID NO: 89 (LCDR1), SEQ ID NO: 90 (LCDR2), and SEQ ID NO: 91 (LCDR3); (II) SEQ ID NO: 79 (HCDR1), SEQ ID NO: 77 (HCDR2), SEQ ID NO: 78 (HCDR3), SEQ ID NO: 89 (LCDR1), SEQ ID NO: 90 (LCDR2), and SEQ ID NO: 91 (LCDR3); (III) SEQ ID NO: 80 (HCDR1), SEQ ID NO: 81 (HCDR2), SEQ ID NO: 78 (HCDR3), SEQ ID NO: 92 (LCDR1), SEQ ID NO: 93 (LCDR2), and SEQ ID NO: 94 (LCDR3); or (IV) SEQ ID NO: 82 (HCDR1), SEQ ID NO: 83 (HCDR2), SEQ ID NO: 84 (HCDR3), SEQ ID NO: 95 (LCDR1), SEQ ID NO: 93 (LCDR2), and SEQ ID NO: 91 (LCDR3).

In some embodiments of the invention, the antibody or antigen binding fragment comprises: (a) a heavy chain variable region comprising an amino acid sequence of SEQ ID NO: 201, and a light chain variable region comprising an amino acid sequence of SEQ ID NO: 136; (b) a heavy chain variable region comprising an amino acid sequence of SEQ ID NO: 122, and a light chain variable region comprising an amino acid sequence of SEQ ID NO: 136; or (c) a heavy chain variable region comprising an amino acid sequence of SEQ ID NO: 37, and a light chain variable region comprising an amino acid sequence of SEQ ID NO: 48.

In some embodiments of the invention, the antibody or antigen binding fragment comprises: a heavy chain variable region comprising an amino acid sequence of SEQ ID NO: 85, and a light chain variable region comprising an amino acid sequence of SEQ ID NO: 96.

In some embodiments of the invention, the antibody or antigen binding fragment comprises: (a) a heavy chain comprising an amino acid sequence of SEQ ID NO: 203, and a light chain comprising an amino acid sequence of SEQ ID NO: 138; (b) a heavy chain comprising an amino acid sequence of SEQ ID NO: 208, and a light chain comprising an amino acid sequence of SEQ ID NO: 138; or (c) a heavy chain comprising an amino acid sequence of SEQ ID NO: 39, and a light chain comprising an amino acid sequence of SEQ ID NO: 50.

In some embodiments of the invention, the antibody or antigen binding fragment comprises: a heavy chain comprising an amino acid sequence of SEQ ID NO: 87, and a light chain comprising an amino acid sequence of SEQ ID NO: 98.

In some embodiments of the invention, the antigen binding fragment is selected from the group consisting of a Fab, Fab', F(ab)$_2$, Fv, single domain antibody (dAb), and a single chain variable fragment (scFv). In some embodiments of the invention, the antibody or antigen binding fragment is therapeutic.

In some aspects of the invention, provided herein is an isolated nucleic acid or nucleic acids encoding the amino acid sequence of any of the antibodies or antigen binding fragments described herein. In some aspects of the invention, provided herein is a vector comprising any of the isolated nucleic acid(s) described herein. In some aspects of the invention, provided herein is a host cell comprising any of the isolated nucleic acid(s) described herein. In some aspects of the invention, provided herein is a method of producing an isolated anti-NPR1 antibody or antigen binding fragment, comprising culturing any of the host cells described herein under conditions suitable for producing the antibody or antigen binding fragment.

In some aspects of the invention, provided herein is a pharmaceutical composition comprising any of the antibodies or antigen binding fragments described herein and a pharmaceutically acceptable carrier. In some embodiments of the invention, the composition further comprises an additional therapeutic agent. In some embodiments of the invention, the additional therapeutic agent is selected from an ACE (angiotensin-converting-enzyme) inhibitor, an angiotensin receptor blocker (ARB), a neprilysin inhibitor, a beta blocker, a diuretic, a calcium channel blocker, a cardiac glycoside, a sodium-glucose co-transporter 2 inhibitor (SGLT2i), an angiotensin receptor-neprilysin inhibitor (ARNi), a corticosteroid, a leukotriene modifier, a bronchodilator, a beta-adrenoceptor antagonist, a carbonic anhydrase inhibitor, an alpha 2-adrenoceptor agonist, a parasympathomimetic, a prostaglandin analog, a rho kinase inhibitor, and combinations thereof. In some embodiments of the invention, the additional therapeutic agent is selected from enalapril, benazepril, captopril, fosinopril, lisinopril, moexipril, perindopril, quinapril, ramipril, trandolapril, valsartan, azilsartan, candesartan, eprosartan, irbesartan, losartan, olmesartan, telmisartan, sacubitril, bisoprolol, carvedilol, propanolol, metoprolol, metoprolol tartrate, metoprolol succinate, thiazide diuretics, loop diuretics, potassium-sparing diuretics, amlodipine, clevidipine, diltiazem, felodipine, isradipine, nicardipine, nifedipine, nisoldipine, verapamil, a digitalis glycoside, canagliflozin, dapagliflozin, empagliflozin, ertugliflozin, chlorothiazide, chlorthalidone, hydrochlorothiazide, indapamide, metolazone, bumetanide, ethacrynic acid, furosemide, torsemide, amiloride, eplerenone, spironolactonem, triamterene, digoxin, fluticasone, budesonide, mometasone, beclomethasone, ciclesonide, fluticasone furoate, prednisone, methylprednisolone, montelukast, zafirlukast, zileuton, a long-acting beta agonist, a short-acting beta agonist, theophylline, ipratropium, salmeterol, formoterol, albuterol, levalbuterol, timolol, levobunolol, metipranolol, carteolol, betaxolol, acetazolamide, dorzolamide, brinzolamide, methazolamide, brimonidine, apraclonidine, a cholinomimetic, latanoprost, latanoprostene bunod, travoprost, bimatoprost, tafluprost, netarsudil, ripasudil, and combinations thereof.

In some aspects of the invention, provided herein is a method of treating a disorder or a disease associated with natriuretic peptide receptor activity in a subject in need thereof, the method comprising administering to the subject a therapeutically effective amount of any of the antibodies or antigen binding fragments described herein.

In some aspects of the invention, provided herein is a method of treating a cardiovascular disorder in a subject in need thereof, the method comprising administering to the subject a therapeutically effective amount of any of the antibodies or antigen binding fragments described herein. In some embodiments of the invention, the cardiovascular disorder is selected from: hypertension, peripheral vascular disease, heart failure, coronary artery disease (CAD), ischemic heart disease (IHD), mitral stenosis and regurgitation, angina, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, and myocardial infarction (MI).

In some aspects of the invention, provided herein is a method of treating heart failure, hypertrophic cardiomyopathy (HCM), hypertension, preeclampsia, asthma, glaucoma, and/or cytokine release syndrome in a subject in need thereof, comprising administering to the subject a therapeutically effective amount of any of the antibodies or antigen binding fragments described herein. In some embodiments of the invention, the subject has heart failure, and the heart failure is selected from a heart failure with reduced ejection fraction (HFrEF), heart failure with preserved ejection fraction (HFpEF), heart failure after acute myocardial infarct, or acute decompensated heart failure. In some embodiments of the invention, the subject has hypertrophic cardiomyopathy, and wherein the hypertrophic cardiomyopathy is ventricular hypertrophy. In some embodiments of the invention, the subject has hypertension, and the hypertension is selected from resistant hypertension, hypertensive heart disease, pulmonary hypertension, pulmonary arterial hypertension, isolated systolic hypertension, resistant hypertension, and pulmonary arterial hypertension. In some embodiments of the invention, the subject has hypertension, and the hypertension is selected from resistant hypertension or hypertensive heart disease.

In some aspects of the invention, provided herein is a method of treating a kidney disorder in a subject in need thereof, the method comprising administering to the subject a therapeutically effective amount of any of the antibodies or antigen binding fragments described herein. In some embodiments of the invention, the kidney disorder is selected from: diabetic renal insufficiency, non-diabetic renal insufficiency, renal failure, diabetic nephropathy, non-diabetic nephropathy, acute renal injury, contrast induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, renal fibrosis, and polycystic kidney disease (PKD).

BRIEF DESCRIPTION OF THE FIGURES

FIGS. 9A and 9B show a set of graphs displaying the results of antibody candidates XX01-XX08, XX10, and XX12 binding to the following antigens (ELISA analysis): human NPR1, constitutively active human NPR1 mutant (W74R), rat NPR1, and human NPR3 (counter target) in the absence of or in the presence of a 250 fold molar excess of ANP.

GENERAL DEFINITIONS

Figure 1:
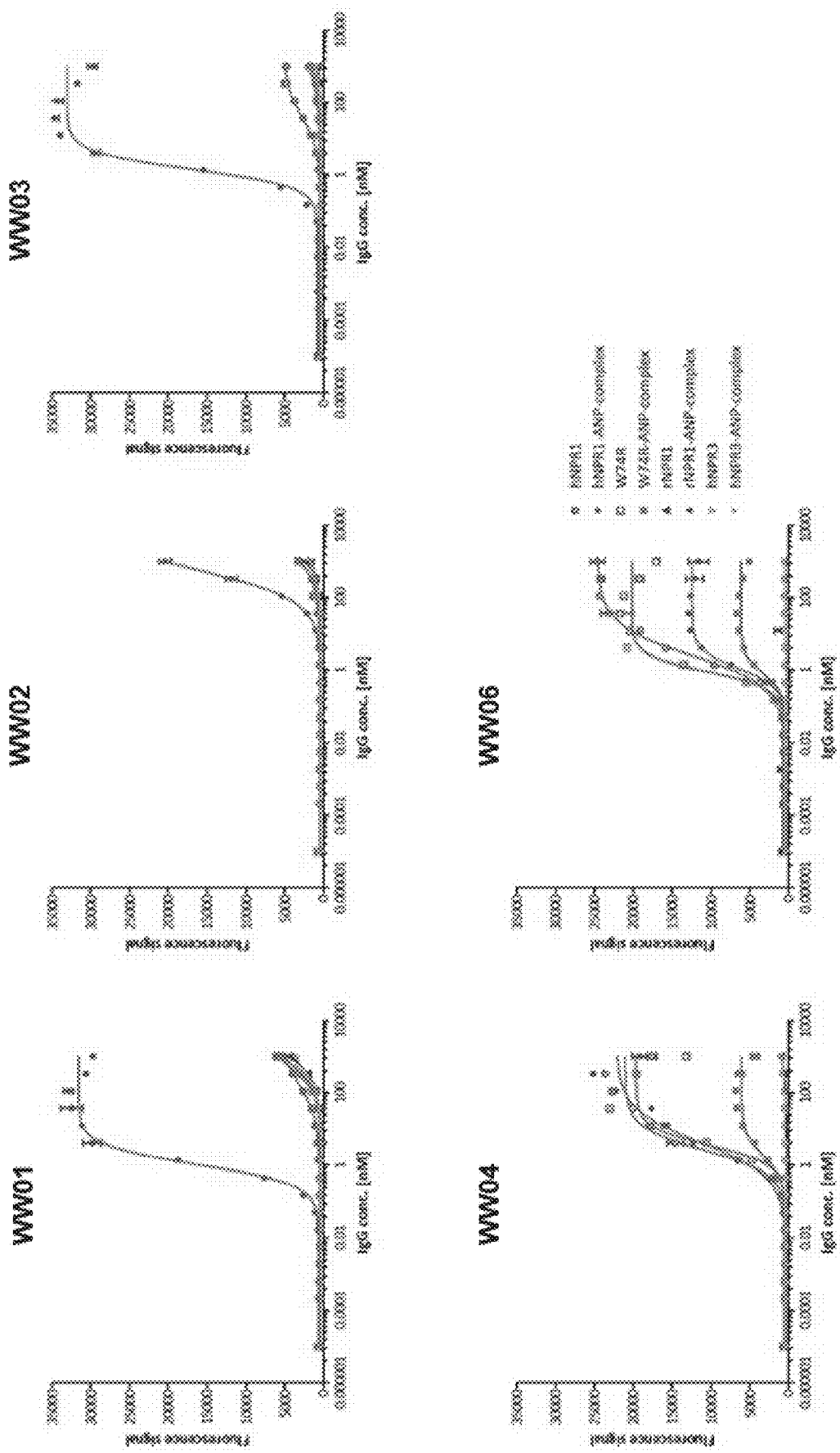
FIG. 1 is a set of graphs displaying the results of antibody candidates WW01, WW02, WW03, WW04, and WW06 binding to the following antigens (ELISA analysis): human NPR1, constitutively active human NPR1 mutant (W74R), rat NPR1, and human NPR3 (counter target) both in the absence of and presence of a 250 fold molar excess of ANP.

In order that the present disclosure may be more readily understood, certain terms are first defined. Additional definitions are set forth throughout the detailed description as required.

Throughout the description and claims of this specification, the words "comprise" and "contain" and variations of the words, for example "comprising" and "comprises", mean "including but not limited to", and do not exclude other components, integers, or steps. Moreover the singular encompasses the plural unless the context otherwise requires: in particular, where the indefinite article is used, the specification is to be understood as contemplating plurality as well as singularity, unless the context requires otherwise.

As used herein, "NPR1" and "NPR1 protein" refers to Natriuretic Peptide Receptor 1. This protein is also known as Atrial natriuretic peptide receptor type A (ANP-A, ANPR-A or NPR-A) and Guanylate cyclase A (GC-A). In some embodiments, the NPR1 referred to is human NPR1. In some embodiments the human NPR1 is has UniProt accession number P16066 or GenBank Accession number EAW53284.1 (SEQ ID NO: 1). In some embodiments, the NPR1 referred to is mouse (*Mus musculus*) NPR1. In some embodiments the mouse NPR1 has NCBI Reference Sequence number NP_032753.5 (SEQ ID NO: 2). In some embodiments, the NPR1 referred to is rat (*Rattus norvegicus*) NPR1. In some embodiments the rat NPR1 has NCBI Reference Sequence number NP_036745.1 (SEQ ID NO: 3). Exemplary NPR1 proteins are shown in Table 1. Where a constitutively active or W74R mutant is discussed herein, this mutant refers to Trp at amino acid 74 of the mature human NPR1 protein, which may also be referred to as the Trp at amino acid 106 of the hNPR1 protein shown in SEQ ID NO: 1.

TABLE 1

NPR1 Protein Sequences

| SEQ ID NO: | Animal | Sequence (amino acid) |
|---|---|---|
| 1 | Human | MPGPRRPAGSRLRLLLLLLLPPLLLLLRGSH AGNLTVAVVLPLANTSYPWSWARVGPAVELA LAQVKARPDLLPGWTVRTVLGSSENALGVCS DTAAPLAAVDLKWEHNPAVFLGPGCVYAAAP VGRFTAHWRVPLLTAGAPALGFGVKDEYALT TRAGPSYAKLGDFVAALHRRLGWERQALMLY AYRPGDEEHCFFLVEGLFMRVRDRLNITVDH LEFAEDDLSHYTRLLRTMPRKGRVIYICSSP DAFRTLMLLALEAGLCGEDYVFFHLDIFGQS LQGGQGPAPRRPWERGDGQDVSARQAFQAAK IITYKDPDNPEYLEFLKQLKHLAYEQFNFTM EDGLVNTIPASFHDGLLLYIQAVTETLAHGG TVTDGENITQRMWNRSFQGVTGYLKIDSSGD RETDFSLWDMDPENGAFRVVLNYNGTSQELV AVSGRKLNWPLGYPPPDIPKCGFDNEDPACN QDHLSTLEVLALVGSLSLLGILIVSFFIYRK MQLEKELASELWRVRWEDVEPSSLERHLRSA GSRLTLSGRGSNYGSLLTTEGQFQVFAKTAY YKGNLVAVKRVNRKRIELTRKVLFELKHMRD VQNEHLTRFVGACTDPPNICILTEYCPRGSL QDILENESITLDWMFRYSLTNDIVKGMLFLH NGAICSHGNLKSSNCVVDGRFVLKITDYGLE SFRDLDPEQGHTVYAKKLWTAPELLRMASPP VRGSQAGDVYSFGIILQEIALRSGVFHVEGL DLSPKEIIERVTRGEQPPFRPSLALQSHLEE LGLLMQRCWAEDPQERPPFQQIRLTLRKFNR ENSSNILDNLLSRMEQYANNLEELVEERTQA YLEEKRKAEALLYQILPHSVAEQLKRGETVQ AEAFDSVTIYFSDIVGFTALSAESTPMQVVT LLNDLYTCFDAVIDNFDVYKVETIGDAYMVV SGLPVRNGRLHACEVARMALALLDAVRSFRI RHRPQEQLRLRIGIHTGPVCAGVVGLKMPRY CLFGDTVNTASRMESNGEALKIHLSSETKAV LEEFGGFELELRGDVEMKGKGKVRTYWLLGE RGSSTRG |
| 2 | Mouse | MPGSRRVRPRLRALLLLPPLLLLRSGH ASDLTVAVVLPLTNTSYPWSWARVGPAVELA LGRVKARPDLLPGWTVRMVLGSSENAAGVCS DTAAPLAAVDLKWEHSPAVFLGPGCVYSAAP VGRFTAHWRVPLLTAGAPALGIGVKDEYALT TRTGPSHVKLGDFVTALHRRLGWEHQALVLY ADRLGDDRPCFFIVEGLYMRVRERLNITVNH QEFVEGDPDHYTKLLRTVQRKGRVIYICSSP DAFRNLMLLALDAGLTGEDYVFFHLDVFGQS LQGAQGPVPRKPWERDDGQDRRARQAFQAAK IITYKEPDNPEYLEFLKQLKLLADKKFNFTM EDGLKNIIPASFHDGLLLYVQAVTETLAQGG TVTDGENITQRMWNRSFQGVTGYLKIDRNGD RDTDFSLWDMDPETGAFRVVLNFNGTSQELM AVSEHRLYWPLGYPPPDIPKCGFDNEDPACN QDHFSTLEVLALVGSLSLVSFLIVSFFIYRK |

TABLE 1-continued

NPR1 Protein Sequences

| SEQ ID NO: | Animal | Sequence (amino acid) |
|---|---|---|
|  |  | MQLEKELVSELWRVRWEDLQPSSLERHLRSA GSRLTLSGRGSNYGSLLTTEGQFQVFAKTAY YKGNLVAVKRVNRKRIELTRKVLFELKHMRD VQNEHLTRFVGACTDPPNICILTEYCPRGSL QDILENESITLDWMFRYSLINDIVKGMLFLH NGAIGSHGNLKSSNCVVDGRFVLKITDYGLE SFRDPEPEQGHTLFAKKLWTAPELLRMASPP ARGSQAGDVYSFGIILQEIALRSGVFYVEGL DLSPKEIIERVTRGEQPPFRPSMDLQSHLEE LGQLMQRCWAEDPQERPPFQQIRLALRKFNK ENSSNILDNLLSRMEQYANNLEELVEERTQA YLEEKRKAEALLYQILPHSVAEQLKRGETVQ AEAFDSVTIYFSDIVGFTALSAESTPMQVVT LLNDLYTCFDAVIDNFDVYKVETIGDAYMVV SGLPVRNGQLHAREVARMALALLLDAVRSFRI RHRPQEQLRLRIGIHTGPVCAGVVGLKMPRY CLFGDTVNTASRMESNGEALRIHLSSETKAV LEEFDGFELELRGDVEMKGKGKVRTYWLLGE RGCSTRG |
| 3 | Rat | MPGSRRVRPRLRALLLLLPPLLLLLRGGH ASDLTVAVVLPLTNTSYPWSWARVGPAVELA LARVKARPDLLPGWTVRMVLGSSENAAGVCS DTAAPLAAVDLKWEHSPAVFLGPGCVYSAAP VGRFTAHWRVPLLTAGAPALGIGVKDEYALT TRTGPSHVKLGDFVTALHRRLGWEHQALVLY ADRLGDDRPCFFIVEGLYMRVRERLNITVNH QEFVEGDPDHYPKLLRAVRRKGRVIYICSSP DAFRNLMLLALNAGLTGEDYVFFHLDVFGQS LKSAQGLVPQKPWERGDGQDRSARQAFQAAK IITYKEPDNPEYLEFLKQLKLLADKKFNFTV EDGLKNIIPASFHDGLLLYVQAVTETLAQGG TVTDGENITQRMWNRSFQGVTGYLKIDRNGD RDTDFSLWDMDPETGAFRVVLNYNGTSQELM AVSEHKLYWPLGYPPPDVPKCGFDNEDPACN QDHFSTLEVLALVGSLSLISFLIVSFFIYRK MQLEKELVSELWRVRWEDLQPSSLERHLRSA GSRLTLSGRGSNYGSLLTTEGQFQVFAKTAY YKGNLVAVKRVNRKRIELTRKVLFELKHMRD VQNEHLTRFVGACTDPPNICILTEYCPRGSL QDILENESITLDWMFRYSLTNDIVKGMLFLH NGAICSHGNLKSSNCVVDGRFVLKITDYGLE SFRDPEPEQGHTLFAKKLWTAPELLRMASPP ARGSQAGDVYSFGIILQEIALRSGVFYVEGL DLSPKEIIERVTRGEQPPFRPSMDLQSHLEE LGQLMQRCWAEDPQERPPFQQIRLALRKFNK ENSSNILDNLLSRMEQYANNLEELVEERTQA YLEEKRKAEALLYQILPHSVAEQLKRGETVQ AEAFDSVTIYFSDIVGFTALSAESTPMQVVT LLNDLYTCFDAVIDNFDVYKVETIGDAYMVV SGLPVRNGQLHAREVARMALALLLDAVRSFRI RHRPQEQLRLRIGIHTGPVCAGVVGLKMPRY CLFGDTVNTASRMESNGEALKIHLSSETKAV LEEFDGFELELRGDVEMKGKGKVRTYWLLGE RGCSTRG |

In various embodiments, the anti-NPR1 antibodies and antigen binding fragments disclosed herein are capable of binding to NPR1 and activating NPR1 in the absence of ANP. By virtue of this activity, the disclosed anti-NPR1 antibodies and antigen binding fragments may be useful in treating undesirable conditions, diseases and disorders including cardiovascular disorders (e.g., hypertension, peripheral vascular disease, heart failure (including but not limited to heart failure with reduced ejection fraction (HFrEF), heart failure with preserved ejection fraction (HFpEF), heart failure after acute myocardial infarct, or acute decompensated heart failure), coronary artery disease (CAD), ischemic heart disease (IHD), mitral stenosis and regurgitation, angina, hypertrophic cardiomyopathy (e.g., ventricular hypertrophy), diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, or myocardial infarction (MI)), hypertension (e.g., resistant hypertension, hypertensive heart disease, pulmonary hypertension, pulmonary arterial hypertension, isolated systolic hypertension, resistant hypertension, or pulmonary arterial hypertension), preeclampsia, asthma, glaucoma, cytokine release syndrome, and/or a kidney disorder (e.g., diabetic renal insufficiency, non-diabetic renal insufficiency, renal failure, diabetic nephropathy, non-diabetic nephropathy, acute renal injury, contrast induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, renal fibrosis, and polycystic kidney disease (PKD)).

The term "antibody" as used herein refers to a whole antibody or antigen binding fragment thereof. A whole antibody is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. The term "antibody" includes, but is not limited to, monoclonal antibodies, human antibodies, humanized antibodies, camelised antibodies, and chimeric antibodies. The antibodies can be of any isotype/class (e.g., IgG, IgE, IgM, IgD, IgA and IgY) or subclass (e.g., $IgG_1$, $IgG_2$, $IgG_3$, $IgG_4$, $IgA_1$, and $IgA_2$).

The term "antigen binding fragment" refers to a fragment of an intact antibody that retains the ability to specifically bind to a given antigen (e.g., NPR1) and/or provide a function of the intact antibody. Such fragments include Fab fragments, Fab' fragments, monovalent fragments consisting of the VL, VH, CL and CH1 domains; F(ab')2 fragments, bivalent fragments comprising two Fab fragments linked by a disulfide bridge at the hinge region; an Fd fragment consisting of the VH and CH1 domains; an Fv fragment consisting of the VL and VH domains, a single chain Fv fragment (scFv) consisting of the VL and VH domains connected by a linker sequence; and a single domain antibody (dAb) fragment (Ward et al., 1989 Nature 341:544-546), which consists of a VH domain or a VL domain.

The term "single chain antibody", "single chain Fv" or "scFv" is refers to a molecule comprising an antibody heavy chain variable domain (or region; VH) and an antibody light chain variable domain (or region; VL) connected by a linker. Such scFv molecules can have the general structures: NH2-VL-linker-VH-COOH or NH2-VH-linker-VL-COOH. Any suitable linker may be used. A non-limiting set of linkers that can be used in such single chain antibodies are described by Holliger et al. (1993), Proc. Natl. Acad. Sci. USA 90:6444-6448, Alfthan et al. (1995), Protein Eng. 8:725-731, Choi et al. (2001), Eur. J. Immunol. 31:94-106, Hu et al. (1996), Cancer Res. 56:3055-3061, Kipriyanov et al. (1999), J. Mol. Biol. 293:41-56 and Roovers et al. (2001), Cancer Immunol; the contents of each of which are herein incorporated by reference for this purpose. Such single chain antibodies are also intended to be encompassed within the term "antigen binding fragment" of an antibody. These antibody fragments are obtained using techniques known to those of skill in the art, and the fragments are screened for utility in the same manner as are intact antibodies. Without limitation, an antigen binding fragment can be produced by any suitable method known in the art. For instance, the various antigen binding fragments described herein can be produced by enzymatic or chemical modification of intact antibodies, synthesized de novo using recombinant DNA methodologies (e.g., single chain Fv), or identified using phage display libraries (see, e.g., Pini and Bracci, Curr Protein Pept Sci 2000; 1(2):155-69, the contents of which are herein incorporated by reference for this purpose). Antigen binding fragments are screened for utility (e.g., binding affinity, activity) in the same manner as are intact antibodies.

Antigen binding fragments can also be incorporated into single domain antibodies, maxibodies, minibodies, intrabodies, diabodies, triabodies, tetrabodies, v-NAR and bis-scFv (see, e.g., Hollinger and Hudson, 2005, Nature Biotechnology, 23, 9, 1126-1136, the contents of which are herein incorporated by reference for this purpose). Antigen binding portions of antibodies can be grafted into scaffolds based on polypeptides such as Fibronectin type III (Fn3) (see e.g., U.S. Pat. No. 6,703,199, which describes fibronectin polypeptide monobodies, the contents of which are herein incorporated by reference for this purpose).

Antigen binding fragments can be incorporated into single chain molecules comprising a pair of tandem Fv segments (VH-CH1-VH-CH1) which, together with complementary light chain polypeptides, form a pair of antigen binding regions (see Zapata et al., 1995 Protein Eng. 8(10):1057-1062; and U.S. Pat. No. 5,641,870; the contents of each of which are herein incorporated by reference for this purpose).

The term "isolated" means throughout this specification, that the immunoglobulin, antibody or polynucleotide, as the case may be, exists in a physical milieu distinct from that in which it may occur in nature. For example, a naturally-occurring polynucleotide or polypeptide present in a living organism is not isolated, but the same polynucleotide or polypeptide separated from some or all of the coexisting materials in the living organism, is isolated.

The term "isolated antibody," as used herein, refers to an antibody that has been identified and separated from one or more (e.g., the majority) of the components (by weight) of its source environment, e.g., from the components of a hybridoma cell culture or a different cell culture that was used for its production (e.g., producer cells including but not limited to the exemplary host cells described herein that recombinantly express the antibody). The separation is performed such that it sufficiently removes components that may otherwise interfere with the suitability of the antibody for the desired applications (e.g., for therapeutic use of an anti-NPR1 antibody). Methods for preparing isolated antibodies are known in the art and include Protein A chromatography, anion exchange chromatography, cation exchange chromatography, virus retentive filtration, and ultrafiltration.

Throughout this specification, complementarity determining regions ("CDR") are defined according to the Kabat definition unless specified that the CDR are defined according to another definition. The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme) and ImMunoGenTics (IMGT) numbering (Lefranc, M.-P., The Immunologist, 7, 132-136 (1999); Lefranc, M.-P. et al., Dev. Comp. Immunol., 27, 55-77 (2003) ("IMGT" numbering scheme); the contents of each of which are herein incorporated by reference for this purpose. For example, for classic formats, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL. Under IMGT the CDR amino acid residues in the VH are numbered approximately 26-35 (CDR1), 51-57 (CDR2) and 93-102 (CDR3), and the CDR amino acid residues in the VL are numbered approximately 27-32 (CDR1), 50-52 (CDR2), and 89-97 (CDR3) (numbering according to "Kabat"). Under IMGT, the CDR regions of an antibody can be determined using the program IMGT/DomainGap Align.

By convention, the CDR regions in the heavy chain are typically referred to as HCDR1, HCDR2 and HCDR3 and in the light chain as LCDR1, LCDR2 and LCDR3. They are numbered sequentially in the direction from the amino terminus to the carboxy terminus.

The term "antibody framework" as used herein refers to the part of the variable domain, either VL or VH, which serves as a scaffold for the antigen binding loops (CDRs) of this variable domain. In essence, it is the variable domain without the CDRs.

The terms "constant region" or "constant domain" refer to a carboxy terminal portion of the light and heavy chain which is not directly involved in binding of the antibody to antigen but exhibits various effector functions, such as interaction with the Fc receptor. The terms refer to the portion of an immunoglobulin molecule having a more conserved amino acid sequence relative to the other portion of the immunoglobulin, the variable domain, which contains the antigen binding site. The constant domain contains the CH1, CH2 and CH3 domains of the heavy chain and the CHL domain of the light chain.

The term "epitope" or "antigenic determinant" refers to a site on an antigen to which an immunoglobulin or antibody specifically binds (e.g., a specific site on the target molecule). An epitope typically includes at least 3, 4, 5, 6, 7, 8, 9, 10, 11, 12, 13, 14, or 15 consecutive or non-consecutive amino acids in a unique spatial conformation. See, e.g., *Epitope Mapping Protocols in Methods in Molecular Biology*, Vol. 66, G. E. Morris, Ed. (1996), the contents of which are herein incorporated by reference for this purpose. In addition, as used herein, an epitope can comprise one or more monosaccharide units of a polysaccharide to which an antibody specifically binds. In specific aspects, an epitope can be a conformational epitope. See, e.g., Thompson et al., 2009, *J. of Biol. Chem.* 51: 35621-35631, the contents of which are herein incorporated by reference for this purpose.

The terms "monoclonal antibody" or "monoclonal antibody composition" as used herein refers to an antibody obtained from a population of substantially homogeneous antibodies produced by a particular cell or cell line, wherein the individual antibodies comprising the population are essentially identical in sequence except for possible naturally-occurring mutations that may be present in minor amounts. A monoclonal antibody preparation displays a single binding specificity and affinity for a particular epitope. In contrast, conventional (polyclonal) antibody preparations typically include a multitude of antibodies directed against or specific for different epitopes. The modifier "monoclonal" indicates the character of the antibody as being obtained from a substantially homogeneous population of antibodies and is not to be construed as requiring production of the antibody by any particular method. Monoclonal antibodies (mAbs) can be produced by a variety of techniques, including conventional methodology, e.g., the standard somatic cell hybridization technique of Kohler and Milstein (Nature 1975; 256(5517):495-7), the contents of which are herein incorporated by reference for this purpose. A monoclonal antibody may also be obtained from other suitable methods, including phage display techniques such as those described in Clackson et al. (Nature 1991; 352 (6336):624-8) or Marks et al. (J Mol Biol 1991; 222(3):581-97), the contents of each of which are herein incorporated by reference for this purpose. The term "monoclonal antibody" is also not limited to antibody sequences from particular species of origin or from one single species of origin. Thus, the meaning of the term "monoclonal antibody" encompasses chimeric monoclonal antibodies such as humanized monoclonal antibodies.

The term "chimeric antibody," as used herein, refers to antibodies in which (a) the constant region is altered, replaced, or exchanged such that the antigen binding site (variable region) is linked to a constant region of a different or altered class, effector function, and/or species; or (b) the variable region, or a portion thereof, is altered, replaced, or exchanged with a variable region, or a portion thereof, having a different or altered antigen specificity. To create a chimeric antibody, the variable region sequences from a non-human donor antibody (e.g., a mouse, rabbit, or rat donor antibody) can be linked to human constant regions using methods known in the art (see, e.g., U.S. Pat. No. 4,816,567 (Cabilly et al.), the contents of which are herein incorporated by reference for this purpose). For instance, a mouse anti-NPR1 antibody can be modified by replacing its constant region with the constant region from a human immunoglobulin. Due to the replacement with a human constant region, the chimeric antibody can retain its specificity in recognizing human NPR1 while having reduced immunogenicity in human as compared to the original mouse antibody.

As used herein, the term "humanized antibody" refers to forms of antibodies that contain at least some human sequence and at least some non-human sequence. Typically, the antibody contains human sequences and a minor portion of non-human sequences which confer binding specificity to the target antigen. Such antibodies are chimeric antibodies which contain minimal sequence derived from a non-human immunoglobulin and retain the reactivity of a non-human antibody while being less immunogenic in humans. Typically, humanized antibodies are generated by replacing hypervariable region sequences from a human acceptor antibody with hypervariable region sequences from a non-human donor antibody (e.g., a mouse, rabbit, or rat donor antibody) that binds to an antigen of interest (e.g., NPR1). In some cases, framework region sequences of the acceptor antibody may also be replaced with the corresponding sequences of the donor antibody (e.g., via affinity maturation). In addition to the sequences derived from the donor and acceptor antibodies, the humanized antibody can be further modified by the substitution of residues, either in the framework region and/or within the replaced non-human residues to refine and optimize antibody specificity, affinity, and/or activity, as discussed herein. Methods to generate humanized antibodies are known in the art. See, e.g., Riechmann et al. (Nature 1988; 332(6162):323-7); Jones et al. (Nature 1986; 321(6069):522-5); U.S. Pat. No. 5,225,539 (Winter); and U.S. Pat. Nos. 5,530,101; 5,585,089; 5,693,762, and 6,180,370 (Queen et al.), the contents of each of which are herein incorporated by reference for this purpose.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik, et al., (2000) J Mol Biol; 296:57-86, the contents of which are herein incorporated by reference for this purpose). Human antibodies may include amino acid residues not encoded by human sequences (e.g., mutations introduced by random or site-specific mutagenesis in vitro or by somatic mutation in vivo).

The antibodies or antigen binding fragments of the disclosure may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The terms "peptide," "polypeptide," and "protein" are used interchangeably herein to refer to a polymer of amino acid residues. The terms encompass amino acid polymers in which one or more amino acid residues is an artificial chemical mimetic of a corresponding naturally-occurring amino acid, as well as naturally-occurring amino acid polymers and non-naturally-occurring amino acid polymers. Unless otherwise indicated, a particular polypeptide sequence also implicitly encompasses conservatively modified variants thereof.

The term "conservatively modified variant" applies to both amino acid and nucleic acid sequences. For nucleic acid sequences, conservatively modified variants refer to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence. For polypeptide sequences, conservatively modified variants include individual substitutions, deletions, or additions to a polypeptide sequence which result in the substitution of an amino acid with a chemically similar amino acid. Conservative substitution tables providing functionally similar amino acids are well known in the art. The following eight groups contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

The term "identity" or "homology" refers to a relationship between the sequences of two or more polypeptides, as determined by comparing the sequences. "Identity" also means the degree of sequence relatedness between polypeptides, as determined by the number of matches between strings of two or more amino acid residues. The percent "identity" between the two sequences is a function of the number of identical positions shared by the sequences (i.e., percent identity equals number of identical positions/total number of positions×100), taking into account the number of gaps, and the length of each gap, which need to be introduced for optimal alignment of the two sequences. The comparison of sequences and determination of percent identity between two sequences can be accomplished using a mathematical algorithm. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Additionally, or alternatively, the protein sequences of the present disclosure can further be used as a "query sequence" to perform a search against public databases to, for example, identify related sequences. For example, such searches can be performed using the BLAST program of Altschul et al. (J Mol Biol 1990; 215(3):403-10), the contents of which are herein incorporated by reference for this purpose.

Two sequences are "substantially identical" if two sequences have a specified percentage of amino acid residues or nucleotides that are the same (e.g., 60% identity, 65% identity, 70% identity, 75% identity, 80% identity, 85% identity, 90% identity, 95% identity, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or exists over a region that is 100 to 500 or 1000 or more nucleotides (or 20, 50, 200 or more amino acids) in length.

Binding "affinity" refers to the strength of interaction between antibody and antigen at single antigenic sites. Within each antigenic site, the variable region of the antibody "arm" interacts through weak non-covalent forces with antigen at numerous sites. In general, the more interactions, the stronger the affinity. Generally, such determinations can be made using a cell-based assay.

The term "Kassoc" or "Ka", as used herein, is intended to refer to the association rate of a particular binding molecule-antigen interaction, whereas the term "Kdis" or "Kd," as used herein, is intended to refer to the dissociation rate of a particular binding molecule-antigen interaction. The term "$K_D$", as used herein, is intended to refer to the equilibrium dissociation constant, which is obtained from the ratio of Kd to Ka (i.e., Kd/Ka) and is expressed as a molar concentration (M). $K_D$ values for antibodies can be determined using methods well established in the art. A method for determining the $K_D$ of an antibody is by using surface plasmon resonance, such as a Biacore® system, or solution equilibrium titration (SET) (see Friguet et al., (1985) J. Immunol. Methods, 77(2):305-319, and Hanel et al., (2005) Anal. Biochem., 339(1):182-184), the contents of each of which are herein incorporated by reference for this purpose.

As used herein, the term "specific," "specifically binds," and "binds specifically" refers to a binding reaction between an antibody or antigen binding fragment (e.g., an anti-NPR1 antibody) and a target antigen (e.g., NPR1) in a heterogeneous population of proteins and other biologics. Antibodies can be tested for specificity of binding by comparing binding to an appropriate antigen to binding to an irrelevant antigen or antigen mixture under a given set of conditions. If the antibody binds to the appropriate antigen with at least 2, 5, 7, and preferably 10 or more times more affinity than to the irrelevant antigen or antigen mixture, then it is considered to be specific. A "specific antibody" or a "target-specific antibody" is one that only binds the target antigen (e.g., NPR1), but does not bind (or exhibits minimal binding) to other antigens. In certain embodiments, an antibody or antigen binding fragment that specifically binds the target antigen (e.g., NPR1) has a $K_D$ of less than $1\times10^{-6}$ M, less than $1\times10^{-7}$ M, less than $1\times10^{-8}$ M, less than $1\times10^{-9}$ M, less than $1\times10^{-10}$ M, less than $1\times10^{-11}$ M, less than $1\times10^{-12}$ M, or less than $1\times10^{-13}$ M. In certain embodiments, the $K_D$ is about 1 pM to about 600 pM. In certain embodiments, the $K_D$ is between 600 pM to 1 µM, 1 µM to 100 nM, or 100 mM to 10 nM (inclusive).

In some embodiments, the antibodies or antigen binding fragments thereof act as non-competitive agonists. A "non-competitive agonist" refers to a molecule which binds to an enzyme or receptor at a site distant from the binding sites of its natural ligands. The non-competitive or allosteric agonism is generally independent of the association or concentration of the natural ligands for the enzyme or receptor. Such non-competitive agonists can, for example, provide for a level of activation that can be substantially independent of natural ligands. In a specific embodiment, the anti-NPR1 antibodies or antigen binding fragments described herein are ANP non-competitive, meaning that the antibody or antigen binding fragment acts as an agonist which binds at site away from ANP binding site of NPR1 and effect agonistic activity regardless of whether or not NPR1 is bound to ANP.

In some embodiments, the antibodies or antigen binding fragments thereof act as competitive agonists. A "competitive agonist" refers to an agonist which interferes or competes with a natural ligand for its binding site on an enzyme or receptor. In a specific embodiment, the anti-NPR1 antibodies or antigen binding fragments described herein are ANP competitive, meaning that the antibody or antigen binding fragment acts as an agonist which competes with ANP at the ANP binding site of NPR1.

In some embodiments, the activation of NPR1 by an antibody or antigen binding fragment may be determined by any suitable assay. An exemplary assay for determination of NPR1 activation is the production of cGMP by mammalian cells (e.g., CHO cells or a human cell line) expressing hNPR1.

Figure 3:
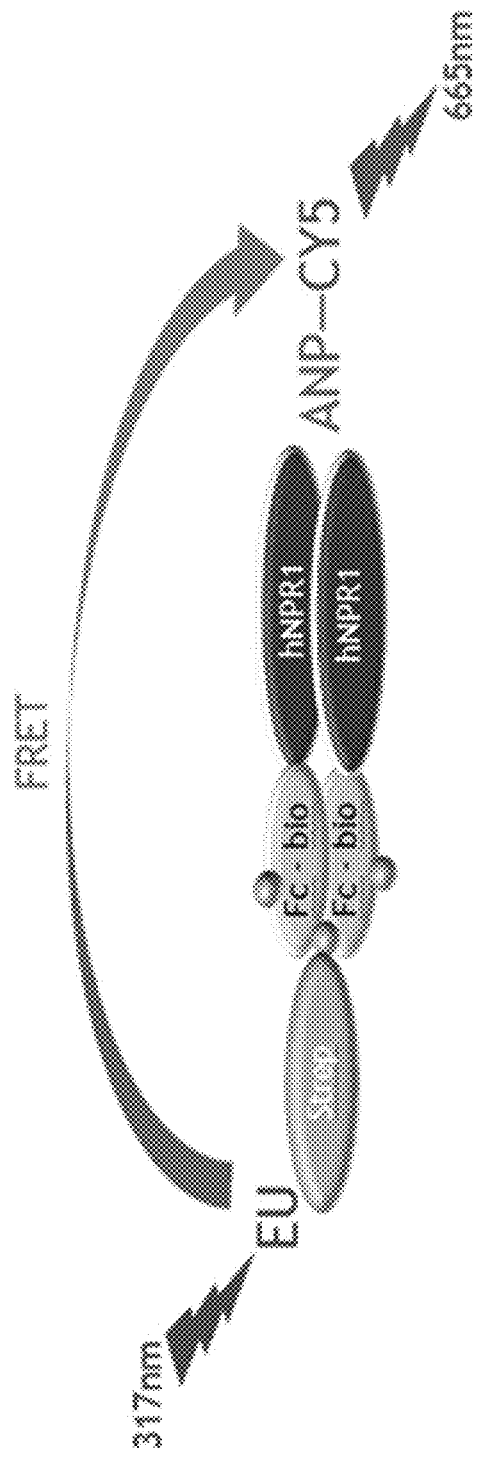
FIG. 3 is a graphical representation of a Fluorescence Resonance Energy Transfer (FRET)-based assay in which the NPR1-specific antibodies competed with ANP for binding to NPR1. In this FRET based assay, Eu-labeled Streptavidin (for measurement of IgGs) or Eu-labeled anti-hFc antibody (for measurement of FabCys) was used as an energy donor, while Cy5-labeled ANP was used as an acceptor.

In some embodiments, the stabilization of the ANP-NPR1 complex may be determined by any suitable assay. An exemplary assay for determination of the stability of the ANP-NPR1 complex is the FRET assay described herein (see, e.g., FIG. 3).

The term "about" in relation to a numerical value x means, for example, x±10%.

Antibodies of the Disclosure

Below are disclosed certain specific anti-NPR1 antibody sequences of the disclosure. As used herein, the term "anti-NPR1 antibody" or "antibody that binds to NPR1" refers to any form of an antibody or antigen binding fragment that specifically binds to NPR1, e.g., those binding with a $K_D$ of less than $1\times10^{-8}$ M, as determined by, e.g., surface plasmon resonance (SPR) spectroscopy (using Biacore™) or solution equilibrium titration (SET). The term encompasses monoclonal antibodies (including intact monoclonal antibodies), polyclonal antibodies, and biologically functional antigen binding fragments so long as they specifically bind to NPR1.

Amino acid and nucleic acid sequences of exemplary anti-NPR1 antibodies of the present disclosure are set forth in Table 2. In some embodiments, the antibody has the heavy and light chain CDRs, VH and VL sequence, and/or the heavy and light chain sequence of any of the antibodies described in Table 2. In some embodiments, the anti-NPR1 antibody is a four-chain antibody (also referred to as an intact antibody), comprising two heavy chains and two light chains. In some embodiments, the anti-NPR1 antibody is an antigen binding fragment of an intact antibody, e.g., a functional fragment of an intact antibody selected from any of those set forth in Table 2 that retains the ability to bind NPR1 and/or provide a function of the intact antibody (e.g., activating NPR1 in the absence of ANP). In some embodiments, the anti-NPR1 antibody is an antibody having the CDRs of any heavy chain variable region and light chain variable region pair shown in Table 2. In some embodiments, the anti-NPR1 antibody is an antibody having the CDRs of any heavy and light chain pair shown in Table 2.

TABLE 2

Exemplary anti-NPR1 antibody sequences

WW01_LALA

| SEQ ID NO: 4 | HCDR1 (Combined) | GFTFNTHYIH |
|---|---|---|
| SEQ ID NO: 5 | HCDR2 (Combined) | SISGSGSNTYYADSVKG |
| SEQ ID NO: 6 | HCDR3 (Combined) | ERGYVYYHMFDP |
| SEQ ID NO: 7 | HCDR1 (Kabat) | THYIH |
| SEQ ID NO: 5 | HCDR2 (Kabat) | SISGSGSNTYYADSVKG |
| SEQ ID NO: 6 | HCDR3 (Kabat) | ERGYVYYHMFDP |
| SEQ ID NO: 8 | HCDR1 (Chothia) | GFTFNTH |
| SEQ ID NO: 9 | HCDR2 (Chothia) | SGSGSN |
| SEQ ID NO: 6 | HCDR3 (Chothia) | ERGYVYYHMFDP |
| SEQ ID NO: 10 | HCDR1 (IMGT) | GFTFNTHY |
| SEQ ID NO: 11 | HCDR2 (IMGT) | ISGSGSNT |
| SEQ ID NO: 12 | HCDR3 (IMGT) | ARERGYVYYHMFDP |
| SEQ ID NO: 13 | VH | QVQLLESGGGLVQPGGSLRLSCAASGFTFNTHYIHWVRQAPGKGLEWVSSI SGSGSNTYYADSVKGRFTISRDNSKNTLYLQMNSLRAEDTAVYYCARERG YVYYHMFDPWGQGTLVTVSS |
| SEQ ID NO: 14 | DNA VH | caggtgcaattgctggaaagcggcggtggcctggtgcagccgggtggcagcctgcgtctgagctgcgcg gcgtccggattcacctttaacactcattacatccattgggtgcgccaggcccccggcaaaggtctcgag tgggtttcctctatctctggttctggttctaacacctactatgcggatagcgtgaaaggccgctttacc atcagccgcgataattcgaaaaacaccctgtatctgcaaatgaacagcctgcgtgccgaagatacggcc gtgtattattgcgcgcgtgaacgtggttacgtttactaccatatgttcgatccgtggggccaaggcacc ctggtgactgttagctca |
| SEQ ID NO: 15 | Heavy Chain | QVQLLESGGGLVQPGGSLRLSCAASGFTFNTHYIHWVRQAPGKGLEWVSSI SGSGSNTYYADSVKGRFTISRDNSKNTLYLQMNSLRAEDTAVYYCARERG YVYYHMFDPWGQGTLVTVSSASTKGPSVFPLAPSSKSTSGGTAALGCLVK DYFPEPVTVSWNSGALTSGVHTFPAVLQSSGLYSLSSVVTVPSSSLGTQTYI CNVNHKPSNTKVDKRVEPKSCDKTHTCPPCPAPEAAGGPSVFLFPPKPKDT LMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSREEMTKNQVSLTCLVKGFYPSDIAVEWESNGQPENNYKTTPPVLDSD GSFFLYSKLTVDKSRWQQGNVFSCSVMHEALHNHYTQKSLSLSPGK |
| SEQ ID NO: 16 | DNA Heavy Chain | caggtgcaattgctggaaagcggcggtggcctggtgcagccgggtggcagcctgcgtctgagctgcgcg gcgtccggattcacctttaacactcattacatccattgggtgcgccaggcccccggcaaaggtctcgag tgggtttcctctatctctggttctggttctaacacctactatgcggatagcgtgaaaggccgctttacc atcagccgcgataattcgaaaaacaccctgtatctgcaaatgaacagcctgcgtgccgaagatacggcc gtgtattattgcgcgcgtgaacgtggttacgtttactaccatatgttcgatccgtggggccaaggcacc ctggtgactgttagctcagcctccaccaagggtccatcggtcttccccctggcaccctcctccaagagc acctctgggggcacagcggccctgggctgcctggtcaaggactacttccccgaaccggtgacggtgtcg tggaactcaggcgccctgaccagcggcgtgcacaccttcccggctgtcctacagtcctcaggactctac tccctcagcagcgtggtgaccgtgccctccagcagcttgggcacccagacctacatctgcaacgtgaat cacaagcccagcaacaccaaggtggacaagagagttgagcccaaatcttgtgacaaaactcacacatgc ccaccgtgcccagcacctgaagcagcggggggaccgtcagtcttcctcttccccccaaaacccaaggac accctcatgatctcccggacccctgaggtcacatgcgtggtggtggacgtgagccacgaagaccctgag gtcaagttcaactggtacgtggacggcgtggaggtgcataatgccaagacaaagccgcgggaggagcag tacaacagcacgtaccgggtggtcagcgtcctcaccgtcctgcaccaggactggctgaatggcaaggag tacaagtgcaaggtctccaacaaagccctcccagcccccatcgagaaaaccatctccaaagccaaaggg cagccccgagaaccacaggtgtacaccctgcccccatcccgggaggagatgaccaagaaccaggtcagc ctgacctgcctggtcaaaggcttctatcccagcgacatcgccgtggagtgggagagcaatgggcagccg gagaacaactacaagaccacgcctcccgtgctggactccgacggctccttcttcctctacagcaagctc accgtggacaagagcaggtggcagcaggggaacgtcttctcatgctccgtgatgcatgaggctctgcac aaccactacacgcagaagagcctctccctgtctccgggtaaa |
| SEQ ID NO: 17 | LCDR1 (Combined) | RASQSITRNYLA |
| SEQ ID NO: 18 | LCDR2 (Combined) | GASSRAT |
| SEQ ID NO: 19 | LCDR3 (Combined) | QQHSMYPRT |
| SEQ ID NO: 17 | LCDR1 (Kabat) | RASQSITRNYLA |
| SEQ ID NO: 18 | LCDR2 (Kabat) | GASSRAT |

TABLE 2-continued

Exemplary anti-NPR1 antibody sequences

| SEQ ID NO: 19 | LCDR3 (Kabat) | QQHSMYPRT |
|---|---|---|
| SEQ ID NO: 20 | LCDR1 (Chothia) | SQSITRNY |
| SEQ ID NO: 21 | LCDR2 (Chothia) | GAS |
| SEQ ID NO: 22 | LCDR3 (Chothia) | HSMYPR |
| SEQ ID NO: 23 | LCDR1 (IMGT) | QSITRNY |
| SEQ ID NO: 21 | LCDR2 (IMGT) | GAS |
| SEQ ID NO: 19 | LCDR3 (IMGT) | QQHSMYPRT |
| SEQ ID NO: 24 | VL | DIVLTQSPATLSLSPGERATLSCRASQSITRNYLAWYQQKPGQAPRLLIYGA<br>SSRATGIPARFSGSGSGTDFTLTISSLEPEDFAVYYCQQHSMYPRTFGQGTK<br>VEIK |
| SEQ ID NO: 25 | DNA VL | gatatcgtgctgacccagagcccggcgacccctgagcctgagcccgggtgaacgtgccacccctgagctgc<br>agagcgagccagtctatcactcgtaactacctggcttggtaccagcagaaaccgggccaggcccccgcgt<br>ctattaatctacggtgcttcttctcgtgcgaccggcattccggcgcgttttagcggcagcggatccggc<br>accgatttcaccctgaccattagcagcctggaaccggaagactttgcggtgtattattgccagcagcat<br>tctatgtacccgcgtaccctttggccagggcacgaaagttgaaattaaa |
| SEQ ID NO: 26 | Light Chain | DIVLTQSPATLSLSPGERATLSCRASQSITRNYLAWYQQKPGQAPRLLIYGA<br>SSRATGIPARFSGSGSGTDFTLTISSLEPEDFAVYYCQQHSMYPRTFGQGTK<br>VEIKRTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGLSSPV<br>TKSFNRGEC |
| SEQ ID NO: 27 | DNA Light Chain | gatatcgtgctgacccagagcccggcgacccctgagcctgagcccgggtgaacgtgccacccctgagctgc<br>agagcgagccagtctatcactcgtaactacctggcttggtaccagcagaaaccgggccaggcccccgcgt<br>ctattaatctacggtgcttcttctcgtgcgaccggcattccggcgcgttttagcggcagcggatccggc<br>accgatttcaccctgaccattagcagcctggaaccggaagactttgcggtgtattattgccagcagcat<br>tctatgtacccgcgtaccctttggccagggcacgaaagttgaaattaaacgtacggtggccgctcccagc<br>gtgttcatcttccccccagcgacgagcagctgaagagcggcaccgccagcgtggtgtgcctgctgaac<br>aacttctaccccgggaggccaaggtgcagtggaaggtggacaacgcgcctgcagagcggcaacagccag<br>gaaagcgtcaccgagcaggacagcaaggactccaccctacagcctgagcagcaccctgaccctgagcaag<br>gccgactacgagaagcacaaggtgtacgcctgcgaggtgacccaccagggcctgtccagcccgtgacc<br>aagagcttcaacggggcgagtgt |

WW03_LALA

| SEQ ID NO: 28 | HCDR1 (Combined) | GFTFSSYWMN |
|---|---|---|
| SEQ ID NO: 29 | HCDR2 (Combined) | AISSDGSYTYYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 29 | HCDR2 (Kabat) | AISSDGSYTYYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 33 | HCDR2 (Chothia) | SSDGSY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 35 | HCDR2 (IMGT) | ISSDGSYT |
| SEQ ID NO: 36 | HCDR3 (IMGT) | ARDRYSMIYSYGAGAFDY |
| SEQ ID NO: 37 | VH | QVQLLESGGGLVQPGGSLRLSCAASGFTFSSYWMNWVRQAPGKGLEWVS<br>AISSDGSYTYYADSVKGRFTISRDNSKNTLYLQMNSLRAEDTAVYYCARD<br>RYSMIYSYGAGAFDYWGQGTLVTVSS |
| SEQ ID NO: 38 | DNA VH | caggtgcaattgctggaaagcggcggtggcctggtgcagccgggtggcagcctgcgtctgagctgcgcg<br>gcgtccggattcaccttttcttcttactggatgaactgggtgcgccaggcccgggcaaaggtctcgag<br>tgggttcccgctatctcttctgacggttcttacacctatatgcggatagcgtgaaaggccgctttacc<br>atcagccgcgataattcgaaaaacacccctgtatctgcaaatgaacagcctgcgtgccgaagatacggcc<br>gtgtattattgcgcgcgtgaccgttactctatgatctactcttacggtgctggtgctttcgattactgg<br>ggccaaggcacccctggtgactgttagctca |

TABLE 2-continued

Exemplary anti-NPR1 antibody sequences

| SEQ ID NO: 39 | Heavy Chain | QVQLLESGGGLVQPGGSLRLSCAASGFTFSSYWMNWVRQAPGKGLEWVS<br>AISSDGSYTYYADSVKGRFTISRDNSKNTLYLQMNSLRAEDTAVYYCARD<br>RYSMIYSYGAGAFDYWGQGTLVTVSSASTKGPSVFPLAPSSKSTSGGTAAL<br>GCLVKDYFPEPVTVSWNSGALTSGVHTFPAVLQSSGLYSLSSVVTVPSSSL<br>GTQTYICNVNHKPSNTKVDKRVEPKSCDKTHTCPPCPAPEAAGGPSVFLFP<br>PKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPR<br>EPQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSP<br>GK |
|---|---|---|
| SEQ ID NO: 40 | DNA Heavy Chain | caggtgcaattgctggaaagcggcggtggcctggtgcagccgggtggcagcctgcgtctgagctgcgcg<br>gcgtccggattcacctttttcttcttactggatgaactgggtgcgccaggccccgggcaaaggtctcgag<br>tgggtttccgctatctcttctgacggttcttacacctactatgcggatagcgtgaaaggccgctttacc<br>atcagccgcgataattcgaaaaacaccctgtatctgcaaatgaacagcctgcgtgcggaagatacggcc<br>gtgtattattgcgcgcgtgaccgttactctatgatctactcttacggtgctggtgctttcgattactgg<br>ggccaaggcaccctggtgactgttagctcagcctccaccaagggtccatcggtcttcccctggcaccc<br>tcctccaagagcacctctgggggcacagcggccctgggctgcctggtcaaggactacttccccgaaccg<br>gtgacggtgtcgtggaactcaggcgccctgaccagcggcgtgcacaccttcccggctgtcctacagtcc<br>tcaggactctactccctcagcagcgtggtgaccgtgccctccagcagcttgggcacccagacctacatc<br>tgcaacgtgaatcacaagcccagcaacaccaaggtggacaagagagttgagcccaaatcttgtgacaaa<br>actcacacatgcccaccgtgcccagcacctgaagcagcggggggaccgtcagtcttcctcttccccca<br>aaacccaaggacaccctcatgatctcccggacccctgaggtcacatgcgtggtggtggacgtgagccac<br>gaagaccctgaggtcaagttcaactggtacgtggacggcgtggaggtgcataatgccaagacaaagccg<br>cgggaggagcagtacaacagcacgtaccgggtggtcagcgtcctcaccgtcctgcaccaggactggctg<br>aatggcaaggagtacaagtgcaaggtctccaacaaagcccccagccccatcgagaaaaccatctcc<br>aaagccaaagggcagccccgagaaccacaggtgtacaccctgcccccatcccgggaggagatgaccaag<br>aaccaggtcagcctgacctgcctggtcaaaggcttctatcccagcgacatcgccgtggagtgggagagc<br>aatgggcagccggagaacaactacaagaccacgcctcccgtgctggactccgacggctccttcttcctc<br>tacagcaagctcaccgtggacaagagcaggtggcagcaggggaacgtcttctcatgctccgtgatgcat<br>gaggctctgcacaaccactacacgcagaagagcctctccctgtctccgggtaaa |
| SEQ ID NO: 41 | LCDR1 (Combined) | RASQGISSYLA |
| SEQ ID NO: 42 | LCDR2 (Combined) | TASTLQS |
| SEQ ID NO: 43 | LCDR3 (Combined) | MQSYEKPRT |
| SEQ ID NO: 41 | LCDR1 (Kabat) | RASQGISSYLA |
| SEQ ID NO: 42 | LCDR2 (Kabat) | TASTLQS |
| SEQ ID NO: 43 | LCDR3 (Kabat) | MQSYEKPRT |
| SEQ ID NO: 44 | LCDR1 (Chothia) | SQGISSY |
| SEQ ID NO: 45 | LCDR2 (Chothia) | TAS |
| SEQ ID NO: 46 | LCDR3 (Chothia) | SYEKPR |
| SEQ ID NO: 47 | LCDR1 (IMGT) | QGISSY |
| SEQ ID NO: 45 | LCDR2 (IMGT) | TAS |
| SEQ ID NO: 43 | LCDR3 (IMGT) | MQSYEKPRT |
| SEQ ID NO: 48 | VL | DIQMTQSPSSLSASVGDRVTITCRASQGISSYLAWYQQKPGKAPKLLIYTAS<br>TLQSGVPSRFSGSGSGTDFTLTISSLQPEDFATYYCMQSYEKPRTFGQGTKV<br>EIK |
| SEQ ID NO: 49 | DNA VL | gatatccagatgacccagagcccgagcagcctgagcgccagcgtgggcgatcgcgtgaccattacctgc<br>agagccagccagggtatttcttcttacctggcttggtaccagcagaaaccgggcaaagcgccgaaacta<br>ttaatctacactgctttctactctgcaaagcggcgtgccgagccgctttagcggcagcggatccggcacc<br>gatttcaccctgaccattagctctctgcaaccggaagactttgcgacctattattgcatgcagtcttac<br>gaaaaaccgcgtaccttggccagggcacgaaagttgaaattaaa |
| SEQ ID NO: 50 | Light Chain | DIQMTQSPSSLSASVGDRVTITCRASQGISSYLAWYQQKPGKAPKLLIYTAS<br>TLQSGVPSRFSGSGSGTDFTLTISSLQPEDFATYYCMQSYEKPRTFGQGTKV<br>EIKRTVAAPSVIFPPSDEQLKSGTASVVCLLNNFYPREAKVQWKVDNALQ<br>SGNSQESVTEQDSKDSTYSLSSTLTLSKADYEKHKVYACEVTHQGLSSPVT<br>KSFNRGEC |
| SEQ ID NO: 51 | DNA Light Chain | gatatccagatgacccagagcccgagcagcctgagcgccagcgtgggcgatcgcgtgaccattacctgc<br>agagccagccagggtatttcttcttacctggcttggtaccagcagaaaccgggcaaagcgccgaaacta<br>ttaatctacactgctttctactctgcaaagcggcgtgccgagccgctttagcggcagcggatccggcacc<br>gatttcaccctgaccattagctctctgcaaccggaagactttgcgacctattattgcatgcagtcttac<br>gaaaaaccgcgtaccttggccagggcacgaaagttgaaattaaacgtacggtggccgctcccagcgtg<br>ttcatcttcccccccagcgacgagcagctgaagagcggcaccgccagcgtggtgtgcctgctgaacaac |

TABLE 2-continued

Exemplary anti-NPR1 antibody sequences

```
ttctacccccgggaggccaaggtgcagtggaaggtggacaacgccctgcagagcggcaacagccaggaa
agcgtcaccgagcaggacagcaaggactccacctacagcctgagcagcaccctgaccctgagcaaggcc
gactacgagaagcacaaggtgtacgcctgcgaggtgacccaccagggcctgtccagccccgtgaccaag
agcttcaaccggggcgagtgt
```

WW05_LALA

| | | |
|---|---|---|
| SEQ ID NO: 52 | HCDR1 (Combined) | GYSFSNYWIG |
| SEQ ID NO: 53 | HCDR2 (Combined) | IIYPDVSYTRYSPSFQG |
| SEQ ID NO: 54 | HCDR3 (Combined) | YWSEAYTFDY |
| SEQ ID NO: 55 | HCDR1 (Kabat) | NYWIG |
| SEQ ID NO: 53 | HCDR2 (Kabat) | IIYPDVSYTRYSPSFQG |
| SEQ ID NO: 54 | HCDR3 (Kabat) | YWSEAYTFDY |
| SEQ ID NO: 56 | HCDR1 (Chothia) | GYSFSNY |
| SEQ ID NO: 57 | HCDR2 (Chothia) | YPDVSY |
| SEQ ID NO: 54 | HCDR3 (Chothia) | YWSEAYTFDY |
| SEQ ID NO: 58 | HCDR1 (IMGT) | GYSFSNYW |
| SEQ ID NO: 59 | HCDR2 (IMGT) | IYPDVSYT |
| SEQ ID NO: 60 | HCDR3 (IMGT) | ARYWSEAYTFDY |
| SEQ ID NO: 61 | VH | QVQLVQSGAEVKKPGESLKISCKGSGYSFSNYWIGWVRQMPGKGLEWMG<br>IIYPDVSYTRYSPSFQGQVTISADKSISTAYLQWSSLKASDTAMYYCARYWS<br>EAYTFDYWGQGTLVTVSS |
| SEQ ID NO: 62 | DNA VH | caggtgcaattggtgcagagcggtgcggaagtgaaaaaaccgggcgaaagcctgaaaattagctgcaaa<br>ggctccggatatagcttctctaactactggatcggttgggtgcgccagatgccgggcaaaggtctcgag<br>tggatgggcatcatctacccggacgttagctacacccgttatagcccgagctttcagggccaggtgacc<br>attagcgcggataaaagcatcagcaccgcgtatctgcaatggagcagcctgaaagcgagcgataccgcg<br>atgtattattgcgcgcgttactggtctgaagcttacacttcgattactggggccaaggcacctggtg<br>actgttagctca |
| SEQ ID NO: 63 | Heavy Chain | QVQLVQSGAEVKKPGESLKISCKGSGYSFSNYWIGWVRQMPGKGLEWMG<br>IIYPDVSYTRYSPSFQGQVTISADKSISTAYLQWSSLKASDTAMYYCARYWS<br>EAYTFDYWGQGTLVTVSSASTKGPSVFPLAPSSKSTSGGTAALGCLVKDYF<br>PEPVTVSWNSGALTSGVHTFPAVLQSSGLYSLSSVVTVPSSSLGTQTYICNV<br>NHKPSNTKVDKRVEPKSCDKTHTCPPCPAPEAAGGPSVFLFPPKPKDTLMIS<br>RTPEVTCVVVDVSHEDPEVKFNWYVDGVEVHNAKTKPREEQYNSTYRVV<br>SVLTVLHQDWLNGKEYKCKVSNKALPAPIEKTISKAKGQPREPQVYTLPPS<br>REEMTKNQVSLTCLVKGFYPSDIAVEWESNGQPENNYKTTPPVLDSDGSFF<br>LYSKLTVDKSRWQQGNVFSCSVMHEALHNHYTQKSLSLSPGK |
| SEQ ID NO: 64 | DNA Heavy Chain | caggtgcaattggtgcagagcggtgcggaagtgaaaaaaccgggcgaaagcctgaaaattagctgcaaa<br>ggctccggatatagcttctctaactactggatcggttgggtgcgccagatgccgggcaaaggtctcgag<br>tggatgggcatcatctacccggacgttagctacacccgttatagcccgagctttcagggccaggtgacc<br>attagcgcggataaaagcatcagcaccgcgtatctgcaatggagcagcctgaaagcgagcgataccgcg<br>atgtattattgcgcgcgttactggtctgaagcttacacttcgattactggggccaaggcacctggtg<br>actgttagctcagcctccaccaagggcccatcggtcttccccctggcaccctcctccaagagcacctct<br>gggggcacagcggccctgggctgcctggtcaaggactacttccccgaaccggtgacggtgtcgtggaac<br>tcaggcgccctgaccagcggcgtgcacaccttcccggctgtcctacagtcctcaggactctactccctc<br>agcagcgtggtgaccgtgccctccagcagcttgggcacccagacctacatctgcaacgtgaatcacaag<br>cccagcaacaccaaggtggacaagagagttgagcccaaatcttgtgacaaaactcacacatgcccaccg<br>tgcccagcacctgaagcagcggggggaccgtcagtcttcctcttccccccaaaacccaaggacaccctc<br>atgatctcccggacccctgaggtcacatgcgtggtggtggacgtgagccacgaagaccctgaggtcaag<br>ttcaactggtacgtggacggcgtggaggtgcataatgccaagacaaagccgcgggaggagcagtacaac<br>agcacgtaccgggtggtcagcgtcctcaccgtcctgcaccaggactggctgaatggcaaggagtacaag<br>tgcaaggtctccaacaaagcccccagccccatcgagaaaaccatctccaaagccaaagggcagccc<br>cgagaaccacaggtgtacaccctgcccccatcccgggaggagatgaccaagaaccaggtcagcctgacc<br>tgcctggtcaaaggcttctatcccagcgacatcgccgtggagtgggagagcaatgggcagccggagaac<br>aactacaagaccacgcctcccgtgctggactccgacggctccttcttcctctacagcaagctcaccgtg<br>gacaagagcaggtggcagcaggggaacgtcttctcatgctccgtgatgcatgaggctctgcacaaccac<br>tacacgcagaagagcctctccctgtctccgggtaaa |
| SEQ ID NO: 65 | LCDR1 (Combined) | SGDNIRKKYVF |
| SEQ ID NO: 66 | LCDR2 (Combined) | GDNDRPS |
| SEQ ID NO: 67 | LCDR3 (Combined) | GTYTLLFTSKV |

TABLE 2-continued

Exemplary anti-NPR1 antibody sequences

| SEQ ID NO: 65 | LCDR1 (Kabat) | SGDNIRKKYVF |
|---|---|---|
| SEQ ID NO: 66 | LCDR2 (Kabat) | GDNDRPS |
| SEQ ID NO: 67 | LCDR3 (Kabat) | GTYTLLFTSKV |
| SEQ ID NO: 68 | LCDR1 (Chothia) | DNIRKKY |
| SEQ ID NO: 69 | LCDR2 (Chothia) | GDN |
| SEQ ID NO: 70 | LCDR3 (Chothia) | YTLLFTSK |
| SEQ ID NO: 71 | LCDR1 (IMGT) | NIRKKY |
| SEQ ID NO: 69 | LCDR2 (IMGT) | GDN |
| SEQ ID NO: 67 | LCDR3 (IMGT) | GTYTLLFTSKV |
| SEQ ID NO: 72 | VL | DIELTQPPSVSVSPGQTASITCSGDNIRKKYVFWYQQKPGQAPVLVIYGDND<br>RPSGIPERFSGSNSGNTATLTISGTQAEDEADYYCGTYTLLFTSKVFGGGTK<br>LTVL |
| SEQ ID NO: 73 | DNA VL | gatatcgaactgacccagccgccgagcgtgagcgtgagtccgggccagaccgcgagcattacctgtagc<br>ggcgataacatccgtaaaaaatacgtttctggtaccagcagaaaccgggccaggcgccggtgctggtg<br>atctacggtgacaacgaccgtccgagcggcatcccggaacgttttagcggatccaacagcggcaacacc<br>gcgaccctgaccattagcggcacccaggcggaagacgaagcggattattactgcggtacttacactctg<br>ctgttcacttctaaagtgtttggcggcggcacgaagttaaccgtccta |
| SEQ ID NO: 74 | Light Chain | DIELTQPPSVSVSPGQTASITCSGDNIRKKYVFWYQQKPGQAPVLVIYGDND<br>RPSGIPERFSGSNSGNTATLTISGTQAEDEADYYCGTYTLLFTSKVFGGGTK<br>LTVLGQPKAAPSVTLFPPSSEELQANKATLVCLISDFYPGAVTVAWKADSS<br>PVKAGVETTTPSKQSNNKYAASSYLSLTPEQWKSHRSYSCQVTHEGSTVEK<br>TVAPTECS |
| SEQ ID NO: 75 | DNA Light Chain | gatatcgaactgacccagccgccgagcgtgagcgtgagtccgggccagaccgcgagcattacctgtagc<br>ggcgataacatccgtaaaaaatacgtttctggtaccagcagaaaccgggccaggcgccggtgctggtg<br>atctacggtgacaacgaccgtccgagcggcatcccggaacgttttagcggatccaacagcggcaacacc<br>gcgaccctgaccattagcggcacccaggcggaagacgaagcggattattactgcggtacttacactctg<br>ctgttcacttctaaagtgtttggcggcggcacgaagttcctaggtcagcccaaggctgccccc<br>tcggtcactctgttcccgccctcctctgaggagcttcaagccaacaaggccacactggtgtgtctcata<br>agtgacttctacccgggagccgtgacagtggcctggaaggcagatagcagccccgtcaaggcgggagtg<br>gagaccaccacccctccaaacaaagcaacaacaagtacgcggccagcagctatctgagcctgacgcct<br>gagcagtggaagtcccacagaaagctacagctgccaggtcacgcatgaaggggagcaccgtggagaagaca<br>gtggcccctacagaatgttca |

WW06_LALA

| SEQ ID NO: 76 | HCDR1 (Combined) | GYSFTSYWIA |
|---|---|---|
| SEQ ID NO: 77 | HCDR2 (Combined) | RIDPDNSYTRYSPSFQG |
| SEQ ID NO: 78 | HCDR3 (Combined) | WLSPGYALGEQPAGMDH |
| SEQ ID NO: 79 | HCDR1 (Kabat) | SYWIA |
| SEQ ID NO: 77 | HCDR2 (Kabat) | RIDPDNSYTRYSPSFQG |
| SEQ ID NO: 78 | HCDR3 (Kabat) | WLSPGYALGEQPAGMDH |
| SEQ ID NO: 80 | HCDR1 (Chothia) | GYSFTSY |
| SEQ ID NO: 81 | HCDR2 (Chothia) | DPDNSY |
| SEQ ID NO: 78 | HCDR3 (Chothia) | WLSPGYALGEQPAGMDH |
| SEQ ID NO: 82 | HCDR1 (IMGT) | GYSFTSYW |
| SEQ ID NO: 83 | HCDR2 (IMGT) | IDPDNSYT |
| SEQ ID NO: 84 | HCDR3 (IMGT) | ARWLSPGYALGEQPAGMDH |
| SEQ ID NO: 85 | VH | QVQLVQSGAEVKKPGESLKISCKGSGYSFTSYWIAWVRQMPGKGLEWMG<br>RIDPDNSYTRYSPSFQGQVTISADKSISTAYLQWSSLKASDTAMYYCARWL<br>SPGYALGEQPAGMDHWGQGTLVTVSS |
| SEQ ID NO: 86 | DNA VH | caggtgcaattggtgcagagcggtgcggaagtgaaaaaaccgggcgaaagcctgaaaattagctgcaaa<br>ggctccggatatagcttcacttcttactggatcgcttgggtgcgccagatgccgggcaaaggtctcgag |

TABLE 2-continued

Exemplary anti-NPR1 antibody sequences

| | | |
|---|---|---|
| | | tggatgggccgtatcgaccggacaacagctacacccgttatagcccgagctttcagggccaggtgacc<br>attagcgcggataaaagcatcagcaccgcgtatctgcaatggagcagcctgaaagcgagcgataccgcg<br>atgtattattgcgcgcgttggctgtctccgggttacgctctgggtgaacagccggctggtatggatcat<br>tggggccaaggcaccctggtgactgttagctca |
| SEQ ID NO: 87 | Heavy Chain | QVQLVQSGAEVKKPGESLKISCKGSGYSFTSYWIAWVRQMPGKGLEWMG<br>RIDPDNSYTRYSPSFQGQVTISADKSISTAYLQWSSLKASDTAMYYCARWL<br>SPGYALGEQPAGMDHWGQGTLVTVSSASTKGPSVFPLAPSSKSTSGGTAAL<br>GCLVKDYFPEPVTVSWNSGALTSGVHTFPAVLQSSGLYSLSSVVTVPSSSL<br>GTQTYICNVNHKPSNTKVDKRVEPKSCDKTHTCPPCPAPEAAGGPSVFLFP<br>PKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPR<br>EPQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSP<br>GK |
| SEQ ID NO: 88 | DNA Heavy Chain | caggtgcaattggtgcagagcggtgcggaagtgaaaaaaccgggcgaaagcctgaaaattagctgcaaa<br>ggctccggatatagcttcacttcttactggatcgcttgggtgcgccagatgccgggcaaaggtctcgag<br>tggatgggccgtatcgaccggacaacagctacacccgttatagcccgagctttcagggccaggtgacc<br>attagcgcggataaaagcatcagcaccgcgtatctgcaatggagcagcctgaaagcgagcgataccgcg<br>atgtattattgcgcgcgttggctgtctccgggttacgctctgggtgaacagccggctggtatggatcat<br>tggggccaaggcaccctggtgactgttagctcagcctccaccaagggtccatcggtcttcccctggca<br>ccctcctccaagagcacctctgggggcacagcggccctgggctgcctggtcaaggactacttccccgaa<br>ccggtgacggtgtcgtggaactcaggcgccctgaccagcggcgtgcacaccttcccggctgtcctacag<br>tcctcaggactctactccctcagcagcgtggtgaccgtgccctccagcagcttgggcacccagacctac<br>atctgcaacgtaatcacaagcccagcaacaccaaggtggacaagagagttgagcccaaatcttgtgac<br>aaaactcacacatgcccaccgtgcccagcacctgaagcagcggggggaccgtcagtcttcctcttccc<br>ccaaaacccaaggacaccctcatgatctcccggacccctgaggtcacatgcgtggtggtggacgtgagc<br>cacgaagaccctgaggtcaagttcaactggtacgtggacggcgtggaggtgcataatgccaagacaaag<br>ccgcgggaggagcagtacaacagcacgtaccgggtggtcagcgtcctcaccgtcctgcaccaggactgg<br>ctgaatggcaaggagtacaagtgcaaggtctccaacaaagccctcccagcccccatcgagaaaaccatc<br>tccaaagccaaagggcagccccgagaaccacaggtgtacaccctgcccccatcccgggaggagatgacc<br>aagaaccaggtcagcctgacctgcctggtcaaaggcttctatcccagcgacatcgccgtggagtgggag<br>agcaatgggcagccggagaacaactacaagaccacgcctcccgtgctggactccgacggctccttcttc<br>ctctacagcaagctcaccgtggacaagagcaggtggcagcaggggaacgtcttctcatgctccgtgatg<br>catgaggctctgcacaaccactacacgcagaagagcctctccctgtctccgggtaaa |
| SEQ ID NO: 89 | LCDR1 (Combined) | TGSSSNIGAGYAVH |
| SEQ ID NO: 90 | LCDR2 (Combined) | SNNKRPS |
| SEQ ID NO: 91 | LCDR3 (Combined) | QSYDLQKSSRV |
| SEQ ID NO: 89 | LCDR1 (Kabat) | TGSSSNIGAGYAVH |
| SEQ ID NO: 90 | LCDR2 (Kabat) | SNNKRPS |
| SEQ ID NO: 91 | LCDR3 (Kabat) | QSYDLQKSSRV |
| SEQ ID NO: 92 | LCDR1 (Chothia) | SSSNIGAGYA |
| SEQ ID NO: 93 | LCDR2 (Chothia) | SNN |
| SEQ ID NO: 94 | LCDR3 (Chothia) | YDLQKSSR |
| SEQ ID NO: 95 | LCDR1 (IMGT) | SSNIGAGYA |
| SEQ ID NO: 93 | LCDR2 (IMGT) | SNN |
| SEQ ID NO: 91 | LCDR3 (IMGT) | QSYDLQKSSRV |
| SEQ ID NO: 96 | VL | DIVLTQPPSVSGAPGQRVTISCTGSSSNIGAGYAVHWYQQLPGTAPKLLIYS<br>NNKRPSGVPDRFSGSKSGTSASLAITGLQAEDEADYYCQSYDLQKSSRVFG<br>GGTKLTVL |
| SEQ ID NO: 97 | DNA VL | gatatcgtgctgacccagccgccgagcgtgagcggtgcaccgggccagcgcgtgaccattagctgtacc<br>ggcagcagcagcaacattggtgctggttacgctgtgcattggtaccagcagctgccgggcacggcgccg<br>aaactgctgatctactctaacaacaaacgcccgagcggcgtgccggatcgctttagcggatccaaaagc<br>ggcaccagcgccagcctggcgattaccggcctgcaagcagaagacgaagcggattattactgccagtct<br>tacgacctgcagaaatcttctcgtgtgtttggcggcggcacgaagttaaccgtccta |
| SEQ ID NO: 98 | Light Chain | DIVLTQPPSVSGAPGQRVTISCTGSSSNIGAGYAVHWYQQLPGTAPKLLIYS<br>NNKRPSGVPDRFSGSKSGTSASLAITGLQAEDEADYYCQSYDLQKSSRVFG<br>GGTKLTVLGQPKAAPSVTLFPPSSEELQANKATLVCLISDFYPGAVTVAWK<br>ADSSPVKAGVETTTPSKQSNNKYAASSYLSLTPEQWKSHRSYSCQVTHEGS<br>TVEKTVAPTECS |

TABLE 2-continued

Exemplary anti-NPR1 antibody sequences

| SEQ ID NO: 99 | DNA Light Chain | gatatcgtgctgacccagccgccgagcgtgagcggtgcaccgggccagcgcgtgaccattagctgtacc
ggcagcagcagcaacattggtgctggttacgctgtgcattggtaccagcagctgctttagcggatccaaaagc
aaactgctgatctactctaacaaacgcccgagcggcgtgccggatcgcttttagcggatccaaaagc
ggcaccagcgccagcctggcgattaccggcctgcaagcagaagacgaagcggattattactgccagtct
tacgacctgcagaaatcttctcgtgtgtttggcggcggcacgaagttaaccgtcctaggtcagcccaag
gctgcccctcggtcactctgttcccgccctcctctgaggagcttcaagccaacaaggcacactggtg
tgtctcataagtgacttctacccgggagccgtgacagtggcctggaaggcagatagcagcccgtcaag
gcggagtggagaccaccacaccctccaaacaaagcaacaacaagtacgcccagcagctatctgagc
ctgacgcctgagcagtggaagtcccacagaagctacagctgccaggtcacgcatgaagggagcaccgtg
gagaagacagtggcccctacagaatgttca |

XX01_LALA

| SEQ ID NO: 4 | HCDR1 (Combined) | GFTFNTHYIH |
| SEQ ID NO: 100 | HCDR2 (Combined) | SISSSGQSTYYADSVKG |
| SEQ ID NO: 6 | HCDR3 (Combined) | ERGYVYYHMFDP |
| SEQ ID NO: 7 | HCDR1 (Kabat) | THYIH |
| SEQ ID NO: 100 | HCDR2 (Kabat) | SISSSGQSTYYADSVKG |
| SEQ ID NO: 6 | HCDR3 (Kabat) | ERGYVYYHMFDP |
| SEQ ID NO: 8 | HCDR1 (Chothia) | GFTFNTH |
| SEQ ID NO: 101 | HCDR2 (Chothia) | SSSGQS |
| SEQ ID NO: 6 | HCDR3 (Chothia) | ERGYVYYHMFDP |
| SEQ ID NO: 10 | HCDR1 (IMGT) | GFTFNTHY |
| SEQ ID NO: 102 | HCDR2 (IMGT) | ISSSGQST |
| SEQ ID NO: 12 | HCDR3 (IMGT) | ARERGYVYYHMFDP |
| SEQ ID NO: 103 | VH | EVQLLESGGGLVQPGGSLRLSCAASGFTFNTHYIHWVRQAPGKGLEWVSSI
SSSGQSTYYADSVKGRFTISRDNSKNTLYLQMNSLRAEDTAVYYCARERG
YVYYHMFDPWGQGTLVTVSS |
| SEQ ID NO: 104 | DNA VH | gaggtgcaattgctggaaagcggcggtggcctggtgcagccgggtggcagcctgcgtctgagctgcgcg
gcgtccggattcacctttaacactcattacatccattgggtgcgccaggccccggcaaaggtctcgag
tgggtttcctctatctcttcttctggccagtctacttactatgcggatagcgtgaaaggccgctttacc
atcagccgcgataattcgaaaaacaccctgtatctgcaaatgaacagcctgcgtgcggaagatacggc
gtgtattattgcgcgcgtgaacgtggttacgtttactaccatatgttcgatccgtggggccaaggcacc
ctggtgactgttagctca |
| SEQ ID NO: 105 | Heavy Chain | EVQLLESGGGLVQPGGSLRLSCAASGFTFNTHYIHWVRQAPGKGLEWVSSI
SSSGQSTYYADSVKGRFTISRDNSKNTLYLQMNSLRAEDTAVYYCARERG
YVYYHMFDPWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYI
CNVNHKPSNTKVDKRVEPKSCDKTHTCPPCPAPEAAGGPSVFLFPPKPKDT
LMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPGK |
| SEQ ID NO: 106 | DNA Heavy Chain | gaggtgcaattgctggaaagcggcggtggcctggtgcagccgggtggcagcctgcgtctgagctgcgcg
gcgtccggattcacctttaacactcattacatccattgggtgcgccaggccccggcaaaggtctcgag
tgggtttcctctatctcttcttctggccagtctacttactatgcggatagcgtgaaaggccgctttacc
atcagccgcgataattcgaaaaacaccctgtatctgcaaatgaacagcctgcgtgcggaagatacggc
gtgtattattgcgcgcgtgaacgtggttacgtttactaccatatgttcgatccgtggggccaaggcacc
ctggtgactgttagctcagcctccaccaagggcccatcggtcttccccctggcacctcctccaagagc
acctctgggggcacagcggccctgggctgcctggtcaaggactacttccccgaaccggtgacggtgtcg
tggaactcaggcgccctgaccagcggcgtgcacaccttcccggctgtcctacagtcctcaggactctac
tccctcagcagcgtggtgaccgtgccctccagcagcttgggcacccagacctacatctgcaacgtgaat
cacaagcccagcaacaccaaggtggacaagagagttgagcccaaatcttgtgacaaaactcacacatgc
ccaccgtgcccagcacctgaagcagcggggggaccgtcagtcttcctcttccccccaaaacccaaggac
accctcatgatctcccggacccctgaggtcacatgcgtggtggtggacgtgagccacgaagaccctgag
gtcaagttcaactggtacgtggacggcgtggaggtgcataatgccaagacaaagccgcgggaggagcag
tacaacagcacgtaccgtgtggtcagcgtcctcaccgtcctgcaccaggactggctgaatggcaaggag
tacaagtgcaaggtctccaacaaagccctcccagcccccatcgagaaaaccatctccaaagccaaaggg
cagccccgagaaccacaggtgtacaccctgcccccatcccgggaggagatgaccaagaaccaggtcagc
ctgacctgcctggtcaaaggcttctatcccagcgacatcgccgtggagtgggagagcaatgggcagccg
gagaacaactacaagaccacgcctcccgtgctggactccgacggctccttcttcctctacagcaagctc
accgtggacaagagcaggtggcagcaggggaacgtcttctcatgctccgtgatgcatgaggctctgcac
aaccactacacgcagaagagcctctccctgtctccgggtaaa |

TABLE 2-continued

Exemplary anti-NPR1 antibody sequences

| SEQ ID NO: 17 | LCDR1 (Combined) | RASQSITRNYLA |
| --- | --- | --- |
| SEQ ID NO: 18 | LCDR2 (Combined) | GASSRAT |
| SEQ ID NO: 19 | LCDR3 (Combined) | QQHSMYPRT |
| SEQ ID NO: 17 | LCDR1 (Kabat) | RASQSITRNYLA |
| SEQ ID NO: 18 | LCDR2 (Kabat) | GASSRAT |
| SEQ ID NO: 19 | LCDR3 (Kabat) | QQHSMYPRT |
| SEQ ID NO: 20 | LCDR1 (Chothia) | SQSITRNY |
| SEQ ID NO: 21 | LCDR2 (Chothia) | GAS |
| SEQ ID NO: 22 | LCDR3 (Chothia) | HSMYPR |
| SEQ ID NO: 23 | LCDR1 (IMGT) | QSITRNY |
| SEQ ID NO: 21 | LCDR2 (IMGT) | GAS |
| SEQ ID NO: 19 | LCDR3 (IMGT) | QQHSMYPRT |
| SEQ ID NO: 24 | VL | DIVLTQSPATLSLSPGERATLSCRASQSITRNYLAWYQQKPGQAPRLLIYGA SSRATGIPARFSGSGSGTDFTLTISSLEPEDFAVYYCQQHSMYPRTFGQGTK VEIK |
| SEQ ID NO: 25 | DNA VL | gatatcgtgctgacccagagcccggcgaccctgagcctgagcccgggtgaacgtgccaccctgagctgc agagcgagccagtctatcactcgtaactacctggcttggtaccagcagaaaccgggccaggcccgcgt ctattaatctacggtgcttcttctcgtgcgaccggcattccggcgcgttttagcggcagcggatccggc accgatttcaccctgaccattagcagcctggaacggaagactttgcggtgtattattgccagcagcat tctatgtacccgcgtacctttggccagggcacgaaagttgaaattaaa |
| SEQ ID NO: 26 | Light Chain | DIVLTQSPATLSLSPGERATLSCRASQSITRNYLAWYQQKPGQAPRLLIYGA SSRATGIPARFSGSGSGTDFTLTISSLEPEDFAVYYCQQHSMYPRTFGQGTK VEIKRTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPV TKSFNRGEC |
| SEQ ID NO: 27 | DNA Light Chain | gatatcgtgctgacccagagcccggcgaccctgagcctgagcccgggtgaacgtgccaccctgagctgc agagcgagccagtctatcactcgtaactacctggcttggtaccagcagaaaccgggccaggcccgcgt ctattaatctacggtgcttcttctcgtgcgaccggcattccggcgcgttttagcggcagcggatccggc accgatttcaccctgaccattagcagcctggaacggaagactttgcggtgtattattgccagcagcat tctatgtacccgcgtacctttggccagggcacgaaagttgaaattaaacgtacggtggccgctcccagc gtgttcatcttccccccagcgacgagcagctgaagagcggcaccgccagcgtggtgtgcctgctgaac aacttctaccccccgggaggccaaggtgcagtggaaggtggacaacgccctgcagagcggcaacagccag gaaagcgtcaccgcaggacagcaaggactccacctacagcctgagcagcaccctgaccctgagcaag gccgactacgagaagcacaaggtgtacgcctgcgaggtgacccaccagggcctgtccagcccgtgacc aagagcttcaaccggggcgagtgt |

XX01_DAPA

| SEQ ID NO: 4 | HCDR1 (Combined) | GFTFNTHYIH |
| --- | --- | --- |
| SEQ ID NO: 100 | HCDR2 (Combined) | SISSSGQSTYYADSVKG |
| SEQ ID NO: 6 | HCDR3 (Combined) | ERGYVYYHMFDP |
| SEQ ID NO: 7 | HCDR1 (Kabat) | THYIH |
| SEQ ID NO: 100 | HCDR2 (Kabat) | SISSSGQSTYYADSVKG |
| SEQ ID NO: 6 | HCDR3 (Kabat) | ERGYVYYHMFDP |
| SEQ ID NO: 8 | HCDR1 (Chothia) | GFTFNTH |
| SEQ ID NO: 101 | HCDR2 (Chothia) | SSSGQS |
| SEQ ID NO: 6 | HCDR3 (Chothia) | ERGYVYYHMFDP |
| SEQ ID NO: 10 | HCDR1 (IMGT) | GFTFNTHY |
| SEQ ID NO: 102 | HCDR2 (IMGT) | ISSSGQST |
| SEQ ID NO: 12 | HCDR3 (IMGT) | ARERGYVYYHMFDP |

TABLE 2-continued

Exemplary anti-NPR1 antibody sequences

| SEQ ID NO: 103 | VH | EVQLLESGGGLVQPGGSLRLSCAASGFTFNTHYIHWVRQAPGKGLEWVSSI<br>SSSGQSTYYADSVKGRFTISRDNSKNTLYLQMNSLRAEDTAVYYCARERG<br>YVYYHMFDPWGQGTLVTVSS |
|---|---|---|
| SEQ ID NO: 107 | DNA VH | gaagtgcagctgcttgagtccggggggtggactggtgcagcccggaggatcctgcgcctgagctgcgct<br>gcatccggcttcaccttcaacacgcactacatccattgggtcagacaggcccaggaaaaggcctggaa<br>tgggtgtcctccatctcctcgtcgggggcagtcaacctactacgcggactccgtcaagggccggtttacc<br>attagccgggacaacagcaagaatacccctgtacctccaaatgaactcgctgagggccgaagataccgcc<br>gtgtattactgtgcccgcgagagaggctacgtgtactaccacatgttcgacccgtggggacagggtact<br>ctcgtgactgtgtcttct |
| SEQ ID NO: 108 | Heavy Chain | EVQLLESGGGLVQPGGSLRLSCAASGFTFNTHYIHWVRQAPGKGLEWVSSI<br>SSSGQSTYYADSVKGRFTISRDNSKNTLYLQMNSLRAEDTAVYYCARERG<br>YVYYHMFDPWGQGTLVTVSSASTKGPSVFPLAPSSKSTSGGTAALGCLVK<br>DYFPEPVTVSWNSGALTSGVHTFPAVLQSSGLYSLSSVVTVPSSSLGTQTYI<br>CNVNHKPSNTKVDKRVEPKSCDKTHTCPPCPAPELLGGPSVFLFPPKPKDT<br>LMISRTPEVTCVVVAVSHEDPEVKFNWYVDGVEVHNAKTKPREEQYNSTY<br>RVVSVLTVLHQDWLNGKEYKCKVSNKALAAPIEKTISKAKGQPREPQVYT<br>LPPSREEMTKNQVSLTCLVKGFYPSDIAVEWESNGQPENNYKTTPPVLDSD<br>GSFFLYSKLTVDKSRWQQGNVFSCSVMHEALHNHYTQKSLSLSPGK |
| SEQ ID NO: 109 | DNA Heavy Chain | gaagtgcagctgcttgagtccggggggtggactggtgcagcccggaggatcctgcgcctgagctgcgct<br>gcatccggcttcaccttcaacacgcactacatccattgggtcagacaggcccaggaaaaggcctggaa<br>tgggtgtcctccatctcctcgtcgggggcagtcaacctactacgcggactccgtcaagggccggtttacc<br>attagccgggacaacagcaagaatacccctgtacctccaaatgaactcgctgagggccgaagataccgcc<br>gtgtattactgtgcccgcgagagaggctacgtgtactaccacatgttcgacccgtggggacagggtact<br>ctcgtgactgtgtcttctgcgagcactaagggcccgtcagtgttcccgctggctccatcgtcgaagtcc<br>acctccggagggaaccagcagccggttgcctggtcaaggactacttccctgagccagtgaccgtgtcg<br>tggaacagcggagccctgacttccggctgcacacttttccccgcggtgctgcagtcctccggtctgtac<br>tcccttcgtccgtggtcaccgtgccgtcgtctagcctgggcacccagacctacatctgcaacgtgaac<br>cacaagccgtccaacaccaagtggataagcgggtggagccgaagtcctgcgataagacacacacgtgc<br>ccgccatgtccagcgcctgaattgcttggcggacctctccgtgttcctgttcccgcctaagcccaagga<br>cccttgatgattagccggactcccgaagtcacctgtggtggtggcagtgtcccacgaggaccccgag<br>gtcaagtttaattggtacgtggacggcgtcgaagtgcacaacgcaagactaagcccgggaggaacag<br>tacaacagcacctaccgggtcgtgtccgtgctgaccgtgctgcaccaggactggctgaatgggaagag<br>tacaagtgcaaagtgtccaacaaggccttggccgctcctatcgaaaaaactatcagcaaggctaaggga<br>cagccgagggaaccccaagtctacacctgccccttcacgcgaagagatgaccaagaatcaagtgtcg<br>ctgacctgcctcgtcaagggattctacccctccgacattgccgtggagtgggagtccaacggccagccc<br>gagaacaactacaagactactccgcccgtgctggactccgacggcagcttcttcctgtattccaagctg<br>accgtggacaagtcccgtggcagcaaggaaacgtgttctcctgctcggtcatgcacgaagcctgcac<br>aaccactacgcagaagtccctgtccttgagcccggggaaa |
| SEQ ID NO: 17 | LCDR1 (Combined) | RASQSITRNYLA |
| SEQ ID NO: 18 | LCDR2 (Combined) | GASSRAT |
| SEQ ID NO: 19 | LCDR3 (Combined) | QQHSMYPRT |
| SEQ ID NO: 17 | LCDR1 (Kabat) | RASQSITRNYLA |
| SEQ ID NO: 18 | LCDR2 (Kabat) | GASSRAT |
| SEQ ID NO: 19 | LCDR3 (Kabat) | QQHSMYPRT |
| SEQ ID NO: 20 | LCDR1 (Chothia) | SQSITRNY |
| SEQ ID NO: 21 | LCDR2 (Chothia) | GAS |
| SEQ ID NO: 22 | LCDR3 (Chothia) | HSMYPR |
| SEQ ID NO: 23 | LCDR1 (IMGT) | QSITRNY |
| SEQ ID NO: 21 | LCDR2 (IMGT) | GAS |
| SEQ ID NO: 19 | LCDR3 (IMGT) | QQHSMYPRT |
| SEQ ID NO: 24 | VL | DIVLTQSPATLSLSPGERATLSCRASQSITRNYLAWYQQKPGQAPRLLIYGA<br>SSRATGIPARFSGSGSGTDFTLTISSLEPEDFAVYYCQQHSMYPRTFGQGTK<br>VEIK |
| SEQ ID NO: 110 | DNA VL | gacatcgtgctgactcagtcccctgcgactctgagcctgtcaccgggagaacgggccaccctctcttgc<br>cgcgcctcccaatccattactcggaactacctggcctggtatcagcagaagccaggacaggcccctagg<br>cttctgatctacggggccagctcaagagcaactggcatcccggctcgcttctccggttcgggaagcggc<br>accgacttcaccctgaccctcgaacccgaggatttcgccgtgtactactgccaacagcac<br>tccatgtaccccgggacctttgggcagggaaccaaagtcgagatcaag |
| SEQ ID NO: 26 | Light Chain | DIVLTQSPATLSLSPGERATLSCRASQSITRNYLAWYQQKPGQAPRLLIYGA<br>SSRATGIPARFSGSGSGTDFTLTISSLEPEDFAVYYCQQHSMYPRTFGQGTK |

TABLE 2-continued

Exemplary anti-NPR1 antibody sequences

|  |  |  |
|---|---|---|
|  |  | VEIKRTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGLSSPV<br>TKSFNRGEC |
| SEQ ID NO: 111 | DNA Light Chain | gacatcgtgctgactcagtccctgcgactctgagcctgtcaccgggagaacgggccaccctctcttgc<br>cgcgcctcccaatccattactcggaactacctggcctggtatcagcagaagccaggacaggcccctagg<br>cttctgatctacggggccagctcaagagcaactggcatcccggctcgcttctccggttcggggaagcggc<br>accgacttcaccctgacaatttcgtccctcgaacccgaggatttcgccgtgtactactgccaacagcac<br>tccatgtaccccccgacctttgggcagggaaccaaagtcgagatcaagcgtacggtggccgctcccagc<br>gtgttcatcttccccccagcgacgagcagctgaagagcggcaccgccagcgtggtgtgcctgctgaac<br>aacttctacccccgggaggccaaggtgcagtggaaggtggacaacgccctgcagagcgggcaacagccag<br>gagagcgtcaccgagcaggacagcaaggactccacctacagcctgagcagcaccctgaccctgagcaag<br>gccgactacgagaagcataaggtgtacgcctgcgaggtgacccaccagggcctgtccagcccgtgacc<br>aagagcttcaacaggggcgagtgc |

XX01_N30S_DAPA

| SEQ ID NO: 112 | HCDR1 (Combined) | GFTFSTHYIH |
| SEQ ID NO: 100 | HCDR2 (Combined) | SISSSGQSTYYADSVKG |
| SEQ ID NO: 6 | HCDR3 (Combined) | ERGYVYYHMFDP |
| SEQ ID NO: 7 | HCDR1 (Kabat) | THYIH |
| SEQ ID NO: 100 | HCDR2 (Kabat) | SISSSGQSTYYADSVKG |
| SEQ ID NO: 6 | HCDR3 (Kabat) | ERGYVYYHMFDP |
| SEQ ID NO: 113 | HCDR1 (Chothia) | GFTFSTH |
| SEQ ID NO: 101 | HCDR2 (Chothia) | SSSGQS |
| SEQ ID NO: 6 | HCDR3 (Chothia) | ERGYVYYHMFDP |
| SEQ ID NO: 114 | HCDR1 (IMGT) | GFTFSTHY |
| SEQ ID NO: 102 | HCDR2 (IMGT) | ISSSGQST |
| SEQ ID NO: 12 | HCDR3 (IMGT) | ARERGYVYYHMFDP |
| SEQ ID NO: 115 | VH | EVQLLESGGGLVQPGGSLRLSCAASGFTFSTHYIHWVRQAPGKGLEWVSSI<br>SSSGQSTYYADSVKGRFTISRDNSKNTLYLQMNSLRAEDTAVYYCARERG<br>YVYYHMFDPWGQGTLVTVSS |
| SEQ ID NO: 116 | DNA VH | gaagtgcagctgcttgagtccggggtggactggtgcagcccggaggatccctgcgcctgagctgcgct<br>gcatccggcttcaccttcagcacgcactacatccattgggtcagacaggcccaggaaaaggcctggaa<br>tgggtgtcctccatctcctcgtcggggcagtcaacctactacgcggactccgtcaagggccggtttacc<br>attagccgggacaacagcaagaataccctgtacctccaaatgaactcgctgagggccgaagataccgcc<br>gtgtattactgtgcccgcgagagaggctacgtgtactaccacatgttcgacccgtggggacagggtact<br>ctcgtgactgtgtcttct |
| SEQ ID NO: 117 | Heavy Chain | EVQLLESGGGLVQPGGSLRLSCAASGFTFSTHYIHWVRQAPGKGLEWVSSI<br>SSSGQSTYYADSVKGRFTISRDNSKNTLYLQMNSLRAEDTAVYYCARERG<br>YVYYHMFDPWGQGTLVTVSSASTKGPSVFPLAPSSKSTSGGTAALGCLVK<br>DYFPEPVTVSWNSGALTSGVHTFPAVLQSSGLYSLSSVVTVPSSSLGTQTYI<br>CNVNHKPSNTKVDKRVEPKSCDKTHTCPPCPAPELLGGPSVFLFPPKPKDT<br>LMISRTPEVTCVVVAVSHEDPEVKFNWYVDGVEVHNAKTKPREEQYNSTY<br>RVVSVLTVLHQDWLNGKEYKCKVSNKALAAPIEKTISKAKGQPREPQVYT<br>LPPSREEMTKNQVSLTCLVKGFYPSDIAVEWESNGQPENNYKTTPPVLDSD<br>GSFFLYSKLTVDKSRWQQGNVFSCSVMHEALHNHYTQKSLSLSPGK |
| SEQ ID NO: 118 | DNA Heavy Chain | gaagtgcagctgcttgagtccggggtggactggtgcagcccggaggatccctgcgcctgagctgcgct<br>gcatccggcttcaccttcagcacgcactacatccattgggtcagacaggcccaggaaaaggcctggaa<br>tgggtgtcctccatctcctcgtcggggcagtcaacctactacgcggactccgtcaagggccggtttacc<br>attagccgggacaacagcaagaataccctgtacctccaaatgaactcgctgagggccgaagataccgcc<br>gtgtattactgtgcccgcgagagaggctacgtgtactaccacatgttcgacccgtggggacagggtact<br>ctcgtgactgtgtcttctgcgagcactaagggcccgtcagtgttcccgctggctccatcgtcgaagtcc<br>acctccggaggaaccgccagcactcggttgcctggtcaaggactacttccctgagccagtgaccgtgtcg<br>tggaacagcggagccctgacttccggcgtgcacacttttcccgcggtgctgcagtcctccggtctgtac<br>tccctttcgtccgtggtcaccgtgccgtcgtctagcctgggcacccagacctacatctgcaacgtgaac<br>cacaagccgtccaacaccaaagtggataagcgggtggagccgaagtcctgcgataagacacacacgtgc<br>ccgccatgtccagcgcctgaattgcttggcggacctccgtgttcctgttcccgcctaagccaaggac<br>accttgatgattagccggactcccgaagtcacctgtgtggtggtggcagtgtcccacgaggacccgag<br>gtcaagtttaattggtacgtggacggcgtcgaagtgcacaacgccaagactaagcccgggaggaacag<br>tacaacagcaccaccgggtcgtgtccgtgctgaccgtgctgcaccaggactggctgaatgggaaagag<br>tacaagtgcaaagtgtccaacaaggccttggccgctcctatcgaaaaaactatcagcaaggctaaggga<br>cagccgagggaaccccaagtctacaccctgccccttcacgcgaagagatgaccaagaatcaagtgtcg |

TABLE 2-continued

Exemplary anti-NPR1 antibody sequences

| | | |
|---|---|---|
| | | ctgacctgcctcgtcaagggattctacccctccgacattgcggtggagtgggagtccaacggccagccc gagaacaactacaagactactccgcccgtgctggactccgacggcagcttcttcctgtattccaagctg accgtggacaagtcccgtggcagcaaggaaacgtgttcctgctcggtcatgcacgaagccctgcac aaccactatacgcagaagtccctgtccttgagcccggggaaa |
| SEQ ID NO: 17 | LCDR1 (Combined) | RASQSITRNYLA |
| SEQ ID NO: 18 | LCDR2 (Combined) | GASSRAT |
| SEQ ID NO: 19 | LCDR3 (Combined) | QQHSMYPRT |
| SEQ ID NO: 17 | LCDR1 (Kabat) | RASQSITRNYLA |
| SEQ ID NO: 18 | LCDR2 (Kabat) | GASSRAT |
| SEQ ID NO: 19 | LCDR3 (Kabat) | QQHSMYPRT |
| SEQ ID NO: 20 | LCDR1 (Chothia) | SQSITRNY |
| SEQ ID NO: 21 | LCDR2 (Chothia) | GAS |
| SEQ ID NO: 22 | LCDR3 (Chothia) | HSMYPR |
| SEQ ID NO: 23 | LCDR1 (IMGT) | QSITRNY |
| SEQ ID NO: 21 | LCDR2 (IMGT) | GAS |
| SEQ ID NO: 19 | LCDR3 (IMGT) | QQHSMYPRT |
| SEQ ID NO: 24 | VL | DIVLTQSPATLSLSPGERATLSCRASQSITRNYLAWYQQKPGQAPRLLIYGA SSRATGIPARFSGSGSGTDFTLTISSLEPEDFAVYYCQQHSMYPRTFGQGTK VEIK |
| SEQ ID NO: 110 | DNA VL | gacatcgtgctgactcagtccctgcgactctgagcctgtcaccgggagaacgggccaccctctcttgc cgcgcctcccaatccattactcggaactacctggcctggtatcagcagaagccaggacaggcccctagg cttctgatctacggggccagctcaagagcaactggcatccggctcgcttctccggttcgggaagcggc accgacttcaccctgacaatttcgtccctcgaacccgaggatttcgccgtgtactactgccaacagcac tccatgtaccccggacctttgggcagggaaccaaagtcgagatcaag |
| SEQ ID NO: 26 | Light Chain | DIVLTQSPATLSLSPGERATLSCRASQSITRNYLAWYQQKPGQAPRLLIYGA SSRATGIPARFSGSGSGTDFTLTISSLEPEDFAVYYCQQHSMYPRTFGQGTK VEIKRTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPV TKSFNRGEC |
| SEQ ID NO: 111 | DNA Light Chain | gacatcgtgctgactcagtccctgcgactctgagcctgtcaccgggagaacgggccaccctctcttgc cgcgcctcccaatccattactcggaactacctggcctggtatcagcagaagccaggacaggcccctagg cttctgatctacggggccagctcaagagcaactggcatccggctcgcttctccggttcgggaagcggc accgacttcaccctgacaatttcgtccctcgaacccgaggatttcgccgtgtactactgccaacagcac tccatgtaccccggacctttgggcagggaaccaaagtcgagatcaagcgtacggtggccgctcccagc gtgttcatcttcccccccagcgacgagcagctgaagagcggcaccgccagcgtggtgtgcctgctgaac aacttctaccccagggaggccaaggtgcagtggaaggtggacaacgccctgcagagcggcaacagccag gagagcgtcaccgagcaggacagcaaggactccacctacagcctgagcagcaccctgaccctgagcaag gccgactacgagaagcataaggtgtacgcctgcgaggtgacccaccagggcctgtccagcccgtgacc aagagcttcaacaggggcgagtgc |
| XX03_LALA | | |
| SEQ ID NO: 28 | HCDR1 (Combined) | GFTFSSYWMN |
| SEQ ID NO: 119 | HCDR2 (Combined) | VIESKGNYIFYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 119 | HCDR2 (Kabat) | VIESKGNYIFYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 120 | HCDR2 (Chothia) | ESKGNY |
| SEQ ID NO: 30 | HCDR3 (Chothia) | DRYSMIYSYGAGAFDY |
| SEQ ID NO: 34 | HCDR1 (IMGT) | GFTFSSYW |

TABLE 2-continued

Exemplary anti-NPR1 antibody sequences

| SEQ ID NO: 121 | HCDR2 (IMGT) | IESKGNYI |
|---|---|---|
| SEQ ID NO: 36 | HCDR3 (IMGT) | ARDRYSMIYSYGAGAFDY |
| SEQ ID NO: 122 | VH | EVQLLESGGGLVQPGGSLRLSCAASGFTFSSYWMNWVRQAPGKGLEWVS<br>VIESKGNYIFYADSVKGRFTISRDNSKNTLYLQMNSLRAEDTAVYYCARDR<br>YSMIYSYGAGAFDYWGQGTLVTVSS |
| SEQ ID NO: 123 | DNA VH | gaggtgcaattgctggaaagcggcggtggcctggtgcagccgggtggcagcctgcgtctgagctgcgcg<br>gcgtccggattcaccttttcttcttactggatgaactgggtgcgccaggccccgggcaaaggtctcgag<br>tgggtttccgttatcgaatctaaaggcaactacatcttctatgcggatagcgtgaaaggccgctttacc<br>atcagccgcgataattcgaaaaacacccctgtatctgcaaatgaacagcctgcgtgcggaagatacggcc<br>gtgtattattgcgcgcgtgaccgttactctatgatctactcttacggtgctggtgctttcgattactgg<br>ggccaaggcaccctggtgactgttagctca |
| SEQ ID NO: 124 | Heavy Chain | EVQLLESGGGLVQPGGSLRLSCAASGFTFSSYWMNWVRQAPGKGLEWVS<br>VIESKGNYIFYADSVKGRFTISRDNSKNTLYLQMNSLRAEDTAVYYCARDR<br>YSMIYSYGAGAFDYWGQGTLVTVSSASTKGPSVFPLAPSSKSTSGGTAALG<br>CLVKDYFPEPVTVSWNSGALTSGVHTFPAVLQSSGLYSLSSVVTVPSSSLGT<br>QTYICNVNHKPSNTKVDKRVEPKSCDKTHTCPPCPAPEAAGGPSVFLFPPKP<br>KDTLMISRTPEVTCVVVDVSHEDPEVKFNWYVDGVEVHNAKTKPREEQY<br>NSTYRVVSVLTVLHQDWLNGKEYKCKVSNKALPAPIEKTISKAKGQPREP<br>QVYTLPPSREEMTKNQVSLTCLVKGFYPSDIAVEWESNGQPENNYKTTPPV<br>LDSDGSFFLYSKLTVDKSRWQQGNVFSCSVMHEALHNHYTQKSLSLSPGK |
| SEQ ID NO: 125 | DNA Heavy Chain | gaggtgcaattgctggaaagcggcggtggcctggtgcagccgggtggcagcctgcgtctgagctgcgcg<br>gcgtccggattcaccttttcttcttactggatgaactgggtgcgccaggccccgggcaaaggtctcgag<br>tgggtttccgttatcgaatctaaaggcaactacatcttctatgcggatagcgtgaaaggccgctttacc<br>atcagccgcgataattcgaaaaacacccctgtatctgcaaatgaacagcctgcgtgcggaagatacggcc<br>gtgtattattgcgcgcgtgaccgttactctatgatctactcttacggtgctggtgctttcgattactgg<br>ggccaaggcaccctggtgactgttagctcagcctccaccaagggtccatcggtcttccccctggcaccc<br>tcctccaagagcacctctgggggcacagcggccctgggctgcctggtcaaggactacttccccgaaccg<br>gtgacggtgtcgtggaactcaggcgccctgaccagcggcgtgcacaccttcccggctgtcctacagtcc<br>tcaggactctactccctcagcagcgtggtgaccgtgccctccagcagcttgggcacccagacctacatc<br>tgcaacgtgaatcacaagcccagcaacaccaaggtggacaagagagttgagcccaaatcttgtgacaaa<br>actcacacatgcccaccgtgcccagcacctgaagcagcgggggaccgtcagtcttcctcttccccccca<br>aaacccaaggacaccctcatgatctcccggacccctgaggtcacatgcgtggtggtggacgtgagccac<br>gaagaccctgaggtcaagttcaactggtacgtggacggcgtggaggtgcataatgccaagacaaagccg<br>cgggaggagcagtacaacagcacgtaccgggtggtcagcgtcctcaccgtcctgcaccaggactggctg<br>aatggcaaggagtacaagtgcaaggtctccaacaaagcccctcccagccccatcgagaaaaccatctcc<br>aaagccaaagggcagccccgagaaccacaggtgtacaccctgcccccatcccgggaggagatgaccaag<br>aaccaggtcagcctgacctgcctggtcaaaggcttctatcccagcgacatcgccgtggagtgggagagc<br>aatgggcagccggagaacaactacaagaccacgcctcccgtgctggactccgacggctccttcttcctc<br>tacagcaagctcaccgtggacaagagcaggtggcagcaggggaacgtcttctcatgctccgtgatgcat<br>gaggctctgcacaaccactacacgcagaagagcctctccctgtctccgggtaaa |
| SEQ ID NO: 41 | LCDR1 (Combined) | RASQGISSYLA |
| SEQ ID NO: 42 | LCDR2 (Combined) | TASTLQS |
| SEQ ID NO: 43 | LCDR3 (Combined) | MQSYEKPRT |
| SEQ ID NO: 41 | LCDR1 (Kabat) | RASQGISSYLA |
| SEQ ID NO: 42 | LCDR2 (Kabat) | TASTLQS |
| SEQ ID NO: 43 | LCDR3 (Kabat) | MQSYEKPRT |
| SEQ ID NO: 44 | LCDR1 (Chothia) | SQGISSY |
| SEQ ID NO: 45 | LCDR2 (Chothia) | TAS |
| SEQ ID NO: 46 | LCDR3 (Chothia) | SYEKPR |
| SEQ ID NO: 47 | LCDR1 (IMGT) | QGISSY |
| SEQ ID NO: 45 | LCDR2 (IMGT) | TAS |
| SEQ ID NO: 43 | LCDR3 (IMGT) | MQSYEKPRT |
| SEQ ID NO: 48 | VL | DIQMTQSPSSLSASVGDRVTITCRASQGISSYLAWYQQKPGKAPKLLIYTAS<br>TLQSGVPSRFSGSGSGTDFTLTISSLQPEDFATYYCMQSYEKPRTFGQGTKV<br>EIK |
| SEQ ID NO: 49 | DNA VL | gatatccagatgacccagagcccgagcagcctgagcgccagcgtgggcgatcgcgtgaccattacctgc<br>agagccagccagggtatttcttcttacctggcttggtaccagcagaaaccgggcaaagcgccgaaacta<br>ttaatctacactgcttctactctgcaaagcggcgtgccgagccgctttagcggcagcggatccggcacc |

TABLE 2-continued

Exemplary anti-NPR1 antibody sequences

| | | |
|---|---|---|
| | | gatttcaccctgaccattagctctctgcaaccggaagactttgcgacctattattgcatgcagtcttac<br>gaaaaaccgcgtacctttggccagggcacgaaagttgaaattaaa |
| SEQ ID NO: 50 | Light Chain | DIQMTQSPSSLSASVGDRVTITCRASQGISSYLAWYQQKPGKAPKLLIYTAS<br>TLQSGVPSRFSGSGSGTDFTLTISSLQPEDFATYYCMQSYEKPRTFGQGTKV<br>EIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVT<br>KSFNRGEC |
| SEQ ID NO: 51 | DNA Light Chain | gatatccagatgacccagagcccgagcagcctgagcgccagcgtgggcgatcgcgtgaccattacctgc<br>agagccagccagggtatttcttcttacctggcttggtaccagcagaaacgggcaaagcgccgaaacta<br>ttaatctacactgcttctactctgcaaagcggcgtgccgagccgctttagcggcagcggatccggcacc<br>gatttcaccctgaccattagctctctgcaaccggaagactttgcgacctattattgcatgcagtcttac<br>gaaaaaccgcgtacctttggccagggcacgaaagttgaaattaaacgtacggtggccgctcccagcgtg<br>ttcatcttccccccagcgacgagcagcagcctgaagagcgccagcgtggtgtgcctgctgaacaac<br>ttctaccccgggaggccaaggtgcagtggaaggtggacaacgcctgcagagcggcaacagccaggaa<br>agcgtcaccgagcaggacagcaaggactccacctacagcctgagcagcaccctgaccctgagcaaggcc<br>gactacgagaagcacaaggtgtacgcctgcgaggtgacccaccagggcctgtccagccccgtgaccaag<br>agcttcaaccggggcgagtgt |

XX04_LALA

| | | |
|---|---|---|
| SEQ ID NO: 28 | HCDR1 (Combined) | GFTFSSYWMN |
| SEQ ID NO: 29 | HCDR2 (Combined) | AISSDGSYTYYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 29 | HCDR2 (Kabat) | AISSDGSYTYYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 33 | HCDR2 (Chothia) | SSDGSY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 35 | HCDR2 (IMGT) | ISSDGSYT |
| SEQ ID NO: 36 | HCDR3 (IMGT) | ARDRYSMIYSYGAGAFDY |
| SEQ ID NO: 37 | VH | QVQLLESGGGLVQPGGSLRLSCAASGFTFSSYWMNWVRQAPGKGLEWVS<br>AISSDGSYTYYADSVKGRFTISRDNSKNTLYLQMNSLRAEDTAVYYCARD<br>RYSMIYSYGAGAFDYWGQGTLVTVSS |
| SEQ ID NO: 38 | DNA VH | caggtgcaattgctggaaagcggcggtggcctggtgcagccgggtggcagcctgcgtctgagctgcgcg<br>gcgtccggattcaccttttcttcttactggatgaactgggtgcgccaggcccccgggcaaaggtctcgag<br>tgggtttccgctatctcttctgacggttcttacacctactatgcggatagcgtgaaaggccgctttacc<br>atcagccgcgataattcgaaaaacaccctgtatctgcaaatgaacagcctgcgtgcggaagatacggcc<br>gtgtattattgcgcgcgtgaccgttactctatgatctactcttacggtgctggtgctttcgattactgg<br>ggccaaggcaccctggtgactgttagctca |
| SEQ ID NO: 39 | Heavy Chain | QVQLLESGGGLVQPGGSLRLSCAASGFTFSSYWMNWVRQAPGKGLEWVS<br>AISSDGSYTYYADSVKGRFTISRDNSKNTLYLQMNSLRAEDTAVYYCARD<br>RYSMIYSYGAGAFDYWGQGTLVTVSSASTKGPSVFPLAPSSKSTSGGTAAL<br>GCLVKDYFPEPVTVSWNSGALTSGVHTFPAVLQSSGLYSLSSVVTVPSSSL<br>GTQTYICNVNHKPSNTKVDKRVEPKSCDKTHTCPPCPAPEAAGGPSVFLFP<br>PKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPR<br>EPQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSP<br>GK |
| SEQ ID NO: 40 | DNA Heavy Chain | caggtgcaattgctggaaagcggcggtggcctggtgcagccgggtggcagcctgcgtctgagctgcgcg<br>gcgtccggattcaccttttcttcttactggatgaactgggtgcgccaggcccccgggcaaaggtctcgag<br>tgggtttccgctatctcttctgacggttcttacacctactatgcggatagcgtgaaaggccgctttacc<br>atcagccgcgataattcgaaaaacaccctgtatctgcaaatgaacagcctgcgtgcggaagatacggcc<br>gtgtattattgcgcgcgtgaccgttactctatgatctactcttacggtgctggtgctttcgattactgg<br>ggccaaggcaccctggtgactgttagctcagcctccaccaagggcccatcggtcttccccctggcaccc<br>tcctccaagagcacctctgggggcacagcggccctgggctgcctggtcaaggactacttccccgaaccg<br>gtgacggtgtcgtggaactcaggcgccctgaccagcggcgtgcacaccttcccggctgtcctacagtcc<br>tcaggactctactccctcagcagcgtggtgaccgtgccctccagcagcttgggcacccagacctacatc<br>tgcaacgtgaatcacaagcccagcaacaccaaggtggacaagagagttgagcccaaatcttgtgacaaa |

TABLE 2-continued

Exemplary anti-NPR1 antibody sequences

|  |  |  |
|---|---|---|
|  |  | actcacacatgcccaccgtgcccagcacctgaagcagcggggggaccgtcagtcttcctcttccccca<br>aaacccaaggacaccctcatgatctccggacccctgaggtcacatgcgtggtggtggacgtgagccac<br>gaagaccctgaggtcaagttcaactggtacgtggacggcgtggaggtgcataatgccaagacaaagccg<br>cgggaggagcagtacaacagcacgtaccgggtggtcagcgtcctcaccgtcctgcaccaggactggctg<br>aatggcaaggagtacaagtgcaaggtctccaacaaagcccctcccagccccatcgagaaaaccatctcc<br>aaagccaaagggcagccccgagaaccacaggtgtacaccctgcccccatcccgggaggagatgaccaag<br>aaccaggtcagcctgacctgcctggtcaaaggcttctatcccagcgacatcgccgtggagtgggagagc<br>aatgggcagccggagaacaactacaagaccacgcctcccgtgctggactccgacggctccttcttcctc<br>tacagcaagctcaccgtggacaagagcaggtggcagcaggggaacgtcttctcatgctccgtgatgcat<br>gaggctctgcacaaccactacacgcagaagagcctctccctgtctccgggtaaa |
| SEQ ID NO: 41 | LCDR1 (Combined) | RASQGISSYLA |
| SEQ ID NO: 42 | LCDR2 (Combined) | TASTLQS |
| SEQ ID NO: 126 | LCDR3 (Combined) | QQEWVKPRT |
| SEQ ID NO: 41 | LCDR1 (Kabat) | RASQGISSYLA |
| SEQ ID NO: 42 | LCDR2 (Kabat) | TASTLQS |
| SEQ ID NO: 126 | LCDR3 (Kabat) | QQEWVKPRT |
| SEQ ID NO: 44 | LCDR1 (Chothia) | SQGISSY |
| SEQ ID NO: 45 | LCDR2 (Chothia) | TAS |
| SEQ ID NO: 127 | LCDR3 (Chothia) | EWVKPR |
| SEQ ID NO: 47 | LCDR1 (IMGT) | QGISSY |
| SEQ ID NO: 45 | LCDR2 (IMGT) | TAS |
| SEQ ID NO: 126 | LCDR3 (IMGT) | QQEWVKPRT |
| SEQ ID NO: 128 | VL | DIQMTQSPSSLSASVGDRVTITCRASQGISSYLAWYQQKPGKAPKLLIYTAS<br>TLQSGVPSRFSGSGSGTDFTLTISSLQPEDFATYYCQQEWVKPRTFGQGTKV<br>EIK |
| SEQ ID NO: 129 | DNA VL | gatatccagatgacccagagcccgagcagcctgagcgccagcgtgggcgatcgcgtgaccattacctgc<br>agagccagccagggtatttcttcttacctggcttggtaccagcagaaaccgggcaaagcgccgaaacta<br>ttaatctacactgcttctactctgcaaagcggcgtgccgagccgctttagcggcagcggatccggcacc<br>gatttcacccctgaccattagctctctgcaaccggaagactttgcgacctattattgccagcaggaatgg<br>gttaaaccgcgtacctttggccagggcacgaaagttgaaattaaa |
| SEQ ID NO: 130 | Light Chain | DIQMTQSPSSLSASVGDRVTITCRASQGISSYLAWYQQKPGKAPKLLIYTAS<br>TLQSGVPSRFSGSGSGTDFTLTISSLQPEDFATYYCQQEWVKPRTFGQGTKV<br>EIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVT<br>KSFNRGEC |
| SEQ ID NO: 131 | DNA Light Chain | gatatccagatgacccagagcccgagcagcctgagcgccagcgtgggcgatcgcgtgaccattacctgc<br>agagccagccagggtatttcttcttacctggcttggtaccagcagaaaccgggcaaagcgccgaaacta<br>ttaatctacactgcttctactctgcaaagcggcgtgccgagccgctttagcggcagcggatccggcacc<br>gatttcacccctgaccattagctctctgcaaccggaagactttgcgacctattattgccagcaggaatgg<br>gttaaaccgcgtacctttggccagggcacgaaagttgaaattaaacgtacggtggccgctcccagcgtg<br>ttcatcttccccccagcgacgagcagctgaagagcggcaccgcagcgtggtgtgcctgctgaacaac<br>ttctaccccgggaggccaaggtgcagtggaaggtggacaacgcccctgcagagcggcaacagccaggaa<br>agcgtcaccgagcaggacagcaaggactccacctacagcctgagcagcaccctgaccctgagcaaggcc<br>gactacgagaagcacaaggtgtacgcctgcgaggtgacccaccagggcctgtccagccccgtgaccaag<br>agcttcaaccggggcgagtgt |
| XX06_LALA |  |  |
| SEQ ID NO: 28 | HCDR1 (Combined) | GFTFSSYWMN |
| SEQ ID NO: 29 | HCDR2 (Combined) | AISSDGSYTYYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 29 | HCDR2 (Kabat) | AISSDGSYTYYADSVKG |
| SEQ ID NO: 30 | HCDR3 (Kabat) | DRYSMIYSYGAGAFDY |
| SEQ ID NO: 32 | HCDR1 (Chothia) | GFTFSSY |

TABLE 2-continued

Exemplary anti-NPR1 antibody sequences

| SEQ ID NO: 33 | HCDR2 (Chothia) | SSDGSY |
|---|---|---|
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 35 | HCDR2 (IMGT) | ISSDGSYT |
| SEQ ID NO: 36 | HCDR3 (IMGT) | ARDRYSMIYSYGAGAFDY |
| SEQ ID NO: 37 | VH | QVQLLESGGGLVQPGGSLRLSCAASGFTFSSYWMNWVRQAPGKGLEWVS<br>AISSDGSYTYYADSVKGRFTISRDNSKNTLYLQMNSLRAEDTAVYYCARD<br>RYSMIYSYGAGAFDYWGQGTLVTVSS |
| SEQ ID NO: 132 | DNA VH | caggtgcaattgctggaaagcggcggtggcctggtgcagccgggtggcagcctgcgtctgagctgcgcg<br>gcgtccggattcacctttcttcttactggatgaactgggtgcgccaggcccaggcaaaggtctcgag<br>tgggtttccgctatctcttctgacggtctttacacctactatgcggatagcgtgaaaggccgctttacc<br>atcagccgcgataattcgaaaaacaccctgtatctgcaaatgaacagcctgcgtgcggaagatacggcc<br>gtgtattattgcgcgcgtgaccgttactctatgatctactcttacggtgctggtgctttcgattactgg<br>ggccaaggcaccctggtgactgttagctca |
| SEQ ID NO: 39 | Heavy Chain | QVQLLESGGGLVQPGGSLRLSCAASGFTFSSYWMNWVRQAPGKGLEWVS<br>AISSDGSYTYYADSVKGRFTISRDNSKNTLYLQMNSLRAEDTAVYYCARD<br>RYSMIYSYGAGAFDYWGQGTLVTVSSASTKGPSVFPLAPSSKSTSGGTAAL<br>GCLVKDYFPEPVTVSWNSGALTSGVHTFPAVLQSSGLYSLSSVVTVPSSSL<br>GTQTYICNVNHKPSNTKVDKRVEPKSCDKTHTCPPCPAPEAAGGPSVFLFP<br>PKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPR<br>EPQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSP<br>GK |
| SEQ ID NO: 133 | DNA Heavy Chain | caggtgcaattgctggaaagcggcggtggcctggtgcagccgggtggcagcctgcgtctgagctgcgcg<br>gcgtccggattcacctttcttcttactggatgaactgggtgcgccaggcccaggcaaaggtctcgag<br>tgggtttccgctatctcttctgacggtctttacacctactatgcggatagcgtgaaaggccgctttacc<br>atcagccgcgataattcgaaaaacaccctgtatctgcaaatgaacagcctgcgtgcggaagatacggcc<br>gtgtattattgcgcgcgtgaccgttactctatgatctactcttacggtgctggtgctttcgattactgg<br>ggccaaggcaccctggtgactgttagctcagcctccaccaagggtccatcggtcttccccctggcaccc<br>tcctccaagagcacctctgggggcacagcggccctgggctgcctggtcaaggactacttccccgaaccg<br>gtgacggtgtcgtggaactcaggcgccctgaccagcggcgtgcacaccttcccggctgtcctacagtcc<br>tcaggactctactccctcagcagcgtggtgaccgtgccctccagcagcttgggcacccagacctacatc<br>tgcaacgtgaatcacaagcccagcaacaccaaggtggacaagagagttgagcccaaatcttgtgacaaa<br>actcacacatgcccaccgtgcccagcacctgaagcagcggggggaccgtcagtcttcctcttccccca<br>aaacccaaggacaccctcatgatctcccggacccctgaggtcacatgcgtggtggtggacgtgagccac<br>gaagaccctgaggtcaagttcaactggtacgtggacggcgtggaggtgcataatgccaagacaaagccg<br>cgggaggagcagtacaacagcacgtaccgggtggtcagcgtcctcaccgtcctgcaccaggactggctg<br>aatggcaaggagtacaagtgcaaggtctccaacaaagcccctcccagcccccatcgagaaaaccatctcc<br>aaagccaaagggcagccccgagaaccacaggtgtacaccctgcccccatcccgggatgagctgaccaag<br>aaccaggtcagcctgacctgcctggtcaaaggcttctatcccagcgacatcgccgtggagtgggagagc<br>aatgggcagccggagaacaactacaagaccacgcctcccgtgctggactccgacggctccttcttcctc<br>tacagcaagctcaccgtggacaagagcaggtggcagcaggggaacgtcttctcatgctccgtgatgcat<br>gaggctctgcacaaccactacacgcagaagagcctctccctgtctccgggtaaa |
| SEQ ID NO: 41 | LCDR1 (Combined) | RASQGISSYLA |
| SEQ ID NO: 42 | LCDR2 (Combined) | TASTLQS |
| SEQ ID NO: 134 | LCDR3 (Combined) | QQTWRKPRT |
| SEQ ID NO: 41 | LCDR1 (Kabat) | RASQGISSYLA |
| SEQ ID NO: 42 | LCDR2 (Kabat) | TASTLQS |
| SEQ ID NO: 134 | LCDR3 (Kabat) | QQTWRKPRT |
| SEQ ID NO: 44 | LCDR1 (Chothia) | SQGISSY |
| SEQ ID NO: 45 | LCDR2 (Chothia) | TAS |
| SEQ ID NO: 135 | LCDR3 (Chothia) | TWRKPR |
| SEQ ID NO: 47 | LCDR1 (IMGT) | QGISSY |
| SEQ ID NO: 45 | LCDR2 (IMGT) | TAS |
| SEQ ID NO: 134 | LCDR3 (IMGT) | QQTWRKPRT |

TABLE 2-continued

Exemplary anti-NPR1 antibody sequences

| SEQ ID NO: 136 | VL | DIQMTQSPSSLSASVGDRVTITCRASQGISSYLAWYQQKPGKAPKLLIYTAS<br>TLQSGVPSRFSGSGSGTDFTLTISSLQPEDFATYYCQQTWRKPRTFGQGTKV<br>EIK |
|---|---|---|
| SEQ ID NO: 137 | DNA VL | gatatccagatgacccagagcccgagcagcctgagcgccagcgtgggcgatcgcgtgaccattacctgc<br>agagccagccagggtatttcttcttacctggcttggtaccagcagaaaccgggcaaagcgccgaaacta<br>ttaatctacactgcttctactctgcaaagcggcgtgccgagccgcttagcggcagcggatccggcacc<br>gatttcaccctgaccattagctctctgcaaccggaagactttgcgacctattattgccagcagacttgg<br>cgtaaaccgcgtacctttggccagggcacgaaagttgaaattaaa |
| SEQ ID NO: 138 | Light Chain | DIQMTQSPSSLSASVGDRVTITCRASQGISSYLAWYQQKPGKAPKLLIYTAS<br>TLQSGVPSRFSGSGSGTDFTLTISSLQPEDFATYYCQQTWRKPRTFGQGTKV<br>EIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVT<br>KSFNRGEC |
| SEQ ID NO: 139 | DNA Light Chain | gatatccagatgacccagagcccgagcagcctgagcgccagcgtgggcgatcgcgtgaccattacctgc<br>agagccagccagggtatttcttcttacctggcttggtaccagcagaaaccgggcaaagcgccgaaacta<br>ttaatctacactgcttctactctgcaaagcggcgtgccgagccgcttagcggcagcggatccggcacc<br>gatttcaccctgaccattagctctctgcaaccggaagactttgcgacctattattgccagcagacttgg<br>cgtaaaccgcgtacctttggccagggcacgaaagttgaaattaaacgtacggtggccgctcccagcgtg<br>ttcatcttcccccccagcgacgagcagctgaagagcggcaccgcccagcgtggtgtgcctgctgaacaac<br>ttctaccccgggaggccaaggtcagtggaaggtggacaacgccctgcagagcggcaacagccaggaa<br>agcgtcaccgagcaggacagcaaggactccacctacagcctgagcagcaccctgaccctgagcaaggcc<br>gactacgagaagcacaaggtgtacgcctgcgaggtgacccaccagggcctgtccagccccgtgaccaag<br>agcttcaaccggggcgagtgt |

XX06_DAPA

| SEQ ID NO: 28 | HCDR1 (Combined) | GFTFSSYWMN |
|---|---|---|
| SEQ ID NO: 29 | HCDR2 (Combined) | AISSDGSYTYYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 29 | HCDR2 (Kabat) | AISSDGSYTYYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 33 | HCDR2 (Chothia) | SSDGSY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 35 | HCDR2 (IMGT) | ISSDGSYT |
| SEQ ID NO: 36 | HCDR3 (IMGT) | ARDRYSMIYSYGAGAFDY |
| SEQ ID NO: 37 | VH | QVQLLESGGGLVQPGGSLRLSCAASGFTFSSYWMNWVRQAPGKGLEWVS<br>AISSDGSYTYYADSVKGRFTISRDNSKNTLYLQMNSLRAEDTAVYYCARD<br>RYSMIYSYGAGAFDYWGQGTLVTVSS |
| SEQ ID NO: 140 | DNA VH | caagtgcagctgcttgagagcggtggcggactggtgcagccaggggatccttgcgcctgtcatgcgct<br>gcgtcggggttcaccttctcgtcctactggatgaactgggtcagacaggctccggggaagggactcgaa<br>tgggtgtccgccatttcctccgacggctcctacacttactacgccgatagcgtcaagggccggttcacc<br>atctcccgggacaattcgaagaacacccgtgacctccaaatgaactcactgcgcgccgaggacactgcg<br>gtgtattactgtgcccgggataggtacagcatgatctactcctacggtgccggagccttgactactgg<br>ggacagggaaccccttgtgaccgtgtctagc |
| SEQ ID NO: 141 | Heavy Chain | QVQLLESGGGLVQPGGSLRLSCAASGFTFSSYWMNWVRQAPGKGLEWVS<br>AISSDGSYTYYADSVKGRFTISRDNSKNTLYLQMNSLRAEDTAVYYCARD<br>RYSMIYSYGAGAFDYWGQGTLVTVSSASTKGPSVFPLAPSSKSTSGGTAAL<br>GCLVKDYFPEPVTVSWNSGALTSGVHTFPAVLQSSGLYSLSSVVTVPSSSL<br>GTQTYICNVNHKPSNTKVDKRVEPKSCDKTHTCPPCPAPELLGGPSVFLFPP<br>KPKDTLMISRTPEVTCVVVAVSHEDPEVKFNWYVDGVEVHNAKTKPREEQ<br>YNSTYRVVSVLTVLHQDWLNGKEYKCKVSNKALAAPIEKTISKAKGQPRE<br>PQVYTLPPSREEMTKNQVSLTCLVKGFYPSDIAVEWESNGQPENNYKTTPP<br>VLDSDGSFFLYSKLTVDKSRWQQGNVFSCSVMHEALHNHYTQKSLSLSPG<br>K |
| SEQ ID NO: 142 | DNA Heavy Chain | caagtgcagctgcttgagagcggtggcggactggtgcagccaggggatccttgcgcctgtcatgcgct<br>gcgtcggggttcaccttctcgtcctactggatgaactgggtcagacaggctccggggaagggactcgaa<br>tgggtgtccgccatttcctccgacggctcctacacttactacgccgatagcgtcaagggccggttcacc |

TABLE 2-continued

Exemplary anti-NPR1 antibody sequences

```
                        atctcccgggacaattcgaagaacaccctgtacctccaaatgaactcactgcgcgccgaggacactgcg
                        gtgtattactgtgcccgggataggtacagcatgatctactcctacggtgccggagccttgactactgg
                        ggacagggaacccttgtgaccgtgtctagcgcgtccactaagggcccgtcagtgttcccgctggctcca
                        tcgtcgaagtccacctccgaggaaccgcagcactcggttgcctggtcaaggactacttccctgagcca
                        gtgaccgtgtcgtggaacagcggagccctgacttccggcgtgcacacttttcccgcggtgctgcagtcc
                        tccggtctgtactcccttcgtccgtggtcaccgtgccgtcgtctagcctgggcacccagacctacatc
                        tgcaacgtgaaccacaagcgtccaacaccaaagtgggataagcgggtggagccgaagtcctgcgataag
                        acacacacgtgcccgccatgtccagcgcctgaattgcttggcggaccttccgtgttcctgttcccgcct
                        aagcccaaggacaccttgatgattagccggactcccgaagtcacctgtgtggtggtggcagtgtcccac
                        gaggaccccgaggtcaagtttaattggtacgtggacggcgtcgaagtgcacaacgccaagactaagccc
                        cgggaggaacagtacaacagcacctaccgggtcgtgtccgtgctgaccgtgctgcaccaggactggctg
                        aatgggaaagagtacaagtgcaaagtgtccaacaaggccttggccgctcctatcgaaaaaactatcagc
                        aaggctaagggacagccgagggaaccccaagtctacaccctgccccttcacgcgaagagatgaccaag
                        aatcaagtgtcgctgacctgcctcgtcaagggattctaccccctccgacattgcggtggagtgggagtcc
                        aacggccagccgagaacaactacaagactactccgcccgtctggactccgacggcagcttcttcctg
                        tattccaagctgaccgtggacaagtcccggtggcagcaaggaaacgtgttctcctgctcggtcatgcac
                        gaagccctgcacaaccactatacgcagaagtccctgtccttgagcccggggaaa
```

| SEQ ID NO: 41 | LCDR1 (Combined) | RASQGISSYLA |
| SEQ ID NO: 42 | LCDR2 (Combined) | TASTLQS |
| SEQ ID NO: 134 | LCDR3 (Combined) | QQTWRKPRT |
| SEQ ID NO: 41 | LCDR1 (Kabat) | RASQGISSYLA |
| SEQ ID NO: 42 | LCDR2 (Kabat) | TASTLQS |
| SEQ ID NO: 134 | LCDR3 (Kabat) | QQTWRKPRT |
| SEQ ID NO: 44 | LCDR1 (Chothia) | SQGISSY |
| SEQ ID NO: 45 | LCDR2 (Chothia) | TAS |
| SEQ ID NO: 135 | LCDR3 (Chothia) | TWRKPR |
| SEQ ID NO: 47 | LCDR1 (IMGT) | QGISSY |
| SEQ ID NO: 45 | LCDR2 (IMGT) | TAS |
| SEQ ID NO: 134 | LCDR3 (IMGT) | QQTWRKPRT |
| SEQ ID NO: 136 | VL | DIQMTQSPSSLSASVGDRVTITCRASQGISSYLAWYQQKPGKAPKLLIYTAS TLQSGVPSRFSGSGSGTDFTLTISSLQPEDFATYYCQQTWRKPRTFGQGTKV EIK |
| SEQ ID NO: 143 | DNA VL | gacatccagatgacccagtctccgtcctccctgtccgcatcagtgggggacagagtgaccatcacttgt cgggcctcccaaggcatctcgtcatacctggcctggtatcagcagaaacccggaaaggctccaaagctg ctcatctacaccgcctcgactctgcaatccggagtgccttcccgcttctccggatccggttcggaacc gacttcaccctcaccattagcagccttcagccggaagatttcgcgacctactactgccagcaaacctgg cggaagcccaggacatttggccagggcactaaggtcgagattaag |
| SEQ ID NO: 138 | Light Chain | DIQMTQSPSSLSASVGDRVTITCRASQGISSYLAWYQQKPGKAPKLLIYTAS TLQSGVPSRFSGSGSGTDFTLTISSLQPEDFATYYCQQTWRKPRTFGQGTKV EIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVT KSFNRGEC |
| SEQ ID NO: 144 | DNA Light Chain | gacatccagatgacccagtctccgtcctccctgtccgcatcagtgggggacagagtgaccatcacttgt cgggcctcccaaggcatctcgtcatacctggcctggtatcagcagaaacccggaaaggctccaaagctg ctcatctacaccgcctcgactctgcaatccggagtgccttcccgcttctccggatccggttcggaacc gacttcaccctcaccattagcagccttcagccggaagatttcgcgacctactactgccagcaaacctgg cggaagcccaggacatttggccagggcactaaggtcgagattaagcgtacggtggccgctcccagcgtg ttcatcttcccccccagcgacgagcagctgaagagcggcaccgccagcgtggtgtgcctgctgaacaac ttctaccccgggaggccaaggtgcagtggaaggtggacaacgccctgcagagcggcaacagccaggag agcgtcaccgagcaggacagcaaggactccacctacagcctgagcagcaccctgaccctgagcaaggcc gactacgagaagcataaggtgtacgcctgcgaggtgacccaccagggcctgtccagccccgtgaccaag agcttcaacagggggcgagtgc |

XX07_LALA

| SEQ ID NO: 28 | HCDR1 (Combined) | GFTFSSYWMN |
| SEQ ID NO: 29 | HCDR2 (Combined) | AISSDGSYTYYADSVKG |
| SEQ ID NO: 30 | HCDR3 (Combined) | DRYSMIYSYGAGAFDY |
| SEQ ID NO: 31 | HCDR1 (Kabat) | SYWMN |

TABLE 2-continued

Exemplary anti-NPR1 antibody sequences

| SEQ ID NO: 29 | HCDR2 (Kabat) | AISSDGSYTYYADSVKG |
|---|---|---|
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 33 | HCDR2 (Chothia) | SSDGSY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 35 | HCDR2 (IMGT) | ISSDGSYT |
| SEQ ID NO: 36 | HCDR3 (IMGT) | ARDRYSMIYSYGAGAFDY |
| SEQ ID NO: 37 | VH | QVQLLESGGGLVQPGGSLRLSCAASGFTFSSYWMNWVRQAPGKGLEWVS<br>AISSDGSYTYYADSVKGRFTISRDNSKNTLYLQMNSLRAEDTAVYYCARD<br>RYSMIYSYGAGAFDYWGQGTLVTVSS |
| SEQ ID NO: 38 | DNA VH | caggtgcaattgctggaaagcggcggtggcctggtgcagccgggtggcagcctgcgtctgagctgcgcg<br>gcgtccggattcaccttttcttcttactggatgaactgggtgcgccaggccccgggcaaaggtctcgag<br>tgggtttccgctatctcttctgacggttcttacacctactatgcggatagcgtgaaaggccgctttacc<br>atcagccgcgataattcgaaaaacaccctgtatctgcaaatgaacagcctgcgtgcggaagatacggcc<br>gtgtattattgcgcgcgtgaccgttactctatgatctactcttacggtgctggtgctttcgattactgg<br>ggccaaggcaccctggtgactgttagctca |
| SEQ ID NO: 39 | Heavy Chain | QVQLLESGGGLVQPGGSLRLSCAASGFTFSSYWMNWVRQAPGKGLEWVS<br>AISSDGSYTYYADSVKGRFTISRDNSKNTLYLQMNSLRAEDTAVYYCARD<br>RYSMIYSYGAGAFDYWGQGTLVTVSSASTKGPSVFPLAPSSKSTSGGTAAL<br>GCLVKDYFPEPVTVSWNSGALTSGVHTFPAVLQSSGLYSLSSVVTVPSSSL<br>GTQTYICNVNHKPSNTKVDKRVEPKSCDKTHTCPPCPAPEAAGGPSVFLFP<br>PKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPR<br>EPQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSP<br>GK |
| SEQ ID NO: 40 | DNA Heavy Chain | caggtgcaattgctggaaagcggcggtggcctggtgcagccgggtggcagcctgcgtctgagctgcgcg<br>gcgtccggattcaccttttcttcttactggatgaactgggtgcgccaggccccgggcaaaggtctcgag<br>tgggtttccgctatctcttctgacggttcttacacctactatgcggatagcgtgaaaggccgctttacc<br>atcagccgcgataattcgaaaaacaccctgtatctgcaaatgaacagcctgcgtgcggaagatacggcc<br>gtgtattattgcgcgcgtgaccgttactctatgatctactcttacggtgctggtgctttcgattactgg<br>ggccaaggcaccctggtgactgttagctcagcctccaccaagggtccatcggtcttcccctggcaccc<br>tcctccaagagcacctctgggggcacagcggccctgggctgcctggtcaaggactacttccccgaaccg<br>gtgacggtgtcgtggaactcaggcgccctgaccagcggcgtgcacaccttcccggctgtcctacagtcc<br>tcaggactctactcccctcagcagcgtggtgaccgtgccctccagcagcttgggcacccagacctacatc<br>tgcaacgtgaatcacaagcccagcaacaccaaggtggacaagagagttgagcccaaatcttgtgacaaa<br>actcacacatgcccaccgtgcccagcacctgaagcagcgggggaccgtcagtcttcctcttccccca<br>aaacccaaggacaccctcatgatctcccggacccctgaggtcacatgcgtggtggtggacgtgagccac<br>gaagaccctgaggtcaagttcaactggtacgtggacggcgtggaggtgcataatgccaagacaaagccg<br>cgggaggagcagtacaacagcacgtaccgtgtggtcagcgtcctcaccgtcctgcaccaggactggctg<br>aatggcaaggagtacaagtgcaaggtctccaacaaagccctcccagcccccatcgagaaaaccatctcc<br>aaagccaaagggcagccccgagaaccacaggtgtacaccctgcccccatcccgggaggagatgaccaag<br>aaccaggtcagcctgacctgcctggtcaaaggcttctatcccagcgacatcgccgtggagtgggagagc<br>aatgggcagccggagaacaactacaagaccacgcctcccgtgctggactccgacggctccttcttcctc<br>tacagcaagctcaccgtggacaagagcaggtggcagcaggggaacgtcttctcatgctccgtgatgcat<br>gaggctctgcacaaccactacacgcagaagagcctctccctgtctccgggtaaa |
| SEQ ID NO: 41 | LCDR1 (Combined) | RASQGISSYLA |
| SEQ ID NO: 42 | LCDR2 (Combined) | TASTLQS |
| SEQ ID NO: 145 | LCDR3 (Combined) | QQIWTVPRT |
| SEQ ID NO: 41 | LCDR1 (Kabat) | RASQGISSYLA |
| SEQ ID NO: 42 | LCDR2 (Kabat) | TASTLQS |
| SEQ ID NO: 145 | LCDR3 (Kabat) | QQIWTVPRT |
| SEQ ID NO: 44 | LCDR1 (Chothia) | SQGISSY |
| SEQ ID NO: 45 | LCDR2 (Chothia) | TAS |
| SEQ ID NO: 146 | LCDR3 (Chothia) | IWTVPR |

TABLE 2-continued

Exemplary anti-NPR1 antibody sequences

| SEQ ID NO: 47 | LCDR1 (IMGT) | QGISSY |
|---|---|---|
| SEQ ID NO: 45 | LCDR2 (IMGT) | TAS |
| SEQ ID NO: 145 | LCDR3 (IMGT) | QQIWTVPRT |
| SEQ ID NO: 147 | VL | DIQMTQSPSSLSASVGDRVTITCRASQGISSYLAWYQQKPGKAPKLLIYTAS TLQSGVPSRFSGSGSGTDFTLTISSLQPEDFATYYCQQIWTVPRTFGQGTKV EIK |
| SEQ ID NO: 148 | DNA VL | gatatccagatgacccagagcccgagcagcctgagcgccagcgtgggcgatcgcgtgaccattacctgc agagccagcagggtatttcttcttacctggcttggtaccagcagaaaccgggcaaagcgccgaaacta ttaatctacactgcttctactctgcaaagcggcgtgccgagccgctttagcggcagcggatccggcacc gatttcacccctgaccattagctctctgcaaccggaagactttgcgacctattattgccagcagatctgg actgttccgcgtacctttggccagggcacgaaagttgaaattaaa |
| SEQ ID NO: 149 | Light Chain | DIQMTQSPSSLSASVGDRVTITCRASQGISSYLAWYQQKPGKAPKLLIYTAS TLQSGVPSRFSGSGSGTDFTLTISSLQPEDFATYYCQQIWTVPRTFGQGTKV EIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVT KSFNRGEC |
| SEQ ID NO: 150 | DNA Light Chain | gatatccagatgacccagagcccgagcagcctgagcgccagcgtgggcgatcgcgtgaccattacctgc agagccagcagggtatttcttcttacctggcttggtaccagcagaaaccgggcaaagcgccgaaacta ttaatctacactgcttctactctgcaaagcggcgtgccgagccgctttagcggcagcggatccggcacc gatttcacccctgaccattagctctctgcaaccggaagactttgcgacctattattgccagcagatctgg actgttccgcgtacctttggccagggcacgaaagttgaaattaaacgtacggtggccgctcccagcgtg ttcatcttccccccagcgacgagcagctgaagagcggcaccggccagcgtggtgtgcctgctgaacaac ttctaccccgggaggccaaggtgcagtggaaggtggacaacgcccctgcagagcggcaacagccaggaa agcgtcaccgagcaggacagcaaggactccacctacagcctgagcagcaccctgaccctgagcaaggcc gactacgagaagcacaaggtgtacgcctgcgaggtgacccaccagggcctgtccagcccgtgaccaag agcttcaaccggggcgagtgt |

XX08_LALA

| SEQ ID NO: 4 | HCDR1 (Combined) | GFTFNTHYIH |
|---|---|---|
| SEQ ID NO: 151 | HCDR2 (Combined) | SIGGQGGMTLYADSVKG |
| SEQ ID NO: 6 | HCDR3 (Combined) | ERGYVYYHMFDP |
| SEQ ID NO: 7 | HCDR1 (Kabat) | THYIH |
| SEQ ID NO: 151 | HCDR2 (Kabat) | SIGGQGGMTLYADSVKG |
| SEQ ID NO: 6 | HCDR3 (Kabat) | ERGYVYYHMFDP |
| SEQ ID NO: 8 | HCDR1 (Chothia) | GFTFNTH |
| SEQ ID NO: 152 | HCDR2 (Chothia) | GGQGGM |
| SEQ ID NO: 6 | HCDR3 (Chothia) | ERGYVYYHMFDP |
| SEQ ID NO: 10 | HCDR1 (IMGT) | GFTFNTHY |
| SEQ ID NO: 153 | HCDR2 (IMGT) | IGGQGGMT |
| SEQ ID NO: 12 | HCDR3 (IMGT) | ARERGYVYYHMFDP |
| SEQ ID NO: 154 | VH | EVQLLESGGGLVQPGGSLRLSCAASGFTFNTHYIHWVRQAPGKGLEWVSSI GGQGGMTLYADSVKGRFTISRDNSKNTLYLQMNSLRAEDTAVYYCARER GYVYYHMFDPWGQGTLVTVSS |
| SEQ ID NO: 155 | DNA VH | gaggtgcaattgctggaaagcggcggtggcctggtgcagccgggtggcagcctgcgtctgagctgcgcg gcgtccggattcaccttaacactcattacatccattgggtgcgccaggcccccggcaaaggtctcgag tgggtttcctctatcggtggtcagggcggtatgactctgtatgcggatagcgtgaaaggccgcttcacc atcagccgcgataattcgaaaaacaccctgtatctgcaaatgaacagcctgcgtgcggaagatacggcc gtgtattattgcgcgcgtgaacgtggttacgtttactaccatatgttcgatccgtggggccaaggcacc ctggtgactgttagctca |
| SEQ ID NO: 156 | Heavy Chain | EVQLLESGGGLVQPGGSLRLSCAASGFTFNTHYIHWVRQAPGKGLEWVSSI GGQGGMTLYADSVKGRFTISRDNSKNTLYLQMNSLRAEDTAVYYCARER GYVYYHMFDPWGQGTLVTVSSASTKGPSVFPLAPSSKSTSGGTAALGCLV KDYFPEPVTVSWNSGALTSGVHTFPAVLQSSGLYSLSSVVTVPSSSLGTQTY ICNVNHKPSNTKVDKRVEPKSCDKTHTCPPCPAPEAAGGPSVFLFPPKPKDT LMISRTPEVTCVVVDVSHEDPEVKFNWYVDGVEVHNAKTKPREEQYNSTY |

TABLE 2-continued

Exemplary anti-NPR1 antibody sequences

|   |   |   |
|---|---|---|
|   |   | RVVSVLTVLHQDWLNGKEYKCKVSNKALPAPIEKTISKAKGQPREPQVYT<br>LPPSREEMTKNQVSLTCLVKGFYPSDIAVEWESNGQPENNYKTTPPVLDSD<br>GSFFLYSKLTVDKSRWQQGNVFSCSVMHEALHNHYTQKSLSLSPGK |
| SEQ ID NO: 157 | DNA Heavy Chain | gaggtgcaattgctggaaagcggcggtggcctggtgcagccgggtggcagcctgcgtctgagctgcgcg<br>gcgtccggattcacctttaacactcattacatccattgggtgcgccaggcccccggcaaaggtctcgag<br>tgggtttcctctatcggtggtcagggcggtatgactctgtatgcggatagcgtgaaaggccgctttacc<br>atcagccgcgataattcgaaaaacacccctgtatctgcaaatgaacagccgcgtgcggaagatacggcc<br>gtgtattattgcgcgcgtaacgtggtacgtttactaccatatgttcgatccgtggggccaaggcacc<br>ctggtgactgttagctcagcctccaccaagggcccatcggtcttccccctggcaccctcctccaagagc<br>acctctgggggcacagcggccctgggctgcctggtcaaggactacttccccgaaccggtgacggtgtcg<br>tggaactcaggcgccctgaccagcggcgtgcacaccttcccggctgtcctacagtcctcaggactctac<br>tccctcagcagcgtggtgaccgtgccctccagcagcttgggcacccagacctacatctgcaacgtgaat<br>cacaagcccagcaacaccaaggtggacaagagagttgagcccaaatcttgtgacaaaactcacacatgc<br>ccaccgtgcccagcacctgaagcagcgggggggaccgtcagtcttcctcttcccccaaaacccaaggac<br>accctcatgatctcccggacccctgaggtcacatgcgtggtggtggacgtgagccacgaagaccctgag<br>gtcaagttcaactggtacgtggacggcgtggaggtgcataatgccaagacaaagccgcgggaggagcag<br>tacaacagcacgtaccgggtggtcagcgtcctcaccgtcctgcaccaggactggctgaatggcaaggag<br>tacaagtgcaaggtctccaacaaagccctcccagcccccatcgagaaaaccatctccaaagccaaaggg<br>cagccccgagaaccacaggtgtacaccctgcccccatcccgggaggagatgaccaagaaccaggtcagc<br>ctgacctgcctggtcaaaggcttctatcccagcgacatcgccgtggagtgggagagcaatgggcagccg<br>gagaacaactacaagaccacgcctcccgtgctggactccgacggctccttcttcctctacagcaagctc<br>accgtggacaagagcaggtggcagcaggggaacgtcttctcatgctccgtgatgcatgaggctctgcac<br>aaccactacacgcagaagagcctctccctgtctccgggtaaa |
| SEQ ID NO: 17 | LCDR1 (Combined) | RASQSITRNYLA |
| SEQ ID NO: 18 | LCDR2 (Combined) | GASSRAT |
| SEQ ID NO: 19 | LCDR3 (Combined) | QQHSMYPRT |
| SEQ ID NO: 17 | LCDR1 (Kabat) | RASQSITRNYLA |
| SEQ ID NO: 18 | LCDR2 (Kabat) | GASSRAT |
| SEQ ID NO: 19 | LCDR3 (Kabat) | QQHSMYPRT |
| SEQ ID NO: 20 | LCDR1 (Chothia) | SQSITRNY |
| SEQ ID NO: 21 | LCDR2 (Chothia) | GAS |
| SEQ ID NO: 22 | LCDR3 (Chothia) | HSMYPR |
| SEQ ID NO: 23 | LCDR1 (IMGT) | QSITRNY |
| SEQ ID NO: 21 | LCDR2 (IMGT) | GAS |
| SEQ ID NO: 19 | LCDR3 (IMGT) | QQHSMYPRT |
| SEQ ID NO: 24 | VL | DIVLTQSPATLSLSPGERATLSCRASQSITRNYLAWYQQKPGQAPRLLIYGA<br>SSRATGIPARFSGSGSGTDFTLTISSLEPEDFAVYYCQQHSMYPRTFGQGTK<br>VEIK |
| SEQ ID NO: 25 | DNA VL | gatatcgtgctgacccagagcccggcgaccctgagcctgagcccgggtgaacgtgccaccctgagctgc<br>agagcgagccagtctatcactcgtaactacctggcttggtaccagcagaaacgggccaggccccgcgt<br>ctattaatctacggtgcttcttctcgtgcgaccggcattccggcgcgttttagcggcagcggatccggc<br>accgatttcaccctgaccattagcagcctggaaccggaagactttgcggtgtattattgccagcagcat<br>tctatgtacccgcgtacctttggccagggcacgaaagttgaaattaaa |
| SEQ ID NO: 26 | Light Chain | DIVLTQSPATLSLSPGERATLSCRASQSITRNYLAWYQQKPGQAPRLLIYGA<br>SSRATGIPARFSGSGSGTDFTLTISSLEPEDFAVYYCQQHSMYPRTFGQGTK<br>VEIKRTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGLSSPV<br>TKSFNRGEC |
| SEQ ID NO: 27 | DNA Light Chain | gatatcgtgctgacccagagcccggcgaccctgagcctgagcccgggtgaacgtgccaccctgagctgc<br>agagcgagccagtctatcactcgtaactacctggcttggtaccagcagaaacgggccaggccccgcgt<br>ctattaatctacggtgcttcttctcgtgcgaccggcattccggcgcgttttagcggcagcggatccggc<br>accgatttcaccctgaccattagcagcctggaaccggaagactttgcggtgtattattgccagcagcat<br>tctatgtacccgcgtacctttggccagggcacgaaagttgaaattaaacgtacggtggccgctcccagc<br>gtgttcatcttcccccccagcgaccagcagcgaagagcggcaccgcgagcgtggtgcctgctgaac<br>aacttctaccccgggaggccaaggtgcagtggaaggtggacaacgccctgcagagcggcaacagccag<br>gaaagcgtcaccgagcaggacagcaaggactccacctacagcctgagcagcaccctgaccctgagcaag<br>gccgactacgagaagcacaaggtgtacgcctgcgaggtgacccaccagggcctgtccagccccgtgacc<br>aagagcttcaaccggggcgagtgt |

TABLE 2-continued

Exemplary anti-NPR1 antibody sequences

XX08_DAPA

| SEQ ID NO: 4 | HCDR1 (Combined) | GFTFNTHYIH |
|---|---|---|
| SEQ ID NO: 151 | HCDR2 (Combined) | SIGGQGGMTLYADSVKG |
| SEQ ID NO: 6 | HCDR3 (Combined) | ERGYVYYHMFDP |
| SEQ ID NO: 7 | HCDR1 (Kabat) | THYIH |
| SEQ ID NO: 151 | HCDR2 (Kabat) | SIGGQGGMTLYADSVKG |
| SEQ ID NO: 6 | HCDR3 (Kabat) | ERGYVYYHMFDP |
| SEQ ID NO: 8 | HCDR1 (Chothia) | GFTFNTH |
| SEQ ID NO: 152 | HCDR2 (Chothia) | GGQGGM |
| SEQ ID NO: 6 | HCDR3 (Chothia) | ERGYVYYHMFDP |
| SEQ ID NO: 10 | HCDR1 (IMGT) | GFTFNTHY |
| SEQ ID NO: 153 | HCDR2 (IMGT) | IGGQGGMT |
| SEQ ID NO: 12 | HCDR3 (IMGT) | ARERGYVYYHMFDP |
| SEQ ID NO: 154 | VH | EVQLLESGGGLVQPGGSLRLSCAASGFTFNTHYIHWVRQAPGKGLEWVSSI GGQGGMTLYADSVKGRFTISRDNSKNTLYLQMNSLRAEDTAVYYCARER GYVYYHMFDPWGQGTLVTVSS |
| SEQ ID NO: 158 | DNA VH | gaagtgcagctcctggagtcgggtggcggactggtgcagcctggcggatcactgcggctgtcatgtgcc gcgagcgggtttactttcaacacccactacatccactgggtccgccaagctcccggaaagggactcgaa tgggtgtcctccattggtggacagggcggcatgacccttacgcggatagcgtgaagggaggttcacc atctctcccgcgacaacagcaagaacaccctgtacctccaaatgaactcgcttcgggccgaggacactgcc gtgtactattgcgcaagagagcggggctacgtgtactaccacatgttcgaccccatgggacagggaacg ctggtcaccgtgtcctcc |
| SEQ ID NO: 159 | Heavy Chain | EVQLLESGGGLVQPGGSLRLSCAASGFTFNTHYIHWVRQAPGKGLEWVSSI GGQGGMTLYADSVKGRFTISRDNSKNTLYLQMNSLRAEDTAVYYCARER GYVYYHMFDPWGQGTLVTVSSASTKGPSVFPLAPSSKSTSGGTAALGCLV KDYFPEPVTVSWNSGALTSGVHTFPAVLQSSGLYSLSSVVTVPSSSLGTQTY ICNVNHKPSNTKVDKRVEPKSCDKTHTCPPCPAPELLGGPSVFLFPPKPKDT LMISRTPEVTCVVVAVSHEDPEVKFNWYVDGVEVHNAKTKPREEQYNSTY RVVSVLTVLHQDWLNGKEYKCKVSNKALAAPIEKTISKAKGQPREPQVYT LPPSREEMTKNQVSLTCLVKGFYPSDIAVEWESNGQPENNYKTTPPVLDSD GSFFLYSKLTVDKSRWQQGNVFSCSVMHEALHNHYTQKSLSLSPGK |
| SEQ ID NO: 160 | DNA Heavy Chain | gaagtgcagctcctggagtcgggtggcggactggtgcagcctggcggatcactgcggctgtcatgtgcc gcgagcgggtttactttcaacacccactacatccactgggtccgccaagctcccggaaagggactcgaa tgggtgtcctccattggtggacagggcggcatgacccttacgcggatagcgtgaagggaggttcacc atctctcccgcgacaacagcaagaacaccctgtacctccaaatgaactcgcttcgggccgaggacactgcc gtgtactattgcgcaagagagcggggctacgtgtactaccacatgttcgaccccatgggacagggaacg ctggtcaccgtgtcctccgcctccactaagggcccgtcagtgttcccgctggctccatcgtcgaagtcc acctccggaggaaccgcagcactcggttgcctggtcaaggactacttccctgagccagtgaccgtgtcg tggaacagcggagccctgacttccggcgtgcacacttttccgcggtgctgcagtcctccggtctgtac tcccttttcgtccgtggtcaccgtgccgtcgtctagcctgggcacccagacctacatctgcaacgtgaac cacaagccgtccaacaccaaagtggataagcgggtggagccgaagtcctgcgataagacacacgtgc ccgccatgtccagcgcctgaattgcttggcggaccttccgtgttcctgttcccgcctaagcccaaggac accttgatgattagccggactcccgaagtcacctgtgtggtggtggcagtgtcccacgaggacccccgag gtcaagtttaattggtacgtggacggcgtcgaagtgcacaacgccaagactaagcccgggaggaacag tacaacagcaccctaccgggtcgtgtccgtgctgaccgtgctgcaccaggactggctgaatggaaaga tacaagtgcaaagtgtccaacaaggccttggccgctcctatcgaaaaaaactatcagcaaggctaaggga cagccgagggaacccccaagtctacaccctgccccttcacgcgaagagatgaccaagaatcaagtgtcg ctgacctgcctcgtcaagggattctaccccctccgacattgcggtggagtgggagtccaacggccagccc gagaacaactacaagactactccgccgtgctggactccgacggcagcttcttcctgtattccaagctg accgtggacaagtcccggtggcagcaaggaaacgtgttctcctgctcggtcatgcacgaagccctgcac aaccactacacgcagaagtccctgtccttgagcccggggaaa |
| SEQ ID NO: 17 | LCDR1 (Combined) | RASQSITRNYLA |
| SEQ ID NO: 18 | LCDR2 (Combined) | GASSRAT |
| SEQ ID NO: 19 | LCDR3 (Combined) | QQHSMYPRT |
| SEQ ID NO: 17 | LCDR1 (Kabat) | RASQSITRNYLA |
| SEQ ID NO: 18 | LCDR2 (Kabat) | GASSRAT |

TABLE 2-continued

Exemplary anti-NPR1 antibody sequences

| SEQ ID NO: 19 | LCDR3 (Kabat) | QQHSMYPRT |
|---|---|---|
| SEQ ID NO: 20 | LCDR1 (Chothia) | SQSITRNY |
| SEQ ID NO: 21 | LCDR2 (Chothia) | GAS |
| SEQ ID NO: 22 | LCDR3 (Chothia) | HSMYPR |
| SEQ ID NO: 23 | LCDR1 (IMGT) | QSITRNY |
| SEQ ID NO: 21 | LCDR2 (IMGT) | GAS |
| SEQ ID NO: 19 | LCDR3 (IMGT) | QQHSMYPRT |
| SEQ ID NO: 24 | VL | DIVLTQSPATLSLSPGERATLSCRASQSITRNYLAWYQQKPGQAPRLLIYGA<br>SSRATGIPARFSGSGSGTDFTLTISSLEPEDFAVYYCQQHSMYPRTFGQGTK<br>VEIK |
| SEQ ID NO: 110 | DNA VL | gacatcgtgctgactcagtcccctgcgactctgagcctgtcaccgggagaacgggccaccctctcttgc<br>cgcgcctcccaatccattactcggaactacctggcctggtatcagcagaagccaggacaggcccctagg<br>cttctgatctacggggccagctcaagagcaactggcatcccggctcgcttctccggttcgggaagcggc<br>accgacttcaccctgacaatttcgtccctcgaacccgaggatttcgccgtgtactactgccaacagcac<br>tccatgtaccccgaccctttgggcagggaaccaaagtcgagatcaag |
| SEQ ID NO: 26 | Light Chain | DIVLTQSPATLSLSPGERATLSCRASQSITRNYLAWYQQKPGQAPRLLIYGA<br>SSRATGIPARFSGSGSGTDFTLTISSLEPEDFAVYYCQQHSMYPRTFGQGTK<br>VEIKRTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGLSSPV<br>TKSFNRGEC |
| SEQ ID NO: 111 | DNA Light Chain | gacatcgtgctgactcagtcccctgcgactctgagcctgtcaccgggagaacgggccaccctctcttgc<br>cgcgcctcccaatccattactcggaactacctggcctggtatcagcagaagccaggacaggcccctagg<br>cttctgatctacggggccagctcaagagcaactggcatcccggctcgcttctccggttcgggaagcggc<br>accgacttcaccctgacaatttcgtccctcgaacccgaggatttcgccgtgtactactgccaacagcac<br>tccatgtaccccgaccctttgggcagggaaccaaagtcgagatcaagcgtacggtggccgctcccagc<br>gtgttcatcttccccccagcgacgagcagctgaagagcggcaccgccagcgtggtgtgcctgctgaac<br>aacttctaccccgggaggccaaggtgcagtggaaggtggacaacgccctgcagagcggcaacagccag<br>gagagcgtcaccgagcaggacagcaaggactccacctacagcctgagcagcaccctgaccctgagcaag<br>gccgactacgagaagcataaggtgtacgcctgcgaggtgaccccaccagggcctgtccagcccgtgacc<br>aagagcttcaacagggggcgagtgc |
| XX08_N30S_DAPA | | |
| SEQ ID NO: 112 | HCDR1 (Combined) | GFTFSTHYIH |
| SEQ ID NO: 151 | HCDR2 (Combined) | SIGGQGGMTLYADSVKG |
| SEQ ID NO: 6 | HCDR3 (Combined) | ERGYVYYHMFDP |
| SEQ ID NO: 7 | HCDR1 (Kabat) | THYIH |
| SEQ ID NO: 151 | HCDR2 (Kabat) | SIGGQGGMTLYADSVKG |
| SEQ ID NO: 6 | HCDR3 (Kabat) | ERGYVYYHMFDP |
| SEQ ID NO: 113 | HCDR1 (Chothia) | GFTFSTH |
| SEQ ID NO: 152 | HCDR2 (Chothia) | GGQGGM |
| SEQ ID NO: 6 | HCDR3 (Chothia) | ERGYVYYHMFDP |
| SEQ ID NO: 114 | HCDR1 (IMGT) | GFTFSTHY |
| SEQ ID NO: 153 | HCDR2 (IMGT) | IGGQGGMT |
| SEQ ID NO: 12 | HCDR3 (IMGT) | ARERGYVYYHMFDP |
| SEQ ID NO: 161 | VH | EVQLLESGGGLVQPGGSLRLSCAASGFTFSTHYIHWVRQAPGKGLEWVSSI<br>GGQGGMTLYADSVKGRFTISRDNSKNTLYLQMNSLRAEDTAVYYCARER<br>GYVYYHMFDPWGQGTLVTVSS |
| SEQ ID NO: 162 | DNA VH | gaagtgcagctcctggagtcggtggcggactggtgcagcctggcggatcactgcggctgtcatgtgcc<br>gcgagcggggtttactttctccaccactacatccactgggtccgcaagctcccggaaagggactgaa<br>tgggtgtcctccattggacagggcggcatgaccctttacgcggatagcgtgaagggaggttcacc<br>atctcccgcgacaacagcaagaacaccctgtacctccaaatgaactcgcttcgggccgaggacactgcc<br>gtgtactattgcgcaagagagcggggctacgtgtactaccacatgttcgaccctggggacagggaacg<br>ctggtcaccgtgtcctcc |

TABLE 2-continued

Exemplary anti-NPR1 antibody sequences

| SEQ ID NO: 163 | Heavy Chain | EVQLLESGGGLVQPGGSLRLSCAASGFTFSTHYIHWVRQAPGKGLEWVSSI<br>GGQGGMTLYADSVKGRFTISRDNSKNTLYLQMNSLRAEDTAVYYCARER<br>GYVYYHMFDPWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQTY<br>ICNVNHKPSNTKVDKRVEPKSCDKTHTCPPCPAPELLGGPSVFLFPPKPKDT<br>LMISRTPEVTCVVVAVSHEDPEVKFNWYVDGVEVHNAKTKPREEQYNSTY<br>RVVSVLTVLHQDWLNGKEYKCKVSNKALAAPIEKTISKAKGQPREPQVYT<br>LPPSREEMTKNQVSLTCLVKGFYPSDIAVEWESNGQPENNYKTTPPVLDSD<br>GSFFLYSKLTVDKSRWQQGNVFSCSVMHEALHNHYTQKSLSLSPGK |
|---|---|---|
| SEQ ID NO: 164 | DNA Heavy Chain | gaagtgcagctcctggagtcgggtggcggactggtgcagcctggcggatcactgcggctgtcatgtgcc<br>gcgagcgggttttactttctccacccactacatccactgggtccgccaagctcccggaaagggactcgaa<br>tgggtgtcctccattggtggacagggcggcatgacccttacgcggatagcgtgaagggaggttcacc<br>atctcccgcgacaacagcaagaacaccctgtacctccaaatgaactcgcttcgggccgaggacactgcc<br>gtgtactattgcgcaagagagcgggggtacgtgtactaccacatgttcgacccatggggacagggaacg<br>ctggtcaccgtgtcctccgcctccactaagggcccgtcagtgttcccgctggctccatcgtcgaagtcc<br>acctccggaggaaccgcagcactcggttgcctggtcaaggactacttccctgagccagtgaccgtgtcg<br>tggaacagcggagccctgacttccggcgtgcacacttttcccgcggtgctgcagtcctccggtctgtac<br>tccctttcgtccgtggtcaccgtgccgtccttcagcctgggcaacagaccctacatctgcaacgtgaac<br>cacaagccgtccaacaccaaagtggataagcgggtggagccgaagtcctgcgataagacacacacgtgc<br>ccgccatgtccagcgcctgaattgcttggcggaccttccgtgttcctgttcccgcctaagcccaaggac<br>accttgatgattagccggactcccgaagtcacctgtgtggtggtggcagtgtcccacgaggaccccgag<br>gtcaagtttaattggtacgtggacggcgtcgaagtgcacaacgccaagactaagcccccggaggaacag<br>tacaacagcacctaccgggtcgtgtccgtgctgaccgtgctgcaccaggactggctgaatgggaaagag<br>tacaagtgcaaagtgtccaacaaggccttggccgctcctatcgaaaaaactatcagcaaggctaaggga<br>cagccgagggaaccccaagtctacaccctgccccttcacgcgaagagatgaccaagaatcaagtgtcg<br>ctgacctgcctcgtcaaggggattctaccctccgacattgcggtggagtgggagtccaacggccagccc<br>gagaacaactacaagactactccgcccgtgctggactccgacggcagcttcttcctgtattccaagctg<br>accgtggacaagtcccggtggcagcaaggaaacgtgttctcctgctcggtcatgcacgaagccctgcac<br>aaccactatacgcagaagtccctgtccttgagcccggggaaa |
| SEQ ID NO: 17 | LCDR1 (Combined) | RASQSITRNYLA |
| SEQ ID NO: 18 | LCDR2 (Combined) | GASSRAT |
| SEQ ID NO: 19 | LCDR3 (Combined) | QQHSMYPRT |
| SEQ ID NO: 17 | LCDR1 (Kabat) | RASQSITRNYLA |
| SEQ ID NO: 18 | LCDR2 (Kabat) | GASSRAT |
| SEQ ID NO: 19 | LCDR3 (Kabat) | QQHSMYPRT |
| SEQ ID NO: 20 | LCDR1 (Chothia) | SQSITRNY |
| SEQ ID NO: 21 | LCDR2 (Chothia) | GAS |
| SEQ ID NO: 22 | LCDR3 (Chothia) | HSMYPR |
| SEQ ID NO: 23 | LCDR1 (IMGT) | QSITRNY |
| SEQ ID NO: 21 | LCDR2 (IMGT) | GAS |
| SEQ ID NO: 19 | LCDR3 (IMGT) | QQHSMYPRT |
| SEQ ID NO: 24 | VL | DIVLTQSPATLSLSPGERATLSCRASQSITRNYLAWYQQKPGQAPRLLIYGA<br>SSRATGIPARFSGSGSGTDFTLTISSLEPEDFAVYYCQQHSMYPRTFGQGTK<br>VEIK |
| SEQ ID NO: 110 | DNA VL | gacatcgtgctgactcagtcccctgcgactctgagcctgtcaccgggagaacgggccaccctctcttgc<br>cgcgcctcccaatcattactcggaactacctggcctggtatcagcagaagccaggacaggccccctagg<br>cttctgatctacggggccagctcaagagcaactggcatcccggctcgcttctccggttcgggaagcggc<br>accgacttcaccctgacaatttcgtccctcgaacccgaggatttcgccgtgtactactgccaacagcac<br>tccatgtaccccgacctttgggcagggaaccaaagtcgagatcaag |
| SEQ ID NO: 26 | Light Chain | DIVLTQSPATLSLSPGERATLSCRASQSITRNYLAWYQQKPGQAPRLLIYGA<br>SSRATGIPARFSGSGSGTDFTLTISSLEPEDFAVYYCQQHSMYPRTFGQGTK<br>VEIKRTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGLSSPV<br>TKSFNRGEC |
| SEQ ID NO: 111 | DNA Light Chain | gacatcgtgctgactcagtcccctgcgactctgagcctgtcaccgggagaacgggccaccctctcttgc<br>cgcgcctcccaatcattactcggaactacctggcctggtatcagcagaagccaggacaggccccctagg<br>cttctgatctacggggccagctcaagagcaactggcatcccggctcgcttctccggttcgggaagcggc<br>accgacttcaccctgacaatttcgtccctcgaacccgaggatttcgccgtgtactactgccaacagcac<br>tccatgtaccccgacctttgggcagggaaccaaagtcgagatcaagcgtacggtggccgctcccagc<br>gtgttcatcttccccccagcgacgagcagctgaagagcggcaccgcagcgtggtgtgcctgctgaac<br>aacttctaccccgggaggccaaggtgcagtggaaggtggacaacgccctgcagagcggcaacagccag |

TABLE 2-continued

Exemplary anti-NPR1 antibody sequences gagagcgtcaccgagcaggacagcaaggactccacctacagcctgagcagcaccctgaccctgagcaag
gccgactacgagaagcataaggtgtacgcctgcgaggtgacccaccagggcctgtccagcccgtgacc
aagagcttcaacaggggcgagtgc

XX08_N30Q_DAPA

| SEQ ID NO: 165 | HCDR1 (Combined) | GFTFQTHYIH |
|---|---|---|
| SEQ ID NO: 151 | HCDR2 (Combined) | SIGGQGGMTLYADSVKG |
| SEQ ID NO: 6 | HCDR3 (Combined) | ERGYVYYHMFDP |
| SEQ ID NO: 7 | HCDR1 (Kabat) | THYIH |
| SEQ ID NO: 151 | HCDR2 (Kabat) | SIGGQGGMTLYADSVKG |
| SEQ ID NO: 6 | HCDR3 (Kabat) | ERGYVYYHMFDP |
| SEQ ID NO: 166 | HCDR1 (Chothia) | GFTFQTH |
| SEQ ID NO: 152 | HCDR2 (Chothia) | GGQGGM |
| SEQ ID NO: 6 | HCDR3 (Chothia) | ERGYVYYHMFDP |
| SEQ ID NO: 167 | HCDR1 (IMGT) | GFTFQTHY |
| SEQ ID NO: 153 | HCDR2 (IMGT) | IGGQGGMT |
| SEQ ID NO: 12 | HCDR3 (IMGT) | ARERGYVYYHMFDP |
| SEQ ID NO: 168 | VH | EVQLLESGGGLVQPGGSLRLSCAASGFTFQTHYIHWVRQAPGKGLEWVSSI<br>GGQGGMTLYADSVKGRFTISRDNSKNTLYLQMNSLRAEDTAVYYCARER<br>GYVYYHMFDPWGQGTLVTVSS |
| SEQ ID NO: 169 | DNA VH | gaagtgcagctcctggagtcgggtggcggactggtgcagcctggcggatcactgcggctgtcatgtgcc<br>gcgagcgggtttactttccagacccactacatccactgggtccgccaagctcccggaaagggactcgaa<br>tgggtgtcctccattggtggacagggcggcatgacccttacgcggatagcgtgaagggaggttcacc<br>atctcccgcgacaacagcaagaacaccctgtacctccaaatgaactcgcttcgggccgaggacactgcc<br>gtgtactattgcgcaagagagcgggggctacgtgtactaccacatgttcgacccatggggacagggaacg<br>ctggtcaccgtgtcctcc |
| SEQ ID NO: 170 | Heavy Chain | EVQLLESGGGLVQPGGSLRLSCAASGFTFQTHYIHWVRQAPGKGLEWVSSI<br>GGQGGMTLYADSVKGRFTISRDNSKNTLYLQMNSLRAEDTAVYYCARER<br>GYVYYHMFDPWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQTY<br>ICNVNHKPSNTKVDKRVEPKSCDKTHTCPPCPAPELLGGPSVFLFPPKPKDT<br>LMISRTPEVTCVVVAVSHEDPEVKFNWYVDGVEVHNAKTKPREEQYNSTY<br>RVVSVLTVLHQDWLNGKEYKCKVSNKALAAPIEKTISKAKGQPREPQVYT<br>LPPSREEMTKNQVSLTCLVKGFYPSDIAVEWESNGQPENNYKTTPPVLDSD<br>GSFFLYSKLTVDKSRWQQGNVFSCSVMHEALHNHYTQKSLSLSPGK |
| SEQ ID NO: 171 | DNA Heavy Chain | gaagtgcagctcctggagtcgggtggcggactggtgcagcctggcggatcactgcggctgtcatgtgcc<br>gcgagcgggtttactttccagacccactacatccactgggtccgccaagctcccggaaagggactcgaa<br>tgggtgtcctccattggtggacagggcggcatgacccttacgcggatagcgtgaagggaggttcacc<br>atctcccgcgacaacagcaagaacaccctgtacctccaaatgaactcgcttcgggccgaggacactgcc<br>gtgtactattgcgcaagagagcgggggctacgtgtactaccacatgttcgacccatggggacagggaacg<br>ctggtcaccgtgtcctccgcctcactaagggccgtcagtgttcccgctgctcccatcgtcgaagtcc<br>acctccggaggaaccgcagcactcggttgcctggtcaaggactacttccctgagccagtgaccgtgtcg<br>tggaacagcggagccctgacttccggcgtgcacacttttcccgcggtgctgcagtcctccggtctgtac<br>tcccttcgtccgtggtcaccgtgccgtcgtctagcctgggcacccagacctacatctgcaacgtgaac<br>cacaagccgtccaacaccaaagtggataagcgggtggagcccaagtcctgcgataagacacacacgtgc<br>ccgccatgtccagcgcctgaattgcttggcggaccttccgtgttcctgttccccgcctaagcccaaggac<br>accttgatgattagccggactcccgaagtcacctgtgtggtggtggcagtgtcccacgaggaccccgag<br>gtcaagtttaattggtacgtggacggcgtcgaagtgcacaacgccaagactaagcccgggaggaacag<br>tacaacagcacctacgggtcgtccgtgctgaccgtgctgcaccaggactggctgaatgggaagaag<br>tacaagtgcaaagtgtccaacaaggccttggccgctcctatcgaaaaaactatcagcaaggctaaggga<br>cagccgagggaaccccaagtctacaccctgccccttcacgcgaagagatgaccaagaatcaagtgtcg<br>ctgacctgcctcgtcaagggattctaccccctccgacattgcggtggagtgggagtccaacggccagccc<br>gagaacaactacaagactactccgcccgtgctggactccgacggcagcttcttcctgtattccaagctg<br>accgtggacaagtccggtggcagcaaggaaacgtgttctcctgctcggtcatgcacgaagccctgcac<br>aaccactatacgcagaagtccctgtccttgagcccggggaaa |
| SEQ ID NO: 17 | LCDR1 (Combined) | RASQSITRNYLA |
| SEQ ID NO: 18 | LCDR2 (Combined) | GASSRAT |
| SEQ ID NO: 19 | LCDR3 (Combined) | QQHSMYPRT |

TABLE 2-continued

Exemplary anti-NPR1 antibody sequences

| SEQ ID NO: 17 | LCDR1 (Kabat) | RASQSITRNYLA |
| --- | --- | --- |
| SEQ ID NO: 18 | LCDR2 (Kabat) | GASSRAT |
| SEQ ID NO: 19 | LCDR3 (Kabat) | QQHSMYPRT |
| SEQ ID NO: 20 | LCDR1 (Chothia) | SQSITRNY |
| SEQ ID NO: 21 | LCDR2 (Chothia) | GAS |
| SEQ ID NO: 22 | LCDR3 (Chothia) | HSMYPR |
| SEQ ID NO: 23 | LCDR1 (IMGT) | QSITRNY |
| SEQ ID NO: 21 | LCDR2 (IMGT) | GAS |
| SEQ ID NO: 19 | LCDR3 (IMGT) | QQHSMYPRT |
| SEQ ID NO: 24 | VL | DIVLTQSPATLSLSPGERATLSCRASQSITRNYLAWYQQKPGQAPRLLIYGA SSRATGIPARFSGSGSGTDFTLTISSLEPEDFAVYYCQQHSMYPRTFGQGTK VEIK |
| SEQ ID NO: 110 | DNA VL | gacatcgtgctgactcagtccctgcgactctgagcctgtcaccgggagaacgggccaccctctcttgc cgcgcctcccaatccattactcggaactacctggcctggtatcagcagaagccaggacaggcccctagg cttctgatctacggggccagctcaagagcaactggcatcccggctcgcttctccggttcgggaagcggc accgacttcaccctgacaatttcgtccctcgaacccgaggatttcgccgtgtactactgccaacagcac tccatgtaccccgaccctttgggcagggaaccaaagtcgagatcaag |
| SEQ ID NO: 26 | Light Chain | DIVLTQSPATLSLSPGERATLSCRASQSITRNYLAWYQQKPGQAPRLLIYGA SSRATGIPARFSGSGSGTDFTLTISSLEPEDFAVYYCQQHSMYPRTFGQGTK VEIKRTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPV TKSFNRGEC |
| SEQ ID NO: 111 | DNA Light Chain | gacatcgtgctgactcagtccctgcgactctgagcctgtcaccgggagaacgggccaccctctcttgc cgcgcctcccaatccattactcggaactacctggcctggtatcagcagaagccaggacaggcccctagg cttctgatctacggggccagctcaagagcaactggcatcccggctcgcttctccggttcgggaagcggc accgacttcaccctgacaatttcgtccctcgaacccgaggatttcgccgtgtactactgccaacagcac tccatgtaccccgaccctttgggcagggaaccaaagtcgagatcaagcgtacggtggccgctcccagc gtgttcatcttccccccagccgacgagcagctgaagagcggcaccgcgtggtgtgcctgctgaac aacttctaccccgggaggccaaggtgcagtggaaggtggacaacgccctgcagagcggcaacagccag gagagcgtcaccgagcaggacagcaaggactccacctacagcctgagcagcaccctgaccctgagcaag gccgactacgagaagcataaggtgtacgcctgcgaggtgaccccaccagggcctgtccagcccgtgacc aagagcttcaacaggggcgagtgc |

XX09_LALA

| SEQ ID NO: 28 | HCDR1 (Combined) | GFTFSSYWMN |
| --- | --- | --- |
| SEQ ID NO: 29 | HCDR2 (Combined) | AISSDGSYTYYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 29 | HCDR2 (Kabat) | AISSDGSYTYYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 33 | HCDR2 (Chothia) | SSDGSY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 35 | HCDR2 (IMGT) | ISSDGSYT |
| SEQ ID NO: 36 | HCDR3 (IMGT) | ARDRYSMIYSYGAGAFDY |
| SEQ ID NO: 37 | VH | QVQLLESGGGLVQPGGSLRLSCAASGFTFSSYWMNWVRQAPGKGLEWVS AISSDGSYTYYADSVKGRFTISRDNSKNTLYLQMNSLRAEDTAVYYCARD RYSMIYSYGAGAFDYWGQGTLVTVSS |
| SEQ ID NO: 38 | DNA VH | caggtgcaattgctggaaagcggcggtggcctggtgcagccgggtggcagcctgcgtctgagctgcgcg gcgtccggattcacctttttcttcttactggatgaactgggtgcgccaggcccgggcaaaggtctcgag tgggtttccgctatctcttctgacggttcttacacctactatgcggatagcgtgaaaggccgcttacc |

TABLE 2-continued

Exemplary anti-NPR1 antibody sequences

| | | |
|---|---|---|
| | | atcagccgcgataattcgaaaaacaccctgtatctgcaaatgaacagcctgcgtgcggaagatacggcc gtgtattattgcgcgcgtgaccgttactctatgatctactcttacggtgctggtgctttcgattactgg ggccaaggcaccctggtgactgttagctca |
| SEQ ID NO: 39 | Heavy Chain | QVQLLESGGGLVQPGGSLRLSCAASGFTFSSYWMNWVRQAPGKGLEWVS AISSDGSYTYYADSVKGRFTISRDNSKNTLYLQMNSLRAEDTAVYYCARD RYSMIYSYGAGAFDYWGQGTLVTVSSASTKGPSVFPLAPSSKSTSGGTAAL GCLVKDYFPEPVTVSWNSGALTSGVHTFPAVLQSSGLYSLSSVVTVPSSSL GTQTYICNVNHKPSNTKVDKRVEPKSCDKTHTCPPCPAPEAAGGPSVFLFP PKPKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKTTP PVLDSDGSFFLYSKLTVDKSRWQQGNVFSCSVMHEALHNHYTQKSLSLSP GK |
| SEQ ID NO: 40 | DNA Heavy Chain | caggtgcaattgctggaaagcggcggtggcctggtgcagccgggtggcagcctgcgtctgagctgcgcg gcgtccggattcacctttttcttcttactggatgaactgggtgcgccaggcccgggcaaaggtctcgag tgggtttccgctatctcttctgacggttcttacacctactatgcggatagcgtgaaaggccgctttacc atcagccgcgataattcgaaaaacaccctgtatctgcaaatgaacagcctgcgtgcggaagatacggcc gtgtattattgcgcgcgtgaccgttactctatgatctactcttacggtgctggtgctttcgattactgg ggccaaggcaccctggtgactgttagctcagcctccaccaagggtccatcggtcttccccctggcaccc tcctccaagagcacctctgggggcacagcggccctgggctgcctggtcaaggactacttccccgaaccg gtgacggtgtcgtggaactcaggcgccctgaccagcggcgtgcacaccttcccggctgtcctacagtcc tcaggactctactccctcagcagcgtggtgaccgtgccctccagcagcttgggcacccagacctacatc tgcaacgtgaatcacaagcccagcaacaccaaggtggacaagagagttgagcccaaatcttgtgacaaa actcacacatgcccaccgtgcccagcacctgaagcagcggggggaccgtcagtcttcctcttccccccca aaacccaaggacaccctcatgatctcccggacccctgaggtcacatgcgtggtggtggacgtgagccac gaagaccctgaggtcaagttcaactggtacgtggacggcgtggaggtgcataatgccaagacaaagccg cgggaggagcagtacaacagcacgtaccgggtggtcagcgtcctcaccgtcctgcaccaggactggctg aatggcaaggagtacaagtgcaaggtctccaacaaagcccctcccagccccatcgagaaaaccatctcc aaagccaaagggcagccccgagaaccacaggtgtacaccctgcccccatcccgggaggagatgaccaag aaccaggtcagcctgacctgcctggtcaaaggcttctatcccagcgacatcgccgtggagtgggagagc aatgggcagccggagaacaactacaagaccacgcctcccgtgctggactccgacggctccttcttcctc tacagcaagctcaccgtggacaagagcaggtggcagcaggggaacgtcttctcatgctccgtgatgcat gaggctctgcacaaccactacacgcagaagagcctctccctgtctccgggtaaa |
| SEQ ID NO: 41 | LCDR1 (Combined) | RASQGISSYLA |
| SEQ ID NO: 42 | LCDR2 (Combined) | TASTLQS |
| SEQ ID NO: 172 | LCDR3 (Combined) | QQEWAKPRT |
| SEQ ID NO: 41 | LCDR1 (Kabat) | RASQGISSYLA |
| SEQ ID NO: 42 | LCDR2 (Kabat) | TASTLQS |
| SEQ ID NO: 172 | LCDR3 (Kabat) | QQEWAKPRT |
| SEQ ID NO: 44 | LCDR1 (Chothia) | SQGISSY |
| SEQ ID NO: 45 | LCDR2 (Chothia) | TAS |
| SEQ ID NO: 173 | LCDR3 (Chothia) | EWAKPR |
| SEQ ID NO: 47 | LCDR1 (IMGT) | QGISSY |
| SEQ ID NO: 45 | LCDR2 (IMGT) | TAS |
| SEQ ID NO: 172 | LCDR3 (IMGT) | QQEWAKPRT |
| SEQ ID NO: 174 | VL | DIQMTQSPSSLSASVGDRVTITCRASQGISSYLAWYQQKPGKAPKLLIYTAS TLQSGVPSRFSGSGSGTDFTLTISSLQPEDFATYYCQQEWAKPRTFGQGTKV EIK |
| SEQ ID NO: 175 | DNA VL | gatatccagatgacccagagcccgagcagcctgagcgccagcgtgggcgatcgcgtgaccattacctgc agagccagccagggtatttcttcttacctggcttggtaccagcagaaaccgggcaaagcgccgaaacta ttaatctacactgcttctactctgcaaagcggcgtgccgagccgctttagcggcagcggatccggcacc gatttcaccctgaccattagctctctgcaaccggaagactttgcgacctattattgccagcaggaatgg gctaaaccgcgtaccctttggccagggcacgaaagttgaaattaaa |
| SEQ ID NO: 176 | Light Chain | DIQMTQSPSSLSASVGDRVTITCRASQGISSYLAWYQQKPGKAPKLLIYTAS TLQSGVPSRFSGSGSGTDFTLTISSLQPEDFATYYCQQEWAKPRTFGQGTKV EIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVT KSFNRGEC |
| SEQ ID NO: 177 | DNA Light Chain | gatatccagatgacccagagcccgagcagcctgagcgccagcgtgggcgatcgcgtgaccattacctgc agagccagccagggtatttcttcttacctggcttggtaccagcagaaaccgggcaaagcgccgaaacta |

TABLE 2-continued

Exemplary anti-NPR1 antibody sequences

```
ttaatctacactgcttctactctgcaaagcggcgtgccgagccgctttagcggcagcggatccggcacc
gatttcaccctgaccattagctctctgcaaccggaagactttgcgacctattattgccagcaggaatgg
gctaaaccgcgtacctttggccagggcacgaaagttgaaattaaacgtacggtggccgctcccagcgtg
ttcatcttcccccccagcgacgagcagctgaagagcggcaccgcgcagcgtggtgtgcctgctgaacaac
ttctaccccggggaggccaaggtgcagtgaaggtggacaacgccctgcagagcggcaacagccaggaa
agcgtcaccgagcaggacagcaaggactccacctacagcctgagcagcaccctgaccctgagcaaggcc
gactacgagaagcacaaggtgtacgcctgcgaggtgacccaccagggcctgtccagcccgtgaccaag
agcttcaaccggggcgagtgt
```

XX11_LALA

| SEQ ID NO: 28 | HCDR1 (Combined) | GFTFSSYWMN |
|---|---|---|
| SEQ ID NO: 29 | HCDR2 (Combined) | AISSDGSYTYYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 29 | HCDR2 (Kabat) | AISSDGSYTYYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 33 | HCDR2 (Chothia) | SSDGSY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 35 | HCDR2 (IMGT) | ISSDGSYT |
| SEQ ID NO: 36 | HCDR3 (IMGT) | ARDRYSMIYSYGAGAFDY |
| SEQ ID NO: 37 | VH | QVQLLESGGGLVQPGGSLRLSCAASGFTFSSYWMNWVRQAPGKGLEWVS<br>AISSDGSYTYYADSVKGRFTISRDNSKNTLYLQMNSLRAEDTAVYYCARD<br>RYSMIYSYGAGAFDYWGQGTLVTVSS |
| SEQ ID NO: 38 | DNA VH | caggtgcaattgctggaaagcggcggtggcctggtgcagccgggtggcagcctgcgtctgagctgcgcg<br>gcgtccggattcaccttttcttcttactggatgaactgggtgcgccaggcccccgggcaaaggtctcgag<br>tgggtttccgctatctcttctgacggttcttacacctactatgcggatagcgtgaaaggccgctttacc<br>atcagccgcgataattcgaaaaacaccctgtatctgcaaatgaacagcctgcgtgcggaagatacggcc<br>gtgtattattgcgcgcgtgaccgttactctatgatctactcttacggtgctggtgctttcgattactgg<br>ggccaaggcaccctggtgactgttagctca |
| SEQ ID NO: 39 | Heavy Chain | QVQLLESGGGLVQPGGSLRLSCAASGFTFSSYWMNWVRQAPGKGLEWVS<br>AISSDGSYTYYADSVKGRFTISRDNSKNTLYLQMNSLRAEDTAVYYCARD<br>RYSMIYSYGAGAFDYWGQGTLVTVSSASTKGPSVFPLAPSSKSTSGGTAAL<br>GCLVKDYFPEPVTVSWNSGALTSGVHTFPAVLQSSGLYSLSSVVTVPSSSL<br>GTQTYICNVNHKPSNTKVDKRVEPKSCDKTHTCPPCPAPEAAGGPSVFLFP<br>PKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPR<br>EPQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSP<br>GK |
| SEQ ID NO: 40 | DNA Heavy Chain | caggtgcaattgctggaaagcggcggtggcctggtgcagccgggtggcagcctgcgtctgagctgcgcg<br>gcgtccggattcaccttttcttcttactggatgaactgggtgcgccaggcccccgggcaaaggtctcgag<br>tgggtttccgctatctcttctgacggttcttacacctactatgcggatagcgtgaaaggccgctttacc<br>atcagccgcgataattcgaaaaacaccctgtatctgcaaatgaacagcctgcgtgcggaagatacggcc<br>gtgtattattgcgcgcgtgaccgttactctatgatctactcttacggtgctggtgctttcgattactgg<br>ggccaaggcaccctggtgactgttagctcagcctccaccaagggtccatcggtcttccctggcaccc<br>tcctccaagagcacctctgggggcacagcggccctgggctgcctggtcaaggactacttccccgaaccg<br>gtgacggtgtcgtggaactcaggcgccctgaccagcggcgtgcacaccttcccggctgtcctacagtcc<br>tcaggactctactccctcagcagcggtgaccgtgccctccagcagcttgggcacccagacctacatc<br>tgcaacgtgaatcacaagcccagcaacaccaaggtggacaagagagttgagcccaaatcttgtgacaaa<br>actcacacatgcccaccgtgcccagcacctgaagcagcggggggaccgtcagtcttcctcttccccca<br>aaacccaaggacaccctcatgatctcccggacccctgaggtcacatgcgtggtggtggacgtgagccac<br>gaagaccctgaggtcaagttcaactggtacgtggacggcgtggaggtgcataatgccaagacaaagccg<br>cgggaggagcagtacaacagcacgtaccgggtggtcagcgtcctcaccgtcctgcaccaggactggctg<br>aatggcaaggagtacaagtgcaaggtctccaacaaagcccctcccagccccatcgagaaaaccatctcc<br>aaagccaaagggcagccccgagaaccacaggtgtacaccctgcccccatcccgggaggagatgaccaag<br>aaccaggtcagcctgacctgcctggtcaaaggcttctatcccagcgacatcgccgtggagtgggagagc<br>aatgggcagccggagaacaactacaagaccacgcctcccgtgctggactccgacggctccttcttcctc<br>tacagcaagctcaccgtggacaagagcaggtggcagcaggggaacgtcttctcatgctccgtgatgcat<br>gaggctctgcacaaccactacacgcagaagagcctctccctgtctccgggtaaa |

TABLE 2-continued

Exemplary anti-NPR1 antibody sequences

| | | |
|---|---|---|
| SEQ ID NO: 41 | LCDR1 (Combined) | RASQGISSYLA |
| SEQ ID NO: 42 | LCDR2 (Combined) | TASTLQS |
| SEQ ID NO: 178 | LCDR3 (Combined) | QQSWTRPRT |
| SEQ ID NO: 41 | LCDR1 (Kabat) | RASQGISSYLA |
| SEQ ID NO: 42 | LCDR2 (Kabat) | TASTLQS |
| SEQ ID NO: 178 | LCDR3 (Kabat) | QQSWTRPRT |
| SEQ ID NO: 44 | LCDR1 (Chothia) | SQGISSY |
| SEQ ID NO: 45 | LCDR2 (Chothia) | TAS |
| SEQ ID NO: 179 | LCDR3 (Chothia) | SWTRPR |
| SEQ ID NO: 47 | LCDR1 (IMGT) | QGISSY |
| SEQ ID NO: 45 | LCDR2 (IMGT) | TAS |
| SEQ ID NO: 178 | LCDR3 (IMGT) | QQSWTRPRT |
| SEQ ID NO: 180 | VL | DIQMTQSPSSLSASVGDRVTITCRASQGISSYLAWYQQKPGKAPKLLIYTAS<br>TLQSGVPSRFSGSGSGTDFTLTISSLQPEDFATYYCQQSWTRPRTFGQGTKV<br>EIK |
| SEQ ID NO: 181 | DNA VL | gatatccagatgacccagagcccgagcagcctgagcgccagcgtgggcgatcgcgtgaccattacctgc<br>agagccagccagggtatttcttcttacctggcttggtaccagcagaaaccgggcaaagcgccgaaacta<br>ttaatctacactgcttctactctgcaaagcggcgtgccgagccgctttagcggcagcggatccggcacc<br>gatttcaccctgaccattagctctctgcaaccggaagactttgcgacctattattgccagcagtcttgg<br>actcgtccgcgtacctttggccagggcacgaaagttgaaattaaa |
| SEQ ID NO: 182 | Light Chain | DIQMTQSPSSLSASVGDRVTITCRASQGISSYLAWYQQKPGKAPKLLIYTAS<br>TLQSGVPSRFSGSGSGTDFTLTISSLQPEDFATYYCQQSWTRPRTFGQGTKV<br>EIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVT<br>KSFNRGEC |
| SEQ ID NO: 183 | DNA Light Chain | Gatatccagatgacccagagcccgagcagcctgagcgccagcgtgggcgatcgcgtgaccattacctgc<br>agagccagccagggtatttcttcttacctggcttggtaccagcagaaaccgggcaaagcgccgaaacta<br>ttaatctacactgcttctactctgcaaagcggcgtgccgagccgctttagcggcagcggatccggcacc<br>gatttcaccctgaccattagctctctgcaaccggaagactttgcgacctattattgccagcagtcttgg<br>actcgtccgcgtacctttggccagggcacgaaagttgaaattaaacgtacggtggccgctcccagcgtg<br>ttcatcttccccccagcgacgagcagctgaaagcggcaccgccagcgtggtgtgcctgctgaacaac<br>ttctaccccgggaggccaaggtcagtggaaggtggacaacgccctgcagagcggcaacagccaggaa<br>agcgtcaccgagcaggacagcaaggactccacctacagcctgagcagcaccctgaccctgagcaaggcc<br>gactacgagaagcacaaggtgtacgcctgcgaggtgacccaccagggcctgtccagccccgtgaccaag<br>agcttcaaccggggcgagtgt |

XX12_LALA

| | | |
|---|---|---|
| SEQ ID NO: 28 | HCDR1 (Combined) | GFTFSSYWMN |
| SEQ ID NO: 29 | HCDR2 (Combined) | AISSDGSYTYYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 29 | HCDR2 (Kabat) | AISSDGSYTYYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 33 | HCDR2 (Chothia) | SSDGSY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 35 | HCDR2 (IMGT) | ISSDGSYT |
| SEQ ID NO: 36 | HCDR3 (IMGT) | ARDRYSMIYSYGAGAFDY |

TABLE 2-continued

Exemplary anti-NPR1 antibody sequences

| SEQ ID NO: 37 | VH | QVQLLESGGGLVQPGGSLRLSCAASGFTFSSYWMNWVRQAPGKGLEWVS
AISSDGSYTYYADSVKGRFTISRDNSKNTLYLQMNSLRAEDTAVYYCARD
RYSMIYSYGAGAFDYWGQGTLVTVSS |
|---|---|---|
| SEQ ID NO: 38 | DNA VH | caggtgcaattgctggaaagcggcggtggcctggtgcagccgggtggcagcctgcgtctgagctgcgcg
gcgtccggattcacctttcttcttactggatgaactgggtgcgccaggccccgggcaaaggtctcgag
tgggtttccgctatctcttctgacggttcttacacctactatgcggatagcgtgaaaggccgctttacc
atcagccgcgataattcgaaaaacacctgtatctgcaaatgaacagcctgcgtgcggaagatacggcc
gtgtattattgcgcgcgtgaccgttactctatgatctactcttacggtgctggtgctttcgattactgg
ggccaaggcaccctggtgactgttagctca |
| SEQ ID NO: 39 | Heavy Chain | QVQLLESGGGLVQPGGSLRLSCAASGFTFSSYWMNWVRQAPGKGLEWVS
AISSDGSYTYYADSVKGRFTISRDNSKNTLYLQMNSLRAEDTAVYYCARD
RYSMIYSYGAGAFDYWGQGTLVTVSSASTKGPSVFPLAPSSKSTSGGTAAL
GCLVKDYFPEPVTVSWNSGALTSGVHTFPAVLQSSGLYSLSSVVTVPSSSL
GTQTYICNVNHKPSNTKVDKRVEPKSCDKTHTCPPCPAPEAAGGPSVFLFP
PKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPR
EPQVYTLPPSREEMTKNQVSLTCLVKGFYPSDIAVEWESNGQPENNYKTTP
PVLDSDGSFFLYSKLTVDKSRWQQGNVFSCSVMHEALHNHYTQKSLSLSP
GK |
| SEQ ID NO: 40 | DNA Heavy Chain | caggtgcaattgctggaaagcggcggtggcctggtgcagccgggtggcagcctgcgtctgagctgcgcg
gcgtccggattcacctttcttcttactggatgaactgggtgcgccaggccccgggcaaaggtctcgag
tgggtttccgctatctcttctgacggttcttacacctactatgcggatagcgtgaaaggccgctttacc
atcagccgcgataattcgaaaaacacctgtatctgcaaatgaacagcctgcgtgcggaagatacggcc
gtgtattattgcgcgcgtgaccgttactctatgatctactcttacggtgctggtgctttcgattactgg
ggccaaggcaccctggtgactgttagctcagcctccaccaagggcccatcggtcttcccctggcaccc
tcctccaagagcacctctggggcacagcggccctgggctgcctggtcaaggactacttccccgaaccg
gtgacggtgtcgtggaactcaggcgccctgaccagcggcgtgcacaccttcccggctgtcctacagtcc
tcaggactctactccctcagcagcgtggtgaccgtgccctccagcagcttgggcacccagacctacatc
tgcaacgtgaatcacaagcccagcaacaccaaggtggacaagagagttgagcccaaatcttgtgacaaa
actcacacatgcccaccgtgcccagcacctgaagcagcggggggaccgtcagtcttcctcttccccca
aaacccaaggacaccctcatgatctcccggacccctgaggtcacatgcgtggtggtggacgtgagccac
gaagaccctgaggtcaagttcaactggtacgtggacggcgtggaggtgcataatgccaagacaaagccg
cgggaggagcagtacaacagcacgtaccgtgtggtcagcgtcctcaccgtcctgcaccaggactggctg
aatggcaaggagtacaagtgcaaggtctccaacaaagccctcccagcccccatcgagaaaaccatctcc
aaagccaaagggcagccccgagaaccacaggtgtacaccctgcccccatcccgggaggagatgaccaag
aaccaggtcagcctgacctgcctggtcaaaggcttctatcccagcgacatcgccgtggagtgggagagc
aatgggcagccggagaacaactacaagaccacgcctcccgtgctggactccgacggctccttcttcctc
tacagcaagctcaccgtggacaagagcaggtggcagcaggggaacgtcttctcatgctccgtgatgcat
gaggctctgcacaaccactacacgcagaagagcctctccctgtctccgggtaaa |
| SEQ ID NO: 41 | LCDR1 (Combined) | RASQGISSYLA |
| SEQ ID NO: 42 | LCDR2 (Combined) | TASTLQS |
| SEQ ID NO: 184 | LCDR3 (Combined) | QQIWMAPRT |
| SEQ ID NO: 41 | LCDR1 (Kabat) | RASQGISSYLA |
| SEQ ID NO: 42 | LCDR2 (Kabat) | TASTLQS |
| SEQ ID NO: 184 | LCDR3 (Kabat) | QQIWMAPRT |
| SEQ ID NO: 44 | LCDR1 (Chothia) | SQGISSY |
| SEQ ID NO: 45 | LCDR2 (Chothia) | TAS |
| SEQ ID NO: 185 | LCDR3 (Chothia) | IWMAPR |
| SEQ ID NO: 47 | LCDR1 (IMGT) | QGISSY |
| SEQ ID NO: 45 | LCDR2 (IMGT) | TAS |
| SEQ ID NO: 184 | LCDR3 (IMGT) | QQIWMAPRT |
| SEQ ID NO: 186 | VL | DIQMTQSPSSLSASVGDRVTITCRASQGISSYLAWYQQKPGKAPKLLIYTAS
TLQSGVPSRFSGSGSGTDFTLTISSLQPEDFATYYCQQIWMAPRTFGQGTKV
EIK |
| SEQ ID NO: 187 | DNA VL | gatatccagatgacccagagcccgagcagcctgagcgccagcgtgggcgatcgcgtgaccattacctgc
agagccagccagggtatttcttcttacctggcttggtaccagcagaaaccgggcaaagcgccgaaacta
ttaatctacactgcttctactctgcaaagcggcgtgccgagccgctttagcggcagcggatccggcacc
gatttcacccctgaccattagctctctgcaaccggaagactttgcgacctattattgccagcagatctgg
atggctccgcgtacctttggccagggcacgaaagttgaaattaaa |

TABLE 2-continued

Exemplary anti-NPR1 antibody sequences

| SEQ ID NO: 188 | Light Chain | DIQMTQSPSSLSASVGDRVTITCRASQGISSYLAWYQQKPGKAPKLLIYTAS<br>TLQSGVPSRFSGSGSGTDFTLTISSLQPEDFATYYCQQIWMAPRTFGQGTKV<br>EIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVT<br>KSFNRGEC |
| --- | --- | --- |
| SEQ ID NO: 189 | DNA Light Chain | gatatccagatgacccagagcccgagcagcctgagcgccagcgtgggcgatcgcgtgaccattacctgc<br>agagccagccagggtatttcttcttacctggcttggtaccagcagaaaccgggcaaagcgccgaaacta<br>ttaatctacactgcttctactctgcaaagcggcgtgccgagccgcttagcggcagcggatccggcacc<br>gatttcacccctgaccattagctctctgcaaccggaagactttgcgacctattattgccagcagatctgg<br>atggctccgcgtacctttggccagggcacgaaagtttgaaattaaacgtacggtggccgctcccagcgtg<br>ttcatcttcccccccagcgacgagcagctgaagagcggcaccgcccagcgtggtgtgcctgctgaacaac<br>ttctaccccggggaggccaaggtcagtgaaggtggacaacgccctgcagagcggcaacagccaggaa<br>agcgtcaccgagcaggacagcaaggactccacctacagcctgagcagcaccctgaccctgagcaaggcc<br>gactacgagaagcacaaggtgtacgcctgcgaggtgacccaccagggcctgtccagccccgtgaccaag<br>agcttcaaccggggcgagtgt |

XX13_LALA

| SEQ ID NO: 28 | HCDR1 (Combined) | GFTFSSYWMN |
| --- | --- | --- |
| SEQ ID NO: 190 | HCDR2 (Combined) | AISSKGSYTYYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 190 | HCDR2 (Kabat) | AISSKGSYTYYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 191 | HCDR2 (Chothia) | SSKGSY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 192 | HCDR2 (IMGT) | ISSKGSYT |
| SEQ ID NO: 36 | HCDR3 (IMGT) | ARDRYSMIYSYGAGAFDY |
| SEQ ID NO: 193 | VH | QVQLLESGGGLVQPGGSLRLSCAASGFTFSSYWMNWVRQAPGKGLEWVS<br>AISSKGSYTYYADSVKGRFTISRDNSKNTLYLQMNSLRAEDTAVYYCARD<br>RYSMIYSYGAGAFDYWGQGTLVTVSS |
| SEQ ID NO: 194 | DNA VH | caagttcagctccttgagtctgggggggcctggtgcaacctgggggctctctgcggctttcatgtgcg<br>gcctcagggttcactttcagctcatactggatgaattgggtacgccaagctccaggcaaaggactcgaa<br>tgggtaagcgctatatccagcaaagggagctataccattacgcggattccgttaagggcaggttcact<br>atatcccgcgacaactccaaaaatactttgtatctgcaaatgaattccctccgagccgaagataccgca<br>gtatattactgtgcgagggacaggtactccatgatttacagctacggtgccggtgctttcgattattgg<br>ggacaggggacacttgtgaccgtcagttct |
| SEQ ID NO: 195 | Heavy Chain | QVQLLESGGGLVQPGGSLRLSCAASGFTFSSYWMNWVRQAPGKGLEWVS<br>AISSKGSYTYYADSVKGRFTISRDNSKNTLYLQMNSLRAEDTAVYYCARD<br>RYSMIYSYGAGAFDYWGQGTLVTVSSASTKGPSVFPLAPSSKSTSGGTAAL<br>GCLVKDYFPEPVTVSWNSGALTSGVHTFPAVLQSSGLYSLSSVVTVPSSSL<br>GTQTYICNVNHKPSNTKVDKRVEPKSCDKTHTCPPCPAPEAAGGPSVFLFP<br>PKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPR<br>EPQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSP<br>GK |
| SEQ ID NO: 196 | DNA Heavy Chain | caagttcagctccttgagtctgggggggcctggtgcaacctgggggctctctgcggctttcatgtgcg<br>gcctcagggttcactttcagctcatactggatgaattgggtacgccaagctccaggcaaaggactcgaa<br>tgggtaagcgctatatccagcaaagggagctataccattacgcggattccgttaagggcaggttcact<br>atatcccgcgacaactccaaaaatactttgtatctgcaaatgaattccctccgagccgaagataccgca<br>gtatattactgtgcgagggacaggtactccatgatttacagctacggtgccggtgctttcgattattgg<br>ggacaggggacacttgtgaccgtcagtctgcaagtaccaaaggcccgtctgttttccattggctccc<br>tcatccaagagcacgagtggaggcaccgccgcgctgggatgcttgtgaaagactatttcccggagccc<br>gtgaccgttagctgaacagcggcgctcttaccagtggcgttcacattcacagttcccagctgtttgcagtg<br>tccgggctctactctctctcatccgtcgtcaccgtgccgtctagttcttgggcacccagaccttactc<br>tgtaacgtaaatcacaaacctgtaatactaaggtggacaagagagttgaaccgaagagctgtgataag<br>acacatacttgtccaccatgtccggcacccgaggcagcggggggcccagtgttttctcttcccaccc<br>aagcccaaagacacattgatgatctcacgaaccccagaggtaacttgtgtcgtggtagatgtaagccat<br>gaggaccccgaagttaagttcaattggtatgttgacggtgtagaggtgcacaatgccaaaactaaaccc |

TABLE 2-continued

Exemplary anti-NPR1 antibody sequences

| | | |
|---|---|---|
| | | cgggaggagcaatacaactcaacttacagagtcgtatccgtgctgaccgttttgcaccaggattggttg<br>aatggtaaggaatacaaatgtaaagtgagcaataaagctctcccagcgcccatcgagaagaccattagc<br>aaagccaagggtcaacccagggaacccccaggtatatacgctgccaccctcaaggggaagagatgacaaag<br>aatcaagtgtcactgacgtgtcttgtcaagggtttctatcctagcgacattgcggtggaatgggagtca<br>aatgggcaacccgagaacaactacaagactactcctcccgtcctggacagcgacggctccttcttcctg<br>tatagtaaactgaccgtcgataaagtaggtggcagcaggggaatgtctttagttgctctgtcatgcat<br>gaggcgctccataaccactacacccaaaaatctttgagcttgagccctgggaaa |
| SEQ ID NO: 41 | LCDR1 (Combined) | RASQGISSYLA |
| SEQ ID NO: 42 | LCDR2 (Combined) | TASTLQS |
| SEQ ID NO: 134 | LCDR3 (Combined) | QQTWRKPRT |
| SEQ ID NO: 41 | LCDR1 (Kabat) | RASQGISSYLA |
| SEQ ID NO: 42 | LCDR2 (Kabat) | TASTLQS |
| SEQ ID NO: 134 | LCDR3 (Kabat) | QQTWRKPRT |
| SEQ ID NO: 44 | LCDR1 (Chothia) | SQGISSY |
| SEQ ID NO: 45 | LCDR2 (Chothia) | TAS |
| SEQ ID NO: 135 | LCDR3 (Chothia) | TWRKPR |
| SEQ ID NO: 47 | LCDR1 (IMGT) | QGISSY |
| SEQ ID NO: 45 | LCDR2 (IMGT) | TAS |
| SEQ ID NO: 134 | LCDR3 (IMGT) | QQTWRKPRT |
| SEQ ID NO: 136 | VL | DIQMTQSPSSLSASVGDRVTITCRASQGISSYLAWYQQKPGKAPKLLIYTAS<br>TLQSGVPSRFSGSGSGTDFTLTISSLQPEDFATYYCQQTWRKPRTFGQGTKV<br>EIK |
| SEQ ID NO: 197 | DNA VL | gacattcaaatgacacaaagtccgtccagtcttagtgcttctgtgggcgatagggtcaccatcacttgt<br>cgggcgtctcaggggatcagctcttacttggcatggtatcaacaaaagccaggaaaagcacctaaattg<br>cttatttatacagcgtccaccctccagtcaggagtgcctagtaggttctcaggctctgggtccggtact<br>gacttcacgctgactatatcaagcttgcaacccgaagattttgcaacatactactgccaacagacatgg<br>aggaagccaagaactttcggtcagggaacgaaagttgagataaag |
| SEQ ID NO: 138 | Light Chain | DIQMTQSPSSLSASVGDRVTITCRASQGISSYLAWYQQKPGKAPKLLIYTAS<br>TLQSGVPSRFSGSGSGTDFTLTISSLQPEDFATYYCQQTWRKPRTFGQGTKV<br>EIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVT<br>KSFNRGEC |
| SEQ ID NO: 198 | DNA Light Chain | gacattcaaatgacacaaagtccgtccagtcttagtgcttctgtgggcgatagggtcaccatcacttgt<br>cgggcgtctcaggggatcagctcttacttggcatggtatcaacaaaagccaggaaaagcacctaaattg<br>cttatttatacagcgtccaccctccagtcaggagtgcctagtaggttctcaggctctgggtccggtact<br>gacttcacgctgactatatcaagcttgcaacccgaagattttgcaacatactactgccaacagacatgg<br>aggaagccaagaactttcggtcagggaacgaaagttgagataaagcgcactgtcgcagcaccttccgtg<br>ttcattttcccgccttccgacgagcagcttaaatcagggaccgcgagtgttgttgcttgcttaataac<br>ttttaccccacgggaagccaagttcagtgaaggtggacaatgcactccaaagcgggaatagtcaggag<br>tcagttactgagcaagatagtaaagactctacttactctttgagttcaaccttgaccctctcaaaagcg<br>gactacgagaagcataaagtgtacgcctgcgaggtgacgcatcaaggtttgtcttcccggttacgaag<br>tcctttaatagggggggaatgt |
| XX14_LALA | | |
| SEQ ID NO: 28 | HCDR1 (Combined) | GFTFSSYWMN |
| SEQ ID NO: 190 | HCDR2 (Combined) | AISSKGSYTYYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 190 | HCDR2 (Kabat) | AISSKGSYTYYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 191 | HCDR2 (Chothia) | SSKGSY |
| SEQ ID NO: 30 | HCDR3 (Chothia) | DRYSMIYSYGAGAFDY |

TABLE 2-continued

Exemplary anti-NPR1 antibody sequences

| SEQ ID NO: 34 | HCDR1 (IMGT) | GFTFSSYW |
|---|---|---|
| SEQ ID NO: 192 | HCDR2 (IMGT) | ISSKGSYT |
| SEQ ID NO: 36 | HCDR3 (IMGT) | ARDRYSMIYSYGAGAFDY |
| SEQ ID NO: 193 | VH | QVQLLESGGGLVQPGGSLRLSCAASGFTFSSYWMNWVRQAPGKGLEWVS<br>AISSKGSYTYYADSVKGRFTISRDNSKNTLYLQMNSLRAEDTAVYYCARD<br>RYSMIYSYGAGAFDYWGQGTLVTVSS |
| SEQ ID NO: 194 | DNA VH | caagttcagctccttgagtctgggggggcctggtgcaacctgggggctctctgcggctttcatgtgcg<br>gcctcagggttcactttcagctcatactggatgaattgggtacgccaagctccaggcaaaggactcgaa<br>tgggtaagcgctatatccagcaaagggagctataccctattacgcggattccgttaagggcaggttcact<br>atatcccgcgacaactccaaaaatactttgtatctgcaaatgaattcctccgagccgaagataccgca<br>gtatattactgtgcgagggacaggtactccatgatttacagctacggtgccggtgctttcgattattgg<br>ggacaggggacacttgtgaccgtcagttct |
| SEQ ID NO: 195 | Heavy Chain | QVQLLESGGGLVQPGGSLRLSCAASGFTFSSYWMNWVRQAPGKGLEWVS<br>AISSKGSYTYYADSVKGRFTISRDNSKNTLYLQMNSLRAEDTAVYYCARD<br>RYSMIYSYGAGAFDYWGQGTLVTVSSASTKGPSVFPLAPSSKSTSGGTAAL<br>GCLVKDYFPEPVTVSWNSGALTSGVHTFPAVLQSSGLYSLSSVVTVPSSSL<br>GTQTYICNVNHKPSNTKVDKRVEPKSCDKTHTCPPCPAPEAAGGPSVFLFP<br>PKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPR<br>EPQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSP<br>GK |
| SEQ ID NO: 196 | DNA Heavy Chain | caagttcagctccttgagtctgggggggcctggtgcaacctgggggctctctgcggctttcatgtgcg<br>gcctcagggttcactttcagctcatactggatgaattgggtacgccaagctccaggcaaaggactcgaa<br>tgggtaagcgctatatccagcaaagggagctataccctattacgcggattccgttaagggcaggttcact<br>atatcccgcgacaactccaaaaatactttgtatctgcaaatgaattcctccgagccgaagataccgca<br>gtatattactgtgcgagggacaggtactccatgatttacagctacggtgccggtgctttcgattattgg<br>ggacaggggacacttgtgaccgtcagttctgcaagtaccaaaggccgtctgttttcccattggctccc<br>tcatccaagagcacgagtggaggcaccgccgcgctgggatgcctttgtgaaagactatttcccggagccc<br>gtgaccgttagctggaacagcggcgctcttaccagtggcgttcacacattcccagctgttttgcagtca<br>tccgggctctactctctcatccgtggtcaccgtgccgtctagttctttgggcacccagacctacatc<br>tgtaacgtaaatcacaaacctagtaatactaaggtggacaagcgagttgaaccgaagagctgtgataag<br>acacatacttgtccaccatgtccggcaccgaggcagcgggggggcccagtgtttttctcttcccaccc<br>aagcccaaagacacattgatgatctcacgaacccagaggtaacttgtgtcgtggtagatgtaagccat<br>gaggaccccgaagttaagttcaattggtatgttgacggtgtagaggtgcacaatgccaaaactaaaccc<br>cgggaggagcaatacaactcaacttacagagtcgtatccgtgctgaccgttttgcaccaggattggttg<br>aatggtaaggaatacaaatgtaaagtgagcaataaagctctcccagcgcccatcgagaagaccattagc<br>aaagccaagggtcaacccagggaaccccaggtatatacgctgccaccctcaagggaagagatgacaaag<br>aatcaagtgtcactgacgtgtcttgtcaagggttttctatcctagcgacattgcggtggaatgggagtca<br>aatgggcaacccgagaacaactacaagactactcctcccgtcctggacagcgacggctccttcttcctg<br>tatagtaaactgaccgtcgataaaagtaggggcagcaggggaatgtctttagttgctctgtcatgcat<br>gaggcgctccataaccactacacccaaaaatctttgagcttgagccctgggaaa |
| SEQ ID NO: 41 | LCDR1 (Combined) | RASQGISSYLA |
| SEQ ID NO: 42 | LCDR2 (Combined) | TASTLQS |
| SEQ ID NO: 172 | LCDR3 (Combined) | QQEWAKPRT |
| SEQ ID NO: 41 | LCDR1 (Kabat) | RASQGISSYLA |
| SEQ ID NO: 42 | LCDR2 (Kabat) | TASTLQS |
| SEQ ID NO: 172 | LCDR3 (Kabat) | QQEWAKPRT |
| SEQ ID NO: 44 | LCDR1 (Chothia) | SQGISSY |
| SEQ ID NO: 45 | LCDR2 (Chothia) | TAS |
| SEQ ID NO: 173 | LCDR3 (Chothia) | EWAKPR |
| SEQ ID NO: 47 | LCDR1 (IMGT) | QGISSY |
| SEQ ID NO: 45 | LCDR2 (IMGT) | TAS |
| SEQ ID NO: 172 | LCDR3 (IMGT) | QQEWAKPRT |
| SEQ ID NO: 174 | VL | DIQMTQSPSSLSASVGDRVTITCRASQGISSYLAWYQQKPGKAPKLLIYTAS<br>TLQSGVPSRFSGSGSGTDFTLTISSLQPEDFATYYCQQEWAKPRTFGQGTKV<br>EIK |

TABLE 2-continued

Exemplary anti-NPR1 antibody sequences

| SEQ ID NO: 199 | DNA VL | gatatacagatgacgcaaagtccctctagtctttctgcaagtgtcggggacagagttaccattacctgc<br>agagcgtcacaaggcatctctagttatctcgcgtggtaccaacagaagccaggtaaagcacctaaactg<br>ttgatttacacggcatcaacattgcagtcaggtgtccctcccgatttagtggcagtggtagcggtaca<br>gatttactcttaccatttcatctcttcagccagaagattttgctacgtactactgtcaacaagaatgg<br>gctaaaccacgaacctttggacagggtacgaaggtcgaaataaa |
| --- | --- | --- |
| SEQ ID NO: 176 | Light Chain | DIQMTQSPSSLSASVGDRVTITCRASQGISSYLAWYQQKPGKAPKLLIYTAS<br>TLQSGVPSRFSGSGSGTDFTLTISSLQPEDFATYYCQQEWAKPRTFGQGTKV<br>EIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVT<br>KSFNRGEC |
| SEQ ID NO: 200 | DNA Light Chain | gatatacagatgacgcaaagtccctctagtctttctgcaagtgtcggggacagagttaccattacctgc<br>agagcgtcacaaggcatctctagttatctcgcgtggtaccaacagaagccaggtaaagcacctaaactg<br>ttgatttacacggcatcaacattgcagtcaggtgtccctcccgatttagtggcagtggtagcggtaca<br>gatttactcttaccatttcatctcttcagccagaagattttgctacgtactactgtcaacaagaatgg<br>gctaaaccacgaacctttggacagggtacgaaggtcgaaataaaacggaccgttgccgcccctccgtc<br>ttcatcttcccccgtctgacgagcagctcaaatccggcacagcttctgtagtctgcttgctgaataac<br>ttctacccaagagaagccaaagttcagtggaaggtcgataatgcattgcaatctggtaatagtcaggaa<br>tctgtgactgagcaggatagcaaagactcaacttacagcctctcttcaaccttgacgttgtccaaagcg<br>gattatgagaaacacaaggtgtacgcttgcgaggtgacgcatcaagggcttagttcccggtaaccaaa<br>tctttcaaccgaggtgaatgc |

XX15_LALA

| SEQ ID NO: 28 | HCDR1 (Combined) | GFTFSSYWMN |
| --- | --- | --- |
| SEQ ID NO: 119 | HCDR2 (Combined) | VIESKGNYIFYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 119 | HCDR2 (Kabat) | VIESKGNYIFYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 120 | HCDR2 (Chothia) | ESKGNY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 121 | HCDR2 (IMGT) | IESKGNYI |
| SEQ ID NO: 36 | HCDR3 (IMGT) | ARDRYSMIYSYGAGAFDY |
| SEQ ID NO: 201 | VH | QVQLLESGGGLVQPGGSLRLSCAASGFTFSSYWMNWVRQAPGKGLEWVS<br>VIESKGNYIFYADSVKGRFTISRDNSKNTLYLQMNSLRAEDTAVYYCARDR<br>YSMIYSYGAGAFDYWGQGTLVTVSS |
| SEQ ID NO: 202 | DNA VH | caagttcaattgctggaaagcggaggtggacttgtccaacctggagggtcactccgactgtcttgcgct<br>gcatcaggattcacctttagtagctattggatgaactgggtccggcaggctcctgggaagggcttgag<br>tgggtaagtgtcattgaatcaaagggcaactacatctctttatgctgattctgtaaagggtaggttcacc<br>atctccagggacaattcaaaaaatacttgtatctgcagatgaactctctcagggcagaagacacggcc<br>gtttattactgcgcccgcgatcgatacagcatgatatactcctacggcgcaggagcttttgactactgg<br>ggtcaaggcacacttgttactgtcagtagc |
| SEQ ID NO: 203 | Heavy Chain | QVQLLESGGGLVQPGGSLRLSCAASGFTFSSYWMNWVRQAPGKGLEWVS<br>VIESKGNYIFYADSVKGRFTISRDNSKNTLYLQMNSLRAEDTAVYYCARDR<br>YSMIYSYGAGAFDYWGQGTLVTVSSASTKGPSVFPLAPSSKSTSGGTAALG<br>CLVKDYFPEPVTVSWNSGALTSGVHTFPAVLQSSGLYSLSSVVTVPSSSLGT<br>QTYICNVNHKPSNTKVDKRVEPKSCDKTHTCPPCPAPEAAGGPSVFLFPPKP<br>KDTLMISRTPEVTCVVVDVSHEDPEVKFNWYVDGVEVHNAKTKPREEQY<br>NSTYRVVSVLTVLHQDWLNGKEYKCKVSNKALPAPIEKTISKAKGQPREP<br>QVYTLPPSREEMTKNQVSLTCLVKGFYPSDIAVEWESNGQPENNYKTTPPV<br>LDSDGSFFLYSKLTVDKSRWQQGNVFSCSVMHEALHNHYTQKSLSLSPGK |
| SEQ ID NO: 204 | DNA Heavy Chain | caagttcaattgctggaaagcggaggtggacttgtccaacctggagggtcactccgactgtcttgcgct<br>gcatcaggattcacctttagtagctattggatgaactgggtccggcaggctcctgggaagggcttgag<br>tgggtaagtgtcattgaatcaaagggcaactacatctctttatgctgattctgtaaagggtaggttcacc<br>atctccagggacaattcaaaaaatacttgtatctgcagatgaactctctcagggcagaagacacggcc<br>gtttattactgcgcccgcgatcgatacagcatgatatactcctacggcgcaggagcttttgactactgg<br>ggtcaaggcacacttgttactgtcagtagcgcctcaacgaaaggaccgtccgtgtttcctcttgctcct<br>agctccaaatccacctcaggtggaacggccgcccctggggtgcctggtaaaggactatttcccagagcca<br>gttactgtgtcttgaattctggtgcattgacaagtggcgtacacacttttcccgcggtcctccaatct |

TABLE 2-continued

Exemplary anti-NPR1 antibody sequences

```
agtggtctgtactcactgtcctccgttgtgactgtcccaagtagctcacttggcacacagacttacatc
tgtaatgttaatcataagccgtcaaacacgaaggtggataagagggtagaacctaagtcatgtgacaaa
acgcatacttgccccccctgccctgcgccggaagccgctggcggaccctccgtattcttgttccctcca
aagccaaaggacactctgatgattagccggacaccggaggtcacttgtgttgtagttgacgtcagccat
gaggatcctgaggtgaaatttaattggtacgtggacggggttgaagtccacaatgctaaaactaaacct
agggaagagcaatataatagtacatacagggttgtcagtgtgctgaccgttctccatcaggactggctg
aacggcaaggaatacaagtgcaaggtcagcaacaaggccttgccggcccccatcgagaagacgatctcc
aaagccaagggggcaaccccgagaaccgcaggtatacacgctcccccctagtagaaaagagatgacaaag
aatcaagtttccttgacgtgccttgtgaaaggcttctaccctagtgacatcgcagtcgaatgggagagc
aacgggcagccggagaataactataaaacaaccccccccgtgcttgactcagacgggtcattttttctg
tatagcaaattgactgttgataaatacggtggcaacaaggaaacgtgtttagttgcagcgtaatgcac
gaagctctccacaatcactatactcaaaagtcactgtcactctcccctggcaag
```

| SEQ ID NO: 41 | LCDR1 (Combined) | RASQGISSYLA |
| SEQ ID NO: 42 | LCDR2 (Combined) | TASTLQS |
| SEQ ID NO: 126 | LCDR3 (Combined) | QQEWVKPRT |
| SEQ ID NO: 41 | LCDR1 (Kabat) | RASQGISSYLA |
| SEQ ID NO: 42 | LCDR2 (Kabat) | TASTLQS |
| SEQ ID NO: 126 | LCDR3 (Kabat) | QQEWVKPRT |
| SEQ ID NO: 44 | LCDR1 (Chothia) | SQGISSY |
| SEQ ID NO: 45 | LCDR2 (Chothia) | TAS |
| SEQ ID NO: 127 | LCDR3 (Chothia) | EWVKPR |
| SEQ ID NO: 47 | LCDR1 (IMGT) | QGISSY |
| SEQ ID NO: 45 | LCDR2 (IMGT) | TAS |
| SEQ ID NO: 126 | LCDR3 (IMGT) | QQEWVKPRT |
| SEQ ID NO: 128 | VL | DIQMTQSPSSLSASVGDRVTITCRASQGISSYLAWYQQKPGKAPKLLIYTAS<br>TLQSGVPSRFSGSGSGTDFTLTISSLQPEDFATYYCQQEWVKPRTFGQGTKV<br>EIK |
| SEQ ID NO: 205 | DNA VL | gacatacaaatgacgcaatctccgagtagcttgtcagcgtccgtaggcgaccgagtaacgattacgtgt<br>agagcgagccagggaatttcatcttatttggcttggtatcagcaaaagccgggaaaagcacccaaactc<br>ctcatttatactgccagcacgttgcaaagcggcgttccgagtcggttctctggatcagggtcgggacg<br>gacttcaccttgacgatttcatctttgcaacctgaagattttgcaacatactactgtcaacaggagtgg<br>gtgaagccaaggaccttcggacaaggcacgaaggtcgaaatcaag |
| SEQ ID NO: 130 | Light Chain | DIQMTQSPSSLSASVGDRVTITCRASQGISSYLAWYQQKPGKAPKLLIYTAS<br>TLQSGVPSRFSGSGSGTDFTLTISSLQPEDFATYYCQQEWVKPRTFGQGTKV<br>EIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVT<br>KSFNRGEC |
| SEQ ID NO: 206 | DNA Light Chain | gacatacaaatgacgcaatctccgagtagcttgtcagcgtccgtaggcgaccgagtaacgattacgtgt<br>agagcgagccagggaatttcatcttatttggcttggtatcagcaaaagccgggaaaagcacccaaactc<br>ctcatttatactgccagcacgttgcaaagcggcgttccgagtcggttctctggatcagggtcgggacg<br>gacttcaccttgacgatttcatctttgcaacctgaagattttgcaacatactactgtcaacaggagtgg<br>gtgaagccaaggaccttcggacaaggcacgaaggtcgaaatcaagcgaaccgtggcagctccgtccgtg<br>tttattttccgcccttccgacgaacaacttaaaagtggaacagctctgtcgtctgtctccttaacaac<br>ttctaccccaggggaagctaaagtacagtggaaggtagataacgctctgcaaagtggtaattctcaggag<br>agcgtcacggaacaggactccaaagactccacctattctctgagctctacactgacgctcagcaaggca<br>gactacgaaaagcacaaagtatatgcgtgtgaggtgacgcatcaaggccttagcagtccagttacaaaa<br>agttttaacaggggagaatgc |

XX15_DAPA

| SEQ ID NO: 28 | HCDR1 (Combined) | GFTFSSYWMN |
| SEQ ID NO: 119 | HCDR2 (Combined) | VIESKGNYIFYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 119 | HCDR2 (Kabat) | VIESKGNYIFYADSVKG |
| SEQ ID NO: 30 | HCDR3 (Kabat) | DRYSMIYSYGAGAFDY |

TABLE 2-continued

Exemplary anti-NPR1 antibody sequences

| SEQ ID NO: 32 | HCDR1 (Chothia) | GFTFSSY |
| --- | --- | --- |
| SEQ ID NO: 120 | HCDR2 (Chothia) | ESKGNY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 121 | HCDR2 (IMGT) | IESKGNYI |
| SEQ ID NO: 36 | HCDR3 (IMGT) | ARDRYSMIYSYGAGAFDY |
| SEQ ID NO: 122 | VH | EVQLLESGGGLVQPGGSLRLSCAASGFTFSSYWMNWVRQAPGKGLEWVS VIESKGNYIFYADSVKGRFTISRDNSKNTLYLQMNSLRAEDTAVYYCARDR YSMIYSYGAGAFDYWGQGTLVTVSS |
| SEQ ID NO: 207 | DNA VH | gaagtgcagctgctggaatccggcggaggtctggtccagcctggaggttccctgcgcctgtcatgcgca gcctccggattcaccttttcgtcgtactggatgaactgggtcagacaggctcctggaaagggcctggaa tgggtgtctgtgattgaatccaagggaactacatcttctacgcggacagcgtgaagggccggttcact atcagcagagacaacagcaagaacaccctgtacctccaaatgaactcgctgagggccgaagatactgcc gtgtactactgtgcccgcgatcgctactgatgatctacagctatggtgccggagcgttcgattactgg ggacagggaaccctcgtgaccgtcagctcc |
| SEQ ID NO: 208 | Heavy Chain | EVQLLESGGGLVQPGGSLRLSCAASGFTFSSYWMNWVRQAPGKGLEWVS VIESKGNYIFYADSVKGRFTISRDNSKNTLYLQMNSLRAEDTAVYYCARDR YSMIYSYGAGAFDYWGQGTLVTVSSASTKGPSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCDKTHTCPPCPAPELLGGPSVFLFPPKP KDTLMISRTPEVTCVVVAVSHEDPEVKFNWYVDGVEVHNAKTKPREEQY NSTYRVVSVLTVLHQDWLNGKEYKCKVSNKALAAPIEKTISKAKGQPREP QVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK |
| SEQ ID NO: 209 | DNA Heavy Chain | gaagtgcagctgctggaatccggcggaggtctggtccagcctggaggttccctgcgcctgtcatgcgca gcctccggattcaccttttcgtcgtactggatgaactgggtcagacaggctcctggaaagggcctggaa tgggtgtctgtgattgaatccaagggaactacatcttctacgcggacagcgtgaagggccggttcact atcagcagagacaacagcaagaacaccctgtacctccaaatgaactcgctgagggccgaagatactgcc gtgtactactgtgcccgcgatcgctactgatgatctacagctatggtgccggagcgttcgattactgg ggacagggaaccctcgtgaccgtcagctccgcctcaaccaagggcccgtcagtgttcccgctggctcca tcgtcgaagtccacctccggaggaaccgcagcactcggttgcctggtcaaggactacttccctgagcca gtgaccgtgtcgtggaacagcggagccctgacttccggcgtgcacacttttcccgcggtgctgcagtcc tccggtctgtactcccttctcgtcgtggtcaccgtgccgtcgtctagcctgggcacccagacctacatc tgcaacgtgaaccacaagccgtccaacaccaaagtggataagcgggtggagccgaagtcctgcgataag acacacagtgccgccatgtccagcgcctgaattgcttggcggaccttccgtgttcctgttcccgcct aagcccaaggacaccttgatgattagccggactcccgaagtcacctgtgtggtggtggcagtgtcccac gaggaccccgaggtcaagtttaattggtacgtggacggcgtcgaagtgcacaacgccaagactaagccc cgggaggaacagtacaacagcacctaccgggtcgtgtccgtgctgaccgtgctgcaccaggactggctg aatgggaaagaatacaagtgcaaagtgtccaacaaggccttggccgctctcgaaaaaactatcagc aaggctaagggacagccgagggaaccccaagtctacaccctgcccccttcacgcgaagagatgaccaag aatcaagtgtcgctgacctgcctcgtcaagggattctaccctccgacattgcggtggagtgggagtcc aacggccagcccgagaacaactacaagactactccgcccgtgctggactccgacggcagcttcttcctg tattccaagctgaccgtggacaagtcccggtggcagcaaggaaacgtgttctcctgctcggtcatgcac gaagcccctgcacaaccactatacgcagaagtccctgtccttgagcccggggaaa |
| SEQ ID NO: 41 | LCDR1 (Combined) | RASQGISSYLA |
| SEQ ID NO: 42 | LCDR2 (Combined) | TASTLQS |
| SEQ ID NO: 126 | LCDR3 (Combined) | QQEWVKPRT |
| SEQ ID NO: 41 | LCDR1 (Kabat) | RASQGISSYLA |
| SEQ ID NO: 42 | LCDR2 (Kabat) | TASTLQS |
| SEQ ID NO: 126 | LCDR3 (Kabat) | QQEWVKPRT |
| SEQ ID NO: 44 | LCDR1 (Chothia) | SQGISSY |
| SEQ ID NO: 45 | LCDR2 (Chothia) | TAS |
| SEQ ID NO: 127 | LCDR3 (Chothia) | EWVKPR |
| SEQ ID NO: 47 | LCDR1 (IMGT) | QGISSY |
| SEQ ID NO: 45 | LCDR2 (IMGT) | TAS |
| SEQ ID NO: 126 | LCDR3 (IMGT) | QQEWVKPRT |

TABLE 2-continued

Exemplary anti-NPR1 antibody sequences

| SEQ ID NO: 128 | VL | DIQMTQSPSSLSASVGDRVTITCRASQGISSYLAWYQQKPGKAPKLLIYTAS
TLQSGVPSRFSGSGSGTDFTLTISSLQPEDFATYYCQQEWVKPRTFGQGTKV
EIK |
|---|---|---|
| SEQ ID NO: 210 | DNA VL | gacatccagatgacccagtctccgtcctccctgtccgcatcagtgggggacagagtgaccatcacttgt
cgggcctcccaaggcatctcgtcatacctggcctggtatcagcagaaacccggaaaggctccaaagctg
ctcatctacaccgcctcgactctgcaatccggagtgccttcccgcttctccggatccggttcgggaacc
gacttcaccctcaccattagcagccttcagccggaagatttcgcgacctactactgccagcaagaatgg
gtgaagcccaggacatttggccagggcactaaggtcgagattaag |
| SEQ ID NO: 130 | Light Chain | DIQMTQSPSSLSASVGDRVTITCRASQGISSYLAWYQQKPGKAPKLLIYTAS
TLQSGVPSRFSGSGSGTDFTLTISSLQPEDFATYYCQQEWVKPRTFGQGTKV
EIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVT
KSFNRGEC |
| SEQ ID NO: 211 | DNA Light Chain | gacatccagatgacccagtctccgtcctccctgtccgcatcagtgggggacagagtgaccatcacttgt
cgggcctcccaaggcatctcgtcatacctggcctggtatcagcagaaacccggaaaggctccaaagctg
ctcatctacaccgcctcgactctgcaatccggagtgccttcccgcttctccggatccggttcgggaacc
gacttcaccctcaccattagcagccttcagccggaagatttcgcgacctactactgccagcaagaatgg
gtgaagcccaggacatttggccagggcactaaggtcgagattaagcgtacggtggccgctcccagcgtg
ttcatcttccccccagcgacgagcagctgaagagcggcaccgccagcgtggtgtgcctgctgaacaac
ttctaccccggaggccaaggtcagtggaaggtggacaacgccctgcagagcggcaacagccaggag
agcgtcaccgagcaggacagcaaggactccacctacagcctgagcagcaccctgaccctgagcaaggcc
gactacgagaagcataaggtgtacgcctgcgaggtgacccaccagggcctgtccagccccgtgaccaag
agcttcaacaggggcgagtgc |

XX16_LALA

| SEQ ID NO: 28 | HCDR1 (Combined) | GFTFSSYWMN |
|---|---|---|
| SEQ ID NO: 119 | HCDR2 (Combined) | VIESKGNYIFYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 119 | HCDR2 (Kabat) | VIESKGNYIFYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 120 | HCDR2 (Chothia) | ESKGNY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 121 | HCDR2 (IMGT) | IESKGNYI |
| SEQ ID NO: 36 | HCDR3 (IMGT) | ARDRYSMIYSYGAGAFDY |
| SEQ ID NO: 201 | VH | QVQLLESGGGLVQPGGSLRLSCAASGFTFSSYWMNWVRQAPGKGLEWVS
VIESKGNYIFYADSVKGRFTISRDNSKNTLYLQMNSLRAEDTAVYYCARDR
YSMIYSYGAGAFDYWGQGTLVTVSS |
| SEQ ID NO: 202 | DNA VH | caagttcaattgctggaaagcggaggtggacttgtccaacctggagggtcactccgactgtcttgcgct
gcatcaggattcacctttagtagctattggatgaactgggtccggcaggctcctgggaagggcttgag
tgggtaagtgtcattgaatcaaagggcaactacatctttttatgctgattctgtaaagggtaggttcacc
atctccagggacaattcaaaaaatactttgtatctgcagatgaactctctcaggcagaagacacggcc
gtttattactgcgcccgcgatcgatacagcatgatatactcctacggcgcaggagcttttgactactgg
ggtcaaggcacacttgttactgtcagtagc |
| SEQ ID NO: 203 | Heavy Chain | QVQLLESGGGLVQPGGSLRLSCAASGFTFSSYWMNWVRQAPGKGLEWVS
VIESKGNYIFYADSVKGRFTISRDNSKNTLYLQMNSLRAEDTAVYYCARDR
YSMIYSYGAGAFDYWGQGTLVTVSSASTKGPSVFPLAPSSKSTSGGTAALG
CLVKDYFPEPVTVSWNSGALTSGVHTFPAVLQSSGLYSLSSVVTVPSSSLGT
QTYICNVNHKPSNTKVDKRVEPKSCDKTHTCPPCPAPEAAGGPSVFLFPPKP
KDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK |
| SEQ ID NO: 204 | DNA Heavy Chain | caagttcaattgctggaaagcggaggtggacttgtccaacctggagggtcactccgactgtcttgcgct
gcatcaggattcacctttagtagctattggatgaactgggtccggcaggctcctgggaagggcttgag
tgggtaagtgtcattgaatcaaagggcaactacatctttttatgctgattctgtaaagggtaggttcacc
atctccagggacaattcaaaaaatactttgtatctgcagatgaactctctcaggcagaagacacggcc |

TABLE 2-continued

Exemplary anti-NPR1 antibody sequences

```
gtttattactgcgcccgcgatcgatacagcatgatatactcctacggcgcaggagcttttgactactgg
ggtcaaggcacacttgttactgtcagtagcgcctcaacgaaaggaccgtccgtgtttcctcttgctcct
agctccaaatccacctcaggtggaacggccgcctgggggtgcctggtaaaggactatttcccagagcca
gttactgtgtcttggaattctggtgcattgacaagtggcgtacacacttttcccgcggtcctccaatct
agtggtctgtactcactgtcctccgttgtgactgtcccaagtagctcacttggcacacagacttacatc
tgtaatgttaatcataagccgtcaaacacgaaggtggataagagggtagaacctaagtcatgtgacaaa
acgcatacttgcccccccctgccctgcgcggaagccgctggcggacccctccgtattcttgttccctcca
aagccaaaggacactctgatgattagccggacaccggaggtcacttgtgttgtagttgacgtcagccat
gaggatcctgaggtgaaatttaattggtacgtggacggggttgaagtccacaatgctaaaactaaacct
agggaagagcaatataatagtacatacaggggtgtcagtgtgctgaccgttctccatcaggactggctg
aacggcaaggaatacaagtgcaaggtcagcaacaaggccttgccggcccccatcgagaagacgatctcc
aaagccaaggggcaaccccgagaaccgcaggtatacacgctccccccagtagagaagagatgacaaag
aatcaagtttccttgacgtgccttgtgaaaggcttctaccctagtgacatcgcagtcgaatgggagagc
aacgggcagccggagaataactataaaacaaccccccccgtgcttgactcagacgggtcatttttctg
tatagcaaattgactgttgataaatacggtggcaacaaggaaacgtgtttagttgcagcgtaatgcac
gaagctctccacaatcactatactcaaaagtcactgtcactcccctggcaag
```

| | | |
|---|---|---|
| SEQ ID NO: 41 | LCDR1 (Combined) | RASQGISSYLA |
| SEQ ID NO: 42 | LCDR2 (Combined) | TASTLQS |
| SEQ ID NO: 134 | LCDR3 (Combined) | QQTWRKPRT |
| SEQ ID NO: 41 | LCDR1 (Kabat) | RASQGISSYLA |
| SEQ ID NO: 42 | LCDR2 (Kabat) | TASTLQS |
| SEQ ID NO: 134 | LCDR3 (Kabat) | QQTWRKPRT |
| SEQ ID NO: 44 | LCDR1 (Chothia) | SQGISSY |
| SEQ ID NO: 45 | LCDR2 (Chothia) | TAS |
| SEQ ID NO: 135 | LCDR3 (Chothia) | TWRKPR |
| SEQ ID NO: 47 | LCDR1 (IMGT) | QGISSY |
| SEQ ID NO: 45 | LCDR2 (IMGT) | TAS |
| SEQ ID NO: 134 | LCDR3 (IMGT) | QQTWRKPRT |
| SEQ ID NO: 136 | VL | DIQMTQSPSSLSASVGDRVTITCRASQGISSYLAWYQQKPGKAPKLLIYTAS TLQSGVPSRFSGSGSGTDFTLTISSLQPEDFATYYCQQTWRKPRTFGQGTKV EIK |
| SEQ ID NO: 197 | DNA VL | gacattcaaatgacacaaagtccgtccagtcttagtgcttctgtgggcgatagggtcaccatcacttgt cgggcgtctcaggggatcagctcttacttggcatggtatcaacaaaagccaggaaaagcacctaaattg cttatttatacagcgtccaccctccagtcaggagtgcctagtaggttctcaggctctgggtccggtact gacttcacgctgactatatcaagcttgcaacccgaagattttgcaacatactactgccaacagacatgg aggaagccaagaactttcggtcagggaacgaaagttgagataaag |
| SEQ ID NO: 138 | Light Chain | DIQMTQSPSSLSASVGDRVTITCRASQGISSYLAWYQQKPGKAPKLLIYTAS TLQSGVPSRFSGSGSGTDFTLTISSLQPEDFATYYCQQTWRKPRTFGQGTKV EIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVT KSFNRGEC |
| SEQ ID NO: 198 | DNA Light Chain | gacattcaaatgacacaaagtccgtccagtcttagtgcttctgtgggcgatagggtcaccatcacttgt cgggcgtctcaggggatcagctcttacttggcatggtatcaacaaaagccaggaaaagcacctaaattg cttatttatacagcgtccaccctccagtcaggagtgcctagtaggttctcaggctctgggtccggtact gacttcacgctgactatatcaagcttgcaacccgaagattttgcaacatactactgccaacagacatgg aggaagccaagaactttcggtcagggaacgaaagttgagataaagcgcactgtcgcagccttccgtg ttcattttcccgcctttcgacgagcagcttaaatcagggaccgcgagtgttgtttgcttgcttaataac ttttaccacgcggaagccaaagttcagtggaaggtggacaatgcactccaaagcgggaatagtcaggag tcagttactgagcaagatagtaaagactctacttactctttgagttcaaccttgaccctctcaaaagcg gactacgagaagcataaagtgtacgcctgcgaggtgacgcatcaaggtttgtcttccccggttacgaag tcctttaataggggggaatgt |

XX16_DAPA

| | | |
|---|---|---|
| SEQ ID NO: 28 | HCDR1 (Combined) | GFTFSSYWMN |
| SEQ ID NO: 119 | HCDR2 (Combined) | VIESKGNYIFYADSVKG |
| SEQ ID NO: 30 | HCDR3 (Combined) | DRYSMIYSGAGAFDY |
| SEQ ID NO: 31 | HCDR1 (Kabat) | SYWMN |

TABLE 2-continued

Exemplary anti-NPR1 antibody sequences

| | | |
|---|---|---|
| SEQ ID NO: 119 | HCDR2 (Kabat) | VIESKGNYIFYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 120 | HCDR2 (Chothia) | ESKGNY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 121 | HCDR2 (IMGT) | IESKGNYI |
| SEQ ID NO: 36 | HCDR3 (IMGT) | ARDRYSMIYSYGAGAFDY |
| SEQ ID NO: 122 | VH | EVQLLESGGGLVQPGGSLRLSCAASGFTFSSYWMNWVRQAPGKGLEWVS<br>VIESKGNYIFYADSVKGRFTISRDNSKNTLYLQMNSLRAEDTAVYYCARDR<br>YSMIYSYGAGAFDYWGQGTLVTVSS |
| SEQ ID NO: 207 | DNA VH | gaagtgcagctgctggaatccggcggaggtctggtccagcctggaggttccctgcgcctgtcatgcgca<br>gcctccggattcaccttttcgtcgtactggatgaactgggtcagacaggctcctggaaagggcctggaa<br>tgggtgtctgtgattgaatccaaggggaactacatcttctacgcggacagcgtgaagggccggttcact<br>atcagcagagacaacagcaagaacaccctgtacctccaaatgaactcgctgagggccgaagatactgcc<br>gtgtactactgtgcccgcgatcgctactgatgatctacagctatggtgccggagcgttcgattactgg<br>ggacagggaaccctcgtgaccgtcagctcc |
| SEQ ID NO: 208 | Heavy Chain | EVQLLESGGGLVQPGGSLRLSCAASGFTFSSYWMNWVRQAPGKGLEWVS<br>VIESKGNYIFYADSVKGRFTISRDNSKNTLYLQMNSLRAEDTAVYYCARDR<br>YSMIYSYGAGAFDYWGQGTLVTVSSASTKGPSVFPLAPSSKSTSGGTAALG<br>CLVKDYFPEPVTVSWNSGALTSGVHTFPAVLQSSGLYSLSSVVTVPSSSLGT<br>QTYICNVNHKPSNTKVDKRVEPKSCDKTHTCPPCPAPELLGGPSVFLFPPKP<br>KDTLMISRTPEVTCVVVAVSHEDPEVKFNWYVDGVEVHNAKTKPREEQY<br>NSTYRVVSVLTVLHQDWLNGKEYKCKVSNKALAAPIEKTISKAKGQPREP<br>QVYTLPPSREEMTKNQVSLTCLVKGFYPSDIAVEWESNGQPENNYKTTPPV<br>LDSDGSFFLYSKLTVDKSRWQQGNVFSCSVMHEALHNHYTQKSLSLSPGK |
| SEQ ID NO: 209 | DNA Heavy Chain | gaagtgcagctgctggaatccggcggaggtctggtccagcctggaggttccctgcgcctgtcatgcgca<br>gcctccggattcaccttttcgtcgtactggatgaactgggtcagacaggctcctggaaagggcctggaa<br>tgggtgtctgtgattgaatccaaggggaactacatcttctacgcggacagcgtgaagggccggttcact<br>atcagcagagacaacagcaagaacaccctgtacctccaaatgaactcgctgagggccgaagatactgcc<br>gtgtactactgtgcccgcgatcgctactgatgatctacagctatggtgccggagcgttcgattactgg<br>ggacagggaaccctcgtgaccgtcagctccgcctcaaccaagggcccgtcagtgttcccgctggctcca<br>tcgtcgaagtcccacctccggaggaaccgcagcactcggttgctggtcaaggactacttccctgagcca<br>gtgaccgtgtcgtggaacagcggagccctgacttccggcgtgcacacttttcccgcggtgctgcagtcc<br>tccggtctgtactcccttttcgtccgtggtcaccgtgccgtcgtctagcctgggcacccagacctacatc<br>tgcaacgtgaaccacaagccgtccaacaccaaagtggataagcgggtggagccgaagtcctgcgataag<br>acacacacgtgcccgccatgtccagccgctcgtgaattgcttggcggaccttccgtgttcctgttcccgcct<br>aagcccaaggacaccttgatgattagccggactcccgaagtcacctgtgtggtggtggcagtgtcccac<br>gaggaccccgaggtcaagtttaattggtacgtggacggcgtcgaagtgcacaacgccaagactaagccc<br>cgggaggaacagtacaacagcacctaccgggtcgtgtccgtgctgaccgtgctgcaccaggactggctg<br>aatgggaaagagtacaagtgcaaagtgtccaacaaggcctttggccgctcctatcgaaaaaactatcagc<br>aaggctaaggggacagccgagggaacccccaagtctacaccctgccccttcacgcgaagagatgaccaag<br>aatcaagtgtcgctgacctgcctcgtcaagggattctaccccctcgacattgcggtggagtgggagtcc<br>aacgccagcccgagaacaactacaagactactccgcccgtgctggactccgacggcagcttcttcctg<br>tattccaagctgaccgtggacaagtcccggtggcagcaaggaaacgtgttctcctgctcggtcatgcac<br>gaagccctgcacaaccactatacgcagaagtccctgtccttgagcccggggaaa |
| SEQ ID NO: 41 | LCDR1 (Combined) | RASQGISSYLA |
| SEQ ID NO: 42 | LCDR2 (Combined) | TASTLQS |
| SEQ ID NO: 134 | LCDR3 (Combined) | QQTWRKPRT |
| SEQ ID NO: 41 | LCDR1 (Kabat) | RASQGISSYLA |
| SEQ ID NO: 42 | LCDR2 (Kabat) | TASTLQS |
| SEQ ID NO: 134 | LCDR3 (Kabat) | QQTWRKPRT |
| SEQ ID NO: 44 | LCDR1 (Chothia) | SQGISSY |
| SEQ ID NO: 45 | LCDR2 (Chothia) | TAS |
| SEQ ID NO: 135 | LCDR3 (Chothia) | TWRKPR |
| SEQ ID NO: 47 | LCDR1 (IMGT) | QGISSY |

TABLE 2-continued

Exemplary anti-NPR1 antibody sequences

| SEQ ID NO: 45 | LCDR2 (IMGT) | TAS |
|---|---|---|
| SEQ ID NO: 134 | LCDR3 (IMGT) | QQTWRKPRT |
| SEQ ID NO: 136 | VL | DIQMTQSPSSLSASVGDRVTITCRASQGISSYLAWYQQKPGKAPKLLIYTAS<br>TLQSGVPSRFSGSGSGTDFTLTISSLQPEDFATYYCQQTWRKPRTFGQGTKV<br>EIK |
| SEQ ID NO: 143 | DNA VL | gacatccagatgacccagtctccgtcctccctgtccgcatcagtgggggacagagtgaccatcacttgt<br>cgggcctcccaaggcatctcgtcatacctggcctggtatcagcagaaacccggaaaggctccaaagctg<br>ctcatctacaccgcctcgactctgcaatccggagtgccttcccgcttctccggatccggttcgggaacc<br>gacttcaccctcaccattagcagccttcagccggaagatttcgcgacctactactgccagcaaacctgg<br>cggaagcccaggacatttggccagggcactaaggtcgagattaag |
| SEQ ID NO: 138 | Light Chain | DIQMTQSPSSLSASVGDRVTITCRASQGISSYLAWYQQKPGKAPKLLIYTAS<br>TLQSGVPSRFSGSGSGTDFTLTISSLQPEDFATYYCQQTWRKPRTFGQGTKV<br>EIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVT<br>KSFNRGEC |
| SEQ ID NO: 144 | DNA Light Chain | gacatccagatgacccagtctccgtcctccctgtccgcatcagtgggggacagagtgaccatcacttgt<br>cgggcctcccaaggcatctcgtcatacctggcctggtatcagcagaaacccggaaaggctccaaagctg<br>ctcatctacaccgcctcgactctgcaatccggagtgccttcccgcttctccggatccggttcgggaacc<br>gacttcaccctcaccattagcagccttcagccggaagatttcgcgacctactactgccagcaaacctgg<br>cggaagcccaggacatttggccagggcactaaggtcgagattaagcgtacggtggccgctcccagcgtg<br>ttcatcttcccccccagcgacgagcagctgaagagcggcaccgccagcgtggtgtgcctgctgaacaac<br>ttctaccccggaggccaaggtgcagtgaaggtggacaacgccctgcagagcggcaacagccaggag<br>agcgtcaccgagcaggacagcaaggactccacctacagcctgagcagcaccctgaccctgagcaaggcc<br>gactacgagaagcataaggtgtacgcctgcgaggtgacccaccagggcctgtccagcccgtgaccaag<br>agcttcaacaggggcgagtgc |

XX17_LALA

| SEQ ID NO: 28 | HCDR1 (Combined) | GFTFSSYWMN |
|---|---|---|
| SEQ ID NO: 119 | HCDR2 (Combined) | VIESKGNYIFYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 119 | HCDR2 (Kabat) | VIESKGNYIFYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 120 | HCDR2 (Chothia) | ESKGNY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 121 | HCDR2 (IMGT) | IESKGNYI |
| SEQ ID NO: 36 | HCDR3 (IMGT) | ARDRYSMIYSYGAGAFDY |
| SEQ ID NO: 201 | VH | QVQLLESGGGLVQPGGSLRLSCAASGFTFSSYWMNWVRQAPGKGLEWVS<br>VIESKGNYIFYADSVKGRFTISRDNSKNTLYLQMNSLRAEDTAVYYCARDR<br>YSMIYSYGAGAFDYWGQGTLVTVSS |
| SEQ ID NO: 202 | DNA VH | caagttcaattgctggaaagcggaggtggacttgtccaacctggagggtcactccgactgtcttgcgct<br>gcatcaggattcaccttagtagctattggatgaactgggtccggcaggctcctgggaaagggcttgag<br>tgggtaagtgtcattgaatcaaagggcaactatctttatgctgattctgtaaagggtaggttcacc<br>atctccagggacaattcaaaaatactttgtatctgcagatgaactctctcagggcagaagacacggcc<br>gtttattactgcgcccgcgatcgatacagcatgatatactcctacggcgcaggagcttttgactactgg<br>ggtcaaggcacacttgttactgtcagtagc |
| SEQ ID NO: 203 | Heavy Chain | QVQLLESGGGLVQPGGSLRLSCAASGFTFSSYWMNWVRQAPGKGLEWVS<br>VIESKGNYIFYADSVKGRFTISRDNSKNTLYLQMNSLRAEDTAVYYCARDR<br>YSMIYSYGAGAFDYWGQGTLVTVSSASTKGPSVFPLAPSSKSTSGGTAALG<br>CLVKDYFPEPVTVSWNSGALTSGVHTFPAVLQSSGLYSLSSVVTVPSSSLGT<br>QTYICNVNHKPSNTKVDKRVEPKSCDKTHTCPPCPAPEAAGGPSVFLFPPKP<br>KDTLMISRTPEVTCVVVDVSHEDPEVKFNWYVDGVEVHNAKTKPREEQY<br>NSTYRVVSVLTVLHQDWLNGKEYKCKVSNKALPAPIEKTISKAKGQPREP<br>QVYTLPPSREEMTKNQVSLTCLVKGFYPSDIAVEWESNGQPENNYKTTPPV<br>LDSDGSFFLYSKLTVDKSRWQQGNVFSCSVMHEALHNHYTQKSLSLSPGK |

TABLE 2-continued

Exemplary anti-NPR1 antibody sequences

| SEQ ID NO: 204 | DNA Heavy Chain | caagttcaattgctggaaagcggaggtggacttgtccaacctggagggtcactccgactgtcttgcgct gcatcaggattcacctttagtagctattggatgaactgggtccggcaggctcctgggaaagggcttgag tgggtaagtgtcattgaatcaaagggcaactacatcttttatgctgattctgtaaagggtaggttcacc atctccagggacaattcaaaaaatactttgtatctgcagatgaactctctcagggcagaagacacggcc gtttattactgcgcccgcgatcgatacagcatgatatactcctacggcgcaggagcttttgactactgg ggtcaaggcacacttgttactgtcagtagcgcctcaacgaaaggaccgtccgtgtttcctcttgctcct agctccaaaatccacctcaggtggaacggccgccctgggggtgcctggtaaaggactatttcccagagca gttactgtgtcttggaattctggtgcattgacaagtggcgtacacttttcccgcggtcctccaatct agtggtctgtactcactgtcctccgttgtgactgtcccaagtagctcacttggcacacagacttacatc tgtaatgttaatcataagccgtcaaacacgaaggtggataagagggtagaacctaagtcatgtgacaaa acgtacttgccccccctgccctgcgccggaagccgctggcggaccctccgtattcttgttccctcca aagccaaaggacactctgatgattagccggacaccggaggtcacttgtgttgtagttgacgtcagccat gaggatcctgaggtgaaatttaattggtacgtggacggggttgaagtccacaatgctaaaactaaacct agggaagagcaatataatagtacatacagggttgtcagtgtgctgaccgttctccatcaggactggctg aacggcaaggaatacaagtgcaaggtcagcaacaaggccttgccggccccatcgagaagagatctcc aaagccaaggggcaaccccgagaaccgcaggtatacacgctccccccagtagagaagagatgacaaag aatcaagtttccttgacgtgccttgtgaaaggcttctacccagtgacatcgcagtcgaatgggagagc aacgggcagccggagaataactataaaacaaccccccccgtgcttgactcagacgggtcattttttctg tatagcaaattgactgttgataaatacggtggcaacaaggaaacgtgtttagttgcagcgtaatgcac gaagctctccacaatcactatactcaaaagtcactgtcactctcccctggcaag |
|---|---|---|
| SEQ ID NO: 41 | LCDR1 (Combined) | RASQGISSYLA |
| SEQ ID NO: 42 | LCDR2 (Combined) | TASTLQS |
| SEQ ID NO: 145 | LCDR3 (Combined) | QQIWTVPRT |
| SEQ ID NO: 41 | LCDR1 (Kabat) | RASQGISSYLA |
| SEQ ID NO: 42 | LCDR2 (Kabat) | TASTLQS |
| SEQ ID NO: 145 | LCDR3 (Kabat) | QQIWTVPRT |
| SEQ ID NO: 44 | LCDR1 (Chothia) | SQGISSY |
| SEQ ID NO: 45 | LCDR2 (Chothia) | TAS |
| SEQ ID NO: 146 | LCDR3 (Chothia) | IWTVPR |
| SEQ ID NO: 47 | LCDR1 (IMGT) | QGISSY |
| SEQ ID NO: 45 | LCDR2 (IMGT) | TAS |
| SEQ ID NO: 145 | LCDR3 (IMGT) | QQIWTVPRT |
| SEQ ID NO: 147 | VL | DIQMTQSPSSLSASVGDRVTITCRASQGISSYLAWYQQKPGKAPKLLIYTAS TLQSGVPSRFSGSGSGTDFTLTISSLQPEDFATYYCQQIWTVPRTFGQGTKV EIK |
| SEQ ID NO: 212 | DNA VL | gacatacagatgactcagagtcctcctccctcagtgcttcagtgggtgatcgcgtgacgatcacgtgc agagcctcacaaggatctccagttacctggcctggtatcaacaaaaaccaggcaaggcgcctaagctg ttgatatatacggcatctactattgcagtctgggggtaccaagtcgattcagtggttctggctcaggcact gactttaccctttacaatatcaagtcttcagccggaggattttcgcaacttactattgccagcagatttgg acggtgccgcgcactttcggtcagggaacaaaggtggaaataaaa |
| SEQ ID NO: 149 | Light Chain | DIQMTQSPSSLSASVGDRVTITCRASQGISSYLAWYQQKPGKAPKLLIYTAS TLQSGVPSRFSGSGSGTDFTLTISSLQPEDFATYYCQQIWTVPRTFGQGTKV EIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVT KSFNRGEC |
| SEQ ID NO: 213 | DNA Light Chain | gacatacagatgactcagagtcctcctccctcagtgcttcagtgggtgatcgcgtgacgatcacgtgc agagcctcacaaggatctccagttacctggcctggtatcaacaaaaaccaggcaaggcgcctaagctg ttgatatatacggcatctactattgcagtctgggggtaccaagtcgattcagtggttctggctcaggcact gactttaccctttacaatatcaagtcttcagccggaggattttcgcaacttactattgccagcagatttgg acggtgccgcgcactttcggtcagggaacaaaggtggaaataaaaagaaccggtcgcagcaccgagtgtt ttcatcttccctccctcgacgagcagcttaaaagcggtacagccagcgtagtgtgtttgttgaataat ttttatccacgcgaagcaaaagttcagtggaaggtagacaacgcattgcaaagcggaaattcccaagaa agtgttacggagcaagacagtaaggactctacatattccttgtcatcaacactcacccttagtaaagca gattacgagaaacacaaggtctatgcatgtgaggtaacgcatcagggcctctccagtcccgtcaccaag tccttcaacagggggtgagtgc |

XX17_DAPA

| SEQ ID NO: 28 | HCDR1 (Combined) | GFTFSSYWMN |
| SEQ ID NO: 119 | HCDR2 (Combined) | VIESKGNYIFYADSVKG |

TABLE 2-continued

Exemplary anti-NPR1 antibody sequences

| SEQ ID NO: 30 | HCDR3 (Combined) | DRYSMIYSYGAGAFDY |
|---|---|---|
| SEQ ID NO: 31 | HCDR1 (Kabat) | SYWMN |
| SEQ ID NO: 119 | HCDR2 (Kabat) | VIESKGNYIFYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 120 | HCDR2 (Chothia) | ESKGNY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 121 | HCDR2 (IMGT) | IESKGNYI |
| SEQ ID NO: 36 | HCDR3 (IMGT) | ARDRYSMIYSYGAGAFDY |
| SEQ ID NO: 122 | VH | EVQLLESGGGLVQPGGSLRLSCAASGFTFSSYWMNWVRQAPGKGLEWVS<br>VIESKGNYIFYADSVKGRFTISRDNSKNTLYLQMNSLRAEDTAVYYCARDR<br>YSMIYSYGAGAFDYWGQGTLVTVSS |
| SEQ ID NO: 207 | DNA VH | gaagtgcagctgctggaatccggcggaggtctggtccagcctggaggttccctgcgcctgtcatgcgca<br>gcctccggattcaccttttcgtcgtactggatgaactgggtcagacaggctcctggaaagggcctggaa<br>tgggtgtctgtgattgaatccaaggggaactacatcttctacgcggacagcgtgaagggccggttcact<br>atcagcagagacaacagcaagaacaccctgtacctccaaatgaactcgctgagggccgaagatactgcc<br>gtgtactactgtgcccgcgatcgctactcgatgatctacagctatggtgccggagcgttcgattactgg<br>ggacagggaaccctcgtgaccgtcagctcc |
| SEQ ID NO: 208 | Heavy Chain | EVQLLESGGGLVQPGGSLRLSCAASGFTFSSYWMNWVRQAPGKGLEWVS<br>VIESKGNYIFYADSVKGRFTISRDNSKNTLYLQMNSLRAEDTAVYYCARDR<br>YSMIYSYGAGAFDYWGQGTLVTVSSASTKGPSVFPLAPSSKSTSGGTAALG<br>CLVKDYFPEPVTVSWNSGALTSGVHTFPAVLQSSGLYSLSSVVTVPSSSLGT<br>QTYICNVNHKPSNTKVDKRVEPKSCDKTHTCPPCPAPELLGGPSVFLFPPKP<br>KDTLMISRTPEVTCVVVAVSHEDPEVKFNWYVDGVEVHNAKTKPREEQY<br>NSTYRVVSVLTVLHQDWLNGKEYKCKVSNKALAAPIEKTISKAKGQPREP<br>QVYTLPPSREEMTKNQVSLTCLVKGFYPSDIAVEWESNGQPENNYKTTPPV<br>LDSDGSFFLYSKLTVDKSRWQQGNVFSCSVMHEALHNHYTQKSLSLSPGK |
| SEQ ID NO: 209 | DNA Heavy Chain | gaagtgcagctgctggaatccggcggaggtctggtccagcctggaggttccctgcgcctgtcatgcgca<br>gcctccggattcaccttttcgtcgtactggatgaactgggtcagacaggctcctggaaagggcctggaa<br>tgggtgtctgtgattgaatccaaggggaactacatcttctacgcggacagcgtgaagggccggttcact<br>atcagcagagacaacagcaagaacaccctgtacctccaaatgaactcgctgagggccgaagatactgcc<br>gtgtactactgtgcccgcgatcgctactcgatgatctacagctatggtgccggagcgttcgattactgg<br>ggacagggaaccctcgtgaccgtcagctccgcctcaaccaagggcccgtcagtgttcccgctggctcca<br>tcgtcgaagtccacctccggaggaaccgcagcactcggttgcctggtcaaggactacttccctgagcga<br>gtgaccgtgtcgtggaacagcggagccctgacttccggcgtgcacacttttcccgcggtgctgcagtcc<br>tccggtctgtactcccttttcgtccgtggtcaccgtgccgtcgtctagcctgggcacccagacctacatc<br>tgcaacgtgaaccacaagccgtccaacaccaaagtggataagcgggtggagccgaagtcctgcgataag<br>acacacgtgccgccatgtccagcgcctgaattgcttggcggaccttccgtgttcctgttcccgcct<br>aagcccaaggacaccttgatgattagccggactcccgaagtcacctgtgtggtggcagtgtcccac<br>gaggaccccgaggtcaagtttaattggtacgtggacggcgtcgaagtgcacaacgccaagactaagccc<br>cgggaggaacagtacaacagcacctaccgggtcgtgtccgtgctgaccgtgctgcaccaggactggctg<br>aatgggaaagagtacaagtgcaaagtgtccaacaaggccttggccgctcctatcgaaaaaactatcagc<br>aaggctaagggacagccgagggaacccaagtctacacccttgcccccttcacgcgaagatgaccaag<br>aatcaagtgtcgctgacctgcctcgtcaagggattctaccccctccgacattgcgttggagtgggagtcc<br>aacggccagcccgagaacaactacaagactactccgcccgtgctggactccgacggcagcttcttcctg<br>tattccaagctgaccgtggacaagtcccggtggcagcaaggaaacgtgttctcctgctcggtcatgcac<br>gaagccctgcacaaccactatacgcagaagtccctgtccttgagcccggggaaa |
| SEQ ID NO: 41 | LCDR1 (Combined) | RASQGISSYLA |
| SEQ ID NO: 42 | LCDR2 (Combined) | TASTLQS |
| SEQ ID NO: 145 | LCDR3 (Combined) | QQIWTVPRT |
| SEQ ID NO: 41 | LCDR1 (Kabat) | RASQGISSYLA |
| SEQ ID NO: 42 | LCDR2 (Kabat) | TASTLQS |
| SEQ ID NO: 145 | LCDR3 (Kabat) | QQIWTVPRT |
| SEQ ID NO: 44 | LCDR1 (Chothia) | SQGISSY |
| SEQ ID NO: 45 | LCDR2 (Chothia) | TAS |

TABLE 2-continued

Exemplary anti-NPR1 antibody sequences

| SEQ ID NO: 146 | LCDR3 (Chothia) | IWTVPR |
|---|---|---|
| SEQ ID NO: 47 | LCDR1 (IMGT) | QGISSY |
| SEQ ID NO: 45 | LCDR2 (IMGT) | TAS |
| SEQ ID NO: 145 | LCDR3 (IMGT) | QQIWTVPRT |
| SEQ ID NO: 147 | VL | DIQMTQSPSSLSASVGDRVTITCRASQGISSYLAWYQQKPGKAPKLLIYTAS<br>TLQSGVPSRFSGSGSGTDFTLTISSLQPEDFATYYCQQIWTVPRTFGQGTKV<br>EIK |
| SEQ ID NO: 214 | DNA VL | gacatccagatgacccagtctccgtcctccctgtccgcatcagtgggggacagagtgaccatcacttgt<br>cgggcctcccaaggcatctcgtcatacctggcctggtatcagcagaaacccggaaaggctccaaagctg<br>ctcatctacaccgcctcgactctgcaatccggagtgccttcccgcttctccggatccggttcgggaacc<br>gacttcaccctcaccattagcagccttcagccggaagatttcgcgacctactactgccagcaaatctgg<br>accgtgcccaggacatttggccagggcactaaggtcgagattaag |
| SEQ ID NO: 149 | Light Chain | DIQMTQSPSSLSASVGDRVTITCRASQGISSYLAWYQQKPGKAPKLLIYTAS<br>TLQSGVPSRFSGSGSGTDFTLTISSLQPEDFATYYCQQIWTVPRTFGQGTKV<br>EIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVT<br>KSFNRGEC |
| SEQ ID NO: 215 | DNA Light Chain | gacatccagatgacccagtctccgtcctccctgtccgcatcagtgggggacagagtgaccatcacttgt<br>cgggcctcccaaggcatctcgtcatacctggcctggtatcagcagaaacccggaaaggctccaaagctg<br>ctcatctacaccgcctcgactctgcaatccggagtgccttcccgcttctccggatccggttcgggaacc<br>gacttcaccctcaccattagcagccttcagccggaagatttcgcgacctactactgccagcaaatctgg<br>accgtgcccaggacatttggccagggcactaaggtcgagattaagcgtacggtggccgctcccagcgtg<br>ttcatcttcccccccagcgacgagcagctgaagagcggcaccgccagcgtggtgtgcctgctgaacaac<br>ttctaccccggggaggccaaggtgcagtggaaggtggacaacgccctgcagagcggcaacagccaggag<br>agcgtcgagcaggacagcaaggactccaccctacagcctgagcagcaccctgaccctgagcaaggcc<br>gactacgagaagcataaggtgtacgcctgcgaggtgacccaccagggcctgtccagcccgtgaccaag<br>agcttcaacaggggcgagtgc |

XX18_LALA

| SEQ ID NO: 28 | HCDR1 (Combined) | GFTFSSYWMN |
|---|---|---|
| SEQ ID NO: 119 | HCDR2 (Combined) | VIESKGNYIFYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 119 | HCDR2 (Kabat) | VIESKGNYIFYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 120 | HCDR2 (Chothia) | ESKGNY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 121 | HCDR2 (IMGT) | IESKGNYI |
| SEQ ID NO: 36 | HCDR3 (IMGT) | ARDRYSMIYSYGAGAFDY |
| SEQ ID NO: 201 | VH | QVQLLESGGGLVQPGGSLRLSCAASGFTFSSYWMNWVRQAPGKGLEWVS<br>VIESKGNYIFYADSVKGRFTISRDNSKNTLYLQMNSLRAEDTAVYYCARDR<br>YSMIYSYGAGAFDYWGQGTLVTVSS |
| SEQ ID NO: 202 | DNA VH | caagttcaattgctggaaagcggaggtggacttgtccaacctggagggtcactccgactgtcttgcgct<br>gcatcaggattcacctttagtagctattggatgaactgggtccgccaggctcctgggaaagggcttgag<br>tgggtaagtgtcattgaatcaaagggcaactatctctttatgctgattctgtaaagggtaggttcacc<br>atctccagggacaattcaaaaatactttgtatctgcagatgaactctctcagggcagaagacacggcc<br>gtttattactgcgcccgcgatcgatacagcatgatatactcctacggcgcaggagcttttgactactgg<br>ggtcaaggcacacttgttactgtcagtagc |
| SEQ ID NO: 203 | Heavy Chain | QVQLLESGGGLVQPGGSLRLSCAASGFTFSSYWMNWVRQAPGKGLEWVS<br>VIESKGNYIFYADSVKGRFTISRDNSKNTLYLQMNSLRAEDTAVYYCARDR<br>YSMIYSYGAGAFDYWGQGTLVTVSSASTKGPSVFPLAPSSKSTSGGTAALG<br>CLVKDYFPEPVTVSWNSGALTSGVHTFPAVLQSSGLYSLSSVVTVPSSSLGT<br>QTYICNVNHKPSNTKVDKRVEPKSCDKTHTCPPCPAPEAAGGPSVFLFPPKP<br>KDTLMISRTPEVTCVVVDVSHEDPEVKFNWYVDGVEVHNAKTKPREEQY |

TABLE 2-continued

Exemplary anti-NPR1 antibody sequences

|  |  |  |
|---|---|---|
|  |  | NSTYRVVSVLTVLHQDWLNGKEYKCKVSNKALPAPIEKTISKAKGQPREP<br>QVYTLPPSREEMTKNQVSLTCLVKGFYPSDIAVEWESNGQPENNYKTTPPV<br>LDSDGSFFLYSKLTVDKSRWQQGNVFSCSVMHEALHNHYTQKSLSLSPGK |
| SEQ ID NO: 204 | DNA Heavy Chain | caagttcaattgctggaaagcggaggtggacttgtccaacctggagggtcactccgactgtcttgcgct<br>gcatcaggattcacctttagtagctattggatgaactgggtccggcaggctcctgggaaagggcttgag<br>tgggtaagtgtcattgaatcaaaggcgaactacatcttttatgctgattctgtaaagggtaggttcacc<br>atctccaggacaattcaaaaaatactttgtatctgcagatgaactctctcagggcagaagacacggcc<br>gtttattactgcgcccgcgatcgatacagcatgatatactcctacggcgcaggagcttttgactactgg<br>ggtcaaggcacacttgttactgtcagtagcgcctcaacgaaaggaccgtccgtgtttcctcttgctcct<br>agctccaaatccacctcaggtggaacggccgcccctggggtgcctggtaaaggactatttcccagagcca<br>gttactgtgtcttggaattctggtgcattgacaagtggcgtacacacttttcccgcggtcctccaatct<br>agtggtctgtactcactgtcctccgttgtgactgtcccaagtagctcacttggcacacagacttacatc<br>tgtaatgttaatcataagccgtcaaacacgaaggtggataagagggtagaacctaagtcatgtgacaaa<br>acgcatacttgccccccctgccctgcgcccgaagccgctggcggaccctccgtattcttgttccctcca<br>aagccaaaggacactctgatgattagccggacaccggaggtcacttgtgttgtagttgacgtcagccat<br>gaggatcctgaggtgaaatttaattggtacgtggacggggttgaagtccacaatgctaaaactaaacct<br>agggaagagcaatataatagtacatacagggttgtcagtgtgctgaccgttctccatcaggactggctg<br>aacggcaaggaaatacaagtgcaaggtcagcaacaaggcctttgccggccccatcgagaagacgatctcc<br>aaagccaaggggcaaccccgagaaccgcaggtatacacgctcccccctagtagagaagagatgacaaag<br>aatcaagtttccttgacgtgccttgtgaaaggcttctaccctagtgacatcgcagtcgaatgggagagc<br>aacgggcagccggagaataactataaaacaaccccccccgtgcttgactcagacgggtcattttttctg<br>tatagcaaattgactgttgataaatacggtggcaacaaggaaacgtgtttagttgcagcgtaatgcac<br>gaagctctccacaatcactatactcaaaagtcactgtcactctcccctggcaag |
| SEQ ID NO: 41 | LCDR1 (Combined) | RASQGISSYLA |
| SEQ ID NO: 42 | LCDR2 (Combined) | TASTLQS |
| SEQ ID NO: 172 | LCDR3 (Combined) | QQEWAKPRT |
| SEQ ID NO: 41 | LCDR1 (Kabat) | RASQGISSYLA |
| SEQ ID NO: 42 | LCDR2 (Kabat) | TASTLQS |
| SEQ ID NO: 172 | LCDR3 (Kabat) | QQEWAKPRT |
| SEQ ID NO: 44 | LCDR1 (Chothia) | SQGISSY |
| SEQ ID NO: 45 | LCDR2 (Chothia) | TAS |
| SEQ ID NO: 173 | LCDR3 (Chothia) | EWAKPR |
| SEQ ID NO: 47 | LCDR1 (IMGT) | QGISSY |
| SEQ ID NO: 45 | LCDR2 (IMGT) | TAS |
| SEQ ID NO: 172 | LCDR3 (IMGT) | QQEWAKPRT |
| SEQ ID NO: 174 | VL | DIQMTQSPSSLSASVGDRVTITCRASQGISSYLAWYQQKPGKAPKLLIYTAS<br>TLQSGVPSRFSGSGSGTDFTLTISSLQPEDFATYYCQQEWAKPRTFGQGTKV<br>EIK |
| SEQ ID NO: 199 | DNA VL | gatatacagatgacgcaaagtccctctagtctttctgcaagtgtcggggacagagttaccattacctgc<br>agagcgtcacaaggcatctctagttatctcgcgtggtaccaacagaagccaggtaaagcacctaaactg<br>ttgatttacacggcatcaacattgcagtcaggtgtcccctcccgatttagtggcagtggtagcggtaca<br>gatttactcttaccatttcatctcttcagccagaagattttgctacgtactactgtcaacaagaatgg<br>gctaaaccacgaacctttggacagggtacgaaggtcgaaataaaa |
| SEQ ID NO: 176 | Light Chain | DIQMTQSPSSLSASVGDRVTITCRASQGISSYLAWYQQKPGKAPKLLIYTAS<br>TLQSGVPSRFSGSGSGTDFTLTISSLQPEDFATYYCQQEWAKPRTFGQGTKV<br>EIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVT<br>KSFNRGEC |
| SEQ ID NO: 200 | DNA Light Chain | gatatacagatgacgcaaagtccctctagtctttctgcaagtgtcggggacagagttaccattacctgc<br>agagcgtcacaaggcatctctagttatctcgcgtggtaccaacagaagccaggtaaagcacctaaactg<br>ttgatttacacggcatcaacattgcagtcaggtgtcccctcccgatttagtggcagtggtagcggtaca<br>gatttactcttaccatttcatctcttcagccagaagattttgctacgtactactgtcaacaagaatgg<br>gctaaaccacgaacctttggacagggtacgaaggtcgaaataaaaacggaccgttgccgccccctccgtc<br>ttcatcttccccccgtctgacgagcagctcaaatccggcacagcttctgtagtctgcttgctgaataac<br>ttctacccaagagaagccaaagttcagtggaaggtcgataatgcattgcaatctggtaatagtcaggaa<br>tctgtgactgagcaggatagcaaagactcaacttacagcctctcttcaaccttgacgttgtccaaagcg<br>gattatgagaaacacaaggtgtacgcttgcgaggtgacgcatcaagggcttagttccccggtaaccaaa<br>tctttcaaccgaggtgaatgc |

TABLE 2-continued

Exemplary anti-NPR1 antibody sequences

XX18_DAPA

| SEQ ID NO: 28 | HCDR1 (Combined) | GFTFSSYWMN |
| --- | --- | --- |
| SEQ ID NO: 119 | HCDR2 (Combined) | VIESKGNYIFYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 119 | HCDR2 (Kabat) | VIESKGNYIFYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 120 | HCDR2 (Chothia) | ESKGNY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 121 | HCDR2 (IMGT) | IESKGNYI |
| SEQ ID NO: 36 | HCDR3 (IMGT) | ARDRYSMIYSYGAGAFDY |
| SEQ ID NO: 122 | VH | EVQLLESGGGLVQPGGSLRLSCAASGFTFSSYWMNWVRQAPGKGLEWVS<br>VIESKGNYIFYADSVKGRFTISRDNSKNTLYLQMNSLRAEDTAVYYCARDR<br>YSMIYSYGAGAFDYWGQGTLVTVSS |
| SEQ ID NO: 207 | DNA VH | gaagtgcagctgctggaatccggcggaggtctggtccagcctggaggttccctgcgcctgtcatgcgca<br>gcctccggattcacctttcgtcgtactggatgaactgggtcagacaggctcctggaaagggcctggaa<br>tgggtgtctgtgattgaatccaaggggaactacatcttctacgcggacagcgtgaagggccggttcact<br>atcagcagagacaacagcaagaacaccctgtacctccaaatgaactcgctgagggccgaagatactgcc<br>gtgtactactgtgcccgcgatcgctactcgatgatctacagctatggtgccggagcgttcgattactgg<br>ggacagggaaccctcgtgaccgtcagctcc |
| SEQ ID NO: 208 | Heavy Chain | EVQLLESGGGLVQPGGSLRLSCAASGFTFSSYWMNWVRQAPGKGLEWVS<br>VIESKGNYIFYADSVKGRFTISRDNSKNTLYLQMNSLRAEDTAVYYCARDR<br>YSMIYSYGAGAFDYWGQGTLVTVSSASTKGPSVFPLAPSSKSTSGGTAALG<br>CLVKDYFPEPVTVSWNSGALTSGVHTFPAVLQSSGLYSLSSVVTVPSSSLGT<br>QTYICNVNHKPSNTKVDKRVEPKSCDKTHTCPPCPAPELLGGPSVFLFPPKP<br>KDTLMISRTPEVTCVVVAVSHEDPEVKFNWYVDGVEVHNAKTKPREEQY<br>NSTYRVVSVLTVLHQDWLNGKEYKCKVSNKALAAPIEKTISKAKGQPREP<br>QVYTLPPSREEMTKNQVSLTCLVKGFYPSDIAVEWESNGQPENNYKTTPPV<br>LDSDGSFFLYSKLTVDKSRWQQGNVFSCSVMHEALHNHYTQKSLSLSPGK |
| SEQ ID NO: 209 | DNA Heavy Chain | gaagtgcagctgctggaatccggcggaggtctggtccagcctggaggttccctgcgcctgtcatgcgca<br>gcctccggattcacctttcgtcgtactggatgaactgggtcagacaggctcctggaaagggcctggaa<br>tgggtgtctgtgattgaatccaaggggaactacatcttctacgcggacagcgtgaagggccggttcact<br>atcagcagagacaacagcaagaacaccctgtacctccaaatgaactcgctgagggccgaagatactgcc<br>gtgtactactgtgcccgcgatcgctactcgatgatctacagctatggtgccggagcgttcgattactgg<br>ggacagggaaccctcgtgaccgtcagctccgcctcaaccaaggggcccgtcagtgttcccgctggctcca<br>tcgtcgaagtccacctccgagggaaccgcagcactcggttgcctggtcaaggactacttccctgagcca<br>gtgaccgtgtcgtggaacagcggagccctgacttccggcgtgcacacttttccgcggtgctgcagtcc<br>tccggtctgtactcccttcgtccgtggtcaccgtgccgtcgtctagcctgggcacccagacctacatc<br>tgcaacgtgaaccacaagccgtccaacaccaaagtggataagcgggtggagccgaagtcctgcgataag<br>acacacacgtgcccgccatgtccagcgcctgaattgcttggcggaccttccgtgttcctgttcccgcct<br>aagcccaaggacaccttgatgattagccggactcccgaagtcacctgtgtggtggtggcagtgtcccac<br>gaggaccccgaggtcaagtttaattggtacgtggacggcgtcgaagtgcacaacgccaagactaagccc<br>cgggaggaacagtacaacagcacctaccgggtcgtgtccgtcctgaccgtgctgcaccaggactgcgtg<br>aatgggaaagagtacaagtgcaaagtgtccaacaaggccttggccgctcctatcgaaaaaactatcagc<br>aaggctaagggacagccgagggaaccccaagtctacaccctgccccttcacgcgaaagagatgaccaag<br>aatcaagtgtcgctgacctgcctcgtcaagggattctaccccctcgacattgcggtggagtgggagtcc<br>aacgggccagcccgagaacaactacaagactactccgcccgtcggactccgacggcagcttcttcctg<br>tattccaagctgaccgtgacaagtcccggtggcagcaaggaaacgtgttctcctgctcggtcatgcac<br>gaagccctgcacaaccactatacgcagaagtccctgtccttgagcccggggaaa |
| SEQ ID NO: 41 | LCDR1 (Combined) | RASQGISSYLA |
| SEQ ID NO: 42 | LCDR2 (Combined) | TASTLQS |
| SEQ ID NO: 172 | LCDR3 (Combined) | QQEWAKPRT |
| SEQ ID NO: 41 | LCDR1 (Kabat) | RASQGISSYLA |
| SEQ ID NO: 42 | LCDR2 (Kabat) | TASTLQS |

TABLE 2-continued

Exemplary anti-NPR1 antibody sequences

| SEQ ID NO: 172 | LCDR3 (Kabat) | QQEWAKPRT |
|---|---|---|
| SEQ ID NO: 44 | LCDR1 (Chothia) | SQGISSY |
| SEQ ID NO: 45 | LCDR2 (Chothia) | TAS |
| SEQ ID NO: 173 | LCDR3 (Chothia) | EWAKPR |
| SEQ ID NO: 47 | LCDR1 (IMGT) | QGISSY |
| SEQ ID NO: 45 | LCDR2 (IMGT) | TAS |
| SEQ ID NO: 172 | LCDR3 (IMGT) | QQEWAKPRT |
| SEQ ID NO: 174 | VL | DIQMTQSPSSLSASVGDRVTITCRASQGISSYLAWYQQKPGKAPKLLIYTAS TLQSGVPSRFSGSGSGTDFTLTISSLQPEDFATYYCQQEWAKPRTFGQGTKV EIK |
| SEQ ID NO: 216 | DNA VL | gacatccagatgacccagtctccgtcctccctgtccgcatcagtgggggacagagtgaccatcacttgt cgggcctcccaaggcatctcgtcatacctggcctggtatcagcagaaacccggaaaggctccaaagctg ctcatctacaccgcctcgactctgcaatccggagtgccttcccgcttctccggatccggttcgggaacc gacttcaccctcaccattagcagccttcagccggaagatttcgcgacctactactgccagcaagaatgg gccaagcccaggacatttggccagggcactaaggtcgagattaag |
| SEQ ID NO: 176 | Light Chain | DIQMTQSPSSLSASVGDRVTITCRASQGISSYLAWYQQKPGKAPKLLIYTAS TLQSGVPSRFSGSGSGTDFTLTISSLQPEDFATYYCQQEWAKPRTFGQGTKV EIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVT KSFNRGEC |
| SEQ ID NO: 217 | DNA Light Chain | gacatccagatgacccagtctccgtcctccctgtccgcatcagtgggggacagagtgaccatcacttgt cgggcctcccaaggcatctcgtcatacctggcctggtatcagcagaaacccggaaaggctccaaagctg ctcatctacaccgcctcgactctgcaatccggagtgccttcccgcttctccggatccggttcgggaacc gacttcaccctcaccattagcagccttcagccggaagatttcgcgacctactactgccagcaagaatgg gccaagcccaggacatttggccagggcactaaggtcgagattaagcgtacggtggccgctcccagcgtg ttcatcttccccccctcagcgacgagcagctgaagagcggcaccgccagcgtggtgctgctgaacaac ttctaccccgggaggccaaggtgcagtggaaggtggacaacgccctgcagagcggcaacagccaggag agcgtcaccgagcaggacagcaaggactccacctacagcctgagcagcaccctgaccctgagcaaggcc gactacgagaagcataaggtgtacgcctgcgaggtgacccaccagggcctgtccagcccgtgaccaag agcttcaacagggggcgagtgc |

XX19_LALA

| SEQ ID NO: 28 | HCDR1 (Combined) | GFTFSSYWMN |
|---|---|---|
| SEQ ID NO: 119 | HCDR2 (Combined) | VIESKGNYIFYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 119 | HCDR2 (Kabat) | VIESKGNYIFYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 120 | HCDR2 (Chothia) | ESKGNY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 121 | HCDR2 (IMGT) | IESKGNYI |
| SEQ ID NO: 36 | HCDR3 (IMGT) | ARDRYSMIYSYGAGAFDY |
| SEQ ID NO: 201 | VH | QVQLLESGGGLVQPGGSLRLSCAASGFTFSSYWMNWVRQAPGKGLEWVS VIESKGNYIFYADSVKGRFTISRDNSKNTLYLQMNSLRAEDTAVYYCARDR YSMIYSYGAGAFDYWGQGTLVTVSS |
| SEQ ID NO: 202 | DNA VH | caagttcaattgctggaaagcggaggtggacttgtccaacctggagggtcactccgactgtcttgcgct gcatcaggattcacctttagtagctattggatgaactgggtccggcaggctcctgggaaagggcttgag tgggtaagtgtcattgaatcaaagggcaactacatcttttatgctgattctgtaaaggtaggttcacc atctccaggacaattcaaaaaatactttgtatctgcagatgaactctctcagggcagaagacacggcc gtttattactgcgcccgcgatcgatacagcatgatatactcctacggcgcaggagcttttgactactgg ggtcaaggcacacttgttactgtcagtagc |

TABLE 2-continued

Exemplary anti-NPR1 antibody sequences

| SEQ ID NO: 203 | Heavy Chain | QVQLLESGGGLVQPGGSLRLSCAASGFTFSSYWMNWVRQAPGKGLEWVS
VIESKGNYIFYADSVKGRFTISRDNSKNTLYLQMNSLRAEDTAVYYCARDR
YSMIYSYGAGAFDYWGQGTLVTVSSASTKGPSVFPLAPSSKSTSGGTAALG
CLVKDYFPEPVTVSWNSGALTSGVHTFPAVLQSSGLYSLSSVVTVPSSSLGT
QTYICNVNHKPSNTKVDKRVEPKSCDKTHTCPPCPAPEAAGGPSVFLFPPKP
KDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK |
| SEQ ID NO: 204 | DNA Heavy Chain | caagttcaattgctggaaagcggaggtggacttgtccaacctggagggtcactccgactgtcttgcgct
gcatcaggattcacctttagtagctattggatgaactgggtccggcaggctcctgggaaagggcttgag
tgggtaagtgtcattgaatcaaagggcaactacatcttttatgctgattctgtaaagggtaggttcacc
atctccagggacaattcaaaaatactttgtatctgcagatgaactctctcaggcagaagacacggcc
gtttattactgcgcccgcgatcgatacagcatgatatactcctacggcgcaggagcttttgactactgg
ggtcaaggcacacttgttactgtcagtagcgcctcaacgaaaggaccgtcgtgtttcctcttgctcct
agctccaaatccacctcaggtggaacggccgccctggggtgcctggtaaaggactatttcccagagcca
gttactgtgtcttggaattctggtgcattgacaagtggcgtacacacttttcccgcggtcctccaatct
agtggtctgtactcactgtcctccgttgtgactgtcccaagtagctcacttggcacacagacttacatc
tgtaatgttaatcataagccgtcaaacacgaaggtggataagagggtagaacctaagtcatgtgacaaa
acgcatacttgcccccctgccctgcgccggaagccgctggcggaccctccgtattcttgttccctcca
aagccaaaggacactctgatgattagccggacaccggaggtcacttgtgttgtagttgacgtcagccat
gaggatcctgaggtgaaatttaattggtacgtggacggggttgaagtccacaatgctaaaactaaacct
agggaagagcaatataatagtacatacaggggttgtcagtgtgctgaccgttctccatcaggactggctg
aacggcaaggaatacaagtgcaaggtcagcaacaaggccttgccggcccccatcgagaagacgatctcc
aaagccaaggggcaaccccgagaaccgcaggtatacacgctccccccagtagagaagagatgacaaag
aatcaagtttccttgacgtgccttgtgaaaggcttctaccctagtgacatcgcagtcgaatgggagagc
aacgggcagccggagaataactataaaacaacccccccgtgcttgactcagacgggtcatttttctg
tatagcaaattgactgttgataaatcacggtggcaacaaggaaacgtgtttagttgcagcgtaatgcac
gaagctctccacaatcactatactcaaaagtcactgtcactctcccctggcaag |
| SEQ ID NO: 41 | LCDR1 (Combined) | RASQGISSYLA |
| SEQ ID NO: 42 | LCDR2 (Combined) | TASTLQS |
| SEQ ID NO: 178 | LCDR3 (Combined) | QQSWTRPRT |
| SEQ ID NO: 41 | LCDR1 (Kabat) | RASQGISSYLA |
| SEQ ID NO: 42 | LCDR2 (Kabat) | TASTLQS |
| SEQ ID NO: 178 | LCDR3 (Kabat) | QQSWTRPRT |
| SEQ ID NO: 44 | LCDR1 (Chothia) | SQGISSY |
| SEQ ID NO: 45 | LCDR2 (Chothia) | TAS |
| SEQ ID NO: 179 | LCDR3 (Chothia) | SWTRPR |
| SEQ ID NO: 47 | LCDR1 (IMGT) | QGISSY |
| SEQ ID NO: 45 | LCDR2 (IMGT) | TAS |
| SEQ ID NO: 178 | LCDR3 (IMGT) | QQSWTRPRT |
| SEQ ID NO: 180 | VL | DIQMTQSPSSLSASVGDRVTITCRASQGISSYLAWYQQKPGKAPKLLIYTAS
TLQSGVPSRFSGSGSGTDFTLTISSLQPEDFATYYCQQSWTRPRTFGQGTKV
EIK |
| SEQ ID NO: 218 | DNA VL | gatattcagatgacgcaatctccgtcttccttgtcagctagtgtaggagaccgcgtcacaattacctgt
agagccagccagggggatttcctcataccttgcatggtaccagcaaaagccaggcaaagcccccaaactg
ctgatctacaccgcgtctaccttgcaatctggtgtgccgtcacgcttttccggctctggctcaggtact
gatttcacattgacgatctcaagtctccagccggaagacttcgcaacttactactgccaacaatcctgg
acgaggccgaggactttcgggcagggaacaaaggttgaaattaaa |
| SEQ ID NO: 182 | Light Chain | DIQMTQSPSSLSASVGDRVTITCRASQGISSYLAWYQQKPGKAPKLLIYTAS
TLQSGVPSRFSGSGSGTDFTLTISSLQPEDFATYYCQQSWTRPRTFGQGTKV
EIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVT
KSFNRGEC |
| SEQ ID NO: 219 | DNA Light Chain | gatattcagatgacgcaatctccgtcttccttgtcagctagtgtaggagaccgcgtcacaattacctgt
agagccagccagggggatttcctcataccttgcatggtaccagcaaaagccaggcaaagcccccaaactg
ctgatctacaccgcgtctaccttgcaatctggtgtgccgtcacgcttttccggctctggctcaggtact
gatttcacattgacgatctcaagtctccagccggaagacttcgcaacttactactgccaacaatcctgg
acgaggccgaggactttcgggcagggaacaaaggttgaaattaaaagaacagtcgcagcaccaagtgtt
tttattttccaccctcagacgagcagctcaagtctggcaccgcgagcgtagtatgtttgttgaataat
ttctaccctagggaagctaaggtacagtggaaagtggataatgctctccaaagtggcaactcccaggaa |

TABLE 2-continued

Exemplary anti-NPR1 antibody sequences tcagtgactgagcaagattcaaaggacagcacgtattctctttcttctacgcttactctctctaaggcc
gactacgaaaaacacaaagtttacgcttgcgaggttacccaccaggggctgtcctcaccagtaacgaaa
agttttaaccggggcgagtgt

XX19_DAPA

| SEQ ID NO: 28 | HCDR1 (Combined) | GFTFSSYWMN |
|---|---|---|
| SEQ ID NO: 119 | HCDR2 (Combined) | VIESKGNYIFYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 119 | HCDR2 (Kabat) | VIESKGNYIFYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 120 | HCDR2 (Chothia) | ESKGNY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 121 | HCDR2 (IMGT) | IESKGNYI |
| SEQ ID NO: 36 | HCDR3 (IMGT) | ARDRYSMIYSYGAGAFDY |
| SEQ ID NO: 122 | VH | EVQLLESGGGLVQPGGSLRLSCAASGFTFSSYWMNWVRQAPGKGLEWVS<br>VIESKGNYIFYADSVKGRFTISRDNSKNTLYLQMNSLRAEDTAVYYCARDR<br>YSMIYSYGAGAFDYWGQGTLVTVSS |
| SEQ ID NO: 207 | DNA VH | gaagtgcagctgctggaatccggcggaggtctggtccagcctggaggttccctgcgcctgtcatgcgca<br>gcctccggattcacctttcgtcgtactggatgaactgggtcagacaggctcctggaaagggcctggaa<br>tgggtgtctgtgattgaatccaaggggaactacatcttctacgcggacagcgtgaagggccggttcact<br>atcagcagagacaacagcaagaacaccctgtacctccaaatgaactcgctgagggccgaagatactgcc<br>gtgtactactgtgcccgcgatcgctactcgatgatctacagctatggtgccggagcgttcgattactgg<br>ggacagggaaccctcgtgaccgtcagctcc |
| SEQ ID NO: 208 | Heavy Chain | EVQLLESGGGLVQPGGSLRLSCAASGFTFSSYWMNWVRQAPGKGLEWVS<br>VIESKGNYIFYADSVKGRFTISRDNSKNTLYLQMNSLRAEDTAVYYCARDR<br>YSMIYSYGAGAFDYWGQGTLVTVSSASTKGPSVFPLAPSSKSTSGGTAALG<br>CLVKDYFPEPVTVSWNSGALTSGVHTFPAVLQSSGLYSLSSVVTVPSSSLGT<br>QTYICNVNHKPSNTKVDKRVEPKSCDKTHTCPPCPAPELLGGPSVFLFPPKP<br>KDTLMISRTPEVTCVVVAVSHEDPEVKFNWYVDGVEVHNAKTKPREEQY<br>NSTYRVVSVLTVLHQDWLNGKEYKCKVSNKALAAPIEKTISKAKGQPREP<br>QVYTLPPSREEMTKNQVSLTCLVKGFYPSDIAVEWESNGQPENNYKTTPPV<br>LDSDGSFFLYSKLTVDKSRWQQGNVFSCSVMHEALHNHYTQKSLSLSPGK |
| SEQ ID NO: 209 | DNA Heavy Chain | gaagtgcagctgctggaatccggcggaggtctggtccagcctggaggttccctgcgcctgtcatgcgca<br>gcctccggattcacctttcgtcgtactggatgaactgggtcagacaggctcctggaaagggcctggaa<br>tgggtgtctgtgattgaatccaaggggaactacatcttctacgcggacagcgtgaagggccggttcact<br>atcagcagagacaacagcaagaacaccctgtacctccaaatgaactcgctgagggccgaagatactgcc<br>gtgtactactgtgcccgcgatcgctactcgatgatctacagctatggtgccggagcgttcgattactgg<br>ggacagggaaccctcgtgaccgtcagctcctccgcctcaaccaaggcccgtcagtgttcccgctggctcca<br>tcgtcgaagtccacctccggaggaaccgcagcactcggttgcctggtcaaggactacttccctgagcca<br>gtgaccgtcgtgaacagcggagccctgacttccggcgtgcacacttttcccgcggtgctgcagtcc<br>tccggtctgtactccctttcgtccgtggtcaccgtgccgtcgtctagcctgggcacccagacctacatc<br>tgcaacgtgaaccacaagccgtccaacaccaaagtggataagcgggtggagcccaagtcctgcgataag<br>acacacacgtgccgccatgtccagcgcctgaattgcttggcggaccttccgtgttcctgttcccgcct<br>aagcccaaggacaccttgatgattagccggactcccgaagtcacctgtgtggtggtggcagtgtcccac<br>gaggaccccgaggtcaagtttaattggtacgtggacggcgtcgaagtgcacaacgccaagactaagccc<br>cgggagaacagtacaacagcacctaccgggtcgtgtccgtgctgaccgtgctgcaccaggactggctg<br>aatgggaaagagtacaagtgcaaagtgtccaacaaggccttggccgctcctatcgaaaaaactatcagc<br>aaggctaagggacagccgagggaaccccaagtctacaccctgcccccttcacgcgaagagatgaccaag<br>aatcaagtgtcgctgacctgcctcgtcaagggattctaccctccgacattgcggtggagtgggagtcc<br>aacggccagcccgagaacaactacaagactactccgcccgtgctggactccgacggcagcttcttcctg<br>tattccaagctgaccgtggacaagtcccggtggcagcaaggaaacgttgttctcctgctcggtcatgcac<br>gaagccctgcacaaccactatacgcagaagtccctgtccttgagcccggggaaa |
| SEQ ID NO: 41 | LCDR1 (Combined) | RASQGISSYLA |
| SEQ ID NO: 42 | LCDR2 (Combined) | TASTLQS |
| SEQ ID NO: 178 | LCDR3 (Combined) | QQSWTRPRT |

TABLE 2-continued

Exemplary anti-NPR1 antibody sequences

| | | |
|---|---|---|
| SEQ ID NO: 41 | LCDR1 (Kabat) | RASQGISSYLA |
| SEQ ID NO: 42 | LCDR2 (Kabat) | TASTLQS |
| SEQ ID NO: 178 | LCDR3 (Kabat) | QQSWTRPRT |
| SEQ ID NO: 44 | LCDR1 (Chothia) | SQGISSY |
| SEQ ID NO: 45 | LCDR2 (Chothia) | TAS |
| SEQ ID NO: 179 | LCDR3 (Chothia) | SWTRPR |
| SEQ ID NO: 47 | LCDR1 (IMGT) | QGISSY |
| SEQ ID NO: 45 | LCDR2 (IMGT) | TAS |
| SEQ ID NO: 178 | LCDR3 (IMGT) | QQSWTRPRT |
| SEQ ID NO: 180 | VL | DIQMTQSPSSLSASVGDRVTITCRASQGISSYLAWYQQKPGKAPKLLIYTAS<br>TLQSGVPSRFSGSGSGTDFTLTISSLQPEDFATYYCQQSWTRPRTFGQGTKV<br>EIK |
| SEQ ID NO: 220 | DNA VL | gacatccagatgacccagtctccgtcctccctgtccgcatcagtgggggacagagtgaccatcacttgt<br>cgggcctcccaaggcatctcgtcatacctggcctggtatcagcagaaacccggaaaggctccaaagctg<br>ctcatctacaccgcctcgactctgcaatccggagtgccttccccgcttctccggatccggttcgggaacc<br>gacttcaccctcaccattagcagccttcagccggaagatttcgcgacctactactgccagcaaagctgg<br>accaggcccaggacatttggccagggcactaaggtcgagattaag |
| SEQ ID NO: 182 | Light Chain | DIQMTQSPSSLSASVGDRVTITCRASQGISSYLAWYQQKPGKAPKLLIYTAS<br>TLQSGVPSRFSGSGSGTDFTLTISSLQPEDFATYYCQQSWTRPRTFGQGTKV<br>EIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVT<br>KSFNRGEC |
| SEQ ID NO: 221 | DNA Light Chain | gacatccagatgacccagtctccgtcctccctgtccgcatcagtgggggacagagtgaccatcacttgt<br>cgggcctcccaaggcatctcgtcatacctggcctggtatcagcagaaacccggaaaggctccaaagctg<br>ctcatctacaccgcctcgactctgcaatccggagtgccttccccgcttctccggatccggttcgggaacc<br>gacttcaccctcaccattagcagccttcagccggaagatttcgcgacctactactgccagcaaagctgg<br>accaggcccaggacatttggccagggcactaaggtcgagattaagcgtacggtggccgctcccagcgtg<br>ttcatcttcccccccagcgacgagcagctgaagagcggcaccgccagcgtggtgtgcctgctgaacaac<br>ttctaccccggggaggccaaggtgcagtggaaggtggacaacgccctgcagagcggcaacagccaggag<br>agcgtcaccgagcaggacagcaaggactccacctacagcctgagcagcaccctgaccctgagcaaggcc<br>gactacgagaagcataaggtgtacgcctgcgaggtgacccaccagggcctgtccagccccgtgaccaag<br>agcttcaacaggggcgagtgc |
| XX20_LALA | | |
| SEQ ID NO: 28 | HCDR1 (Combined) | GFTFSSYWMN |
| SEQ ID NO: 119 | HCDR2 (Combined) | VIESKGNYIFYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 119 | HCDR2 (Kabat) | VIESKGNYIFYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 120 | HCDR2 (Chothia) | ESKGNY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 121 | HCDR2 (IMGT) | IESKGNYI |
| SEQ ID NO: 36 | HCDR3 (IMGT) | ARDRYSMIYSYGAGAFDY |
| SEQ ID NO: 201 | VH | QVQLLESGGGLVQPGGSLRLSCAASGFTFSSYWMNWVRQAPGKGLEWVS<br>VIESKGNYIFYADSVKGRFTISRDNSKNTLYLQMNSLRAEDTAVYYCARDR<br>YSMIYSYGAGAFDYWGQGTLVTVSS |
| SEQ ID NO: 202 | DNA VH | caagttcaattgctggaaagcggaggtggacttgtccaacctggagggtcactccgactgtcttgcgct<br>gcatcaggattcaccttttagtagctattggatgaactgggtccggcaggctcctgggaaagggcttgag<br>tgggtaagtgtcattgaatcaaaggggaactacatctcttttatgctgattctgtaaagggtaggttcacc |

TABLE 2-continued

Exemplary anti-NPR1 antibody sequences

| | | |
|---|---|---|
| | | atctccagggacaattcaaaaaatactttgtatctgcagatgaactctctcagggcagaagacacggcc<br>gtttattactgcgcccgcgatcgatacagcatgatatactcctacgcgcaggagcttttgactactgg<br>ggtcaaggcacacttgttactgtcagtagc |
| SEQ ID NO: 203 | Heavy Chain | QVQLLESGGGLVQPGGSLRLSCAASGFTFSSYWMNWVRQAPGKGLEWVS<br>VIESKGNYIFYADSVKGRFTISRDNSKNTLYLQMNSLRAEDTAVYYCARDR<br>YSMIYSYGAGAFDYWGQGTLVTVSSASTKGPSVFPLAPSSKSTSGGTAALG<br>CLVKDYFPEPVTVSWNSGALTSGVHTFPAVLQSSGLYSLSSVVTVPSSSLGT<br>QTYICNVNHKPSNTKVDKRVEPKSCDKTHTCPPCPAPEAAGGPSVFLFPPKP<br>KDTLMISRTPEVTCVVVDVSHEDPEVKFNWYVDGVEVHNAKTKPREEQY<br>NSTYRVVSVLTVLHQDWLNGKEYKCKVSNKALPAPIEKTISKAKGQPREP<br>QVYTLPPSREEMTKNQVSLTCLVKGFYPSDIAVEWESNGQPENNYKTTPPV<br>LDSDGSFFLYSKLTVDKSRWQQGNVFSCSVMHEALHNHYTQKSLSLSPGK |
| SEQ ID NO: 204 | DNA Heavy Chain | caagttcaattgctggaaagcggaggtggacttgtccaacctggagggtcactccgactgtcttgcgct<br>gcatcaggattcacctttagtagctattggatgaactgggtccggcaggctcctgggaaagggcttgag<br>tgggtaagtgtcattgaatcaaagggcaactacatcttttatgctgattctgtaaagggtaggttcacc<br>atctccagggacaattcaaaaaatactttgtatctgcagatgaactctctcagggcagaagacacggcc<br>gtttattactgcgcccgcgatcgatacagcatgatatactcctacgcgcaggagcttttgactactgg<br>ggtcaaggcacacttgttactgtcagtagcgcctcaacgaaaggaccgtccgtgtttcctcttgctcct<br>agctccaaatccacctcaggtggaacggccgccctggggtgcctggtaaaggactatttcccagagcca<br>gttactgtgtcttggaattctggtgcattgacaagtggcgtacacacttttcccgcggtcctccaatct<br>agtggtctgtactcactgtcctccgttgtgactgtcccaagtagctcacttggcacacagacttacatc<br>tgtaatgttaatcataagccgtcaaacacgaaggtggataagagggtagaacctaagtcatgtgacaaa<br>acgcatacttgcccccctgccctgcgccggaagccgctggcggaccctccgtattcttgttcctcca<br>aagccaaaggacactctgatgattagccggacaccggaggtcacttgtgttgtagttgacgtcagccat<br>gaggatcctgaggtgaaatttaattggtacgtggacggggttgaagtccacaatgctaaaactaaacct<br>agggaagagcaatataatagtacatacagggttgtcagtgtgctgaccgttctccatcaggactggctg<br>aacggcaaggaatacaagtgcaaggtcagcaacaaggccttgccggcccccatcgagaagacgatctcc<br>aaagccaaggggcaaccccgagaaccgcaggtatacacgctccccctagtagaagagatgacaaag<br>aatcaagtttccttgacgtgccttgtgaaaggcttctaccctagtgacatcgcagtcgaatgggagagc<br>aacggccagccggagaataactataaaacaaccccccgtgcttgctcagcagggtcatttttttctg<br>tatagcaaattgactgttgataaatcacggtggcaacaaggaaacgtgtttagttgcagcgtaatgcac<br>gaagctctccacaatcactatactcaaaagtcactgtcactctccctggcaag |
| SEQ ID NO: 41 | LCDR1 (Combined) | RASQGISSYLA |
| SEQ ID NO: 42 | LCDR2 (Combined) | TASTLQS |
| SEQ ID NO: 184 | LCDR3 (Combined) | QQIWMAPRT |
| SEQ ID NO: 41 | LCDR1 (Kabat) | RASQGISSYLA |
| SEQ ID NO: 42 | LCDR2 (Kabat) | TASTLQS |
| SEQ ID NO: 184 | LCDR3 (Kabat) | QQIWMAPRT |
| SEQ ID NO: 44 | LCDR1 (Chothia) | SQGISSY |
| SEQ ID NO: 45 | LCDR2 (Chothia) | TAS |
| SEQ ID NO: 185 | LCDR3 (Chothia) | IWMAPR |
| SEQ ID NO: 47 | LCDR1 (IMGT) | QGISSY |
| SEQ ID NO: 45 | LCDR2 (IMGT) | TAS |
| SEQ ID NO: 184 | LCDR3 (IMGT) | QQIWMAPRT |
| SEQ ID NO: 186 | VL | DIQMTQSPSSLSASVGDRVTITCRASQGISSYLAWYQQKPGKAPKLLIYTAS<br>TLQSGVPSRFSGSGSGTDFTLTISSLQPEDFATYYCQQIWMAPRTFGQGTKV<br>EIK |
| SEQ ID NO: 222 | DNA VL | gacattcaaatgactcagtctccctcatctttgtcagcatcagttggggacagggtgacaatcacatgc<br>cgagcctcacagggattttctagctatcttgcatggtaccaacagaagcccggcaaagcccccaagctt<br>ttgatatatacggcatccactcttcagagcggagtacccagtaggtttagtggctccggagtggtacg<br>gactttactctgacgatttcctcccttcaacctgaagactttgcaacgtattactgtcagcaaatatgg<br>atggctcccagaacgtttggtcaaggtactaaagttgaaataaag |
| SEQ ID NO: 188 | Light Chain | DIQMTQSPSSLSASVGDRVTITCRASQGISSYLAWYQQKPGKAPKLLIYTAS<br>TLQSGVPSRFSGSGSGTDFTLTISSLQPEDFATYYCQQIWMAPRTFGQGTKV<br>EIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVT<br>KSFNRGEC |
| SEQ ID NO: 223 | DNA Light Chain | gacattcaaatgactcagtctccctcatctttgtcagcatcagttggggacagggtgacaatcacatgc<br>cgagcctcacagggattttctagctatcttgcatggtaccaacagaagcccggcaaagcccccaagctt<br>ttgatatatacggcatccactcttcagagcggagtacccagtaggtttagtggctccggagtggtacg |

TABLE 2-continued

Exemplary anti-NPR1 antibody sequences

```
gactttactctgacgatttcctcccttcaacctgaagactttgcaacgtattactgtcagcaaatatgg
atggctcccagaacgtttggtcaaggtactaaagttgaaataaagcgaactgtagcagcacctagtgta
tttatcttccccccttctgatgaacagttgaagtccgggacggcttccgtcgtatgtctcctgaacaac
ttttacccaagggaggcaaaggtgcaatgaaggtggataatgcactccagagtggcaatagccaagaa
tcagtaaccgaacaggattccaaggattctacctacagcctttcctctacgcttacattgagcaaggcg
gactatgaaaagcataaggtgtatgcgtgcgaagtaacacaccagggtctcagcagtccagttacgaag
tctttcaatcggggagaatgt
```

XX20_DAPA

| SEQ ID NO: 28 | HCDR1 (Combined) | GFTFSSYWMN |
| SEQ ID NO: 119 | HCDR2 (Combined) | VIESKGNYIFYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 119 | HCDR2 (Kabat) | VIESKGNYIFYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 120 | HCDR2 (Chothia) | ESKGNY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 121 | HCDR2 (IMGT) | IESKGNYI |
| SEQ ID NO: 36 | HCDR3 (IMGT) | ARDRYSMIYSYGAGAFDY |
| SEQ ID NO: 122 | VH | EVQLLESGGGLVQPGGSLRLSCAASGFTFSSYWMNWVRQAPGKGLEWVS<br>VIESKGNYIFYADSVKGRFTISRDNSKNTLYLQMNSLRAEDTAVYYCARDR<br>YSMIYSYGAGAFDYWGQGTLVTVSS |
| SEQ ID NO: 207 | DNA VH | gaagtgcagctgctggaatccggcggaggtctggtccagcctggaggttccctgcgcctgtcatgcgca<br>gcctccggattcaccttttcgtcgtactggatgaactgggtcagacaggctcctggaaagggcctggaa<br>tgggtgtctgtgattgaatccaaggggaactacatcttctacgcggacagcgtgaagggccggttcact<br>atcagcagagacaacagcaagaacaccctgtacctccaaatgaactcgctgagggccgaagatactgcc<br>gtgtactactgtgcccgcgatcgctactcgatgatctacagctatggtgccggagcgttcgattactgg<br>ggacagggaaccctcgtgaccgtcagctcc |
| SEQ ID NO: 208 | Heavy Chain | EVQLLESGGGLVQPGGSLRLSCAASGFTFSSYWMNWVRQAPGKGLEWVS<br>VIESKGNYIFYADSVKGRFTISRDNSKNTLYLQMNSLRAEDTAVYYCARDR<br>YSMIYSYGAGAFDYWGQGTLVTVSSASTKGPSVFPLAPSSKSTSGGTAALG<br>CLVKDYFPEPVTVSWNSGALTSGVHTFPAVLQSSGLYSLSSVVTVPSSSLGT<br>QTYICNVNHKPSNTKVDKRVEPKSCDKTHTCPPCPAPELLGGPSVFLFPPKP<br>KDTLMISRTPEVTCVVVAVSHEDPEVKFNWYVDGVEVHNAKTKPREEQY<br>NSTYRVVSVLTVLHQDWLNGKEYKCKVSNKALAAPIEKTISKAKGQPREP<br>QVYTLPPSREEMTKNQVSLTCLVKGFYPSDIAVEWESNGQPENNYKTTPPV<br>LDSDGSFFLYSKLTVDKSRWQQGNVFSCSVMHEALHNHYTQKSLSLSPGK |
| SEQ ID NO: 209 | DNA Heavy Chain | gaagtgcagctgctggaatccggcggaggtctggtccagcctggaggttccctgcgcctgtcatgcgca<br>gcctccggattcaccttttcgtcgtactggatgaactgggtcagacaggctcctggaaagggcctggaa<br>tgggtgtctgtgattgaatccaaggggaactacatcttctacgcggacagcgtgaagggccggttcact<br>atcagcagagacaacagcaagaacaccctgtacctccaaatgaactcgctgagggccgaagatactgcc<br>gtgtactactgtgcccgcgatcgctactcgatgatctacagctatggtgccggagcgttcgattactgg<br>ggacagggaaccctcgtgaccgtcagctccgcctcaaccaagggcccgtcagtgttccctggctgccca<br>tcgtcgaagtccacctccgaggaaccgcagcactcggttgcctggtcaaggactacttccctgagcca<br>gtgaccgtgtcgtggaacagcggagccctgacttccggcgtgcacacttttccggcggtgctgcagtcc<br>tccggtctgtactcccttcgtccgtggtcaccgtgccgtcgtctagcctgggcacccagacctacatc<br>tgcaacgtgaaccacaagcctccaacaccaaagtggataagcgggtggagccgaagtcctgcgataag<br>acacacgtgccgcctgtccagcgcctgaattgcttggcggaccttccgtgttcctgttcccgcct<br>aagcccaaggacaccttgatgattagccggactcccgaagtcacctgtgtggtggtggcagtgtcccac<br>gaggaccccgaggtcaagtttaattggtacgtggacggcgtcgaagtgcacaacgccaagactaagccc<br>cgggaggaacagtacaacagcacctaccgggtcgtgtccgtgctgaccgtgctgcaccaggactggctg<br>aatgggaaagagtacaagtgcaaagtgtccaacaaggccttggccgctcctatcgaaaaaactatcagc<br>aaggctaagggacagccgagggaaccccaagtctacaccctgccccttcacgcgaagagtgaccaag<br>aatcaagtgtcgctgacctgcctcgtcaagggattctaccccctccgacattgcgtggagtgggagtcc<br>aacggccagcccgagaacaactacaagactactccgcccgtgctggactccgacggcagcttcttcctg<br>tattccaagctgaccgtggacaagtcccggtggcagcaaggaaacgtgttctcctgtcggtcatgcac<br>gaagcctgcacaaccactatacgcagaagtccctgtccttgagcccggggaaa |

TABLE 2-continued

Exemplary anti-NPR1 antibody sequences

| | | |
|---|---|---|
| SEQ ID NO: 41 | LCDR1 (Combined) | RASQGISSYLA |
| SEQ ID NO: 42 | LCDR2 (Combined) | TASTLQS |
| SEQ ID NO: 184 | LCDR3 (Combined) | QQIWMAPRT |
| SEQ ID NO: 41 | LCDR1 (Kabat) | RASQGISSYLA |
| SEQ ID NO: 42 | LCDR2 (Kabat) | TASTLQS |
| SEQ ID NO: 184 | LCDR3 (Kabat) | QQIWMAPRT |
| SEQ ID NO: 44 | LCDR1 (Chothia) | SQGISSY |
| SEQ ID NO: 45 | LCDR2 (Chothia) | TAS |
| SEQ ID NO: 185 | LCDR3 (Chothia) | IWMAPR |
| SEQ ID NO: 47 | LCDR1 (IMGT) | QGISSY |
| SEQ ID NO: 45 | LCDR2 (IMGT) | TAS |
| SEQ ID NO: 184 | LCDR3 (IMGT) | QQIWMAPRT |
| SEQ ID NO: 186 | VL | DIQMTQSPSSLSASVGDRVTITCRASQGISSYLAWYQQKPGKAPKLLIYTAS<br>TLQSGVPSRFSGSGSGTDFTLTISSLQPEDFATYYCQQIWMAPRTFGQGTKV<br>EIK |
| SEQ ID NO: 224 | DNA VL | gacatccagatgacccagtctccgtcctccctgtccgcatcagtgggggacagagtgaccatcacttgt<br>cgggcctcccaaggcatctcgtcatacctggcctggtatcagcagaaacccggaaaggctccaaagctg<br>ctcatctacaccgcctcgactctgcaatccggagtgccttcccgcttctccggatccggttcgggaacc<br>gacttcaccctcaccattagcagccttcagccggaagatttcgcgacctactactgccagcaaatctgg<br>atggcccccaggacatttggccagggcactaaggtcgagattaag |
| SEQ ID NO: 188 | Light Chain | DIQMTQSPSSLSASVGDRVTITCRASQGISSYLAWYQQKPGKAPKLLIYTAS<br>TLQSGVPSRFSGSGSGTDFTLTISSLQPEDFATYYCQQIWMAPRTFGQGTKV<br>EIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVT<br>KSFNRGEC |
| SEQ ID NO: 225 | DNA Light Chain | gacatccagatgacccagtctccgtcctccctgtccgcatcagtgggggacagagtgaccatcacttgt<br>cgggcctcccaaggcatctcgtcatacctggcctggtatcagcagaaacccggaaaggctccaaagctg<br>ctcatctacaccgcctcgactctgcaatccggagtgccttcccgcttctccggatccggttcgggaacc<br>gacttcaccctcaccattagcagccttcagccggaagatttcgcgacctactactgccagcaaatctgg<br>atggcccccaggacatttggccagggcactaaggtcgagattaagcgtacggtggccgctcccagcgtg<br>ttcatcttccccccagcgacgagcagctgaagagcggcaccgccagcgtggtgtgcctgctgaacaac<br>ttctaccccggaggccaaggtcagtggaaggtggacaacgccctgcagagcggcaacagccaggag<br>agcgtcaccgagcaggacagcaaggactccacctacagcctgagcagcaccctgaccctgagcaaggcc<br>gactacgagaagcataaggtgtacgcctgcgaggtgacccaccagggcctgtccagccccgtgaccaag<br>agcttcaacagggggcgagtgc |

YY01_LALA

| | | |
|---|---|---|
| SEQ ID NO: 226 | HCDR1 (Combined) | GFTFSSYWIS |
| SEQ ID NO: 227 | HCDR2 (Combined) | NIKQSGSETYYVESVKG |
| SEQ ID NO: 228 | HCDR3 (Combined) | SLRRRSTEHAGFDV |
| SEQ ID NO: 229 | HCDR1 (Kabat) | SYWIS |
| SEQ ID NO: 227 | HCDR2 (Kabat) | NIKQSGSETYYVESVKG |
| SEQ ID NO: 228 | HCDR3 (Kabat) | SLRRRSTEHAGFDV |
| SEQ ID NO: 32 | HCDR1 (Chothia) | GFTFSSY |
| SEQ ID NO: 230 | HCDR2 (Chothia) | KQSGSE |
| SEQ ID NO: 228 | HCDR3 (Chothia) | SLRRRSTEHAGFDV |
| SEQ ID NO: 34 | HCDR1 (IMGT) | GFTFSSYW |
| SEQ ID NO: 231 | HCDR2 (IMGT) | IKQSGSET |
| SEQ ID NO: 232 | HCDR3 (IMGT) | ARSLRRRSTEHAGFDV |

TABLE 2-continued

Exemplary anti-NPR1 antibody sequences

| SEQ ID NO: 233 | VH | EVQLVESGGGLVQPGGSLRLSCAASGFTFSSYWISWVRQAPGKGLEWVAN IKQSGSETYYVESVKGRFTISRDNAKNSLYLQMNSLRAEDTAVYYCARSLR RRSTEHAGFDVWGQGTLVTVSS |
|---|---|---|
| SEQ ID NO: 234 | DNA VH | gaagtgcagctggtggaaagcggcggtggcctggtgcagccaggtggtagcctgcgcctgagctgcgcc gccagcggctttacctttagcagctattggattagctgggttcgccaggcccaggcaaaggcctggaa tgggtggcgaacatcaaacagagcggcagcgagacctactatgtggagagcgtgaaaggccgctttacc attagccgcgataacgccaaaaacagcctgtatctgcaaatgaacagcctgcgggccgaagataccgcc gtgtattattgcgcgcgtagcctgcgtcgtcgtagcactgagcacgcaggattcgacgtttggggccag ggcaccctggttactgtctcgagc |
| SEQ ID NO: 235 | Heavy Chain | EVQLVESGGGLVQPGGSLRLSCAASGFTFSSYWISWVRQAPGKGLEWVAN IKQSGSETYYVESVKGRFTISRDNAKNSLYLQMNSLRAEDTAVYYCARSLR RRSTEHAGFDVWGQGTLVTVSSASTKGPSVFPLAPSSKSTSGGTAALGCLV KDYFPEPVTVSWNSGALTSGVHTFPAVLQSSGLYSLSSVVTVPSSSLGTQTY ICNVNHKPSNTKVDKRVEPKSCDKTHTCPPCPAPEAAGGPSVFLFPPKPKDT LMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSREEMTKNQVSLTCLVKGFYPSDIAVEWESNGQPENNYKTTPPVLDSD GSFFLYSKLTVDKSRWQQGNVFSCSVMHEALHNHYTQKSLSLSPGK |
| SEQ ID NO: 236 | DNA Heavy Chain | gaagtgcagctggtggaaagcggcggtggcctggtgcagccaggtggtagcctgcgcctgagctgcgcc gccagcggctttacctttagcagctattggattagctgggttcgccaggcccaggcaaaggcctggaa tgggtggcgaacatcaaacagagcggcagcgagacctactatgtggagagcgtgaaaggccgctttacc attagccgcgataacgccaaaaacagcctgtatctgcaaatgaacagcctgcgggccgaagataccgcc gtgtattattgcgcgcgtagcctgcgtcgtcgtagcactgagcacgcaggattcgacgtttggggccag ggcaccctggttactgtctcgagcgcgtcgaccaaaggcccagcgtgttccctggccccagcagc aagagcacctctggcggcacagcccgctgggctgcctggtcaaggactacttcccccgaaccgtgagc gtgtcctggaactctggcgccctgaccagcggcgtgcacacctttccagccgtgctccagagcagcggc ctgtacagcctgagcagcgtcgtgaccgtgcccagcagcagcctgggcacccagacctacatctgcaac gtgaaccacaagcccagcaacacaaaggtggacaagcgggtggaacccaagagctgcgacaagacccac acctgtccccctgccctgcccctgaagcggcggaggcccctcgtgttcctgttccccccaaagcct aaggacaccctgatgatcagccggacccccgaagtgacctgcgtggtggtggacgtgtcccacgaggac cctgaagtgaagtttaattggtacgtggacggcgtggaagtgcacaacgccaagaccaagcccagagag gaacagtacaacagcacctaccgggtggtgtccgtgctgaccgtgctgcaccaggactggctgaacggc aagaagtacaagtgcaaggtgtccaacaaggcccctgctccccccatcgagaaaaccatcagcaaggcc aaaggccagccccgcgagccccaggtgtacacactgccccctagccgggaagagatgaccaagaaccag gtgtccctgacctgcctcgtgaagggcttctaccccagcgacattgccgtggaatgggagagcaacggc cagcccgagaacaactacaagaccacccccctgtgctggacagcgacggctcattcttcctgtacagc aagctgaccgtggacaagagccggtggcagcagggcaacgtgttcagctgctccgtgatgcacgaggcc ctgcacaaccactacacccagaagtccctgagcctgagccccggcaag |
| SEQ ID NO: 237 | LCDR1 (Combined) | RASQGISNYLA |
| SEQ ID NO: 238 | LCDR2 (Combined) | AASTLQS |
| SEQ ID NO: 239 | LCDR3 (Combined) | QQADKFPYT |
| SEQ ID NO: 237 | LCDR1 (Kabat) | RASQGISNYLA |
| SEQ ID NO: 238 | LCDR2 (Kabat) | AASTLQS |
| SEQ ID NO: 239 | LCDR3 (Kabat) | QQADKFPYT |
| SEQ ID NO: 240 | LCDR1 (Chothia) | SQGISNY |
| SEQ ID NO: 241 | LCDR2 (Chothia) | AAS |
| SEQ ID NO: 242 | LCDR3 (Chothia) | ADKFPY |
| SEQ ID NO: 243 | LCDR1 (IMGT) | QGISNY |
| SEQ ID NO: 241 | LCDR2 (IMGT) | AAS |
| SEQ ID NO: 239 | LCDR3 (IMGT) | QQADKFPYT |
| SEQ ID NO: 244 | VL | DIQMTQSPSSLSASVGDRVTITCRASQGISNYLAWYQQKPGKVPKLLIYAAS TLQSGVPSRFSGSGSGTDFTLTISSLQPEDVATYYCQQADKFPYTFGQGTKV EIK |
| SEQ ID NO: 245 | DNA VL | gatattcagatgacccagagcccgagcagcctgagcgcaagcgtgggcgatcgcgtgaccattacctgc cgcgccagccagggcattagcaactatctggcctggtatcagcagaaaccgggcaaagtgccgaaactg ctgatctatgccgcgagcaccctgcaaagcggcgtgccaagtcgctttagcggcagcggtagcggcacc gatttcaccctgaccattagcagcctgcaaccggaagacgtggcgacctattattgccagcaggctgac aaatttccgtacaccttcggccagggtaccaaagtggaaatcaag |
| SEQ ID NO: 246 | Light Chain | DIQMTQSPSSLSASVGDRVTITCRASQGISNYLAWYQQKPGKVPKLLIYAAS TLQSGVPSRFSGSGSGTDFTLTISSLQPEDVATYYCQQADKFPYTFGQGTKV |

TABLE 2-continued

Exemplary anti-NPR1 antibody sequences

| | | |
|---|---|---|
| | | EIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVT<br>KSFNRGEC |
| SEQ ID NO: 247 | DNA Light Chain | gatattcagatgacccagagcccgagcagcctgagcgcaagcgtgggcgatcgcgtgaccattacctgc<br>cgcgccagccagggcattagcaactatctggcctggtatcagcagaaacgggcaaagtgccgaaactg<br>ctgatctatgccgccagcacccctgcaaagcggcgtgccaagtcgctttagcggcagcggtagcggcacc<br>gatttcacccctgaccattagcagcctgcaaccggaagacgtggcgacctattattgccagcaggctgac<br>aaattcccgtacaccttcggccagggtaccaaagtggaaatcaagcggaccgtggccgctccctccgtg<br>ttcatcttcccaccagcgacgagcagctgaagtccggcacagccagcgtcgtgtgcctgctgaacaac<br>ttctacccccgcgaggccaaagtgcagtggaaggtggacaacgcccctccagagcggcaacagccaggaa<br>agcgtcaccgagcaggacagcaaggactccacctacagcctgagcagcaccctgaccctgagcaaggcc<br>gactacgagaagcacaaggtgtacgcctgcgaagtgacccaccagggcctgtccagccccgtgaccaag<br>agcttcaaccggggcgagtgt |

YY02_LALA

| SEQ ID NO: 248 | HCDR1 (Combined) | GFTFSSYSMN |
|---|---|---|
| SEQ ID NO: 249 | HCDR2 (Combined) | SISSSSSYIYYADSVKG |
| SEQ ID NO: 250 | HCDR3 (Combined) | SGYRGVYGFDY |
| SEQ ID NO: 251 | HCDR1 (Kabat) | SYSMN |
| SEQ ID NO: 249 | HCDR2 (Kabat) | SISSSSSYIYYADSVKG |
| SEQ ID NO: 250 | HCDR3 (Kabat) | SGYRGVYGFDY |
| SEQ ID NO: 32 | HCDR1 (Chothia) | GFTFSSY |
| SEQ ID NO: 252 | HCDR2 (Chothia) | SSSSSY |
| SEQ ID NO: 250 | HCDR3 (Chothia) | SGYRGVYGFDY |
| SEQ ID NO: 253 | HCDR1 (IMGT) | GFTFSSYS |
| SEQ ID NO: 254 | HCDR2 (IMGT) | ISSSSSYI |
| SEQ ID NO: 255 | HCDR3 (IMGT) | ARSGYRGVYGFDY |
| SEQ ID NO: 256 | VH | EVQLVESGGGLVKPGGSLRLSCAASGFTFSSYSMNWVRQAPGKGLEWVSS<br>ISSSSSYIYYADSVKGRFTISRDNAKNSLYLQMNSLRAEDTAVYYCARSGY<br>RGVYGFDYWGQGTLVTVSS |
| SEQ ID NO: 257 | DNA VH | gaagtgcagctggtggaaagcggcggtggcctggtgaaaccaggcggtagcctgcgcctgagctgcgcc<br>gccagcggctttaccttagcagctatagcatgaactgggttcgccaggcccaggcaaaggcctggaa<br>tgggttagcagcatcagcagcagtagcagctatatctattacgccgatagcgtgaaaggccgctttacc<br>attagccgcgataacgccaaaaacagcctgtatctgcaaatgaacagcctgcgggccgaagataccgcc<br>gtgtattattgcgcgcgaagcggatatcgtggagtttacggatttgattattggggccagggcaccctg<br>gttactgtctcgagc |
| SEQ ID NO: 258 | Heavy Chain | EVQLVESGGGLVKPGGSLRLSCAASGFTFSSYSMNWVRQAPGKGLEWVSS<br>ISSSSSYIYYADSVKGRFTISRDNAKNSLYLQMNSLRAEDTAVYYCARSGY<br>RGVYGFDYWGQGTLVTVSSASTKGPSVFPLAPSSKSTSGGTAALGCLVKD<br>YFPEPVTVSWNSGALTSGVHTFPAVLQSSGLYSLSSVVTVPSSSLGTQTYIC<br>NVNHKPSNTKVDKRVEPKSCDKTHTCPPCPAPEAAGGPSVFLFPPKPKDTL<br>MISRTPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQVYTLP<br>PSREEMTKNQVSLTCLVKGFYPSDIAVEWESNGQPENNYKTTPPVLDSDGS<br>FFLYSKLTVDKSRWQQGNVFSCSVMHEALHNHYTQKSLSLSPGK |
| SEQ ID NO: 259 | DNA Heavy Chain | gaagtgcagctggtggaaagcggcggtggcctggtgaaaccaggcggtagcctgcgcctgagctgcgcc<br>gccagcggctttaccttagcagctatagcatgaactgggttcgccaggcccaggcaaaggcctggaa<br>tgggttagcagcatcagcagcagtagcagctatatctattacgccgatagcgtgaaaggccgctttacc<br>attagccgcgataacgccaaaaacagcctgtatctgcaaatgaacagcctgcgggccgaagataccgcc<br>gtgtattattgcgcgcgaagcggatatcgtggagtttacggatttgattattggggccagggcaccctg<br>gttactgtctcgagcgcgtcgaccaaaggcccagcgtgttccctctggcccccagcagcaagagcacc<br>tctggcggaacagccgccctgggctgcctggtcaaggactacttcccgagcccgtgaccgtgtcctgg<br>aactcaggcgccctgaccagcggcgtgcacacctttccagccgtgctccagagcagcggcctgtacagc<br>ctgagcagcgtcgtgaccgtgccagcagcagcctgggcacccagacctacatctgcaacgtgaaccac<br>aagcccagcaacacaaaggtggacaagcgggtggaacccaagagctgcgacaagacccacacctgtccc<br>ccctgccctgaagcggcgggacccctccgtgttcctgttccccccaaagcctaaggacaccc<br>ctgatgatcagcccggaccccgaagtgacctgcgtggtggacgtgtccacgaggaccctgaagtg<br>aagtttaattggtacgtggacggcgtggaagtgcacaacgccaagaccaagccagagaggaacagtac<br>aacagcacctaccggggtggtgtccgtgctgaccgtgctgcaccaggactggctgaacggcaaagagtac<br>aagtgcaaggtgtccaacaaggcccgctgcccccatcgagaaaaccatcagcaaggccaaaggccag<br>ccccgcgagccccaggtgtacacactgccccctagccgggaagagatgaccaagaaccaggtgtccctg </tr>

TABLE 2-continued

Exemplary anti-NPR1 antibody sequences

|  |  |  | acctgcctcgtgaagggcttctaccccagcgacattgccgtggaatgggagagcaacggccagcccgag<br>aacaactacaagaccaccccccctgtgctggacagcgacggctcattcttcctgtacagcaagctgacc<br>gtggacaagagccggtggcagcagggcaacgtgttcagctgctccgtgatgcacgaggccctgcacaac<br>cactacacccagaagtccctgagcctgagccccggcaag |
|---|---|---|---|
| SEQ ID NO: 260 | LCDR1 (Combined) | | RASQGISSWLA |
| SEQ ID NO: 261 | LCDR2 (Combined) | | AASSLQS |
| SEQ ID NO: 262 | LCDR3 (Combined) | | QQYYHSPLT |
| SEQ ID NO: 260 | LCDR1 (Kabat) | | RASQGISSWLA |
| SEQ ID NO: 261 | LCDR2 (Kabat) | | AASSLQS |
| SEQ ID NO: 262 | LCDR3 (Kabat) | | QQYYHSPLT |
| SEQ ID NO: 263 | LCDR1 (Chothia) | | SQGISSW |
| SEQ ID NO: 241 | LCDR2 (Chothia) | | AAS |
| SEQ ID NO: 264 | LCDR3 (Chothia) | | YYHSPL |
| SEQ ID NO: 265 | LCDR1 (IMGT) | | QGISSW |
| SEQ ID NO: 241 | LCDR2 (IMGT) | | AAS |
| SEQ ID NO: 262 | LCDR3 (IMGT) | | QQYYHSPLT |
| SEQ ID NO: 266 | VL | | DIQMTQSPSSVSASVGDRVTITCRASQGISSWLAWYQQKPGKAPKLLIYAA<br>SSLQSGVPSRFSGSGSGTDFTLTISSLQPEDFATYYCQQYYHSPLTFGQGTK<br>VEIK |
| SEQ ID NO: 267 | DNA VL | | gatattcagatgacccagagcccgagcagcgttagcgccagcgtgggcgatcgcgtgaccattacctgc<br>cgcgccagtcagggcattagcagctggctggcctggtatcagcagaaaccgggcaaagcccccgaaactg<br>ctgatctatgccgccagcagcctgcaaagcggcgtgccaagtcgctttagcggcagcggtagcggcacc<br>gatttcaccctgaccattagcagtctgcaaccggaagactttgccacctattattgccagcagtactac<br>cattctccgctgaccttcggccagggtaccaaagtggaaatcaag |
| SEQ ID NO: 268 | Light Chain | | DIQMTQSPSSVSASVGDRVTITCRASQGISSWLAWYQQKPGKAPKLLIYAA<br>SSLQSGVPSRFSGSGSGTDFTLTISSLQPEDFATYYCQQYYHSPLTFGQGTK<br>VEIKRTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGLSSPV<br>TKSFNRGEC |
| SEQ ID NO: 269 | DNA Light Chain | | gatattcagatgacccagagcccgagcagcgttagcgccagcgtgggcgatcgcgtgaccattacctgc<br>cgcgccagtcagggcattagcagctggctggcctggtatcagcagaaaccgggcaaagcccccgaaactg<br>ctgatctatgccgccagcagcctgcaaagcggcgtgccaagtcgctttagcggcagcggtagcggcacc<br>gatttcaccctgaccattagcagtctgcaaccggaagactttgccacctattattgccagcagtactac<br>cattctccgctgaccttcggccagggtaccaaagtggaaatcaagcggaccgtggccgctcccctccgtg<br>ttcatcttcccaccagcgacgagcagctgaagtccggcacagccagcgtcgtgtgcctgctgaacaac<br>ttctaccccgcgaggccaaagtcagtggaaggtggacaacgcccctccagagcggcaacagccaggaa<br>agcgtcaccgagcaggacagcaaggactccacctacagcctgagcagcaccctgaccctgagcaaggcc<br>gactacgagaagcacaaggtgtacgcctgcgaagtgacccaccagggcctgtccagccccgtgaccaag<br>agcttcaaccggggcgagtgt |
| YY03_LALA | | | |
| SEQ ID NO: 270 | HCDR1 (Combined) | | GFTFSSYAIS |
| SEQ ID NO: 271 | HCDR2 (Combined) | | AISGSGGSTYYAESVKG |
| SEQ ID NO: 272 | HCDR3 (Combined) | | ESGYVYYLKFDY |
| SEQ ID NO: 273 | HCDR1 (Kabat) | | SYAIS |
| SEQ ID NO: 271 | HCDR2 (Kabat) | | AISGSGGSTYYAESVKG |
| SEQ ID NO: 272 | HCDR3 (Kabat) | | ESGYVYYLKFDY |
| SEQ ID NO: 32 | HCDR1 (Chothia) | | GFTFSSY |
| SEQ ID NO: 274 | HCDR2 (Chothia) | | SGSGGS |
| SEQ ID NO: 272 | HCDR3 (Chothia) | | ESGYVYYLKFDY |
| SEQ ID NO: 275 | HCDR1 (IMGT) | | GFTFSSYA |

TABLE 2-continued

Exemplary anti-NPR1 antibody sequences

| SEQ ID NO: 276 | HCDR2 (IMGT) | ISGSGGST |
|---|---|---|
| SEQ ID NO: 277 | HCDR3 (IMGT) | ARESGYVYYLKFDY |
| SEQ ID NO: 278 | VH | EVQLLESGGGLVQPGGSLRLSCAASGFTFSSYAISWVRQAPGKGLEWVSAI SGSGGSTYYAESVKGRFTISRDNSKNTLYLQMNSLRAEDTAVYYCARESG YVYYLKFDYWGQGTLVTVSS |
| SEQ ID NO: 279 | DNA VH | gaagtgcagctgctggaaagcggtggcggtctggtgcagccaggtggtagcctgcgcctgagctgtgcc gcaagcggctttacctttagcagctatgccattagctgggtgcgccaagcaccaggcaaaggcctggaa tgggtgagcgccattagcggcagcggtggcagcacctattatgccgagagcgtgaaaggtcgctttacc attagtcgcgataacagcaaaaacaccctgtatctgcaaatgaacagcctgcgggcagaagataccgca gtttattattgcgcgcgtgagagcggatacgtttactatctgaaattcgattattggggccagggcacc ctggttactgtctcgagc |
| SEQ ID NO: 280 | Heavy Chain | EVQLLESGGGLVQPGGSLRLSCAASGFTFSSYAISWVRQAPGKGLEWVSAI SGSGGSTYYAESVKGRFTISRDNSKNTLYLQMNSLRAEDTAVYYCARESG YVYYLKFDYWGQGTLVTVSSASTKGPSVFPLAPSSKSTSGGTAALGCLVK DYFPEPVTVSWNSGALTSGVHTFPAVLQSSGLYSLSSVVTVPSSSLGTQTYI CNVNHKPSNTKVDKRVEPKSCDKTHTCPPCPAPEAAGGPSVFLFPPKPKDT LMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSREEMTKNQVSLTCLVKGFYPSDIAVEWESNGQPENNYKTTPPVLDSD GSFFLYSKLTVDKSRWQQGNVFSCSVMHEALHNHYTQKSLSLSPGK |
| SEQ ID NO: 281 | DNA Heavy Chain | gaagtgcagctgctggaaagcggtggcggtctggtgcagccaggtggtagcctgcgcctgagctgtgcc gcaagcggctttacctttagcagctatgccattagctgggtgcgccaagcaccaggcaaaggcctggaa tgggtgagcgccattagcggcagcggtggcagcacctattatgccgagagcgtgaaaggtcgctttacc attagtcgcgataacagcaaaaacaccctgtatctgcaaatgaacagcctgcgggcagaagataccgca gtttattattgcgcgcgtgagagcggatacgtttactatctgaaattcgattattggggccagggcacc ctggttactgtctcgagcgcgtcgaccaaaggcccccagcgtgttcctctggcccccagcagcaagagc acctctggcggaacagccgcctgggctgcctggtcaaggactacttccccgagccgtgaccgtgtcc tggaactctggcgccctgaccagcggcgtgcacacctttccagccgtgctccagagcagcggcctgtac agcctgagcagcgtcgtgaccgtgcccagcagcagcctgggcacccagacctacatctgcaacgtgaac cacaagcccagcaacacaaaggtggacaagcgggtggaacccaagagctgcgacaagacccacacctgt ccccctgccctgcccctgaagcggcggaggccccctccgtgttcctgttccccccaaagcctaaggac accctgatgatcagccggaccccgaagtgacctgcgtggtggtggacgtgtcccacgaggaccctgaa gtgaagtttaattggtacgtggacggcgtggaagtgcacaacgccaagaccaagcccagagaggaacag tacaacagcacctacgggtggtgtccgtgctgaccgtgctgcaccaggactggctgaacggcaaagag tacaagtgcaaggtgtccaacaagcctgcctgcccccatcgagaaaaccatcagcaaggccaaaggc cagcccgcgagccccaggtgtacacactgccccctagccgggaagagatgaccaagaaccaggtgtcc ctgacctgcctcgtgaagggcttctacccagcgacattgccgtggaatgggagagcaacggccagccc gagaacaactacaagaccaccccctgtgctggacagcgacggctcattcttcctgtacagcaagctg accgtggacaagagccgtggcagcagggcaacgtgttcagctgctccgtgatgcacgaggcctgcac aaccactacacccagaagtccctgagcctgagccccggcaag |
| SEQ ID NO: 282 | LCDR1 (Combined) | RASQSISSYLN |
| SEQ ID NO: 261 | LCDR2 (Combined) | AASSLQS |
| SEQ ID NO: 283 | LCDR3 (Combined) | QQHVRVPIT |
| SEQ ID NO: 282 | LCDR1 (Kabat) | RASQSISSYLN |
| SEQ ID NO: 261 | LCDR2 (Kabat) | AASSLQS |
| SEQ ID NO: 283 | LCDR3 (Kabat) | QQHVRVPIT |
| SEQ ID NO: 284 | LCDR1 (Chothia) | SQSISSY |
| SEQ ID NO: 241 | LCDR2 (Chothia) | AAS |
| SEQ ID NO: 285 | LCDR3 (Chothia) | HVRVPI |
| SEQ ID NO: 286 | LCDR1 (IMGT) | QSISSY |
| SEQ ID NO: 241 | LCDR2 (IMGT) | AAS |
| SEQ ID NO: 283 | LCDR3 (IMGT) | QQHVRVPIT |
| SEQ ID NO: 287 | VL | DIQMTQSPSSLSASVGDRVTITCRASQSISSYLNWYQQKPGKAPKLLIYAAS SLQSGVPSRFSGSGSGTDFTLTISSLQPEDFATYYCQQHVRVPITFGQGTKVE IK |
| SEQ ID NO: 288 | DNA VL | gatattcagatgacccagagcccgagcagcctgagcgccagcgtgggtgatcgcgtgaccattacctgt cgcgcaagccagagcattagcagctatctgaactggtatcagcagaaaccaggcaaagcccccaaactg ctgatttatgccgcaagcagcctgcaaagcggtgtgccgagccgctttagcggcagcggtagcggcacc |

TABLE 2-continued

Exemplary anti-NPR1 antibody sequences

|  |  |  |
|---|---|---|
|  |  | gattttaccctgaccattagtagcctgcaaccggaagactttgccacctattattgccagcagcatgtt<br>cgtgttccgatcaccttcggccagggtaccaaagtggaaatcaag |
| SEQ ID NO: 289 | Light Chain | DIQMTQSPSSLSASVGDRVTITCRASQSISSYLNWYQQKPGKAPKLLIYAAS<br>SLQSGVPSRFSGSGSGTDFTLTISSLQPEDFATYYCQQHVRVPITFGQTKVE<br>IKRTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPVTK<br>SFNRGEC |
| SEQ ID NO: 290 | DNA Light Chain | gatattcagatgacccagagcccgagcagcctgagcgccagcgtgggtgatcgcgtgaccattacctgt<br>cgcgcaagccagagcattagcagctatctgaactggtatcagcagaaaccaggcaaagcccaaaactg<br>ctgatttatgccgcaagcagcctgcaaagcggtgtgccgagccgctttagcggcagcggtagcggcacc<br>gattttaccctgaccattagtagcctgcaaccggaagactttgccacctattattgccagcagcatgtt<br>cgtgttccgatcaccttcggccagggtaccaaagtggaaatcaagcggaccgtggccgctcccctccgtg<br>ttcatcttcccaccagcgacgagcagcctgaagtccggcaccgcagcgtcgtgtgcctgctgaacaac<br>ttctaccccgcgaggccaaagtgcagtggaaggtggacaacgcctccagagcggcaacagccaggaa<br>agcgtcaccgagcaggacagcaaggactccacctacagcctgagcagcaccctgaccctgagcaaggcc<br>gactacgagaagcacaaggtgtacgcctgcgaagtgacccaccagggcctgtccagcccgtgaccaag<br>agcttcaacggggcgagtgt |

YY04_LALA

| SEQ ID NO: 291 | HCDR1 (Combined) | GFTFSNYWIS |
| SEQ ID NO: 292 | HCDR2 (Combined) | RIKSKTYGGTTDYAEPVKG |
| SEQ ID NO: 293 | HCDR3 (Combined) | EKYSIRARGHGDYGFDV |
| SEQ ID NO: 294 | HCDR1 (Kabat) | NYWIS |
| SEQ ID NO: 292 | HCDR2 (Kabat) | RIKSKTYGGTTDYAEPVKG |
| SEQ ID NO: 293 | HCDR3 (Kabat) | EKYSIRARGHGDYGFDV |
| SEQ ID NO: 295 | HCDR1 (Chothia) | GFTFSNY |
| SEQ ID NO: 296 | HCDR2 (Chothia) | KSKTYGGT |
| SEQ ID NO: 293 | HCDR3 (Chothia) | EKYSIRARGHGDYGFDV |
| SEQ ID NO: 297 | HCDR1 (IMGT) | GFTFSNYW |
| SEQ ID NO: 298 | HCDR2 (IMGT) | IKSKTYGGTT |
| SEQ ID NO: 299 | HCDR3 (IMGT) | AREKYSIRARGHGDYGFDV |
| SEQ ID NO: 300 | VH | EVQLVESGGGLVKPGGSLRLSCAASGFTFSNYWISWVRQAPGKGLEWVGR<br>IKSKTYGGTTDYAEPVKGRFTISRDDSKNTLYLQMNSLKTEDTAVYYCARE<br>KYSIRARGHGDYGFDVWGQGTLVTVSS |
| SEQ ID NO: 301 | DNA VH | gaagtgcagctggtggaaagcggcggtggcctggtgaaaccaggcggtagcctgcgcctgagctgcgcc<br>gccagcggctttacctttagcaactattggattagctgggttcgccaggcccaggcaaaggcctggaa<br>tgggttggccgcatcaaaagcaaaaccatgcggcaccaccgattatgccgagccagtgaaaggccgc<br>tttaccattagccgcgacgatagcaaaaacaccctgtacctgcaaatgaacagcctgaaaaccgaagat<br>accgccgtgtattattgcgcgcgtgagaaatattccatccgtgcacgtggtcacggagactacggattt<br>gatgtgtggggccagggcaccctggttactgtctcgagc |
| SEQ ID NO: 302 | Heavy Chain | EVQLVESGGGLVKPGGSLRLSCAASGFTFSNYWISWVRQAPGKGLEWVGR<br>IKSKTYGGTTDYAEPVKGRFTISRDDSKNTLYLQMNSLKTEDTAVYYCARE<br>KYSIRARGHGDYGFDVWGQGTLVTVSSASTKGPSVFPLAPSSKSTSGGTAA<br>LGCLVKDYFPEPVTVSWNSGALTSGVHTFPAVLQSSGLYSLSSVVTVPSSSL<br>GTQTYICNVNHKPSNTKVDKRVEPKSCDKTHTCPPCPAPEAAGGPSVFLFP<br>PKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPR<br>EPQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSP<br>GK |
| SEQ ID NO: 303 | DNA Heavy Chain | gaagtgcagctggtggaaagcggcggtggcctggtgaaaccaggcggtagcctgcgcctgagctgcgcc<br>gccagcggctttacctttagcaactattggattagctgggttcgccaggcccaggcaaaggcctggaa<br>tgggttggccgcatcaaaagcaaaaccatgcggcggcaccaccgattatgccgagccagtgaaaggccgc<br>tttaccattagccgcgacgatagcaaaaacaccctgtacctgcaaatgaacagcctgaaaaccgaagat<br>accgccgtgtattattgcgcgcgtgagaaatattccatccgtgcacgtggtcacggagactacggattt<br>gatgtgtggggccagggcaccctggttactgtctcgagcgcgtccaccaagggcccagcgtgttcct<br>ctggcccccagcagcaagagcacctctggcggaacagcgccctgggctgcctggtcaaggactacttc<br>cccgagccgtgaccgtgtcctggaactctggcgccctgaccagcggcgtgcacacctccagccgtg<br>ctccagcagcggcctgtacagcctgagcagcgtcgtgaccgtgcccagcagcagcctgggcacccag<br>acctacatctgcaacgtgaaccacaagcccagcaacacaaaggtggacaagcgggtggaacccaaagagc |

TABLE 2-continued

Exemplary anti-NPR1 antibody sequences

| | | |
|---|---|---|
| | | tgcgacaagacccacacctgtccccctgccctgcccctgaagcggcgggaggcccctccgtgttcctg<br>ttccccccaaagcctaaggacaccctgatgatcagccggacccccgaagtgacctgcgtggtggtggac<br>gtgtcccacgaggaccctgaagtgaagtttaattggtacgtggacggcgtggaagtgcacaacgccaag<br>accaagccagagaggaacagtacaacagcacctaccgggtggtgtccgtgctgaccgtgctgcaccag<br>gactggctgaacggcaaagagtacaagtgcaaggtgtccaacaaggcctgcctgcccccatcgagaaa<br>accatcagcaaggccaaaggccagccccgcgagccccaggtgtacacactgcccctagccgggaagag<br>atgaccaagaaccaggtgtccctgacctgcctcgtgaagggcttctaccccagcgacattgccgtggaa<br>tgggagagcaacggccagcccgagaacaactacaagaccacccccctgtgctggacagcgacggctca<br>ttcttcctgtacagcaagctgaccgtggacaagagccggtggcagcagggcaacgtgttcagctgctcc<br>gtgatgcacgaggccctgcacaaccactacacccagaagtccctgagcctgagccccggcaag |
| SEQ ID NO: 237 | LCDR1 (Combined) | RASQGISNYLA |
| SEQ ID NO: 238 | LCDR2 (Combined) | AASTLQS |
| SEQ ID NO: 304 | LCDR3 (Combined) | QQGYHAPFT |
| SEQ ID NO: 237 | LCDR1 (Kabat) | RASQGISNYLA |
| SEQ ID NO: 238 | LCDR2 (Kabat) | AASTLQS |
| SEQ ID NO: 304 | LCDR3 (Kabat) | QQGYHAPFT |
| SEQ ID NO: 240 | LCDR1 (Chothia) | SQGISNY |
| SEQ ID NO: 241 | LCDR2 (Chothia) | AAS |
| SEQ ID NO: 305 | LCDR3 (Chothia) | GYHAPF |
| SEQ ID NO: 243 | LCDR1 (IMGT) | QGISNY |
| SEQ ID NO: 241 | LCDR2 (IMGT) | AAS |
| SEQ ID NO: 304 | LCDR3 (IMGT) | QQGYHAPFT |
| SEQ ID NO: 306 | VL | DIQMTQSPSSLSASVGDRVTITCRASQGISNYLAWYQQKPGKVPKLLIYAAS<br>TLQSGVPSRFSGSGSGTDFTLTISSLQPEDVATYYCQQGYHAPFTFGQGTKV<br>EIK |
| SEQ ID NO: 307 | DNA VL | gatattcagatgacccagagcccgagcagcctgagcgcaagcgtgggcgatcgcgtgaccattacctgc<br>cgcgccagccagggcattagcaactatctggcctggtatcagcagaaaccgggcaaagtgccgaaactg<br>ctgatctatgccgccagcaccctgcaaagcggcgtgccaagtcgctttagcggcagcggtagcggcacc<br>gatttcaccctgaccattagcagcctgcaaccggaagacgtggcgacctattattgccagcagggttac<br>catgctccgttcaccttcggccagggtaccaaagtggaaatcaag |
| SEQ ID NO: 308 | Light Chain | DIQMTQSPSSLSASVGDRVTITCRASQGISNYLAWYQQKPGKVPKLLIYAAS<br>TLQSGVPSRFSGSGSGTDFTLTISSLQPEDVATYYCQQGYHAPFTFGQGTKV<br>EIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVT<br>KSFNRGEC |
| SEQ ID NO: 309 | DNA Light Chain | gatattcagatgacccagagcccgagcagcctgagcgcaagcgtgggcgatcgcgtgaccattacctgc<br>cgcgccagccagggcattagcaactatctggcctggtatcagcagaaaccgggcaaagtgccgaaactg<br>ctgatctatgccgccagcaccctgcaaagcggcgtgccaagtcgctttagcggcagcggtagcggcacc<br>gatttcaccctgaccattagcagcctgcaaccggaagacgtggcgacctattattgccagcagggttac<br>catgctccgttcaccttcggccagggtaccaaagtggaaatcaagcggaccgtggccgctcccctccgtg<br>ttcatcttcccaccccagcgacgagcagctgaagtccggcaccgccagcgtcgtgtgcctgctgaacaa<br>ttctaccccgcgaggccaaagtgcagtggaaggtggacaacgcccctccagagcggcaacagccaggaa<br>agcgtcaccgagcaggacagcaaggactccacctacagcctgagcagcaccctgaccctgagcaaggcc<br>gactacgagaagcacaaggtgtacgcctgcgaagtgacccaccagggcctgtccagcccgtgaccaag<br>agcttcaaccggggcgagtgt |
| YY05_LALA | | |
| SEQ ID NO: 310 | HCDR1 (Combined) | GYSFTSYWIS |
| SEQ ID NO: 311 | HCDR2 (Combined) | IIYPGTSYTRYSPSFQG |
| SEQ ID NO: 312 | HCDR3 (Combined) | GAVAGQLGFDH |
| SEQ ID NO: 229 | HCDR1 (Kabat) | SYWIS |
| SEQ ID NO: 311 | HCDR2 (Kabat) | IIYPGTSYTRYSPSFQG |
| SEQ ID NO: 312 | HCDR3 (Kabat) | GAVAGQLGFDH |
| SEQ ID NO: 80 | HCDR1 (Chothia) | GYSFTSY |

TABLE 2-continued

Exemplary anti-NPR1 antibody sequences

| SEQ ID NO: 313 | HCDR2 (Chothia) | YPGTSY |
|---|---|---|
| SEQ ID NO: 312 | HCDR3 (Chothia) | GAVAGQLGFDH |
| SEQ ID NO: 82 | HCDR1 (IMGT) | GYSFTSYW |
| SEQ ID NO: 314 | HCDR2 (IMGT) | IYPGTSYT |
| SEQ ID NO: 315 | HCDR3 (IMGT) | ARGAVAGQLGFDH |
| SEQ ID NO: 316 | VH | EVQLVQSGAEVKKPGESLKISCKGSYSFTSYWISWVRQMPGKGLEWMGII<br>YPGTSYTRYSPSFQGQVTISADKSISTAYLQWSSLKASDTAMYYCARGAVA<br>GQLGFDHWGQGTLVTVSS |
| SEQ ID NO: 317 | DNA VH | gaagtgcagctggtgcagagcggtgccgaagtgaaaaaaccgggcgaaagcctgaaaatcagctgcaaa<br>ggcagcggctatagctttaccagctattggattagctgggttcgccagatgccgggcaaaggcctggaa<br>tggatgggcattatctatccgggcaccagctatacccgctatagcccgagctttcagggccaggttaca<br>attagcgccgacaaaagcatcagcaccgcctatctgcaatggagcagcctgaaagccagcgataccgcc<br>atgtattattgcgcgcgtggtgcagttgcaggacaactgggatttgatcactggggccagggcaccctg<br>gttactgtctcgagc |
| SEQ ID NO: 318 | Heavy Chain | EVQLVQSGAEVKKPGESLKISCKGSYSFTSYWISWVRQMPGKGLEWMGII<br>YPGTSYTRYSPSFQGQVTISADKSISTAYLQWSSLKASDTAMYYCARGAVA<br>GQLGFDHWGQGTLVTVSSASTKGPSVFPLAPSSKSTSGGTAALGCLVKDYF<br>PEPVTVSWNSGALTSGVHTFPAVLQSSGLYSLSSVVTVPSSSLGTQTYICNV<br>NHKPSNTKVDKRVEPKSCDKTHTCPPCPAPEAAGGPSVFLFPPKPKDTLMIS<br>RTPEVTCVVVDVSHEDPEVKFNWYVDGVEVHNAKTKPREEQYNSTYRVV<br>SVLTVLHQDWLNGKEYKCKVSNKALPAPIEKTISKAKGQPREPQVYTLPPS<br>REEMTKNQVSLTCLVKGFYPSDIAVEWESNGQPENNYKTTPPVLDSDGSFF<br>LYSKLTVDKSRWQQGNVFSCSVMHEALHNHYTQKSLSLSPGK |
| SEQ ID NO: 319 | DNA Heavy Chain | gaagtgcagctggtgcagagcggtgccgaagtgaaaaaaccgggcgaaagcctgaaaatcagctgcaaa<br>ggcagcggctatagctttaccagctattggattagctgggttcgccagatgccgggcaaaggcctggaa<br>tggatgggcattatctatccgggcaccagctatacccgctatagcccgagctttcagggccaggttaca<br>attagcgccgacaaaagcatcagcaccgcctatctgcaatggagcagcctgaaagccagcgataccgcc<br>atgtattattgcgcgcgtggtgcagttgcaggacaactgggatttgatcactggggccagggcaccctg<br>gttactgtctcgagcgcgtcgaccaaaggccccagcgtgttcctctggcccccagcagcaagagcacc<br>tctggcggaacagccgccctgggctgcctggtcaaggactacttccccgagcccgtgaccgtgtcctgg<br>aactctggcgccctgaccagcggcgtgcacacctttccagccgtgctgcagagcagcggcctgtacagc<br>ctgagcagcgtcgtgaccgtgcccagcagcagcctgggcacccagacctacatctgcaacgtgaaccac<br>aagcccagcaacacaaaggtggacaagcgggtggaacccaagagctgcgacaagacccacacctgtccc<br>ccctgccctgccctgaagcggcgggaggcccctccgtgttcctgttccccccaaagcctaaggacacc<br>ctgatgatcagccgaccccccgaagtgacctgcgtggtggtggacgtgtcccacgaggaccctgaagtg<br>aagtttaattggtacgtggacggcgtggaagtgcacaacgccaagaccaagcccagagaggaacagtac<br>aacagcacctaccgggtggtgtccgtgctgaccgtgctgcaccaggactggctgaacggcaaagagtac<br>aagtgcaaggtgtccaacaaggccctgcctgcccccatcgagaaaaccatcagcaaggccaaaggccag<br>ccccgcgagccccaggtgtacacactgcccccagcggggaagagatgaccaagaaccaggtgtccctg<br>acctgcctcgtgaagggcttctaccccagcgacattgccgtggaatgggagagcaacggccagcccgag<br>aacaactacaagaccaccccccctgtgctggacagcgacggctcattcttcctgtacagcaagctgacc<br>gtggacaagagccggtggcagcagggcaacgtgttcagctgctccgtgatgcacgaggccctgcacaac<br>cactacacccagaagtccctgagcctgagccccggcaag |
| SEQ ID NO: 320 | LCDR1 (Combined) | TGSSSNIGAGYDVH |
| SEQ ID NO: 321 | LCDR2 (Combined) | GNSNRPS |
| SEQ ID NO: 322 | LCDR3 (Combined) | QSYYTSSHGPV |
| SEQ ID NO: 320 | LCDR1 (Kabat) | TGSSSNIGAGYDVH |
| SEQ ID NO: 321 | LCDR2 (Kabat) | GNSNRPS |
| SEQ ID NO: 322 | LCDR3 (Kabat) | QSYYTSSHGPV |
| SEQ ID NO: 323 | LCDR1 (Chothia) | SSSNIGAGYD |
| SEQ ID NO: 324 | LCDR2 (Chothia) | GNS |
| SEQ ID NO: 325 | LCDR3 (Chothia) | YYTSSHGP |
| SEQ ID NO: 326 | LCDR1 (IMGT) | SSNIGAGYD |
| SEQ ID NO: 324 | LCDR2 (IMGT) | GNS |
| SEQ ID NO: 322 | LCDR3 (IMGT) | QSYYTSSHGPV |

TABLE 2-continued

Exemplary anti-NPR1 antibody sequences

| SEQ ID NO: 327 | VL | QSVLTQPPSVSGAPGQRVTISCTGSSSNIGAYDVHWYQQLPGTAPKLLIYG
NSNRPSGVPDRFSGSKSGTSASLAITGLQAEDEADYYCQSYYTSSHGPVFG
GGTKLTVL |
|---|---|---|
| SEQ ID NO: 328 | DNA VL | cagagcgtgctgacccagccaccaagcgtgagcggtgcaccaggtcagcgcgtgaccattagctgcacc
ggcagcagcagcaacattggcgcaggctatgatgtgcattggtatcagcagctgccaggcaccgcaccg
aaactgctgatttatggcaacagcaatcgcccaagcggtgtgccggatcgctttagcggcagcaaaagc
ggcaccagcgccagcctggcgattaccggtctgcaagccgaagacgaagccgattattactgccagtct
tactacacttcttctcatggtccggtgtttggcggcggtaccaagctgaccgtgctg |
| SEQ ID NO: 329 | Light Chain | QSVLTQPPSVSGAPGQRVTISCTGSSSNIGAYDVHWYQQLPGTAPKLLIYG
NSNRPSGVPDRFSGSKSGTSASLAITGLQAEDEADYYCQSYYTSSHGPVFG
GGTKLTVLGQPKAAPSVTLFPPSSEELQANKATLVCLISDFYPGAVTVAWK
ADSSPVKAGVETTTPSKQSNNKYAASSYLSLTPEQWKSHRSYSCQVTHEGS
TVEKTVAPTECS |
| SEQ ID NO: 330 | DNA Light Chain | cagagcgtgctgacccagccaccaagcgtgagcggtgcaccaggtcagcgcgtgaccattagctgcacc
ggcagcagcagcaacattggcgcaggctatgatgtgcattggtatcagcagctgccaggcaccgcaccg
aaactgctgatttatggcaacagcaatcgcccaagcggtgtgccggatcgctttagcggcagcaaaagc
ggcaccagcgccagcctggcgattaccggtctgcaagccgaagacgaagccgattattactgccagtct
tactacacttcttctcatggtccggtgtttggcggcggtaccaagctgaccgtgctgggccagcccaaa
gccgcccctagcgtgaccctgttcccccccaagcagcgaggaactccaggccaacaaggccaccctcgtg
tgcctgatcagcgacttctacccgggcgtgaccgtggcctggaaggccgatagcagccctgtgaag
gccggcgtggaaaccaccaccccagcaagcagacaacaaaatacgccgccagcagctacctgagc
ctgacccccgagcagtggaagtcccacagatcctacagctgccaggtcacacacgagggcagcaccgtg
gaaaagaccgtggcccccaccgagtgcagc |

YY06_LALA

| SEQ ID NO: 270 | HCDR1 (Combined) | GFTFSSYAIS |
|---|---|---|
| SEQ ID NO: 271 | HCDR2 (Combined) | AISGSGGSTYYAESVKG |
| SEQ ID NO: 331 | HCDR3 (Combined) | PYLGDRRSYGFDH |
| SEQ ID NO: 273 | HCDR1 (Kabat) | SYAIS |
| SEQ ID NO: 271 | HCDR2 (Kabat) | AISGSGGSTYYAESVKG |
| SEQ ID NO: 331 | HCDR3 (Kabat) | PYLGDRRSYGFDH |
| SEQ ID NO: 32 | HCDR1 (Chothia) | GFTFSSY |
| SEQ ID NO: 274 | HCDR2 (Chothia) | SGSGGS |
| SEQ ID NO: 331 | HCDR3 (Chothia) | PYLGDRRSYGFDH |
| SEQ ID NO: 275 | HCDR1 (IMGT) | GFTFSSYA |
| SEQ ID NO: 276 | HCDR2 (IMGT) | ISGSGGST |
| SEQ ID NO: 332 | HCDR3 (IMGT) | ARPYLGDRRSYGFDH |
| SEQ ID NO: 333 | VH | EVQLLESGGGLVQPGGSLRLSCAASGFTFSSYAISWVRQAPGKGLEWVSAI
SGSGGSTYYAESVKGRFTISRDNSKNTLYLQMNSLRAEDTAVYYCARPYL
GDRRSYGFDHWGQGTLVTVSS |
| SEQ ID NO: 334 | DNA VH | gaagtgcagctgctggaaagcggtggcggtctggtgcagccaggtggtagcctgcgcctgagctgtgcc
gcaagcggctttacctttagcagctatgccattagctgggtgcgccaagcaccaggcaaaggcctggaa
tgggtgagcgccattagcggcagcggtggcagcacctattatgccgagagcgtgaaaggtcgctttacc
attagtcgcgataacagcaaaaacaccctgtatctgcaaatgaacagcctgcgggcagaagataccgca
gtttattattgcgcgcgaccttatctgggtgaccgtcgtagctatggtttcgaccactggggccagggc
accctggttactgtctcgagc |
| SEQ ID NO: 335 | Heavy Chain | EVQLLESGGGLVQPGGSLRLSCAASGFTFSSYAISWVRQAPGKGLEWVSAI
SGSGGSTYYAESVKGRFTISRDNSKNTLYLQMNSLRAEDTAVYYCARPYL
GDRRSYGFDHWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYI
CNVNHKPSNTKVDKRVEPKSCDKTHTCPPCPAPEAAGGPSVFLFPPKPKDT
LMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPGK |
| SEQ ID NO: 336 | DNA Heavy Chain | gaagtgcagctgctggaaagcggtggcggtctggtgcagccaggtggtagcctgcgcctgagctgtgcc
gcaagcggctttacctttagcagctatgccattagctgggtgcgccaagcaccaggcaaaggcctggaa
tgggtgagcgccattagcggcagcggtggcagcacctattatgccgagagcgtgaaaggtcgctttacc
attagtcgcgataacagcaaaaacaccctgtatctgcaaatgaacagcctgcgggcagaagataccgca |

TABLE 2-continued

Exemplary anti-NPR1 antibody sequences

|  |  |  |
|---|---|---|
|  |  | gtttattattgcgcgcgaccttatctgggtgaccgtcgtagctatggtttcgaccactgggccagggc<br>accctggttactgtctcgagcgcgtcgaccaaaggccccagcgtgttccctctggcccccagcagcaag<br>agcacctctggcggaacagccgccctgggctggtcaaggactacttccccgagcccgtgaccgtg<br>tcctggaactctggcgccctgaccagcggcgtgcacacctttccagccgtgctccagagcagcggcctg<br>tacagcctgagcagcgtcgtgaccgtgcccagcagcagcctgggcacccagacctacatctgcaacgtg<br>aaccacaagcccagcaacacaaaggtggacaagcgggtggaacccaagagctgcgacaagacccacacc<br>tgtccccccctgccctgccctgaagcggcgggaggccccctccgtgttcctgttccccccaaagctaag<br>gacacccctgatgatcagccggaccccgaagtgacctgcgtggtggtggacgtgtcccacgaggaccct<br>gaagtgaagtttaattggtacgtgacggcgtggaagtgcacaacgccaagaccaagcccagagaggaa<br>cagtacaacagcacctaccgggtggtgtccgtgctgaccgtgctgcaccaggactggctgaacggcaaa<br>gagtacaagtgcaaggtgtccaacaaggccctgcctgcccccatcgagaaaaccatcagcaaggccaaa<br>ggccagccccgcgagccccaggtgtacacactgcccctagccgggaagagatgaccaagaaccaggtg<br>tccctgacctgcctcgtgaagggcttctaccccagcgacattgccgtggaatgggagagcaacggccag<br>cccgagaacaactaaagaccaccccctgtgctggacagcgacggctcattcttcctgtacagcaag<br>ctgaccgtggacaagagccgtggcagcagggcaacgtgttcagctgctccgtgatgcacgaggccctg<br>cacaaccactacacccagaagtccctgagcctgagccccggcaag |
| SEQ ID NO: 337 | LCDR1 (Combined) | TGTSSDVGSYNLVS |
| SEQ ID NO: 338 | LCDR2 (Combined) | EGSKRPS |
| SEQ ID NO: 339 | LCDR3 (Combined) | SSYGFHIVVVV |
| SEQ ID NO: 337 | LCDR1 (Kabat) | TGTSSDVGSYNLVS |
| SEQ ID NO: 338 | LCDR2 (Kabat) | EGSKRPS |
| SEQ ID NO: 339 | LCDR3 (Kabat) | SSYGFHIVVVV |
| SEQ ID NO: 340 | LCDR1 (Chothia) | TSSDVGSYNL |
| SEQ ID NO: 341 | LCDR2 (Chothia) | EGS |
| SEQ ID NO: 342 | LCDR3 (Chothia) | YGFHIVVV |
| SEQ ID NO: 343 | LCDR1 (IMGT) | SSDVGSYNL |
| SEQ ID NO: 341 | LCDR2 (IMGT) | EGS |
| SEQ ID NO: 339 | LCDR3 (IMGT) | SSYGFHIVVVV |
| SEQ ID NO: 344 | VL | QSALTQPASVSGSPGQSITISCTGTSSDVGSYNLVSWYQQHPGKAPKLMIYE<br>GSKRPSGVSNRFSGSKSGNTASLTISGLQAEDEADYYCSSYGFHIVVVVFGG<br>GTKLTVL |
| SEQ ID NO: 345 | DNA VL | cagagcgccctgacccagccagccagcgttagcggtagcccaggccagagcattaccattagctgcacc<br>ggcaccagcagcgacgtgggcagctataacctggttagctggtatcagcagcatccgggcaaagccccg<br>aaactgatgatctatgaaggcagcaaacgcccgagcggcgttagcaaccgctttagtggcagcaaaagc<br>ggcaacaccgccagcctgaccattagcggcctgcaagccgaagacgaagccgattattactgctcctct<br>tacggttttccatatcgttgttgttgtgtttggcggcggtaccaagctgaccgtgctg |
| SEQ ID NO: 346 | Light Chain | QSALTQPASVSGSPGQSITISCTGTSSDVGSYNLVSWYQQHPGKAPKLMIYE<br>GSKRPSGVSNRFSGSKSGNTASLTISGLQAEDEADYYCSSYGFHIVVVVFGG<br>GTKLTVLGQPKAAPSVTLFPPSSEELQANKATLVCLISDFYPGAVTVAWKA<br>DSSPVKAGVETTTPSKQSNNKYAASSYLSLTPEQWKSHRSYSCQVTHEGST<br>VEKTVAPTECS |
| SEQ ID NO: 347 | DNA Light Chain | cagagcgccctgacccagccagccagcgttagcggtagcccaggccagagcattaccattagctgcacc<br>ggcaccagcagcgacgtgggcagctataacctggttagctggtatcagcagcatccgggcaaagccccg<br>aaactgatgatctatgaaggcagcaaacgcccgagcggcgttagcaaccgctttagtggcagcaaaagc<br>ggcaacaccgccagcctgaccattagcggcctgcaagccgaagacgaagccgattattactgctcctct<br>tacggttttccatatcgttgttgttgtgtttggcggcggtaccaagctgaccgtgctgggccagcccaaa<br>gccgcccctagcgtgaccctgttccccccaagcagcgaggaactccaggccaacaaggccaccctcgtg<br>tgcctgatcagcgacttctaccctggcgccgtgaccgtggcctggaaggccgatagcagccctgtgaag<br>gccggcgtggaaaccaccacccccagcaagcagagcaacaacaaatacgccgccagcagctacctgagc<br>ctgaccccgagcagtggaagtcccacagatcctacagctgccaggtcacacacgagggcagcaccgtg<br>gaaaagaccgtggcccccaccgagtgcagc |

YY07_LALA

| SEQ ID NO: 310 | HCDR1 (Combined) | GYSFTSYWIS |
| SEQ ID NO: 311 | HCDR2 (Combined) | IIYPGTSYTRYSPSFQG |
| SEQ ID NO: 348 | HCDR3 (Combined) | GSLPGLLGFDH |
| SEQ ID NO: 229 | HCDR1 (Kabat) | SYWIS |

TABLE 2-continued

Exemplary anti-NPR1 antibody sequences

| SEQ ID NO: 311 | HCDR2 (Kabat) | IIYPGTSYTRYSPSFQG |
|---|---|---|
| SEQ ID NO: 348 | HCDR3 (Kabat) | GSLPGLLGFDH |
| SEQ ID NO: 80 | HCDR1 (Chothia) | GYSFTSY |
| SEQ ID NO: 313 | HCDR2 (Chothia) | YPGTSY |
| SEQ ID NO: 348 | HCDR3 (Chothia) | GSLPGLLGFDH |
| SEQ ID NO: 82 | HCDR1 (IMGT) | GYSFTSYW |
| SEQ ID NO: 314 | HCDR2 (IMGT) | IYPGTSYT |
| SEQ ID NO: 349 | HCDR3 (IMGT) | ARGSLPGLLGFDH |
| SEQ ID NO: 350 | VH | EVQLVQSGAEVKKPGESLKISCKGSYSFTSYWISWVRQMPGKGLEWMGII<br>YPGTSYTRYSPSFQGQVTISADKSISTAYLQWSSLKASDTAMYYCARGSLP<br>GLLGFDHWGQGTLVTVSS |
| SEQ ID NO: 351 | DNA VH | gaagtgcagctggtgcagagcggtgccgaagtgaaaaaaccgggcgaaagcctgaaaatcagctgcaaa<br>ggcagcggctatagctttaccagctattggattagctgggttcgccagatgccgggcaaaggcctggaa<br>tggatgggcattatctatccgggcaccagctataccgctatagcccgagctttcagggccaggttaca<br>attagcgccgacaaaagcatcagcaccgcctatctgcaatggagcagcctgaaagccagcgataccgcc<br>atgtattattgcgcgcgtggaagcctgcctggtctgctgggttttgatcactggggccagggcaccctg<br>gttactgtctcgagc |
| SEQ ID NO: 352 | Heavy Chain | EVQLVQSGAEVKKPGESLKISCKGSYSFTSYWISWVRQMPGKGLEWMGII<br>YPGTSYTRYSPSFQGQVTISADKSISTAYLQWSSLKASDTAMYYCARGSLP<br>GLLGFDHWGQGTLVTVSSASTKGPSVFPLAPSSKSTSGGTAALGCLVKDYF<br>PEPVTVSWNSGALTSGVHTFPAVLQSSGLYSLSSVVTVPSSSLGTQTYICNV<br>NHKPSNTKVDKRVEPKSCDKTHTCPPCPAPEAAGGPSVFLFPPKPKDTLMIS<br>RTPEVTCVVVDVSHEDPEVKFNWYVDGVEVHNAKTKPREEQYNSTYRVV<br>SVLTVLHQDWLNGKEYKCKVSNKALPAPIEKTISKAKGQPREPQVYTLPPS<br>REEMTKNQVSLTCLVKGFYPSDIAVEWESNGQPENNYKTTPPVLDSDGSFF<br>LYSKLTVDKSRWQQGNVFSCSVMHEALHNHYTQKSLSLSPGK |
| SEQ ID NO: 353 | DNA Heavy Chain | gaagtgcagctggtgcagagcggtgccgaagtgaaaaaaccgggcgaaagcctgaaaatcagctgcaaa<br>ggcagcggctatagctttaccagctattggattagctgggttcgccagatgccgggcaaaggcctggaa<br>tggatgggcattatctatccgggcaccagctataccgctatagcccgagctttcagggccaggttaca<br>attagcgccgacaaaagcatcagcaccgcctatctgcaatggagcagcctgaaagccagcgataccgcc<br>atgtattattgcgcgcgtggaagcctgcctggtctgctgggttttgatcactggggccagggcaccctg<br>gttactgtctcgagcgcgtcgaccaaaggcccagcgtgttccctctggccccagcagcaagagcacc<br>tctggcggaacagccgccctgggctgcctggtcaaggactacttccccgagccggtgaccgtgtcctgg<br>aactctggcgccctgaccagcggcgtgcacacctttccagccgtgctccagagcagcggcctgtacagc<br>ctgagcagcgtcgtgaccgtgcccagcagcagcctgggcacccagacctacatctgcaacgtgaaccac<br>aagcccagcaacacaaaggtggacaagcgggtggaacccaagagctgcgacaagacccacacctgtccc<br>ccctgccctgccctgaagcggcgggaggcccctcccgtgttcctgttccccccaaagcctaaggacacc<br>ctgatgatcagccggacccccgaagtgacctgcgtggtggtggacgtgtcccacgaggaccctgaagtg<br>aagtttaattggtacgtggacggcgtggaagtgcacaacgccaagaccaagcccagagaggaacagtac<br>aacagcacctaccgggtggtgtccgtgctgaccgtgctgcaccaggactggctgaacggcaaagagtac<br>aagtgcaaggtgtccaacaaggcccctgcccccatcgagaaaaccatcagcaaggccaaagggcag<br>ccccgcgagccccaggtgtacactgcccccctagccgggaagagatgaccaagaaccaggtgtccctg<br>acctgcctcgtgaagggcttctaccccagcgacattgccgtggaatgggagagcaacggccagcccgag<br>aacaactacaagaccacccccctgtgctggacagcgacggctcattcttcctgtacagcaagctgacc<br>gtggacaagagccggtggcagcagggcaacgtgttcagctgctccgtgatgcacgaggccctgcacaac<br>cactacacccagaagtccctgagcctgagccccggcaag |
| SEQ ID NO: 320 | LCDR1 (Combined) | TGSSSNIGAGYDVH |
| SEQ ID NO: 354 | LCDR2 (Combined) | GNSNRPN |
| SEQ ID NO: 355 | LCDR3 (Combined) | QSYDSPTSSSV |
| SEQ ID NO: 320 | LCDR1 (Kabat) | TGSSSNIGAGYDVH |
| SEQ ID NO: 354 | LCDR2 (Kabat) | GNSNRPN |
| SEQ ID NO: 355 | LCDR3 (Kabat) | QSYDSPTSSSV |
| SEQ ID NO: 323 | LCDR1 (Chothia) | SSSNIGAGYD |
| SEQ ID NO: 324 | LCDR2 (Chothia) | GNS |
| SEQ ID NO: 356 | LCDR3 (Chothia) | YDSPTSSS |
| SEQ ID NO: 326 | LCDR1 (IMGT) | SSNIGAGYD |

TABLE 2-continued

Exemplary anti-NPR1 antibody sequences

| SEQ ID NO: 324 | LCDR2 (IMGT) | GNS |
|---|---|---|
| SEQ ID NO: 355 | LCDR3 (IMGT) | QSYDSPTSSSV |
| SEQ ID NO: 357 | VL | QSVLTQPPSVSGAPGQRVTISCTGSSSNIGAGYDVHWYQQLPGTAPKLLIYG<br>NSNRPNGVPDRFSGSKSGTSASLAITGLQAEDEADYYCQSYDSPTSSSVFGG<br>GTKLTVL |
| SEQ ID NO: 358 | DNA VL | cagagcgtgctgacccagccaccaagcgtgagcggtgcaccaggtcagcgcgtgaccattagctgcacc<br>ggcagcagcagcaacattggcgcaggctatgatgtgcattggtatcagcagctgccaggcaccgcaccg<br>aaactgctgatttatggcaacagcaatcgcccaaacggtgtgccggatcgctttagcggcagcaaaagc<br>ggcaccagcgccagcctggcgattaccggtctgcaagccgaagacgaagccgattattactgccagtct<br>tacgactctccgacttcttcttctgtgtttggcggcggtaccaagctgaccgtgctg |
| SEQ ID NO: 359 | Light Chain | QSVLTQPPSVSGAPGQRVTISCTGSSSNIGAGYDVHWYQQLPGTAPKLLIYG<br>NSNRPNGVPDRFSGSKSGTSASLAITGLQAEDEADYYCQSYDSPTSSSVFGG<br>GTKLTVLGQPKAAPSVTLFPPSSEELQANKATLVCLISDFYPGAVTVAWKA<br>DSSPVKAGVETTTPSKQSNNKYAASSYLSLTPEQWKSHRSYSCQVTHEGST<br>VEKTVAPTECS |
| SEQ ID NO: 360 | DNA Light Chain | cagagcgtgctgacccagccaccaagcgtgagcggtgcaccaggtcagcgcgtgaccattagctgcacc<br>ggcagcagcagcaacattggcgcaggctatgatgtgcattggtatcagcagctgccaggcaccgcaccg<br>aaactgctgatttatggcaacagcaatcgcccaaacggtgtgccggatcgctttagcggcagcaaaagc<br>ggcaccagcgccagcctggcgattaccggtctgcaagccgaagacgaagccgattattactgccagtct<br>tacgactctccgacttcttcttctgtgtttggcggcggtaccaagctgaccgtgctgggccagcccaaa<br>gccgcccctagcgtgaccctgttcccccccaagcagcgaggaactccaggccaacaaggccacccctcgtg<br>tgcctgatcagcgacttctaccctggcgccgtgaccgtggcctggaaggccgatagcagccctgtgaag<br>gccggcgtggaaaccaccacccccagcaagcagagcaacaacaaatacgccgccagcagctacctgagc<br>ctgaccccccgagcagtggaagtcccacagatcctacagctgccaggtcacacacgagggcagcaccgtg<br>gaaaagaccgtggcccccaccgagtgcagc |

ZZ05_LALA

| SEQ ID NO: 310 | HCDR1 (Combined) | GYSFTSYWIS |
|---|---|---|
| SEQ ID NO: 311 | HCDR2 (Combined) | IIYPGTSYTRYSPSFQG |
| SEQ ID NO: 348 | HCDR3 (Combined) | GSLPGLLGFDH |
| SEQ ID NO: 229 | HCDR1 (Kabat) | SYWIS |
| SEQ ID NO: 311 | HCDR2 (Kabat) | IIYPGTSYTRYSPSFQG |
| SEQ ID NO: 348 | HCDR3 (Kabat) | GSLPGLLGFDH |
| SEQ ID NO: 80 | HCDR1 (Chothia) | GYSFTSY |
| SEQ ID NO: 313 | HCDR2 (Chothia) | YPGTSY |
| SEQ ID NO: 348 | HCDR3 (Chothia) | GSLPGLLGFDH |
| SEQ ID NO: 82 | HCDR1 (IMGT) | GYSFTSYW |
| SEQ ID NO: 314 | HCDR2 (IMGT) | IYPGTSYT |
| SEQ ID NO: 349 | HCDR3 (IMGT) | ARGSLPGLLGFDH |
| SEQ ID NO: 350 | VH | EVQLVQSGAEVKKPGESLKISCKGSGYSFTSYWISWVRQMPGKGLEWMGII<br>YPGTSYTRYSPSFQGQVTISADKSISTAYLQWSSLKASDTAMYYCARGSLP<br>GLLGFDHWGQGTLVTVSS |
| SEQ ID NO: 351 | DNA VH | gaagtgcagctggtgcagagcggtgccgaagtgaaaaaaccgggcgaaagcctgaaaatcagctgcaaa<br>ggcagcggctatagctttaccagctattggattagctgggttcgccagatgccgggcaaaggcctggaa<br>tggatgggcattatctatccgggcaccagctatacccgctatagcccgagctttcagggccaggttaca<br>attagcgccgacaaaaagcatcagcaccgccatctgcaatggagcagcctgaaagccagcgataccgcc<br>atgtattattgcgcgcgtggaagccgcctggtctgctggttttgatcactggggccagggcaccctg<br>gttactgtctcgagc |
| SEQ ID NO: 352 | Heavy Chain | EVQLVQSGAEVKKPGESLKISCKGSGYSFTSYWISWVRQMPGKGLEWMGII<br>YPGTSYTRYSPSFQGQVTISADKSISTAYLQWSSLKASDTAMYYCARGSLP<br>GLLGFDHWGQGTLVTVSSASTKGPSVFPLAPSSKSTSGGTAALGCLVKDYF<br>PEPVTVSWNSGALTSGVHTFPAVLQSSGLYSLSSVVTVPSSSLGTQTYICNV<br>NHKPSNTKVDKRVEPKSCDKTHTCPPCPAPEAAGGPSVFLFPPKPKDTLMIS<br>RTPEVTCVVVDVSHEDPEVKFNWYVDGVEVHNAKTKPREEQYNSTYRVV<br>SVLTVLHQDWLNGKEYKCKVSNKALPAPIEKTISKAKGQPREPQVYTLPPS<br>REEMTKNQVSLTCLVKGFYPSDIAVEWESNGQPENNYKTTPPVLDSDGSFF<br>LYSKLTVDKSRWQQGNVFSCSVMHEALHNHYTQKSLSLSPGK |

TABLE 2-continued

Exemplary anti-NPR1 antibody sequences

| | | |
|---|---|---|
| SEQ ID NO: 353 | DNA Heavy Chain | gaagtgcagctggtgcagagcggtgccgaagtgaaaaaaccgggcgaaagcctgaaaatcagctgcaaa<br>ggcagcggctatatagctttaccagctattggattagctgggttcgccagatgccgggcaaaggcctggaa<br>tggatgggcattatctatccgggcaccagctataccgctatagcccgagctttcagggccaggttaca<br>attagcgccgacaaaagcatcagcaccgcctatctgcaatggagcagcctgaaagccagcgataccgcc<br>atgtattattgcgcgcgtgaaagcctgcctggtctgctgggttttgatcactggggccagggcacccctg<br>gttactgtctcgagcgcgtcgaccaaaggccccagcgtgttcctctggccccagcagcaagagcacc<br>tctggcggaacagccgcccttgggctgcctggtcaaggactacttccccgaaccggtgaccgtgtcctgg<br>aactctggcgccctgaccagcggcgtgcacacctttccagccgtgctccagagcagcggcctgtacagc<br>ctgagcagcgtcgtgaccgtgccagcagcagcctgggcacccagacctacatctgcaacgtgaaccac<br>aagcccagcaacacaaaggtggacaagcgggtggaacccaagagctgcgacaagacccacacctgtccc<br>ccctgccctgcccctgaagcggcgggaggcccctccgtgttcctgttccccccaaagcctaaggacacc<br>ctgatgatcagccggaccccgaagtgacctgcgtggtggtggacgtgtcccacgaggaccctgaagtg<br>aagtttaattggtacgtggacggcgtggaagtgcacaacgccaagaccaagcccagagaggaacagtac<br>aacagcacctaccgggtggtgtccgtgctgaccgtgctgcaccaggactggctgaacggcaaagagtac<br>aagtgcaaggtgtccaacaaggccctgcctgccccatcgagaaaaccatcagcaaggccaaaggccag<br>ccccgcgagccccaggtgtacacactgccccctagccgggaagagatgaccaagaaccaggtgtccctg<br>acctgcctcgtgaagggcttctaccccagcgacattgccgtggaatgggagagcaacggccagcccgag<br>aacaactacaagaccacccccctgtgctggacagcgacggctcattcttcctgtacagcaagctgacc<br>gtggacaagagccgtggcagcagggcaacgtgttcagctgctccgtgatgcacgaggccctgcacaac<br>cactacacccagaagtccctgagcctgagccccggcaag |
| SEQ ID NO: 320 | LCDR1 (Combined) | TGSSSNIGAGYDVH |
| SEQ ID NO: 354 | LCDR2 (Combined) | GNSNRPN |
| SEQ ID NO: 361 | LCDR3 (Combined) | QSYGAFPRFVV |
| SEQ ID NO: 320 | LCDR1 (Kabat) | TGSSSNIGAGYDVH |
| SEQ ID NO: 354 | LCDR2 (Kabat) | GNSNRPN |
| SEQ ID NO: 361 | LCDR3 (Kabat) | QSYGAFPRFVV |
| SEQ ID NO: 323 | LCDR1 (Chothia) | SSSNIGAGYD |
| SEQ ID NO: 324 | LCDR2 (Chothia) | GNS |
| SEQ ID NO: 362 | LCDR3 (Chothia) | YGAFPRFV |
| SEQ ID NO: 326 | LCDR1 (IMGT) | SSNIGAGYD |
| SEQ ID NO: 324 | LCDR2 (IMGT) | GNS |
| SEQ ID NO: 361 | LCDR3 (IMGT) | QSYGAFPRFVV |
| SEQ ID NO: 363 | VL | QSVLTQPPSVSGAPGQRVTISCTGSSSNIGAGYDVHWYQQLPGTAPKLLIYG<br>NSNRPNGVPDRFSGSKSGTSASLAITGLQAEDEADYYCQSYGAFPRFVVFG<br>GGTKLTVL |
| SEQ ID NO: 364 | DNA VL | cagagcgtgctgacccagccaccaagcgtgagcggtgcaccaggtcagcgcgtgaccattagctgcacc<br>ggcagcagcagcaacattggcgcaggctatgatgtgcattggtatcagcagctgccaggcaccgcaccg<br>aaactgctgatttatggcaacagcaatcgcccaaacggtgtgccggatcgctttagcggcagcaaaagc<br>ggcaccagcgccagcctggcgattaccggtctgcaagccgaagacgaagccgattattactgccaatcc<br>tatggtgccttccctcgtttcgttgttttggcggcggtaccaagctgaccgtgctg |
| SEQ ID NO: 365 | Light Chain | QSVLTQPPSVSGAPGQRVTISCTGSSSNIGAGYDVHWYQQLPGTAPKLLIYG<br>NSNRPNGVPDRFSGSKSGTSASLAITGLQAEDEADYYCQSYGAFPRFVVFG<br>GGTKLTVLGQPKAAPSVTLFPPSSEELQANKATLVCLISDFYPGAVTVAWK<br>ADSSPVKAGVETTTPSKQSNNKYAASSYLSLTPEQWKSHRSYSCQVTHEGS<br>TVEKTVAPTECS |
| SEQ ID NO: 366 | DNA Light Chain | cagagcgtgctgacccagccaccaagcgtgagcggtgcaccaggtcagcgcgtgaccattagctgcacc<br>ggcagcagcagcaacattggcgcaggctatgatgtgcattggtatcagcagctgccaggcaccgcaccg<br>aaactgctgatttatggcaacagcaatcgcccaaacggtgtgccggatcgctttagcggcagcaaaagc<br>ggcaccagcgccagcctggcgattaccggtctgcaagccgaagacgaagccgattattactgccaatcc<br>tatggtgccttccctcgtttcgttgttttggcggcggtaccaagctgaccgtgctgggccagcccaaa<br>gccgcccctagcgtgaccctgttccccccaagcagcgaggaactccaggccaacaaggccaccctcgtg<br>tgcctgatcagcgacttctaccctggcgccgtgaccgtggcctggaaggccgatagcagccctgtgaag<br>gccggcgtggaaaccaccacccccagcaagcagagcaacaacaaatacgccgccagcagctacctgagc<br>ctgaccccgagcagtggaagtcccacagatcctacagctgccaggtcacacgagggcagcaccgtg<br>gaaaagaccgtggcccccaccgagtgcagc |
| ZZ12_LALA | | |
| SEQ ID NO: 367 | HCDR1 (Combined) | GFSFSKYYLN |
| SEQ ID NO: 368 | HCDR2 (Combined) | SIHQQAHEKKYVESVKG |

TABLE 2-continued

Exemplary anti-NPR1 antibody sequences

| SEQ ID NO: 228 | HCDR3 (Combined) | SLRRRSTEHAGFDV |
|---|---|---|
| SEQ ID NO: 369 | HCDR1 (Kabat) | KYYLN |
| SEQ ID NO: 368 | HCDR2 (Kabat) | SIHQQAHEKKYVESVKG |
| SEQ ID NO: 228 | HCDR3 (Kabat) | SLRRRSTEHAGFDV |
| SEQ ID NO: 370 | HCDR1 (Chothia) | GFSFSKY |
| SEQ ID NO: 371 | HCDR2 (Chothia) | HQQAHE |
| SEQ ID NO: 228 | HCDR3 (Chothia) | SLRRRSTEHAGFDV |
| SEQ ID NO: 372 | HCDR1 (IMGT) | GFSFSKYY |
| SEQ ID NO: 373 | HCDR2 (IMGT) | IHQQAHEK |
| SEQ ID NO: 232 | HCDR3 (IMGT) | ARSLRRRSTEHAGFDV |
| SEQ ID NO: 374 | VH | EVQLVESGGGLVQPGGSLRLSCAASGFSFSKYYLNWVRQAPGKGLEWVAS<br>IHQQAHEKKYVESVKGRFTISRDNAKNSLYLQMNSLRAEDTAVYYCARSL<br>RRRSTEHAGFDVWGQGTLVTVSS |
| SEQ ID NO: 375 | DNA VH | gaagtgcagctggtggaaagcggcggtggcctggtgcagccaggtggtagcctgcgcctgagctgcgcc<br>gccagcggctttagcttcagcaaatattacttgaactgggttcgccaggcccaggcaaaggcctggaa<br>tgggtggccagcattcaccagcaagcacacgagaaaaaatacgtggagtccgtgaaaggccgctttacc<br>attagccgcgataacgccaaaaacagcctgtatctgcaaatgaacagcctgcgggccgaagataccgcc<br>gtgtattattgcgcgcgtagcctgcgtcgtcgtagcactgagcacgcaggattcgacgtttggggccag<br>ggcaccctggttactgtctcgagc |
| SEQ ID NO: 376 | Heavy Chain | EVQLVESGGGLVQPGGSLRLSCAASGFSFSKYYLNWVRQAPGKGLEWVAS<br>IHQQAHEKKYVESVKGRFTISRDNAKNSLYLQMNSLRAEDTAVYYCARSL<br>RRRSTEHAGFDVWGQGTLVTVSSASTKGPSVFPLAPSSKSTSGGTAALGCL<br>VKDYFPEPVTVSWNSGALTSGVHTFPAVLQSSGLYSLSSVVTVPSSSLGTQT<br>YICNVNHKPSNTKVDKRVEPKSCDKTHTCPPCPAPEAAGGPSVFLFPPKPK<br>DTLMISRTPEVTCVVVDVSHEDPEVKFNWYVDGVEVHNAKTKPREEQYNS<br>TYRVVSVLTVLHQDWLNGKEYKCKVSNKALPAPIEKTISKAKGQPREPQV<br>YTLPPSREEMTKNQVSLTCLVKGFYPSDIAVEWESNGQPENNYKTTPPVLD<br>SDGSFFLYSKLTVDKSRWQQGNVFSCSVMHEALHNHYTQKSLSLSPGK |
| SEQ ID NO: 377 | DNA Heavy Chain | gaagtgcagctggtggaaagcggcggtggcctggtgcagccaggtggtagcctgcgcctgagctgcgcc<br>gccagcggctttagcttcagcaaatattacttgaactgggttcgccaggcccaggcaaaggcctggaa<br>tgggtggccagcattcaccagcaagcacacgagaaaaaatacgtggagtccgtgaaaggccgctttacc<br>attagccgcgataacgccaaaaacagcctgtatctgcaaatgaacagcctgcgggccgaagataccgcc<br>gtgtattattgcgcgcgtagcctgcgtcgtcgtagcactgagcacgcaggattcgacgtttggggccag<br>ggcaccctggttactgtctcgagcgcgtcgaccaaaggcccagcgtgttccctctggccccagcagc<br>aagagcacctctggcggaacagccgccctgggctgcctggtcaaggactacttccccgagccagtgacc<br>gtgtcctggaactctggcgccctgaccagcggcgtgcacacctttccagccgtgctccagagcagcggc<br>ctgtacagcctgagcagcgtcgtgaccgtgcccagcagcagcctgggcacccagacctacatctgcaac<br>gtgaaccacaagcccagcaacacaaaggtggacaagcgggtggaacccaagagctgcgacaagacccac<br>acctgtcccccctgccctgccccctgaagcggcgggaggccccctcgtgttcctgttccccccaaagcct<br>aaggacaccctgatgatcagccggacccccgaagtgacctgcgtggtggtggacgtgtcccacgaggac<br>cctgaagtgaagtttaattggtacgtggacggcgtggaagtgcacaacgccaagaccaagcccagagag<br>gaacagtacaacagcacctaccgggtggtgtccgtgctgaccgtgctgcaccaggactggctgaacggc<br>aaagagtacaagtgcaaggtgtccaacaaggcctgcctgccccatcgagaaaaccatcagcaaggcc<br>aaaggccagccccgcgagccccaggtgtacacactgccccctagccgggaagagatgaccaagaaccag<br>gtgtccctgacctgcctcgtgaagggcttctaccccagcgacattgccgtggaatgggagagcaacggc<br>cagcccgagaacaactacaagaccacccccctgtgctggacagcgacggctcattcttcctgtacagc<br>aagctgaccgtggacaagagccggtggcagcagggcaacgtgttcagctgctccgtgatgcacgaggcc<br>ctgcacaaccactacacccagaagtccctgagcctgagccccggcaag |
| SEQ ID NO: 237 | LCDR1 (Combined) | RASQGISNYLA |
| SEQ ID NO: 238 | LCDR2 (Combined) | AASTLQS |
| SEQ ID NO: 239 | LCDR3 (Combined) | QQADKFPYT |
| SEQ ID NO: 237 | LCDR1 (Kabat) | RASQGISNYLA |
| SEQ ID NO: 238 | LCDR2 (Kabat) | AASTLQS |
| SEQ ID NO: 239 | LCDR3 (Kabat) | QQADKFPYT |
| SEQ ID NO: 240 | LCDR1 (Chothia) | SQGISNY |
| SEQ ID NO: 241 | LCDR2 (Chothia) | AAS |

TABLE 2-continued

Exemplary anti-NPR1 antibody sequences

| | | |
|---|---|---|
| SEQ ID NO: 242 | LCDR3 (Chothia) | ADKFPY |
| SEQ ID NO: 243 | LCDR1 (IMGT) | QGISNY |
| SEQ ID NO: 241 | LCDR2 (IMGT) | AAS |
| SEQ ID NO: 239 | LCDR3 (IMGT) | QQADKFPYT |
| SEQ ID NO: 244 | VL | DIQMTQSPSSLSASVGDRVTITCRASQGISNYLAWYQQKPGKVPKLLIYAAS<br>TLQSGVPSRFSGSGSGTDFTLTISSLQPEDVATYYCQQADKFPYTFGQGTKV<br>EIK |
| SEQ ID NO: 245 | DNA VL | gatattcagatgacccagagcccgagcagcctgagcgcaagcgtgggcgatcgcgtgaccattacctgc<br>cgcgccagccagggcattagcaactatctggcctggtatcagcagaaaccgggcaaagtgccgaaactg<br>ctgatctatgccgccagcaccctgcaaagcggcgtgccaagtcgctttagcggcagcggtagcggcacc<br>gatttcaccctgaccattagcagcctgcaaccggaagacgtggcgacctattattgccagcaggctgac<br>aaatttccgtacaccttcggccagggtaccaaagtggaaatcaag |
| SEQ ID NO: 246 | Light Chain | DIQMTQSPSSLSASVGDRVTITCRASQGISNYLAWYQQKPGKVPKLLIYAAS<br>TLQSGVPSRFSGSGSGTDFTLTISSLQPEDVATYYCQQADKFPYTFGQGTKV<br>EIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVT<br>KSFNRGEC |
| SEQ ID NO: 247 | DNA Light Chain | gatattcagatgacccagagcccgagcagcctgagcgcaagcgtgggcgatcgcgtgaccattacctgc<br>cgcgccagccagggcattagcaactatctggcctggtatcagcagaaaccgggcaaagtgccgaaactg<br>ctgatctatgccgccagcaccctgcaaagcggcgtgccaagtcgctttagcggcagcggtagcggcacc<br>gatttcaccctgaccattagcagcctgcaaccggaagacgtggcgacctattattgccagcaggctgac<br>aaatttccgtacaccttcggccagggtaccaaagtggaaatcaagcggaccgtggccgctcccctccgtg<br>ttcatcttcccaccccagcgacgagcagctgaagtccggcacagccagcgtcgtgtgcctgctgaacaac<br>ttctaccccgcgaggccaaagtgcagtggaaggtggacaacgccctccagagcggcaacagccaggaa<br>agcgtcaccgagcaggacagcaaggactccacctacagcctgagcagcaccctgaccctgagcaaggcc<br>gactacgagaagcacaaggtgtacgcctgcgaagtgacccaccagggcctgtccagccccgtgaccaag<br>agcttcaaccggggcgagtgt |

ZZ13_LALA

| | | |
|---|---|---|
| SEQ ID NO: 378 | HCDR1 (Combined) | GFTFSRYYIN |
| SEQ ID NO: 379 | HCDR2 (Combined) | SIHQHGLETRYVESVKG |
| SEQ ID NO: 228 | HCDR3 (Combined) | SLRRRSTEHAGFDV |
| SEQ ID NO: 380 | HCDR1 (Kabat) | RYYIN |
| SEQ ID NO: 379 | HCDR2 (Kabat) | SIHQHGLETRYVESVKG |
| SEQ ID NO: 228 | HCDR3 (Kabat) | SLRRRSTEHAGFDV |
| SEQ ID NO: 381 | HCDR1 (Chothia) | GFTFSRY |
| SEQ ID NO: 382 | HCDR2 (Chothia) | HQHGLE |
| SEQ ID NO: 228 | HCDR3 (Chothia) | SLRRRSTEHAGFDV |
| SEQ ID NO: 383 | HCDR1 (IMGT) | GFTFSRYY |
| SEQ ID NO: 384 | HCDR2 (IMGT) | IHQHGLET |
| SEQ ID NO: 232 | HCDR3 (IMGT) | ARSLRRRSTEHAGFDV |
| SEQ ID NO: 385 | VH | EVQLVESGGGLVQPGGSLRLSCAASGFTFSRYYINWVRQAPGKGLEWVASI<br>HQHGLETRYVESVKGRFTISRDNAKNSLYLQMNSLRAEDTAVYYCARSLR<br>RRSTEHAGFDVWGQGTLVTVSS |
| SEQ ID NO: 386 | DNA VH | gaagtgcagctggtggaaagcggcggtggcctggtgcagccaggtggtagcctgcgcctgagctgcgcc<br>gccagcgggtttactttttccagatattacattaattgggttcgccaggccccaggcaaaggcctggaa<br>tgggtggcgagcatccaccagcacggcctggagaccagatatgtggaatctgtcaaagggcgctttacc<br>attagccgcgataacgccaaaaacagcctgtatctgcaaatgaacagcctgcgggccgaagataccgcc<br>gtgtattattgcgcgcgtagcctgcgtcgtcgtagcactgagcacgcaggattcgacgtttggggccag<br>ggcaccctggttactgtctcgagc |
| SEQ ID NO: 387 | Heavy Chain | EVQLVESGGGLVQPGGSLRLSCAASGFTFSRYYINWVRQAPGKGLEWVASI<br>HQHGLETRYVESVKGRFTISRDNAKNSLYLQMNSLRAEDTAVYYCARSLR<br>RRSTEHAGFDVWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQTY<br>ICNVNHKPSNTKVDKRVEPKSCDKTHTCPPCPAPEAAGGPSVFLFPPKPKDT<br>LMISRTPEVTCVVVDVSHEDPEVKFNWYVDGVEVHNAKTKPREEQYNSTY |

TABLE 2-continued

Exemplary anti-NPR1 antibody sequences

|  |  |  |
|---|---|---|
|  |  | RVVSVLTVLHQDWLNGKEYKCKVSNKALPAPIEKTISKAKGQPREPQVYT<br>LPPSREEMTKNQVSLTCLVKGFYPSDIAVEWESNGQPENNYKTTPPVLDSD<br>GSFFLYSKLTVDKSRWQQGNVFSCSVMHEALHNHYTQKSLSLSPGK |
| SEQ ID NO: 388 | DNA Heavy Chain | gaagtgcagctggtggaaagcggcggtggcctggtgcagccaggtggtagcctgcgcctgagctgcgcc<br>gccagcgggtttacttttccagatattacattaattgggttcgccaggccccaggcaaaggcctggaa<br>tgggtggcgagcatccaccagcacggcctggagaccagatatgtggaatctgtcaaaggcgctttacc<br>attagccgcgataacgccaaaaacagcctgtatctgcaaatgaacagcctgcgggccgaagataccgcc<br>gtgtattattgcgcgcgtagcctgcgtcgtcgtagcactgagcacgcaggattcgacgtttggggccag<br>ggcacccctggttactgtctcgagcgcgtcgaccaaaggccccagcgtgttccctctggccccagcagc<br>aagagcacctctggcggaacagccctgggctgcctggtcaaggactacttccccgagcccgtgacc<br>gtgtcctggaactctggcgccctgaccagcggcgtgcacacctttccagccgtgctccagagcagcggc<br>ctgtacagcctgagcagcgtcgtgaccgtgcccagcagcagcctgggcacccagacctacatctgcaac<br>gtgaaccacaagcccagcaacacaaaggtggacaagcgggtggaacccaagagctgcgacaagacccac<br>acctgtcccccctgccctgccctgaagcggcgggaggcccctccgtgttcctgttcccccccaaagcct<br>aaggacaccctgatgatcagccggaccccgaagtgacctgcgtggtggtggacgtgtcccacgaggac<br>cctgaagtgaagtttaattggtacgtggacggcgtggaagtgcacaacgccaagaccaagcccagagag<br>gaacagtacaacagcacctaccgggtggtgtccgtgctgaccgtgctgcaccaggactggctgaacggc<br>aaagagtacaagtgcaaggtgtccaacaaggccctgcctgcccccatcgagaaaaccatcagcaaggcc<br>aaaggccagccccgcgagccccaggtgtacacactgcccccta gccggggaagagatgaccaagaaccag<br>gtgtccctgacctgcctcgtgaagggcttctaccccagcgacattgccgtggaatgggagagcaacggc<br>cagcccgagaacaactacaagaccaccccccctgtgctggacagcgacggctcattcttcctgtacagc<br>aagctgaccgtggacaagagccggtggcagcagggcaacgtgttcagctgctccgtgatgcacgaggcc<br>ctgcacaaccactacacccagaagtccctgagcctgagccccggcaag |
| SEQ ID NO: 237 | LCDR1 (Combined) | RASQGISNYLA |
| SEQ ID NO: 238 | LCDR2 (Combined) | AASTLQS |
| SEQ ID NO: 239 | LCDR3 (Combined) | QQADKFPYT |
| SEQ ID NO: 237 | LCDR1 (Kabat) | RASQGISNYLA |
| SEQ ID NO: 238 | LCDR2 (Kabat) | AASTLQS |
| SEQ ID NO: 239 | LCDR3 (Kabat) | QQADKFPYT |
| SEQ ID NO: 240 | LCDR1 (Chothia) | SQGISNY |
| SEQ ID NO: 241 | LCDR2 (Chothia) | AAS |
| SEQ ID NO: 242 | LCDR3 (Chothia) | ADKFPY |
| SEQ ID NO: 243 | LCDR1 (IMGT) | QGISNY |
| SEQ ID NO: 241 | LCDR2 (IMGT) | AAS |
| SEQ ID NO: 239 | LCDR3 (IMGT) | QQADKFPYT |
| SEQ ID NO: 244 | VL | DIQMTQSPSSLSASVGDRVTITCRASQGISNYLAWYQQKPGKVPKLLIYAAS<br>TLQSGVPSRFSGSGSGTDFTLTISSLQPEDVATYYCQQADKFPYTFGQGTKV<br>EIK |
| SEQ ID NO: 245 | DNA VL | gatattcagatgacccagagcccgagcagcctgagcgcaagcgtgggcgatcgcgtgaccattacctgc<br>cgcgccagccagggcattagcaactatctggcctggtatcagcagaaacggggcaaagtgccgaaactg<br>ctgatctatgccgccagcaccctgcaaagcggcgtgccaagtcgctttagcggcagcggtagcggcacc<br>gatttcaccctgaccattagcagcctgcaaccggaagacgtggcgacctattattgccagcaggctgac<br>aaattcccgtacaccttcggccagggtaccaaagtggaaatcaag |
| SEQ ID NO: 246 | Light Chain | DIQMTQSPSSLSASVGDRVTITCRASQGISNYLAWYQQKPGKVPKLLIYAAS<br>TLQSGVPSRFSGSGSGTDFTLTISSLQPEDVATYYCQQADKFPYTFGQGTKV<br>EIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVT<br>KSFNRGEC |
| SEQ ID NO: 247 | DNA Light Chain | gatattcagatgacccagagcccgagcagcctgagcgcaagcgtgggcgatcgcgtgaccattacctgc<br>cgcgccagccagggcattagcaactatctggcctggtatcagcagaaacggggcaaagtgccgaaactg<br>ctgatctatgccgccagcaccctgcaaagcggcgtgccaagtcgctttagcggcagcggtagcggcacc<br>gatttcaccctgaccattagcagcctgcaaccggaagacgtggcgacctattattgccagcaggctgac<br>aaattcccgtacaccttcggccagggtaccaaagtggaaatcaagcggaccgtggccgctcccctccgtg<br>ttcatcttcccaccagccagcgacgagcagctgaagtccggcaccagctgtgtgctgctgaacaac<br>ttctaccccgcgaggccaaagtgcagtggaaggtggacaacgccctccagagcggcaacagccaggaa<br>agcgtcaccgagcaggacagcaaggactccacctacagcctgagcagcaccctgaccctgagcaaggcc<br>gactacgagaagcacaaggtgtacgcctgcgaagtgacccaccggggcctgtccagcccgtgaccaag<br>agcttcaaccggggcgagtgt |

TABLE 2-continued

Exemplary anti-NPR1 antibody sequences

ZZ14_LALA

| SEQ ID NO: 270 | HCDR1 (Combined) | GFTFSSYAIS |
| --- | --- | --- |
| SEQ ID NO: 389 | HCDR2 (Combined) | SISSHGYYTRYAESVKG |
| SEQ ID NO: 331 | HCDR3 (Combined) | PYLGDRRSYGFDH |
| SEQ ID NO: 273 | HCDR1 (Kabat) | SYAIS |
| SEQ ID NO: 389 | HCDR2 (Kabat) | SISSHGYYTRYAESVKG |
| SEQ ID NO: 331 | HCDR3 (Kabat) | PYLGDRRSYGFDH |
| SEQ ID NO: 32 | HCDR1 (Chothia) | GFTFSSY |
| SEQ ID NO: 390 | HCDR2 (Chothia) | SSHGYY |
| SEQ ID NO: 331 | HCDR3 (Chothia) | PYLGDRRSYGFDH |
| SEQ ID NO: 275 | HCDR1 (IMGT) | GFTFSSYA |
| SEQ ID NO: 391 | HCDR2 (IMGT) | ISSHGYYT |
| SEQ ID NO: 332 | HCDR3 (IMGT) | ARPYLGDRRSYGFDH |
| SEQ ID NO: 392 | VH | EVQLLESGGGLVQPGGSLRLSCAASGFTFSSYAISWVRQAPGKGLEWVSSIS SHGYYTRYAESVKGRFTISRDNSKNTLYLQMNSLRAEDTAVYYCARPYLG DRRSYGFDHWGQGTLVTVSS |
| SEQ ID NO: 393 | DNA VH | gaagtgcagctgctggaaagcggtggcggtctggtgcagccaggtggtagcctgcgcctgagctgtgcc gcaagcgggtttacattttccagctatgctatcagctgggtgcgccaagcaccaggcaaaggcctggaa tgggtgagcagcattagctcacatggatattacacccggtatgccgagtccgtgaaaggtcgctttacc attagtcgcgataacagcaaaaacacccttgtatctgcaaatgaacagcctgcgggcagaagataccgca gtttattattgcgcgcgaccttatctgggtgaccgtcgtagctatggtttcgaccactggggccagggc accctggttactgtctcgagc |
| SEQ ID NO: 394 | Heavy Chain | EVQLLESGGGLVQPGGSLRLSCAASGFTFSSYAISWVRQAPGKGLEWVSSIS SHGYYTRYAESVKGRFTISRDNSKNTLYLQMNSLRAEDTAVYYCARPYLG DRRSYGFDHWGQGTLVTVSSASTKGPSVFPLAPSSKSTSGGTAALGCLVKD YFPEPVTVSWNSGALTSGVHTFPAVLQSSGLYSLSSVVTVPSSSLGTQTYIC NVNHKPSNTKVDKRVEPKSCDKTHTCPPCPAPEAAGGPSVFLFPPKPKDTL MISRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVYTLP PSREEMTKNQVSLTCLVKGFYPSDIAVEWESNGQPENNYKTTPPVLDSDGS FFLYSKLTVDKSRWQQGNVFSCSVMHEALHNHYTQKSLSLSPGK |
| SEQ ID NO: 395 | DNA Heavy Chain | gaagtgcagctgctggaaagcggtggcggtctggtgcagccaggtggtagcctgcgcctgagctgtgcc gcaagcgggtttacattttccagctatgctatcagctgggtgcgccaagcaccaggcaaaggcctggaa tgggtgagcagcattagctcacatggatattacacccggtatgccgagtccgtgaaaggtcgctttacc attagtcgcgataacagcaaaaacacccttgtatctgcaaatgaacagcctgcgggcagaagataccgca gtttattattgcgcgcgaccttatctgggtgaccgtcgtagctatggtttcgaccactggggccagggc accctggttactgtctcgagcgcgtccaaaagggcccagcgtgtttccctggcccctgctcaaagcagcaag agcacctctggcggaacagccgccctgggctgcctggtcaaggactacttccccgagcccgtgaccgtg tcctggaactctggcgccctgaccagcggcgtgcacacctttccagccgtgctccagagcagcggcctg tacagcctgagcagcgtcgtgaccgtgcccagcagcagcctgggcacccagacctacatctgcaacgtg aaccacaagcccagcaacacaaaggttggacaagcgggtggaaccccaaggagctgcgacaagacccacac tgtccccctgccctgccctgaagcggcgggaggccccttccgtgttcctgttccccccaaaagcctaag gacaccctgatgatcagccggacccccgaagtgacctgcgtggtggtggacgtgtcccacgaggaccct gaagtgaagtttaattggtacgtggacggcgtggaagtgcacaacgccaagaccaagcccagagaggaa cagtacaacagcacctaccgggtggtgtccgtgctgaccgtgctgcaccaggactggctgaacggcaaa gagtacaagtgcaaggtgtccaacaaggcccctgcctgccccatcgagaaaaccatcagcaaggccaaa ggccagccccgcgagccccaggtgtacacactgcccccctagccgggaagagatgaccaagaaccaggtg tccctgacctgcctcgtgaagggcttctaccccagcgacattgccgtggaatgggagagcaacggccag cccgagaacaactacaagaccacccccccctgtgctggacagcgacggctcattcttcctgtacagcaag ctgaccgtggacaagagccggtggcagcagggcaacgtgttcagctgctccgtgatgcacgaggccctg cacaaccactacacccagaagtccctgagcctgagccccggcaag |
| SEQ ID NO: 337 | LCDR1 (Combined) | TGTSSDVGSYNLVS |
| SEQ ID NO: 338 | LCDR2 (Combined) | EGSKRPS |
| SEQ ID NO: 339 | LCDR3 (Combined) | SSYGFHIVVVV |
| SEQ ID NO: 337 | LCDR1 (Kabat) | TGTSSDVGSYNLVS |
| SEQ ID NO: 338 | LCDR2 (Kabat) | EGSKRPS |

TABLE 2-continued

Exemplary anti-NPR1 antibody sequences

| SEQ ID NO: 339 | LCDR3 (Kabat) | SSYGFHIVVVV |
|---|---|---|
| SEQ ID NO: 340 | LCDR1 (Chothia) | TSSDVGSYNL |
| SEQ ID NO: 341 | LCDR2 (Chothia) | EGS |
| SEQ ID NO: 342 | LCDR3 (Chothia) | YGFHIVVV |
| SEQ ID NO: 343 | LCDR1 (IMGT) | SSDVGSYNL |
| SEQ ID NO: 341 | LCDR2 (IMGT) | EGS |
| SEQ ID NO: 339 | LCDR3 (IMGT) | SSYGFHIVVVV |
| SEQ ID NO: 344 | VL | QSALTQPASVSGSPGQSITISCTGTSSDVGSYNLVSWYQQHPGKAPKLMIYE GSKRPSGVSNRFSGSKSGNTASLTISGLQAEDEADYYCSSYGFHIVVVVFGG GTKLTVL |
| SEQ ID NO: 345 | DNA VL | cagagcgccctgacccagccagccagcgttagcggtagcccaggccagagcattaccattagctgcacc ggcaccagcagcgacgtgggcagctataacctggttagctggtatcagcagcatccgggcaaagccccg aaactgatgatctatgaaggcagcaaacgcccgagcggcgttagcaaccgctttagtggcagcaaaagc ggcaacaccgccagcctgaccattagcggcctgcaagccgaagacgaagccgattattactgctcctct tacggtttccatatcgttgttgttgtgtttggcggcggtaccaagctgaccgtgctg |
| SEQ ID NO: 346 | Light Chain | QSALTQPASVSGSPGQSITISCTGTSSDVGSYNLVSWYQQHPGKAPKLMIYE GSKRPSGVSNRFSGSKSGNTASLTISGLQAEDEADYYCSSYGFHIVVVVFGG GTKLTVLGQPKAAPSVTLFPPSSEELQANKATLVCLISDFYPGAVTVAWKA DSSPVKAGVETTTPSKQSNNKYAASSYLSLTPEQWKSHRSYSCQVTHEGST VEKTVAPTECS |
| SEQ ID NO: 347 | DNA Light Chain | cagagcgccctgacccagccagccagcgttagcggtagcccaggccagagcattaccattagctgcacc ggcaccagcagcgacgtgggcagctataacctggttagctggtatcagcagcatccgggcaaagccccg aaactgatgatctatgaaggcagcaaacgcccgagcggcgttagcaaccgctttagtggcagcaaaagc ggcaacaccgccagcctgaccattagcggcctgcaagccgaagacgaagccgattattactgctcctct tacggtttccatatcgttgttgttgtgtttggcggcggtaccaagctgaccgtgctgggccagcccaaa gccgcccctagcgtgaccctgttcccccccaagcagcgaggaactccaggccaacaaggccaccctcgtg tgcctgatcagcgacttctaccctggcgccgtgaccgtggcctggaaggccgatagcagccctgtgaag gccggcgtggaaaccaccacccccagcaagcagagcaacaacaaatacgccgccagcagctacctgagc ctgaccccgagcagtggaagtcccacagatcctacagctgccaggtcacacacgagggcagcaccgtg gaaaagaccgtggccccaccgagtgcagc |
| ZZ15_LALA | | |
| SEQ ID NO: 396 | HCDR1 (Combined) | GFTFASYAIT |
| SEQ ID NO: 397 | HCDR2 (Combined) | TISGSGVYTYYAESVKG |
| SEQ ID NO: 331 | HCDR3 (Combined) | PYLGDRRSYGFDH |
| SEQ ID NO: 398 | HCDR1 (Kabat) | SYAIT |
| SEQ ID NO: 397 | HCDR2 (Kabat) | TISGSGVYTYYAESVKG |
| SEQ ID NO: 331 | HCDR3 (Kabat) | PYLGDRRSYGFDH |
| SEQ ID NO: 399 | HCDR1 (Chothia) | GFTFASY |
| SEQ ID NO: 400 | HCDR2 (Chothia) | SGSGVY |
| SEQ ID NO: 331 | HCDR3 (Chothia) | PYLGDRRSYGFDH |
| SEQ ID NO: 401 | HCDR1 (IMGT) | GFTFASYA |
| SEQ ID NO: 402 | HCDR2 (IMGT) | ISGSGVYT |
| SEQ ID NO: 332 | HCDR3 (IMGT) | ARPYLGDRRSYGFDH |
| SEQ ID NO: 403 | VH | EVQLLESGGGLVQPGGSLRLSCAASGFTFASYAITWVRQAPGKGLEWVSTI SGSGVYTYYAESVKGRFTISRDNSKNTLYLQMNSLRAEDTAVYYCARPYL GDRRSYGFDHWGQGTLVTVSS |
| SEQ ID NO: 404 | DNA VH | gaagtgcagctgctggaaagcggtggcggtctggtgcagccaggtggtagcctgcgcctgagctgtgcc gcaagcgggttcacattcgcatcctatgcaattacttgggtgcgccaagcaccaggcaaaggcctggaa tgggtgagcaccatttccgggtccggtgtgtacacctattacgccgagtccgtcaaaggccgcttttacc attagtcgcgataacagcaaaaacaccctgtatctgcaaatgaacagcctgcgggcagaagataccgca gtttattattgcgcgcgacctatctgggtgaccgtcgtagctatggttttcgaccactgggccagggc acccttggttactgtctcgagc |

TABLE 2-continued

Exemplary anti-NPR1 antibody sequences

| SEQ ID NO: 405 | Heavy Chain | EVQLLESGGGLVQPGGSLRLSCAASGFTFASYAITWVRQAPGKGLEWVSTI
SGSGVYTYYAESVKGRFTISRDNSKNTLYLQMNSLRAEDTAVYYCARPYL
GDRRSYGFDHWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYI
CNVNHKPSNTKVDKRVEPKSCDKTHTCPPCPAPEAAGGPSVFLFPPKPKDT
LMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPGK |
|---|---|---|
| SEQ ID NO: 406 | DNA Heavy Chain | gaagtgcagctgctggaaagcggtggcggtctggtgcagccaggtggtagcctgcgcctgagctgtgcc
gcaagcgggttcacattcgcatcctatgcaattacttgggtgcgccaagcaccaggcaaaggcctggaa
tgggtgagcaccatttccgggtccggtgtgtacacctattacgccgagtccgtcaaaggccgctttacc
attagtcgcgataacagcaaaaacaccctgtatctgcaaatgaacagcctgcgggcagaagataccgca
gtttattattgcgcgcgacctatctgggtgaccgtcgtagtatggtttcgaccactggggcagggc
accctggttactgtctcgagcgcgtcgaccaaaggccccagcgtgttccctctggccccagcagcaag
agcacctctggcggaacagccgccctgggctgcctggtcaaggactactcccgagcccgtgaccgtg
tcctggaactctggcgccctgaccagcggcgtgcacacctttccagccgtgctccagagcagcggcctg
tacagcctgagcagcgtcgtgaccgtgccagcgccagcaccagcatcctgcaacgtg
aaccacaagcccagcaacacaaaggtggacaagcggtggaacccaagagctgcgacaagacccacacc
tgtcccccctgcccgcccctgaagcggcgggaggcccccgtgttcctgttccccccaaagcctaag
gacacccctgatgatcagccggaccccgaagtgacctgcgtggtggtggacgtgtcccacgaggaccct
gaagtgaagttcaattggtacgtggacggcgtggaagtgcacaacgccaagacaaagccccagagaggaa
cagtacaacagcacctaccgggtggtgtccgtgctgaccgtgctgcaccaggactggctgaacggcaaa
gagtacaagtgcaaggtgtccaacaaggcccctgcctgccccatcgagaaaaccatcagcaaggccaaa
ggccagcccgcgagccccaggtgtacacactgccccctagccgggaagagatgaccaagaaccaggtg
tccctgacctgcctcgtgaaggcttctaccccagcgacattgccgtggaatgggagagcaacggccag
ccgagaacaactacaagaccaccccccctgtgctggacagcgacggctcattcttcctgtacagcaag
ctgaccgtggacaagagccggtggcagcagggcaacgtgttcagctgctccgtgatgcacgaggccctg
cacaaccactacacccagaagtccctgagcctgagccccggcaag |
| SEQ ID NO: 337 | LCDR1 (Combined) | TGTSSDVGSYNLVS |
| SEQ ID NO: 338 | LCDR2 (Combined) | EGSKRPS |
| SEQ ID NO: 339 | LCDR3 (Combined) | SSYGFHIVVVV |
| SEQ ID NO: 337 | LCDR1 (Kabat) | TGTSSDVGSYNLVS |
| SEQ ID NO: 338 | LCDR2 (Kabat) | EGSKRPS |
| SEQ ID NO: 339 | LCDR3 (Kabat) | SSYGFHIVVVV |
| SEQ ID NO: 340 | LCDR1 (Chothia) | TSSDVGSYNL |
| SEQ ID NO: 341 | LCDR2 (Chothia) | EGS |
| SEQ ID NO: 342 | LCDR3 (Chothia) | YGFHIVVV |
| SEQ ID NO: 343 | LCDR1 (IMGT) | SSDVGSYNL |
| SEQ ID NO: 341 | LCDR2 (IMGT) | EGS |
| SEQ ID NO: 339 | LCDR3 (IMGT) | SSYGFHIVVVV |
| SEQ ID NO: 344 | VL | QSALTQPASVSGSPGQSITISCTGTSSDVGSYNLVSWYQQHPGKAPKLMIYE
GSKRPSGVSNRFSGSKSGNTASLTISGLQAEDEADYYCSSYGFHIVVVVFGG
GTKLTVL |
| SEQ ID NO: 345 | DNA VL | cagagcgccctgacccagccagccagcgttagcggtagcccaggccagagcattaccattagctgcacc
ggcaccagcagcgacgtgggcagctatataacctggttagctggtatcagcagcatccgggcaaagcccg
aaactgatgatctatgaaggcagcaaacgcccgagcggcgttagcaaccgctttagtggcagcaaaagc
ggcaacaccgccagcctgaccattagcggcctgcaagccgaagacgaagccgattattactgctcctct
tacggttttccatatcgttgttgttgtgtttggcggcggtaccaagctgaccgtgctg |
| SEQ ID NO: 346 | Light Chain | QSALTQPASVSGSPGQSITISCTGTSSDVGSYNLVSWYQQHPGKAPKLMIYE
GSKRPSGVSNRFSGSKSGNTASLTISGLQAEDEADYYCSSYGFHIVVVVFGG
GTKLTVLGQPKAAPSVTLFPPSSEELQANKATLVCLISDFYPGAVTVAWKA
DSSPVKAGVETTTPSKQSNNKYAASSYLSLTPEQWKSHRSYSCQVTHEGST
VEKTVAPTECS |
| SEQ ID NO: 347 | DNA Light Chain | cagagcgccctgacccagccagccagcgttagcggtagcccaggccagagcattaccattagctgcacc
ggcaccagcagcgacgtgggcagctatataacctggttagctggtatcagcagcatccgggcaaagcccg
aaactgatgatctatgaaggcagcaaacgcccgagcggcgttagcaaccgctttagtggcagcaaaagc
ggcaacaccgccagcctgaccattagcggcctgcaagccgaagacgaagccgattattactgctcctct
tacggttttccatatcgttgttgttgtgtttggcggcggtaccaagctgaccgtgctgggccagcccaaa
gccgcccctagcgtgaccctgttccccccaagcagcgaggaactccaggccaacaaggccaccctcgtg
tgcctgatcagcgacttctaccctggcgccgtgaccgtggcctggaaggccgatagcagccctgtgaag |

TABLE 2-continued

Exemplary anti-NPR1 antibody sequences

|  |  |  |
|---|---|---|
|  |  | gccggcgtggaaaccaccacccccagcaagcagagcaacaacaaatacgccgccagcagctacctgagc<br>ctgacccccgagcagtggaagtcccacagatcctacagctgccaggtcacacacgagggcagcaccgtg<br>gaaaagaccgtggcccccaccgagtgcagc |
| ZZ16_LALA |  |  |
| SEQ ID NO: 407 | HCDR1 (Combined) | GFTFGTYAMT |
| SEQ ID NO: 408 | HCDR2 (Combined) | SISASGYYANYAGSVKG |
| SEQ ID NO: 331 | HCDR3 (Combined) | PYLGDRRSYGFDH |
| SEQ ID NO: 409 | HCDR1 (Kabat) | TYAMT |
| SEQ ID NO: 408 | HCDR2 (Kabat) | SISASGYYANYAGSVKG |
| SEQ ID NO: 331 | HCDR3 (Kabat) | PYLGDRRSYGFDH |
| SEQ ID NO: 410 | HCDR1 (Chothia) | GFTFGTY |
| SEQ ID NO: 411 | HCDR2 (Chothia) | SASGYY |
| SEQ ID NO: 331 | HCDR3 (Chothia) | PYLGDRRSYGFDH |
| SEQ ID NO: 412 | HCDR1 (IMGT) | GFTFGTYA |
| SEQ ID NO: 413 | HCDR2 (IMGT) | ISASG |
| SEQ ID NO: 332 | HCDR3 (IMGT) | ARPYLGDRRSYGFDH |
| SEQ ID NO: 414 | VH | EVQLLESGGGLVQPGGSLRLSCAASGFTFGTYAMTWVRQAPGKGLEWVSS<br>ISASGYYANYAGSVKGRFTISRDNSKNTLYLQMNSLRAEDTAVYYCARPY<br>LGDRRSYGFDHWGQGTLVTVSS |
| SEQ ID NO: 415 | DNA VH | gaagtgcagctgctggaaagcggtggcggtctggtgcagccaggtggtagcctgcgcctgagctgtgcc<br>gcaagcgggtttacattcggcacctatgcaatgacttgggtgcgccaagcaccaggcaaaggcctggaa<br>tgggtgagtagcattagcgcatccggatattacgctaactacgcaggcagcgtcaaaggccgctttacc<br>attagtcgcgataacagcaaaaacaccctgtatctgcaaatgaacagcctgcgggcagaagataccgca<br>gtttattattgcgcgcgaccttatctgggtgaccgtcgtagctatggtttcgaccactggggccagggc<br>accctggttactgtctcgagc |
| SEQ ID NO: 416 | Heavy Chain | EVQLLESGGGLVQPGGSLRLSCAASGFTFGTYAMTWVRQAPGKGLEWVSS<br>ISASGYYANYAGSVKGRFTISRDNSKNTLYLQMNSLRAEDTAVYYCARPY<br>LGDRRSYGFDHWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQTY<br>ICNVNHKPSNTKVDKRVEPKSCDKTHTCPPCPAPEAAGGPSVFLFPPKPKDT<br>LMISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYT<br>LPPSREEMTKNQVSLTCLVKGFYPSDIAVEWESNGQPENNYKTTPPVLDSD<br>GSFFLYSKLTVDKSRWQQGNVFSCSVMHEALHNHYTQKSLSLSPGK |
| SEQ ID NO: 417 | DNA Heavy Chain | gaagtgcagctgctggaaagcggtggcggtctggtgcagccaggtggtagcctgcgcctgagctgtgcc<br>gcaagcgggtttacattcggcacctatgcaatgacttgggtgcgccaagcaccaggcaaaggcctggaa<br>tgggtgagtagcattagcgcatccggatattacgctaactacgcaggcagcgtcaaaggccgctttacc<br>attagtcgcgataacagcaaaaacaccctgtatctgcaaatgaacagcctgcgggcagaagataccgca<br>gtttattattgcgcgcgaccttatctgggtgaccgtcgtagctatggtttcgaccactggggccagggc<br>accctggttactgtctcgagcgcgtcaaaggcccttctgttccctctgtgcccccagcagcaag<br>agcacctctggcggaacagccgccctgggctgcctggtcaaggactacttccccgagcccgtgaccgtg<br>tcctggaactctggcgccctgaccagcggcgtgcacacctttccagccgtgctccagagcagcggcctg<br>tacagcctgagcagcgtcgtgaccgtgcccagcagcagcctgggcacccagacctacatctgcaacgtg<br>aaccacaagcccagcaacacaaaggtggacaagcgggtggaacccaagagctgcgacaagacccacacc<br>tgtccccctgcctgccctgaagcggcgggggccctccgtgttcctgttcccccaaaagcctaag<br>gacacccctgatgatcagccggacccccgaagtgacctgcgtggtggtggacgtgtcccacgaggaccct<br>gaagtgaagtttaattggtacgtggacggcgtggaagtgcacaacgccaagaccaagcccagagaggaa<br>cagtacaacagcacctaccgggtggtgtccgtgctgctgcaccaggactggctgaacggcaaa<br>gagtacaagtgcaaggtgtccaacaaggcccctgcctgccccatcgagaaaaccatcagcaaggccaaa<br>ggccagccccgcgagccccaggtgtacacactgcccctagccgggaagagatgaccaagaaccaggtg<br>tccctgacctgcctcgtgaagggcttctaccccagcgacattgccgtggaatgggagagcaacggccag<br>cccgagaacaactacaagaccacccccctgtgctggacagcgacggctcattcttcctgtacagcaag<br>ctgaccgtggacaagagccggtggcagcagggcaacgtgttcagctgctccgtgatgcacgaggccctg<br>cacaaccactacacccagaagtccctgagcctgagccccggcaag |
| SEQ ID NO: 337 | LCDR1 (Combined) | TGTSSDVGSYNLVS |
| SEQ ID NO: 338 | LCDR2 (Combined) | EGSKRPS |
| SEQ ID NO: 339 | LCDR3 (Combined) | SSYGFHIVVVV |

TABLE 2-continued

Exemplary anti-NPR1 antibody sequences

| SEQ ID NO: 337 | LCDR1 (Kabat) | TGTSSDVGSYNLVS |
|---|---|---|
| SEQ ID NO: 338 | LCDR2 (Kabat) | EGSKRPS |
| SEQ ID NO: 339 | LCDR3 (Kabat) | SSYGFHIVVVV |
| SEQ ID NO: 340 | LCDR1 (Chothia) | TSSDVGSYNL |
| SEQ ID NO: 341 | LCDR2 (Chothia) | EGS |
| SEQ ID NO: 342 | LCDR3 (Chothia) | YGFHIVVV |
| SEQ ID NO: 343 | LCDR1 (IMGT) | SSDVGSYNL |
| SEQ ID NO: 341 | LCDR2 (IMGT) | EGS |
| SEQ ID NO: 339 | LCDR3 (IMGT) | SSYGFHIVVVV |
| SEQ ID NO: 344 | VL | QSALTQPASVSGSPGQSITISCTGTSSDVGSYNLVSWYQQHPGKAPKLMIYE GSKRPSGVSNRFSGSKSGNTASLTISGLQAEDEADYYCSSYGFHIVVVVFGG GTKLTVL |
| SEQ ID NO: 345 | DNA VL | cagagcgccctgacccagccagccagcgttagcggtagcccaggccagagcattaccattagctgcacc ggcaccagcagcgacgtgggcagctataacctggttagctggtatcagcagcatccgggcaaagccccg aaactgatgatctatgaaggcagcaaacgcccgagcggcgttagcaaccgctttagtggcagcaaaagc ggcaacaccgccagcctgaccattagcggcctgcaagccgaagacgaagccgattattactgctcctct tacggttttccatatcgttgttgttgtgtttggcggcggtaccaagctgaccgtgctg |
| SEQ ID NO: 346 | Light Chain | QSALTQPASVSGSPGQSITISCTGTSSDVGSYNLVSWYQQHPGKAPKLMIYE GSKRPSGVSNRFSGSKSGNTASLTISGLQAEDEADYYCSSYGFHIVVVVFGG GTKLTVLGQPKAAPSVTLFPPSSEELQANKATLVCLISDFYPGAVTVAWKA DSSPVKAGVETTTPSKQSNNKYAASSYLSLTPEQWKSHRSYSCQVTHEGST VEKTVAPTECS |
| SEQ ID NO: 347 | DNA Light Chain | cagagcgccctgacccagccagccagcgttagcggtagcccaggccagagcattaccattagctgcacc ggcaccagcagcgacgtgggcagctataacctggttagctggtatcagcagcatccgggcaaagccccg aaactgatgatctatgaaggcagcaaacgcccgagcggcgttagcaaccgctttagtggcagcaaaagc ggcaacaccgccagcctgaccattagcggcctgcaagccgaagacgaagccgattattactgctcctct tacggttttccatatcgttgttgttgtgtttggcggcggtaccaagctgaccgtgctgggccagcccaaa gccgccccgagcgtgaccctgttcccccccaagcagcgaggaactccaggccaacaaggccacccctcgtg tgcctgatcagcgacttctaccctggcgccgtgaccgtggcctggaaggccgatagcagccctgtgaag gccggcgtggaaaccaccaccccccagcaagcagagcaacaacaaatacgccgccagcagctacctgagc ctgaccccccgagcagtggaagtcccacagatcctacagctgccaggtcacacacgagggcagcaccgtg gaaaagaccgtggccccccaccgagtgcagc |

ZZ17_LALA

| SEQ ID NO: 418 | HCDR1 (Combined) | GFTFSDYAIS |
|---|---|---|
| SEQ ID NO: 419 | HCDR2 (Combined) | SISGGGYHTQYAGSVKG |
| SEQ ID NO: 331 | HCDR3 (Combined) | PYLGDRRSYGFDH |
| SEQ ID NO: 420 | HCDR1 (Kabat) | DYAIS |
| SEQ ID NO: 419 | HCDR2 (Kabat) | SISGGGYHTQYAGSVKG |
| SEQ ID NO: 331 | HCDR3 (Kabat) | PYLGDRRSYGFDH |
| SEQ ID NO: 421 | HCDR1 (Chothia) | GFTFSDY |
| SEQ ID NO: 422 | HCDR2 (Chothia) | SGGGYH |
| SEQ ID NO: 331 | HCDR3 (Chothia) | PYLGDRRSYGFDH |
| SEQ ID NO: 423 | HCDR1 (IMGT) | GFTFSDYA |
| SEQ ID NO: 424 | HCDR2 (IMGT) | ISGGGYHT |
| SEQ ID NO: 332 | HCDR3 (IMGT) | ARPYLGDRRSYGFDH |
| SEQ ID NO: 425 | VH | EVQLLESGGGLVQPGGSLRLSCAASGFTFSDYAISWVRQAPGKGLEWVSSI SGGGYHTQYAGSVKGRFTISRDNSKNTLYLQMNSLRAEDTAVYYCARPYL GDRRSYGFDHWGQGTLVTVSS |
| SEQ ID NO: 426 | DNA VH | gaagtgcagctgctggaaagcggtggcggtctggtgcagccaggtggtagcctgcgcctgagctgtgcc gcaagcggctttaccttttccgactatgcaatcagctgggtgcgccaagcaccaggcaaaggcctggaa tgggtgagcagcatttccgggggggggtatcatacacaatatgcaggatccgtgaaaggccgctttacc TABLE 2-continued Exemplary anti-NPR1 antibody sequences

|  |  |  |
|---|---|---|
|  |  | attagtcgcgataacagcaaaaacaccctgtatctgcaaatgaacagcctgcgggcagaagataccgca<br>gtttattattgcgcgcgaccttatctgggtgaccgtcgtagctatggtttcgaccactggggccagggc<br>accctggttactgtctcgagc |
| SEQ ID NO: 427 | Heavy Chain | EVQLLESGGGLVQPGGSLRLSCAASGFTFSDYAISWVRQAPGKGLEWVSSI<br>SGGGYHTQYAGSVKGRFTISRDNSKNTLYLQMNSLRAEDTAVYYCARPYL<br>GDRRSYGFDHWGQGTLVTVSSASTKGPSVFPLAPSSKSTSGGTAALGCLVK<br>DYFPEPVTVSWNSGALTSGVHTFPAVLQSSGLYSLSSVVTVPSSSLGTQTYI<br>CNVNHKPSNTKVDKRVEPKSCDKTHTCPPCPAPEAAGGPSVFLFPPKPKDT<br>LMISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYT<br>LPPSREEMTKNQVSLTCLVKGFYPSDIAVEWESNGQPENNYKTTPPVLDSD<br>GSFFLYSKLTVDKSRWQQGNVFSCSVMHEALHNHYTQKSLSLSPGK |
| SEQ ID NO: 428 | DNA Heavy Chain | gaagtgcagctgctggaaagcggtggcggtctggtgcagccaggtggtagcctgcgcctgagctgtgcc<br>gcaagcggctttacctttcccgactatgcaatcagctgggtgcgccaagcaccaggcaaaggcctggaa<br>tgggtgagcagcatttccggggggggtatcatacacaatatgcaggatccgtgaaaggccgctttacc<br>attagtcgcgataacagcaaaaacaccctgtatctgcaaatgaacagcctgcgggcagaagataccgca<br>gtttattattgcgcgcgaccttatctgggtgaccgtcgtagctatggtttcgaccactggggccagggc<br>accctggttactgtctcgagcgcgtcgaccaaaggcccagcgtgttcctctggccccagcagcaag<br>agcacctctggcggaacagccgcccgggctgcctggtcaaggactacttccccgagcccgtgaccgtg<br>tcctggaactctggcgccctgaccagcggcgtgcacacctttccagccgtgctccagagcagcggcctg<br>tacagcctgagcagcgtcgtgaccgtgccacagcagcagcgcctgggcacccagacctacatctgcaacgtg<br>aaccacaagcccagcaacacaaaggtggacaagcgggtggaacccaagagctgcgacaagacccacacc<br>tgtcccccctgccctgccctgaagcggcgggaggcccctcgcgtgttcctgttccccccaaagcctaag<br>gacaccctgatgatcagccggaccccgaagtgacctgcgtggtggtggacgtgtcccacgaggaccct<br>gaagtgaagtttaattggtacgtggacggcgtggaagtgcacaacgccaagaccaagcccagagaggaa<br>cagtacaacagcacctaccgggtggtgtccgtgctggtgctgcaccaggactggctgaacggcaaa<br>gagtacaagtgcaaggtgtccaacaaggccctgcctgccccatcgagaaaaccatcagcaaggccaaa<br>ggccagccccgcgagcccaggtgtacacactgccccctagccgggaagagatgaccaagaaccaggtg<br>tccctgacctgcctcgtgaaggggcttctaccccagcgacattgccgtggaatgggagagcaacggccag<br>cccgagaacaactacaagaccaccccccctgtgctggacagcgacggctcattcttcctgtacagcaag<br>ctgaccgtggacaagagccggtggcagcagggcaacgtgttcagctgctccgtgatgcacgaggccctg<br>cacaaccactacacccagaagtccctgagcctgagccccggcaag |
| SEQ ID NO: 337 | LCDR1 (Combined) | TGTSSDVGSYNLVS |
| SEQ ID NO: 338 | LCDR2 (Combined) | EGSKRPS |
| SEQ ID NO: 339 | LCDR3 (Combined) | SSYGFHIVVVV |
| SEQ ID NO: 337 | LCDR1 (Kabat) | TGTSSDVGSYNLVS |
| SEQ ID NO: 338 | LCDR2 (Kabat) | EGSKRPS |
| SEQ ID NO: 339 | LCDR3 (Kabat) | SSYGFHIVVVV |
| SEQ ID NO: 340 | LCDR1 (Chothia) | TSSDVGSYNL |
| SEQ ID NO: 341 | LCDR2 (Chothia) | EGS |
| SEQ ID NO: 342 | LCDR3 (Chothia) | YGFHIVVV |
| SEQ ID NO: 343 | LCDR1 (IMGT) | SSDVGSYNL |
| SEQ ID NO: 341 | LCDR2 (IMGT) | EGS |
| SEQ ID NO: 339 | LCDR3 (IMGT) | SSYGFHIVVVV |
| SEQ ID NO: 344 | VL | QSALTQPASVSGSPGQSITISCTGTSSDVGSYNLVSWYQQHPGKAPKLMIYE<br>GSKRPSGVSNRFSGSKSGNTASLTISGLQAEDEADYYCSSYGFHIVVVVFGG<br>GTKLTVL |
| SEQ ID NO: 345 | DNA VL | cagagcgccctgacccagccagccagcgttagcggtagcccaggccagagcattaccattagctgcacc<br>ggcaccagcagcgacgtgggcagctataacctggttagctggtatcagcagcatccgggcaaagcccg<br>aaactgatgatctatgaaggcagcaaacgcccgagcggcgttagcaaccgctttagtggcagcaaaagc<br>ggcaacaccgccagcctgaccattagcggcctgcaagccgaagacgaagccgattattactgctcctct<br>tacggttttccatatcgttgttgttgtgtttggcggcggtaccaagctgaccgtgctg |
| SEQ ID NO: 346 | Light Chain | QSALTQPASVSGSPGQSITISCTGTSSDVGSYNLVSWYQQHPGKAPKLMIYE<br>GSKRPSGVSNRFSGSKSGNTASLTISGLQAEDEADYYCSSYGFHIVVVVFGG<br>GTKLTVLGQPKAAPSVTLFPPSSEELQANKATLVCLISDFYPGAVTVAWKA<br>DSSPVKAGVETTTPSKQSNNKYAASSYLSLTPEQWKSHRSYSCQVTHEGST<br>VEKTVAPTECS |
| SEQ ID NO: 347 | DNA Light Chain | cagagcgccctgacccagccagccagcgttagcggtagcccaggccagagcattaccattagctgcacc<br>ggcaccagcagcgacgtgggcagctataacctggttagctggtatcagcagcatccgggcaaagcccg<br>aaactgatgatctatgaaggcagcaaacgcccgagcggcgttagcaaccgctttagtggcagcaaaagc |

TABLE 2-continued

Exemplary anti-NPR1 antibody sequences

```
ggcaacaccgccagcctgaccattagcggcctgcaagccgaagacgaagccgattattactgctcctct
tacggtttccatatcgttgttgttgtgtttggcggcggtaccaagctgaccgtgctgggccagcccaaa
gccgccccctagcgtgaccctgttccccccaagcagcgaggaactccaggccaacaaggccaccctcgtg
tgcctgatcagcgacttctaccctggcgccgtgaccgtggcctggaaggccgatagcagcctgtgaag
gccggcgtggaaaccaccaccccagcaagcagagcaacaacaaatacgccgccagcagctacctgagc
ctgaccccgagcagtggaagtcccacagatcctacagctgccaggtcacacacgagggcagcaccgtg
gaaaagaccgtggcccccaccgagtgcagc
```

For example, WW01_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 4 (HCDR1), SEQ ID NO: 5 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 5 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 8 (HCDR1), SEQ ID NO: 9 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 10 (HCDR1), SEQ ID NO: 11 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, WW11_LALA may be defined as comprising or having amino acid sequences of SEQ ID NO: 4 (HCDR1), SEQ ID NO: 5 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, WW01_LALA may be defined as comprising or having amino acid sequences of SEQ ID NO: 7 (HCDR1), SEQ ID NO: 5 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, WW01_LALA may be defined as comprising or having amino acid sequences of SEQ ID NO: 8 (HCDR1), SEQ ID NO: 9 (HCDR2), SEQ ID NO: 6 (HCDR3), SEQ ID NO: 20 (LCDR1), SEQ ID NO: 21 (LCDR2), and SEQ ID NO: 22 (LCDR3). In some embodiments, WW01_LALA may be defined as comprising or having amino acid sequences of SEQ ID NO: 10 (HCDR1), SEQ ID NO: 11 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, WW01_LALA may be defined as comprising or having a heavy chain variable region comprising or having an amino acid sequence of SEQ ID NO: 13, and a light chain variable region comprising or having an amino acid sequence of SEQ ID NO: 24. In some embodiments, WW01_LALA may be defined as comprising or having a heavy chain comprising or having an amino acid sequence of SEQ ID NO: 15, and a light chain comprising or having an amino acid sequence of SEQ ID NO: 26.

For example, WW03_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 43 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 43 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 46 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 43 (LCDR3). In some embodiments, WW03_LALA may be defined as comprising or having amino acid sequences of SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 43 (LCDR3). In some embodiments, WW03_LALA may be defined as comprising or having amino acid sequences of SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 43 (LCDR3). In some embodiments, WW03_LALA may be defined as comprising or having amino acid sequences of SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 46 (LCDR3). In some embodiments, WW03_LALA may be defined as comprising or having amino acid sequences of SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 43 (LCDR3). In some embodiments, WW03_LALA may be defined as comprising or having a heavy chain variable region comprising or having an amino acid sequence of SEQ ID NO: 37, and a light chain variable region comprising or having an amino acid sequence of SEQ ID NO: 48. In some embodiments, WW03_LALA may be defined as comprising or having a heavy chain comprising or having an amino acid sequence of SEQ ID NO: 39, and a light chain comprising or having an amino acid sequence of SEQ ID NO: 50.

For example, WW05_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 52 (HCDR1), SEQ ID NO: 53 (HCDR2), SEQ ID NO: 54 (HCDR3), SEQ ID NO: 65 (LCDR1), SEQ ID NO: 66 (LCDR2), and SEQ ID NO: 67 (LCDR3); (II) SEQ ID NO: 55 (HCDR1), SEQ ID NO: 53 (HCDR2), SEQ ID NO: 54 (HCDR3), SEQ ID NO: 65 (LCDR1), SEQ ID NO: 66 (LCDR2), and SEQ ID NO: 67 (LCDR3); (III) SEQ ID NO: 56 (HCDR1), SEQ ID NO: 57 (HCDR2), SEQ ID NO: 54 (HCDR3), SEQ ID NO: 68 (LCDR1), SEQ ID NO: 69 (LCDR2), and SEQ ID NO: 70 (LCDR3); or (IV) SEQ ID NO: 58 (HCDR1), SEQ ID NO: 59 (HCDR2), SEQ ID NO: 60 (HCDR3), SEQ ID NO: 71 (LCDR1), SEQ ID NO: 69 (LCDR2), and SEQ ID NO: 67 (LCDR3). In some embodiments, WW05_LALA may be defined as comprising or having amino acid sequences of SEQ ID NO: 52 (HCDR1), SEQ ID NO: 53 (HCDR2), SEQ ID NO: 54 (HCDR3), SEQ ID NO: 65 (LCDR1), SEQ ID NO: 66 (LCDR2), and SEQ ID NO: 67 (LCDR3). In some embodiments, WW05_LALA may be defined as comprising or having amino acid sequences of SEQ ID NO: 55 (HCDR1), SEQ ID NO: 53 (HCDR2), SEQ ID NO: 54 (HCDR3), SEQ ID NO: 65 (LCDR1), SEQ ID NO: 66 (LCDR2), and SEQ ID NO: 67 (LCDR3). In some embodiments, WW05_LALA may be defined as comprising or having amino acid sequences of SEQ ID NO: 56 (HCDR1), SEQ ID NO: 57 (HCDR2), SEQ ID NO: 54 (HCDR3), SEQ ID NO: 68 (LCDR1), SEQ ID NO: 69 (LCDR2), and SEQ ID NO: 70 (LCDR3). In some embodiments, WW05_LALA may be defined as comprising or having amino acid sequences of SEQ ID NO: 58 (HCDR1), SEQ ID NO: 59 (HCDR2), SEQ ID NO: 60 (HCDR3), SEQ ID NO: 71 (LCDR1), SEQ ID NO: 69 (LCDR2), and SEQ ID NO: 67 (LCDR3). In some embodiments, WW05_LALA may be defined as comprising or having a heavy chain variable region comprising or having an amino acid sequence of SEQ ID NO: 61, and a light chain variable region comprising or having an amino acid sequence of SEQ ID NO: 72. In some embodiments, WW05_LALA may be defined as comprising or having a heavy chain comprising or having an amino acid sequence of SEQ ID NO: 63, and a light chain comprising or having an amino acid sequence of SEQ ID NO: 74.

For example, WW06_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 76 (HCDR1), SEQ ID NO: 77 (HCDR2), SEQ ID NO: 78 (HCDR3), SEQ ID NO: 89 (LCDR1), SEQ ID NO: 90 (LCDR2), and SEQ ID NO: 91 (LCDR3); (II) SEQ ID NO: 79 (HCDR1), SEQ ID NO: 77 (HCDR2), SEQ ID NO: 78 (HCDR3), SEQ ID NO: 89 (LCDR1), SEQ ID NO: 90 (LCDR2), and SEQ ID NO: 91 (LCDR3); (III) SEQ ID NO: 80 (HCDR1), SEQ ID NO: 81 (HCDR2), SEQ ID NO: 78 (HCDR3), SEQ ID NO: 92 (LCDR1), SEQ ID NO: 93 (LCDR2), and SEQ ID NO: 94 (LCDR3); or (IV) SEQ ID NO: 82 (HCDR1), SEQ ID NO: 83 (HCDR2), SEQ ID NO: 84 (HCDR3), SEQ ID NO: 95 (LCDR1), SEQ ID NO: 93 (LCDR2), and SEQ ID NO: 91 (LCDR3). In some embodiments, WW06_LALA may be defined as comprising or having amino acid sequences of SEQ ID NO: 76 (HCDR1), SEQ ID NO: 77 (HCDR2), SEQ ID NO: 78 (HCDR3), SEQ ID NO: 89 (LCDR1), SEQ ID NO: 90 (LCDR2), and SEQ ID NO: 91 (LCDR3). In some embodiments, WW06_LALA may be defined as comprising or having amino acid sequences of SEQ ID NO: 79 (HCDR1), SEQ ID NO: 77 (HCDR2), SEQ ID NO: 78 (HCDR3), SEQ ID NO: 89 (LCDR1), SEQ ID NO: 90 (LCDR2), and SEQ ID NO: 91 (LCDR3). In some embodiments, WW06_LALA may be defined as comprising or having amino acid sequences of SEQ ID NO: 80 (HCDR1), SEQ ID NO: 81 (HCDR2), SEQ ID NO: 78 (HCDR3), SEQ ID NO: 92 (LCDR1), SEQ ID NO: 93 (LCDR2), and SEQ ID NO: 94 (LCDR3). In some embodiments, WW06_LALA may be defined as comprising or having amino acid sequences of SEQ ID NO: 82 (HCDR1), SEQ ID NO: 83 (HCDR2), SEQ ID NO: 84 (HCDR3), SEQ ID NO: 95 (LCDR1), SEQ ID NO: 93 (LCDR2), and SEQ ID NO: 91 (LCDR3). In some embodiments, WW06_LALA may be defined as comprising or having a heavy chain variable region comprising or having an amino acid sequence of SEQ ID NO: 85, and a light chain variable region comprising or having an amino acid sequence of SEQ ID NO: 96. In some embodiments, WW06_LALA may be defined as comprising or having a heavy chain comprising or having an amino acid sequence of SEQ ID NO: 87, and a light chain comprising or having an amino acid sequence of SEQ ID NO: 98.

For example, XX01_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 4 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 8 (HCDR1), SEQ ID NO: 101 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 10 (HCDR1), SEQ ID NO: 102 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX01_LALA may be defined as comprising or having amino acid sequences of SEQ ID NO: 4 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX01_LALA may be defined as comprising or having amino acid sequences of SEQ ID NO: 7 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX01_LALA may be defined as comprising or having amino acid sequences of SEQ ID NO: 8 (HCDR1), SEQ ID NO: 101 (HCDR2), SEQ ID NO: 6 (HCDR3), SEQ ID NO: 20 (LCDR1), SEQ ID NO: 21 (LCDR2), and SEQ ID NO: 22 (LCDR3). In some embodiments, XX01_LALA may be defined as comprising or having amino acid sequences of SEQ ID NO: 10 (HCDR1), SEQ ID NO: 102 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX01_LALA may be defined as comprising or having a heavy chain variable region comprising or having an amino acid sequence of SEQ ID NO: 103, and a light chain variable region comprising or having an amino acid sequence of SEQ ID NO: 24. In some embodiments, XX01_LALA may be defined as comprising or having a heavy chain comprising or having an amino acid sequence of SEQ ID NO: 105, and a light chain comprising or having an amino acid sequence of SEQ ID NO: 26.

For example, XX01_DAPA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 4 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 8 (HCDR1), SEQ ID NO: 101 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 10 (HCDR1), SEQ ID NO: 102 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX01_DAPA may be defined as comprising or having amino acid sequences of SEQ ID NO: 4 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX01_DAPA may be defined as comprising or having amino acid sequences of SEQ ID NO: 7 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX01_DAPA may be defined as comprising or having amino acid sequences of SEQ ID NO: 8 (HCDR1), SEQ ID NO: 101 (HCDR2), SEQ ID NO: 6 (HCDR3), SEQ ID NO: 20 (LCDR1), SEQ ID NO: 21 (LCDR2), and SEQ ID NO: 22 (LCDR3). In some embodiments, XX01_DAPA may be defined as comprising or having amino acid sequences of SEQ ID NO: 10 (HCDR1), SEQ ID NO: 102 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX01_DAPA may be defined as comprising or having a heavy chain variable region comprising or having an amino acid sequence of SEQ ID NO: 103, and a light chain variable region comprising or having an amino acid sequence of SEQ ID NO: 24. In some embodiments, XX01_DAPA may be defined as comprising or having a heavy chain comprising or having an amino acid sequence of SEQ ID NO: 108, and a light chain comprising or having an amino acid sequence of SEQ ID NO: 26.

For example, XX01_N30S_DAPA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 112 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 113 (HCDR1), SEQ ID NO: 101 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 114 (HCDR1), SEQ ID NO: 102 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX01_N305_DAPA may be defined as comprising or having amino acid sequences of SEQ ID NO: 112 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX01_N30S_DAPA may be defined as comprising or having amino acid sequences of SEQ ID NO: 7 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX01_N30S_DAPA may be defined as comprising or having amino acid sequences of SEQ ID NO: 113 (HCDR1), SEQ ID NO: 101 (HCDR2), SEQ ID NO: 6 (HCDR3), SEQ ID NO: 20 (LCDR1), SEQ ID NO: 21 (LCDR2), and SEQ ID NO: 22 (LCDR3). In some embodiments, XX01_N30S_DAPA may be defined as comprising or having amino acid sequences of SEQ ID NO: 114 (HCDR1), SEQ ID NO: 102 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX01_N30S_DAPA may be defined as comprising or having a heavy chain variable region comprising or having an amino acid sequence of SEQ ID NO: 115, and a light chain variable region comprising or having an amino acid sequence of SEQ ID NO: 24. In some embodiments, XX01_N30S_DAPA may be defined as comprising or having a heavy chain comprising or having an amino acid sequence of SEQ ID NO: 117, and a light chain comprising or having an amino acid sequence of SEQ ID NO: 26.

For example, XX03_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 43 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 43 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 46 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 43 (LCDR3). In some embodiments, XX03_LALA may be defined as comprising or having amino acid sequences of SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 43 (LCDR3). In some embodiments, XX03_LALA may be defined as comprising or having amino acid sequences of SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 43 (LCDR3). In some embodiments, XX03_LALA may be defined as comprising or having amino acid sequences of SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 46 (LCDR3). In some embodiments, XX03_LALA may be defined as comprising or having amino acid sequences of SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 43 (LCDR3). In some embodiments, XX03_LALA may be defined as comprising or having a heavy chain variable region comprising or having an amino acid sequence of SEQ ID NO: 122, and a light chain variable region comprising or having an amino acid sequence of SEQ ID NO: 48. In some embodiments, XX03_LALA may be defined as comprising or having a heavy chain comprising or having an amino acid sequence of SEQ ID NO: 124, and a light chain comprising or having an amino acid sequence of SEQ ID NO: 50.

For example, XX04_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 126 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 126 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 127 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 126 (LCDR3). In some embodiments, XX04_LALA may be defined as comprising or having amino acid sequences of SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 126 (LCDR3). In some embodiments, XX04_LALA may be defined as comprising or having amino acid sequences of SEQ ID NO: 31

(HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 126 (LCDR3). In some embodiments, XX04_LALA may be defined as comprising or having amino acid sequences of SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 127 (LCDR3). In some embodiments, XX04_LALA may be defined as comprising or having amino acid sequences of SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 126 (LCDR3). In some embodiments, XX04_LALA may be defined as comprising or having a heavy chain variable region comprising or having an amino acid sequence of SEQ ID NO: 37, and a light chain variable region comprising or having an amino acid sequence of SEQ ID NO: 128. In some embodiments, XX04_LALA may be defined as comprising or having a heavy chain comprising or having an amino acid sequence of SEQ ID NO: 39, and a light chain comprising or having an amino acid sequence of SEQ ID NO: 130.

For example, XX06_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 134 (LCDR3). In some embodiments, XX06_LALA may be defined as comprising or having amino acid sequences of SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3). In some embodiments, XX06_LALA may be defined as comprising or having amino acid sequences of SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3). In some embodiments, XX06_LALA may be defined as comprising or having amino acid sequences of SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 135 (LCDR3). In some embodiments, XX06_LALA may be defined as comprising or having amino acid sequences of SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 134 (LCDR3). In some embodiments, XX06_LALA may be defined as comprising or having a heavy chain variable region comprising or having an amino acid sequence of SEQ ID NO: 37, and a light chain variable region comprising or having an amino acid sequence of SEQ ID NO: 136. In some embodiments, XX06_LALA may be defined as comprising or having a heavy chain comprising or having an amino acid sequence of SEQ ID NO: 39, and a light chain comprising or having an amino acid sequence of SEQ ID NO: 138.

For example, XX06_DAPA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 134 (LCDR3). In some embodiments, XX06_DAPA may be defined as comprising or having amino acid sequences of SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3). In some embodiments, XX06_DAPA may be defined as comprising or having amino acid sequences of SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3). In some embodiments, XX06_DAPA may be defined as comprising or having amino acid sequences of SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 135 (LCDR3). In some embodiments, XX06_DAPA may be defined as comprising or having amino acid sequences of SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 134 (LCDR3). In some embodiments, XX06_DAPA may be defined as comprising or having a heavy chain variable region comprising or having an amino acid sequence of SEQ ID NO: 37, and a light chain variable region comprising or having an amino acid sequence of SEQ ID NO: 136. In some embodiments, XX06_DAPA may be defined as comprising or having a heavy chain comprising or having an amino acid sequence of SEQ ID NO: 141, and a light chain comprising or having an amino acid sequence of SEQ ID NO: 138.

For example, XX07_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 145 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 145 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 146 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 145 (LCDR3). In some embodiments, XX07_LALA may be defined as comprising or having amino acid sequences of SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 145 (LCDR3). In some embodiments, XX07_LALA may be defined as comprising or having amino acid sequences of SEQ ID NO: 31 (HCDR1), SEQ ID NO: 29 (HCDR2), SEQ ID NO: 30 (HCDR3), SEQ ID NO: 41 (LCDR1), SEQ ID NO: 42

(LCDR2), and SEQ ID NO: 145 (LCDR3). In some embodiments, XX07_LALA may be defined as comprising or having amino acid sequences of SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 146 (LCDR3). In some embodiments, XX07_LALA may be defined as comprising or having amino acid sequences of SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 145 (LCDR3). In some embodiments, XX07_LALA may be defined as comprising or having a heavy chain variable region comprising or having an amino acid sequence of SEQ ID NO: 37, and a light chain variable region comprising or having an amino acid sequence of SEQ ID NO: 147. In some embodiments, XX07_LALA may be defined as comprising or having a heavy chain comprising or having an amino acid sequence of SEQ ID NO: 39, and a light chain comprising or having an amino acid sequence of SEQ ID NO: 149.

For example, XX08_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 4 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 8 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 10 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX08_LALA may be defined as comprising or having amino acid sequences of SEQ ID NO: 4 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX08_LALA may be defined as comprising or having amino acid sequences of SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX08_LALA may be defined as comprising or having amino acid sequences of SEQ ID NO: 8 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3). In some embodiments, XX08_LALA may be defined as comprising or having amino acid sequences of SEQ ID NO: 10 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX08_LALA may be defined as comprising or having a heavy chain variable region comprising or having an amino acid sequence of SEQ ID NO: 154, and a light chain variable region comprising or having an amino acid sequence of SEQ ID NO: 24. In some embodiments, XX08_LALA may be defined as comprising or having a heavy chain comprising or having an amino acid sequence of SEQ ID NO: 156, and a light chain comprising or having an amino acid sequence of SEQ ID NO: 26.

For example, XX08_DAPA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 4 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 8 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 10 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX08_DAPA may be defined as comprising or having amino acid sequences of SEQ ID NO: 4 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX08_DAPA may be defined as comprising or having amino acid sequences of SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX08_DAPA may be defined as comprising or having amino acid sequences of SEQ ID NO: 8 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3). In some embodiments, XX08_DAPA may be defined as comprising or having amino acid sequences of SEQ ID NO: 10 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX08_DAPA may be defined as comprising or having a heavy chain variable region comprising or having an amino acid sequence of SEQ ID NO: 154, and a light chain variable region comprising or having an amino acid sequence of SEQ ID NO: 24. In some embodiments, XX08_DAPA may be defined as comprising or having a heavy chain comprising or having an amino acid sequence of SEQ ID NO: 159, and a light chain comprising or having an amino acid sequence of SEQ ID NO: 26.

For example, XX08_N30S_DAPA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 112 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 113 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 114 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX08_N30S_DAPA may be defined as comprising or having amino acid sequences of SEQ ID NO: 112 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX08_N30S_DAPA may be defined as comprising or having amino acid sequences of SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX08_N30S_DAPA may be defined as comprising or having amino acid sequences of SEQ ID NO: 113 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3). In some embodiments, XX08_N30S_DAPA may be defined as comprising or having amino acid sequences of SEQ ID NO: 114 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX08_N30S_DAPA may be defined as comprising or having a heavy chain variable region comprising or having an amino acid sequence of SEQ ID NO: 161, and a light chain variable region comprising or having an amino acid sequence of SEQ ID NO: 24. In some embodiments, XX08_N30S_DAPA may be defined as comprising or having a heavy chain comprising or having an amino acid sequence of SEQ ID NO: 163, and a light chain comprising or having an amino acid sequence of SEQ ID NO: 26.

For example, XX08_N30Q_DAPA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 165 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 166 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 167 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX08_N30Q_DAPA may be defined as comprising or having amino acid sequences of SEQ ID NO: 165 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX08_N30Q_DAPA may be defined as comprising or having amino acid sequences of SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX08_N30Q_DAPA may be defined as comprising or having amino acid sequences of SEQ ID NO: 166 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3). In some embodiments, XX08_N30Q_DAPA may be defined as comprising or having amino acid sequences of SEQ ID NO: 167 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX08_N30Q_DAPA may be defined as comprising or having a heavy chain variable region comprising or having an amino acid sequence of SEQ ID NO: 168, and a light chain variable region comprising or having an amino acid sequence of SEQ ID NO: 24. In some embodiments, XX08_N30Q_DAPA may be defined as comprising or having a heavy chain comprising or having an amino acid sequence of SEQ ID NO: 170, and a light chain comprising or having an amino acid sequence of SEQ ID NO: 26.

For example, XX09_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 172 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 172 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 173 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 172 (LCDR3). In some embodiments, XX09_LALA may be defined as comprising or having amino acid sequences of SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 172 (LCDR3). In some embodiments, XX09_LALA may be defined as comprising or having amino acid sequences of SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 172 (LCDR3). In some embodiments, XX09_LALA may be defined as comprising or having amino acid sequences of SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 173 (LCDR3). In some embodiments, XX09_LALA may be defined as comprising or having amino acid sequences of SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 172 (LCDR3). In some embodiments, XX09_LALA may be defined as comprising or having a heavy chain variable region comprising or having an amino acid sequence of SEQ ID NO: 37, and a light chain variable region comprising or having an amino acid sequence of SEQ ID NO: 174. In some embodiments, XX09_LALA may be defined as comprising or having a heavy chain comprising or having an amino acid sequence of SEQ ID NO: 39, and a light chain comprising or having an amino acid sequence of SEQ ID NO: 176.

For example, XX11_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 178 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 178 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 179 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 178 (LCDR3). In some embodiments, XX11_LALA may be defined as comprising or having amino acid sequences of SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 178 (LCDR3). In some embodiments, XX11_LALA may be defined as comprising or having amino acid sequences of SEQ ID NO: 31 (HCDR1), SEQ ID NO: 29 (HCDR2), SEQ ID NO: 30 (HCDR3), SEQ ID NO: 41 (LCDR1), SEQ ID NO: 42

(LCDR2), and SEQ ID NO: 178 (LCDR3). In some embodiments, XX11_LALA may be defined as comprising or having amino acid sequences of SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 179 (LCDR3). In some embodiments, XX11_LALA may be defined as comprising or having amino acid sequences of SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 178 (LCDR3). In some embodiments, XX11_LALA may be defined as comprising or having a heavy chain variable region comprising or having an amino acid sequence of SEQ ID NO: 37, and a light chain variable region comprising or having an amino acid sequence of SEQ ID NO: 180. In some embodiments, XX11_LALA may be defined as comprising or having a heavy chain comprising or having an amino acid sequence of SEQ ID NO: 39, and a light chain comprising or having an amino acid sequence of SEQ ID NO: 182.

For example, XX12_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 184 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 184 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 185 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 184 (LCDR3). In some embodiments, XX12_LALA may be defined as comprising or having amino acid sequences of SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 184 (LCDR3). In some embodiments, XX12_LALA may be defined as comprising or having amino acid sequences of SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 184 (LCDR3). In some embodiments, XX12_LALA may be defined as comprising or having amino acid sequences of SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 185 (LCDR3). In some embodiments, XX12_LALA may be defined as comprising or having amino acid sequences of SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 184 (LCDR3). In some embodiments, XX12_LALA may be defined as comprising or having a heavy chain variable region comprising or having an amino acid sequence of SEQ ID NO: 37, and a light chain variable region comprising or having an amino acid sequence of SEQ ID NO: 186. In some embodiments, XX12_LALA may be defined as comprising or having a heavy chain comprising or having an amino acid sequence of SEQ ID NO: 39, and a light chain comprising or having an amino acid sequence of SEQ ID NO: 188.

For example, XX13_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 191 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 192 (HCDR2), SEQ ID NO: 36 (HCDR3), SEQ ID NO: 47 (LCDR1), SEQ ID NO: 45 (LCDR2), and SEQ ID NO: 134 (LCDR3). In some embodiments, XX13_LALA may be defined as comprising or having amino acid sequences of SEQ ID NO: 28 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 134 (LCDR3). In some embodiments, XX13_LALA may be defined as comprising or having amino acid sequences of SEQ ID NO: 31 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 134 (LCDR3). In some embodiments, XX13_LALA may be defined as comprising or having amino acid sequences of SEQ ID NO: 32 (HCDR1), SEQ ID NO: 191 (HCDR2), SEQ ID NO: 30 (HCDR3), SEQ ID NO: 44 (LCDR1), SEQ ID NO: 45 (LCDR2), and SEQ ID NO: 135 (LCDR3). In some embodiments, XX13_LALA may be defined as comprising or having amino acid sequences of SEQ ID NO: 34 (HCDR1), SEQ ID NO: 192 (HCDR2), SEQ ID NO: 36 (HCDR3), SEQ ID NO: 47 (LCDR1), SEQ ID NO: 45 (LCDR2), and SEQ ID NO: 134 (LCDR3). In some embodiments, XX13_LALA may be defined as comprising or having a heavy chain variable region comprising or having an amino acid sequence of SEQ ID NO: 193, and a light chain variable region comprising or having an amino acid sequence of SEQ ID NO: 136. In some embodiments, XX13_LALA may be defined as comprising or having a heavy chain comprising or having an amino acid sequence of SEQ ID NO: 195, and a light chain comprising or having an amino acid sequence of SEQ ID NO: 138.

For example, XX14_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 172 (LCDR3); (II) SEQ ID NO: 31 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 172 (LCDR3); (III) SEQ ID NO: 32 (HCDR1), SEQ ID NO: 191 (HCDR2), SEQ ID NO: 30 (HCDR3), SEQ ID NO: 44 (LCDR1), SEQ ID NO: 45 (LCDR2), and SEQ ID NO: 173 (LCDR3); or (IV) SEQ ID NO: 34 (HCDR1), SEQ ID NO: 192 (HCDR2), SEQ ID NO: 36 (HCDR3), SEQ ID NO: 47 (LCDR1), SEQ ID NO: 45 (LCDR2), and SEQ ID NO: 172 (LCDR3). In some embodiments, XX14_LALA may be defined as comprising or having amino acid sequences of SEQ ID NO: 28 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 172 (LCDR3). In some embodiments, XX14_LALA may be defined as comprising or having amino acid sequences of SEQ ID NO: 31 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 172 (LCDR3). In some embodiments, XX14_LALA may be defined as comprising or having amino acid sequences of SEQ ID NO: 32 (HCDR1), SEQ ID NO: 191 (HCDR2), SEQ ID NO: 30 (HCDR3), SEQ ID NO: 44 (LCDR1), SEQ ID NO: 45 (LCDR2), and SEQ ID NO: 173 (LCDR3). In some embodiments, XX14_LALA may be defined as comprising or having amino acid sequences of SEQ ID NO: 34 (HCDR1), SEQ ID NO: 192 (HCDR2), SEQ ID NO: 36 (HCDR3), SEQ ID NO: 47 (LCDR1), SEQ ID NO: 45 (LCDR2), and SEQ ID NO: 172 (LCDR3). In some embodiments, XX14_LALA may be defined as comprising or having a heavy chain variable region comprising or having an amino acid sequence of SEQ ID NO: 193, and a light chain variable region comprising or having an amino acid sequence of SEQ ID NO: 174. In some embodiments, XX14_LALA may be defined as comprising or having a heavy chain comprising or having an amino acid sequence of SEQ ID NO: 195, and a light chain comprising or having an amino acid sequence of SEQ ID NO: 176.

For example, XX15_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 126 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 126 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 127 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 126 (LCDR3). In some embodiments, XX15_LALA may be defined as comprising or having amino acid sequences of SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 126 (LCDR3). In some embodiments, XX15_LALA may be defined as comprising or having amino acid sequences of SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 126 (LCDR3). In some embodiments, XX15_LALA may be defined as comprising or having amino acid sequences of SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 127 (LCDR3). In some embodiments, XX15_LALA may be defined as comprising or having amino acid sequences of SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 126 (LCDR3). In some embodiments, XX15_LALA may be defined as comprising or having a heavy chain variable region comprising or having an amino acid sequence of SEQ ID NO: 201, and a light chain variable region comprising or having an amino acid sequence of SEQ ID NO: 128. In some embodiments, XX15_LALA may be defined as comprising or having a heavy chain comprising or having an amino acid sequence of SEQ ID NO: 203, and a light chain comprising or having an amino acid sequence of SEQ ID NO: 130.

For example, XX15_DAPA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 126 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 126 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 127 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 126 (LCDR3). In some embodiments, XX15_DAPA may be defined as comprising or having amino acid sequences of SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 126 (LCDR3). In some embodiments, XX15_DAPA may be defined as comprising or having amino acid sequences of SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 126 (LCDR3). In some embodiments, XX15_DAPA may be defined as comprising or having amino acid sequences of SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 127 (LCDR3). In some embodiments, XX15_DAPA may be defined as comprising or having amino acid sequences of SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 126 (LCDR3). In some embodiments, XX15_DAPA may be defined as comprising or having a heavy chain variable region comprising or having an amino acid sequence of SEQ ID NO: 122, and a light chain variable region comprising or having an amino acid sequence of SEQ ID NO: 128. In some embodiments, XX15_DAPA may be defined as comprising or having a heavy chain comprising or having an amino acid sequence of SEQ ID NO: 208, and a light chain comprising or having an amino acid sequence of SEQ ID NO: 130.

For example, XX16_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 134 (LCDR3). In some embodiments, XX16_LALA may be defined as comprising or having amino acid sequences of SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3). In some embodiments, XX16_LALA may be defined as comprising or having amino acid sequences of SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3). In some embodiments, XX16_LALA may be defined as comprising or having amino acid sequences of SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 135 (LCDR3). In some embodiments, XX16_LALA may be defined as comprising or having amino acid sequences of SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 134 (LCDR3). In some embodiments, XX16_LALA may be defined as comprising or having a heavy chain variable region comprising or having an amino acid sequence of SEQ ID NO: 201, and a light chain variable region comprising or having an amino acid sequence of SEQ ID NO: 136. In some embodiments, XX16_LALA may be defined as comprising or having a heavy chain comprising or having an amino acid sequence of SEQ ID NO: 203, and a light chain comprising or having an amino acid sequence of SEQ ID NO: 138.

For example, XX16_DAPA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 134 (LCDR3). In some embodiments, XX16_DAPA may be defined as comprising or having amino acid sequences of SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3). In some embodiments, XX16_DAPA may be defined as comprising or having amino acid sequences of SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3). In some embodiments, XX16_DAPA may be defined as comprising or having amino acid sequences of SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 135 (LCDR3). In some embodiments, XX16_DAPA may be defined as comprising or having amino acid sequences of SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 134 (LCDR3). In some embodiments, XX16_DAPA may be defined as comprising or having a heavy chain variable region comprising or having an amino acid sequence of SEQ ID NO: 122, and a light chain variable region comprising or having an amino acid sequence of SEQ ID NO: 136. In some embodiments, XX16_DAPA may be defined as comprising or having a heavy chain comprising or having an amino acid sequence of SEQ ID NO: 208, and a light chain comprising or having an amino acid sequence of SEQ ID NO: 138.

For example, XX17_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 146 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 145 (LCDR3). In some embodiments, XX17_LALA may be defined as comprising or having amino acid sequences of SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3). In some embodiments, XX17_LALA may be defined as comprising or having amino acid sequences of SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3). In some embodiments, XX17_LALA may be defined as comprising or having amino acid sequences of SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 146 (LCDR3). In some embodiments, XX17_LALA may be defined as comprising or having amino acid sequences of SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 145 (LCDR3). In some embodiments, XX17_LALA may be defined as comprising or having a heavy chain variable region comprising or having an amino acid sequence of SEQ ID NO: 201, and a light chain variable region comprising or having an amino acid sequence of SEQ ID NO: 147. In some embodiments, XX17_LALA may be defined as comprising or having a heavy chain comprising or having an amino acid sequence of SEQ ID NO: 203, and a light chain comprising or having an amino acid sequence of SEQ ID NO: 149.

For example, XX17_DAPA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 146 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 145 (LCDR3). In some embodiments, XX17_DAPA may be defined as comprising or having amino acid sequences of SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3). In some embodiments, XX17_DAPA may be defined as comprising or having amino acid sequences of SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3). In some embodiments, XX17_DAPA may be defined as comprising or having amino acid sequences of SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 146 (LCDR3). In some embodiments, XX17_DAPA may be defined as comprising or having amino acid sequences of (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 145 (LCDR3). In some embodiments, XX17_DAPA may be defined as comprising or having a heavy chain variable region comprising or having an amino acid sequence of SEQ ID NO: 122, and a light chain variable region comprising or having an amino acid sequence of SEQ ID NO: 147. In some embodiments, XX17_DAPA may be defined as comprising or having a heavy chain comprising or having an amino acid sequence of SEQ ID NO: 208, and a light chain comprising or having an amino acid sequence of SEQ ID NO: 149.

For example, XX18_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 173 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 172 (LCDR3). In some embodiments, XX18_LALA may be defined as comprising or having amino acid sequences of SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3). In some embodiments, XX18_LALA may be defined as comprising or having amino acid sequences of SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3). In some embodiments, XX18_LALA may be defined as comprising or having amino acid sequences of SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 173 (LCDR3). In some embodiments, XX18_LALA may be defined as comprising or having amino acid sequences of SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 172 (LCDR3). In some embodiments, XX18_LALA may be defined as comprising or having a heavy chain variable region comprising or having an amino acid sequence of SEQ ID NO: 201, and a light chain variable region comprising or having an amino acid sequence of SEQ ID NO: 174. In some embodiments, XX18_LALA may be defined as comprising or having a heavy chain comprising or having an amino acid sequence of SEQ ID NO: 203, and a light chain comprising or having an amino acid sequence of SEQ ID NO: 176.

For example, XX18_DAPA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 173 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 172 (LCDR3). In some embodiments, XX18_DAPA may be defined as comprising or having amino acid sequences of SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3). In some embodiments, XX18_DAPA may be defined as comprising or having amino acid sequences of SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3). In some embodiments, XX18_DAPA may be defined as comprising or having amino acid sequences of SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 173 (LCDR3). In some embodiments, XX18_DAPA may be defined as comprising or having amino acid sequences of SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 172 (LCDR3). In some embodiments, XX18_DAPA may be defined as comprising or having a heavy chain variable region comprising or having an amino acid sequence of SEQ ID NO: 122, and a light chain variable region comprising or having an amino acid sequence of SEQ ID NO: 174. In some embodiments, XX18_DAPA may be defined as comprising or having a heavy chain comprising or having an amino acid sequence of SEQ ID NO: 208, and a light chain comprising or having an amino acid sequence of SEQ ID NO: 176.

For example, XX19_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 179 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 178 (LCDR3). In some embodiments, XX19_LALA may be defined as comprising or having amino acid sequences of SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3). In some embodiments, XX19_LALA may be defined as comprising or having amino acid sequences of SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3). In some embodiments, XX19_LALA may be defined as comprising or having amino acid sequences of SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 179 (LCDR3). In some embodiments, XX19_LALA may be defined as comprising or having amino acid sequences of SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 178 (LCDR3). In some embodiments, XX19_LALA may be defined as comprising or having a heavy chain variable region comprising or having an amino acid sequence of SEQ ID NO: 201, and a light chain variable region comprising or having an amino acid sequence of SEQ ID NO: 180. In some embodiments, XX19_LALA may be defined as comprising or having a heavy chain comprising or having an amino acid sequence of SEQ ID NO: 203, and a light chain comprising or having an amino acid sequence of SEQ ID NO: 182.

For example, XX19_DAPA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 179 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 178 (LCDR3). In some embodiments, XX19_DAPA may be defined as comprising or having amino acid sequences of SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3). In some embodiments, XX19_DAPA may be defined as comprising or having amino acid sequences of SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3). In some embodiments, XX19_DAPA may be defined as comprising or having amino acid sequences of SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 179 (LCDR3). In some embodiments, XX19_DAPA may be defined as comprising or having amino acid sequences of SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 178 (LCDR3). In some embodiments, XX19_DAPA may be defined as comprising or having a heavy chain variable region comprising or having an amino acid sequence of SEQ ID NO: 122, and a light chain variable region comprising or having an amino acid sequence of SEQ ID NO: 180. In some embodiments, XX19_DAPA may be defined as comprising or having a heavy chain comprising or having an amino acid sequence of SEQ ID NO: 208, and a light chain comprising or having an amino acid sequence of SEQ ID NO: 182.

For example, XX20_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 185 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 184 (LCDR3). In some embodiments, XX20_LALA may be defined as comprising or having amino acid sequences of SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3). In some embodiments, XX20_LALA may be defined as comprising or having amino acid sequences of SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3). In some embodiments, XX20_LALA may be defined as comprising or having amino acid sequences of SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 185 (LCDR3). In some embodiments, XX20_LALA may be defined as comprising or having amino acid sequences of SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 184 (LCDR3). In some embodiments, XX20_LALA may be defined as comprising or having a heavy chain variable region comprising or having an amino acid sequence of SEQ ID NO: 201, and a light chain variable region comprising or having an amino acid sequence of SEQ ID NO: 186. In some embodiments, XX20_LALA may be defined as comprising or having a heavy chain comprising or having an amino acid sequence of SEQ ID NO: 203, and a light chain comprising or having an amino acid sequence of SEQ ID NO: 188.

For example, XX20_DAPA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 185 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 184 (LCDR3). In some embodiments, XX20_DAPA may be defined as comprising or having amino acid sequences of SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3). In some embodiments, XX20_DAPA may be defined as comprising or having amino acid sequences of SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3). In some embodiments, XX20_DAPA may be defined as comprising or having amino acid sequences of SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 185 (LCDR3). In some embodiments, XX20_DAPA may be defined as comprising or having amino acid sequences of SEQ ID NO: 34 (HCDR1), SEQ ID NO: 121 (HCDR2), SEQ ID NO: 36 (HCDR3), SEQ ID NO:

47 (LCDR1), SEQ ID NO: 45 (LCDR2), and SEQ ID NO: 184 (LCDR3). In some embodiments, XX20_DAPA may be defined as comprising or having a heavy chain variable region comprising or having an amino acid sequence of SEQ ID NO: 122, and a light chain variable region comprising or having an amino acid sequence of SEQ ID NO: 186. In some embodiments, XX20_DAPA may be defined as comprising or having a heavy chain comprising or having an amino acid sequence of SEQ ID NO: 208, and a light chain comprising or having an amino acid sequence of SEQ ID NO: 188.

For example, YY01_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 226 (HCDR1), SEQ ID NO: 227 (HCDR2), SEQ ID NO: 228 (HCDR3), SEQ ID NO: 237 (LCDR1), SEQ ID NO: 238 (LCDR2), and SEQ ID NO: 239 (LCDR3); (II) SEQ ID NO: 229 (HCDR1), SEQ ID NO: 227 (HCDR2), SEQ ID NO: 228 (HCDR3), SEQ ID NO: 237 (LCDR1), SEQ ID NO: 238 (LCDR2), and SEQ ID NO: 239 (LCDR3); (III) SEQ ID NO: 32 (HCDR1), SEQ ID NO: 230 (HCDR2), SEQ ID NO: 228 (HCDR3), SEQ ID NO: 240 (LCDR1), SEQ ID NO: 241 (LCDR2), and SEQ ID NO: 242 (LCDR3); or (IV) SEQ ID NO: 34 (HCDR1), SEQ ID NO: 231 (HCDR2), SEQ ID NO: 232 (HCDR3), SEQ ID NO: 243 (LCDR1), SEQ ID NO: 241 (LCDR2), and SEQ ID NO: 239 (LCDR3). In some embodiments, YY01_LALA may be defined as comprising or having amino acid sequences of SEQ ID NO: 226 (HCDR1), SEQ ID NO: 227 (HCDR2), SEQ ID NO: 228 (HCDR3), SEQ ID NO: 237 (LCDR1), SEQ ID NO: 238 (LCDR2), and SEQ ID NO: 239 (LCDR3). In some embodiments, YY01_LALA may be defined as comprising or having amino acid sequences of SEQ ID NO: 229 (HCDR1), SEQ ID NO: 227 (HCDR2), SEQ ID NO: 228 (HCDR3), SEQ ID NO: 237 (LCDR1), SEQ ID NO: 238 (LCDR2), and SEQ ID NO: 239 (LCDR3). In some embodiments, YY01_LALA may be defined as comprising or having amino acid sequences of SEQ ID NO: 32 (HCDR1), SEQ ID NO: 230 (HCDR2), SEQ ID NO: 228 (HCDR3), SEQ ID NO: 240 (LCDR1), SEQ ID NO: 241 (LCDR2), and SEQ ID NO: 242 (LCDR3). In some embodiments, YY01_LALA may be defined as comprising or having amino acid sequences of SEQ ID NO: 34 (HCDR1), SEQ ID NO: 231 (HCDR2), SEQ ID NO: 232 (HCDR3), SEQ ID NO: 243 (LCDR1), SEQ ID NO: 241 (LCDR2), and SEQ ID NO: 239 (LCDR3). In some embodiments, YY01_LALA may be defined as comprising or having a heavy chain variable region comprising or having an amino acid sequence of SEQ ID NO: 233, and a light chain variable region comprising or having an amino acid sequence of SEQ ID NO: 244. In some embodiments, YY01_LALA may be defined as comprising or having a heavy chain comprising or having an amino acid sequence of SEQ ID NO: 235, and a light chain comprising or having an amino acid sequence of SEQ ID NO: 246.

For example, YY02_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 248 (HCDR1), SEQ ID NO: 249 (HCDR2), SEQ ID NO: 250 (HCDR3), SEQ ID NO: 260 (LCDR1), SEQ ID NO: 261 (LCDR2), and SEQ ID NO: 262 (LCDR3); (II) SEQ ID NO: 251 (HCDR1), SEQ ID NO: 249 (HCDR2), SEQ ID NO: 250 (HCDR3), SEQ ID NO: 260 (LCDR1), SEQ ID NO: 261 (LCDR2), and SEQ ID NO: 262 (LCDR3); (III) SEQ ID NO: 32 (HCDR1), SEQ ID NO: 252 (HCDR2), SEQ ID NO: 250 (HCDR3), SEQ ID NO: 263 (LCDR1), SEQ ID NO: 241 (LCDR2), and SEQ ID NO: 264 (LCDR3); or (IV) SEQ ID NO: 253 (HCDR1), SEQ ID NO: 254 (HCDR2), SEQ ID NO: 255 (HCDR3), SEQ ID NO: 265 (LCDR1), SEQ ID NO: 241 (LCDR2), and SEQ ID NO: 262 (LCDR3). In some embodiments, YY02_LALA may be defined as comprising or having amino acid sequences of SEQ ID NO: 248 (HCDR1), SEQ ID NO: 249 (HCDR2), SEQ ID NO: 250 (HCDR3), SEQ ID NO: 260 (LCDR1), SEQ ID NO: 261 (LCDR2), and SEQ ID NO: 262 (LCDR3). In some embodiments, YY02_LALA may be defined as comprising or having amino acid sequences of SEQ ID NO: 251 (HCDR1), SEQ ID NO: 249 (HCDR2), SEQ ID NO: 250 (HCDR3), SEQ ID NO: 260 (LCDR1), SEQ ID NO: 261 (LCDR2), and SEQ ID NO: 262 (LCDR3). In some embodiments, YY02_LALA may be defined as comprising or having amino acid sequences of SEQ ID NO: 32 (HCDR1), SEQ ID NO: 252 (HCDR2), SEQ ID NO: 250 (HCDR3), SEQ ID NO: 263 (LCDR1), SEQ ID NO: 241 (LCDR2), and SEQ ID NO: 264 (LCDR3). In some embodiments, YY02_LALA may be defined as comprising or having amino acid sequences of SEQ ID NO: 253 (HCDR1), SEQ ID NO: 254 (HCDR2), SEQ ID NO: 255 (HCDR3), SEQ ID NO: 265 (LCDR1), SEQ ID NO: 241 (LCDR2), and SEQ ID NO: 262 (LCDR3). In some embodiments, YY02_LALA may be defined as comprising or having a heavy chain variable region comprising or having an amino acid sequence of SEQ ID NO: 256, and a light chain variable region comprising or having an amino acid sequence of SEQ ID NO: 266. In some embodiments, YY02_LALA may be defined as comprising or having a heavy chain comprising or having an amino acid sequence of SEQ ID NO: 258, and a light chain comprising or having an amino acid sequence of SEQ ID NO: 268.

For example, YY03_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 270 (HCDR1), SEQ ID NO: 271 (HCDR2), SEQ ID NO: 272 (HCDR3), SEQ ID NO: 282 (LCDR1), SEQ ID NO: 261 (LCDR2), and SEQ ID NO: 283 (LCDR3); (II) SEQ ID NO: 273 (HCDR1), SEQ ID NO: 271 (HCDR2), SEQ ID NO: 272 (HCDR3), SEQ ID NO: 282 (LCDR1), SEQ ID NO: 261 (LCDR2), and SEQ ID NO: 283 (LCDR3); (III) SEQ ID NO: 32 (HCDR1), SEQ ID NO: 274 (HCDR2), SEQ ID NO: 272 (HCDR3), SEQ ID NO: 284 (LCDR1), SEQ ID NO: 241 (LCDR2), and SEQ ID NO: 285 (LCDR3); or (IV) SEQ ID NO: 275 (HCDR1), SEQ ID NO: 276 (HCDR2), SEQ ID NO: 277 (HCDR3), SEQ ID NO: 286 (LCDR1), SEQ ID NO: 241 (LCDR2), and SEQ ID NO: 283 (LCDR3). In some embodiments, YY03_LALA may be defined as comprising or having amino acid sequences of SEQ ID NO: 270 (HCDR1), SEQ ID NO: 271 (HCDR2), SEQ ID NO: 272 (HCDR3), SEQ ID NO: 282 (LCDR1), SEQ ID NO: 261 (LCDR2), and SEQ ID NO: 283 (LCDR3). In some embodiments, YY03_LALA may be defined as comprising or having amino acid sequences of SEQ ID NO: 273 (HCDR1), SEQ ID NO: 271 (HCDR2), SEQ ID NO: 272 (HCDR3), SEQ ID NO: 282 (LCDR1), SEQ ID NO: 261 (LCDR2), and SEQ ID NO: 283 (LCDR3). In some embodiments, YY03_LALA may be defined as comprising or having amino acid sequences of SEQ ID NO: 32 (HCDR1), SEQ ID NO: 274 (HCDR2), SEQ ID NO: 272 (HCDR3), SEQ ID NO: 284 (LCDR1), SEQ ID NO: 241 (LCDR2), and SEQ ID NO: 285 (LCDR3). In some embodiments, YY03_LALA may be defined as comprising or having amino acid sequences of SEQ ID NO: 275 (HCDR1), SEQ ID NO: 276 (HCDR2), SEQ ID NO:

277 (HCDR3), SEQ ID NO: 286 (LCDR1), SEQ ID NO: 241 (LCDR2), and SEQ ID NO: 283 (LCDR3). In some embodiments, YY03_LALA may be defined as comprising or having a heavy chain variable region comprising or having an amino acid sequence of SEQ ID NO: 278, and a light chain variable region comprising or having an amino acid sequence of SEQ ID NO: 287. In some embodiments, YY03_LALA may be defined as comprising or having a heavy chain comprising or having an amino acid sequence of SEQ ID NO: 280, and a light chain comprising or having an amino acid sequence of SEQ ID NO: 289.

For example, YY04_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 291 (HCDR1), SEQ ID NO: 292 (HCDR2), SEQ ID NO: 293 (HCDR3), SEQ ID NO: 237 (LCDR1), SEQ ID NO: 238 (LCDR2), and SEQ ID NO: 304 (LCDR3); (II) SEQ ID NO: 294 (HCDR1), SEQ ID NO: 292 (HCDR2), SEQ ID NO: 293 (HCDR3), SEQ ID NO: 237 (LCDR1), SEQ ID NO: 238 (LCDR2), and SEQ ID NO: 304 (LCDR3); (III) SEQ ID NO: 295 (HCDR1), SEQ ID NO: 296 (HCDR2), SEQ ID NO: 293 (HCDR3), SEQ ID NO: 240 (LCDR1), SEQ ID NO: 241 (LCDR2), and SEQ ID NO: 305 (LCDR3); or (IV) SEQ ID NO: 297 (HCDR1), SEQ ID NO: 298 (HCDR2), SEQ ID NO: 299 (HCDR3), SEQ ID NO: 243 (LCDR1), SEQ ID NO: 241 (LCDR2), and SEQ ID NO: 304 (LCDR3). In some embodiments, YY04_LALA may be defined as comprising or having amino acid sequences of SEQ ID NO: 291 (HCDR1), SEQ ID NO: 292 (HCDR2), SEQ ID NO: 293 (HCDR3), SEQ ID NO: 237 (LCDR1), SEQ ID NO: 238 (LCDR2), and SEQ ID NO: 304 (LCDR3). In some embodiments, YY04_LALA may be defined as comprising or having amino acid sequences of SEQ ID NO: 294 (HCDR1), SEQ ID NO: 292 (HCDR2), SEQ ID NO: 293 (HCDR3), SEQ ID NO: 237 (LCDR1), SEQ ID NO: 238 (LCDR2), and SEQ ID NO: 304 (LCDR3). In some embodiments, YY04_LALA may be defined as comprising or having amino acid sequences of SEQ ID NO: 295 (HCDR1), SEQ ID NO: 296 (HCDR2), SEQ ID NO: 293 (HCDR3), SEQ ID NO: 240 (LCDR1), SEQ ID NO: 241 (LCDR2), and SEQ ID NO: 305 (LCDR3). In some embodiments, YY04_LALA may be defined as comprising or having amino acid sequences of SEQ ID NO: 297 (HCDR1), SEQ ID NO: 298 (HCDR2), SEQ ID NO: 299 (HCDR3), SEQ ID NO: 243 (LCDR1), SEQ ID NO: 241 (LCDR2), and SEQ ID NO: 304 (LCDR3). In some embodiments, YY04_LALA may be defined as comprising or having a heavy chain variable region comprising or having an amino acid sequence of SEQ ID NO: 300, and a light chain variable region comprising or having an amino acid sequence of SEQ ID NO: 306. In some embodiments, YY04_LALA may be defined as comprising or having a heavy chain comprising or having an amino acid sequence of SEQ ID NO: 302, and a light chain comprising or having an amino acid sequence of SEQ ID NO: 308.

For example, YY05_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 310 (HCDR1), SEQ ID NO: 311 (HCDR2), SEQ ID NO: 312 (HCDR3), SEQ ID NO: 320 (LCDR1), SEQ ID NO: 321 (LCDR2), and SEQ ID NO: 322 (LCDR3); (II) SEQ ID NO: 229 (HCDR1), SEQ ID NO: 311 (HCDR2), SEQ ID NO: 312 (HCDR3), SEQ ID NO: 320 (LCDR1), SEQ ID NO: 321 (LCDR2), and SEQ ID NO: 322 (LCDR3); (III) SEQ ID NO: 80 (HCDR1), SEQ ID NO: 313 (HCDR2), SEQ ID NO: 312 (HCDR3), SEQ ID NO: 323 (LCDR1), SEQ ID NO: 324 (LCDR2), and SEQ ID NO: 325 (LCDR3); or (IV) SEQ ID NO: 82 (HCDR1), SEQ ID NO: 314 (HCDR2), SEQ ID NO: 315 (HCDR3), SEQ ID NO: 326 (LCDR1), SEQ ID NO: 324 (LCDR2), and SEQ ID NO: 322 (LCDR3). In some embodiments, YY05_LALA may be defined as comprising or having amino acid sequences of SEQ ID NO: 310 (HCDR1), SEQ ID NO: 311 (HCDR2), SEQ ID NO: 312 (HCDR3), SEQ ID NO: 320 (LCDR1), SEQ ID NO: 321 (LCDR2), and SEQ ID NO: 322 (LCDR3). In some embodiments, YY05_LALA may be defined as comprising or having amino acid sequences of SEQ ID NO: 229 (HCDR1), SEQ ID NO: 311 (HCDR2), SEQ ID NO: 312 (HCDR3), SEQ ID NO: 320 (LCDR1), SEQ ID NO: 321 (LCDR2), and SEQ ID NO: 322 (LCDR3). In some embodiments, YY05_LALA may be defined as comprising or having amino acid sequences of SEQ ID NO: 80 (HCDR1), SEQ ID NO: 313 (HCDR2), SEQ ID NO: 312 (HCDR3), SEQ ID NO: 323 (LCDR1), SEQ ID NO: 324 (LCDR2), and SEQ ID NO: 325 (LCDR3). In some embodiments, YY05_LALA may be defined as comprising or having amino acid sequences of SEQ ID NO: 82 (HCDR1), SEQ ID NO: 314 (HCDR2), SEQ ID NO: 315 (HCDR3), SEQ ID NO: 326 (LCDR1), SEQ ID NO: 324 (LCDR2), and SEQ ID NO: 322 (LCDR3). In some embodiments, YY05_LALA may be defined as comprising or having a heavy chain variable region comprising or having an amino acid sequence of SEQ ID NO: 316, and a light chain variable region comprising or having an amino acid sequence of SEQ ID NO: 327. In some embodiments, YY05_LALA may be defined as comprising or having a heavy chain comprising or having an amino acid sequence of SEQ ID NO: 318, and a light chain comprising or having an amino acid sequence of SEQ ID NO: 329.

For example, YY06_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 270 (HCDR1), SEQ ID NO: 271 (HCDR2), SEQ ID NO: 331 (HCDR3), SEQ ID NO: 337 (LCDR1), SEQ ID NO: 338 (LCDR2), and SEQ ID NO: 339 (LCDR3); (II) SEQ ID NO: 273 (HCDR1), SEQ ID NO: 271 (HCDR2), SEQ ID NO: 331 (HCDR3), SEQ ID NO: 337 (LCDR1), SEQ ID NO: 338 (LCDR2), and SEQ ID NO: 339 (LCDR3); (III) SEQ ID NO: 32 (HCDR1), SEQ ID NO: 274 (HCDR2), SEQ ID NO: 331 (HCDR3), SEQ ID NO: 340 (LCDR1), SEQ ID NO: 341 (LCDR2), and SEQ ID NO: 342 (LCDR3); or (IV) SEQ ID NO: 275 (HCDR1), SEQ ID NO: 276 (HCDR2), SEQ ID NO: 332 (HCDR3), SEQ ID NO: 343 (LCDR1), SEQ ID NO: 341 (LCDR2), and SEQ ID NO: 339 (LCDR3). In some embodiments, YY06_LALA may be defined as comprising or having amino acid sequences of SEQ ID NO: 270 (HCDR1), SEQ ID NO: 271 (HCDR2), SEQ ID NO: 331 (HCDR3), SEQ ID NO: 337 (LCDR1), SEQ ID NO: 338 (LCDR2), and SEQ ID NO: 339 (LCDR3). In some embodiments, YY06_LALA may be defined as comprising or having amino acid sequences of SEQ ID NO: 273 (HCDR1), SEQ ID NO: 271 (HCDR2), SEQ ID NO: 331 (HCDR3), SEQ ID NO: 337 (LCDR1), SEQ ID NO: 338 (LCDR2), and SEQ ID NO: 339 (LCDR3). In some embodiments, YY06_LALA may be defined as comprising or having amino acid sequences of SEQ ID NO: 32 (HCDR1), SEQ ID NO: 274 (HCDR2), SEQ ID NO: 331 (HCDR3), SEQ ID NO: 340 (LCDR1), SEQ ID NO: 341 (LCDR2), and SEQ ID NO: 342 (LCDR3). In some embodiments, YY06_LALA may be defined as comprising or having amino acid sequences of SEQ ID NO:

275 (HCDR1), SEQ ID NO: 276 (HCDR2), SEQ ID NO: 332 (HCDR3), SEQ ID NO: 343 (LCDR1), SEQ ID NO: 341 (LCDR2), and SEQ ID NO: 339 (LCDR3). In some embodiments, YY06_LALA may be defined as comprising or having a heavy chain variable region comprising or having an amino acid sequence of SEQ ID NO: 333, and a light chain variable region comprising or having an amino acid sequence of SEQ ID NO: 344. In some embodiments, YY06_LALA may be defined as comprising or having a heavy chain comprising or having an amino acid sequence of SEQ ID NO: 335, and a light chain comprising or having an amino acid sequence of SEQ ID NO: 346.

For example, YY07_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 310 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 355 (LCDR3); (II) SEQ ID NO: 229 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 355 (LCDR3); (III) SEQ ID NO: 80 (HCDR1), SEQ ID NO: 313 (HCDR2), SEQ ID NO: 348 (HCDR3), SEQ ID NO: 323 (LCDR1), SEQ ID NO: 324 (LCDR2), and SEQ ID NO: 356 (LCDR3); or (IV) SEQ ID NO: 82 (HCDR1), SEQ ID NO: 314 (HCDR2), SEQ ID NO: 349 (HCDR3), SEQ ID NO: 326 (LCDR1), SEQ ID NO: 324 (LCDR2), and SEQ ID NO: 355 (LCDR3). In some embodiments, YY07_LALA may be defined as comprising or having amino acid sequences of SEQ ID NO: 310 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 355 (LCDR3). In some embodiments, YY07_LALA may be defined as comprising or having amino acid sequences of SEQ ID NO: 229 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 355 (LCDR3). In some embodiments, YY07_LALA may be defined as comprising or having amino acid sequences of SEQ ID NO: 80 (HCDR1), SEQ ID NO: 313 (HCDR2), SEQ ID NO: 348 (HCDR3), SEQ ID NO: 323 (LCDR1), SEQ ID NO: 324 (LCDR2), and SEQ ID NO: 356 (LCDR3). In some embodiments, YY07_LALA may be defined as comprising or having amino acid sequences of SEQ ID NO: 82 (HCDR1), SEQ ID NO: 314 (HCDR2), SEQ ID NO: 349 (HCDR3), SEQ ID NO: 326 (LCDR1), SEQ ID NO: 324 (LCDR2), and SEQ ID NO: 355 (LCDR3). In some embodiments, YY07_LALA may be defined as comprising or having a heavy chain variable region comprising or having an amino acid sequence of SEQ ID NO: 350, and a light chain variable region comprising or having an amino acid sequence of SEQ ID NO: 357. In some embodiments, YY07_LALA may be defined as comprising or having a heavy chain comprising or having an amino acid sequence of SEQ ID NO: 352, and a light chain comprising or having an amino acid sequence of SEQ ID NO: 359.

For example, ZZ05_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 310 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 361 (LCDR3); (II) SEQ ID NO: 229 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 361 (LCDR3); (III) SEQ ID NO: 80 (HCDR1), SEQ ID NO: 313 (HCDR2), SEQ ID NO: 348 (HCDR3), SEQ ID NO: 323 (LCDR1), SEQ ID NO: 324 (LCDR2), and SEQ ID NO: 362 (LCDR3); or (IV) SEQ ID NO: 82 (HCDR1), SEQ ID NO: 314 (HCDR2), SEQ ID NO: 349 (HCDR3), SEQ ID NO: 326 (LCDR1), SEQ ID NO: 324 (LCDR2), and SEQ ID NO: 361 (LCDR3). In some embodiments, ZZ05_LALA may be defined as comprising or having amino acid sequences of SEQ ID NO: 310 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 361 (LCDR3). In some embodiments, ZZ05_LALA may be defined as comprising or having amino acid sequences of SEQ ID NO: 229 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 361 (LCDR3). In some embodiments, ZZ05_LALA may be defined as comprising or having amino acid sequences of SEQ ID NO: 80 (HCDR1), SEQ ID NO: 313 (HCDR2), SEQ ID NO: 348 (HCDR3), SEQ ID NO: 323 (LCDR1), SEQ ID NO: 324 (LCDR2), and SEQ ID NO: 362 (LCDR3). In some embodiments, ZZ05_LALA may be defined as comprising or having amino acid sequences of SEQ ID NO: 82 (HCDR1), SEQ ID NO: 314 (HCDR2), SEQ ID NO: 349 (HCDR3), SEQ ID NO: 326 (LCDR1), SEQ ID NO: 324 (LCDR2), and SEQ ID NO: 361 (LCDR3). In some embodiments, ZZ05_LALA may be defined as comprising or having a heavy chain variable region comprising or having an amino acid sequence of SEQ ID NO: 350, and a light chain variable region comprising or having an amino acid sequence of SEQ ID NO: 363. In some embodiments, ZZ05_LALA may be defined as comprising or having a heavy chain comprising or having an amino acid sequence of SEQ ID NO: 352, and a light chain comprising or having an amino acid sequence of SEQ ID NO: 365.

For example, ZZ12_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 367 (HCDR1), SEQ ID NO: 368 (HCDR2), SEQ ID NO: 228 (HCDR3), SEQ ID NO: 237 (LCDR1), SEQ ID NO: 238 (LCDR2), and SEQ ID NO: 239 (LCDR3); (II) SEQ ID NO: 369 (HCDR1), SEQ ID NO: 368 (HCDR2), SEQ ID NO: 228 (HCDR3), SEQ ID NO: 237 (LCDR1), SEQ ID NO: 238 (LCDR2), and SEQ ID NO: 239 (LCDR3); (III) SEQ ID NO: 370 (HCDR1), SEQ ID NO: 371 (HCDR2), SEQ ID NO: 228 (HCDR3), SEQ ID NO: 240 (LCDR1), SEQ ID NO: 241 (LCDR2), and SEQ ID NO: 242 (LCDR3); or (IV) SEQ ID NO: 372 (HCDR1), SEQ ID NO: 373 (HCDR2), SEQ ID NO: 232 (HCDR3), SEQ ID NO: 243 (LCDR1), SEQ ID NO: 241 (LCDR2), and SEQ ID NO: 239 (LCDR3). In some embodiments, ZZ12_LALA may be defined as comprising or having amino acid sequences of SEQ ID NO: 367 (HCDR1), SEQ ID NO: 368 (HCDR2), SEQ ID NO: 228 (HCDR3), SEQ ID NO: 237 (LCDR1), SEQ ID NO: 238 (LCDR2), and SEQ ID NO: 239 (LCDR3). In some embodiments, ZZ12_LALA may be defined as comprising or having amino acid sequences of SEQ ID NO: 369 (HCDR1), SEQ ID NO: 368 (HCDR2), SEQ ID NO: 228 (HCDR3), SEQ ID NO: 237 (LCDR1), SEQ ID NO: 238 (LCDR2), and SEQ ID NO: 239 (LCDR3). In some embodiments, ZZ12_LALA may be defined as comprising or having amino acid sequences of SEQ ID NO: 370 (HCDR1), SEQ ID NO: 371 (HCDR2), SEQ ID NO: 228 (HCDR3), SEQ ID NO: 240 (LCDR1), SEQ ID NO: 241 (LCDR2), and SEQ ID NO: 242 (LCDR3). In some embodiments, ZZ12_LALA may be defined as comprising or having amino acid sequences of SEQ ID NO: 372 (HCDR1), SEQ ID NO: 373 (HCDR2), SEQ ID NO: 232 (HCDR3), SEQ ID NO: 243 (LCDR1), SEQ ID NO: 241 (LCDR2), and SEQ ID NO: 239 (LCDR3). In some embodiments, ZZ12_LALA may be defined as comprising or having a heavy chain variable region comprising or having an amino acid sequence of SEQ ID NO: 374, and a light chain variable region comprising or having an amino acid sequence of SEQ ID NO: 244. In some embodiments, ZZ12_LALA may be defined as comprising or having a heavy chain comprising or having an amino acid sequence of SEQ ID NO: 376, and a light chain comprising or having an amino acid sequence of SEQ ID NO: 246.

For example, ZZ13_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 378 (HCDR1), SEQ ID NO: 379 (HCDR2), SEQ ID NO: 228 (HCDR3), SEQ ID NO: 237 (LCDR1), SEQ ID NO: 238 (LCDR2), and SEQ ID NO: 239 (LCDR3); (II) SEQ ID NO: 380 (HCDR1), SEQ ID NO: 379 (HCDR2), SEQ ID NO: 228 (HCDR3), SEQ ID NO: 237 (LCDR1), SEQ ID NO: 238 (LCDR2), and SEQ ID NO: 239 (LCDR3); (III) SEQ ID NO: 381 (HCDR1), SEQ ID NO: 382 (HCDR2), SEQ ID NO: 228 (HCDR3), SEQ ID NO: 240 (LCDR1), SEQ ID NO: 241 (LCDR2), and SEQ ID NO: 242 (LCDR3); or (IV) SEQ ID NO: 383 (HCDR1), SEQ ID NO: 384 (HCDR2), SEQ ID NO: 232 (HCDR3), SEQ ID NO: 243 (LCDR1), SEQ ID NO: 241 (LCDR2), and SEQ ID NO: 239 (LCDR3). In some embodiments, ZZ13_LALA may be defined as comprising or having amino acid sequences of SEQ ID NO: 378 (HCDR1), SEQ ID NO: 379 (HCDR2), SEQ ID NO: 228 (HCDR3), SEQ ID NO: 237 (LCDR1), SEQ ID NO: 238 (LCDR2), and SEQ ID NO: 239 (LCDR3). In some embodiments, ZZ13_LALA may be defined as comprising or having amino acid sequences of SEQ ID NO: 380 (HCDR1), SEQ ID NO: 379 (HCDR2), SEQ ID NO: 228 (HCDR3), SEQ ID NO: 237 (LCDR1), SEQ ID NO: 238 (LCDR2), and SEQ ID NO: 239 (LCDR3). In some embodiments, ZZ13_LALA may be defined as comprising or having amino acid sequences of SEQ ID NO: 381 (HCDR1), SEQ ID NO: 382 (HCDR2), SEQ ID NO: 228 (HCDR3), SEQ ID NO: 240 (LCDR1), SEQ ID NO: 241 (LCDR2), and SEQ ID NO: 242 (LCDR3). In some embodiments, ZZ13_LALA may be defined as comprising or having amino acid sequences of (IV) SEQ ID NO: 383 (HCDR1), SEQ ID NO: 384 (HCDR2), SEQ ID NO: 232 (HCDR3), SEQ ID NO: 243 (LCDR1), SEQ ID NO: 241 (LCDR2), and SEQ ID NO: 239 (LCDR3). In some embodiments, ZZ13_LALA may be defined as comprising or having a heavy chain variable region comprising or having an amino acid sequence of SEQ ID NO: 385, and a light chain variable region comprising or having an amino acid sequence of SEQ ID NO: 244. In some embodiments, ZZ13_LALA may be defined as comprising or having a heavy chain comprising or having an amino acid sequence of SEQ ID NO: 387, and a light chain comprising or having an amino acid sequence of SEQ ID NO: 246.

For example, ZZ14_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 270 (HCDR1), SEQ ID NO: 389 (HCDR2), SEQ ID NO: 331 (HCDR3), SEQ ID NO: 337 (LCDR1), SEQ ID NO: 338 (LCDR2), and SEQ ID NO: 339 (LCDR3); (II) SEQ ID NO: 273 (HCDR1), SEQ ID NO: 389 (HCDR2), SEQ ID NO: 331 (HCDR3), SEQ ID NO: 337 (LCDR1), SEQ ID NO: 338 (LCDR2), and SEQ ID NO: 339 (LCDR3); (III) SEQ ID NO: 32 (HCDR1), SEQ ID NO: 390 (HCDR2), SEQ ID NO: 331 (HCDR3), SEQ ID NO: 340 (LCDR1), SEQ ID NO: 341 (LCDR2), and SEQ ID NO: 342 (LCDR3); or (IV) SEQ ID NO: 275 (HCDR1), SEQ ID NO: 391 (HCDR2), SEQ ID NO: 332 (HCDR3), SEQ ID NO: 343 (LCDR1), SEQ ID NO: 341 (LCDR2), and SEQ ID NO: 339 (LCDR3). In some embodiments, ZZ14_LALA may be defined as comprising or having amino acid sequences of SEQ ID NO: 270 (HCDR1), SEQ ID NO: 389 (HCDR2), SEQ ID NO: 331 (HCDR3), SEQ ID NO: 337 (LCDR1), SEQ ID NO: 338 (LCDR2), and SEQ ID NO: 339 (LCDR3). In some embodiments, ZZ14_LALA may be defined as comprising or having amino acid sequences of SEQ ID NO: 273 (HCDR1), SEQ ID NO: 389 (HCDR2), SEQ ID NO: 331 (HCDR3), SEQ ID NO: 337 (LCDR1), SEQ ID NO: 338 (LCDR2), and SEQ ID NO: 339 (LCDR3). In some embodiments, ZZ14_LALA may be defined as comprising or having amino acid sequences of SEQ ID NO: 32 (HCDR1), SEQ ID NO: 390 (HCDR2), SEQ ID NO: 331 (HCDR3), SEQ ID NO: 340 (LCDR1), SEQ ID NO: 341 (LCDR2), and SEQ ID NO: 342 (LCDR3). In some embodiments, ZZ14_LALA may be defined as comprising or having amino acid sequences of SEQ ID NO: 275 (HCDR1), SEQ ID NO: 391 (HCDR2), SEQ ID NO: 332 (HCDR3), SEQ ID NO: 343 (LCDR1), SEQ ID NO: 341 (LCDR2), and SEQ ID NO: 339 (LCDR3). In some embodiments, ZZ14_LALA may be defined as comprising or having a heavy chain variable region comprising or having an amino acid sequence of SEQ ID NO: 392, and a light chain variable region comprising or having an amino acid sequence of SEQ ID NO: 344. In some embodiments, ZZ14_LALA may be defined as comprising or having a heavy chain comprising or having an amino acid sequence of SEQ ID NO: 394, and a light chain comprising or having an amino acid sequence of SEQ ID NO: 346.

For example, ZZ15_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 396 (HCDR1), SEQ ID NO: 397 (HCDR2), SEQ ID NO: 331 (HCDR3), SEQ ID NO: 337 (LCDR1), SEQ ID NO: 338 (LCDR2), and SEQ ID NO: 339 (LCDR3); (II) SEQ ID NO: 398 (HCDR1), SEQ ID NO: 397 (HCDR2), SEQ ID NO: 331 (HCDR3), SEQ ID NO: 337 (LCDR1), SEQ ID NO: 338 (LCDR2), and SEQ ID NO: 339 (LCDR3); (III) SEQ ID NO: 399 (HCDR1), SEQ ID NO: 400 (HCDR2), SEQ ID NO: 331 (HCDR3), SEQ ID NO: 340 (LCDR1), SEQ ID NO: 341 (LCDR2), and SEQ ID NO: 342 (LCDR3); or (IV) SEQ ID NO: 401 (HCDR1), SEQ ID NO: 402 (HCDR2), SEQ ID NO: 332 (HCDR3), SEQ ID NO: 343 (LCDR1), SEQ ID NO: 341 (LCDR2), and SEQ ID NO: 339 (LCDR3). In some embodiments, ZZ15_LALA may be defined as comprising or having amino acid sequences of SEQ ID NO: 396 (HCDR1), SEQ ID NO: 397 (HCDR2), SEQ ID NO: 331 (HCDR3), SEQ ID NO: 337 (LCDR1), SEQ ID NO: 338 (LCDR2), and SEQ ID NO: 339 (LCDR3). In some embodiments, ZZ15_LALA may be defined as comprising or having amino acid sequences of SEQ ID NO: 398 (HCDR1), SEQ ID NO: 397 (HCDR2), SEQ ID NO: 331 (HCDR3), SEQ ID NO: 337 (LCDR1), SEQ ID NO: 338 (LCDR2), and SEQ ID NO: 339 (LCDR3). In some embodiments, ZZ15_LALA may be defined as comprising or having amino acid sequences of SEQ ID NO: 399 (HCDR1), SEQ ID NO: 400 (HCDR2), SEQ ID NO: 331 (HCDR3), SEQ ID NO: 340 (LCDR1), SEQ ID NO: 341 (LCDR2), and SEQ ID NO: 342 (LCDR3). In some embodiments, ZZ15_LALA may be defined as comprising or having amino acid sequences of SEQ ID NO: 401 (HCDR1), SEQ ID NO: 402 (HCDR2), SEQ ID NO: 332 (HCDR3), SEQ ID NO: 343 (LCDR1), SEQ ID NO: 341 (LCDR2), and SEQ ID NO: 339 (LCDR3). In some embodiments, ZZ15_LALA may be defined as comprising or having a heavy chain variable region comprising or having an amino acid sequence of SEQ ID NO: 403, and a light chain variable region comprising or having an amino acid sequence of SEQ ID NO: 344. In some embodiments, ZZ15_LALA may be defined as comprising or having a heavy chain comprising or having an amino acid sequence of SEQ ID NO: 405, and a light chain comprising or having an amino acid sequence of SEQ ID NO: 346.

For example, ZZ16_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 407 (HCDR1), SEQ ID NO: 408 (HCDR2), SEQ ID NO: 331 (HCDR3), SEQ ID NO: 337 (LCDR1), SEQ ID NO: 338 (LCDR2), and SEQ ID NO: 339 (LCDR3); (II) SEQ ID NO: 409 (HCDR1), SEQ ID NO: 408 (HCDR2), SEQ ID NO: 331 (HCDR3), SEQ ID NO: 337 (LCDR1), SEQ ID NO: 338 (LCDR2), and SEQ ID NO: 339 (LCDR3); (III) SEQ ID NO: 410 (HCDR1), SEQ ID NO: 411 (HCDR2), SEQ ID NO: 331 (HCDR3), SEQ ID NO: 340 (LCDR1), SEQ ID NO: 341 (LCDR2), and SEQ ID NO: 342 (LCDR3); or (IV) SEQ ID NO: 412 (HCDR1), SEQ ID NO: 413 (HCDR2), SEQ ID NO: 332 (HCDR3), SEQ ID NO: 343 (LCDR1), SEQ ID NO: 341 (LCDR2), and SEQ ID NO: 339 (LCDR3). In some embodiments, ZZ16_LALA may be defined as comprising or having amino acid sequences of SEQ ID NO: 407 (HCDR1), SEQ ID NO: 408 (HCDR2), SEQ ID NO: 331 (HCDR3), SEQ ID NO: 337 (LCDR1), SEQ ID NO: 338 (LCDR2), and SEQ ID NO: 339 (LCDR3). In some embodiments, ZZ16_LALA may be defined as comprising or having amino acid sequences of SEQ ID NO: 409 (HCDR1), SEQ ID NO: 408 (HCDR2), SEQ ID NO: 331 (HCDR3), SEQ ID NO: 337 (LCDR1), SEQ ID NO: 338 (LCDR2), and SEQ ID NO: 339 (LCDR3). In some embodiments, ZZ16_LALA may be defined as comprising or having amino acid sequences of SEQ ID NO: 410 (HCDR1), SEQ ID NO: 411 (HCDR2), SEQ ID NO: 331 (HCDR3), SEQ ID NO: 340 (LCDR1), SEQ ID NO: 341 (LCDR2), and SEQ ID NO: 342 (LCDR3). In some embodiments, ZZ16_LALA may be defined as comprising or having amino acid sequences of SEQ ID NO: 412 (HCDR1), SEQ ID NO: 413 (HCDR2), SEQ ID NO: 332 (HCDR3), SEQ ID NO: 343 (LCDR1), SEQ ID NO: 341 (LCDR2), and SEQ ID NO: 339 (LCDR3). In some embodiments, ZZ16_LALA may be defined as comprising or having a heavy chain variable region comprising or having an amino acid sequence of SEQ ID NO: 414, and a light chain variable region comprising or having an amino acid sequence of SEQ ID NO: 344. In some embodiments, ZZ16_LALA may be defined as comprising or having a heavy chain comprising or having an amino acid sequence of SEQ ID NO: 416, and a light chain comprising or having an amino acid sequence of SEQ ID NO: 346.

For example, ZZ17_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 418 (HCDR1), SEQ ID NO: 419 (HCDR2), SEQ ID NO: 331 (HCDR3), SEQ ID NO: 337 (LCDR1), SEQ ID NO: 338 (LCDR2), and SEQ ID NO: 339 (LCDR3); (II) SEQ ID NO: 420 (HCDR1), SEQ ID NO: 419 (HCDR2), SEQ ID NO: 331 (HCDR3), SEQ ID NO: 337 (LCDR1), SEQ ID NO: 338 (LCDR2), and SEQ ID NO: 339 (LCDR3); (III) SEQ ID NO: 421 (HCDR1), SEQ ID NO: 422 (HCDR2), SEQ ID NO: 331 (HCDR3), SEQ ID NO: 340 (LCDR1), SEQ ID NO: 341 (LCDR2), and SEQ ID NO: 342 (LCDR3); or (IV) SEQ ID NO: 423 (HCDR1), SEQ ID NO: 424 (HCDR2), SEQ ID NO: 332 (HCDR3), SEQ ID NO: 343 (LCDR1), SEQ ID NO: 341 (LCDR2), and SEQ ID NO: 339 (LCDR3). In some embodiments, ZZ17_LALA may be defined as comprising or having amino acid sequences of SEQ ID NO: 418 (HCDR1), SEQ ID NO: 419 (HCDR2), SEQ ID NO: 331 (HCDR3), SEQ ID NO: 337 (LCDR1), SEQ ID NO: 338 (LCDR2), and SEQ ID NO: 339 (LCDR3). In some embodiments, ZZ17_LALA may be defined as comprising or having amino acid sequences of SEQ ID NO: 420 (HCDR1), SEQ ID NO: 419 (HCDR2), SEQ ID NO: 331 (HCDR3), SEQ ID NO: 337 (LCDR1), SEQ ID NO: 338 (LCDR2), and SEQ ID NO: 339 (LCDR3). In some embodiments, ZZ17_LALA may be defined as comprising or having amino acid sequences of SEQ ID NO: 421 (HCDR1), SEQ ID NO: 422 (HCDR2), SEQ ID NO: 331 (HCDR3), SEQ ID NO: 340 (LCDR1), SEQ ID NO: 341 (LCDR2), and SEQ ID NO: 342 (LCDR3). In some embodiments, ZZ17_LALA may be defined as comprising or having amino acid sequences of SEQ ID NO: 423 (HCDR1), SEQ ID NO: 424 (HCDR2), SEQ ID NO: 332 (HCDR3), SEQ ID NO: 343 (LCDR1), SEQ ID NO: 341 (LCDR2), and SEQ ID NO: 339 (LCDR3). In some embodiments, ZZ17_LALA may be defined as comprising or having a heavy chain variable region comprising or having an amino acid sequence of SEQ ID NO: 425, and a light chain variable region comprising or having an amino acid sequence of SEQ ID NO: 344. In some embodiments, ZZ17_LALA may be defined as comprising or having a heavy chain comprising or having an amino acid sequence of SEQ ID NO: 427, and a light chain comprising or having an amino acid sequence of SEQ ID NO: 346.

In some embodiments, the antibody or antigen binding fragment comprises a heavy chain variable region comprising or having an amino acid sequence of SEQ ID NO: 13 or a sequence having at least 95%, 96%, 97%, 98%, or 99% identity with SEQ ID NO: 13, and a light chain variable region comprising or having an amino acid sequence of SEQ ID NO: 24 or a sequence having at least 95%, 96%, 97%, 98%, or 99% identity with SEQ ID NO: 24. In some other embodiments, the antibody or antigen binding fragment comprises a heavy chain comprising or having an amino acid sequence of SEQ ID NO: 15 or a sequence having at least 95%, 96%, 97%, 98%, or 99% identity with SEQ ID NO: 15, and a light chain comprising or having an amino acid sequence of SEQ ID NO: 26 or a sequence having at least 95%, 96%, 97%, 98%, or 99% identity with SEQ ID NO: 26.

In some embodiments, the antibody or antigen binding fragment comprises a heavy chain variable region comprising or having an amino acid sequence of SEQ ID NO: 37 or a sequence having at least 95%, 96%, 97%, 98%, or 99% identity with SEQ ID NO: 37, and a light chain variable region comprising or having an amino acid sequence of SEQ ID NO: 48 or a sequence having at least 95%, 96%, 97%, 98%, or 99% identity with SEQ ID NO: 48. In some embodiments, the antibody or antigen binding fragment comprises a heavy chain comprising or having an amino acid sequence of SEQ ID NO: 39 or a sequence having at least 95%, 96%, 97%, 98%, or 99% identity with SEQ ID NO: 39, and a light chain comprising or having an amino acid sequence of SEQ ID NO: 50 or a sequence having at least 95%, 96%, 97%, 98%, or 99% identity with SEQ ID NO: 50.

In some embodiments, the antibody or antigen binding fragment comprises a heavy chain variable region comprising or having an amino acid sequence of SEQ ID NO: 61 or a sequence having at least 95%, 96%, 97%, 98%, or 99% identity with SEQ ID NO: 61, and a light chain variable region comprising or having an amino acid sequence of SEQ ID NO: 72 or a sequence having at least 95%, 96%, 97%, 98%, or 99% identity with SEQ ID NO: 72. In some embodiments, the antibody or antigen binding fragment comprises a heavy chain comprising or having an amino acid sequence of SEQ ID NO: 63 or a sequence having at least 95%, 96%, 97%, 98%, or 99% identity with SEQ ID NO: 63, and a light chain comprising or having an amino acid sequence of SEQ ID NO: 74 or a sequence having at least 95%, 96%, 97%, 98%, or 99% identity with SEQ ID NO: 74.

In some embodiments, the antibody or antigen binding fragment comprises a heavy chain variable region comprising or having an amino acid sequence of SEQ ID NO: 85 or a sequence having at least 95%, 96%, 97%, 98%, or 99% identity with SEQ ID NO: 85, and a light chain variable region comprising or having an amino acid sequence of SEQ ID NO: 96 or a sequence having at least 95%, 96%, 97%, 98%, or 99% identity with SEQ ID NO: 96. In some embodiments, the antibody or antigen binding fragment comprises a heavy chain comprising or having an amino acid sequence of SEQ ID NO: 87 or a sequence having at least 95%, 96%, 97%, 98%, or 99% identity with SEQ ID NO: 87, and a light chain comprising or having an amino acid sequence of SEQ ID NO: 98 or a sequence having at least 95%, 96%, 97%, 98%, or 99% identity with SEQ ID NO: 98.

In some embodiments, the antibody or antigen binding fragment comprises a heavy chain variable region comprising or having an amino acid sequence of SEQ ID NO: 103 or a sequence having at least 95%, 96%, 97%, 98%, or 99% identity with SEQ ID NO: 103, and a light chain variable region comprising or having an amino acid sequence of SEQ ID NO: 24 or a sequence having at least 95%, 96%, 97%, 98%, or 99% identity with SEQ ID NO: 24. In some embodiments, the antibody or antigen binding fragment comprises a heavy chain comprising or having an amino acid sequence of SEQ ID NO: 105 or a sequence having at least 95%, 96%, 97%, 98%, or 99% identity with SEQ ID NO: 105, and a light chain comprising or having an amino acid sequence of SEQ ID NO: 26 or a sequence having at least 95%, 96%, 97%, 98%, or 99% identity with SEQ ID NO: 26.

In some embodiments, the antibody or antigen binding fragment comprises a heavy chain variable region comprising or having an amino acid sequence of SEQ ID NO: 103 or a sequence having at least 95%, 96%, 97%, 98%, or 99% identity with SEQ ID NO: 103, and a light chain variable region comprising or having an amino acid sequence of SEQ ID NO: 24 or a sequence having at least 95%, 96%, 97%, 98%, or 99% identity with SEQ ID NO: 24. In some embodiments, the antibody or antigen binding fragment comprises a heavy chain comprising or having an amino acid sequence of SEQ ID NO: 108 or a sequence having at least 95%, 96%, 97%, 98%, or 99% identity with SEQ ID NO: 108, and a light chain comprising or having an amino acid sequence of SEQ ID NO: 26 or a sequence having at least 95%, 96%, 97%, 98%, or 99% identity with SEQ ID NO: 26.

In some embodiments, the antibody or antigen binding fragment comprises a heavy chain variable region comprising or having an amino acid sequence of SEQ ID NO: 115 or a sequence having at least 95%, 96%, 97%, 98%, or 99% identity with SEQ ID NO: 115, and a light chain variable region comprising or having an amino acid sequence of SEQ ID NO: 24 or a sequence having at least 95%, 96%, 97%, 98%, or 99% identity with SEQ ID NO: 24. In some embodiments, the antibody or antigen binding fragment comprises a heavy chain comprising or having an amino acid sequence of SEQ ID NO: 117 or a sequence having at least 95%, 96%, 97%, 98%, or 99% identity with SEQ ID NO: 117, and a light chain comprising or having an amino acid sequence of SEQ ID NO: 26 or a sequence having at least 95%, 96%, 97%, 98%, or 99% identity with SEQ ID NO: 26.

In some embodiments, the antibody or antigen binding fragment comprises a heavy chain variable region comprising or having an amino acid sequence of SEQ ID NO: 122 or a sequence having at least 95%, 96%, 97%, 98%, or 99% identity with SEQ ID NO: 122, and a light chain variable region comprising or having an amino acid sequence of SEQ ID NO: 48 or a sequence having at least 95%, 96%, 97%, 98%, or 99% identity with SEQ ID NO: 48. In some embodiments, the antibody or antigen binding fragment comprises a heavy chain comprising or having an amino acid sequence of SEQ ID NO: 124 or a sequence having at least 95%, 96%, 97%, 98%, or 99% identity with SEQ ID NO: 124, and a light chain comprising or having an amino acid sequence of SEQ ID NO: 50 or a sequence having at least 95%, 96%, 97%, 98%, or 99% identity with SEQ ID NO: 50.

In some embodiments, the antibody or antigen binding fragment comprises a heavy chain variable region comprising or having an amino acid sequence of SEQ ID NO: 37 or a sequence having at least 95%, 96%, 97%, 98%, or 99% identity with SEQ ID NO: 37, and a light chain variable region comprising or having an amino acid sequence of SEQ ID NO: 128 or a sequence having at least 95%, 96%, 97%, 98%, or 99% identity with SEQ ID NO: 128. In some embodiments, the antibody or antigen binding fragment comprises a heavy chain comprising or having an amino acid sequence of SEQ ID NO: 39 or a sequence having at least 95%, 96%, 97%, 98%, or 99% identity with SEQ ID NO: 39, and a light chain comprising or having an amino acid sequence of SEQ ID NO: 130 or a sequence having at least 95%, 96%, 97%, 98%, or 99% identity with SEQ ID NO: 130.

In some embodiments, the antibody or antigen binding fragment comprises a heavy chain variable region comprising or having an amino acid sequence of SEQ ID NO: 37 or a sequence having at least 95%, 96%, 97%, 98%, or 99% identity with SEQ ID NO: 37, and a light chain variable region comprising or having an amino acid sequence of SEQ ID NO: 136 or a sequence having at least 95%, 96%, 97%, 98%, or 99% identity with SEQ ID NO: 136. In some embodiments, the antibody or antigen binding fragment comprises a heavy chain comprising or having an amino acid sequence of SEQ ID NO: 39 or a sequence having at least 95%, 96%, 97%, 98%, or 99% identity with SEQ ID NO: 39, and a light chain comprising or having an amino acid sequence of SEQ ID NO: 138 or a sequence having at least 95%, 96%, 97%, 98%, or 99% identity with SEQ ID NO: 138.

In some embodiments, the antibody or antigen binding fragment comprises a heavy chain variable region comprising or having an amino acid sequence of SEQ ID NO: 37 or a sequence having at least 95%, 96%, 97%, 98%, or 99% identity with SEQ ID NO: 37, and a light chain variable region comprising or having an amino acid sequence of SEQ ID NO: 136 or a sequence having at least 95%, 96%, 97%, 98%, or 99% identity with SEQ ID NO: 136. In some embodiments, the antibody or antigen binding fragment comprises a heavy chain comprising or having an amino acid sequence of SEQ ID NO: 141 or a sequence having at least 95%, 96%, 97%, 98%, or 99% identity with SEQ ID NO: 141, and a light chain comprising or having an amino acid sequence of SEQ ID NO: 138 or a sequence having at least 95%, 96%, 97%, 98%, or 99% identity with SEQ ID NO: 138.

In some embodiments, the antibody or antigen binding fragment comprises a heavy chain variable region comprising or having an amino acid sequence of SEQ ID NO: 37 or a sequence having at least 95%, 96%, 97%, 98%, or 99% identity with SEQ ID NO: 37, and a light chain variable region comprising or having an amino acid sequence of SEQ ID NO: 147 or a sequence having at least 95%, 96%, 97%, 98%, or 99% identity with SEQ ID NO: 147. In some embodiments, the antibody or antigen binding fragment comprises a heavy chain comprising or having an amino acid sequence of SEQ ID NO: 39 or a sequence having at least 95%, 96%, 97%, 98%, or 99% identity with SEQ ID NO: 39, and a light chain comprising or having an amino acid sequence of SEQ ID NO: 149 or a sequence having at least 95%, 96%, 97%, 98%, or 99% identity with SEQ ID NO: 149.

In some embodiments, the antibody or antigen binding fragment comprises a heavy chain variable region comprising or having an amino acid sequence of SEQ ID NO: 154 or a sequence having at least 95%, 96%, 97%, 98%, or 99% identity with SEQ ID NO: 154, and a light chain variable region comprising or having an amino acid sequence of SEQ ID NO: 24 or a sequence having at least 95%, 96%, 97%, 98%, or 99% identity with SEQ ID NO: 24. In some embodiments, the antibody or antigen binding fragment comprises a heavy chain comprising or having an amino acid sequence of SEQ ID NO: 156 or a sequence having at least 95%, 96%, 97%, 98%, or 99% identity with SEQ ID NO: 156, and a light chain comprising or having an amino acid sequence of SEQ ID NO: 26 or a sequence having at least 95%, 96%, 97%, 98%, or 99% identity with SEQ ID NO: 26.

In some embodiments, the antibody or antigen binding fragment comprises a heavy chain variable region comprising or having an amino acid sequence of SEQ ID NO: 154 or a sequence having at least 95%, 96%, 97%, 98%, or 99% identity with SEQ ID NO: 154, and a light chain variable region comprising or having an amino acid sequence of SEQ ID NO: 24 or a sequence having at least 95%, 96%, 97%, 98%, or 99% identity with SEQ ID NO: 24. In some embodiments, the antibody or antigen binding fragment comprises a heavy chain comprising or having an amino acid sequence of SEQ ID NO: 159 or a sequence having at least 95%, 96%, 97%, 98%, or 99% identity with SEQ ID NO: 159, and a light chain comprising or having an amino acid sequence of SEQ ID NO: 26 or a sequence having at least 95%, 96%, 97%, 98%, or 99% identity with SEQ ID NO: 26.

In some embodiments, the antibody or antigen binding fragment comprises a heavy chain variable region comprising or having an amino acid sequence of SEQ ID NO: 161 or a sequence having at least 95%, 96%, 97%, 98%, or 99% identity with SEQ ID NO: 161, and a light chain variable region comprising or having an amino acid sequence of SEQ ID NO: 24 or a sequence having at least 95%, 96%, 97%, 98%, or 99% identity with SEQ ID NO: 24. In some embodiments, the antibody or antigen binding fragment comprises a heavy chain comprising or having an amino acid sequence of SEQ ID NO: 163 or a sequence having at least 95%, 96%, 97%, 98%, or 99% identity with SEQ ID NO: 163, and a light chain comprising or having an amino acid sequence of SEQ ID NO: 26 or a sequence having at least 95%, 96%, 97%, 98%, or 99% identity with SEQ ID NO: 26.

In some embodiments, the antibody or antigen binding fragment comprises a heavy chain variable region comprising or having an amino acid sequence of SEQ ID NO: 168 or a sequence having at least 95%, 96%, 97%, 98%, or 99% identity with SEQ ID NO: 168, and a light chain variable region comprising or having an amino acid sequence of SEQ ID NO: 24 or a sequence having at least 95%, 96%, 97%, 98%, or 99% identity with SEQ ID NO: 24. In some embodiments, the antibody or antigen binding fragment comprises a heavy chain comprising or having an amino acid sequence of SEQ ID NO: 170 or a sequence having at least 95%, 96%, 97%, 98%, or 99% identity with SEQ ID NO: 170, and a light chain comprising or having an amino acid sequence of SEQ ID NO: 26 or a sequence having at least 95%, 96%, 97%, 98%, or 99% identity with SEQ ID NO: 26.

In some embodiments, the antibody or antigen binding fragment comprises a heavy chain variable region comprising or having an amino acid sequence of SEQ ID NO: 37 or a sequence having at least 95%, 96%, 97%, 98%, or 99% identity with SEQ ID NO: 37, and a light chain variable region comprising or having an amino acid sequence of SEQ ID NO: 174 or a sequence having at least 95%, 96%, 97%, 98%, or 99% identity with SEQ ID NO: 174. In some embodiments, the antibody or antigen binding fragment comprises a heavy chain comprising or having an amino acid sequence of SEQ ID NO: 39 or a sequence having at least 95%, 96%, 97%, 98%, or 99% identity with SEQ ID NO: 39, and a light chain comprising or having an amino acid sequence of SEQ ID NO: 176 or a sequence having at least 95%, 96%, 97%, 98%, or 99% identity with SEQ ID NO: 176.

In some embodiments, the antibody or antigen binding fragment comprises a heavy chain variable region comprising or having an amino acid sequence of SEQ ID NO: 37 or a sequence having at least 95%, 96%, 97%, 98%, or 99% identity with SEQ ID NO: 37, and a light chain variable region comprising or having an amino acid sequence of SEQ ID NO: 180 or a sequence having at least 95%, 96%, 97%, 98%, or 99% identity with SEQ ID NO: 180. In some embodiments, the antibody or antigen binding fragment comprises a heavy chain comprising or having an amino acid sequence of SEQ ID NO: 39 or a sequence having at least 95%, 96%, 97%, 98%, or 99% identity with SEQ ID NO: 39, and a light chain comprising or having an amino acid sequence of SEQ ID NO: 182 or a sequence having at least 95%, 96%, 97%, 98%, or 99% identity with SEQ ID NO: 182.

In some embodiments, the antibody or antigen binding fragment comprises a heavy chain variable region comprising or having an amino acid sequence of SEQ ID NO: 37 or a sequence having at least 95%, 96%, 97%, 98%, or 99% identity with SEQ ID NO: 37, and a light chain variable region comprising or having an amino acid sequence of SEQ ID NO: 186 or a sequence having at least 95%, 96%, 97%, 98%, or 99% identity with SEQ ID NO: 186. In some embodiments, the antibody or antigen binding fragment comprises a heavy chain comprising or having an amino acid sequence of SEQ ID NO: 39 or a sequence having at least 95%, 96%, 97%, 98%, or 99% identity with SEQ ID NO: 39, and a light chain comprising or having an amino acid sequence of SEQ ID NO: 188 or a sequence having at least 95%, 96%, 97%, 98%, or 99% identity with SEQ ID NO: 188.

In some embodiments, the antibody or antigen binding fragment comprises a heavy chain variable region comprising or having an amino acid sequence of SEQ ID NO: 193 or a sequence having at least 95%, 96%, 97%, 98%, or 99% identity with SEQ ID NO: 193, and a light chain variable region comprising or having an amino acid sequence of SEQ ID NO: 136 or a sequence having at least 95%, 96%, 97%, 98%, or 99% identity with SEQ ID NO: 136. In some embodiments, the antibody or antigen binding fragment comprises a heavy chain comprising or having an amino acid sequence of SEQ ID NO: 195 or a sequence having at least 95%, 96%, 97%, 98%, or 99% identity with SEQ ID NO: 195, and a light chain comprising or having an amino acid sequence of SEQ ID NO: 138 or a sequence having at least 95%, 96%, 97%, 98%, or 99% identity with SEQ ID NO: 138.

In some embodiments, the antibody or antigen binding fragment comprises a heavy chain variable region comprising or having an amino acid sequence of SEQ ID NO: 193 or a sequence having at least 95%, 96%, 97%, 98%, or 99% identity with SEQ ID NO: 193, and a light chain variable region comprising or having an amino acid sequence of SEQ ID NO: 174 or a sequence having at least 95%, 96%, 97%, 98%, or 99% identity with SEQ ID NO: 174. In some embodiments, the antibody or antigen binding fragment comprises a heavy chain comprising or having an amino acid sequence of SEQ ID NO: 195 or a sequence having at least 95%, 96%, 97%, 98%, or 99% identity with SEQ ID NO: 195, and a light chain comprising or having an amino acid sequence of SEQ ID NO: 176 or a sequence having at least 95%, 96%, 97%, 98%, or 99% identity with SEQ ID NO: 176.

In some embodiments, the antibody or antigen binding fragment comprises a heavy chain variable region comprising or having an amino acid sequence of SEQ ID NO: 201 or a sequence having at least 95%, 96%, 97%, 98%, or 99% identity with SEQ ID NO: 201, and a light chain variable region comprising or having an amino acid sequence of SEQ ID NO: 128 or a sequence having at least 95%, 96%, 97%, 98%, or 99% identity with SEQ ID NO: 128. In some embodiments, the antibody or antigen binding fragment comprises a heavy chain comprising or having an amino acid sequence of SEQ ID NO: 203 or a sequence having at least 95%, 96%, 97%, 98%, or 99% identity with SEQ ID NO: 203, and a light chain comprising or having an amino acid sequence of SEQ ID NO: 130 or a sequence having at least 95%, 96%, 97%, 98%, or 99% identity with SEQ ID NO: 130.

In some embodiments, the antibody or antigen binding fragment comprises a heavy chain variable region comprising or having an amino acid sequence of SEQ ID NO: 122 or a sequence having at least 95%, 96%, 97%, 98%, or 99% identity with SEQ ID NO: 122, and a light chain variable region comprising or having an amino acid sequence of SEQ ID NO: 128 or a sequence having at least 95%, 96%, 97%, 98%, or 99% identity with SEQ ID NO: 128. In some embodiments, the antibody or antigen binding fragment comprises a heavy chain comprising or having an amino acid sequence of SEQ ID NO: 208 or a sequence having at least 95%, 96%, 97%, 98%, or 99% identity with SEQ ID NO: 208, and a light chain comprising or having an amino acid sequence of SEQ ID NO: 130 or a sequence having at least 95%, 96%, 97%, 98%, or 99% identity with SEQ ID NO: 130.

In some embodiments, the antibody or antigen binding fragment comprises a heavy chain variable region comprising or having an amino acid sequence of SEQ ID NO: 201 or a sequence having at least 95%, 96%, 97%, 98%, or 99% identity with SEQ ID NO: 201, and a light chain variable region comprising or having an amino acid sequence of SEQ ID NO: 136 or a sequence having at least 95%, 96%, 97%, 98%, or 99% identity with SEQ ID NO: 136. In some embodiments, the antibody or antigen binding fragment comprises a heavy chain comprising or having an amino acid sequence of SEQ ID NO: 203 or a sequence having at least 95%, 96%, 97%, 98%, or 99% identity with SEQ ID NO: 203, and a light chain comprising or having an amino acid sequence of SEQ ID NO: 138 or a sequence having at least 95%, 96%, 97%, 98%, or 99% identity with SEQ ID NO: 138.

In some embodiments, the antibody or antigen binding fragment comprises a heavy chain variable region comprising or having an amino acid sequence of SEQ ID NO: 122 or a sequence having at least 95%, 96%, 97%, 98%, or 99% identity with SEQ ID NO: 122, and a light chain variable region comprising or having an amino acid sequence of SEQ ID NO: 136 or a sequence having at least 95%, 96%, 97%, 98%, or 99% identity with SEQ ID NO: 136. In some embodiments, the antibody or antigen binding fragment comprises a heavy chain comprising or having an amino acid sequence of SEQ ID NO: 208 or a sequence having at least 95%, 96%, 97%, 98%, or 99% identity with SEQ ID NO: 208, and a light chain comprising or having an amino acid sequence of SEQ ID NO: 138 or a sequence having at least 95%, 96%, 97%, 98%, or 99% identity with SEQ ID NO: 138.

In some embodiments, the antibody or antigen binding fragment comprises a heavy chain variable region comprising or having an amino acid sequence of SEQ ID NO: 201 or a sequence having at least 95%, 96%, 97%, 98%, or 99% identity with SEQ ID NO: 201, and a light chain variable region comprising or having an amino acid sequence of SEQ ID NO: 147 or a sequence having at least 95%, 96%, 97%, 98%, or 99% identity with SEQ ID NO: 147. In some embodiments, the antibody or antigen binding fragment comprises a heavy chain comprising or having an amino acid sequence of SEQ ID NO: 203 or a sequence having at least 95%, 96%, 97%, 98%, or 99% identity with SEQ ID NO: 203, and a light chain comprising or having an amino acid sequence of SEQ ID NO: 149 or a sequence having at least 95%, 96%, 97%, 98%, or 99% identity with SEQ ID NO: 149.

In some embodiments, the antibody or antigen binding fragment comprises a heavy chain variable region comprising or having an amino acid sequence of SEQ ID NO: 122 or a sequence having at least 95%, 96%, 97%, 98%, or 99% identity with SEQ ID NO: 122, and a light chain variable region comprising or having an amino acid sequence of SEQ ID NO: 147 or a sequence having at least 95%, 96%, 97%, 98%, or 99% identity with SEQ ID NO: 147. In some embodiments, the antibody or antigen binding fragment comprises a heavy chain comprising or having an amino acid sequence of SEQ ID NO: 208 or a sequence having at least 95%, 96%, 97%, 98%, or 99% identity with SEQ ID NO: 208, and a light chain comprising or having an amino acid sequence of SEQ ID NO: 149 or a sequence having at least 95%, 96%, 97%, 98%, or 99% identity with SEQ ID NO: 149.

In some embodiments, the antibody or antigen binding fragment comprises a heavy chain variable region comprising or having an amino acid sequence of SEQ ID NO: 201 or a sequence having at least 95%, 96%, 97%, 98%, or 99% identity with SEQ ID NO: 201, and a light chain variable region comprising or having an amino acid sequence of SEQ ID NO: 174 or a sequence having at least 95%, 96%, 97%, 98%, or 99% identity with SEQ ID NO: 174. In some embodiments, the antibody or antigen binding fragment comprises a heavy chain comprising or having an amino acid sequence of SEQ ID NO: 203 or a sequence having at least 95%, 96%, 97%, 98%, or 99% identity with SEQ ID NO: 203, and a light chain comprising or having an amino acid sequence of SEQ ID NO: 176 or a sequence having at least 95%, 96%, 97%, 98%, or 99% identity with SEQ ID NO: 176.

In some embodiments, the antibody or antigen binding fragment comprises a heavy chain variable region comprising or having an amino acid sequence of SEQ ID NO: 122 or a sequence having at least 95%, 96%, 97%, 98%, or 99% identity with SEQ ID NO: 122, and a light chain variable region comprising or having an amino acid sequence of SEQ ID NO: 174 or a sequence having at least 95%, 96%, 97%, 98%, or 99% identity with SEQ ID NO: 174. In some embodiments, the antibody or antigen binding fragment comprises a heavy chain comprising or having an amino acid sequence of SEQ ID NO: 208 or a sequence having at least 95%, 96%, 97%, 98%, or 99% identity with SEQ ID NO: 208, and a light chain comprising or having an amino acid sequence of SEQ ID NO: 176 or a sequence having at least 95%, 96%, 97%, 98%, or 99% identity with SEQ ID NO: 176.

In some embodiments, the antibody or antigen binding fragment comprises a heavy chain variable region comprising or having an amino acid sequence of SEQ ID NO: 201 or a sequence having at least 95%, 96%, 97%, 98%, or 99% identity with SEQ ID NO: 201, and a light chain variable region comprising or having an amino acid sequence of SEQ ID NO: 180 or a sequence having at least 95%, 96%, 97%, 98%, or 99% identity with SEQ ID NO: 180. In some embodiments, the antibody or antigen binding fragment comprises a heavy chain comprising or having an amino acid sequence of SEQ ID NO: 203 or a sequence having at least 95%, 96%, 97%, 98%, or 99% identity with SEQ ID NO: 203, and a light chain comprising or having an amino acid sequence of SEQ ID NO: 182 or a sequence having at least 95%, 96%, 97%, 98%, or 99% identity with SEQ ID NO: 182.

In some embodiments, the antibody or antigen binding fragment comprises a heavy chain variable region comprising or having an amino acid sequence of SEQ ID NO: 122 or a sequence having at least 95%, 96%, 97%, 98%, or 99% identity with SEQ ID NO: 122, and a light chain variable region comprising or having an amino acid sequence of SEQ ID NO: 180 or a sequence having at least 95%, 96%, 97%, 98%, or 99% identity with SEQ ID NO: 180. In some embodiments, the antibody or antigen binding fragment comprises a heavy chain comprising or having an amino acid sequence of SEQ ID NO: 208 or a sequence having at least 95%, 96%, 97%, 98%, or 99% identity with SEQ ID NO: 208, and a light chain comprising or having an amino acid sequence of SEQ ID NO: 182 or a sequence having at least 95%, 96%, 97%, 98%, or 99% identity with SEQ ID NO: 182.

In some embodiments, the antibody or antigen binding fragment comprises a heavy chain variable region comprising or having an amino acid sequence of SEQ ID NO: 201 or a sequence having at least 95%, 96%, 97%, 98%, or 99% identity with SEQ ID NO: 201, and a light chain variable region comprising or having an amino acid sequence of SEQ ID NO: 186 or a sequence having at least 95%, 96%, 97%, 98%, or 99% identity with SEQ ID NO: 186. In some embodiments, the antibody or antigen binding fragment comprises a heavy chain comprising or having an amino acid sequence of SEQ ID NO: 203 or a sequence having at least 95%, 96%, 97%, 98%, or 99% identity with SEQ ID NO: 203, and a light chain comprising or having an amino acid sequence of SEQ ID NO: 188 or a sequence having at least 95%, 96%, 97%, 98%, or 99% identity with SEQ ID NO: 188.

In some embodiments, the antibody or antigen binding fragment comprises a heavy chain variable region comprising or having an amino acid sequence of SEQ ID NO: 122 or a sequence having at least 95%, 96%, 97%, 98%, or 99% identity with SEQ ID NO: 122, and a light chain variable region comprising or having an amino acid sequence of SEQ ID NO: 186 or a sequence having at least 95%, 96%, 97%, 98%, or 99% identity with SEQ ID NO: 186. In some embodiments, the antibody or antigen binding fragment comprises a heavy chain comprising or having an amino acid sequence of SEQ ID NO: 208 or a sequence having at least 95%, 96%, 97%, 98%, or 99% identity with SEQ ID NO: 208, and a light chain comprising or having an amino acid sequence of SEQ ID NO: 188 or a sequence having at least 95%, 96%, 97%, 98%, or 99% identity with SEQ ID NO: 188.

In some embodiments, the antibody or antigen binding fragment comprises a heavy chain variable region comprising or having an amino acid sequence of SEQ ID NO: 233 or a sequence having at least 95%, 96%, 97%, 98%, or 99% identity with SEQ ID NO: 233, and a light chain variable region comprising or having an amino acid sequence of SEQ ID NO: 244 or a sequence having at least 95%, 96%, 97%, 98%, or 99% identity with SEQ ID NO: 244. In some embodiments, the antibody or antigen binding fragment comprises a heavy chain comprising or having an amino acid sequence of SEQ ID NO: 235 or a sequence having at least 95%, 96%, 97%, 98%, or 99% identity with SEQ ID NO: 235, and a light chain comprising or having an amino acid sequence of SEQ ID NO: 246 or a sequence having at least 95%, 96%, 97%, 98%, or 99% identity with SEQ ID NO: 246.

In some embodiments, the antibody or antigen binding fragment comprises a heavy chain variable region comprising or having an amino acid sequence of SEQ ID NO: 256 or a sequence having at least 95%, 96%, 97%, 98%, or 99% identity with SEQ ID NO: 256, and a light chain variable region comprising or having an amino acid sequence of SEQ ID NO: 266 or a sequence having at least 95%, 96%, 97%, 98%, or 99% identity with SEQ ID NO: 266. In some embodiments, the antibody or antigen binding fragment comprises a heavy chain comprising or having an amino acid sequence of SEQ ID NO: 258 or a sequence having at least 95%, 96%, 97%, 98%, or 99% identity with SEQ ID NO: 258, and a light chain comprising or having an amino acid sequence of SEQ ID NO: 268 or a sequence having at least 95%, 96%, 97%, 98%, or 99% identity with SEQ ID NO: 268.

In some embodiments, the antibody or antigen binding fragment comprises a heavy chain variable region comprising or having an amino acid sequence of SEQ ID NO: 278 or a sequence having at least 95%, 96%, 97%, 98%, or 99% identity with SEQ ID NO: 278, and a light chain variable region comprising or having an amino acid sequence of SEQ ID NO: 287 or a sequence having at least 95%, 96%, 97%, 98%, or 99% identity with SEQ ID NO: 287. In some embodiments, the antibody or antigen binding fragment comprises a heavy chain comprising or having an amino acid sequence of SEQ ID NO: 280 or a sequence having at least 95%, 96%, 97%, 98%, or 99% identity with SEQ ID NO: 280, and a light chain comprising or having an amino acid sequence of SEQ ID NO: 289 or a sequence having at least 95%, 96%, 97%, 98%, or 99% identity with SEQ ID NO: 289.

In some embodiments, the antibody or antigen binding fragment comprises a heavy chain variable region comprising or having an amino acid sequence of SEQ ID NO: 300 or a sequence having at least 95%, 96%, 97%, 98%, or 99% identity with SEQ ID NO: 300, and a light chain variable region comprising or having an amino acid sequence of SEQ ID NO: 306 or a sequence having at least 95%, 96%, 97%, 98%, or 99% identity with SEQ ID NO: 306. In some embodiments, the antibody or antigen binding fragment comprises a heavy chain comprising or having an amino acid sequence of SEQ ID NO: 302 or a sequence having at least 95%, 96%, 97%, 98%, or 99% identity with SEQ ID NO: 302, and a light chain comprising or having an amino acid sequence of SEQ ID NO: 308 or a sequence having at least 95%, 96%, 97%, 98%, or 99% identity with SEQ ID NO: 308.

In some embodiments, the antibody or antigen binding fragment comprises a heavy chain variable region comprising or having an amino acid sequence of SEQ ID NO: 316 or a sequence having at least 95%, 96%, 97%, 98%, or 99% identity with SEQ ID NO: 316, and a light chain variable region comprising or having an amino acid sequence of SEQ ID NO: 327 or a sequence having at least 95%, 96%, 97%, 98%, or 99% identity with SEQ ID NO: 327. In some embodiments, the antibody or antigen binding fragment comprises a heavy chain comprising or having an amino acid sequence of SEQ ID NO: 318 or a sequence having at least 95%, 96%, 97%, 98%, or 99% identity with SEQ ID NO: 318, and a light chain comprising or having an amino acid sequence of SEQ ID NO: 329 or a sequence having at least 95%, 96%, 97%, 98%, or 99% identity with SEQ ID NO: 329.

In some embodiments, the antibody or antigen binding fragment comprises a heavy chain variable region comprising or having an amino acid sequence of SEQ ID NO: 333 or a sequence having at least 95%, 96%, 97%, 98%, or 99% identity with SEQ ID NO: 333, and a light chain variable region comprising or having an amino acid sequence of SEQ ID NO: 344 or a sequence having at least 95%, 96%, 97%, 98%, or 99% identity with SEQ ID NO: 344. In some embodiments, the antibody or antigen binding fragment comprises a heavy chain comprising or having an amino acid sequence of SEQ ID NO: 335 or a sequence having at least 95%, 96%, 97%, 98%, or 99% identity with SEQ ID NO: 335, and a light chain comprising or having an amino acid sequence of SEQ ID NO: 346 or a sequence having at least 95%, 96%, 97%, 98%, or 99% identity with SEQ ID NO: 346.

In some embodiments, the antibody or antigen binding fragment comprises a heavy chain variable region comprising or having an amino acid sequence of SEQ ID NO: 350 or a sequence having at least 95%, 96%, 97%, 98%, or 99% identity with SEQ ID NO: 350, and a light chain variable region comprising or having an amino acid sequence of SEQ ID NO: 357 or a sequence having at least 95%, 96%, 97%, 98%, or 99% identity with SEQ ID NO: 357. In some embodiments, the antibody or antigen binding fragment comprises a heavy chain comprising or having an amino acid sequence of SEQ ID NO: 352 or a sequence having at least 95%, 96%, 97%, 98%, or 99% identity with SEQ ID NO: 352, and a light chain comprising or having an amino acid sequence of SEQ ID NO: 359 or a sequence having at least 95%, 96%, 97%, 98%, or 99% identity with SEQ ID NO: 359.

In some embodiments, the antibody or antigen binding fragment comprises a heavy chain variable region comprising or having an amino acid sequence of SEQ ID NO: 350 or a sequence having at least 95%, 96%, 97%, 98%, or 99% identity with SEQ ID NO: 350, and a light chain variable region comprising or having an amino acid sequence of SEQ ID NO: 363 or a sequence having at least 95%, 96%, 97%, 98%, or 99% identity with SEQ ID NO: 363. In some embodiments, the antibody or antigen binding fragment comprises a heavy chain comprising or having an amino acid sequence of SEQ ID NO: 352 or a sequence having at least 95%, 96%, 97%, 98%, or 99% identity with SEQ ID NO: 352, and a light chain comprising or having an amino acid sequence of SEQ ID NO: 365 or a sequence having at least 95%, 96%, 97%, 98%, or 99% identity with SEQ ID NO: 365.

In some embodiments, the antibody or antigen binding fragment comprises a heavy chain variable region comprising or having an amino acid sequence of SEQ ID NO: 374 or a sequence having at least 95%, 96%, 97%, 98%, or 99% identity with SEQ ID NO: 374, and a light chain variable region comprising or having an amino acid sequence of SEQ ID NO: 244 or a sequence having at least 95%, 96%, 97%, 98%, or 99% identity with SEQ ID NO: 244. In some embodiments, the antibody or antigen binding fragment comprises a heavy chain comprising or having an amino acid sequence of SEQ ID NO: 376 or a sequence having at least 95%, 96%, 97%, 98%, or 99% identity with SEQ ID NO: 376, and a light chain comprising or having an amino acid sequence of SEQ ID NO: 246 or a sequence having at least 95%, 96%, 97%, 98%, or 99% identity with SEQ ID NO: 246.

In some embodiments, the antibody or antigen binding fragment comprises a heavy chain variable region comprising or having an amino acid sequence of SEQ ID NO: 385 or a sequence having at least 95%, 96%, 97%, 98%, or 99% identity with SEQ ID NO: 385, and a light chain variable region comprising or having an amino acid sequence of SEQ ID NO: 244 or a sequence having at least 95%, 96%, 97%, 98%, or 99% identity with SEQ ID NO: 244. In some embodiments, the antibody or antigen binding fragment comprises a heavy chain comprising or having an amino acid sequence of SEQ ID NO: 387 or a sequence having at least 95%, 96%, 97%, 98%, or 99% identity with SEQ ID NO: 387, and a light chain comprising or having an amino acid sequence of SEQ ID NO: 246 or a sequence having at least 95%, 96%, 97%, 98%, or 99% identity with SEQ ID NO: 246.

In some embodiments, the antibody or antigen binding fragment comprises a heavy chain variable region comprising or having an amino acid sequence of SEQ ID NO: 392 or a sequence having at least 95%, 96%, 97%, 98%, or 99% identity with SEQ ID NO: 392, and a light chain variable region comprising or having an amino acid sequence of SEQ ID NO: 344 or a sequence having at least 95%, 96%, 97%, 98%, or 99% identity with SEQ ID NO: 344. In some embodiments, the antibody or antigen binding fragment comprises a heavy chain comprising or having an amino acid sequence of SEQ ID NO: 394 or a sequence having at least 95%, 96%, 97%, 98%, or 99% identity with SEQ ID NO: 394, and a light chain comprising or having an amino acid sequence of SEQ ID NO: 346 or a sequence having at least 95%, 96%, 97%, 98%, or 99% identity with SEQ ID NO: 346.

In some embodiments, the antibody or antigen binding fragment comprises a heavy chain variable region comprising or having an amino acid sequence of SEQ ID NO: 403 or a sequence having at least 95%, 96%, 97%, 98%, or 99% identity with SEQ ID NO: 403, and a light chain variable region comprising or having an amino acid sequence of SEQ ID NO: 344 or a sequence having at least 95%, 96%, 97%, 98%, or 99% identity with SEQ ID NO: 344. In some embodiments, the antibody or antigen binding fragment comprises a heavy chain comprising or having an amino acid sequence of SEQ ID NO: 405 or a sequence having at least 95%, 96%, 97%, 98%, or 99% identity with SEQ ID NO: 405, and a light chain comprising or having an amino acid sequence of SEQ ID NO: 346 or a sequence having at least 95%, 96%, 97%, 98%, or 99% identity with SEQ ID NO: 346.

In some embodiments, the antibody or antigen binding fragment comprises a heavy chain variable region comprising or having an amino acid sequence of SEQ ID NO: 414 or a sequence having at least 95%, 96%, 97%, 98%, or 99% identity with SEQ ID NO: 414, and a light chain variable region comprising or having an amino acid sequence of SEQ ID NO: 344 or a sequence having at least 95%, 96%, 97%, 98%, or 99% identity with SEQ ID NO: 344. In some embodiments, the antibody or antigen binding fragment comprises a heavy chain comprising or having an amino acid sequence of SEQ ID NO: 416 or a sequence having at least 95%, 96%, 97%, 98%, or 99% identity with SEQ ID NO: 416, and a light chain comprising or having an amino acid sequence of SEQ ID NO: 346 or a sequence having at least 95%, 96%, 97%, 98%, or 99% identity with SEQ ID NO: 346.

In some embodiments, the antibody or antigen binding fragment comprises a heavy chain variable region comprising or having an amino acid sequence of SEQ ID NO: 425 or a sequence having at least 95%, 96%, 97%, 98%, or 99% identity with SEQ ID NO: 425, and a light chain variable region comprising or having an amino acid sequence of SEQ ID NO: 344 or a sequence having at least 95%, 96%, 97%, 98%, or 99% identity with SEQ ID NO: 344. In some embodiments, the antibody or antigen binding fragment comprises a heavy chain comprising or having an amino acid sequence of SEQ ID NO: 427 or a sequence having at least 95%, 96%, 97%, 98%, or 99% identity with SEQ ID NO: 427, and a light chain comprising or having an amino acid sequence of SEQ ID NO: 346 or a sequence having at least 95%, 96%, 97%, 98%, or 99% identity with SEQ ID NO: 346.

Groups of exemplary anti-NPR1 antibodies of the present disclosure are set forth in Table 3 or Table 4 by CDR (i.e., numerical values in these tables represent sequence identifiers such that "28" represents "SEQ ID NO: 28") or amino acid consensus sequences. When multiple numerical values are presented in Table 3, they may be used in the alternative for that CDR (i.e., when SEQ ID Nos: 29, 119, and 190 are listed for HCDR2, they may be used in the alternative for that CDR). In Table 4, those amino acids presented in parentheses and separated by a slash represent alternative amino acids in that position (e.g., "(A/V)" represents a position at which the amino acid may be alanine or valine). In some embodiments, the antibody has the heavy and light chain CDRs of any of the antibodies described in Table 3 or Table 4. In some embodiments, the anti-NPR1 antibody is a four-chain antibody (also referred to as an intact antibody), comprising two heavy chains and two light chains. In some embodiments, the anti-NPR1 antibody is an antigen binding fragment of an intact antibody, e.g., a functional fragment of an intact antibody selected from any of those set forth in Table 3 or Table 4 that retains the ability to bind NPR1 and/or provide a function of the intact antibody (e.g., activating NPR1 in the absence of ANP).

TABLE 3

Exemplary anti-NPR1 antibody groups by CDR

| | HCDR1 | HCDR2 | HCDR3 | LCDR1 | LCDR2 | LCDR3 |
|---|---|---|---|---|---|---|
| ANP non-competitive group 1 | | | | | | |
| Combined | 28 | 29<br>119<br>190 | 30 | 41 | 42 | 43<br>126<br>134<br>145<br>172<br>178<br>184 |
| Kabat | 31 | 29<br>119<br>190 | 30 | 41 | 42 | 43<br>126<br>134<br>145<br>172<br>178<br>184 |
| Chothia | 32 | 33<br>120<br>191 | 30 | 44 | 45 | 46<br>127<br>135<br>146<br>173<br>179<br>185 |
| IMGT | 34 | 35<br>121<br>192 | 36 | 47 | 45 | 43<br>126<br>134<br>145<br>172<br>178<br>184 |
| ANP non-competitive group 2 | | | | | | |
| Combined | 28 | 119 | 30 | 41 | 42 | 126<br>134<br>145<br>172<br>178<br>184 |
| Kabat | 31 | 119 | 30 | 41 | 42 | 126<br>134<br>145<br>172<br>178<br>184 |

TABLE 3-continued

Exemplary anti-NPR1 antibody groups by CDR

| | HCDR1 | HCDR2 | HCDR3 | LCDR1 | LCDR2 | LCDR3 |
|---|---|---|---|---|---|---|
| Chothia | 32 | 120 | 30 | 44 | 45 | 127 |
| | | | | | | 135 |
| | | | | | | 146 |
| | | | | | | 173 |
| | | | | | | 179 |
| | | | | | | 185 |
| IMGT | 34 | 121 | 36 | 47 | 45 | 126 |
| | | | | | | 134 |
| | | | | | | 145 |
| | | | | | | 172 |
| | | | | | | 178 |
| | | | | | | 184 |
| ANP non-competitive group 3 | | | | | | |
| Combined | 4 | 5 | 6 | 17 | 18 | 19 |
| | 112 | 100 | | | | |
| | 165 | 151 | | | | |
| Kabat | 7 | 5 | 6 | 17 | 18 | 19 |
| | | 100 | | | | |
| | | 151 | | | | |
| Chothia | 8 | 9 | 6 | 20 | 21 | 22 |
| | 113 | 101 | | | | |
| | 166 | 152 | | | | |
| IMGT | 10 | 11 | 12 | 23 | 21 | 19 |
| | 114 | 102 | | | | |
| | 167 | 153 | | | | |
| ANP non-competitive group 4 | | | | | | |
| Combined | 4 | 5 | 6 | 17 | 18 | 19 |
| | 112 | 100 | | | | |
| | 165 | | | | | |
| Kabat | 7 | 5 | 6 | 17 | 18 | 19 |
| | | 100 | | | | |
| Chothia | 8 | 9 | 6 | 20 | 21 | 22 |
| | 113 | 101 | | | | |
| | 166 | | | | | |
| IMGT | 10 | 11 | 12 | 23 | 21 | 19 |
| | 114 | 102 | | | | |
| | 167 | | | | | |
| ANP non-competitive group 5 | | | | | | |
| Combined | 226 | 227 | 228 | 237 | 238 | 239 |
| | 367 | 368 | | | | |
| | 378 | 379 | | | | |
| Kabat | 229 | 227 | 228 | 237 | 238 | 239 |
| | 369 | 368 | | | | |
| | 380 | 379 | | | | |
| Chothia | 32 | 230 | 228 | 240 | 241 | 242 |
| | 370 | 371 | | | | |
| | 381 | 382 | | | | |
| IMGT | 34 | 231 | 232 | 243 | 241 | 239 |
| | 372 | 373 | | | | |
| | 383 | 384 | | | | |
| ANP non-competitive group 6 | | | | | | |
| Combined | 226 | 227 | 228 | 237 | 238 | 239 |
| | 378 | 368 | | | | |
| | | 379 | | | | |
| Kabat | 229 | 227 | 228 | 237 | 238 | 239 |
| | 380 | 368 | | | | |
| | | 379 | | | | |
| Chothia | 32 | 230 | 228 | 240 | 241 | 242 |
| | 381 | 371 | | | | |
| | | 382 | | | | |
| IMGT | 34 | 231 | 232 | 243 | 241 | 239 |
| | 383 | 373 | | | | |
| | | 384 | | | | |
| ANP non-competitive group 7 | | | | | | |
| Combined | 226 | 368 | 228 | 237 | 238 | 239 |
| | 367 | 379 | | | | |
| | 378 | | | | | |
| Kabat | 229 | 368 | 228 | 237 | 238 | 239 |
| | 369 | 379 | | | | |
| | 380 | | | | | |
| Chothia | 32 | 371 | 228 | 240 | 241 | 242 |
| | 370 | 382 | | | | |
| | 381 | | | | | |
| IMGT | 34 | 373 | 232 | 243 | 241 | 239 |
| | 372 | 384 | | | | |
| | 383 | | | | | |
| ANP non-competitive group 8 | | | | | | |
| Combined | 226 | 368 | 228 | 237 | 238 | 239 |
| | 378 | 379 | | | | |
| Kabat | 229 | 368 | 228 | 237 | 238 | 239 |
| | 380 | 379 | | | | |
| Chothia | 32 | 371 | 228 | 240 | 241 | 242 |
| | 381 | 382 | | | | |
| IMGT | 34 | 373 | 232 | 243 | 241 | 239 |
| | 383 | 384 | | | | |
| ANP competitive group 1 | | | | | | |
| Combined | 310 | 311 | 312 | 320 | 321 | 322 |
| | | | 348 | | 354 | 355 |
| | | | | | | 361 |
| Kabat | 229 | 311 | 312 | 320 | 321 | 322 |
| | | | 348 | | 354 | 355 |
| | | | | | | 361 |
| Chothia | 80 | 313 | 312 | 323 | 324 | 325 |
| | | | 348 | | | 356 |
| | | | | | | 362 |
| IMGT | 82 | 314 | 315 | 326 | 324 | 322 |
| | | | 349 | | | 355 |
| | | | | | | 361 |
| ANP competitive group 2 | | | | | | |
| Combined | 270 | 271 | 331 | 337 | 338 | 339 |
| | 407 | 389 | | | | |
| | | 408 | | | | |
| Kabat | 273 | 271 | 331 | 337 | 338 | 339 |
| | 409 | 389 | | | | |
| | | 408 | | | | |
| Chothia | 32 | 274 | 331 | 340 | 341 | 342 |
| | 410 | 390 | | | | |
| | | 411 | | | | |
| IMGT | 275 | 276 | 332 | 343 | 341 | 339 |
| | 412 | 391 | | | | |
| | | 413 | | | | |
| ANP competitive group 3 | | | | | | |
| Combined | 270 | 389 | 331 | 337 | 338 | 339 |
| | 407 | 408 | | | | |
| Kabat | 273 | 389 | 331 | 337 | 338 | 339 |
| | 409 | 408 | | | | |
| Chothia | 32 | 390 | 331 | 340 | 341 | 342 |
| | 410 | 411 | | | | |
| IMGT | 275 | 276 | 332 | 343 | 341 | 339 |
| | 412 | 391 | | | | |
| | | 413 | | | | |

TABLE 4

Exemplary anti-NPR1 antibody groups by consensus sequence

| | HCDR1 | HCDR2 | HCDR3 | LCDR1 | LC

TABLE 4-continued

| Exemplary anti-NPR1 antibody groups by consensus sequence | | | | | | |
|---|---|---|---|---|---|---|
| | HCDR1 | HCDR2 | HCDR3 | LCDR1 | LCDR2 | LCDR3 |
| ANP non-competitive group D | | | | | | |
| Combined | GFTF(N/S/Q)T HYIH (SEQ ID NO: 436) | SI(S/G)(S/G)(S/Q) G(S/Q/G)(S/N/M)T (Y/L)YADSVKG (SEQ ID NO: 437) | 6 | 17 | 18 | 19 |
| Kabat | 7 | SI(S/G)(S/G)(S/Q) G(S/Q/G)(S/N/M)T (Y/L)YADSVKG (SEQ ID NO: 437) | 6 | 17 | 18 | 19 |
| Chothia | GFTF(N/S/Q)TH (SEQ ID NO: 438) | (S/G)(S/G)(S/Q)G (S/Q/G)(S/N/M) (SEQ ID NO: 439) | 6 | 20 | 21 | 22 |
| IMGT | GFTF(N/S/Q)THY (SEQ ID NO: 440) | I(S/G)(S/G)(S/Q)G (S/Q/G)(S/N/M)T (SEQ ID NO: 441) | 12 | 23 | 21 | 19 |
| ANP non-competitive group E | | | | | | |
| Combined | GFTF(N/S/Q)T HYIH (SEQ ID NO: 436) | SIS(S/G)SG(S/Q) (S/N)TYYADSVKG (SEQ ID NO: 442) | 6 | 17 | 18 | 19 |
| Kabat | 7 | SIS(S/G)SG(S/Q) (S/N)TYYADSVKG (SEQ ID NO: 442) | 6 | 17 | 18 | 19 |
| Chothia | GFTF(N/S/Q)TH (SEQ ID NO: 438) | S(S/G)SG(S/Q) (S/N) (SEQ ID NO: 443) | 6 | 20 | 21 | 22 |
| IMGT | GFTF(N/S/Q)THY (SEQ ID NO: 440) | IS(S/G)SG(S/Q) (S/N)T (SEQ ID NO: 444) | 12 | 23 | 21 | 19 |
| ANP non-competitive group F | | | | | | |
| Combined | GF(S/T)FS(S/K/ R)Y(W/Y)(I/L) (S/N) (SEQ ID NO: 445) | (N/S)I(K/H)Q(S/Q/ H)(G/A)(S/H/L)E(T/ K)(Y/K/R)YVESVKG (SEQ ID NO: 446) | 228 | 237 | 238 | 239 |
| Kabat | (S/K/R)Y(W/Y) (I/L)(S/N) (SEQ ID NO: 447) | (N/S)I(K/H)Q(S/Q/ H)(G/A)(S/H/L)E(T/ K)(Y/K/R)YVESVKG (SEQ ID NO: 446) | 228 | 237 | 238 | 239 |
| Chothia | GF(S/T)FS(S/K/ R)Y (SEQ ID NO: 448) | (K/H)Q(S/Q/H)(G/ A)(S/H/L)E (SEQ ID NO: 449) | 228 | 240 | 241 | 242 |
| IMGT | GF(S/T)FS(S/K/ R)Y(W/Y) (SEQ ID NO: 450) | I(K/H)Q(S/Q/H)(G/ A)(S/H/L)E(T/K) (SEQ ID NO: 451) | 232 | 243 | 241 | 239 |
| ANP non-competitive group G | | | | | | |
| Combined | GFTFS(S/R)Y (W/Y)I(S/N) (SEQ ID NO: 452) | (N/S)I(K/H)Q(S/Q/ H)(G/A)(S/H/L)E(T/ K)(Y/K/R)YVESVKG (SEQ ID NO: 446) | 228 | 237 | 238 | 239 |

TABLE 4-continued

Exemplary anti-NPR1 antibody groups by consensus sequence

| | HCDR1 | HCDR2 | HCDR3 | LCDR1 | LCDR2 | LCDR3 |
|---|---|---|---|---|---|---|
| Kabat | (S/R)Y(W/Y)I(S/N) (SEQ ID NO: 454) | (N/S)I(K/H)Q(S/Q/H)(G/A)(S/H/L)E(T/K)(Y/K/R)YVESVKG (SEQ ID NO: 446) | 228 | 237 | 238 | 239 |
| Chothia | GFTFS(S/R)Y (SEQ ID NO: 455) | (K/H)Q(S/Q/H)(G/A)(S/H/L)E (SEQ ID NO: 449) | 228 | 240 | 241 | 242 |
| IMGT | GFTFS(S/R)Y(W/Y) (SEQ ID NO: 457) | I(K/H)Q(S/Q/H)(G/A)(S/H/L)E(T/K) (SEQ ID NO: 451) | 232 | 243 | 241 | 239 |
| ANP non-competitive group H | | | | | | |
| Combined | GF(S/T)FS(S/K/R)Y(W/Y)(I/L)(S/N) (SEQ ID NO: 445) | SIHQ(Q/H)(G/A)(H/L)E(T/K)(K/R)YVESVKG (SEQ ID NO: 453) | 228 | 237 | 238 | 239 |
| Kabat | (S/K/R)Y(W/Y)(I/L)(S/N) (SEQ ID NO: 447) | SIHQ(Q/H)(G/A)(H/L)E(T/K)(K/R)YVESVKG (SEQ ID NO: 453) | 228 | 237 | 238 | 239 |
| Chothia | GF(S/T)FS(S/K/R)Y (SEQ ID NO: 448) | HQ(Q/H)(G/A)(H/L)E (SEQ ID NO: 456) | 228 | 240 | 241 | 242 |
| IMGT | GF(S/T)FS(S/K/R)Y(W/Y) (SEQ ID NO: 450) | IHQ(Q/H)(G/A)(H/L)E(T/K) (SEQ ID NO: 458) | 232 | 243 | 241 | 239 |
| ANP non-competitive group I | | | | | | |
| Combined | GFTFS(S/R)Y(W/Y)I(S/N) (SEQ ID NO: 452) | SIHQ(Q/H)(G/A)(H/L)E(T/K)(K/R)YVESVKG (SEQ ID NO: 453) | 228 | 237 | 238 | 239 |
| Kabat | (S/R)Y(W/Y)I(S/N) (SEQ ID NO: 454) | SIHQ(Q/H)(G/A)(H/L)E(T/K)(K/R)YVESVKG (SEQ ID NO: 453) | 228 | 237 | 238 | 239 |
| Chothia | GFTFS(S/R)Y (SEQ ID NO: 455) | HQ(Q/H)(G/A)(H/L)E (SEQ ID NO: 456) | 228 | 240 | 241 | 242 |
| IMGT | GFTFS(S/R)Y(W/Y) (SEQ ID NO: 457) | IHQ(Q/H)(G/A)(H/L)E(T/K) (SEQ ID NO: 458) | 232 | 243 | 241 | 239 |
| ANP competitive group A | | | | | | |
| Combined | 310 | 311 | G(A/S)(V/L)(A/P)G(Q/L)LGFDH (SEQ ID NO: 459) | 320 | GNSNRP(S/N) (SEQ ID NO: 460) | QSY(Y/D/G)(T/S/A)(S/P/F)(S/T/P)(H/S/R)(G/S/F)(P/S/V)V (SEQ ID NO: 461) |
| Kabat | 229 | 311 | G(A/S)(V/L)(A/P)G(Q/L)LGFDH (SEQ ID NO: 459) | 320 | GNSNRP(S/N) (SEQ ID NO: 460) | QSY(Y/D/G)(T/S/A)(S/P/F)(S/T/P)(H/S/R)(G/S/F)(P/S/V)V (SEQ ID NO: 461) |

TABLE 4-continued

Exemplary anti-NPR1 antibody groups by consensus sequence

| | HCDR1 | HCDR2 | HCDR3 | LCDR1 | LCDR2 | LCDR3 |
|---|---|---|---|---|---|---|
| Chothia | 80 | 313 | G(A/S)(V/L)(A/P)G(Q/L)L GFDH (SEQ ID NO: 459) | 323 | 324 | Y(Y/D/G)(T/S/A)(S/P/F)(S/T/P)(H/S/R)(G/S/F)(P/S/V) (SEQ ID NO: 462) |
| IMGT | 82 | 314 | ARG(A/S)(V/L)(A/P)G(Q/L)LGFDH (SEQ ID NO: 463) | 326 | 324 | QSY(Y/D/G)(T/S/A)(S/P/F)(S/T/P)(H/S/R)(G/S/F)(P/S/V)V (SEQ ID NO: 461) |
| ANP competitive group B | | | | | | |
| Combined | GFTF(S/G)(S/T)YA(I/M)(S/T) (SEQ ID NO: 464) | (A/S)IS(A/S/G)(S/H)G(G/Y)(S/Y)(T/A)(Y/R/N)YA(E/G)SVKG (SEQ ID NO: 465) | 331 | 337 | 338 | 339 |
| Kabat | (S/T)YA(I/M)(S/T) (SEQ ID NO: 466) | (A/S)IS(A/S/G)(S/H)G(G/Y)(S/Y)(T/A)(Y/R/N)YA(E/G)SVKG (SEQ ID NO: 465) | 331 | 337 | 338 | 339 |
| Chothia | GFTF(S/G)(S/T)Y (SEQ ID NO: 467) | S(A/S/G)(S/H)G(G/Y)(S/Y) (SEQ ID NO: 468) | 331 | 340 | 341 | 342 |
| IMGT | GFTF(S/G)(S/T)YA (SEQ ID NO: 469) | IS(S/G)(S/H)G(G/Y)(S/Y)T (SEQ ID NO: 470) | 332 | 343 | 341 | 339 |
| ANP competitive group C | | | | | | |
| Combined | GFTF(S/G)(S/T)YA(I/M)(S/T) (SEQ ID NO: 464) | SIS(A/S)(S/H)GYY(T/A)(R/N)YA(E/G)SVKG (SEQ ID NO: 471) | 331 | 337 | 338 | 339 |
| Kabat | (S/T)YA(I/M)(S/T) (SEQ ID NO: 466) | SIS(A/S)(S/H)GYY(T/A)(R/N)YA(E/G)SVKG (SEQ ID NO: 471) | 331 | 337 | 338 | 339 |
| Chothia | GFTF(S/G)(S/T)Y (SEQ ID NO: 467) | S(A/S)(S/H)GYY (SEQ ID NO: 472) | 331 | 340 | 341 | 342 |
| IMGT | GFTF(S/G)(S/T)YA NO: 469) | IS(A/S/G)(S/H)G (SEQ ID NO: 473) | 332 | 343 | 341 | 339 |

In some embodiments, an antibody or antigen-binding fragment thereof as provided herein binds to (a) human NPR1; and (b) mouse NPR1 and/or rat NPR1.

In some embodiments, an antibody or antigen-binding fragment thereof as provided herein binds to (a) human NPR1; and (b) cyno NPR1. In some embodiments, the antibody or antigen binding fragment thereof is therapeutic. A therapeutic antibody, as defined herein, is an antibody that is both efficacious and stable.

Antibodies that Bind to the Same Epitope as Anti-NPR1 Antibodies of the Disclosure In another embodiment, the disclosure provides antibodies or antigen-binding fragments thereof that bind to the same epitope as one or more of the anti-NPR1 antibodies described herein (e.g., WW06). Such antibodies:
(i) bind NPR1;
(ii) are agonists of NPR1;
(iii) are ANP competitive; and
bind the same epitope in NPR1 as antibody WW06.

In another embodiment, the disclosure provides antibodies or antigen-binding fragments thereof that bind to the same epitope as one or more of the anti-NPR1 antibodies described herein (e.g., XX16). Such antibodies:
(i) bind NPR1;
(ii) are agonists of NPR1;
(iii) are ANP non-competitive; and
bind the same epitope in NPR1 as XX16.

In another embodiment, the disclosure provides antibodies or antigen-binding fragments thereof that bind to the same epitope as one or more of the anti-NPR1 antibodies described herein (e.g., WW03). Such antibodies:
(i) bind NPR1;
(ii) are agonists of NPR1;
(iii) are ANP non-competitive; and
bind the same epitope in NPR1 as WW03.

Following the crystallisation and structure determination, the binding regions of the preferred antibodies of the disclosure have been more clearly defined. Such binding is defined herein as being inclusive of both covalent and non-covalent bonds.

Thus, the disclosure provides an ANP competitive antibody that binds the same epitope as WW06. In some embodiments, the disclosure provides an antibody that binds to an epitope of human NPR1 protein (Accession no. P16066; SEQ ID NO: 1) comprising amino acids 188, 192, 194, 197, 201, 208, and 219. In some embodiments, the disclosure provides an antibody that binds to an epitope of human NPR1 protein (Accession no. P16066; SEQ ID NO: 1) comprising amino acids 188, 192, 194, 197, 201, 208, 219, and 295. In some embodiments, the disclosure provides an antibody that binds to an epitope within amino acid numbers 188-198 of SEQ ID NO: 1. In some embodiments, the disclosure provides an antibody that binds to at least 2, 3, or 4 amino acid residues within amino acid numbers 188-198 of SEQ ID NO: 1. In some embodiments, the disclosure provides an antibody that binds to an epitope within amino acid numbers 201-208 of SEQ ID NO: 1. In some embodiments, the disclosure provides an antibody that binds to at least 2 amino acids within amino acid numbers 201-208 of SEQ ID NO: 1. In some embodiments, the disclosure provides an antibody that binds to at least 2, 3, or 4 amino acid residues within amino acid numbers 188-198 of SEQ ID NO: 1, and binds to at least 2 amino acids within amino acid numbers 201-208 of SEQ ID NO: 1. In some embodiments, the disclosure provides an antibody that binds to an epitope comprising at least one amino acid residue within each of (i) amino acids 188-198 of SEQ ID NO: 1, (ii) amino acids 201-208 of SEQ ID NO: 1, (iii) amino acids 215-238 of SEQ ID NO: 1, and (iv) amino acids 294-297 of SEQ ID NO: 1.

The disclosure provides an ANP non-competitive antibody that binds the same epitope as WW03. In some embodiments, the disclosure provides an antibody that binds to an epitope of human NPR1 protein (Accession no. P16066; SEQ ID NO: 1) comprising amino acids 82, 102, 103, 105, 106, 109, 132, and 375. In some embodiments, the disclosure provides an antibody that binds to an epitope of human NPR1 protein (Accession no. P16066; SEQ ID NO: 1) comprising amino acids 79, 82, 99, 102, 103, 105, 106, 109, 131, 132, and 375. In some embodiments, the disclosure provides an antibody that binds to an epitope within amino acid numbers 99-111 of SEQ ID NO: 1. In some embodiments, the disclosure provides an antibody that binds to at least 2, 3, 4, 5, or 6 amino acids within amino acid numbers 99-111 of SEQ ID NO: 1. In some embodiments, the disclosure provides an antibody that binds to at least 2, 3, 4, 5, 6, 7, or 8 amino acid residues within amino acid numbers 99-133 of SEQ ID NO: 1. In some embodiments, the disclosure provides an antibody that binds to an epitope within amino acid numbers 131-134 of SEQ ID NO: 1. In some embodiments, the disclosure provides an antibody that binds to at least 2 amino acids within amino acid numbers 131-134 of SEQ ID NO: 1. In some embodiments, the disclosure provides an antibody that binds to at least 2, 3, 4, 5, or 6 amino acids within amino acid numbers 99-111 of SEQ ID NO: 1, and binds to at least 2 amino acids within amino acid numbers 131-134 of SEQ ID NO: 1. In some embodiments, the disclosure provides an antibody that binds to an epitope comprising at least one amino acid residue within each of (i) amino acids 99-111 of SEQ ID NO: 1, (ii) amino acids 131-134 of SEQ ID NO: 1, and (iii) amino acids 374-375 of SEQ ID NO: 1. Optionally, the antibody may additionally bind to amino acids 79 and/or 82 of SEQ ID NO: 1.

The disclosure additionally provides an ANP non-competitive antibody that binds the same epitope as XX16. In some embodiments, the disclosure provides an antibody that binds to an epitope of human NPR1 protein (Accession no. P16066; SEQ ID NO: 1) comprising amino acids 82, 102, 103, 105, 106, 109, 132, and 375. In some embodiments, the disclosure provides an antibody that binds to an epitope of human NPR1 protein (Accession no. P16066; SEQ ID NO: 1) comprising amino acids 34, 82, 102, 103, 105, 106, 107, 109, 132, 133, 375, and 378. In some embodiments, the disclosure provides an antibody that binds to an epitope within amino acid numbers 102-111 of SEQ ID NO: 1. In some embodiments, the disclosure provides an antibody that binds to at least 2, 3, 4, 5, or 6 amino acids within amino acid numbers 102-111 of SEQ ID NO: 1. In some embodiments, the disclosure provides an antibody that binds to an epitope within amino acid numbers 131-134 of SEQ ID NO: 1. In some embodiments, the disclosure provides an antibody that binds to at least 2 amino acids within amino acid numbers 131-134 of SEQ ID NO: 1. In some embodiments, the disclosure provides an antibody that binds to at least 2, 3, 4, 5, or 6 amino acids within amino acid numbers 102-111 of SEQ ID NO: 1, and binds to at least 2 amino acids within amino acid numbers 131-134 of SEQ ID NO: 1. In some embodiments, the disclosure provides an antibody that binds to an epitope comprising at least one amino acid residue within each of (i) amino acids 102-111 of SEQ ID NO: 1, (ii) amino acids 131-134 of SEQ ID NO: 1, and (iii) amino acids 374-378 of SEQ ID NO: 1. Optionally, the antibody may additionally bind to amino acids 34, 76, and/or 82 of SEQ ID NO: 1.

Additional antibodies can be identified based on their ability to cross-compete (e.g., to competitively inhibit the binding of, in a statistically significant manner) with other antibodies of the disclosure in standard NPR1 binding assays (e.g., XX16, WW06, or WW03). The ability of a test antibody to inhibit the binding of antibodies of the present disclosure to human NPR1 demonstrates that the test antibody can compete with that antibody for binding to human NPR1; such an antibody may, according to non-limiting theory, bind to the same or a related (e.g., a structurally similar or spatially proximal) epitope on human NPR1 as the antibody with which it competes. In a certain embodiment, the antibody that binds to the same epitope on human NPR1 as the antibodies of the present disclosure is a human antibody (e.g., a human monoclonal antibody or antigen binding fragment thereof). Such antibodies can be prepared and isolated as described herein.

Engineered and Modified Antibodies

An antibody of the disclosure can be prepared using an antibody having one or more of the VH and/or VL sequences shown herein as starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is antibody binding region/paratope or CDR grafting. Because paratope sequences are responsible for most antibody-antigen interactions, it is possible to express recombinant antibodies that mimic the properties of specific naturally occurring antibodies by constructing expression vectors that include CDR/paratope sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad. See. U.S.A. 86:10029-10033; U.S. Pat. Nos. 5,225,539, and 5,530,101; 5,585,089; 5,693,762 and 6,180,370; the contents of each of which are herein incorporated by reference for this purpose).

Accordingly, another embodiment of the disclosure pertains to an isolated anti-NPR1 antibody, or a antigen-binding fragment thereof, comprising an antigen binding portion thereof, comprising a heavy chain variable region comprising the CDR sequences of an antibody or group of antibodies shown in Table 2, Table 3, or Table 4. Thus, such antibodies contain the $V_H$ and $V_L$ CDR sequences of monoclonal antibodies, yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www [dot] mrc-cpe [dot] cam [dot] ac [dot] uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. fol. Biol. 227:776-798; and Cox, J. P. L. et al., 1994 Eur. J Immunol. 24:827-836; the contents of each of which are herein incorporated by reference for this purpose.

An example of framework sequences for use in the antibodies or antigen binding fragments of the disclosure are those that are structurally similar to the framework sequences used by selected antibodies of the disclosure, e.g., consensus sequences and/or framework sequences used by the antibodies or antigen binding fragments of the disclosure. The $V_H$ CDR1, 2 and 3 sequences, and the $V_L$ CDR1, 2 and 3 sequences, can be grafted onto framework regions that have an identical sequence to that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180, 370; the contents of each of which are herein incorporated by reference for this purpose).

Another type of variable region modification is to mutate amino acid residues within the $V_H$ and/or $V_L$ CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein. Conservative modifications (as discussed above) can also be introduced. The mutations may be amino acid substitutions, additions or deletions. Moreover, typically no more than one, two, three, four or five residues within a CDR region are altered.

Grafting Antigen Binding Domains into Alternative Frameworks or Scaffolds

A wide variety of antibody/immunoglobulin frameworks or scaffolds can be employed so long as the resulting polypeptide includes at least one binding region which specifically binds to NPR1. Such frameworks or scaffolds include the 5 main idiotypes of human immunoglobulins, or fragments thereof (such as those disclosed elsewhere herein), and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

In one aspect, the disclosure pertains to generating non-immunoglobulin based antibodies using non-immunoglobulin scaffolds onto which CDRs of the disclosure can be grafted. Known or future non-immunoglobulin frameworks and scaffolds may be employed, as long as they comprise a binding region specific for NPR1, e.g., such as those disclosed for an antibody described herein including, but not limited to, XX16, WW03, or WW06. Such compounds are known herein as "polypeptides comprising a target-specific binding region". Examples of non-immunoglobulin framework are further described in the sections below (camelid antibodies and non-antibody scaffold).

Camelid Antibodies

Antibody proteins obtained from members of the camel and dromedary (*Camelus bactrianus* and *Camelus dromaderius*) family including new world members such as llama species (*Lama paccos, Lama glama*, and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals, see WO94/04678, the contents of which are herein incorporated by reference for this purpose.

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J 17: 3512-3520; the contents of each of which are herein incorporated by reference for this purpose. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier, see US2004/0161738, the contents of which are herein incorporated by reference for this purpose. These features combined with the low antigenicity to humans indicate great therapeutic potential. Further, these molecules can be fully expressed in prokaryotic cells such as *E. coli* and may be expressed as functional fusion proteins with bacteriophage.

Accordingly, a feature of the present disclosure is a camelid antibody or nanobody having high affinity for NPR1. In one embodiment, the camelid antibody or nanobody is obtained by grafting the CDRs sequences of the heavy or light chain of the human antibodies of the disclosure into nanobody or single domain antibody framework sequences as described, for example, in WO94/04678 (the contents of which are herein incorporated by reference for this purpose).

Framework or Fc Engineering

Engineered antibodies of the disclosure include those in which modifications have been made to framework residues within VH and/or VL, e.g., to improve one or more properties of the antibody. Typically such framework modifications are made to decrease the immunogenicity of the antibody. Antibodies of the disclosure may be modified in one or more ways, including each of the ways described herein.

For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies and additional modifications described herein are also intended to be encompassed by the disclosure.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in US2003/0153043, the contents of which are herein incorporated by reference for this purpose.

In addition or alternative to modifications made within the framework or CDR regions, antibodies of the disclosure may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the disclosure may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425, the contents of which are herein incorporated by reference for this purpose. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745, the contents of which are herein incorporated by reference for this purpose.

In another embodiment, the antibody is modified to increase its biological half-life. Various approaches are possible. For example, one or more of the following mutations can be introduced: T252L, T254S, T256F, as described in U.S. Pat. No. 6,277,375, the contents of which are herein incorporated by reference for this purpose. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022, the contents of each of which are herein incorporated by reference for this purpose.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, the contents of each of which are herein incorporated by reference for this purpose.

In order to minimize the ADCC activity of an antibody, specific mutations in the Fc region result in "Fc silent" antibodies that have minimal interaction with effector cells. In general, the "IgG Fc region" is used to define the C-terminal region of an immunoglobulin heavy chain, including native sequence Fc region and variant Fc regions. The human IgG heavy chain Fc region is generally defined as comprising the amino acid residue from position C226 or from P230 to the carboxyl-terminus of the IgG antibody. The numbering of residues in the Fc region is that of the EU index of Kabat. The C-terminal lysine (residue K447) of the Fc region may be removed, for example, during production or purification of the antibody.

Silenced effector functions can be obtained by mutation in the Fc region of the antibodies. See, for example, LALA and N297A (Strohl, W., 2009, Curr. Opin. Biotechnol. vol. 20(6):685-691); and D265A (Baudino et al., 2008, J. Immunol. 181: 6664-69) see also Heusser et al., WO2012065950; the contents of each of which are herein incorporated by reference for this purpose. In particular, residues 234 and/or 235 may be mutated, optionally to alanine. Thus, in one embodiment, an antibody according to the disclosure has a mutation in the Fc region at one or both of amino acids 234 and 235. Such substitution of both amino acids 234 and 235 results in reduced ADCC activity. One example of such a mutation is the LALA mutant comprising L234A and L235A mutation in the IgG1 Fc amino acid sequence. Another example of a silent IgG1 antibody is the DAPA (D265A, P329A) mutation (U.S. Pat. No. 6,737,056, the contents of which are herein incorporated by reference for this purpose). Another silent IgG1 antibody comprises the N297A mutation, which results in aglycosylated/non-glycosylated antibodies. Fc silent antibodies result in no or low ADCC activity, meaning that an Fc silent antibody exhibits an ADCC activity that is below 50% specific cell lysis. No ADCC activity means that the Fc silent antibody exhibits an ADCC activity (specific cell lysis) that is below 1%.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551, the contents of which are herein incorporated by reference for this purpose.

In another embodiment, one or more amino acid residues are altered to thereby alter the ability of the antibody to fix complement. This approach is described further in WO94/29351, the contents of which are herein incorporated by reference for this purpose.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in WO00/42072, the contents of which are herein incorporated by reference for this purpose. Moreover, the binding sites on human IgG1 for FcγR1, FcγRII, FcγRIII and FcRn have been mapped and variants with improved binding have been described (see Shields, R. L. et al., 2001 J. Biol. Chen. 276:6591-6604, the contents of which are herein incorporated by reference for this purpose).

In still another embodiment, the glycosylation of an antibody is modified. For example, an aglycoslated antibody can be made (i.e., the antibody lacks glycosylation). Glycosylation can be altered to, for example, increase the affinity of the antibody for "antigen". Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861, the contents of each of which are herein incorporated by reference for this purpose.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. For example, EP 1,176,195 (the contents of which are herein incorporated by reference for this purpose) describes a cell line with a functionally disrupted FUT8 gene, which encodes a fucosyl transferase, such that antibodies expressed in such a cell line exhibit hypofucosylation. WO03/035835 describes a variant CHO cell line, Lec13 cells, with reduced ability to attach fucose to Asn (297)-linked carbohydrates, also resulting in hypofucosylation of antibodies expressed in that host cell (see also Shields, R. L. et al., 2002 J. Biol. Chem. 277:26733-26740). WO99/54342 describes cell lines engineered to express glycoprotein-modifying glycosyl transferases (e.g., beta(1, 4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180). The contents of each of the foregoing applications and references are herein incorporated by reference for this purpose Another modification of the antibodies herein that is contemplated by the disclosure is pegylation. An antibody can be pegylated, for example, to increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the disclosure. See, for example, EP0154316 and EP0401384, the contents of each of which are herein incorporated by reference for this purpose.

Another modification of the antibodies that is contemplated by the disclosure is a conjugate or a protein fusion of at least the antigen-binding region of the antibody of the disclosure to serum protein, such as human serum albumin or a fragment thereof to increase half-life of the resulting molecule. Such an approach is described, for example, in EP0322094, the contents of which are herein incorporated by reference for this purpose.

Another possibility is a fusion of at least the antigen-binding region of the antibody of the disclosure to proteins capable of binding to serum proteins, such human serum albumin to increase half-life of the resulting molecule. Such approach is described, for example, in EP0486525, the contents of which are herein incorporated by reference for this purpose.

Nucleic Acid Molecules Encoding Antibodies of the Disclosure

Another aspect of the disclosure pertains to nucleic acid molecules that encode the antibodies of the disclosure. The term "nucleic acid" is used herein interchangeably with the term "polynucleotide," and refers to deoxyribonucleotides or ribonucleotides and polymers thereof in either single- or double-stranded form. The term encompasses nucleic acids containing known nucleotide analogs or modified backbone residues or linkages, which are synthetic, naturally-occurring, and non-naturally-occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). In some embodiments, the nucleic acid may be an mRNA.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (See: Batzer et al., Nucleic Acids Res 1991; 25(19):5081; Ohtsuka et al., J Biol Chem 1985; 260(5):2605-8; Rossolini et al., Mol Cell Probes 1994; 8(2):91-8; the contents of each of which are herein incorporated by reference for this purpose).

Provided herein are exemplary full length heavy and light chain nucleotide sequences of anti-NPR1 antibodies. In some embodiments, the nucleic acid molecules are one or more of those identified in Table 2, e.g., those encoding an anti-NPR1 antibody or antigen binding fragment thereof. In some other embodiments, the nucleic acid molecules described herein comprise nucleotide sequences that are substantially identical (e.g., at least 80%, 85%, 90%, 91%, 92%, 93%, 94%, 95%, 96%, 97%, 98%, or 99%) to the nucleotide sequences of those identified in Table 2. When expressed from appropriate expression vectors, polypeptides encoded by these polynucleotides are capable of binding to a NPR1 protein (e.g., human NPR1).

Also provided herein are polynucleotides which encode at least one CDR region, and usually all three CDR regions, from the heavy and/or light chain of an anti-NPR1 antibody or antigen binding fragment of the disclosure. Further provided herein are polynucleotides which encode all or substantially all of the variable region sequence of the heavy chain and/or the light chain of an exemplary anti-NPR1 antibody or antigen binding fragment of the disclosure. Because of the degeneracy of the genetic code, a variety of nucleic acid sequences will encode each of the immunoglobulin amino acid sequences.

In some embodiments, the nucleic acid molecules disclosed herein encode both a variable region and a constant region of an antibody. In some embodiments, the nucleic acid molecules disclosed herein comprise nucleotides encoding a full-length heavy chain sequence that is substantially identical (e.g., at least 80%, 85%, 90%, 91%, 92%, 93%, 94%, 95%, 96%, 97%, 98%, or 99%) to the heavy chain sequence of one of the antibodies described herein including those in Table 2. In some embodiments, the nucleic acid molecules disclosed herein comprise nucleotides encoding a full-length light chain sequence that is substantially identical (e.g., at least 80%, 85%, 90%, 91%, 92%, 93%, 94%, 95%, 96%, 97%, 98%, or 99%) to the light chain sequence of one of the antibodies described herein including those in Table 2.

The nucleic acids may be present in whole cells, in a cell lysate, or may be nucleic acids in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. 1987 Current Protocols in Molecular Biology, Greene Publishing and Wiley Interscience, New York, the contents of which are herein incorporated by reference for this purpose. A nucleic acid of the disclosure can be, for example, DNA or RNA and may or may not contain intronic sequences. In an embodiment, the nucleic acid is a cDNA molecule. The nucleic acid may be present in a vector such as a phage display vector, or in a recombinant plasmid vector.

Nucleic acids of the disclosure can be obtained using standard molecular biology techniques. For antibodies expressed by hybridomas (e.g., hybridomas prepared from transgenic mice carrying human immunoglobulin genes as described further herein), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from various phage clones that are members of the library.

The polynucleotide sequences can be produced by de novo solid-phase DNA synthesis or by PCR mutagenesis of an existing sequence (e.g., sequences as described herein in, for example, Table 2). Direct chemical synthesis of nucleic acids can be accomplished by methods known in the art, such as the phosphotriester method of Narang et al., 1979, Meth. Enzymol. 68:90; the phosphodiester method of Brown et al., Meth. Enzymol. 68: 109, 1979; the diethylphosphoramidite method of Beaucage et al., Tetra. Lett., 22: 1859, 1981; and the solid support method of U.S. Pat. No. 4,458,066 (the contents of each of which are herein incorporated by reference for this purpose). Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Manila et al., Nucleic Acids Res. 19:967, 1991; and Eckert et al., PCR Methods and Applications 1:17, 1991.

Once DNA fragments encoding VH and VL segments are obtained, these DNA fragments can be further manipulated by standard recombinant DNA techniques, for example to convert the variable region genes to full-length antibody chain genes, to Fab fragment genes or to an scFv gene. In these manipulations, a VL- or VH-encoding DNA fragment is operatively linked to another DNA molecule, or to a fragment encoding another protein, such as an antibody constant region or a flexible linker. The term "operatively linked", as used in this context, is intended to mean that the two DNA fragments are joined in a functional manner, for example, such that the amino acid sequences encoded by the two DNA fragments remain in-frame, or such that the protein is expressed under control of a desired promoter.

The isolated DNA encoding the VH region can be converted to a full-length heavy chain gene by operatively linking the VH-encoding DNA to another DNA molecule encoding heavy chain constant regions (CHL CH2 and CH3). The sequences of human heavy chain constant region genes are known in the art (see e.g., Kabat, E. A., el al., 1991 Sequences of Proteins of Immunological Interest, Fifth Edition, U.S. Department of Health and Human Services, NIH Publication No. 91-3242, the contents of which are herein incorporated by reference for this purpose) and DNA fragments encompassing these regions can be obtained by standard PCR amplification. The heavy chain constant region can be an IgG1, IgG2, IgG3, IgG4, IgA, IgE, IgM, or IgD constant region. In some embodiments, the heavy chain constant region is an IgG1 isotype. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as to a Fab light chain gene) by operatively linking the VL-encoding DNA to another DNA molecule encoding the light chain constant region, CL. The sequences of human light chain constant region genes are known in the art (see, e.g., Kabat, E. A., et al., 1991 Sequences of Proteins of Immunological Interest, Fifth Edition, U.S. Department of Health and Human Services, NIH Publication No. 91-3242, the contents of which are herein incorporated by reference for this purpose) and DNA fragments encompassing these regions can be obtained by standard PCR amplification. The light chain constant region can be a kappa or a lambda constant region.

To create an scFv gene, the VH- and VL-encoding DNA fragments are operatively linked to another fragment encoding a flexible linker, such that the VH and VL sequences can be expressed as a contiguous single-chain protein, with the VL and VH regions joined by the flexible linker (see e.g., Bird et al., 1988 Science 242:423-426; Huston et al., 1988 Proc. Natl. Acad. Sci. USA 85:5879-5883; McCafferty et al., 1990 Nature 348:552-554; the contents of each of which are herein incorporated by reference for this purpose).

Vectors

Various expression vectors can be employed to express the polynucleotides encoding the antibody of the disclosure or antigen-binding fragment thereof. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet. 15:345, 1997, the contents of which are herein incorporated by reference for this purpose). For example, nonviral vectors useful for expression of the polynucleotides and polypeptides of the multispecific antibody of the disclosure or domains thereof in mammalian (e.g., human) cells include pThioHis A, B and C, pcDNA3.1/His, pEBVHis A, B and C, (Invitrogen, San Diego, Calif.), MPS V vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68: 143, 1992, the contents of each of which are herein incorporated by reference for this purpose.

The choice of expression vector depends on the intended host cells in which the vector is to be expressed. Expression vectors for mammalian host cells can include expression control sequences, such as an origin of replication, a promoter, and an enhancer (see, e.g., Queen, et al., Immunol. Rev. 89:49-68, 1986, the contents of which are herein incorporated by reference for this purpose), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPS V promoter, the tetracycline-inducible CMV promoter (such as the human immediate-early CMV promoter), the constitutive CMV promoter, and known promoter-enhancer combinations.

Cultures of transformed organisms can be expanded under non-inducing conditions without biasing the population for coding sequences whose expression products are better tolerated by the host cells. In addition to promoters, other regulatory elements may also be required or desired for efficient expression of the antibody of the disclosure or fragments thereof. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20: 125, 1994; and Bittner et al., Meth. Enzymol., 153:516, 1987; the contents of each of which are herein incorporated by reference for this purpose). For example, the SV40 enhancer or CMV enhancer may be used to increase expression in mammalian host cells.

Accordingly, the disclosure provides a cloning or expression vector comprising one or more of the nucleic acid sequences of the antibodies shown in Table 2. Furthermore, the disclosure provides a cloning or expression vector comprising a nucleic acid encoding one or more of the nucleotide sequences shown in Table 2.

Host Cells

For expression of the light and heavy chains, the expression vector or expression vectors encoding the heavy and light chains may be transferred into a host cell by standard techniques.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra, the contents of which are herein incorporated by reference for this purpose). Other methods include, e.g., electroporation, calcium phosphate treatment, liposome-mediated transformation, injection and microinjection, ballistic methods, virosomes, immunoliposomes, polycatiomnucleic acid conjugates, naked DNA, artificial virions, fusion to the herpes virus structural protein VP22 (Elliot and O'Hare, Cell 88:223, 1997, the contents of which are herein incorporated by reference for this purpose), agent-enhanced uptake of DNA, and ex vivo transduction.

It is theoretically possible to express the antibodies of the disclosure in either prokaryotic or eukaryotic host cells. Expression of antibodies in eukaryotic cells, in particular mammalian host cells, is discussed because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R., 1985 Immunology Today 6:12-13, the contents of which are herein incorporated by reference for this purpose).

For long-term, high-yield production of recombinant proteins, stable expression will often be desired. For example, cell lines which stably express the antibodies or antigen-binding fragments thereof of the disclosure can be prepared using expression vectors of the disclosure which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type. The present disclosure thus provides a method of producing the antibodies or antigen-binding fragments of the disclosure, wherein said method comprises the step of culturing a host cell comprising a nucleic acid encoding the antibodies or antigen-binding fragments.

In some embodiments, mammalian host cells are used to express and produce the anti-NPR1 antibodies or antigen binding fragments of the present disclosure. For example, they can be either a hybridoma cell line expressing endogenous immunoglobulin genes or a mammalian cell line harboring an exogenous expression vector. These include any normal mortal or normal or abnormal immortal animal or human cell. For example, a number of suitable host cell lines capable of secreting intact immunoglobulins have been developed including the CHO cell lines, various COS cell lines, HeLa cells, myeloma cell lines, transformed B-cells, and hybridomas. Exemplary host cells include but are not limited to Chinese hamster ovary (CHO) cells, human embryonic kidney (HEK) cells (e.g., HEK293, HEK293T, HEK293F), monkey kidney (COS) cells (e.g., COS-1, COS-7), baby hamster kidney (BHK) cells (e.g., BHK-21), African green monkey kidney cells (e.g. BSC-1), HeLa cells, human hepatocellular carcinoma cells (e.g., Hep G2), myeloma cells (e.g., NSO, 653, SP2/0), lymphoma cells, oocyte cells, and cells from a transgenic animal (e.g., mammary epithelial cells), or any derivative, immortalized, or transformed cell thereof. In particular, for use with NSO myeloma cells, another expression system is the GS gene expression system shown in WO87/04462, WO89/01036 and EP0338841, the contents of each of which are herein incorporated by reference for this purpose. When recombinant expression vectors encoding antibody nucleic acid are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Such purified antibodies of the disclosure may be used for any purpose including, but not limited to, the methods and uses described herein, and/or as part of a pharmaceutical composition as described herein.

In a further alternative, the host cell may be a yeast or a filamentous fungi engineered for mammalian-like glycosylation pattern, and capable for producing antibodies lacking fucose as glycosylation pattern (see, for example, EP1297172, the contents of which are herein incorporated by reference for this purpose).

Accordingly, the disclosure provides a host cell comprising one or more of the vectors, or nucleic acid sequences of the disclosure described above.

Generation of Monoclonal Antibodies of the Disclosure

Monoclonal antibodies (mAbs) can be produced by a variety of techniques, including conventional monoclonal antibody methodology e.g., the somatic cell hybridization technique of Kohler and Milstein, 1975 Nature 256: 495, the contents of which are herein incorporated by reference for this purpose. Many techniques for producing monoclonal antibody can be employed e.g., viral or oncogenic transformation of B lymphocytes.

Hybridomas may be prepared using, for example, the murine system. Immunization protocols and isolation of immunized splenocytes for fusion may be performed according to any appropriate procedure. Chimeric or humanized antibodies can be prepared based on the sequence of a murine monoclonal antibody prepared as described herein. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using any known methods (see e.g., U.S. Pat. No. 4,816,567, the contents of which are herein incorporated by reference for this purpose). To create a humanized antibody, the murine CDR regions can be inserted into a human framework using any known methods. See e.g., U.S. Pat. Nos. 5,225,539, and 5,530,101; 5,585,089; 5,693,762 and 6,180,370, the contents of each of which are herein incorporated by reference for this purpose.

Human monoclonal antibodies can also be generated using transgenic or transchromosomic mice carrying parts of the human immune system rather than the mouse system. These transgenic and transchromosomic mice include mice referred to herein as HuMAb Mice® and KM mice, respectively, and are collectively referred to herein as "human Ig mice."

The HuMAb Mouse® (Medarex, Inc.) contains human immunoglobulin gene miniloci that encode un-rearranged human heavy (μ and γ) and κ light chain immunoglobulin sequences, together with targeted mutations that inactivate the endogenous μ and κ chain loci (see e.g., Lonberg, et al., 1994 Nature 368(6474): 856-859, the contents of which are herein incorporated by reference for this purpose). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al., 1994 supra; reviewed in Lonberg, N., 1994 Handbook of Experimental Pharmacology 113:49-101; Lonberg, N. and Huszar, D., 1995 Intern. Rev. Immunol. 13: 65-93, and Harding, F. and Lonberg, N., 1995 Ann. N. Y. Acad. Sci. 764:536-546; the contents of each of which are herein incorporated by reference for this purpose). The preparation and use of HuMAb Mice®, and the genomic modifications carried by such mice, is further described in Taylor, L. et al., 1992 Nucleic Acids Research 20:6287-6295; Chen, J. et al., 1993 International Immunology 5: 647-656; Tuaillon et al., 1993 Proc. Natl. Acad. Sci. USA 94:3720-3724; Choi et al., 1993 Nature Genetics 4:117-123; Chen, J. et al., 1993 EMBO J. 12: 821-830; Tuaillon et al., 1994 J. Immunol. 152:2912-2920; Taylor, L. et al., 1994 International Immunology 579-591; and Fishwild, D. et al., 1996 Nature Biotechnology 14: 845-851, the contents of each of which are hereby incorporated by reference for this purpose. See further, U.S. Pat. Nos. 5,545,806; 5,569,825; 5,625,126; 5,633,425; 5,789,650; 5,877,397; 5,661,016; 5,814,318; 5,874,299; and 5,770,429; 5,545,807; WO92/103918, WO93/12227, WO94/25585, WO97/113852, WO98/24884 and WO99/45962; and WO01/14424; the contents of each of which are hereby incorporated by reference for this purpose.

In another embodiment, human antibodies can be raised using a mouse that carries human immunoglobulin sequences on transgenes and transchomosomes such as a mouse that carries a human heavy chain transgene and a human light chain transchromosome. Such mice, referred to herein as "KM mice", are described in detail in WO02/43478, the contents of which are hereby incorporated by reference for this purpose.

Still further, alternative transgenic animal systems expressing human immunoglobulin genes are available in the art and can be used to raise antibodies of the disclosure. For example, an alternative transgenic system referred to as the Xenomouse (Abgenix, Inc.) can be used. Such mice are described in, e.g., U.S. Pat. Nos. 5,939,598; 6,075,181; 6,114,598; 6,150,584 and 6,162,963, the contents of each of which are hereby incorporated by reference for this purpose.

Moreover, alternative transchromosomic animal systems expressing human immunoglobulin genes are available in the art and can be used to raise antibodies of the disclosure. For example, mice carrying both a human heavy chain transchromosome and a human light chain tranchromosome, referred to as "TC mice" can be used; such mice are described in Tomizuka et al., 2000 Proc. Natl. Acad. Sci. USA 97:722-727, the contents of which are hereby incorporated by reference for this purpose. Furthermore, cows carrying human heavy and light chain transchromosomes have been described in the art (Kuroiwa et al., 2002 Nature Biotechnology 20:889-894, the contents of which are hereby incorporated by reference for this purpose) and can be used to raise antibodies of the disclosure.

Human monoclonal antibodies of the disclosure can also be prepared using phage display methods for screening libraries of human immunoglobulin genes. Such phage display methods for isolating human antibodies are established in the art or described in the examples below. See for example: U.S. Pat. Nos. 5,223,409; 5,403,484; and 5,571,698; 5,427,908 and 5,580,717; 5,969,108 and 6,172,197; and 5,885,793; 6,521,404; 6,544,731; 6,555,313; 6,582,915 and 6,593,081, the contents of each of which are hereby incorporated by reference for this purpose.

Human antibodies or antigen binding fragments of the disclosure can also be prepared using SCID mice into which human immune cells have been reconstituted such that a human antibody response can be generated upon immunization. Such mice are described in, for example, U.S. Pat. Nos. 5,476,996 and 5,698,767, the contents of each of which are hereby incorporated by reference for this purpose.

Antibodies of the disclosure may be prepared by any of the methods described herein.

Generation of Hybridomas Producing Antibodies or Antigen Binding Fragments of the Disclosure To generate hybridomas producing the antibodies or antigen binding fragments of the disclosure, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Cells are plated at approximately 2×145 in flat bottom microtiter plates, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify antibodies or antigen binding fragments thereof, selected hybridomas can be grown in two-liter spinner-flasks for antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The antibodies or antigen binding fragments can be aliquoted and stored at −80° C.

Hybridomas producing the antibodies or antigen binding fragments of the disclosure may be produced, for example, using the methods described herein.

Generation of Transfectomas Producing Antibodies or Antigen Binding Fragments of the Disclosure Antibodies or antigen binding fragments of the disclosure can also be produced in a host cell transfectoma using, for example, a combination of suitable recombinant DNA techniques and gene transfection methods (e.g., Morrison, S. (1985) Science 229:1202, the contents of which are incorporated herein by reference for this purpose).

For example, to express the antibodies, or antigen-binding fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or both genes may be inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the CH segment(s) within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology; Methods in Enzymology 185, Academic Press, San Diego, Calif. 1990, the contents of which are incorporated herein by reference for this purpose). It will be appreciated by those skilled in the art that the design of the expression vector, including the selection of regulatory sequences, may depend on such factors as the choice of the host cell to be transformed, the level of expression of protein desired, etc. Regulatory sequences for mammalian host cell expression include viral elements that direct high levels of protein expression in mammalian cells, such as promoters and/or enhancers derived from cytomegalovirus (CMV), Simian Virus 40 (SV40), adenovirus (e.g., the adenovirus major late promoter (AdMLP)), and polyoma. Alternatively, nonviral regulatory sequences may be used, such as the ubiquitin promoter or P-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al., 1988 Mol. Cell. Biol. 8:466-472, the contents of which are incorporated herein by reference for this purpose).

In addition to the antibody chain genes and regulatory sequences, the recombinant expression vectors of the disclosure may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, the contents of each of which are incorporated herein by reference for this purpose). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is or are transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is theoretically possible to express the antibodies of the disclosure in either prokaryotic or eukaryotic host cells. Expression of antibodies in eukaryotic cells, in particular mammalian host cells, is discussed because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R., 1985 Immunology Today 6:12-13, the contents of which are incorporated herein by reference for this purpose).

Mammalian host cells for expressing the antibodies of the disclosure are described elsewhere herein. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Accordingly, the disclosure provides a process for the production of an anti-NPR1 antibody of the disclosure, or antigen-binding fragment thereof, comprising culturing a host cell of the disclosure and isolating the antibody or antigen-binding fragment thereof Uses and Methods of Treatment Methods of Treatment Provided herein are methods of treating a disease associated with NPR1 loss of function by using the anti-NPR1 antibodies or antigen binding fragments thereof disclosed herein (e.g., an antibody or group of antibodies as defined in Table 2, Table 3, or Table 4). In some embodiments, the antibody or antigen binding fragment thereof may be selected from WW01_LALA, WW03_LALA, WW05_LALA, WW06_LALA, XX01_LALA, XX01_DAPA, XX01_N30S_DAPA, XX03_LALA, XX04_LALA, XX06_LALA, XX06_DAPA, XX07_LALA, XX08_LALA, XX08_DAPA, XX08_N30S_DAPA, XX08_N30Q_DAPA, XX09_LALA, XX11_LALA, XX12_LALA, XX13_LALA, XX14_LALA, XX15_LALA, XX15_DAPA, XX16_LALA, XX16_DAPA, XX17_LALA, XX17_DAPA, XX18_LALA, XX18_DAPA, XX19_LALA, XX19_DAPA, XX20_LALA, XX20_DAPA, YY01_LALA, YY02_LALA, YY03_LALA, YY04_LALA, YY05_LALA, YY06_LALA, YY07_LALA, ZZ05_LALA, ZZ12_LALA, ZZ13_LALA, ZZ14_LALA, ZZ15_LALA, ZZ16_LALA, and ZZ17_LALA.

In some embodiments, the antibody or antigen binding fragment thereof may be selected from WW01_LALA, WW03_LALA, XX01_LALA, XX01_DAPA, XX01_N30S_DAPA, XX03_LALA, XX04_LALA, XX06_LALA, XX06_DAPA, XX07_LALA, XX08_LALA, XX08_DAPA, XX08_N30S_DAPA, XX08_N30Q_DAPA, XX09_LALA, XX11_LALA, XX12_LALA, XX13_LALA, XX14_LALA, XX15_LALA, XX15_DAPA, XX16_LALA, XX16_DAPA, XX17_LALA, XX17_DAPA, XX18_LALA, XX18_DAPA, XX19_LALA, XX19_DAPA, XX20_LALA, XX20_DAPA, YY01_LALA, YY03_LALA, YY04_LALA, ZZ12_LALA, and ZZ13_LALA. In some embodiments, the antibody or antigen binding fragment thereof may be selected from WW05_LALA, WW06_LALA, YY05_LALA, YY06_LALA, YY07_LALA, ZZ05_LALA, ZZ14_LALA, and ZZ16_LALA. In some embodiments, the antibody or antigen binding fragment thereof may be XX16_DAPA. In some embodiments, the antibody or antigen binding fragment thereof may be XX16_LALA.

In some embodiments, the disease associated with NPR1 loss of function is a cardiovascular disorder. In some embodiments, the cardiovascular disorder is selected from: hypertension, peripheral vascular disease, heart failure, coronary artery disease (CAD), ischemic heart disease (IHD), mitral stenosis and regurgitation, angina, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, and myocardial infarction (MI). In some embodiments, the disease associated with NPR1 loss of function is heart failure, hypertrophic cardiomyopathy (HCM), hypertension, preeclampsia, asthma, glaucoma, or cytokine release syndrome. In some embodiments, the heart failure is selected from a heart failure with reduced ejection fraction (HFrEF), heart failure with preserved ejection fraction (HFpEF), heart failure after acute myocardial infarct, or acute decompensated heart failure. In some embodiments, the hypertrophic cardiomyopathy is ventricular hypertrophy. In some embodiments, the hypertension is selected from resistant hypertension, hypertensive heart disease, pulmonary hypertension, pulmonary arterial hypertension, isolated systolic hypertension, resistant hypertension, and pulmonary arterial hypertension. In some embodiments, the hypertension is selected from resistant hypertension and hypertensive heart disease.

In some embodiments, the disease associated with NPR1 loss of function is a kidney disorder. In some embodiments, the kidney disorder is selected from: diabetic renal insufficiency, non-diabetic renal insufficiency, renal failure, diabetic nephropathy, non-diabetic nephropathy, acute renal injury, contrast induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, renal fibrosis, and polycystic kidney disease (PKD).

NPR1-related disorders also include any other disorders which are directly or indirectly associated with aberrant NPR1 activity and/or expression. Provided herein are also methods of treating a NPR1 related disorder directly or indirectly associated with aberrant NPR1 activity and/or expression by using the anti-NPR1 antibodies or antigen binding fragments disclosed herein (e.g., from Table 2, Table 3, or Table 4, such as XX16_DAPA or XX16_LALA).

In some embodiments, the present disclosure provides methods of treating an undesirable condition, disease, or disorder associated with natriuretic peptide receptor activity in a subject in need thereof, the method comprising administering to the subject a therapeutically effective amount of an antibody or antigen binding fragment disclosed herein. In some embodiments, the present disclosure provides a use of an antibody or antigen binding fragment disclosed herein for treatment of an undesirable condition, disease or disorder associated with natriuretic peptide receptor activity in a subject in need thereof. In some embodiments, the present disclosure provides an antibody or antigen binding fragment disclosed herein for use in a method for treating an undesirable condition, disease or disorder associated with natriuretic peptide receptor activity. In some embodiments, the present disclosure provides an antibody or antigen binding fragment disclosed herein for use in manufacturing a medicament for treating an undesirable condition, disease or disorder associated with natriuretic peptide receptor activity. Such conditions, diseases and disorders include, but are not limited to, cardiovascular disorders (e.g., hypertension, peripheral vascular disease, heart failure (including but not limited to heart failure with reduced ejection fraction (HFrEF), heart failure with preserved ejection fraction (HFpEF), heart failure after acute myocardial infarct, or acute decompensated heart failure), coronary artery disease (CAD), ischemic heart disease (IHD), mitral stenosis and regurgitation, angina, hypertrophic cardiomyopathy (e.g., ventricular hypertrophy), diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, or myocardial infarction (MI)), hypertension (e.g., resistant hypertension, hypertensive heart disease, pulmonary hypertension, pulmonary arterial hypertension, isolated systolic hypertension, resistant hypertension, or pulmonary arterial hypertension), preeclampsia, asthma, glaucoma, cytokine release syndrome, and/or a kidney disorder (e.g., diabetic renal insufficiency, non-diabetic renal insufficiency, renal failure, diabetic nephropathy, non-diabetic nephropathy, acute renal injury, contrast induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, renal fibrosis, and polycystic kidney disease (PKD)).

In some embodiments, such methods include administering to a subject in need of treatment a therapeutically effective amount of an antibody or antigen-binding fragment thereof that specifically binds to the same epitope as one of the antibodies described herein. For example, such methods include administering to a subject in need of treatment a therapeutically effective amount of an antibody or antigen-binding fragment thereof that specifically binds to the same epitope as XX16. In another embodiment, such methods include administering to a subject in need of treatment a therapeutically effective amount of an antibody or antigen-binding fragment thereof that specifically binds to the same epitope as WW03. In another embodiment, such methods include administering to a subject in need of treatment a therapeutically effective amount of an antibody or antigen-binding fragment thereof that specifically binds to the same epitope as WW06.

All the aforementioned embodiments for the methods of protection and treatment according to the present invention are equally applicable to
   the use of any one of the antibodies or antigen binding fragments as described herein for the manufacture of a medicament for use according to the present invention,
   the use of any one of the antibodies or antigen binding fragments described herein according to the present invention,
   any one of the antibodies or antigen binding fragments described herein for use according to the present invention, the pharmaceutical compositions comprising any one of the antibodies or antigen binding fragments described herein for the use according to the present invention, the use of the pharmaceutical compositions comprising any one of the antibodies or antigen binding fragments described herein according to the present invention, and the use of the pharmaceutical compositions comprising any one of the antibodies or antigen binding fragments described herein for the manufacture of a medicament for use according to the present invention.

Combination Therapies

The various treatments described above can be combined with other treatment partners or therapeutic agents such as the current standard of care for a disease associated with NPR1 loss of function, e.g., the current standard of care for one or more of the diseases or disorders discussed herein. For example, the NPR1 antibodies or an antigen-binding fragment thereof described herein can be combined with one or more of an ACE (angiotensin-converting-enzyme) inhibitor, an angiotensin receptor blocker (ARB), a neprilysin inhibitor, a beta blocker, a diuretic, a calcium channel blocker, a cardiac glycoside, a sodium-glucose co-transporter 2 inhibitor (SGLT2i), or combinations thereof. As a non-limiting set of examples, the NPR1 antibody or antigen binding from may be combined with an additional therapeutic agent selected from enalapril, benazepril, captopril, fosinopril, lisinopril, moexipril, perindopril, quinapril, ramipril, trandolapril, valsartan, azilsartan, candesartan, eprosartan, irbesartan, losartan, olmesartan, telmisartan, sacubitril, bisoprolol, carvedilol, propanolol, metoprolol, metoprolol tartrate, metoprolol succinate, thiazide diuretics, loop diuretics, potassium-sparing diuretics, amlodipine, clevidipine, diltiazem, felodipine, isradipine, nicardipine, nifedipine, nisoldipine, verapamil, a digitalis glycoside, canagliflozin, dapagliflozin, empagliflozin, ertugliflozin, and combinations thereof. Exemplary diuretics and digitalis glycosides include, but are not limited to, chlorothiazide, chlorthalidone, hydrochlorothiazide, indapamide, metolazone, bumetanide, ethacrynic acid, furosemide, torsemide, amiloride, eplerenone, spironolactonem, triamterene, digoxin, and combinations thereof. In some embodiments, the NPR1 antibodies or an antigen-binding fragment thereof described herein may be combined with an angiotensin receptor-neprilysin inhibitor (ARNi) such as a combination of sacubitril and valsartan (e.g., Entresto®). In some embodiments, the NPR1 antibodies or an antigen-binding fragment thereof described herein can be combined with one or more of a corticosteroid (e.g., an inhaled corticosteroid such as fluticasone, budesonide, mometasone, beclomethasone, ciclesonide, or fluticasone furoate; or an oral or intravenous corticosteroid such as prednisone or methylprednisolone), a leukotriene modifier (e.g., montelukast, zafirlukast, or zileuton), a bronchodilator (e.g., a long-acting beta agonist (e.g., salmeterol or formoterol), a short-acting beta agonist (e.g., albuterol or levalbuterol), theophylline or ipratropium), or combinations thereof (e.g., a combination of fluticasone and salmeterol, a combination of budesonide and formoterol, or a combination of formoterol and mometasone). In some embodiments, the NPR1 antibodies or an antigen-binding fragment thereof described herein can be combined with one or more of a beta-adrenoceptor antagonist (e.g., timolol, levobunolol, metipranolol, carteolol, or betaxolol), a carbonic anhydrase inhibitor (e.g., acetazolamide, dorzolamide, brinzolamide, or methazolamide), an alpha 2-adrenoceptor agonist (e.g., brimonidine or apraclonidine), a parasympathomimetic (e.g., cholinomimetics like pilocarpine), a prostaglandin analog (e.g., latanoprost, latanoprostene bunod, travoprost, bimatoprost, or tafluprost), a rho kinase inhibitor (e.g., netarsudil or ripasudil), or combinations thereof (e.g., a combination of rho kinase inhibitor and latanoprost).

Accordingly, the methods of treating a disease associated with NPR1 loss of function described herein can further include administering a second agent to the subject in need of treatment.

The term "combination" refers to either a fixed combination in one dosage unit form, or a combined administration where an anti-NPR1 antibody or antigen-binding fragment thereof described herein and a combination partner (e.g., another drug as explained below, also referred to as "therapeutic agent" or "co-agent") may be administered independently at the same time or separately within time intervals, especially where these time intervals allow that the combination partners show a cooperative, e.g., synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration and/or at the same time. The term "pharmaceutical combination" as used herein means a product that results from the mixing or combining of more than one therapeutic agent and includes both fixed and non-fixed combinations of the therapeutic agents. The term "fixed combination" means that the therapeutic agents, e.g., a compound of the present invention and a combination partner, are both administered to a patient simultaneously in the form of a single entity or dosage. The term "non-fixed combination" means that the therapeutic agents, e.g., a compound of the present invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more therapeutic agent.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g., synergistic effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., tablets, capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

Pharmaceutical Compositions, Dosages, and Methods of Administration

Also provided herein are compositions, e.g., pharmaceutical compositions, for use in treatment of an NPR1-associated disease. Such compositions include one or more anti-NPR1 antibodies or an antigen-binding fragment thereof as described herein and may include a pharmaceutically acceptable carrier. Such compositions can further include another agent, e.g., a current standard of care for the disease to be treated.

Pharmaceutical compositions typically include a pharmaceutically acceptable carrier. As used herein the term "pharmaceutically acceptable carrier" refers to a carrier or a diluent that does not cause significant irritation to a subject and does not abrogate the biological activity and properties of the administered anti-NPR1 antibody or antigen binding fragment and/or any additional therapeutic agent in the composition. Pharmaceutically acceptable carriers may enhance or stabilize the composition or can be used to facilitate preparation of the composition. Pharmaceutically acceptable carriers may include saline, solvents, dispersion media, coatings, antibacterial and antifungal agents, isotonic and absorption delaying agents, and the like, compatible with pharmaceutical administration. An adjuvant may also be included in any of these formulations. Pharmaceutical compositions are typically formulated to be compatible with its intended route of administration. Examples of routes of administration include parenteral (e.g., intravenous, intraarterial, intraperitoneal), oral, intracranial, intrathecal, or intranasal (e.g., inhalation), intradermal, subcutaneous, or transmucosal administration. In some embodiments, the pharmaceutical compositions are formulated to deliver anti-NPR1 antibodies or antigen-binding fragments thereof to cross the blood-brain barrier. The phrases "physiologically acceptable carrier" and "pharmaceutically acceptable carrier" may be used interchangeably.

As used herein, the term "excipient" refers to an inert substance added to a pharmaceutical composition to further facilitate administration of an active ingredient. Formulations for parenteral administration can, for example, contain excipients such as sterile water or saline, polyalkylene glycols such as polyethylene glycol, vegetable oils, or hydrogenated napthalenes. Other exemplary excipients include, but are not limited to, calcium bicarbonate, calcium phosphate, various sugars and types of starch, cellulose derivatives, gelatin, ethylene-vinyl acetate co-polymer particles, and surfactants, including, for example, polysorbate 20.

A pharmaceutical composition of the present disclosure can be administered by a variety of methods known in the art. The route and/or mode of administration may vary depending upon the desired results. In some embodiments, the administration is intravitreal, intravenous, intramuscular, intraperitoneal, or subcutaneous. The pharmaceutically acceptable carrier should be suitable for intravitreal, intravenous, intramuscular, subcutaneous, parenteral, spinal, or epidermal administration (e.g., by injection or infusion). Depending on the route of administration, the active compound(s), i.e., the anti-NPR1 antibody or antigen binding fragment and optionally the additional therapeutic agent, may be coated in a material to protect the compound(s) from the action of acids and other natural conditions that may inactivate the compound(s).

Typically, a therapeutically effective dose or efficacious dose of the anti-NPR1 antibodies or antigen binding fragments is employed in the pharmaceutical compositions of the present disclosure. The anti-NPR1 antibodies or antigen binding fragments may be formulated into pharmaceutically acceptable dosage forms by conventional methods known to those of skill in the art.

Methods of formulating suitable pharmaceutical compositions are known in the art, see, e.g., Remington: The Science and Practice of Pharmacy. $21^{st}$ ed., 2005; and the books in the series Drugs and the Pharmaceutical Sciences: a Series of Textbooks and Monographs (Dekker, NY), the contents of each of which are incorporated by reference herein for this purpose. For example, solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Dosage regimens for anti-NPR1 antibodies and antigen binding fragments with or without an additional therapeutic agent may be adjusted to provide the optimum desired response (e.g., a therapeutic response). For example, a single bolus of one or both agents may be administered at one time, several divided doses may be administered over a predetermined period of time, or the dose of one or both agents may be proportionally reduced or increased as indicated by the exigencies of the therapeutic situation. For any particular subject, specific dosage regimens may be adjusted over time according to the individual's need, and the professional judgment of the treating clinician. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The skilled artisan (such as a medical doctor) will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Dosage regimens for anti-NPR1 antibodies and antigen binding fragments alone or in combination with an additional therapeutic agent may be adjusted to provide the optimum desired response (e.g., a therapeutic response). For example, a single bolus of one or both agents may be administered at one time, several divided doses may be administered over a predetermined period of time, or the dose of one or both agents may be proportionally reduced or increased as indicated by the exigencies of the therapeutic situation. For any particular subject, specific dosage regimens may be adjusted over time according to the individual's need, and the professional judgment of the treating clinician. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Dosage values for compositions comprising an anti-NPR1 antibody or antigen binding fragment, and/or any additional therapeutic agent(s), may be selected based on the unique characteristics of the active compound(s), and the particular therapeutic effect to be achieved. A physician or veterinarian can start doses of the antibodies of the disclosure employed in the pharmaceutical composition at levels lower than that required to achieve the desired therapeutic effect and gradually increase the dosage until the desired effect is achieved. In general, effective doses of the compositions of the present disclosure, for the treatment of obesity or another disorder described herein may vary depending upon many different factors, including means of administration, target site, physiological state of the patient, whether the patient is human or an animal, other medications administered, and whether treatment is prophylactic or therapeutic. The selected dosage level may also depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors. Treatment dosages may be titrated to optimize safety and efficacy.

Kits

Also provided herein are kits including one or more of the compositions provided herein (e.g., an antibody or antigen binding fragment thereof described in Table 2, Table 3, or Table 4) and instructions for use. Instructions for use can include instructions for diagnosis or treatment of an NPR1-associated disease. Kits as provided herein may be used in accordance with any of the methods described herein. Those skilled in the art will be aware of other suitable uses for kits provided herein, and will be able to employ the kits for such uses. Kits as provided herein can also include a mailer (e.g., a postage paid envelope or mailing pack) that can be used to return the sample for analysis, e.g., to a laboratory. The kit can include one or more containers for the sample, or the sample can be in a standard blood collection vial. The kit can also include one or more of an informed consent form, a test requisition form, and instructions on how to use the kit in a method described herein. Methods for using such kits are also included herein. One or more of the forms (e.g., the test requisition form) and the container holding the sample can be coded, for example, with a bar code for identifying the subject who provided the sample.

The disclosure is further illustrated by the following examples and claims, which are illustrative and are not meant to be further limiting. One skilled in the art will recognize many methods and materials similar or equivalent to those described herein, which could be used in the practice of the described compositions and methods. Such equivalents are within the scope of the present disclosure and claims. The contents of all references, including issued patents and published patent applications, cited throughout this application are hereby incorporated by reference.

EMBODIMENTS

In more detail, the disclosure provides the following embodiments:

Embodiment 1. An isolated antibody or antigen binding fragment that (i) binds to natriuretic peptide receptor 1 (NPR1); and (ii) is capable of activating NPR1 in the absence of atrial natriuretic peptide (ANP).

Embodiment 2. An isolated anti-NPR1 antibody or antigen binding fragment; or the isolated antibody or antigen-binding fragment thereof of embodiment 1, which does not bind to and/or does not activate natriuretic peptide receptor 2 (NPR2) and/or natriuretic peptide receptor 3 (NPR3).

Embodiment 3. An isolated anti-NPR1 antibody or antigen binding fragment; or the isolated antibody or antigen binding fragment of embodiment 1 or embodiment 2 which binds to (a) human NPR1; and (b) mouse NPR1 and/or rat NPR1.

Embodiment 4. An isolated anti-NPR1 antibody or antigen binding fragment; or the isolated antibody or antigen binding fragment of embodiment 1 or embodiment 2 which binds to (a) human NPR1; and (b) cyno NPR1.

Embodiment 5. An isolated anti-NPR1 antibody or antigen binding fragment; or the isolated antibody or antigen-binding fragment thereof of any one of embodiments 1-4, which is ANP non-competitive.

Embodiment 6. An isolated anti-NPR1 antibody or antigen binding fragment; or the isolated antibody or antigen-binding fragment thereof of any one of embodiments 1, 2, or 4, which is ANP competitive.

Embodiment 7. An isolated anti-NPR1 antibody or antigen binding fragment; or the isolated antibody or antigen binding fragment of any one of embodiments 1-5 which is capable of stabilizing the ANP-NPR1 complex.

Embodiment 8. An isolated anti-NPR1 antibody or antigen binding fragment; or the isolated antibody or antigen binding fragment of any one of embodiments 1-5 or 7, wherein the antibody or antigen binding fragment thereof binds to an epitope within amino acids 99-133 of SEQ ID NO: 1.

Embodiment 9. An isolated anti-NPR1 antibody or antigen binding fragment; or the isolated antibody or antigen binding fragment of any one of embodiments 1-5, 7, or 8, wherein the antibody or antigen binding fragment thereof binds to an epitope comprising at least two amino acid residues within amino acids 99-133 of SEQ ID NO: 1.

Embodiment 10. An isolated anti-NPR1 antibody or antigen binding fragment; or the isolated antibody or antigen binding fragment of any one of embodiments 1-5 or 7-9, wherein the antibody or antigen binding fragment thereof binds to an epitope comprising at least 3, 4, 5, 6, 7, or 8 amino acid residues within amino acids 99-133 of SEQ ID NO: 1.

Embodiment 11. An isolated anti-NPR1 antibody or antigen binding fragment; or the isolated antibody or antigen binding fragment of any one of embodiments 1-5 or 7-10, wherein the antibody or antigen binding fragment thereof binds to an epitope within amino acids 99-111 of SEQ ID NO: 1.

Embodiment 12. An isolated anti-NPR1 antibody or antigen binding fragment; or the isolated antibody or antigen binding fragment of any one of embodiments 1-5 or 7-11, wherein the antibody or antigen binding fragment thereof binds to an epitope within amino acids 99-103 of SEQ ID NO: 1.

Embodiment 13. An isolated anti-NPR1 antibody or antigen binding fragment; or the isolated antibody or antigen binding fragment of any one of embodiments 1-5 or 7-12, wherein the antibody or antigen binding fragment thereof binds to an epitope within amino acids 105-111 of SEQ ID NO: 1.

Embodiment 14. An isolated anti-NPR1 antibody or antigen binding fragment; or the isolated antibody or antigen binding fragment of any one of embodiments 1-5 or 7-13, wherein the antibody or antigen binding fragment thereof binds to an epitope comprising at least 2, 3, or 4 amino acid residues within amino acids 105-111 of SEQ ID NO: 1.

Embodiment 15. An isolated anti-NPR1 antibody or antigen binding fragment; or the isolated antibody or antigen binding fragment of any one of embodiments 1-5 or 7-14, wherein the antibody or antigen binding fragment thereof binds to a conformational epitope of human NPR1, and wherein the conformational epitope comprises at least one amino acid residue within each of (i) amino acids 99-103 of SEQ ID NO: 1, (ii) 105-111 of SEQ ID NO: 1, (iii) 131-134 of SEQ ID NO: 1, and additionally binds to amino acid 375 and/or 378 of SEQ ID NO: 1.

Embodiment 16. An isolated anti-NPR1 antibody or antigen binding fragment; or the isolated antibody or antigen binding fragment of any one of embodiments 8-14, wherein the epitope is a conformational epitope, and wherein the conformational epitope additionally comprises at least one amino acid residue selected from the group consisting of amino acids 33, 34, 76, 82, and 104 of SEQ ID NO: 1.

Embodiment 17. An isolated anti-NPR1 antibody or antigen binding fragment; or the isolated antibody or antigen binding fragment of embodiment 15, wherein the conformational epitope additionally comprises at least one amino acid residue selected from the group consisting of amino acids 33, 34, 76, 82, 104, 374, and 375 of SEQ ID NO: 1.

Embodiment 18. An isolated anti-NPR1 antibody or antigen binding fragment; or the isolated antibody or antigen binding fragment of any one of embodiments 1-5 or 7-17, wherein the antibody or antigen binding fragment thereof binds to at least amino acids 82, 102, 103, 105, 106, 109, 132, and 375 of SEQ ID NO: 1.

Embodiment 19. An isolated anti-NPR1 antibody or antigen binding fragment; or the isolated antibody or antigen binding fragment of any one of embodiments 1-5 or 7-18, wherein the antibody or antigen binding fragment thereof binds to at least amino acids 34, 82, 102, 103, 105, 106, 107, 109, 132, 133, 375, and 378 of SEQ ID NO: 1.

Embodiment 20. An isolated anti-NPR1 antibody or antigen binding fragment; or the isolated antibody or antigen binding fragment of any one of embodiments 1-5 or 7-18, wherein the antibody or antigen binding fragment thereof binds to at least amino acids 79, 82, 99, 102, 103, 105, 106, 109, 131, 132, and 375 of SEQ ID NO: 1.

Embodiment 21. An isolated anti-NPR1 antibody or antigen binding fragment; or the isolated antibody or antigen binding fragment of any one of embodiments 1, 2, 4, or 6, wherein the antibody or antigen binding fragment thereof binds to an epitope within amino acids 188-219 of SEQ ID NO: 1.

Embodiment 22. An isolated anti-NPR1 antibody or antigen binding fragment; or the isolated antibody or antigen binding fragment of any one of embodiments 1, 2, 4, 6, or 21, wherein the antibody or antigen binding fragment thereof binds to an epitope comprising at least 2, 3, 4, 5, 6, or 7 amino acids within amino acids 188-219 of SEQ ID NO: 1.

Embodiment 23. An isolated anti-NPR1 antibody or antigen binding fragment; or the isolated antibody or antigen binding fragment of any one of embodiments 1, 2, 4, 6, 21, or 22, wherein the antibody or antigen binding fragment thereof binds to a conformational epitope within NPR1, and wherein the conformational epitope comprises at least one amino acid residue within each of (i) amino acids 188-198 of SEQ ID NO: 1, (ii) 201-208 of SEQ ID NO: 1, (iii) 215-238 of SEQ ID NO: 1, and (iv) 294-297 of SEQ ID NO: 1.

Embodiment 24. An isolated anti-NPR1 antibody or antigen binding fragment; or the isolated antibody or antigen binding fragment of any one of embodiments 1, 2, 4, 6, or 21-23, wherein the antibody or antigen binding fragment thereof binds to at least amino acids 188, 192, 194, 197, 201, 208, and 219 of SEQ ID NO: 1.

Embodiment 25. An isolated anti-NPR1 antibody or antigen binding fragment; or the isolated antibody or antigen binding fragment of any one of embodiments 1, 2, 4, 6, or 21-24, wherein the antibody or antigen binding fragment thereof binds to at least amino acids 188, 192, 194, 197, 201, 208, 219, and 295 of SEQ ID NO: 1.

Embodiment 26. An isolated anti-NPR1 antibody or antigen binding fragment; or the antibody or antigen binding fragment of any one of embodiments 1-5 or 7-20, wherein the antibody or antigen binding fragment comprises three heavy chain complementarity determining regions (HCDR1, HCDR2, and HCDR3) and three light chain complementarity determining regions (LCDR1, LCDR2, and LCDR3), and wherein the antibody or antigen binding fragment comprises the CDRs of one of the ANP non-competitive groups described in Table 3 or Table 4.

Embodiment 27. An isolated anti-NPR1 antibody or antigen binding fragment; or the antibody or antigen binding fragment of any one of embodiments 1, 2, 4, 6, or 21-25, wherein the antibody or antigen binding fragment comprises three heavy chain complementarity determining regions (HCDR1, HCDR2, and HCDR3) and three light chain complementarity determining regions (LCDR1, LCDR2, and LCDR3), and wherein wherein the antibody or antigen binding fragment comprises the CDRs of one of the ANP competitive groups described in Table 3 or Table 4.

Embodiment 28. An isolated anti-NPR1 antibody or antigen binding fragment; or the antibody or antigen binding fragment of any one of embodiments 1-5, 7-20, or 26, wherein the antibody or antigen binding fragment is WW01_LALA, WW03_LALA, XX01_LALA, XX01_DAPA, XX01_N30S_DAPA, XX03_LALA, XX04_LALA, XX06_LALA, XX06_DAPA, XX07_LALA, XX08_LALA, XX08_DAPA, XX08_N30S_DAPA, XX08_N30Q_DAPA, XX09_LALA, XX11_LALA, XX12_LALA, XX13_LALA, XX14_LALA, XX15_LALA, XX15_DAPA, XX16_LALA, XX16_DAPA, XX17_LALA, XX17_DAPA, XX18_LALA, XX18_DAPA, XX19_LALA, XX19_DAPA, XX20_LALA, XX20_DAPA, YY01_LALA, YY03_LALA, YY04_LALA, ZZ12_LALA, and ZZ13_LALA.

Embodiment 29. An isolated anti-NPR1 antibody or antigen binding fragment; or the antibody or antigen binding fragment of any one of embodiments 1, 2, 4, 6, 21-25, or 27, wherein the antibody or antigen binding fragment is WW05_LALA, WW06_LALA, YY05_LALA, YY06_LALA, YY07_LALA, ZZ05_LALA, ZZ14_LALA, and ZZ16_LALA.

Embodiment 30. An isolated anti-NPR1 antibody or antigen binding fragment; or the antibody or antigen binding fragment of any one of embodiments 1-5, 7-20, 26, or 28, wherein the antibody or antigen binding fragment comprises three heavy chain complementarity determining regions (HCDR1, HCDR2, and HCDR3) and three light chain complementarity determining regions (LCDR1, LCDR2, and LCDR3), and wherein:

(a) (I) HCDR1 comprises or consists of an amino acid sequence as set forth in SEQ ID NO: 28; HCDR2 comprises or consists of an amino acid sequence as set forth in $X_1IX_2SX_3GX_4YX_5X_6YADSVKG$ (SEQ ID NO: 429), wherein $X_1$ is A or V, $X_2$ is S or E, $X_3$ is D or K, $X_4$ is S or N, $X_5$ is I or T, and $X_6$ is Y or F; HCDR3 comprises or consists of an amino acid sequence as set forth in SEQ ID NO: 30; LCDR1 comprises or consists of an amino acid sequence as set forth in SEQ ID NO: 41; LCDR2 comprises or consists of an amino acid sequence as set forth in SEQ ID NO: 42; and LCDR3 comprises or consists of an amino acid sequence as set forth in $Y_1QY_2Y_3Y_4Y_5PRT$ (SEQ ID NO: 430); wherein $Y_1$ is M or Q, $Y_2$ is S, E, T, or I, $Y_3$ is Y or W, $Y_4$ is E, V, R, A, T, or M, and $Y_5$ is K, V, R, or A;

(II) HCDR1 comprises or consists of an amino acid sequence as set forth in SEQ ID NO: 31; HCDR2 comprises or consists of an amino acid sequence as set forth in $X_1IX_2SX_3GX_4YX_5X_6YADSVKG$ (SEQ ID NO: 429), wherein $X_1$ is A or V, $X_2$ is S or E, $X_3$ is D or K, $X_4$ is S or N, $X_5$ is I or T, and $X_6$ is Y or F; HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in $Y_1QY_2Y_3Y_4Y_5PRT$ (SEQ ID NO: 430); wherein $Y_1$ is M or Q, $Y_2$ is S, E, T, or I, $Y_3$ is Y or W, $Y_4$ is E, V, R, A, T, or M, and $Y_5$ is K, V, R, or A;

(III) HCDR1 comprises or consists of an amino acid sequence as set forth in SEQ ID NO: 32, HCDR2 comprises or consists of an amino acid sequence as set forth in $X_1SX_2GX_3Y$ (SEQ ID NO: 431), wherein $X_1$ is S or E, $X_2$ is D or K, or $X_3$ is S or N, HCDR3 comprises or consists of an amino acid sequence as set forth in SEQ ID NO: 30, LCDR1 comprises or consists of an amino acid sequence as set forth in SEQ ID NO: 44, LCDR2 comprises or consists of an amino acid sequence as set forth in SEQ ID NO: 45, and LCDR3 comprises or consists of an amino acid sequence as set forth in $Y_1Y_2Y_3Y_4PR$ (SEQ ID NO: 432); wherein $Y_1$ is S, E, T, or I, $Y_2$ is Y or W, $Y_3$ is E, V, R, A, T, or M, and $Y_4$ is K, V, R, or A; or (IV) HCDR1 comprises or consists of an amino acid sequence as set forth in SEQ ID NO: 34, HCDR2 comprises or consists of an amino acid sequence as set forth in $IX_1SX_2GX_3YX_4$ (SEQ ID NO: 433), wherein $X_1$ is S or E, $X_2$ is D or K, $X_3$ is S or N, and $X_4$ is I or T, HCDR3 comprises or consists of an amino acid sequence as set forth in SEQ ID NO: 36, LCDR1 comprises or consists of an amino acid sequence as set forth in SEQ ID NO: 47, LCDR2 comprises or consists of an amino acid sequence as set forth in SEQ ID NO: 45, and LCDR3 comprises or consists of an amino acid sequence as set forth in $Y_1QY_2Y_3Y_4Y_5PRT$ (SEQ ID NO: 430); wherein $Y_1$ is M or Q, $Y_2$ is S, E, T, or I, $Y_3$ is Y or W, $Y_4$ is E, V, R, A, T, or M, and $Y_5$ is K, V, R, or A;

(b) (I) HCDR1 comprises or consists of an amino acid sequence as set forth in SEQ ID NO: 28; HCDR2 comprises or consists of an amino acid sequence as set forth in $X_1IX_2SX_3GX_4YX_5X_6YADSVKG$ (SEQ ID NO: 429), wherein $X_1$ is A or V, $X_2$ is S or E, $X_3$ is D or K, $X_4$ is S or N, $X_5$ is I or T, and $X_6$ is Y or F; HCDR3 comprises or consists of an amino acid sequence as set forth in SEQ ID NO: 30; LCDR1 comprises or consists of an amino acid sequence as set forth in SEQ ID NO: 41; LCDR2 comprises or consists of an amino acid sequence as set forth in SEQ ID NO: 42; and LCDR3 comprises or consists of an amino acid sequence as set forth in $QQY_1WY_2Y_3PRT$ (SEQ ID NO: 434); wherein $Y_1$ is S, E, T, or I, $Y_2$ is V, R, A, T, or M, and $Y_3$ is K, V, R, or A;

(II) HCDR1 comprises or consists of an amino acid sequence as set forth in SEQ ID NO: 31; HCDR2 comprises or consists of an amino acid sequence as set forth in $X_1IX_2SX_3GX_4YX_5X_6YADSVKG$ (SEQ ID NO: 429), wherein $X_1$ is A or V, $X_2$ is S or E, $X_3$ is D or K, $X_4$ is S or N, $X_5$ is I or T, and $X_6$ is Y or F; HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in $QQY_1WY_2Y_3PRT$ (SEQ ID NO: 434); wherein $Y_1$ is S, E, T, or I, $Y_2$ is V, R, A, T, or M, and $Y_3$ is K, V, R, or A;

(III) HCDR1 comprises or consists of an amino acid sequence as set forth in SEQ ID NO: 32, HCDR2 comprises or consists of an amino acid sequence as set forth in $X_1SX_2GX_3Y$ (SEQ ID NO: 431), wherein $X_1$ is S or E, $X_2$ is D or K, or $X_3$ is S or N, HCDR3 comprises or consists of an amino acid sequence as set forth in SEQ ID NO: 30, LCDR1 comprises or consists of an amino acid sequence as set forth in SEQ ID NO: 44, LCDR2 comprises or consists of an amino acid sequence as set forth in SEQ ID NO: 45, and LCDR3 comprises or consists of an amino acid sequence as set forth in $Y_1WY_2Y_3PR$ (SEQ ID NO: 435); wherein $Y_1$ is S, E, T, or I, $Y_2$ is V, R, A, T, or M, and $Y_3$ is K, V, R, or A; or (IV) HCDR1 comprises or consists of an amino acid sequence as set forth in SEQ ID NO: 34, HCDR2 comprises or consists of an amino acid sequence as set forth in IX$_1$SX$_2$GX$_3$YX$_4$ (SEQ ID NO: 433), wherein X$_1$ is S or E, X$_2$ is D or K, X$_3$ is S or N, and X$_4$ is I or T, HCDR3 comprises or consists of an amino acid sequence as set forth in SEQ ID NO: 36, LCDR1 comprises or consists of an amino acid sequence as set forth in SEQ ID NO: 47, LCDR2 comprises or consists of an amino acid sequence as set forth in SEQ ID NO: 45, and LCDR3 comprises or consists of an amino acid sequence as set forth in QQY$_1$WY$_2$Y$_3$PRT (SEQ ID NO: 434); wherein Y$_1$ is S, E, T, or I, Y$_2$ is V, R, A, T, or M, and Y$_3$ is K, V, R, or A;

(c) (I) HCDR1 comprises or consists of an amino acid sequence as set forth in SEQ ID NO: 28; HCDR2 comprises or consists of an amino acid sequence as set forth in SEQ ID NO: 119; HCDR3 comprises or consists of an amino acid sequence as set forth in SEQ ID NO: 30; LCDR1 comprises or consists of an amino acid sequence as set forth in SEQ ID NO: 41; LCDR2 comprises or consists of an amino acid sequence as set forth in SEQ ID NO: 42; and LCDR3 comprises or consists of an amino acid sequence as set forth in QQY$_1$WY$_2$Y$_3$PRT (SEQ ID NO: 434); wherein Y$_1$ is S, E, T, or I, Y$_2$ is V, R, A, T, or M, and Y$_3$ is K, V, R, or A;

(II) HCDR1 comprises or consists of an amino acid sequence as set forth in SEQ ID NO: 31; HCDR2 comprises or consists of an amino acid sequence as set forth in SEQ ID NO: 119; HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in QQY$_1$WY$_2$Y$_3$PRT (SEQ ID NO: 434); wherein Y$_1$ is S, E, T, or I, Y$_2$ is V, R, A, T, or M, and Y$_3$ is K, V, R, or A;

(III) HCDR1 comprises or consists of an amino acid sequence as set forth in SEQ ID NO: 32, HCDR2 comprises or consists of an amino acid sequence as set forth in SEQ ID NO: 120, HCDR3 comprises or consists of an amino acid sequence as set forth in SEQ ID NO: 30, LCDR1 comprises or consists of an amino acid sequence as set forth in SEQ ID NO: 44, LCDR2 comprises or consists of an amino acid sequence as set forth in SEQ ID NO: 45, and LCDR3 comprises or consists of an amino acid sequence as set forth in Y$_1$WY$_2$Y$_3$PR (SEQ ID NO: 435); wherein Y$_1$ is S, E, T, or I, Y$_2$ is V, R, A, T, or M, and Y$_3$ is K, V, R, or A; or (IV) HCDR1 comprises or consists of an amino acid sequence as set forth in SEQ ID NO: 34, HCDR2 comprises or consists of an amino acid sequence as set forth in SEQ ID NO: 121, HCDR3 comprises or consists of an amino acid sequence as set forth in SEQ ID NO: 36, LCDR1 comprises or consists of an amino acid sequence as set forth in SEQ ID NO: 47, LCDR2 comprises or consists of an amino acid sequence as set forth in SEQ ID NO: 45, and LCDR3 comprises or consists of an amino acid sequence as set forth in QQY$_1$WY$_2$Y$_3$PRT (SEQ ID NO: 434); wherein Y$_1$ is S, E, T, or I, Y$_2$ is V, R, A, T, or M, and Y$_3$ is K, V, R, or A;

(d) (I) HCDR1 comprises or consists of an amino acid sequence as set forth in GFTFX$_1$THYIH (SEQ ID NO: 436), wherein X$_1$ is N, S, or Q, HCDR2 comprises or consists of an amino acid sequence as set forth in SIY$_1$Y$_2$Y$_3$GY$_4$Y$_5$TY$_6$YADSVKG (SEQ ID NO: 437), wherein Y$_1$ is S or G, Y$_2$ is S or G, Y$_3$ is S or Q, Y$_4$ is 5, Q, or G, Y$_5$ is 5, N, or M, and Y$_6$ is Y or L, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19;

(II) HCDR1 comprises or consists of an amino acid sequence as set forth in SEQ ID NO: 7, HCDR2 comprises or consists of an amino acid sequence as set forth in SIY$_1$Y$_2$Y$_3$GY$_4$Y$_5$TY$_6$YADSVKG (SEQ ID NO: 437), wherein Y$_1$ is S or G, Y$_2$ is S or G, Y$_3$ is S or Q, Y$_4$ is S, Q, or G, Y$_5$ is S, N, or M, and Y$_6$ is Y or L, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19;

(III) HCDR1 comprises or consists of an amino acid sequence as set forth in GFTFX$_1$TH (SEQ ID NO: 438), wherein X$_1$ is N, S, or Q, HCDR2 comprises or consists of an amino acid sequence as set forth in Y$_1$Y$_2$Y$_3$GY$_4$Y$_5$ (SEQ ID NO: 439), wherein Y$_1$ is S or G, Y$_2$ is S or G, Y$_3$ is S or Q, Y$_4$ is S, Q, or G, and Y$_5$ is S, N, or M, HCDR3 comprises or consists of an amino acid sequence as set forth in SEQ ID NO: 6, LCDR1 comprises or consists of an amino acid sequence as set forth in SEQ ID NO: 20, LCDR2 comprises or consists of an amino acid sequence as set forth in SEQ ID NO: 21, and LCDR3 comprises or consists of an amino acid sequence as set forth in SEQ ID NO: 22; or (IV) HCDR1 comprises or consists of an amino acid sequence as set forth in GFTFX$_1$THY (SEQ ID NO: 440), wherein X$_1$ is N, S, or Q, HCDR2 comprises or consists of an amino acid sequence as set forth in IY$_1$Y$_2$Y$_3$GY$_4$Y$_5$T (SEQ ID NO: 441), wherein Y$_1$ is S or G, Y$_2$ is S or G, Y$_3$ is S or Q, Y$_4$ is S, Q, or G, and Y$_5$ is S, N, or M, HCDR3 comprises or consists of an amino acid sequence as set forth in SEQ ID NO: 12, LCDR1 comprises or consists of an amino acid sequence as set forth in SEQ ID NO: 23, LCDR2 comprises or consists of an amino acid sequence as set forth in SEQ ID NO: 21, and LCDR3 comprises or consists of an amino acid sequence as set forth in SEQ ID NO: 19;

(e) (I) HCDR1 comprises or consists of an amino acid sequence as set forth in GFTFX$_1$THYIH (SEQ ID NO: 436), wherein X$_1$ is N, S, or Q, HCDR2 comprises or consists of an amino acid sequence as set forth in SISY$_1$SGY$_2$Y$_3$TYYADSVKG (SEQ ID NO: 442), wherein Y$_1$ is S or G, Y$_2$ is S or Q, and Y$_3$ is S or N, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19;

(II) HCDR1 comprises or consists of an amino acid sequence as set forth in SEQ ID NO: 7, HCDR2 comprises or consists of an amino acid sequence as set forth in SISY$_1$SGY$_2$Y$_3$TYYADSVKG (SEQ ID NO: 442), wherein Y$_1$ is S or G, Y$_2$ is S or Q, and Y$_3$ is S or N, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19;

(III) HCDR1 comprises or consists of an amino acid sequence as set forth in GFTFX$_1$TH (SEQ ID NO: 438), wherein X$_1$ is N, S, or Q, HCDR2 comprises or consists of an amino acid sequence as set forth in SY$_1$SGY$_2$Y$_3$ (SEQ ID NO: 443), wherein Y$_1$ is S or G, Y$_2$ is S or Q, and Y$_3$ is S or N, HCDR3 comprises or consists of an amino acid sequence as set forth in SEQ ID NO: 6, LCDR1 comprises or consists of an amino acid sequence as set forth in SEQ ID NO: 20, LCDR2 comprises or consists of an amino acid sequence as set forth in SEQ ID NO: 21, and LCDR3 comprises or consists of an amino acid sequence as set forth in SEQ ID NO: 22; or (IV) HCDR1 comprises or consists of an amino acid sequence as set forth in GFTFX$_1$THY (SEQ ID NO: 440), wherein X$_1$ is N, S, or Q, HCDR2 comprises or consists of an amino acid sequence as set forth in ISY$_1$SGY$_2$Y$_3$T (SEQ ID NO: 444), wherein Y$_1$ is S or G, Y$_2$ is S or Q, and Y$_3$ is S or N, HCDR3 comprises or consists of an amino acid sequence as set forth in SEQ ID NO: 12, LCDR1 comprises or consists of an amino acid sequence as set forth in SEQ ID NO: 23, LCDR2 comprises or consists of an amino acid sequence as set forth in SEQ ID NO: 21, and LCDR3 comprises or consists of an amino acid sequence as set forth in SEQ ID NO: 19;

(f) (I) HCDR1 comprises or consists of an amino acid sequence as set forth in GFX$_1$FSX$_2$YX$_3$X$_4$X$_5$ (SEQ ID NO: 445), wherein X$_1$ is S or T, X$_2$ is S, K, or R, X$_3$ is W or Y, X$_4$ is I or L, and X$_5$ is S or N, HCDR2 comprises or consists of an amino acid sequence as set forth in Y$_1$IY$_2$QY$_3$Y$_4$Y$_5$EY$_6$Y$_7$YVESVKG (SEQ ID NO: 446), wherein Y$_1$ is S or N, Y$_2$ is K or H, Y$_3$ is S, Q, or H, Y$_4$ is G or A, Y$_5$ is S, H, or L, Y$_6$ is T or K, and Y$_7$ is Y, K, or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239;

(II) HCDR1 comprises or consists of an amino acid sequence as set forth in X$_1$YX$_2$X$_3$X$_4$ (SEQ ID NO: 447), wherein X$_1$ is S, K, or R, X$_2$ is W or Y, X$_3$ is I or L, and X$_4$ is S or N, HCDR2 comprises or consists of an amino acid sequence as set forth in Y$_1$IY$_2$QY$_3$Y$_4$Y$_5$EY$_6$Y$_7$YVESVKG (SEQ ID NO: 446), wherein Y$_1$ is S or N, Y$_2$ is K or H, Y$_3$ is S, Q, or H, Y$_4$ is G or A, Y$_5$ is S, H, or L, Y$_6$ is T or K, and Y$_7$ is Y, K, or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239;

(III) HCDR1 comprises or consists of an amino acid sequence as set forth in GFX$_1$FSX$_2$Y (SEQ ID NO: 448), wherein X$_1$ is S or T, and X$_2$ is S, K, or R, HCDR2 comprises or consists of an amino acid sequence as set forth in Y$_1$QY$_2$Y$_3$Y$_4$E (SEQ ID NO: 449), wherein Y$_1$ is K or H, Y$_2$ is S, Q, or H, Y$_3$ is G or A, and Y$_4$ is S, H, or L, HCDR3 comprises or consists of an amino acid sequence as set forth in SEQ ID NO: 228, LCDR1 comprises or consists of an amino acid sequence as set forth in SEQ ID NO: 240, LCDR2 comprises or consists of an amino acid sequence as set forth in SEQ ID NO: 241, and LCDR3 comprises or consists of an amino acid sequence as set forth in SEQ ID NO: 242; or (IV) HCDR1 comprises or consists of an amino acid sequence as set forth in GFX$_1$FSX$_2$YX$_3$ (SEQ ID NO: 450), wherein X$_1$ is S or T, X$_2$ is S, K, or R, and X$_3$ is W or Y, HCDR2 comprises or consists of an amino acid sequence as set forth in IY$_1$QY$_2$Y$_3$Y$_4$EY$_5$ (SEQ ID NO: 451), wherein Y$_1$ is K or H, Y$_2$ is S, Q, or H, Y$_3$ is G or A, Y$_4$ is S, H, or L, and Y$_5$ is T or K, HCDR3 comprises or consists of an amino acid sequence as set forth in SEQ ID NO: 232, LCDR1 comprises or consists of an amino acid sequence as set forth in SEQ ID NO: 243, LCDR2 comprises or consists of an amino acid sequence as set forth in SEQ ID NO: 241, and LCDR3 comprises or consists of an amino acid sequence as set forth in SEQ ID NO: 239;

(g) (I) HCDR1 comprises or consists of an amino acid sequence as set forth in GFX$_1$FSX$_2$YX$_3$X$_4$X$_5$ (SEQ ID NO: 445), wherein X$_1$ is S or T, X$_2$ is S, K, or R, X$_3$ is W or Y, X$_4$ is I or L, and X$_5$ is S or N, HCDR2 comprises or consists of an amino acid sequence as set forth in SIHQY$_1$Y$_2$Y$_3$EY$_4$Y$_5$YVESVKG (SEQ ID NO: 453), wherein Y$_1$ is Q or H, Y$_2$ is G or A, Y$_3$ is H or L, Y$_4$ is T or K, and Y$_5$ is K or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239;

(II) HCDR1 comprises or consists of an amino acid sequence as set forth in X$_1$YX$_2$X$_3$X$_4$ (SEQ ID NO: 447), wherein X$_1$ is S, K, or R, X$_2$ is W or Y, X$_3$ is I or L, and X$_4$ is S or N, HCDR2 comprises or consists of an amino acid sequence as set forth in SIHQY$_1$Y$_2$Y$_3$EY$_4$Y$_5$YVESVKG (SEQ ID NO: 453), wherein Y$_1$ is Q or H, Y$_2$ is G or A, Y$_3$ is H or L, Y$_4$ is T or K, and Y$_5$ is K or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239;

(III) HCDR1 comprises or consists of an amino acid sequence as set forth in GFX$_1$FSX$_2$Y (SEQ ID NO: 448), wherein X$_1$ is S or T, and X$_2$ is S, K, or R, HCDR2 comprises or consists of an amino acid sequence as set forth in HQY$_1$Y$_2$Y$_3$E (SEQ ID NO: 456), wherein Y$_1$ is Q or H, Y$_2$ is G or A, and Y$_3$ is H or L, HCDR3 comprises or consists of an amino acid sequence as set forth in SEQ ID NO: 228, LCDR1 comprises or consists of an amino acid sequence as set forth in SEQ ID NO: 240, LCDR2 comprises or consists of an amino acid sequence as set forth in SEQ ID NO: 241, and LCDR3 comprises or consists of an amino acid sequence as set forth in SEQ ID NO: 242; or (IV) HCDR1 comprises or consists of an amino acid sequence as set forth in GFX$_1$FSX$_2$YX$_3$ (SEQ ID NO: 450), wherein X$_1$ is S or T, X$_2$ is S, K, or R, and X$_3$ is W or Y, HCDR2 comprises or consists of an amino acid sequence as set forth in IHQY$_1$Y$_2$Y$_3$EY$_4$ (SEQ ID NO: 458), wherein Y$_1$ is Q or H, Y$_2$ is G or A, Y$_3$ is H or L, and Y$_4$ is T or K, HCDR3 comprises or consists of an amino acid sequence as set forth in SEQ ID NO: 232, LCDR1 comprises or consists of an amino acid sequence as set forth in SEQ ID NO: 243, LCDR2 comprises or consists of an amino acid sequence as set forth in SEQ ID NO: 241, and LCDR3 comprises or consists of an amino acid sequence as set forth in SEQ ID NO: 239;

(h) (I) HCDR1 comprises or consists of an amino acid sequence as set forth in GFTFSX$_1$YX$_2$IX$_3$ (SEQ ID NO: 452), wherein X$_1$ is S or R, X$_2$ is W or Y, and X$_3$ is S or N, HCDR2 comprises or consists of an amino acid sequence as set forth in Y$_1$IY$_2$QY$_3$Y$_4$Y$_5$EY$_6$Y$_7$YVESVKG (SEQ ID NO: 446), wherein Y$_1$ is S or N, Y$_2$ is K or H, Y$_3$ is S, Q, or H, Y$_4$ is G or A, Y$_5$ is S, H, or L, Y$_6$ is T or K, and Y$_7$ is Y, K, or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239;

(II) HCDR1 comprises or consists of an amino acid sequence as set forth in X$_1$YX$_2$IX$_3$ (SEQ ID NO: 454), wherein X$_1$ is S or R, X$_2$ is W or Y, and X$_3$ is S or N, HCDR2 comprises or consists of an amino acid sequence as set forth in Y$_1$IY$_2$QY$_3$Y$_4$Y$_5$EY$_6$Y$_7$YVESVKG (SEQ ID NO: 446), wherein Y$_1$ is S or N, Y$_2$ is K or H, Y$_3$ is S, Q, or H, Y$_4$ is G or A, Y$_5$ is S, H, or L, Y$_6$ is T or K, and Y$_7$ is Y, K, or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239;

(III) HCDR1 comprises or consists of an amino acid sequence as set forth in GFTFSX$_1$Y (SEQ ID NO: 455), wherein X$_1$ is S or R, HCDR2 comprises or consists of an amino acid sequence as set forth in Y$_1$QY$_2$Y$_3$Y$_4$E (SEQ ID NO: 449), wherein Y$_1$ is K or H, Y$_2$ is S, Q, or H, Y$_3$ is G or A, and Y$_4$ is S, H, or L, HCDR3 comprises or consists of an amino acid sequence as set forth in SEQ ID NO: 228, LCDR1 comprises or consists of an amino acid sequence as set forth in SEQ ID NO: 240, LCDR2 comprises or consists of an amino acid sequence as set forth in SEQ ID NO: 241, and LCDR3 comprises or consists of an amino acid sequence as set forth in SEQ ID NO: 242; or (IV) HCDR1 comprises or consists of an amino acid sequence as set forth in GFTFSX$_1$YX$_2$ (SEQ ID NO: 457), wherein X$_1$ is S or R, and X$_2$ is W or Y, HCDR2 comprises or consists of an amino acid sequence as set forth in IY$_1$QY$_2$Y$_3$Y$_4$EY$_5$ (SEQ ID NO: 451), wherein Y$_1$ is K or H, Y$_2$ is S, Q, or H, Y$_3$ is G or A, Y$_4$ is S, H, or L, and Y$_5$ is T or K, HCDR3 comprises or consists of an amino acid sequence as set forth in SEQ ID NO: 232, LCDR1 comprises or consists of an amino acid sequence as set forth in SEQ ID NO: 243, LCDR2 comprises or consists of an amino acid sequence as set forth in SEQ ID NO: 241, and LCDR3 comprises or consists of an amino acid sequence as set forth in SEQ ID NO: 239; or (i) (I) HCDR1 comprises or consists of an amino acid sequence as set forth in GFTFSX$_1$YX$_2$IX$_3$ (SEQ ID NO: 452), wherein X$_1$ is S or R, X$_2$ is W or Y, and X$_3$ is S or N, HCDR2 comprises or consists of an amino acid sequence as set forth in SIHQY$_1$Y$_2$Y$_3$EY$_4$Y$_5$YVESVKG (SEQ ID NO: 453), wherein Y$_1$ is Q or H, Y$_2$ is G or A, Y$_3$ is H or L, Y$_4$ is T or K, and Y$_5$ is K or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239;

(II) HCDR1 comprises or consists of an amino acid sequence as set forth in X$_1$YX$_2$IX$_3$ (SEQ ID NO: 454), wherein X$_1$ is S or R, X$_2$ is W or Y, and X$_3$ is S or N, HCDR2 comprises or consists of an amino acid sequence as set forth in SIHQY$_1$Y$_2$Y$_3$EY$_4$Y$_5$YVESVKG (SEQ ID NO: 453), wherein Y$_1$ is Q or H, Y$_2$ is G or A, Y$_3$ is H or L, Y$_4$ is T or K, and Y$_5$ is K or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239;

(III) HCDR1 comprises or consists of an amino acid sequence as set forth in GFTFSX$_1$Y (SEQ ID NO: 455), wherein X$_1$ is S or R, HCDR2 comprises or consists of an amino acid sequence as set forth in HQY$_1$Y$_2$Y$_3$E (SEQ ID NO: 456), wherein Y$_1$ is Q or H, Y$_2$ is G or A, and Y$_3$ is H or L, HCDR3 comprises or consists of an amino acid sequence as set forth in SEQ ID NO: 228, LCDR1 comprises or consists of an amino acid sequence as set forth in SEQ ID NO: 240, LCDR2 comprises or consists of an amino acid sequence as set forth in SEQ ID NO: 241, and LCDR3 comprises or consists of an amino acid sequence as set forth in SEQ ID NO: 242; or (IV) HCDR1 comprises or consists of an amino acid sequence as set forth in GFTFSX$_1$YX$_2$ (SEQ ID NO: 457), wherein X$_1$ is S or R, and X$_2$ is W or Y, HCDR2 comprises or consists of an amino acid sequence as set forth in IHQY$_1$Y$_2$Y$_3$EY$_4$ (SEQ ID NO: 458), wherein Y$_1$ is Q or H, Y$_2$ is G or A, Y$_3$ is H or L, and Y$_4$ is T or K, HCDR3 comprises or consists of an amino acid sequence as set forth in SEQ ID NO: 232, LCDR1 comprises or consists of an amino acid sequence as set forth in SEQ ID NO: 243, LCDR2 comprises or consists of an amino acid sequence as set forth in SEQ ID NO: 241, and LCDR3 comprises or consists of an amino acid sequence as set forth in SEQ ID NO: 239.

Embodiment 31. An isolated anti-NPR1 antibody or antigen binding fragment; or the antibody or antigen binding fragment of any one of embodiments 1, 2, 4, 6, 21-25, 27, or 29, wherein the antibody or antigen binding fragment comprises three heavy chain complementarity determining regions (HCDR1, HCDR2, and HCDR3) and three light chain complementarity determining regions (LCDR1, LCDR2, and LCDR3), and wherein:

(a) (I) HCDR1 comprises or consists of an amino acid sequence as set forth in SEQ ID NO: 310, HCDR2 comprises or consists of an amino acid sequence as set forth in SEQ ID NO: 311, HCDR3 comprises or consists of an amino acid sequence as set forth in $GX_1X_2X_3GX_4LGFDH$ (SEQ ID NO: 459), wherein $X_1$ is A or S, $X_2$ is V or L, $X_3$ is A or P, and $X_4$ is Q or L, LCDR1 comprises or consists of an amino acid sequence as set forth in SEQ ID NO: 320, LCDR2 comprises or consists of an amino acid sequence as set forth in $GNSNRPY_1$ (SEQ ID NO: 460), wherein $Y_1$ is S or N, and LCDR3 comprises or consists of an amino acid sequence as set forth in $QSYZ_1Z_2Z_3Z_4Z_5Z_6Z_7V$ (SEQ ID NO: 461), wherein $Z_1$ is Y, D, or G, $Z_2$ is T, S, or A, $Z_3$ is S, P, or F, $Z_4$ is S, T, or P, $Z_5$ is H, S, or R, $Z_6$ is G, S, or F, and $Z_7$ is P, S, or V;

(II) HCDR1 comprises or consists of an amino acid sequence as set forth in SEQ ID NO: 229, HCDR2 comprises or consists of an amino acid sequence as set forth in SEQ ID NO: 311, HCDR3 comprises or consists of an amino acid sequence as set forth in $GX_1X_2X_3GX_4LGFDH$ (SEQ ID NO: 459), wherein $X_1$ is A or S, $X_2$ is V or L, $X_3$ is A or P, and $X_4$ is Q or L, LCDR1 comprises or consists of an amino acid sequence as set forth in SEQ ID NO: 320, LCDR2 comprises or consists of an amino acid sequence as set forth in $GNSNRPY_1$ (SEQ ID NO: 460), wherein $Y_1$ is S or N, and LCDR3 comprises or consists of an amino acid sequence as set forth in $QSYZ_1Z_2Z_3Z_4Z_5Z_6Z_7V$ (SEQ ID NO: 461), wherein $Z_1$ is Y, D, or G, $Z_2$ is T, S, or A, $Z_3$ is S, P, or F, $Z_4$ is S, T, or P, $Z_5$ is H, S, or R, $Z_6$ is G, S, or F, and $Z_7$ is P, S, or V;

(III) HCDR1 comprises or consists of an amino acid sequence as set forth in SEQ ID NO: 80, HCDR2 comprises or consists of an amino acid sequence as set forth in SEQ ID NO: 313, HCDR3 comprises or consists of an amino acid sequence as set forth in $GX_1X_2X_3GX_4LGFDH$ (SEQ ID NO: 459), wherein $X_1$ is A or S, $X_2$ is V or L, $X_3$ is A or P, and $X_4$ is Q or L, LCDR1 comprises or consists of an amino acid sequence as set forth in SEQ ID NO: 323, LCDR2 comprises or consists of an amino acid sequence as set forth in SEQ ID NO: 324, and LCDR3 comprises or consists of an amino acid sequence as set forth in $YZ_1Z_2Z_3Z_4Z_5Z_6Z_7$ (SEQ ID NO: 462), wherein $Z_1$ is Y, D, or G, $Z_2$ is T, S, or A, $Z_3$ is S, P, or F, $Z_4$ is S, T, or P, $Z_5$ is H, S, or R, $Z_6$ is G, S, or F, and $Z_7$ is P, S, or V; or (IV) HCDR1 comprises or consists of an amino acid sequence as set forth in SEQ ID NO: 82, HCDR2 comprises or consists of an amino acid sequence as set forth in SEQ ID NO: 314, HCDR3 comprises or consists of an amino acid sequence as set forth in $ARGX_1X_2X_3GX_4LGFDH$ (SEQ ID NO: 463), wherein $X_1$ is A or S, $X_2$ is V or L, $X_3$ is A or P, and $X_4$ is Q or L, LCDR1 comprises or consists of an amino acid sequence as set forth in SEQ ID NO: 326, LCDR2 comprises or consists of an amino acid sequence as set forth in SEQ ID NO: 324, and LCDR3 comprises or consists of an amino acid sequence as set forth in $QSYZ_1Z_2Z_3Z_4Z_5Z_6Z_7V$ (SEQ ID NO: 461), wherein $Z_1$ is Y, D, or G, $Z_2$ is T, S, or A, $Z_3$ is S, P, or F, $Z_4$ is S, T, or P, $Z_5$ is H, S, or R, $Z_6$ is G, S, or F, and $Z_7$ is P, S, or V;

(b) (I) HCDR1 comprises or consists of an amino acid sequence as set forth in $GFTFX_1X_2YAX_3X_4$ (SEQ ID NO: 464), wherein $X_1$ is S or G, $X_2$ is S or T, $X_3$ is I or M, and $X_4$ is S or T, HCDR2 comprises or consists of an amino acid sequence as set forth in $Y_1ISY_2Y_3GY_4Y_5Y_6Y_7YAY_8SVKG$ (SEQ ID NO: 465), wherein $Y_1$ is A or S, $Y_2$ is A, S, or G, $Y_3$ is S or H, $Y_4$ is G or Y, $Y_5$ is S or Y, $Y_6$ is T or A, $Y_7$ is Y, R, or N, and $Y_8$ is E or G, HCDR3 comprises or consists of an amino acid sequence as set forth in SEQ ID NO: 331, LCDR1 comprises or consists of an amino acid sequence as set forth in SEQ ID NO: 337, LCDR2 comprises or consists of an amino acid sequence as set forth in SEQ ID NO: 338, and LCDR3 comprises or consists of an amino acid sequence as set forth in SEQ ID NO: 339;

(II) HCDR1 comprises or consists of an amino acid sequence as set forth in $X_1YAX_2X_3$ (SEQ ID NO: 466), wherein $X_1$ is S or T, $X_2$ is I or M, and $X_3$ is S or T, HCDR2 comprises or consists of an amino acid sequence as set forth in $Y_1ISY_2Y_3GY_4Y_5Y_6Y_7YAY_8SVKG$ (SEQ ID NO: 465), wherein $Y_1$ is A or S, $Y_2$ is A, S, or G, $Y_3$ is S or H, $Y_4$ is G or Y, $Y_5$ is S or Y, $Y_6$ is T or A, $Y_7$ is Y, R, or N, and $Y_8$ is E or G, HCDR3 comprises or consists of an amino acid sequence as set forth in SEQ ID NO: 331, LCDR1 comprises or consists of an amino acid sequence as set forth in SEQ ID NO: 337, LCDR2 comprises or consists of an amino acid sequence as set forth in SEQ ID NO: 338, and LCDR3 comprises or consists of an amino acid sequence as set forth in SEQ ID NO: 339;

(III) HCDR1 comprises or consists of an amino acid sequence as set forth in $GFTFX_1X_2Y$ (SEQ ID NO: 467), wherein $X_1$ is S or G, and $X_2$ is S or T, HCDR2 comprises or consists of an amino acid sequence as set forth in $SY_1Y_2GY_3Y_4$ (SEQ ID NO: 468), wherein $Y_1$ is A, S, or G, $Y_2$ is S or H, $Y_3$ is G or Y, and $Y_4$ is S or Y, HCDR3 comprises or consists of an amino acid sequence as set forth in SEQ ID NO: 331, LCDR1 comprises or consists of an amino acid sequence as set forth in SEQ ID NO: 340, LCDR2 comprises or consists of an amino acid sequence as set forth in SEQ ID NO: 341, and LCDR3 comprises or consists of an amino acid sequence as set forth in SEQ ID NO: 342; or (IV) HCDR1 comprises or consists of an amino acid sequence as set forth in $GFTFX_1X_2YA$ (SEQ ID NO: 469), wherein $X_1$ is S or G, and $X_2$ is S or T, HCDR2 comprises or consists of an amino acid sequence as set forth in $ISY_1Y_2GY_3Y_4T$ (SEQ ID NO: 470), wherein $Y_1$ is S or G, $Y_2$ is S or H, $Y_3$ is G or Y, and $Y_4$ is S or Y, HCDR3 comprises or consists of an amino acid sequence as set forth in SEQ ID NO: 332, LCDR1 comprises or consists of an amino acid sequence as set forth in SEQ ID NO: 343, LCDR2 comprises or consists of an amino acid sequence as set forth in SEQ ID NO: 341, and LCDR3 comprises or consists of an amino acid sequence as set forth in SEQ ID NO: 339; or (c) (I) HCDR1 comprises or consists of an amino acid sequence as set forth in $GFTFX_1X_2YAX_3X_4$ (SEQ ID NO: 464), wherein $X_1$ is S or G, $X_2$ is S or T, $X_3$ is I or M, and $X_4$ is S or T, HCDR2 comprises or consists of an amino acid sequence as set forth in SISY$_1$Y$_2$GYYY$_3$Y$_4$YAY$_5$SVKG (SEQ ID NO: 471), wherein $Y_1$ is A or S, $Y_2$ is S or H, $Y_3$ is T or A, $Y_4$ is R or N, and $Y_5$ is E or G, HCDR3 comprises or consists of an amino acid sequence as set forth in SEQ ID NO: 331, LCDR1 comprises or consists of an amino acid sequence as set forth in SEQ ID NO: 337, LCDR2 comprises or consists of an amino acid sequence as set forth in SEQ ID NO: 338, and LCDR3 comprises or consists of an amino acid sequence as set forth in SEQ ID NO: 339;

(II) HCDR1 comprises or consists of an amino acid sequence as set forth in $X_1$YAX$_2$X$_3$ (SEQ ID NO: 466), wherein $X_1$ is S or T, $X_2$ is I or M, and $X_3$ is S or T, HCDR2 comprises or consists of an amino acid sequence as set forth in SISY$_1$Y$_2$GYYY$_3$Y$_4$YAY$_5$SVKG (SEQ ID NO: 471), wherein $Y_1$ is A or S, $Y_2$ is S or H, $Y_3$ is T or A, $Y_4$ is R or N, and $Y_5$ is E or G, HCDR3 comprises or consists of an amino acid sequence as set forth in SEQ ID NO: 331, LCDR1 comprises or consists of an amino acid sequence as set forth in SEQ ID NO: 337, LCDR2 comprises or consists of an amino acid sequence as set forth in SEQ ID NO: 338, and LCDR3 comprises or consists of an amino acid sequence as set forth in SEQ ID NO: 339;

(III) HCDR1 comprises or consists of an amino acid sequence as set forth in GFTFX$_1$X$_2$Y (SEQ ID NO: 467), wherein $X_1$ is S or G, and $X_2$ is S or T, HCDR2 comprises or consists of an amino acid sequence as set forth in SY$_1$Y$_2$GYY (SEQ ID NO: 472), wherein $Y_1$ is A or S, and $Y_2$ is S or H, HCDR3 comprises or consists of an amino acid sequence as set forth in SEQ ID NO: 331, LCDR1 comprises or consists of an amino acid sequence as set forth in SEQ ID NO: 340, LCDR2 comprises or consists of an amino acid sequence as set forth in SEQ ID NO: 341, and LCDR3 comprises or consists of an amino acid sequence as set forth in SEQ ID NO: 342; or (IV) HCDR1 comprises or consists of an amino acid sequence as set forth in GFTFX$_1$X$_2$YA (SEQ ID NO: 469), wherein $X_1$ is S or G, and $X_2$ is S or T, HCDR2 comprises or consists of an amino acid sequence as set forth in ISY$_1$Y$_2$G (SEQ ID NO: 473), wherein $Y_1$ is A, S, or G, and $Y_2$ is S or H, HCDR3 comprises or consists of an amino acid sequence as set forth in SEQ ID NO: 332, LCDR1 comprises or consists of an amino acid sequence as set forth in SEQ ID NO: 343, LCDR2 comprises or consists of an amino acid sequence as set forth in SEQ ID NO: 341, and LCDR3 comprises or consists of an amino acid sequence as set forth in SEQ ID NO: 339.

Embodiment 32. An isolated anti-NPR1 antibody or antigen binding fragment; or the antibody or antigen binding fragment of any one of embodiments 1-5, 7-20, 26, 28, or 30, wherein the antibody or antigen binding fragment comprises three heavy chain complementarity determining regions (HCDR1, HCDR2, and HCDR3) and three light chain complementarity determining regions (LCDR1, LCDR2, and LCDR3), and wherein:

(a) (I) HCDR1 comprises or consists of an amino acid sequence as set forth in SEQ ID NO: 28, HCDR2 comprises or consists of an amino acid sequence as set forth in any one of comprises or consists of an amino acid sequence as set forth in any one of SEQ ID NOs: 29, 119, and 190, HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in any one of SEQ ID NOs: 43, 126, 134, 145, 172, 178, and 184;

(II) HCDR1 comprises or consists of an amino acid sequence as set forth in SEQ ID NO: 31, HCDR2 comprises or consists of an amino acid sequence as set forth in any one of SEQ ID NOs: 29, 119, and 190, HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in any one of SEQ ID NOs: 43, 126, 134, 145, 172, 178, and 184; (III) HCDR1 comprises or consists of an amino acid sequence as set forth in SEQ ID NO: 32, HCDR2 comprises or consists of an amino acid sequence as set forth in any one of SEQ ID NOs: 33, 120, and 191, HCDR3 comprises or consists of an amino acid sequence as set forth in SEQ ID NO: 30, LCDR1 comprises or consists of an amino acid sequence as set forth in SEQ ID NO: 44, LCDR2 comprises or consists of an amino acid sequence as set forth in SEQ ID NO: 45, and LCDR3 comprises or consists of an amino acid sequence as set forth in any one of SEQ ID NOs: 46, 127, 135, 146, 173, 179, and 185; or (IV) HCDR1 comprises or consists of an amino acid sequence as set forth in SEQ ID NO: 34, HCDR2 comprises or consists of an amino acid sequence as set forth in any one of SEQ ID NOs: 35, 121, and 192, HCDR3 comprises or consists of an amino acid sequence as set forth in SEQ ID NO: 36, LCDR1 comprises or consists of an amino acid sequence as set forth in SEQ ID NO: 47, LCDR2 comprises or consists of an amino acid sequence as set forth in SEQ ID NO: 45, and LCDR3 comprises or consists of an amino acid sequence as set forth in any one of SEQ ID NOs: 43, 126, 134, 145, 172, 178, and 184;

(b) (I) HCDR1 comprises or consists of an amino acid sequence as set forth in any one of SEQ ID NOs: 4, 112, and 165, HCDR2 comprises or consists of an amino acid sequence as set forth in any one of SEQ ID NOs: 5, 100, and 151, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19; (II) HCDR1 comprises or consists of an amino acid sequence as set forth in SEQ ID NO: 7, HCDR2 comprises or consists of an amino acid sequence as set forth in any one of SEQ ID NOs: 5, 100, and 151, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19; (III) HCDR1 comprises or consists of an amino acid sequence as set forth in any one of SEQ ID NOs: 8, 113, and 166, HCDR2 comprises or consists of an amino acid sequence as set forth in any one of SEQ ID NOs: 9, 101, and 152, HCDR3 comprises or consists of an amino acid sequence as set forth in SEQ ID NO: 6, LCDR1 comprises or consists of an amino acid sequence as set forth in SEQ ID NO: 20, LCDR2 comprises or consists of an amino acid sequence as set forth in SEQ ID NO: 21, and LCDR3 comprises or consists of an amino acid sequence as set forth in SEQ ID NO: 22; or (IV) HCDR1 comprises or consists of an amino acid sequence as set forth in any one of SEQ ID NOs: 10, 114, and 167, HCDR2 comprises or consists of an amino acid sequence as set forth in any one of SEQ ID NOs: 11, 102, and 153, HCDR3 comprises or consists of an amino acid sequence as set forth in SEQ ID NO: 12, LCDR1 comprises or consists of an amino acid sequence as set forth in SEQ ID NO: 23, LCDR2 comprises or consists of an amino acid sequence as set forth in SEQ ID NO: 21, and LCDR3 comprises or consists of an amino acid sequence as set forth in SEQ ID NO: 19; or (c) (I) HCDR1 comprises or consists of an amino acid sequence as set forth in any one of SEQ ID NOs: 226, 367, and 378, HCDR2 comprises or consists of an amino acid sequence as set forth in any one of SEQ ID NOs: 227, 368, and 379, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239; (II) HCDR1 comprises or consists of an amino acid sequence as set forth in any one of SEQ ID NOs: 229, 369, and 380, HCDR2 comprises or consists of an amino acid sequence as set forth in any one of SEQ ID NOs: 227, 368, and 379, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239; (III) HCDR1 comprises or consists of an amino acid sequence as set forth in any one of SEQ ID NOs: 32, 370, and 381, HCDR2 comprises or consists of an amino acid sequence as set forth in any one of SEQ ID NOs: 230, 371, and 382, HCDR3 comprises or consists of an amino acid sequence as set forth in SEQ ID NO: 228, LCDR1 comprises or consists of an amino acid sequence as set forth in SEQ ID NO: 240, LCDR2 comprises or consists of an amino acid sequence as set forth in SEQ ID NO: 241, and LCDR3 comprises or consists of an amino acid sequence as set forth in SEQ ID NO: 242; or (IV) HCDR1 comprises or consists of an amino acid sequence as set forth in any one of SEQ ID NOs: 34, 372, and 383, HCDR2 comprises or consists of an amino acid sequence as set forth in any one of SEQ ID NOs: 231, 373, and 384, HCDR3 comprises or consists of an amino acid sequence as set forth in SEQ ID NO: 232, LCDR1 comprises or consists of an amino acid sequence as set forth in SEQ ID NO: 243, LCDR2 comprises or consists of an amino acid sequence as set forth in SEQ ID NO: 241, and LCDR3 comprises or consists of an amino acid sequence as set forth in SEQ ID NO: 239.

Embodiment 33. An isolated anti-NPR1 antibody or antigen binding fragment; or the antibody or antigen binding fragment of any one of embodiments 1, 2, 4, 6, 21-25, 27, 29, or 31, wherein the antibody or antigen binding fragment comprises three heavy chain complementarity determining regions (HCDR1, HCDR2, and HCDR3) and three light chain complementarity determining regions (LCDR1, LCDR2, and LCDR3), and wherein:

(a) (I) HCDR1 comprises or consists of an amino acid sequence as set forth in SEQ ID NO: 310, HCDR2 comprises or consists of an amino acid sequence as set forth in SEQ ID NO: 311, HCDR3 comprises or consists of an amino acid sequence as set forth in any one of SEQ ID NOs: 312 and 348, LCDR1 comprises or consists of an amino acid sequence as set forth in SEQ ID NO: 320, LCDR2 comprises or consists of an amino acid sequence as set forth in any one of SEQ ID NOs: 321 and 354, and LCDR3 comprises or consists of an amino acid sequence as set forth in any one of SEQ ID NOs: 322, 355, and 361; (II) HCDR1 comprises or consists of an amino acid sequence as set forth in SEQ ID NO: 229, HCDR2 comprises or consists of an amino acid sequence as set forth in SEQ ID NO: 311, HCDR3 comprises or consists of an amino acid sequence as set forth in any one of SEQ ID NOs: 312 and 348, LCDR1 comprises or consists of an amino acid sequence as set forth in SEQ ID NO: 320, LCDR2 comprises or consists of an amino acid sequence as set forth in any one of SEQ ID NOs: 321 and 354, and LCDR3 comprises or consists of an amino acid sequence as set forth in any one of SEQ ID NOs: 322, 355, and 361; (III) HCDR1 comprises or consists of an amino acid sequence as set forth in SEQ ID NO: 80, HCDR2 comprises or consists of an amino acid sequence as set forth in SEQ ID NO: 313, HCDR3 comprises or consists of an amino acid sequence as set forth in any one of SEQ ID NOs: 312 and 348, LCDR1 comprises or consists of an amino acid sequence as set forth in SEQ ID NO: 323, LCDR2 comprises or consists of an amino acid sequence as set forth in SEQ ID NO: 324, and LCDR3 comprises or consists of an amino acid sequence as set forth in any one of SEQ ID NOs: 325, 356, and 362; or (IV) HCDR1 comprises or consists of an amino acid sequence as set forth in SEQ ID NO: 82, HCDR2 comprises or consists of an amino acid sequence as set forth in SEQ ID NO: 314, HCDR3 comprises or consists of an amino acid sequence as set forth in any one of SEQ ID NOs: 315 and 349, LCDR1 comprises or consists of an amino acid sequence as set forth in SEQ ID NO: 326, LCDR2 comprises or consists of an amino acid sequence as set forth in SEQ ID NO: 324, and LCDR3 comprises or consists of an amino acid sequence as set forth in any one of SEQ ID NOs: 322, 355, and 361; or (b) (I) HCDR1 comprises or consists of an amino acid sequence as set forth in any one of SEQ ID NOs: 270 and 407, HCDR2 comprises or consists of an amino acid sequence as set forth in any one of SEQ ID NOs: 271, 389, and 408, HCDR3 comprises or consists of an amino acid sequence as set forth in SEQ ID NO: 331, LCDR1 comprises or consists of an amino acid sequence as set forth in SEQ ID NO: 337, LCDR2 comprises or consists of an amino acid sequence as set forth in SEQ ID NO: 338, and LCDR3 comprises or consists of an amino acid sequence as set forth in SEQ ID NO: 339; (II) HCDR1 comprises or consists of an amino acid sequence as set forth in any one of SEQ ID NOs: 273 and 409, HCDR2 comprises or consists of an amino acid sequence as set forth in any one of SEQ ID NOs: 271, 389, and 408, HCDR3 comprises or consists of an amino acid sequence as set forth in SEQ ID NO: 331, LCDR1 comprises or consists of an amino acid sequence as set forth in SEQ ID NO: 337, LCDR2 comprises or consists of an amino acid sequence as set forth in SEQ ID NO: 338, and LCDR3 comprises or consists of an amino acid sequence as set forth in SEQ ID NO: 339; (III) HCDR1 comprises or consists of an amino acid sequence as set forth in any one of SEQ ID NOs:32 and 410, HCDR2 comprises or consists of an amino acid sequence as set forth in any one of SEQ ID NOs: 274, 390, and 411, HCDR3 comprises or consists of an amino acid sequence as set forth in SEQ ID NO: 331, LCDR1 comprises or consists of an amino acid sequence as set forth in SEQ ID NO: 340, LCDR2 comprises or consists of an amino acid sequence as set forth in SEQ ID NO: 341, and LCDR3 comprises or consists of an amino acid sequence as set forth in SEQ ID NO: 342; or (IV) HCDR1 comprises or consists of an amino acid sequence as set forth in any one of SEQ ID NOs: 275 and 412, HCDR2 comprises or consists of an amino acid sequence as set forth in any one of SEQ ID NOs: 276, 391, and 413, HCDR3 comprises or consists of an amino acid sequence as set forth in SEQ ID NO: 332, LCDR1 comprises or consists of an amino acid sequence as set forth in SEQ ID NO: 343, LCDR2 comprises or consists of an amino acid sequence as set forth in SEQ ID NO: 341, and LCDR3 comprises or consists of an amino acid sequence as set forth in SEQ ID NO: 339.

Embodiment 34. An isolated anti-NPR1 antibody or antigen binding fragment; or the antibody or antigen binding fragment of any one of embodiments 1-5, 7-20, 26, 28, 30, or 32, wherein the antibody or antigen binding fragment comprises three heavy chain complementarity determining regions (HCDR1, HCDR2, and HCDR3) and three light chain complementarity determining regions (LCDR1, LCDR2, and LCDR3) selected from:

(a) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 134 (LCDR3);

(b) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 126 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 126 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 127 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 126 (LCDR3);

(c) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 146 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 145 (LCDR3);

(d) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 173 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 172 (LCDR3);

(e) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 179 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 178 (LCDR3);

(f) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 185 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 184 (LCDR3);

(g) (I) SEQ ID NO: 4 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 8 (HCDR1), SEQ ID NO: 101 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 10 (HCDR1), SEQ ID NO: 102 (HCDR2), SEQ ID NO: 12 (HCDR3), SEQ ID NO: 23 (LCDR1), SEQ ID NO: 21 (LCDR2), and SEQ ID NO: 19 (LCDR3);

(h) (I) SEQ ID NO: 112 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 113 (HCDR1), SEQ ID NO: 101 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 114 (HCDR1), SEQ ID NO: 102 (HCDR2), SEQ ID NO: 12 (HCDR3), SEQ ID NO: 23 (LCDR1), SEQ ID NO: 21 (LCDR2), and SEQ ID NO: 19 (LCDR3);

(i) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 43 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 43 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 46 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 43 (LCDR3);

(j) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 126 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 126 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 127 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 126 (LCDR3);

(k) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 134 (LCDR3);

(l) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 145 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 145 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 146 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 145 (LCDR3);

(m) (I) SEQ ID NO: 4 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 8 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 10 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3);

(n) (I) SEQ ID NO: 112 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 113 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 114 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3);

(o) (I) SEQ ID NO: 165 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 166 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 167 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3);

(p) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 172 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 172 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 173 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 172 (LCDR3);

(q) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 178 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 178 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 179 (LCDR3); or (IV) SEQ ID NO: 34 (HCDR1), SEQ ID NO: 35 (HCDR2), SEQ ID NO:

36 (HCDR3), SEQ ID NO: 47 (LCDR1), SEQ ID NO: 45 (LCDR2), and SEQ ID NO: 178 (LCDR3);

(r) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 184 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 184 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 185 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 184 (LCDR3);

(s) (I) SEQ ID NO: 28 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 191 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 192 (HCDR2), SEQ ID NO: 36 (HCDR3), SEQ ID NO: 47 (LCDR1), SEQ ID NO: 45 (LCDR2), and SEQ ID NO: 134 (LCDR3);

(t) (I) SEQ ID NO: 28 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 172 (LCDR3); (II) SEQ ID NO: 31 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 172 (LCDR3); (III) SEQ ID NO: 32 (HCDR1), SEQ ID NO: 191 (HCDR2), SEQ ID NO: 30 (HCDR3), SEQ ID NO: 44 (LCDR1), SEQ ID NO: 45 (LCDR2), and SEQ ID NO: 173 (LCDR3); or (IV) SEQ ID NO: 34 (HCDR1), SEQ ID NO: 192 (HCDR2), SEQ ID NO: 36 (HCDR3), SEQ ID NO: 47 (LCDR1), SEQ ID NO: 45 (LCDR2), and SEQ ID NO: 172 (LCDR3);

(u) (I) SEQ ID NO: 4 (HCDR1), SEQ ID NO: 5 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 5 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 8 (HCDR1), SEQ ID NO: 9 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 10 (HCDR1), SEQ ID NO: 11 (HCDR2), SEQ ID NO: 12 (HCDR3), SEQ ID NO: 23 (LCDR1), SEQ ID NO: 21 (LCDR2), and SEQ ID NO: 19 (LCDR3);

(v) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 43 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 43 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 46 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 43 (LCDR3);

(w) (I) SEQ ID NO: 367 (HCDR1), SEQ ID NO: 368 (HCDR2), SEQ ID NO: 228 (HCDR3), SEQ ID NO: 237 (LCDR1), SEQ ID NO: 238 (LCDR2), and SEQ ID NO: 239 (LCDR3); (II) SEQ ID NO: 369 (HCDR1), SEQ ID NO: 368 (HCDR2), SEQ ID NO: 228 (HCDR3), SEQ ID NO: 237 (LCDR1), SEQ ID NO: 238 (LCDR2), and SEQ ID NO: 239 (LCDR3); (III) SEQ ID NO: 370 (HCDR1), SEQ ID NO: 371 (HCDR2), SEQ ID NO: 228 (HCDR3), SEQ ID NO: 240 (LCDR1), SEQ ID NO: 241 (LCDR2), and SEQ ID NO: 242 (LCDR3); or (IV) SEQ ID NO: 372 (HCDR1), SEQ ID NO: 373 (HCDR2), SEQ ID NO: 232 (HCDR3), SEQ ID NO: 243 (LCDR1), SEQ ID NO: 241 (LCDR2), and SEQ ID NO: 239 (LCDR3);

(x) (I) SEQ ID NO: 378 (HCDR1), SEQ ID NO: 379 (HCDR2), SEQ ID NO: 228 (HCDR3), SEQ ID NO: 237 (LCDR1), SEQ ID NO: 238 (LCDR2), and SEQ ID NO: 239 (LCDR3); (II) SEQ ID NO: 380 (HCDR1), SEQ ID NO: 379 (HCDR2), SEQ ID NO: 228 (HCDR3), SEQ ID NO: 237 (LCDR1), SEQ ID NO: 238 (LCDR2), and SEQ ID NO: 239 (LCDR3); (III) SEQ ID NO: 381 (HCDR1), SEQ ID NO: 382 (HCDR2), SEQ ID NO: 228 (HCDR3), SEQ ID NO: 240 (LCDR1), SEQ ID NO: 241 (LCDR2), and SEQ ID NO: 242 (LCDR3); or (IV) SEQ ID NO: 383 (HCDR1), SEQ ID NO: 384 (HCDR2), SEQ ID NO: 232 (HCDR3), SEQ ID NO: 243 (LCDR1), SEQ ID NO: 241 (LCDR2), and SEQ ID NO: 239 (LCDR3);

(y) (I) SEQ ID NO: 226 (HCDR1), SEQ ID NO: 227 (HCDR2), SEQ ID NO: 228 (HCDR3), SEQ ID NO: 237 (LCDR1), SEQ ID NO: 238 (LCDR2), and SEQ ID NO: 239 (LCDR3); (II) SEQ ID NO: 229 (HCDR1), SEQ ID NO: 227 (HCDR2), SEQ ID NO: 228 (HCDR3), SEQ ID NO: 237 (LCDR1), SEQ ID NO: 238 (LCDR2), and SEQ ID NO: 239 (LCDR3); (III) SEQ ID NO: 32 (HCDR1), SEQ ID NO: 230 (HCDR2), SEQ ID NO: 228 (HCDR3), SEQ ID NO: 240 (LCDR1), SEQ ID NO: 241 (LCDR2), and SEQ ID NO: 242 (LCDR3); or (IV) SEQ ID NO: 34 (HCDR1), SEQ ID NO: 231 (HCDR2), SEQ ID NO: 232 (HCDR3), SEQ ID NO: 243 (LCDR1), SEQ ID NO: 241 (LCDR2), and SEQ ID NO: 239 (LCDR3);

(z) (I) SEQ ID NO: 270 (HCDR1), SEQ ID NO: 271 (HCDR2), SEQ ID NO: 272 (HCDR3), SEQ ID NO: 282 (LCDR1), SEQ ID NO: 261 (LCDR2), and SEQ ID NO: 283 (LCDR3); (II) SEQ ID NO: 273 (HCDR1), SEQ ID NO: 271 (HCDR2), SEQ ID NO: 272 (HCDR3), SEQ ID NO: 282 (LCDR1), SEQ ID NO: 261 (LCDR2), and SEQ ID NO: 283 (LCDR3); (III) SEQ ID NO: 32 (HCDR1), SEQ ID NO: 274 (HCDR2), SEQ ID NO: 272 (HCDR3), SEQ ID NO: 284 (LCDR1), SEQ ID NO: 241 (LCDR2), and SEQ ID NO: 285 (LCDR3); or (IV) SEQ ID NO: 275 (HCDR1), SEQ ID NO: 276 (HCDR2), SEQ ID NO: 277 (HCDR3), SEQ ID NO: 286 (LCDR1), SEQ ID NO: 241 (LCDR2), and SEQ ID NO: 283 (LCDR3); or (aa) (I) SEQ ID NO: 291 (HCDR1), SEQ ID NO: 292 (HCDR2), SEQ ID NO: 293 (HCDR3), SEQ ID NO: 237 (LCDR1), SEQ ID NO: 238 (LCDR2), and SEQ ID NO: 304 (LCDR3); (II) SEQ ID NO: 294 (HCDR1), SEQ ID NO: 292 (HCDR2), SEQ ID NO: 293 (HCDR3), SEQ ID NO: 237 (LCDR1), SEQ ID NO: 238 (LCDR2), and SEQ ID NO: 304 (LCDR3); (III) SEQ ID NO: 295 (HCDR1), SEQ ID NO: 296 (HCDR2), SEQ ID NO: 293 (HCDR3), SEQ ID NO:

240 (LCDR1), SEQ ID NO: 241 (LCDR2), and SEQ ID NO: 305 (LCDR3); or (IV) SEQ ID NO: 297 (HCDR1), SEQ ID NO: 298 (HCDR2), SEQ ID NO: 299 (HCDR3), SEQ ID NO: 243 (LCDR1), SEQ ID NO: 241 (LCDR2), and SEQ ID NO: 304 (LCDR3).

Embodiment 35. An isolated anti-NPR1 antibody or antigen binding fragment; or the antibody or antigen binding fragment of any one of embodiments 1, 2, 4, 6, 21-25, 27, 29, 31, or 33, wherein the antibody or antigen binding fragment comprises three heavy chain complementarity determining regions (HCDR1, HCDR2, and HCDR3) and three light chain complementarity determining regions (LCDR1, LCDR2, and LCDR3) selected from:

(a) (I) SEQ ID NO: 52 (HCDR1), SEQ ID NO: 53 (HCDR2), SEQ ID NO: 54 (HCDR3), SEQ ID NO: 65 (LCDR1), SEQ ID NO: 66 (LCDR2), and SEQ ID NO: 67 (LCDR3); (II) SEQ ID NO: 55 (HCDR1), SEQ ID NO: 53 (HCDR2), SEQ ID NO: 54 (HCDR3), SEQ ID NO: 65 (LCDR1), SEQ ID NO: 66 (LCDR2), and SEQ ID NO: 67 (LCDR3); (III) SEQ ID NO: 56 (HCDR1), SEQ ID NO: 57 (HCDR2), SEQ ID NO: 54 (HCDR3), SEQ ID NO: 68 (LCDR1), SEQ ID NO: 69 (LCDR2), and SEQ ID NO: 70 (LCDR3); or (IV) SEQ ID NO: 58 (HCDR1), SEQ ID NO: 59 (HCDR2), SEQ ID NO: 60 (HCDR3), SEQ ID NO: 71 (LCDR1), SEQ ID NO: 69 (LCDR2), and SEQ ID NO: 67 (LCDR3);

(b) (I) SEQ ID NO: 76 (HCDR1), SEQ ID NO: 77 (HCDR2), SEQ ID NO: 78 (HCDR3), SEQ ID NO: 89 (LCDR1), SEQ ID NO: 90 (LCDR2), and SEQ ID NO: 91 (LCDR3); (II) SEQ ID NO: 79 (HCDR1), SEQ ID NO: 77 (HCDR2), SEQ ID NO: 78 (HCDR3), SEQ ID NO: 89 (LCDR1), SEQ ID NO: 90 (LCDR2), and SEQ ID NO: 91 (LCDR3); (III) SEQ ID NO: 80 (HCDR1), SEQ ID NO: 81 (HCDR2), SEQ ID NO: 78 (HCDR3), SEQ ID NO: 92 (LCDR1), SEQ ID NO: 93 (LCDR2), and SEQ ID NO: 94 (LCDR3); or (IV) SEQ ID NO: 82 (HCDR1), SEQ ID NO: 83 (HCDR2), SEQ ID NO: 84 (HCDR3), SEQ ID NO: 95 (LCDR1), SEQ ID NO: 93 (LCDR2), and SEQ ID NO: 91 (LCDR3);

(c) (I) SEQ ID NO: 310 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 361 (LCDR3); (II) SEQ ID NO: 229 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 361 (LCDR3); (III) SEQ ID NO: 80 (HCDR1), SEQ ID NO: 313 (HCDR2), SEQ ID NO: 348 (HCDR3), SEQ ID NO: 323 (LCDR1), SEQ ID NO: 324 (LCDR2), and SEQ ID NO: 362 (LCDR3); or (IV) SEQ ID NO: 82 (HCDR1), SEQ ID NO: 314 (HCDR2), SEQ ID NO: 349 (HCDR3), SEQ ID NO: 326 (LCDR1), SEQ ID NO: 324 (LCDR2), and SEQ ID NO: 361 (LCDR3);

(d) (I) SEQ ID NO: 270 (HCDR1), SEQ ID NO: 389 (HCDR2), SEQ ID NO: 331 (HCDR3), SEQ ID NO: 337 (LCDR1), SEQ ID NO: 338 (LCDR2), and SEQ ID NO: 339 (LCDR3); (II) SEQ ID NO: 273 (HCDR1), SEQ ID NO: 389 (HCDR2), SEQ ID NO: 331 (HCDR3), SEQ ID NO: 337 (LCDR1), SEQ ID NO: 338 (LCDR2), and SEQ ID NO: 339 (LCDR3); (III) SEQ ID NO: 32 (HCDR1), SEQ ID NO: 390 (HCDR2), SEQ ID NO: 331 (HCDR3), SEQ ID NO: 340 (LCDR1), SEQ ID NO: 341 (LCDR2), and SEQ ID NO: 342 (LCDR3); or (IV) SEQ ID NO: 275 (HCDR1), SEQ ID NO: 391 (HCDR2), SEQ ID NO: 332 (HCDR3), SEQ ID NO: 343 (LCDR1), SEQ ID NO: 341 (LCDR2), and SEQ ID NO: 339 (LCDR3);

(e) (I) SEQ ID NO: 407 (HCDR1), SEQ ID NO: 408 (HCDR2), SEQ ID NO: 331 (HCDR3), SEQ ID NO: 337 (LCDR1), SEQ ID NO: 338 (LCDR2), and SEQ ID NO: 339 (LCDR3); (II) SEQ ID NO: 409 (HCDR1), SEQ ID NO: 408 (HCDR2), SEQ ID NO: 331 (HCDR3), SEQ ID NO: 337 (LCDR1), SEQ ID NO: 338 (LCDR2), and SEQ ID NO: 339 (LCDR3); (III) SEQ ID NO: 410 (HCDR1), SEQ ID NO: 411 (HCDR2), SEQ ID NO: 331 (HCDR3), SEQ ID NO: 340 (LCDR1), SEQ ID NO: 341 (LCDR2), and SEQ ID NO: 342 (LCDR3); or (IV) SEQ ID NO: 412 (HCDR1), SEQ ID NO: 413 (HCDR2), SEQ ID NO: 332 (HCDR3), SEQ ID NO: 343 (LCDR1), SEQ ID NO: 341 (LCDR2), and SEQ ID NO: 339 (LCDR3);

(f) (I) SEQ ID NO: 310 (HCDR1), SEQ ID NO: 311 (HCDR2), SEQ ID NO: 312 (HCDR3), SEQ ID NO: 320 (LCDR1), SEQ ID NO: 321 (LCDR2), and SEQ ID NO: 322 (LCDR3); (II) SEQ ID NO: 229 (HCDR1), SEQ ID NO: 311 (HCDR2), SEQ ID NO: 312 (HCDR3), SEQ ID NO: 320 (LCDR1), SEQ ID NO: 321 (LCDR2), and SEQ ID NO: 322 (LCDR3); (III) SEQ ID NO: 80 (HCDR1), SEQ ID NO: 313 (HCDR2), SEQ ID NO: 312 (HCDR3), SEQ ID NO: 323 (LCDR1), SEQ ID NO: 324 (LCDR2), and SEQ ID NO: 325 (LCDR3); or (IV) SEQ ID NO: 82 (HCDR1), SEQ ID NO: 314 (HCDR2), SEQ ID NO: 315 (HCDR3), SEQ ID NO: 326 (LCDR1), SEQ ID NO: 324 (LCDR2), and SEQ ID NO: 322 (LCDR3);

(g) (I) SEQ ID NO: 270 (HCDR1), SEQ ID NO: 271 (HCDR2), SEQ ID NO: 331 (HCDR3), SEQ ID NO: 337 (LCDR1), SEQ ID NO: 338 (LCDR2), and SEQ ID NO: 339 (LCDR3); (II) SEQ ID NO: 273 (HCDR1), SEQ ID NO: 271 (HCDR2), SEQ ID NO: 331 (HCDR3), SEQ ID NO: 337 (LCDR1), SEQ ID NO: 338 (LCDR2), and SEQ ID NO: 339 (LCDR3); (III) SEQ ID NO: 32 (HCDR1), SEQ ID NO: 274 (HCDR2), SEQ ID NO: 331 (HCDR3), SEQ ID NO: 340 (LCDR1), SEQ ID NO: 341 (LCDR2), and SEQ ID NO: 342 (LCDR3); or (IV) SEQ ID NO: 275 (HCDR1), SEQ ID NO: 276 (HCDR2), SEQ ID NO: 332 (HCDR3), SEQ ID NO: 343 (LCDR1), SEQ ID NO: 341 (LCDR2), and SEQ ID NO: 339 (LCDR3); or (h) (I) SEQ ID NO: 310 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 355 (LCDR3); (II) SEQ ID NO: 229 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 355 (LCDR3); (III) SEQ ID NO: 80 (HCDR1), SEQ ID NO: 313 (HCDR2), SEQ ID NO: 348 (HCDR3), SEQ ID NO: 323 (LCDR1), SEQ ID NO: 324 (LCDR2), and SEQ ID NO: 356 (LCDR3); or (IV) SEQ ID NO: 82 (HCDR1), SEQ ID NO: 314 (HCDR2), SEQ ID NO: 349 (HCDR3), SEQ ID NO: 326 (LCDR1), SEQ ID NO: 324 (LCDR2), and SEQ ID NO: 355 (LCDR3).

Embodiment 36. An isolated anti-NPR1 antibody or antigen binding fragment; or the antibody or antigen binding fragment of any one of embodiments 1-5, 7-20, 26, 28, 30, 32, or 34, wherein the antibody or antigen binding fragment comprises:

(a) a heavy chain variable region comprising an amino acid sequence of SEQ ID NO: 201, and a light chain variable region comprising an amino acid sequence of SEQ ID NO: 136;

(b) a heavy chain variable region comprising an amino acid sequence of SEQ ID NO: 122, and a light chain variable region comprising an amino acid sequence of SEQ ID NO: 136;

(c) a heavy chain variable region comprising an amino acid sequence of SEQ ID NO: 201, and a light chain variable region comprising an amino acid sequence of SEQ ID NO: 128;

(d) a heavy chain variable region comprising an amino acid sequence of SEQ ID NO: 122, and a light chain variable region comprising an amino acid sequence of SEQ ID NO: 128;

(e) a heavy chain variable region comprising an amino acid sequence of SEQ ID NO: 201, and a light chain variable region comprising an amino acid sequence of SEQ ID NO: 147;

(f) a heavy chain variable region comprising an amino acid sequence of SEQ ID NO: 122, and a light chain variable region comprising an amino acid sequence of SEQ ID NO: 147;

(g) a heavy chain variable region comprising an amino acid sequence of SEQ ID NO: 201, and a light chain variable region comprising an amino acid sequence of SEQ ID NO: 174;

(h) a heavy chain variable region comprising an amino acid sequence of SEQ ID NO: 122, and a light chain variable region comprising an amino acid sequence of SEQ ID NO: 174;

(i) a heavy chain variable region comprising an amino acid sequence of SEQ ID NO: 201, and a light chain variable region comprising an amino acid sequence of SEQ ID NO: 180;

(j) a heavy chain variable region comprising an amino acid sequence of SEQ ID NO: 122, and a light chain variable region comprising an amino acid sequence of SEQ ID NO: 180;

(k) a heavy chain variable region comprising an amino acid sequence of SEQ ID NO: 201, and a light chain variable region comprising an amino acid sequence of SEQ ID NO: 186;

(l) a heavy chain variable region comprising an amino acid sequence of SEQ ID NO: 122, and a light chain variable region comprising an amino acid sequence of SEQ ID NO: 186;

(m) a heavy chain variable region comprising an amino acid sequence of SEQ ID NO: 103, and a light chain variable region comprising an amino acid sequence of SEQ ID NO: 24;

(n) a heavy chain variable region comprising an amino acid sequence of SEQ ID NO: 115, and a light chain variable region comprising an amino acid sequence of SEQ ID NO: 24;

(o) a heavy chain variable region comprising an amino acid sequence of SEQ ID NO: 122, and a light chain variable region comprising an amino acid sequence of SEQ ID NO: 48;

(p) a heavy chain variable region comprising an amino acid sequence of SEQ ID NO: 37, and a light chain variable region comprising an amino acid sequence of SEQ ID NO: 128;

(q) a heavy chain variable region comprising an amino acid sequence of SEQ ID NO: 37, and a light chain variable region comprising an amino acid sequence of SEQ ID NO: 136;

(r) a heavy chain variable region comprising an amino acid sequence of SEQ ID NO: 37, and a light chain variable region comprising an amino acid sequence of SEQ ID NO: 147;

(s) a heavy chain variable region comprising an amino acid sequence of SEQ ID NO: 154, and a light chain variable region comprising an amino acid sequence of SEQ ID NO: 24;

(t) a heavy chain variable region comprising an amino acid sequence of SEQ ID NO: 161, and a light chain variable region comprising an amino acid sequence of SEQ ID NO: 24;

(u) a heavy chain variable region comprising an amino acid sequence of SEQ ID NO: 168, and a light chain variable region comprising an amino acid sequence of SEQ ID NO: 24;

(v) a heavy chain variable region comprising an amino acid sequence of SEQ ID NO: 37, and a light chain variable region comprising an amino acid sequence of SEQ ID NO: 174;

(w) a heavy chain variable region comprising an amino acid sequence of SEQ ID NO: 37, and a light chain variable region comprising an amino acid sequence of SEQ ID NO: 180;

(x) a heavy chain variable region comprising an amino acid sequence of SEQ ID NO: 37, and a light chain variable region comprising an amino acid sequence of SEQ ID NO: 186;

(y) a heavy chain variable region comprising an amino acid sequence of SEQ ID NO: 193, and a light chain variable region comprising an amino acid sequence of SEQ ID NO: 136;

(z) a heavy chain variable region comprising an amino acid sequence of SEQ ID NO: 193, and a light chain variable region comprising an amino acid sequence of SEQ ID NO: 174;

(aa) a heavy chain variable region comprising an amino acid sequence of SEQ ID NO: 13, and a light chain variable region comprising an amino acid sequence of SEQ ID NO: 24;

(bb) a heavy chain variable region comprising an amino acid sequence of SEQ ID NO: 37, and a light chain variable region comprising an amino acid sequence of SEQ ID NO: 48;

(cc) a heavy chain variable region comprising an amino acid sequence of SEQ ID NO: 374, and a light chain variable region comprising an amino acid sequence of SEQ ID NO: 244;

(dd) a heavy chain variable region comprising an amino acid sequence of SEQ ID NO: 385, and a light chain variable region comprising an amino acid sequence of SEQ ID NO: 244;

(ee) a heavy chain variable region comprising an amino acid sequence of SEQ ID NO: 233, and a light chain variable region comprising an amino acid sequence of SEQ ID NO: 244;

(ff) a heavy chain variable region comprising an amino acid sequence of SEQ ID NO: 278, and a light chain variable region comprising an amino acid sequence of SEQ ID NO: 287; or (gg) a heavy chain variable region comprising an amino acid sequence of SEQ ID NO: 300, and a light chain variable region comprising an amino acid sequence of SEQ ID NO: 306.

Embodiment 37. An isolated anti-NPR1 antibody or antigen binding fragment; or the antibody or antigen binding fragment of any one of embodiments 1, 2, 4, 6, 21-25, 27, 29, 31, 33, or 35, wherein the antibody or antigen binding fragment comprises:
(a) a heavy chain variable region comprising an amino acid sequence of SEQ ID NO: 61, and a light chain variable region comprising an amino acid sequence of SEQ ID NO: 72;
(b) a heavy chain variable region comprising an amino acid sequence of SEQ ID NO: 85, and a light chain variable region comprising an amino acid sequence of SEQ ID NO: 96;
(c) a heavy chain variable region comprising an amino acid sequence of SEQ ID NO: 350, and a light chain variable region comprising an amino acid sequence of SEQ ID NO: 363;
(d) a heavy chain variable region comprising an amino acid sequence of SEQ ID NO: 392, and a light chain variable region comprising an amino acid sequence of SEQ ID NO: 344;
(e) a heavy chain variable region comprising an amino acid sequence of SEQ ID NO: 414, and a light chain variable region comprising an amino acid sequence of SEQ ID NO: 344;
(f) a heavy chain variable region comprising an amino acid sequence of SEQ ID NO: 316, and a light chain variable region comprising an amino acid sequence of SEQ ID NO: 327;
(g) a heavy chain variable region comprising an amino acid sequence of SEQ ID NO: 333, and a light chain variable region comprising an amino acid sequence of SEQ ID NO: 344; or
(h) a heavy chain variable region comprising an amino acid sequence of SEQ ID NO: 350, and a light chain variable region comprising an amino acid sequence of SEQ ID NO: 357.

Embodiment 38. An isolated anti-NPR1 antibody or antigen binding fragment; or the antibody or antigen binding fragment of any one of embodiments 1-5, 7-20, 26, 28, 30, 32, 34, or 36, wherein the antibody or antigen binding fragment comprises:
(a) a heavy chain comprising an amino acid sequence of SEQ ID NO: 203, and a light chain comprising an amino acid sequence of SEQ ID NO: 138;
(b) a heavy chain comprising an amino acid sequence of SEQ ID NO: 208, and a light chain comprising an amino acid sequence of SEQ ID NO: 138;
(c) a heavy chain comprising an amino acid sequence of SEQ ID NO: 203, and a light chain comprising an amino acid sequence of SEQ ID NO: 130;
(d) a heavy chain comprising an amino acid sequence of SEQ ID NO: 208, and a light chain comprising an amino acid sequence of SEQ ID NO: 130;
(e) a heavy chain comprising an amino acid sequence of SEQ ID NO: 203, and a light chain comprising an amino acid sequence of SEQ ID NO: 149;
(f) a heavy chain comprising an amino acid sequence of SEQ ID NO: 208, and a light chain comprising an amino acid sequence of SEQ ID NO: 149;
(g) a heavy chain comprising an amino acid sequence of SEQ ID NO: 203, and a light chain comprising an amino acid sequence of SEQ ID NO: 176;
(h) a heavy chain comprising an amino acid sequence of SEQ ID NO: 208, and a light chain comprising an amino acid sequence of SEQ ID NO: 176;
(i) a heavy chain comprising an amino acid sequence of SEQ ID NO: 203, and a light chain comprising an amino acid sequence of SEQ ID NO: 182;
(j) a heavy chain comprising an amino acid sequence of SEQ ID NO: 208, and a light chain comprising an amino acid sequence of SEQ ID NO: 182;
(k) a heavy chain comprising an amino acid sequence of SEQ ID NO: 203, and a light chain comprising an amino acid sequence of SEQ ID NO: 188;
(l) a heavy chain comprising an amino acid sequence of SEQ ID NO: 208, and a light chain comprising an amino acid sequence of SEQ ID NO: 188;
(m) a heavy chain comprising an amino acid sequence of SEQ ID NO: 105, and a light chain comprising an amino acid sequence of SEQ ID NO: 26;
(n) a heavy chain comprising an amino acid sequence of SEQ ID NO: 108, and a light chain comprising an amino acid sequence of SEQ ID NO: 26;
(o) a heavy chain comprising an amino acid sequence of SEQ ID NO: 117, and a light chain comprising an amino acid sequence of SEQ ID NO: 26;
(p) a heavy chain comprising an amino acid sequence of SEQ ID NO: 124, and a light chain comprising an amino acid sequence of SEQ ID NO: 50;
(q) a heavy chain comprising an amino acid sequence of SEQ ID NO: 39, and a light chain comprising an amino acid sequence of SEQ ID NO: 130;
(r) a heavy chain comprising an amino acid sequence of SEQ ID NO: 39, and a light chain comprising an amino acid sequence of SEQ ID NO: 138;
(s) a heavy chain comprising an amino acid sequence of SEQ ID NO: 141, and a light chain comprising an amino acid sequence of SEQ ID NO: 138;
(t) a heavy chain comprising an amino acid sequence of SEQ ID NO: 39, and a light chain comprising an amino acid sequence of SEQ ID NO: 149;
(u) a heavy chain comprising an amino acid sequence of SEQ ID NO: 156, and a light chain comprising an amino acid sequence of SEQ ID NO: 26;
(v) a heavy chain comprising an amino acid sequence of SEQ ID NO: 159, and a light chain comprising an amino acid sequence of SEQ ID NO: 26;
(w) a heavy chain comprising an amino acid sequence of SEQ ID NO: 163, and a light chain comprising an amino acid sequence of SEQ ID NO: 26;
(x) a heavy chain comprising an amino acid sequence of SEQ ID NO: 170, and a light chain comprising an amino acid sequence of SEQ ID NO: 26;
(y) a heavy chain comprising an amino acid sequence of SEQ ID NO: 39, and a light chain comprising an amino acid sequence of SEQ ID NO: 176;
(z) a heavy chain comprising an amino acid sequence of SEQ ID NO: 39, and a light chain comprising an amino acid sequence of SEQ ID NO: 182;
(aa) a heavy chain comprising an amino acid sequence of SEQ ID NO: 39, and a light chain comprising an amino acid sequence of SEQ ID NO: 188;
(bb) a heavy chain comprising an amino acid sequence of SEQ ID NO: 195, and a light chain comprising an amino acid sequence of SEQ ID NO: 138;
(cc) a heavy chain comprising an amino acid sequence of SEQ ID NO: 195, and a light chain comprising an amino acid sequence of SEQ ID NO: 176;
(dd) a heavy chain comprising an amino acid sequence of SEQ ID NO: 15, and a light chain comprising an amino acid sequence of SEQ ID NO: 26;
(ee) a heavy chain comprising an amino acid sequence of SEQ ID NO: 39, and a light chain comprising an amino acid sequence of SEQ ID NO: 50;

(ff) a heavy chain comprising an amino acid sequence of SEQ ID NO: 376, and a light chain comprising an amino acid sequence of SEQ ID NO: 246;
(gg) a heavy chain comprising an amino acid sequence of SEQ ID NO: 387, and a light chain comprising an amino acid sequence of SEQ ID NO: 246;
(hh) a heavy chain comprising an amino acid sequence of SEQ ID NO: 235, and a light chain comprising an amino acid sequence of SEQ ID NO: 246;
(ii) a heavy chain comprising an amino acid sequence of SEQ ID NO: 280, and a light chain comprising an amino acid sequence of SEQ ID NO: 289; or
(jj) a heavy chain comprising an amino acid sequence of SEQ ID NO: 302, and a light chain comprising an amino acid sequence of SEQ ID NO: 308.

Embodiment 39. An isolated anti-NPR1 antibody or antigen binding fragment; or the antibody or antigen binding fragment of any one of embodiments 1, 2, 4, 6, 21-25, 27, 29, 31, 33, 35, or 37, wherein the antibody or antigen binding fragment comprises:
(a) a heavy chain comprising an amino acid sequence of SEQ ID NO: 63, and a light chain comprising an amino acid sequence of SEQ ID NO: 74;
(b) a heavy chain comprising an amino acid sequence of SEQ ID NO: 87, and a light chain comprising an amino acid sequence of SEQ ID NO: 98;
(c) a heavy chain comprising an amino acid sequence of SEQ ID NO: 352, and a light chain comprising an amino acid sequence of SEQ ID NO: 365;
(d) a heavy chain comprising an amino acid sequence of SEQ ID NO: 394, and a light chain comprising an amino acid sequence of SEQ ID NO: 346;
(e) a heavy chain comprising an amino acid sequence of SEQ ID NO: 416, and a light chain comprising an amino acid sequence of SEQ ID NO: 346;
(f) a heavy chain comprising an amino acid sequence of SEQ ID NO: 318, and a light chain comprising an amino acid sequence of SEQ ID NO: 329;
(g) a heavy chain comprising an amino acid sequence of SEQ ID NO: 335, and a light chain comprising an amino acid sequence of SEQ ID NO: 346; or
(h) a heavy chain comprising an amino acid sequence of SEQ ID NO: 352, and a light chain comprising an amino acid sequence of SEQ ID NO: 359.

Embodiment 40. The antibody or antigen binding fragment of any one of embodiments 1-39, which is an antigen binding fragment selected from the group consisting of a Fab, Fab', F(ab)$_2$, Fv, single domain antibody (dAb), and a single chain variable fragment (scFv), optionally wherein the antigen binding fragment is selected from the group consisting of a Fab, Fab', Fv, single domain antibody (dAb), and a single chain variable fragment (scFv).

Embodiment 41. The antibody or antigen binding fragment of any one of embodiments 1-40, which is monoclonal.

Embodiment 42. The antibody or antigen binding fragment of any one of embodiments 1-41, which is fully human.

Embodiment 43. The antibody or antigen binding fragment of any one of embodiments 1-42, which is an IgG antibody, optionally which is an IgG1 antibody.

Embodiment 44. The antibody or antigen binding fragment of any one of embodiments 1-43, which is an IgG1 antibody having a kappa light chain.

Embodiment 45. The antibody or antigen binding fragment of any one of embodiments 1-44, which is a fully human antibody of the IgG1 isotype and has a kappa light chain.

Embodiment 46. The antibody or antigen binding fragment of any one of embodiments 1-45, wherein the antibody or antigen binding fragment has further modifications as described herein, e.g., wherein the antibody or antigen binding fragment additionally has mutations in the Fc region according to the EU index of Kabat, wherein the mutations comprise at least D265A and P329A; or wherein the mutations comprise at least L234A and L235A.

Embodiment 47. The antibody or antigen binding fragment of any one of embodiments 1-40, wherein the antibody or antigen binding fragment is: a) monoclonal; and/or b) fully human; and/or c) an IgG antibody, optionally an IgG1 antibody; and/or d) has a kappa light chain; and/or e) has mutations in the Fc region according to the EU index of Kabat, optionally wherein the mutations comprise at least D265A and P329A; and/or f) has mutations in the Fc region according to the EU index of Kabat, optionally wherein the mutations comprise at least L234A and L235A.

Embodiment 48. The antibody or antigen binding fragment of any one of embodiments 1-47, wherein the antibody or antigen binding fragment is therapeutic.

Embodiment 49. An isolated antibody or antigen binding fragment that binds to the same epitope on human NPR1 as the antibody or antigen binding fragment of any one of embodiments 1 to 48.

Embodiment 50. An isolated antibody or antigen binding fragment that competes for binding to human NPR1 with the antibody or antigen binding fragment of any one of embodiments 1 to 49.

Embodiment 51. An isolated nucleic acid or nucleic acids encoding the amino acid sequence of the antibody or antigen binding fragment of any one of embodiments 1 to 50.

Embodiment 52. A vector comprising the isolated nucleic acid(s) of embodiment 51.

Embodiment 53. A host cell comprising the isolated nucleic acid(s) of embodiment 51 or the vector of embodiment 52.

Embodiment 54. A method of producing the antibody or antigen binding fragment of any one of embodiments 1 to 50, comprising culturing the host cell of embodiment 53 under conditions suitable to produce the antibody or antigen binding fragment.

Embodiment 55. The method of embodiment 54, wherein the method additionally comprises purification of the antibody or antigen binding fragment.

Embodiment 56. A pharmaceutical composition comprising a purified antibody or antigen binding fragment produced by the method of embodiment 55 and a pharmaceutically acceptable carrier.

Embodiment 57. A pharmaceutical composition comprising an antibody or antigen binding fragment of any one of embodiments 1 to 50 and a pharmaceutically acceptable carrier.

Embodiment 58. The pharmaceutical composition of embodiment 56 or 57 or a combination comprising an antibody or antigen binding fragment of any one of embodiments 1 to 50, wherein the composition further comprises an additional therapeutic agent.

Embodiment 59. The pharmaceutical composition or combination of embodiment 58, wherein the additional therapeutic agent is selected from an ACE (angiotensin-converting-enzyme) inhibitor, an angiotensin receptor blocker (ARB), a neprilysin inhibitor, a beta blocker, a diuretic, a calcium channel blocker, a cardiac glycoside, a sodium-glucose co-transporter 2 inhibitor (SGLT2i), and combinations thereof.

Embodiment 60. The pharmaceutical composition or combination of embodiment 58 or embodiment 59, wherein the additional therapeutic agent is selected from enalapril, benazepril, captopril, fosinopril, lisinopril, moexipril, perindopril, quinapril, ramipril, trandolapril, valsartan, azilsartan, candesartan, eprosartan, irbesartan, losartan, olmesartan, telmisartan, sacubitril, bisoprolol, carvedilol, propanolol, metoprolol, metoprolol tartrate, metoprolol succinate, thiazide diuretics, loop diuretics, potassium-sparing diuretics, amlodipine, clevidipine, diltiazem, felodipine, isradipine, nicardipine, nifedipine, nisoldipine, verapamil, a digitalis glycoside, canagliflozin, dapagliflozin, empagliflozin, ertugliflozin, and combinations thereof.

Embodiment 61. The pharmaceutical composition or combination of embodiment 58 or embodiment 59, wherein the additional therapeutic agent is selected from chlorothiazide, chlorthalidone, hydrochlorothiazide, indapamide, metolazone, bumetanide, ethacrynic acid, furosemide, torsemide, amiloride, eplerenone, spironolactonem, triamterene, digoxin, and combinations thereof.

Embodiment 62. The pharmaceutical composition or combination of any one of embodiments 58-61, wherein the additional therapeutic agent is an angiotensin receptor-neprilysin inhibitor (ARNi).

Embodiment 63. The pharmaceutical composition or combination of embodiment 58, wherein the additional therapeutic agent is selected from a corticosteroid, a leukotriene modifier, a bronchodilator, and combinations thereof.

Embodiment 64. The pharmaceutical composition or combination of embodiment 63, wherein the additional therapeutic agent is selected from fluticasone, budesonide, mometasone, beclomethasone, ciclesonide, fluticasone furoate, prednisone, methylprednisolone, montelukast, zafirlukast, zileuton, a long-acting beta agonist, a short-acting beta agonist, theophylline and ipratropium, and combinations thereof.

Embodiment 65. The pharmaceutical composition or combination of embodiment 63 or embodiment 64, wherein the additional therapeutic agent is selected from salmeterol, formoterol, albuterol, and levalbuterol, and combinations thereof.

Embodiment 66. The pharmaceutical composition or combination of embodiment 58, wherein the additional therapeutic agent is selected from a beta-adrenoceptor antagonist, a carbonic anhydrase inhibitor, an alpha 2-adrenoceptor agonist, a parasympathomimetic, a prostaglandin analog, a rho kinase inhibitor, and combinations thereof, and combinations thereof.

Embodiment 67. The pharmaceutical composition or combination of embodiment 66, wherein the additional therapeutic agent is selected from timolol, levobunolol, metipranolol, carteolol, betaxolol, acetazolamide, dorzolamide, brinzolamide, methazolamide, brimonidine, apraclonidine, a cholinomimetic, latanoprost, latanoprostene bunod, travoprost, bimatoprost, tafluprost, netarsudil and ripasudil, and combinations thereof.

Embodiment 68. The pharmaceutical composition of embodiment 58, wherein the additional therapeutic agent is selected from an ACE (angiotensin-converting-enzyme) inhibitor, an angiotensin receptor blocker (ARB), a neprilysin inhibitor, a beta blocker, a diuretic, a calcium channel blocker, a cardiac glycoside, a sodium-glucose co-transporter 2 inhibitor (SGLT2i), an angiotensin receptor-neprilysin inhibitor (ARNi), a corticosteroid, a leukotriene modifier, a bronchodilator, a beta-adrenoceptor antagonist, a carbonic anhydrase inhibitor, an alpha 2-adrenoceptor agonist, a parasympathomimetic, a prostaglandin analog, a rho kinase inhibitor, and combinations thereof.

Embodiment 69. The pharmaceutical composition of embodiment 68, wherein the additional therapeutic agent is selected from enalapril, benazepril, captopril, fosinopril, lisinopril, moexipril, perindopril, quinapril, ramipril, trandolapril, valsartan, azilsartan, candesartan, eprosartan, irbesartan, losartan, olmesartan, telmisartan, sacubitril, bisoprolol, carvedilol, propanolol, metoprolol, metoprolol tartrate, metoprolol succinate, thiazide diuretics, loop diuretics, potassium-sparing diuretics, amlodipine, clevidipine, diltiazem, felodipine, isradipine, nicardipine, nifedipine, nisoldipine, verapamil, a digitalis glycoside, canagliflozin, dapagliflozin, empagliflozin, ertugliflozin, chlorothiazide, chlorthalidone, hydrochlorothiazide, indapamide, metolazone, bumetanide, ethacrynic acid, furosemide, torsemide, amiloride, eplerenone, spironolactonem, triamterene, digoxin, fluticasone, budesonide, mometasone, beclomethasone, ciclesonide, fluticasone furoate, prednisone, methylprednisolone, montelukast, zafirlukast, zileuton, a long-acting beta agonist, a short-acting beta agonist, theophylline, ipratropium, salmeterol, formoterol, albuterol, and levalbuterol, timolol, levobunolol, metipranolol, carteolol, betaxolol, acetazolamide, dorzolamide, brinzolamide, methazolamide, brimonidine, apraclonidine, a cholinomimetic, latanoprost, latanoprostene bunod, travoprost, bimatoprost, tafluprost, netarsudil and ripasudil, and combinations thereof.

Embodiment 70. The antibody or antigen binding fragment thereof of any of embodiments 1-50, the isolated nucleic acid or nucleic acids of embodiment 51, the vector of embodiment 52, the host cell of embodiment 53 or pharmaceutical composition of any of embodiments 56-69 for use (i) in therapy, (ii) as a medicament or (iii) in the manufacture of a medicament for the treatment of a disease.

Embodiment 71. Use of the antibody or antigen binding fragment of any of embodiments 1-50, the isolated nucleic acid or nucleic acids of embodiment 51, the vector of embodiment 52, the host cell of embodiment 53 or pharmaceutical composition of any of embodiments 56-69 for the manufacture of a medicament for the treatment of a disorder or disease associated with natriuretic peptide receptor activity in a subject in need of such treatment.

Embodiment 72. Use of the antibody or antigen binding fragment of any one of embodiments 1-50, the isolated nucleic acid or nucleic acids of embodiment 51, the vector of embodiment 52, the host cell of embodiment 53 or pharmaceutical composition of any of embodiments 56-69 for the manufacture of a medicament for the treatment of a cardiovascular disorder in a subject in need of such treatment.

Embodiment 73. The use of embodiment 72, wherein the cardiovascular disorder is selected from: hypertension, peripheral vascular disease, heart failure, coronary artery disease (CAD), ischemic heart disease (IHD), mitral stenosis and regurgitation, angina, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, and myocardial infarction (MI).

Embodiment 74. Use of the antibody or antigen binding fragment of any one of embodiments 1-50, the isolated nucleic acid or nucleic acids of embodiment 51, the vector of embodiment 52, the host cell of embodiment 53 or pharmaceutical composition of any of embodiments 56-69, for the manufacture of a medicament for the treatment of heart failure, hypertrophic cardiomyopathy (HCM), hypertension, preeclampsia, asthma, glaucoma, and/or cytokine release syndrome in a subject in need of such treatment.

Embodiment 75. The use of embodiment 73 or embodiment 74, wherein the subject has heart failure, and wherein the heart failure is selected from a heart failure with reduced ejection fraction (HFrEF), heart failure with preserved ejection fraction (HFpEF), heart failure after acute myocardial infarct, or acute decompensated heart failure.

Embodiment 76. The use of embodiment 73 or embodiment 74, wherein the subject has hypertrophic cardiomyopathy, and wherein the hypertrophic cardiomyopathy is ventricular hypertrophy.

Embodiment 77. The use of embodiment 73 or embodiment 74, wherein the subject has hypertension, and wherein the hypertension is selected from resistant hypertension, hypertensive heart disease, pulmonary hypertension, pulmonary arterial hypertension, isolated systolic hypertension, resistant hypertension, and pulmonary arterial hypertension.

Embodiment 78. The use of any one of embodiments 73, 74, or 77, wherein the subject has hypertension, and wherein the hypertension is selected from resistant hypertension or hypertensive heart disease.

Embodiment 79. Use of the antibody or antigen binding fragment of any one of embodiments 1-50, the isolated nucleic acid or nucleic acids of embodiment 51, the vector of embodiment 52, the host cell of embodiment 53 or pharmaceutical composition of any of embodiments 56-69, for the manufacture of a medicament for the treatment of a kidney disorder in a subject in need of such treatment.

Embodiment 80. The use of embodiment 79, wherein the kidney disorder is selected from: diabetic renal insufficiency, non-diabetic renal insufficiency, renal failure, diabetic nephropathy, non-diabetic nephropathy, acute renal injury, contrast induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, renal fibrosis, and polycystic kidney disease (PKD).

Embodiment 81. The antibody or antigen binding fragment of any of embodiments 1-50, the isolated nucleic acid or nucleic acids of embodiment 51, the vector of embodiment 52, the host cell of embodiment 53 or pharmaceutical composition or combination of any of embodiments 56-69 for use in the treatment of a disorder or disease associated with natriuretic peptide receptor activity in a subject in need of such treatment.

Embodiment 82. The antibody or antigen binding fragment of any one of embodiments 1-50, the isolated nucleic acid or nucleic acids of embodiment 51, the vector of embodiment 52, the host cell of embodiment 53 or pharmaceutical composition or combination of any of embodiments 56-69 for use in the treatment of a cardiovascular disorder in a subject in need of such treatment.

Embodiment 83. The antibody or antigen binding fragment, isolated nucleic acid or nucleic acids, vector, host cell, pharmaceutical composition, or combination of embodiment 82, wherein the cardiovascular disorder is selected from: hypertension, peripheral vascular disease, heart failure, coronary artery disease (CAD), ischemic heart disease (IHD), mitral stenosis and regurgitation, angina, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, and myocardial infarction (MI).

Embodiment 84. The antibody or antigen binding fragment of any one of embodiments 1-50, the isolated nucleic acid or nucleic acids of embodiment 51, the vector of embodiment 52, the host cell of embodiment 53 or pharmaceutical composition or combination of any of embodiments 56-69, for use in the treatment of heart failure, hypertrophic cardiomyopathy (HCM), hypertension, preeclampsia, asthma, glaucoma, and/or cytokine release syndrome in a subject in need of such treatment.

Embodiment 85. The antibody or antigen binding fragment, isolated nucleic acid or nucleic acids, vector, host cell, pharmaceutical composition, or combination of embodiment 83 or embodiment 84, wherein the subject has heart failure, and wherein the heart failure is selected from a heart failure with reduced ejection fraction (HFrEF), heart failure with preserved ejection fraction (HFpEF), heart failure after acute myocardial infarct, or acute decompensated heart failure.

Embodiment 86. The antibody or antigen binding fragment, isolated nucleic acid or nucleic acids, vector, host cell, pharmaceutical composition, or combination of embodiment 83 or embodiment 84, wherein the subject has hypertrophic cardiomyopathy, and wherein the hypertrophic cardiomyopathy is ventricular hypertrophy.

Embodiment 87. The antibody or antigen binding fragment, isolated nucleic acid or nucleic acids, vector, host cell, pharmaceutical composition, or combination of embodiment 83 or embodiment 84, wherein the subject has hypertension, and wherein the hypertension is selected from resistant hypertension, hypertensive heart disease, pulmonary hypertension, pulmonary arterial hypertension, isolated systolic hypertension, resistant hypertension, and pulmonary arterial hypertension.

Embodiment 88. The antibody or antigen binding fragment, isolated nucleic acid or nucleic acids, vector, host cell, pharmaceutical composition, or combination of embodiments 83, 84, or 87, wherein the subject has hypertension, and wherein the hypertension is selected from resistant hypertension or hypertensive heart disease.

Embodiment 89. The antibody or antigen binding fragment of any one of embodiments 1-50, the isolated nucleic acid or nucleic acids of embodiment 51, the vector of embodiment 52, the host cell of embodiment 53 or pharmaceutical composition or combination of any of embodiments 56-69, for use in the the treatment of a kidney disorder in a subject in need of such treatment.

Embodiment 90. The antibody or antigen binding fragment, isolated nucleic acid or nucleic acids, vector, host cell, pharmaceutical composition, or combination of embodiment 89, wherein the kidney disorder is selected from: diabetic renal insufficiency, non-diabetic renal insufficiency, renal failure, diabetic nephropathy, non-diabetic nephropathy, acute renal injury, contrast induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, renal fibrosis, and polycystic kidney disease (PKD).

EXAMPLES

The following examples provide illustrative embodiments of the disclosure. One of ordinary skill in the art will recognize the numerous modifications and variations that may be performed without altering the spirit or scope of the disclosure. Such modifications and variations are encompassed within the scope of the disclosure. The examples provided do not in any way limit the disclosure.

This disclosure provides anti-NPR1 antibodies that specifically bind and activate NPR1, e.g., antibodies and antigen binding fragments that (i) bind to NPR1; and (ii) activate NPR1 in the absence of ANP. Antibodies that specifically bind and activate NPR1 could have different possible modes of action: (1) the antibody induces a conformational change within the NPR1 monomers to activate the receptor; (2) the antibody directly mimics the structure and function of the natural ligand ANP and activates the receptor by binding in the ANP binding pocket of NPR1; or (3) the antibody stabilizes the preformed functionally active complex of hNPR1 and ANP (NPR1-ANP-complex).

Example 1: HuCAL® Phage Library Panning and Screening

For the selection of NPR1-specific antibodies covering the described different methods of action, 13 different panning strategies were applied (see Table 5). Ten strategies were performed exclusively on protein (strategies 1-6 and 10-13). In addition, three differential cell pannings were performed (strategies 7-9). In total, four panning strategies (strategies 3 and 11-13) aimed for the enrichment of ANP competing antibodies (elution with ANP, pre-adsorption of phage on NPR1-ANP-complexes, and anti-idiotype pannings on murine anti-ANP antibodies).

TABLE 5

Overview of HuCAL® panning strategies

| Strategy | 1st round | 2nd round | 3rd round | comments |
|---|---|---|---|---|
| 1 | hNPR1 solution | hNPR1 solution | hNPR1 solution | Solution panning with human antigen only |
| 2 | hNPR1 capture | hNPR1 capture | hNPR1 capture | Fc capture panning with human antigen only |
| 3 | hNPR1 solution | hNPR1 solution + ANP elution | hNPR1 solution + ANP elution | Solution panning aiming for enrichment of ANP competitors |
| 4 | hNPR1 solution | hNPR1 solution + pH 5.8 elution | hNPR1 solution + pH 5.8 elution | Solution panning aiming for enrichment of pH dependent binders |
| 5 | hNPR1 solution | rNPR1 capture | hNPR1 solution | Solution/Fc capture panning aiming for rat crossreactivity |
| 6 | rNPR1 capture | hNPR1 capture | rNPR1 capture | Fc capture panning aiming for rat crossreactivity |
| 7 | hNPR1 capture | CHO-K1 NPR1 cells | rNPR1 capture | Fc capture/cell panning aiming for rat crossreactivity |
| 8 | hNPR1 solution | CHO-K1 NPR1 cells | hNPR1 solution | Solution/cell panning with human antigen only |
| 9 | CHO-K1 NPR1 cells | hNPR1 solution | CHO-K1 NPR1 cells | Solution/cell panning with human antigen only |
| 10 | hNPR1-ANP-complex solution | rNPR1-ANP-complex capture | hNPR1-ANP-complex solution | Solution panning aiming for enrichment of NPR-ANP complex stabilizers and rat crossreactivity |
| 11 | pre-adsorption on NPR1-ANP complex, save the unbound phage still in solution, bind to hNPR1 in solution without ANP and capture NPR1/phage complexes | pre-adsorption on NPR1-ANP complex, save the unbound phage still in solution, bind to hNPR1 in solution without ANP and capture NPR1/phage complexes | pre-adsorption on NPR1-ANP complex, save the unbound phage still in solution, bind to hNPR1 in solution without ANP and capture NPR1/phage complexes | Solution panning aiming for enrichment of ANP competitors |
| 12 | mouse anti-ANP-mAb capture | hNPR1 solution | mouse anti-ANP-mAb capture | Fc capture/cell panning with anti-ANP mAb |
| 13 | mouse anti-ANP mix of two mAbs capture | mouse anti-ANP mix of two mAbs capture + ANP elution | mouse anti-ANP mix of two mAbs + ANP elution | Fc capture panning with anti-ANP mAb aiming for enrichment of ANP competitors |

For Fc capture panning, NPR1-hFc was immobilized on a 96-well plate via an appropriate capture antibody (a goat or mouse anti-human Fc antibody). The antigen was immobilized in an appropriate number of wells of a 96-well plate and wells were subsequently blocked prior to the addition of phage-antibodies. In parallel to well preparation, phage-antibodies were blocked. During blocking of phage, additional blocking reagents were added to the blocking buffer to avoid selection of antibodies against the hFc-tag or the capture antibody (goat or mouse γ globulin). Following the blocking procedure, two pre-adsorption steps on human γ globulin and on the counter-target hNPR3-hFc were performed to avoid selection of antibodies against the Fc-tag or the counter-target. The pre-blocked and pre-adsorbed phage mix was added to each well with immobilized NPR1-hFc and the phage-antibodies were allowed to bind to the antigen. Intensive washing ensured removal of non-specifically bound phage, followed by elution of specifically bound phage. The second and third round of solid phase panning was performed according to the protocol of the first panning round. Amounts of antigen were decreased and washing conditions with increased stringency were applied.

For solution panning, NPR1 was biotinylated and the retained activity of biotinylated NPR1 for ANP binding was confirmed. During solution panning, the Fab displaying phage and the biotinylated NPR1-hFc were incubated in solution, which facilitated the accessibility of the antigen by the phage. An appropriate amount of Streptavidin beads was blocked and, in parallel, an appropriate amount of phage-antibodies was blocked. During blocking of phage, human γ globulin, the counter-target hNPR3-hFc and the Flag-TEV linker peptide were added to the blocking buffer to avoid selection of antibodies against the hFc-tag, the counter-target, or the linker peptide. For removal of Streptavidin-, Biotin-, or bead-binding phage, pre-adsorption steps of blocked phage particles were performed using blocked Streptavidin beads with and without coupled biotinylated irrelevant antigen. Subsequently, biotinylated NPR1-hFc/NPR1-hFc-ANP-complex was added to the pre-adsorbed and blocked phage particles and the phage-antibodies were allowed to bind to the antigen in solution. For enrichment of antibody phage binding to the ANP-binding site of NPR1 (ANP competitive antibodies) the pre-formed NPR1-ANP-complex was added to the phage blocking solution or the ANP peptide was used for elution of the bound phage. Thereby, the ANP peptide was used at least in 250-fold molar excess to the NPR1 antigen or the NPR1 expressing cells. The phage-antigen complexes were captured using blocked Streptavidin beads and phage particles bound to the Streptavidin beads were collected with a magnetic separator. Phage bound nonspecifically were washed off by several washing steps. Specifically bound phage were eluted from Streptavidin beads. The eluate was transferred to an *E. coli* culture for phage infection. The second and third round of bead-based solution panning was performed according to the protocol of the first panning round. Amounts of antigen were decreased and washing conditions with increased stringency were applied.

For whole cell panning, an appropriate amount of phage-antibodies was blocked. During blocking of phage, counter-target hNPR3-hFc was added to the blocking buffer to avoid selection of antibodies against the counter-target. In parallel, an appropriate amount of target cells expressing NPR1 and an appropriate amount of adsorption cells without expression of antigen (parental cells) per phage pool were blocked. The blocked target cells were spun down, resuspended in the pre-blocked phage particles and the phage-antibodies were allowed to bind to the NPR1 presented on the cell. The phage-cell complexes were washed several times. For enrichment of antibody phage binding to the ANP-binding site of NPR1 (ANP competitive antibodies) the pre-formed NPR1-ANP-complex was added to the phage blocking solution or the ANP peptide was used for elution of the bound phage. Thereby, the ANP peptide was used at least in 250-fold molar excess to the NPR1 antigen or the NPR1 expressing cells. Specifically bound phage were eluted from target cells. After centrifugation, the supernatant (eluate) was applied to adsorption cells for removal of phage binding to cell surface molecules other than the target antigen (post-adsorption). The final supernatant was transferred to an *E. coli* culture for phage infection. The second and third round of the whole cell panning were performed according to the protocol of the first panning round. Washing conditions with increased stringency were applied.

The outputs of the panning rounds were subsequently subcloned into bacterial expression vectors and bacterial lysates (BEL) were used for primary and secondary screening. The outputs were analyzed for binding to human and rat NPR1 during the primary screening (ELISA-based). Clones binding to human NPR3 were deselected. Secondary screening was performed on hNPR1 expressing CHO-K1 cells. Further screenings regarding ANP competition and binding solely in presence of ANP were performed. Approximately 1700 clones fulfilled the screening selection criteria and 760 clones were selected for sequencing. The sequencing of 760 clones resulted in 210 HCDR3 unique hits, whose binding properties are summarized in Table 6. Of these clones, 72 demonstrated significant ANP competition, while 7 clones bound only in presence of ANP.

TABLE 6

Binding properties of 210 HCDR3 unique hits (HuCAL ®)

| Number of HCDR3 unique candidates | | | Binding to | | |
|---|---|---|---|---|---|
| | | | hNPR1 | rNPR1 | hNPR1 expr. cells |
| 210 of which 7 clones only bind in presence of ANP | 47 human/ rat cross reactive | 28 human/rat cross reactive cell binders | Yes | Yes | Yes |
| | | 19 human/rat cross reactive (not binding to cells) | Yes | Yes | No |
| | 156 human specific | 53 human specific cell binders | Yes | No | Yes |
| | | 103 human specific (not binding to cells) | Yes | No | No |

Example 2: Antibody Reformatting, Expression, and Purification

After confirmation of binding, the VH and VL domains of the 210 HCDR3 unique clones were subcloned into a vector with a human IgG constant region. 180 of the 210 clones were selected for expression and 166 of the 180 passed the production quality control. They were characterized in regard to binding to relevant cell lines and functional activity. 40 of the 166 candidates were then selected for exploratory scale production, and 31 of these candidates were characterized in detail as shown below with respect to binding to relevant antigens and cell lines, ANP competition, and functionality in a cell based cGMP production assay.

For production of the IgG candidates, eukaryotic HKB11 cells were transfected with mammalian expression vector DNA encoding both heavy and light chains of IgG. Cell culture supernatants were harvested at appropriate times and subjected to Protein A affinity chromatography. If needed, a second purification step was performed to remove aggregates. Buffer exchange was performed to 1× Dulbecco's PBS (pH 7.2) and samples were sterile filtered (0.2 μm pore size).

Figure 2:
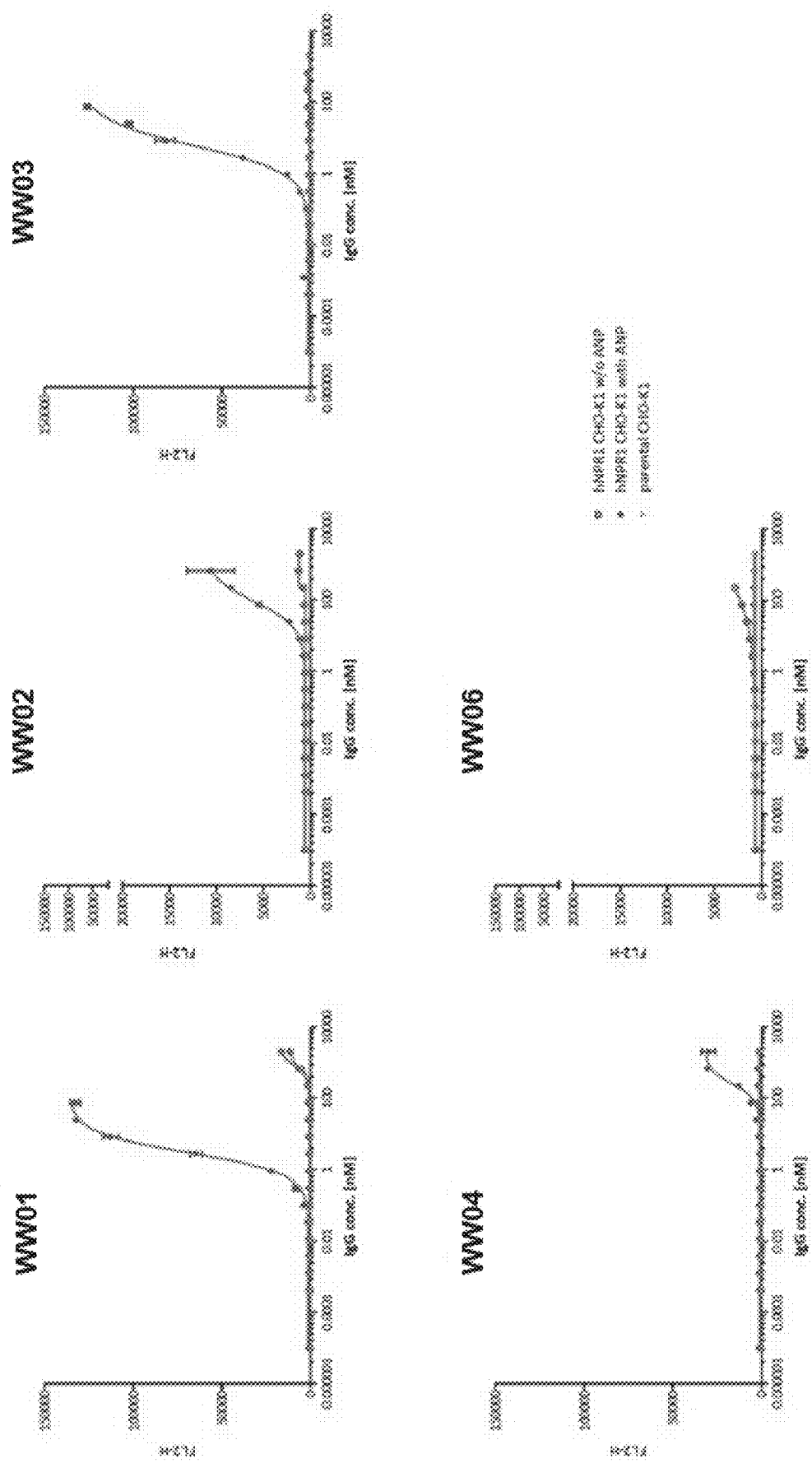
FIG. 2 is a set of graphs displaying the results of flow cytometry analysis of antibody candidates WW01, WW02, WW03, WW04, and WW06 for binding to human NPR1 expressing CHO-K1 cells in the absence and presence of a saturating concentration of ANP and on parental CHO-K1 cells.

Example 3: Antigen Binding, ANP Competition and Cellular cGMP Production—HuCAL® Candidates The 31 IgGs which passed the exploratory scale production quality control were tested via ELISA for binding to the following antigens: human NPR1, constitutively active human NPR1 mutant (W74R), rat NPR1, and human NPR3 (counter target). The clones were also tested by flow cytometry for binding to human NPR1 expressing CHO K1 cells in the absence and presence of ANP and on parental CHO K1 cells. The binding properties of the five functional candidates are shown in FIG. 1 and FIG. 2.

The same 31 IgGs were tested for ANP competition using a Fluorescence Resonance Energy Transfer (FRET)-based assay in which the NPR1-specific antibodies competed with ANP for binding to NPR1. In this FRET based assay (see FIG. 3), Eu-labeled Streptavidin (for measurement of IgGs) or Eu-labeled anti-hFc antibody (for measurement of FabCys) was used as an energy donor, while Cy5-labeled ANP was used as an acceptor (for all measurements). The resulting fluorescent signal was decreased by ANP-competitive antibodies. The assay was performed as follows: antibodies were mixed with NPR1 and incubated for 5 minutes at room temperature. After addition of the Eu-labeled donor and incubation for 30 minutes at room temperature, the Cy5-ANP solution was added. After a further 60-minute incubation, readout was performed using a TECAN Infinite M1000 Pro using an excitation wavelength of 317 nm and an emission wavelength of 665 nm. Percentage of ANP competition was calculated according to the following formulae:

$$\text{Ratio}^* = [(A_{665}\,nm/A_{620}\,nm)*10^4]$$

$$\text{Ratio} = (\text{Ratio}^* - \text{Ratio}_{neg})$$

$$\text{Competition \%} = [100 - (\text{Ratio}/(\text{Ratio}_{pos}/100))]$$

$\text{Ratio}_{neg}$: mean Ratio*data values of control without NPR1

$\text{Ratio}_{pos}$: mean Ratio data values of control without agonist (reaction buffer)

Figure 4:
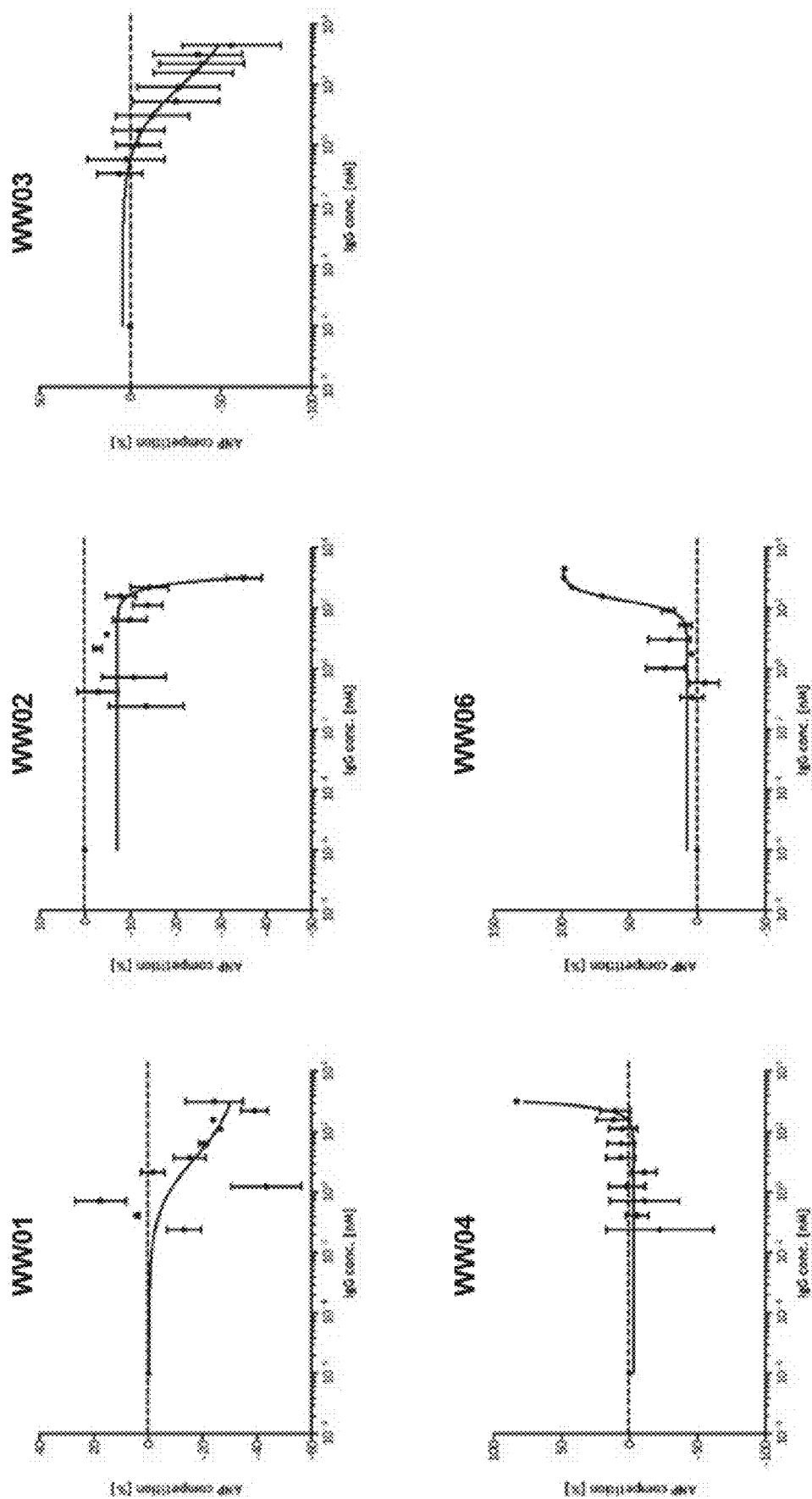
FIG. 4 is a set of graphs displaying the results of ANP competition analyses of candidates WW01, WW02, WW03, WW04, and WW06 using the FRET-based assay depicted in FIG. 3.

15 of the 31 IgGs were ANP competitive, but only two of these candidates showed functionality in the cGMP assay (WW04 and WW06). The other three functional candidates WW01, WW02 and WW03 demonstrated a "negative" ANP competition in this assay indicating the stabilization of the NPR1-ANP-complex. The FRET assay results for the five functional candidates are depicted in FIG. 4.

Additionally, as discussed above, the 31 IgGs were tested for their functional activity in a cellular cGMP production assay using human NPR1 expressing CHO-K1 cells. For the functional characterization of the selected antibodies the production of cyclic guanosine 3',5'-cyclic monophosphate (cGMP) upon binding to and stimulation of NPR1 expressed on the cell surface of CHO-K1 cells was monitored. Cellular cGMP is a major second messenger that mediates cell activities and is synthesized by activated NPR1 triggered by ANP or NPR1-specific antibodies. Therefore, a commercial assay kit was used (Cisbio Bioassays CisBio HTRF Assay Kit CisBio (Cat. #62GM2PEB)). The assay was performed according to manufacturer's instructions with minor deviations. In brief, cells were adjusted to 1×10⁵ cells/mL, 20 μL/well were seeded in 96 well microtiter plates and were incubated overnight. After addition of 10 μL/well of the antibodies in different concentrations, the plate was incubated for 30 min at 37° C. to allow for cGMP production. In parallel, a standard curve using a calibrator (contained in the kit) was generated. The cells were lysed and a mix of cGMP-d2 and anti-cGMP-Cryptate was added and incubated for 1 h at room temperature. The readout was performed using a Tecan M1000 Pro using an excitation wavelength of 317 nm and an emission wavelength of 665 nm. cGMP concentration (Delta F [%]) was calculated according to the following formulae:

$$\text{Ratio} = [(A_{665\,nm}/B_{620\,nm})*10^4]$$

$$\text{Mean Ratio} = (\Sigma\text{ratios}/2)$$

$$CV = [(\text{Std deviation}/\text{Mean ratio})*100]$$

$$\text{Delta } F = [((\text{Calibrator or sample Ratio} - \text{Ratio}_{neg})/\text{Ratio}_{Neg})*100]$$

$\text{Ratio}_{neg}$: negative control

Figure 5:
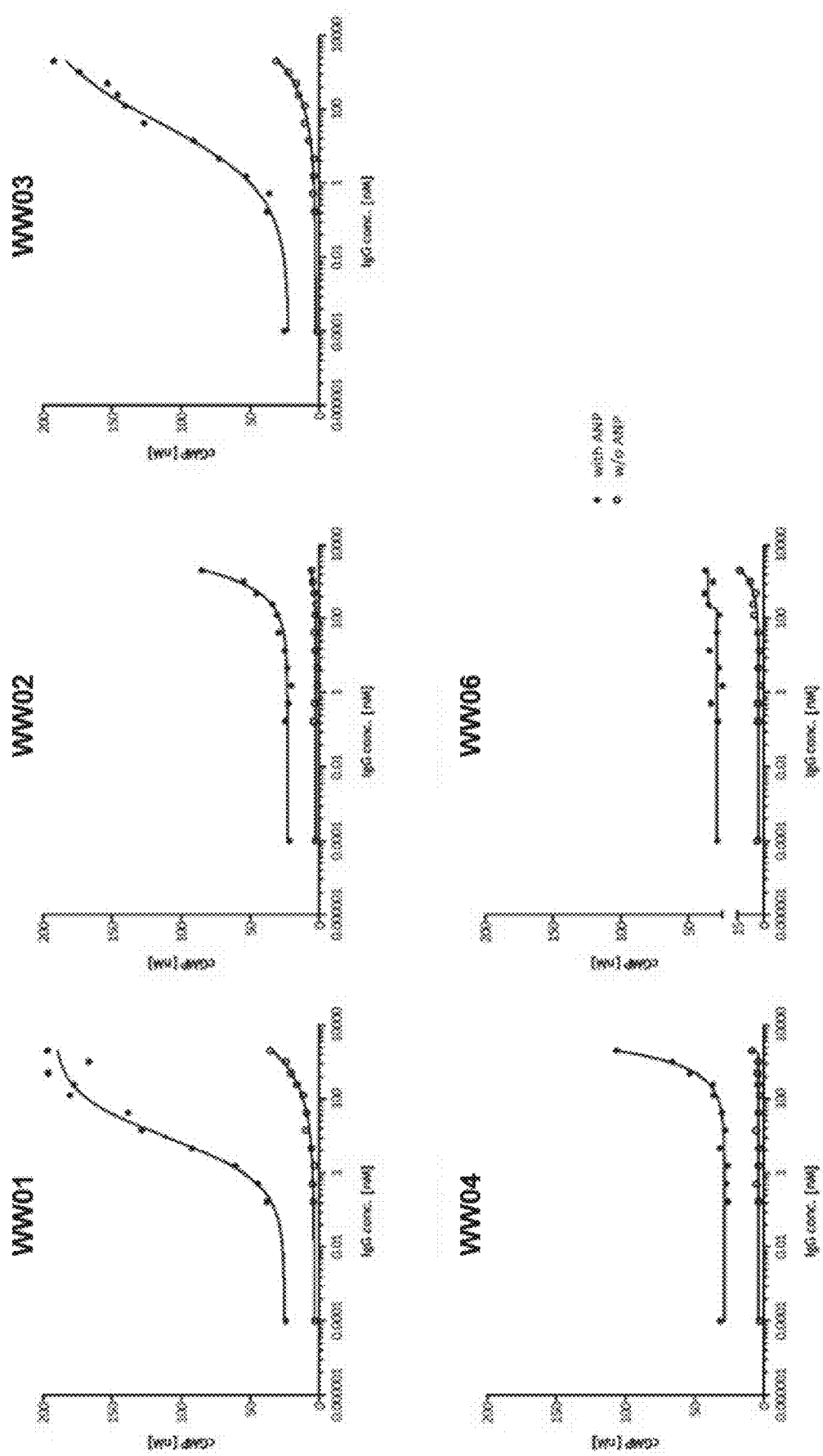
FIG. 5 is a set of graphs depicting the results of functional activity analyses of candidates WW01, WW02, WW03, WW04, and WW06 in a cellular cGMP production assay using human NPR1 expressing CHO-K1 cells. Results represent the cellular production of cGMP [nM] in the absence or presence of 0.075 nM ANP.

Five candidates with significant functional activity were identified using the cellular cGMP assay: WW01, WW02, WW03, WW04, and WW06. These five candidates were functionally active and could be assigned to different methods of action. WW01, WW02, and WW03 were able to stabilize the NPR1-ANP-complex, while WW06 was determined to be ANP competitive. These candidates were all derived from initial panning codes 10 and 11 (aiming for method of action 2 or 3). The results of the assay for the cellular production of cGMP in the absence or presence of 0.075 nM ANP induced by the five functional candidates (IgG format) are shown in FIG. 5.

Example 4: Production and Characterization of HuCAL® Candidates in FabCys Format The functional clones were also tested for functionality in FabCys format. Eukaryotic HKB11 cells were transfected with mammalian expression vector DNA encoding both heavy and light chains of disulfide-bridged FabCys. Cell culture supernatants were harvested at appropriate times and subjected to metal ion affinity chromatography using a liquid handling station. Buffer exchange was performed to 1× Dulbecco's PBS (pH 7.2) and samples were sterile filtered (0.2 μm pore size).

The five functional candidates WW01, WW02, WW03, WW04 and WW06 were additionally analyzed with regard to their monovalent affinities for human and rat NPR1 and the counter-target human NPR3 in absence and presence of ANP in monovalent FabCys format. The results of the affinity determination, epitope binning, and cGMP assay are summarized in Table 7.

TABLE 7

Summary of Affinity, Epitope, and cGMP data for WW01, WW02, WW03, WW04, and WW06 in FabCys Format

| | Characterization in monovalent FabCys format | | | | | | |
|---|---|---|---|---|---|---|---|
| | Affinity FabCys $K_D$ [nM] | | | Epitope | Bin on hNPR1 (-ANP-complex) | cGMP assay cGMP conc [nM] at 2 µM FabCys | |
| Antibody | hNPR1 | hNPR1 + ANP | rNPR1 | rNPR1 + ANP | | Without ANP | +0.075 nM ANP |
| WW01 | — | 1.5 | — | 2.0 | B | 30 | 121 |
| WW02 | weak | weak | weak | weak | n.a. | 4 | 20 |
| WW03 | 1000 | 0.1 | 2600 | 1.0 | B | 32 | 108 |
| WW04 | 0.8 | 0.4 | 66 | 73 | A | 4 | 19 |
| WW06 | 5.3 | 12 | weak | weak | A | 281 | 251 |

For candidates WW01 and WW03 no or very weak binding to human and rat NPR1 was observed in the absence of ANP, while the affinities in the presence of ANP were in the low nanomolar to subnanomolar range. Both shared the same epitope bin "B". The affinity of candidates WW02 was too weak for adequate determination of $K_D$ values and the epitope bin. WW04 and WW06 had affinities in the double-digit nanomolar to subnanomolar range, which were independent from the presence or absence of ANP. Both shared the same epitope bin "A". WW06 was the only candidate which did not exhibit rat cross-reactivity.

While for WW02, WW03 and WW04 no binding to the counter-target hNPR3 in the absence or presence of ANP was observed, additional binding to the counter-target was detected for WW01 as well as for WW06 at higher concentrations.

Example 5: Reformatting HuCAL® Candidates Into IgG Format

Subcloning from the FabCys vector into an IgG1_LALA vector for expression in mammalian cells was performed via amplification of the Fab-encoding insert using one biotinylated primer and one non-biotinylated primer. The amplified product was bound on streptavidin beads, digested using restriction enzymes, and washed, resulting in the release of the purified insert into the supernatant. The insert was cloned into the acceptor vector, the DNA was transformed and single clones were quality controlled via colony PCR and sequencing.

Figure 6:
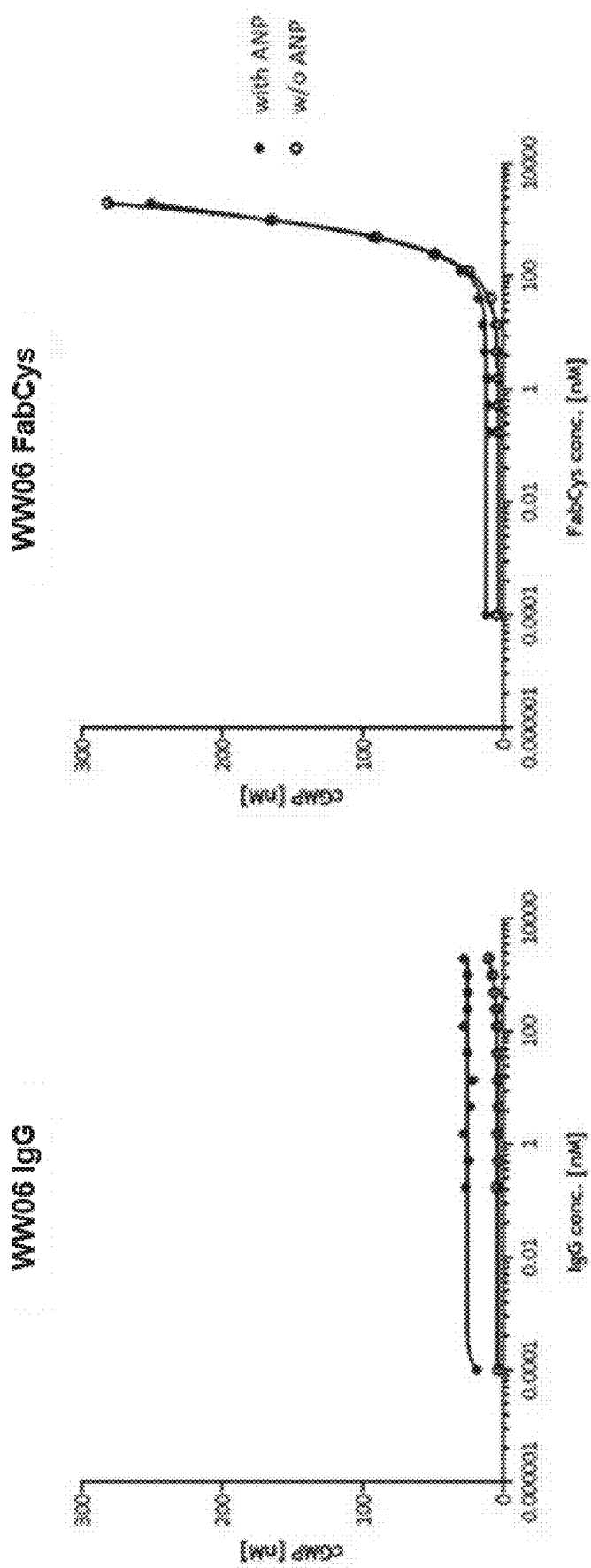
FIG. 6 is a set of graphs depicting the results of functional activity analyses of candidate WW06 in IgG or FabCys format in a cellular cGMP production assay using human NPR1 expressing CHO-K1 cells. Results represent the cellular production of cGMP [nM] in the absence or presence of 0.075 nM ANP.

The five functional candidates WW01, WW02, WW03, WW04, and WW06 in IgG format were characterized as described above. Binding data (ELISA, flow cytometry, ANP competition) and functional data (cGMP assay) as well as affinities, and epitope bins are shown in Table 8. Interestingly, WW06 had a significantly increased functional activity in FabCys format compared to IgG format as shown in FIG. 6.

TABLE 8

Summary of Affinity, Epitope, and cGMP data for WW01, WW02, WW03, WW04, and WW06 in IgG Format

| | Characterization in bivalent IgG format | | | | | | | | | | | |
|---|---|---|---|---|---|---|---|---|---|---|---|---|
| | Elisa +/− 100 nM ANP IgG binding/EC$_{50}$ [nM] | | | | | | | | Flow Cytometry [S/BG] at 2 µM IgG | ANP competition | cGMP assay cGMP conc [nM] at 2 µM IgG | |
| Antibody | hNPR1 | hNPR1 + 100 nm ANP | W74R | W74R + 100 nm ANP | rNPR1 | rNPR1 + 100 nm ANP | hNPR3 | hNPR3 + 100 nm ANP | hNPR1 CHO K1 | hNPR1 CHO KI + 100 nm ANP | competition by IgG | Without ANP | +0.075 nm ANP |
| WW01 | no specific binding | 1.0 | no specific binding | no specific binding | no specific binding | no specific binding | no specific binding | no specific binding | 19.9 | 222.2 | No | 36 | 197 |
| WW02 | no specific binding | 531.6 | no specific binding | no specific binding | no specific binding | no specific binding | no specific binding | no specific binding | 2.0 | 17.4 | No | 6 | 85 |
| WW03 | 42.7 | 1.4 | no specific binding | no specific binding | no specific binding | no specific binding | no specific binding | no specific binding | 2.2 | 214.3 | No | 31 | 192 |
| WW04 | 2.5 | 4.2 | 3.5 | 1.8 | no specific binding | no specific binding | no specific binding | no specific binding | 1.9 | 46.6 | Yes | 8 | 107 |

TABLE 8-continued

Summary of Affinity, Epitope, and cGMP data for WW01, WW02, WW03, WW04, and WW06 in IgG Format

| | Characterization in bivalent IgG format | | | | | | | | | | | |
|---|---|---|---|---|---|---|---|---|---|---|---|---|
| | Elisa +/− 100 nM ANP IgG binding/EC$_{50}$ [nM] | | | | | | | Flow Cytometry [S/BG] at 2 µM IgG | ANP competition | | cGMP assay cGMP conc | |
| | | | W74R | | | | | hNPR1 | assay | | [nM] at | |
| | | | | | | | | CHO | ANP | | 2 µM IgG | |
| Antibody | hNPR1 | hNPR1 + 100 nm ANP | W74R | W74R + 100 nm ANP | rNPR1 | rNPR1 + 100 nm ANP | hNPR3 | hNPR3 _+ 100 nm ANP | hNPR1 CHO K1 | KI + 100 nm ANP | competition by IgG | Without ANP | +0.075 nm ANP |
| WW06 | 2.5 | 1.1 | 0.9 | 0.8 | no specific binding | no specific binding | no specific binding | no specific binding | 4.6 | 1.1 | Yes | 13 | 38 |

Example 6: Generation of HuCAL® Maturation Libraries

To increase affinity and biological activity of the selected antibody fragments (WW01, WW02, WW03, WW04, and WW06), LCDR3 and HCDR2 regions were exchanged in parallel by diversified cassettes/modules (Prassler et al. (2009): In vitro affinity maturation of HuCAL® antibodies: complementarity determining region exchange and Rap-MAT technology; *Immunotherapy* 1 (4), pp. 571-583, the contents of which are hereby incorporated by reference for this purpose), while the framework regions were kept constant. Parental Fab fragments were transferred from the corresponding expression vector into a library cloning vector for affinity maturation.

The generation of HuCAL® maturation libraries was performed for each maturation candidate individually. For LCDR3 optimization, an approximately 400 bp DNA fragment encoding for the LCDR3, framework 4 as well as the constant region of the light chain was removed from the sequence encoding the parental antibody by restriction digest. In order to reduce the background of the parental undiversified sequence the excised fragment was replaced by an approximately 520 bp dummy sequence via ligation, before a repertoire of DNA fragments encoding for diversified LCDR3 regions together with framework 4 and the constant domain (diversified LCDR3 cassette) was inserted via restriction digest and ligation.

In a second library set the HCDR2-encoding sequence was diversified, while the connecting framework regions were kept constant. In order to reduce the background of the parental undiversified sequence an approximately 150 bp DNA fragment containing the parental HCDR2 and the framework 3 sequences was replaced by an approximately 590 bp dummy sequence via restriction digest and ligation, before the diversified HCDR2 cassette (including framework 3) was inserted also via restriction digest and ligation.

The ten maturation libraries were successfully cloned and had library sizes between $9.2 \times 10^8$ and $2.2 \times 10^9$ cfu. Ligation mixtures were electroporated into *E. coli* cells yielding $>10^8$ independent colonies. Amplification of the library was performed as described previously (Rauchenberger et al. (2003): Human combinatorial Fab library yielding specific and functional antibodies against the human fibroblast growth factor receptor 3; *J Biol Chem* 278 (40), pp. 38194-38205, the contents of which are hereby incorporated by reference for this purpose). For quality control, approx. 10-20 single clones per library were picked randomly and sequenced.

For the selection of affinity improved candidates, phage derived from maturation libraries were subjected to three rounds of maturation panning as described further below. Panning stringency was increased by prolonged washing steps. In addition, off-rate selection was performed (Hawkins et al. (1992): Selection of phage antibodies by binding affinity. Mimicking affinity maturation. In *J. Mol. Biol.* 226 (3), pp. 889-896, the contents of which are hereby incorporated by reference for this purpose).

Example 7: Pannings and Screenings—HuCAL®

The maturation libraries were used for four different maturation panning strategies. Strategies #3 and #4 aimed for the enrichment of progenies with improved affinities compared to the parental clones. In addition, strategies #1 and #2 aimed for the enrichment of clones with improved affinities for NPR1 instead of NPR1-ANP-complex. The rationale behind that was the idea to generate candidates which are able to directly active NPR1 by a conformational change. During the panning process, all maturation libraries were kept separately. The panning strategies are summarized in Table 9 in detail. The outputs of the third panning rounds were subsequently sub-cloned into a bacterial expression vector and bacterial lysates (BEL) were used for SET screening.

TABLE 9

Overview of HuCAL ® Maturation Panning Strategies

| Strategy | Parental antibodies | 1st round | 2nd round | 3rd round | comments |
|---|---|---|---|---|---|
| 1 | WW01 WW02 WW03 WW04 WW06 | CHO-K1 NPR1 cells | hNPR1 solution | CHO-K1 NPR1 cells | Cell/solution panning aiming for improved candidates |
| 2 | WW01 WW02 WW03 WW04 | CHO-K1 NPR1 cells | hNPR1-ANP-complex solution | CHO-K1 NPR1 cells | Cell/solution panning aiming for improved candidates |
| 3 | WW01 WW02 WW03 WW04 | hNPR1-ANP-complex solution | CHO-K1 NPR1-ANP-complex Cells | hNPR1-ANP-complex solution | Solution/cell aiming for improved NPR1-ANP-complex |
| 4 | WW04 WW06 | Preadsorption on NPR1-ANP complex CHO-K1 NPR1 cells | Preadsorption on NPR1-ANP complex hNPR1 solution | Preadsorption on NPR1-ANP complex CHO-K1 NPR1 cells | Cell/solution palming aiming for improved ANP competitors |

The outputs of the 3rd panning rounds were used for Solution Equilibrium Titration (SET) screening. 88 clones per subcode (2640 clones in total) were analyzed in SET screening for improved affinity for hNPR1 and/or hNPR1-ANP-complex compared to the parental clones.

Figure 7:
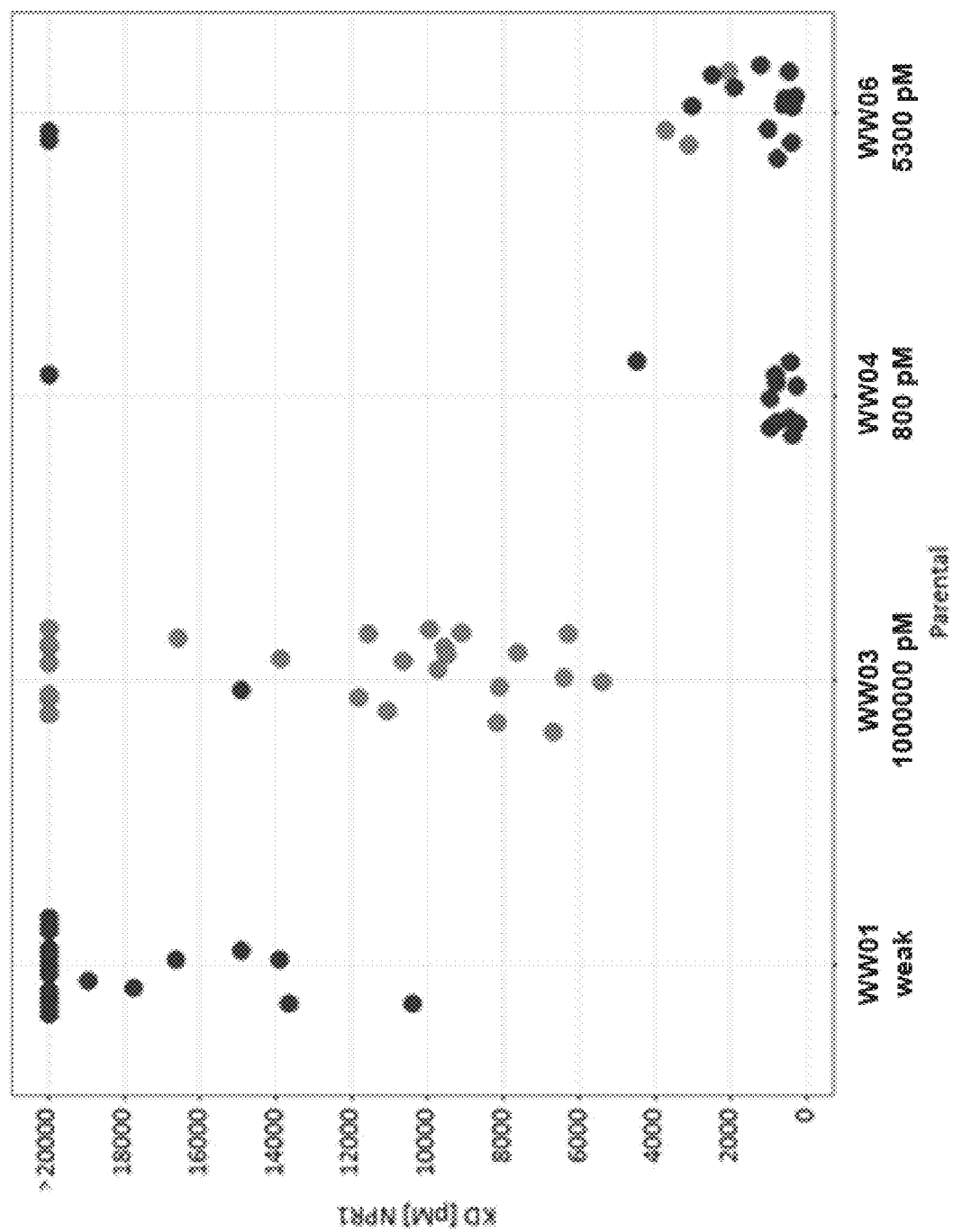
FIG. 7 demonstrates the results of SET screening (hNPR1 affinity) of 82 HCDR2 or LCDR3 unique improved HuCAL® derivatives based on the parental antibody.
Figure 8:
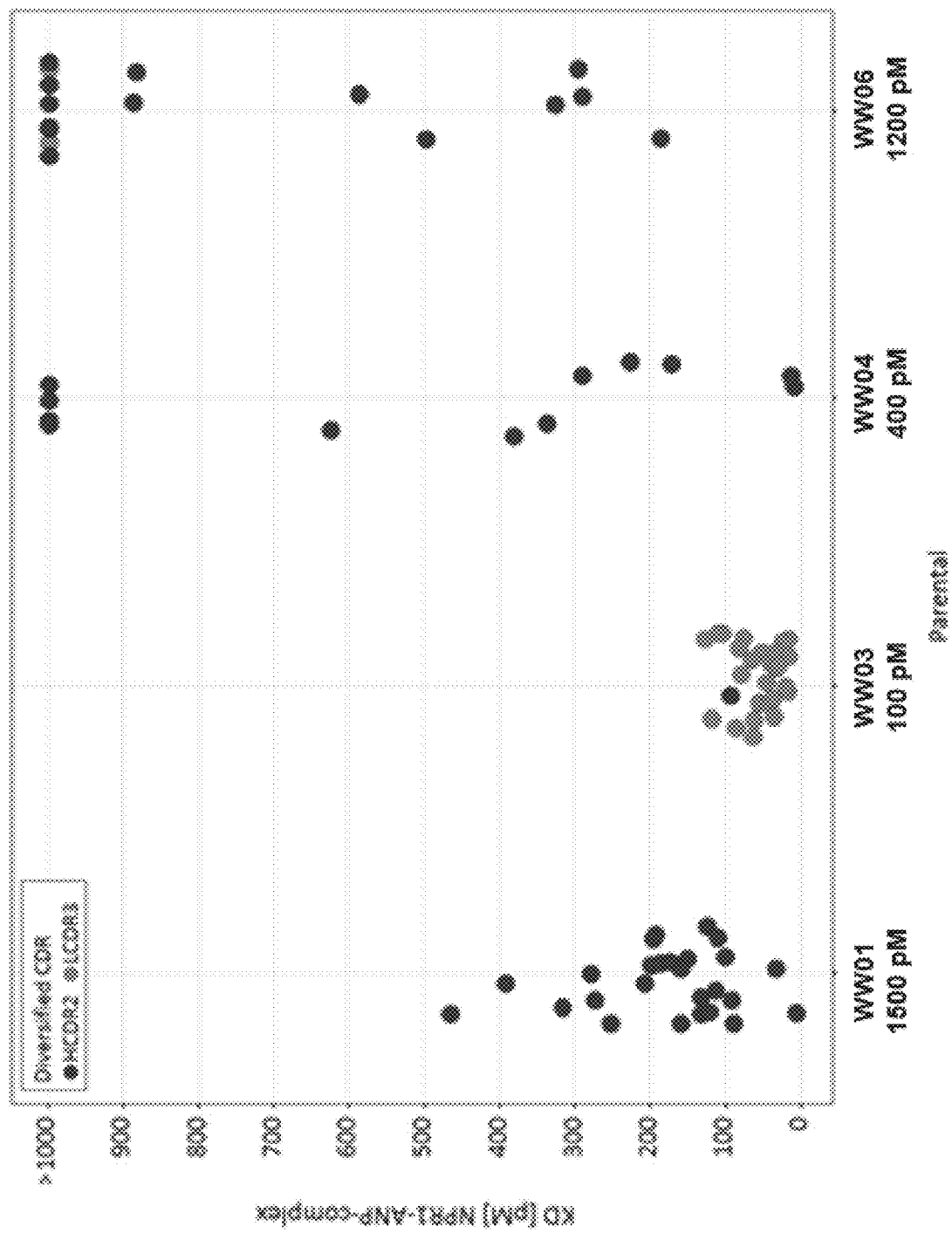
FIG. 8 demonstrates the results of SET screening (hNPR1-ANP complex affinity) of 82 HCDR2 or LCDR3 unique improved HuCAL® derivatives based on the parental antibody.
Figure 9A:
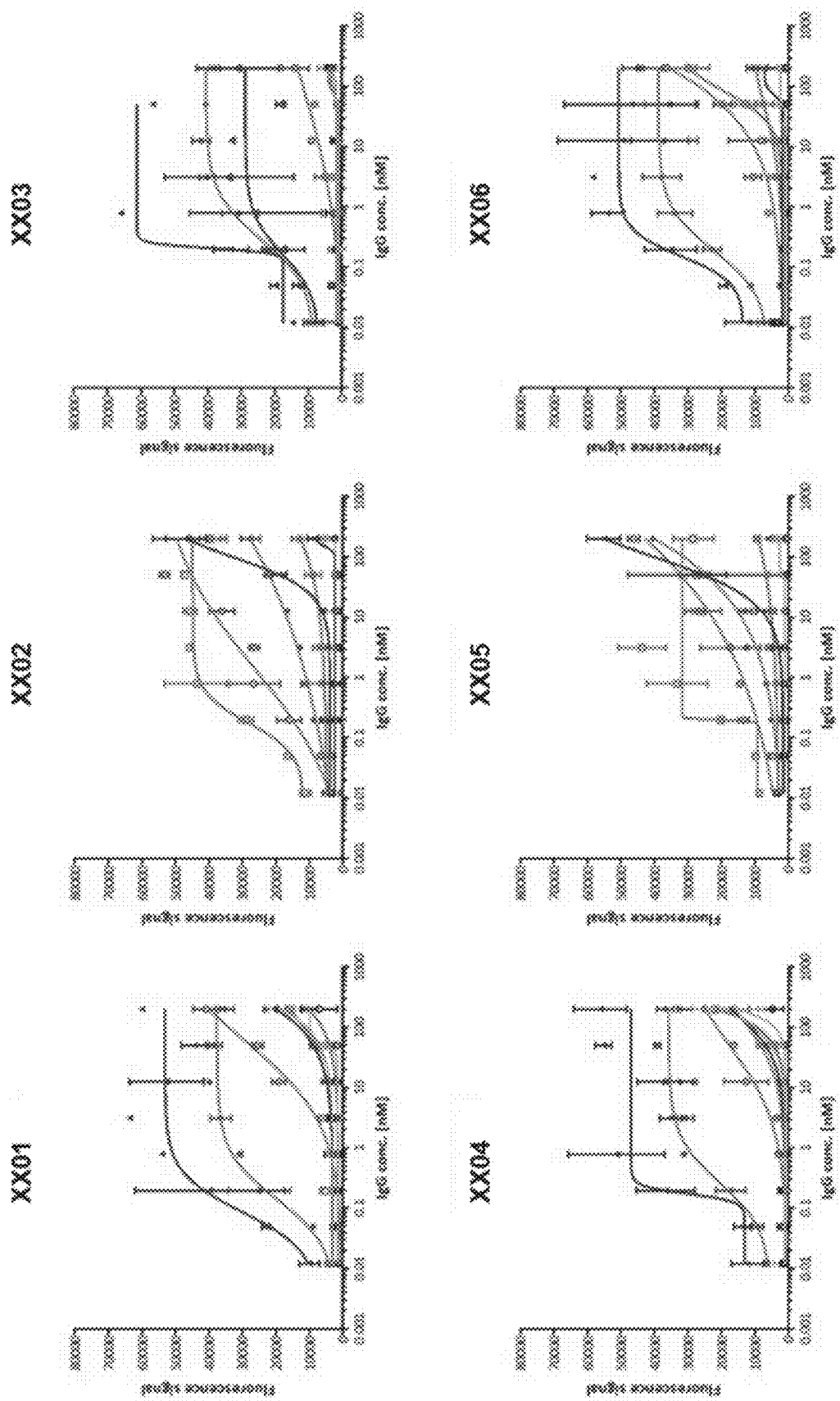
Figure 10A:
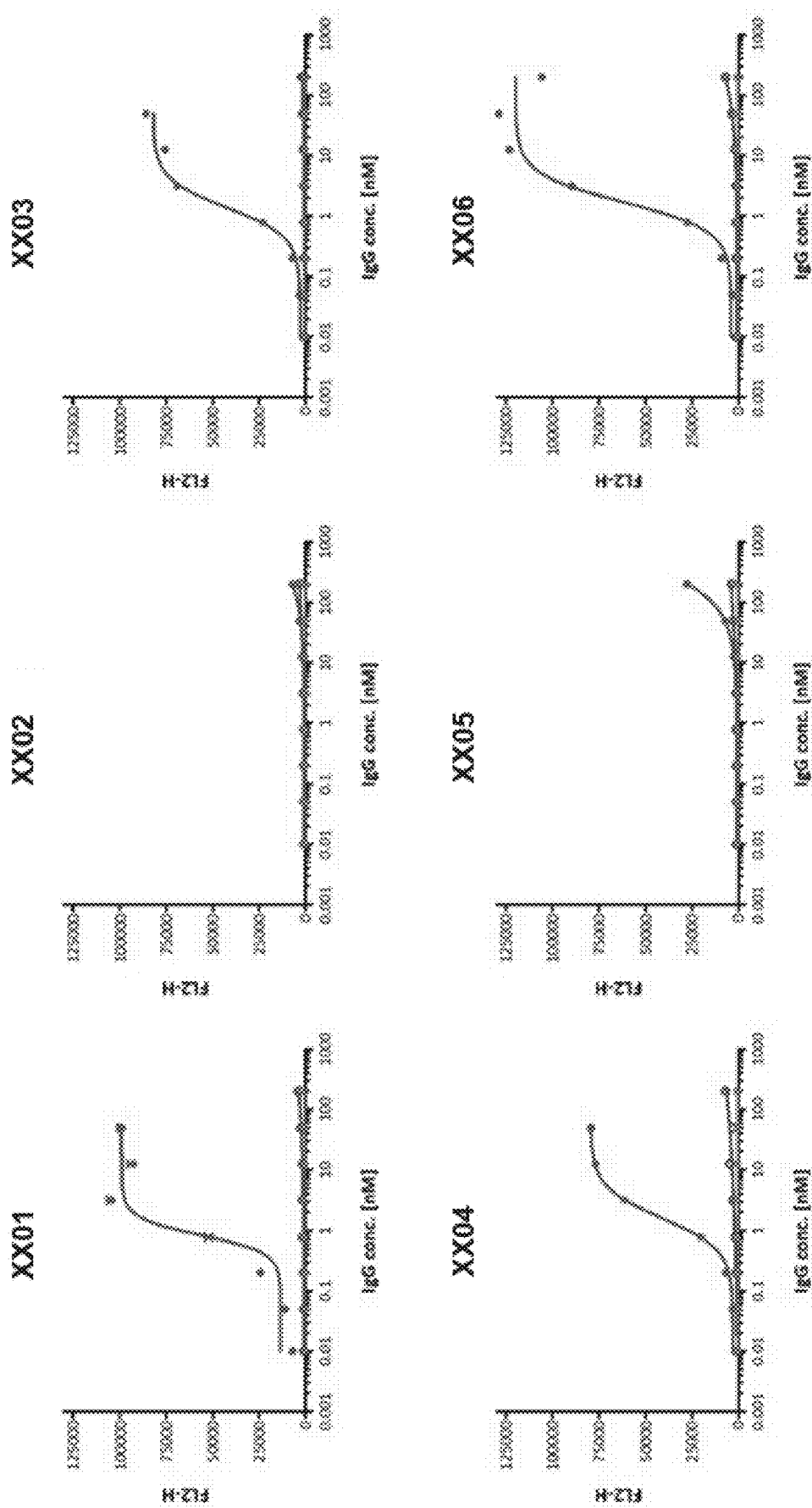
FIGS. 10A and 10B show a set of graphs displaying the results of flow cytometry analysis of antibody candidates XX01-XX08, XX10, and XX12 for binding to human NPR1 expressing CHO-K1 cells in the absence or presence of a saturating concentration of ANP and on parental CHO-K1 cells.
Figure 10B:
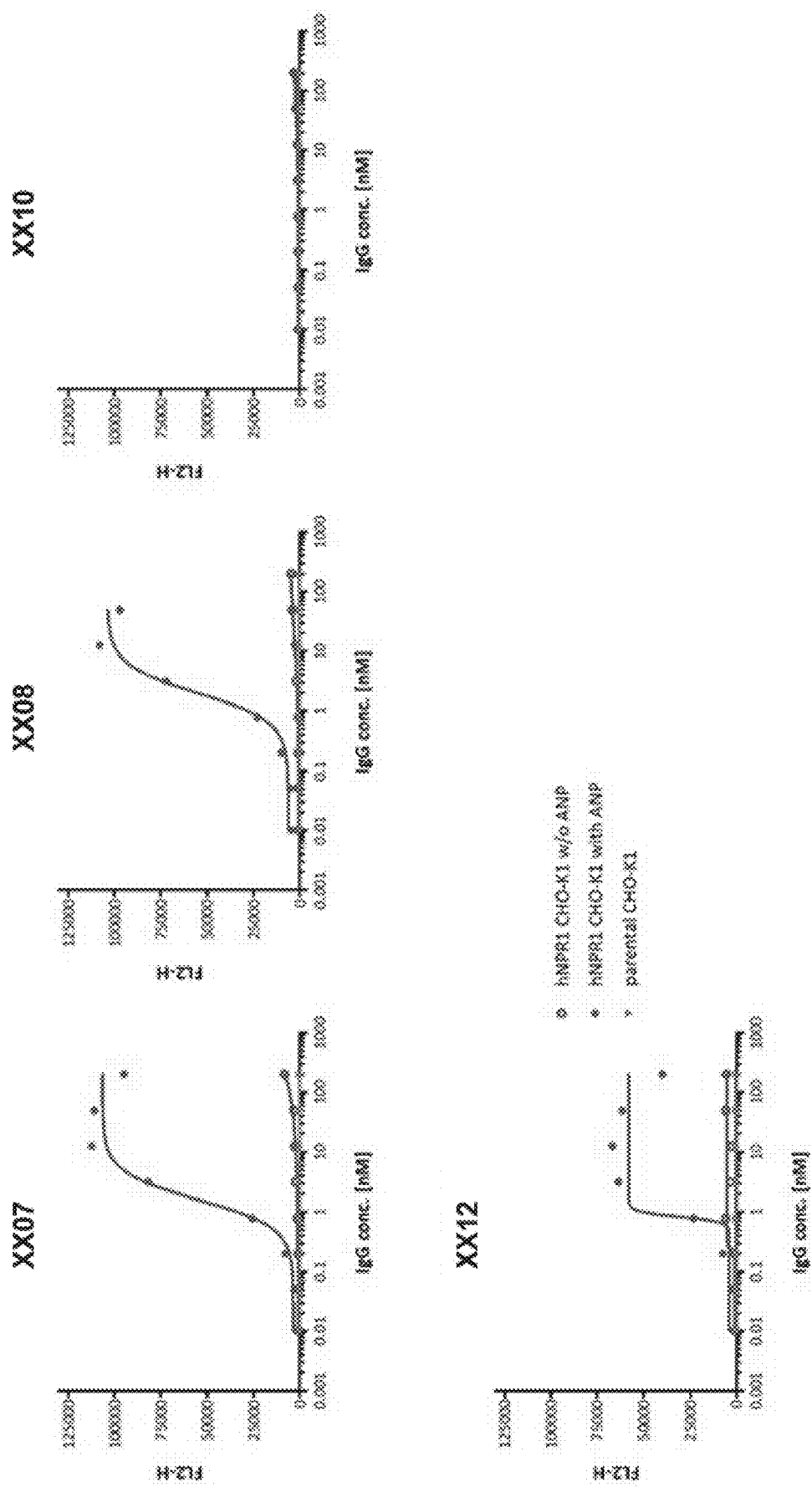

During SET screening, 82 HCDR2 or LCDR3 unique improved derivatives were identified. Compared to their parental clones, the affinities of WW01 and WW03 derivatives were improved up to 20-fold both for hNPR1 and hNPR1-ANP-complex. The affinities of the WW04 derivatives were not improved significantly, while the WW06 derivatives had up to 3-fold improved affinities compared to the parental clone. See FIG. 7 (which shows affinities for hNPR1) and FIG. 8 (which shows affinities for hNPR1-ANP complex) Affinities ($K_D$ [pM]) are indicated at the x-axis below the parental clone name for both figures.

Example 8: Characterization of Matured Candidates—HuCAL®

74 of the 82 improved candidates were successfully subcloned into FabCys format and 61 of the 74 clones passed the production quality control and were characterized in regard to binding to relevant antigens, binding to relevant cell lines, ANP competition, and functional activity in the cGMP production assay in comparison to their parental clones. All 16 derivatives of WW01 and all 27 derivatives of WW03 had up to 20-fold improved binding and functional activity. The majority of the derivatives also showed improved binding and functionality in the presence of ANP. Some derivatives showed binding to W74R (constitutively active hNPR1 mutant), which was not true for the parental FabCys. One of the four derivatives of WW04 had two-fold improved binding and functional activity, while the rest behaved like the parental FabCys. All 14 derivatives of WW06 had improved binding for NPR1 and remained competitive with ANP. The functional activities of 10 of the 14 progenies were improved up to three-fold compared to the parental FabCys. Some derivatives displayed rat cross-reactivity, which was not true for the parental FabCys.

After FabCys characterization, a further 40 of the 61 derivatives were selected for IgG conversion and further characterization. Ten potential candidates shown in Table 10 were then assayed with respect to binding to relevant antigens, binding to relevant cell lines, ANP competition, and functional activity in the cGMP production assay in comparison to their parental clones. They were further analyzed via 3P assay and their affinities for human and rat NPR1 in absence and presence of ANP were determined via SET $K_D$ measurement. WW01 and WW03 derivative antibodies were analyzed in IgG format and the WW06 derivatives in FabCys format.

For protein panel profiling (Frese et al. (2013): An automated immunoassay for early specificity profiling of antibodies; mAbs 5 (2), pp. 279-287, the contents of which are herein incorporated by reference for this purpose), 32 different proteins and controls were coated on two 384-well MSD standard plates at a concentration of 1.0 µg/mL at 4° C. overnight. The coating solution was discarded and plates were blocked with 50 µL 3% (w/v) BSA in PBS for one hour at RT on a microtiter plate shaker (~500 rpm) followed by three washing steps with 50 µL washing buffer (PBS with 0.05% (v/v) Tween 20). Antibody samples were diluted to 100 nM and 10 nM in assay buffer (PBS with 0.5% (w/v) BSA, 0.05% (v/v) Tween 20). As controls, a reference antibody (Fab or IgG, depending on the sample format) and assay buffer were used. Samples and controls were added at 304/well and incubated for three hours at RT on a microtiter plate shaker. The plates were washed three times and 304 detection antibody (ECL-labeled anti-human Fab) were added per well and incubated for one hour on a microtiter plate shaker (~500 rpm). After washing the MSD plate and adding 35 µL/well MSD Read Buffer T with surfactant, electrochemiluminescence signals were detected using a Sector Imager 6000 (Meso Scale Discovery; Gaithersburg, Md., USA). For evaluation, signals of the antibody sample on a certain protein were divided by the respective signals of the reference mAb resulting in a binding ratio (BR). The cumulative binding ratio (CBR) of all proteins except the controls (25 in total) was then calculated: CBR up to 150 represented an antibody or fragment thereof without detectable non-specific binding. Values above represented an antibody or fragment thereof with increased non-specific binding compared to a reference mAb.

TABLE 10

Overview of Matured HuCAL ® Candidates

| Matured antibody | Parental antibody | Matured CDR |
|---|---|---|
| XX01 | WW01 | HCDR2 |
| XX02 | WW06 | HCDR2 |
| XX03 | WW03 | HCDR2 |
| XX04 | WW03 | LCDR3 |
| XX05 | WW06 | HCDR2 |
| XX06 | WW03 | LCDR3 |
| XX07 | WW03 | LCDR3 |
| XX08 | WW01 | HCDR2 |
| XX10 | WW06 | HCDR2 |
| XX12 | WW03 | LCDR3 |

Figure 11A:
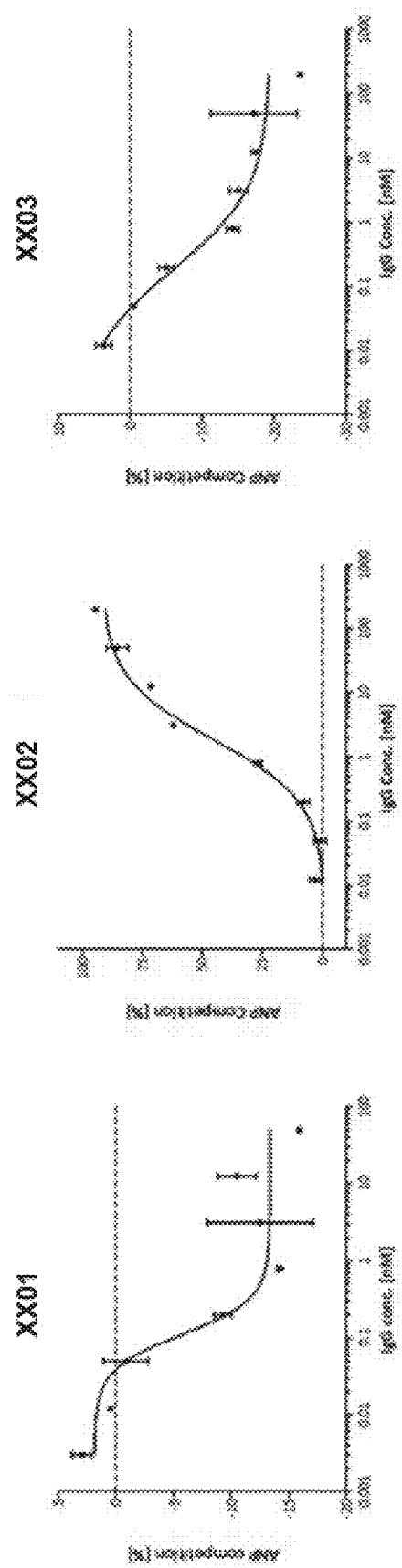
FIGS. 11A, 11B, and 11C show a set of graphs displaying the results of ANP competition analyses of candidates XX01-XX07, XX10, and XX12 using the FRET-based assay depicted in FIG. 3.
Figure 11B:
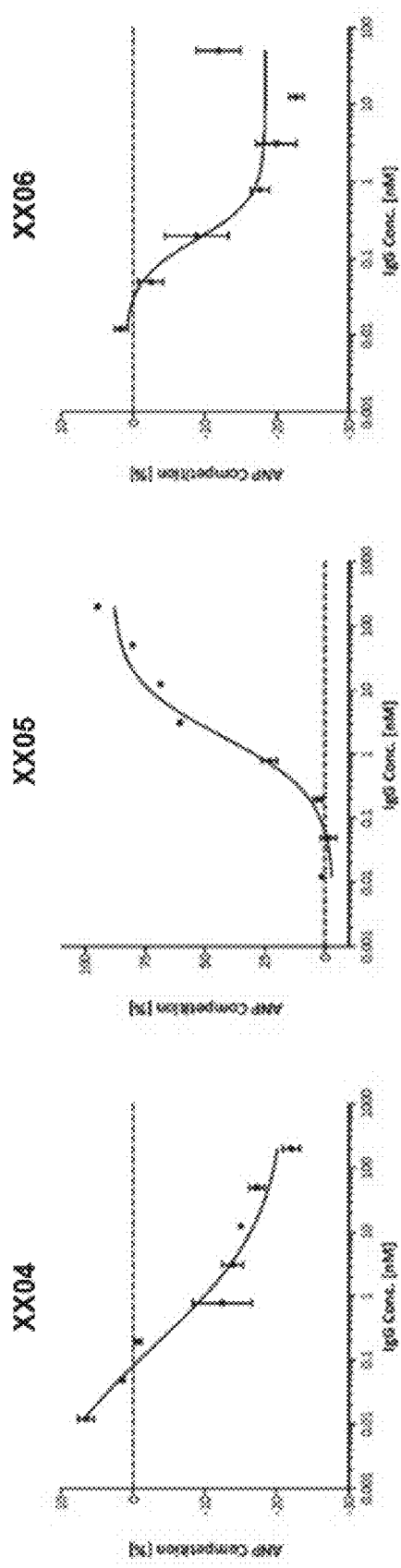
Figure 11C:
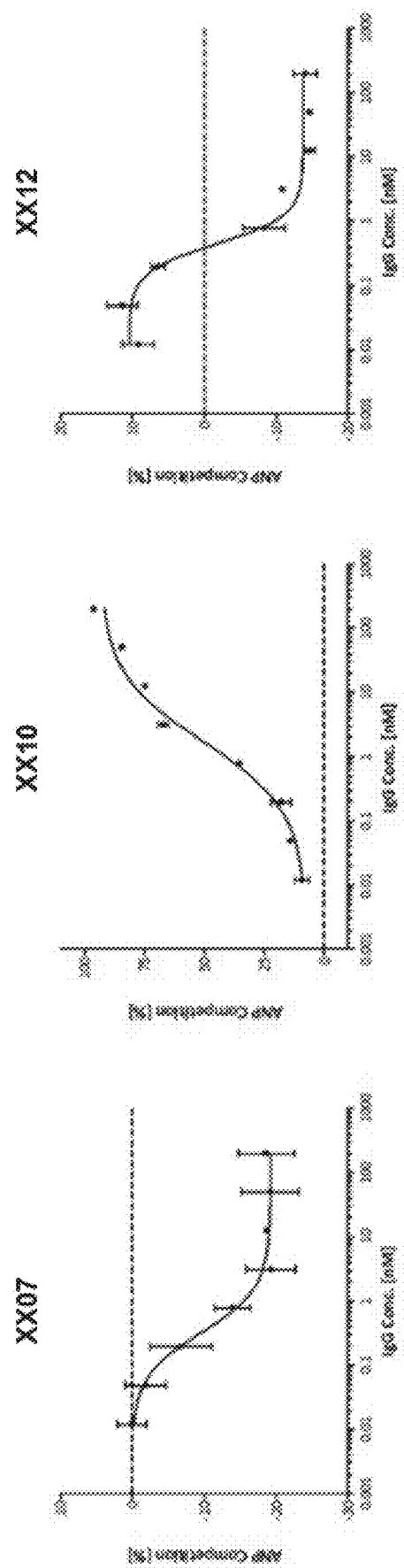

Furthermore, the clones were tested via ELISA for binding to the following antigens: human NPR1, constitutively active human NPR1 mutant (W74R), rat NPR1, human NPR3 (counter target), each in the absence and presence of ANP, and BSA. The clones were also analyzed by flow cytometry for binding to human NPR1 expressing CHO K1 cells in absence and presence of ANP (100 nM) and to parental CHO K1 cells. The binding properties of the 10 candidates are shown in FIGS. 9A, 9B, 10A and 10B. The ANP competition results for nine of the candidates are shown in FIGS. 11A, 11B, and 11C.

Figure 12A:
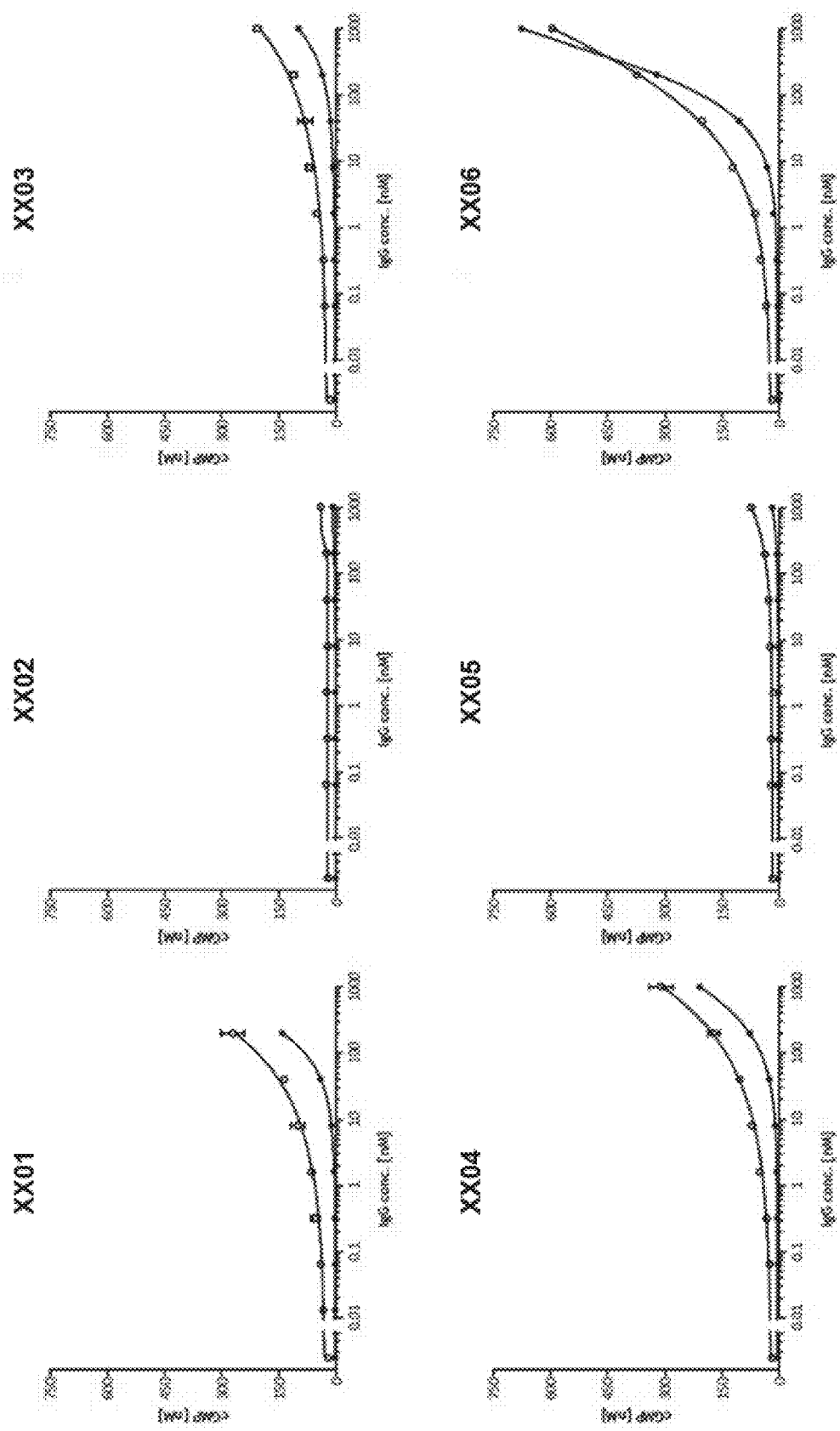
FIGS. 12A and 12B show a set of graphs depicting the results of functional activity analyses of candidates XX01-XX08, XX10, and XX12 in a cellular cGMP production assay using human NPR1 expressing CHO-K1 cells. Results represent the cellular production of cGMP [nM] in the absence or presence of 0.075 nM ANP.
Figure 12B:
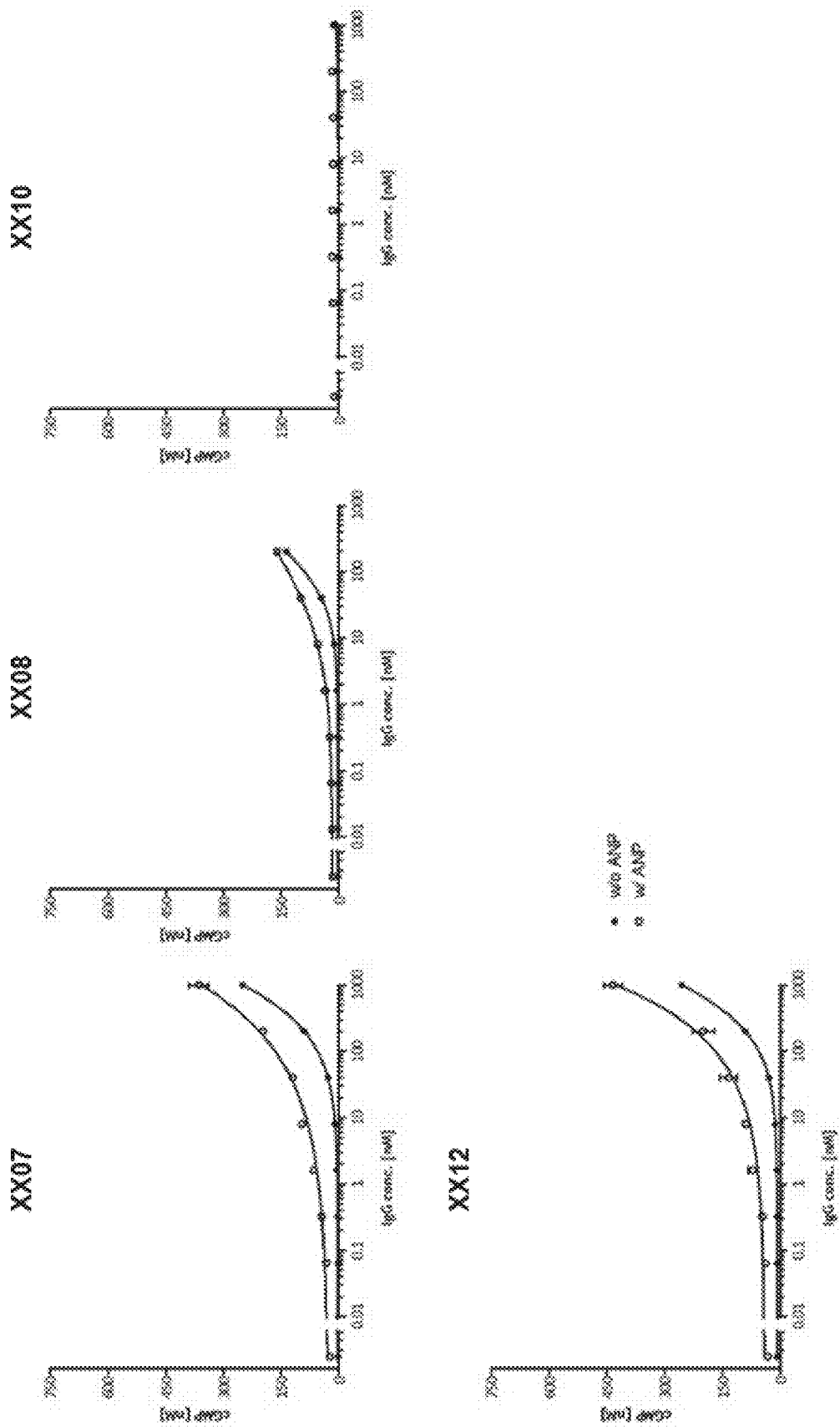

Negative values for XX01, XX03, XX04, XX06, XX07, and XX12 suggest enhancement of ANP binding by these antibodies. The functional activity of the 10 candidates was analyzed using the cellular cGMP production assay and results are shown in FIGS. 12A and 12B. As expected from the functional data of the parental clone WW06, its derivatives XX02, XX05, and XX10 showed weak to no functional activity in the IgG format, whereas they had very high functionality in monovalent FabCys format.

The affinities for XX01-XX08, XX10, and XX12 in monovalent FabCys format were determined via SET $K_D$ measurement. The results are summarized in Table 11 in comparison to the affinities of the parental clones (determined in another experiment via Biacore®). The affinities for human and rat NPR1 of WW01 and WW03 derivatives were improved up to 2,300-fold, while the affinities for the NPR1-ANP-complexes were only slightly improved (maximal 5-fold). They had affinities between 10 and 46 nM for hNPR1 and between 100 and 300 pM for hNPR1-ANP-complex. All WW01 and WW03 progenies displayed rat cross-reactivity with rat/human $K_D$ ratios<5. The affinities of the WW06 derivatives for human NPR1 and hNPR1-ANP-complex were improved maximally 8-fold and had $K_D$ values between 1 and 5 nM, while no binding to rat NPR1 or rat NPR1-ANP-complex could be observed.

TABLE 11

Affinities of Parental and Matured HuCAL ® Candidates

| | Affinity (SET measurement) FabCys $K_D$ [nM] | | | |
|---|---|---|---|---|
| Antibody | hNPR1 | hNPR1 + ANP | rNPR1 | rNPR1 + ANP |
| WW01 | weak | 1.5 | weak | 2.0 |
| XX01 | 43 | 0.3 | 1.4 | 0.5 |
| XX08 | 46 | 0.3 | 1.8 | 0.2 |
| WW03 | 1000 | 0.1 | 2600 | 1.0 |
| XX03 | 22 | 0.2 | 1.1 | 0.1 |
| XX04 | 32 | 0.1 | 3.3 | 0.3 |
| XX06 | 10 | 0.1 | 2.3 | 0.3 |
| XX07 | 21 | 0.2 | 2.9 | 0.5 |

TABLE 11-continued

Affinities of Parental and Matured HuCAL ® Candidates

| | Affinity (SET measurement) FabCys $K_D$ [nM] | | | |
|---|---|---|---|---|
| Antibody | hNPR1 | hNPR1 + ANP | rNPR1 | rNPR1 + ANP |
| XX12 | 16 | 0.2 | 3.0 | 0.5 |
| WW06 | 5.3 | 12 | — | — |
| XX02 | 1.0 | 1.4 | — | — |
| XX05 | 3.2 | 5.1 | — | — |
| XX10 | 2.2 | 4.0 | — | — |

Example 9: Cross-Cloning and PTM Removal

Parental clone WW03 had a 'DG' site in HCDR2. The majority of the WW03 derivatives (26 out of 27) were diversified in LCDR3. Only one candidate (XX03) was diversified in HCDR2 including the mutation of 'DG' into 'DK' at amino acid position 54 in the heavy chain variable region (see, e.g., position 54 of SEQ ID NO: 122). The light chains of the functional LCDR3 diversified clones were cross-cloned with the heavy chain of XX03 to engineer these clones without loss of functionality. Furthermore, the 'DG' to 'DK' mutation was inserted in the original heavy chains of several LCDR3 diversified derivatives. An overview of exemplary cross-cloned and D54K engineered candidates is shown in Table 12.

TABLE 12

Overview of VL-VH Cross-cloned and D54K Engineered Clones (WW03 derivatives)

| Antibody | Light chain origin | Heavy chain origin |
|---|---|---|
| XX13 | XX06 | WW03 D54K |
| XX14 | XX09 | |
| XX15 | XX04 | XX03 |
| XX16 | XX06 | |
| XX17 | XX07 | |
| XX18 | XX09 | |
| XX19 | XX11 | |
| XX20 | XX12 | |

Figure 13:
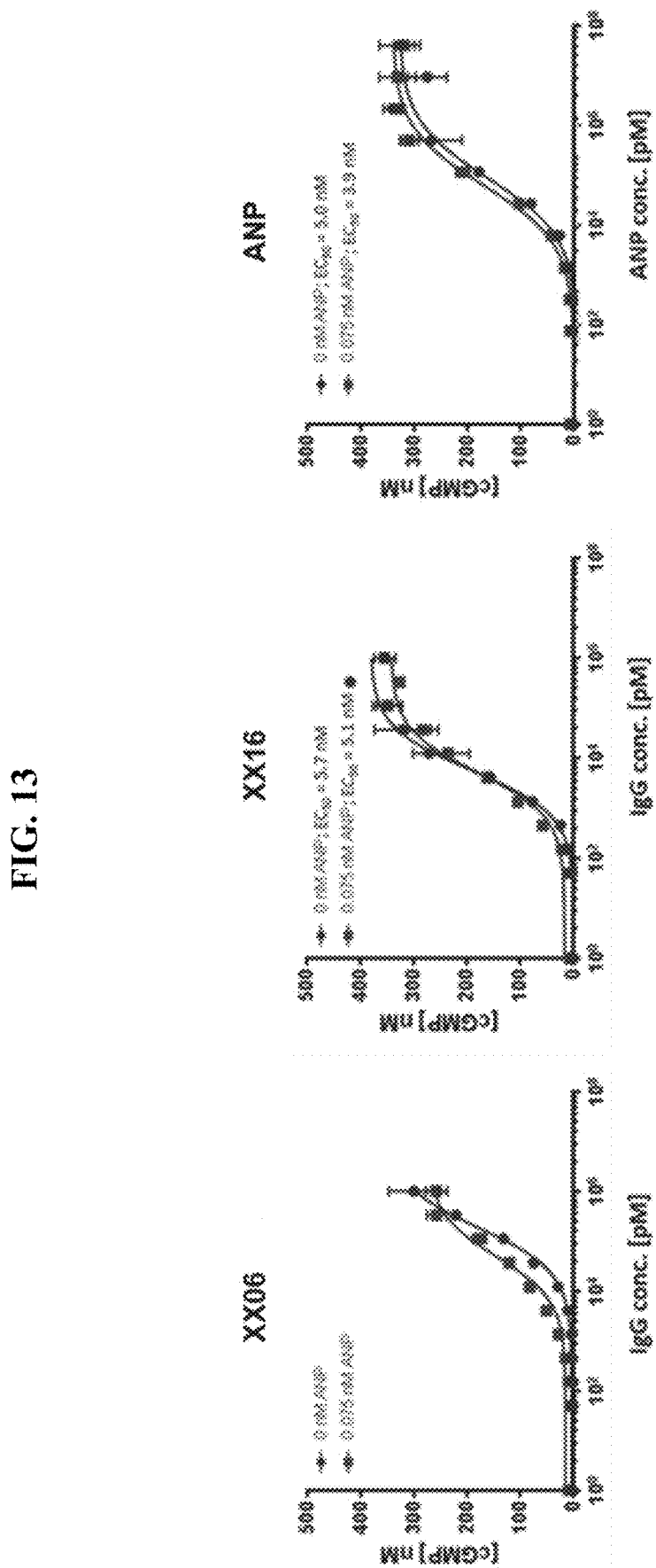
FIG. 13 is a set of graphs depicting the results of functional activity analyses of candidates XX06 and XX16 alongside natural ligand ANP in a cellular cGMP production assay using human NPR1 expressing CHO-K1 cells. Results represent the cellular production of cGMP [nM] in the absence or presence of 0.075 nM ANP.
Figure 14:
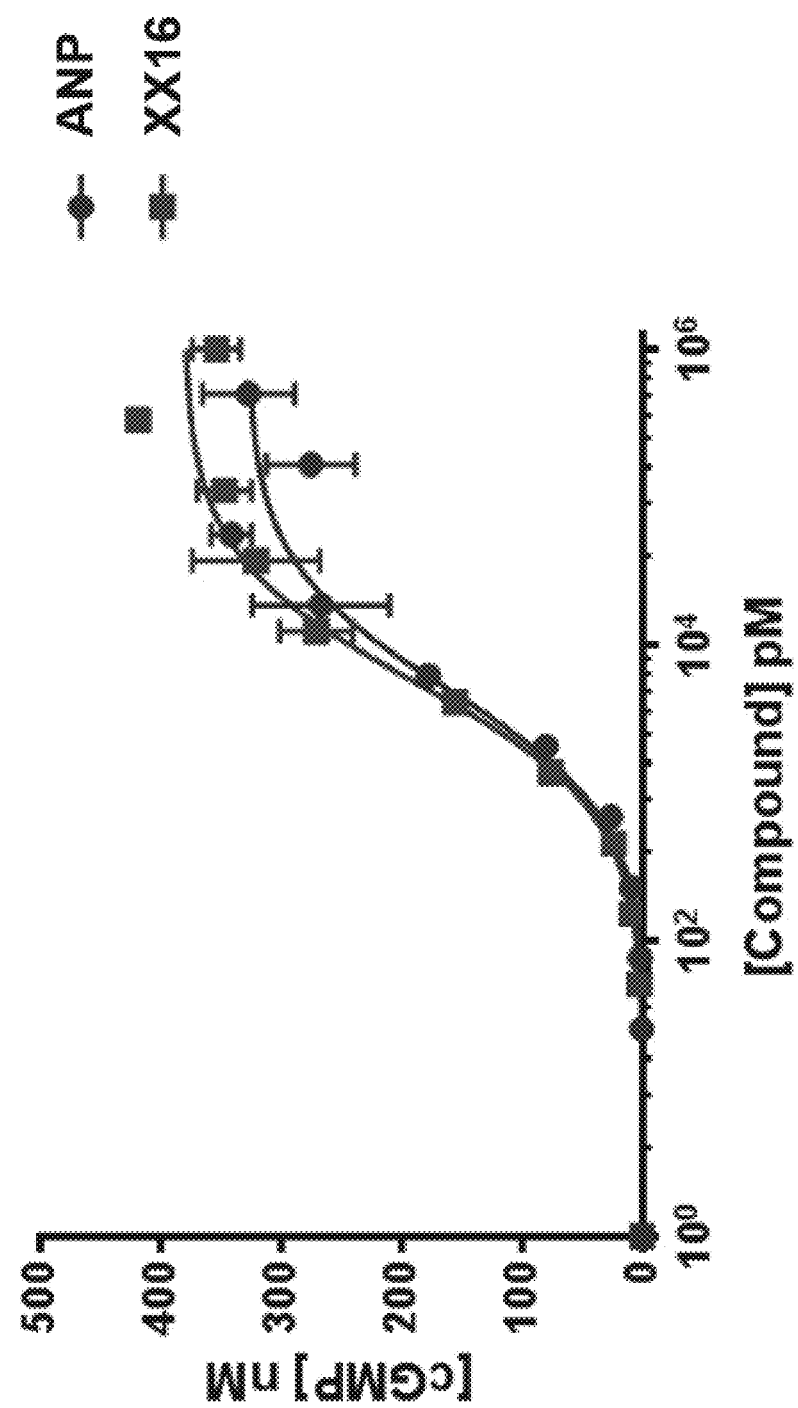
FIG. 14 is a graph depicting the results of functional activity analyses of candidate XX16 alongside natural ligand ANP in a cellular cGMP production assay using human NPR1 expressing CHO-K1 cells. Results represent the cellular production of cGMP [nM] as a function of either ANP or XX16.

Exemplary functional data of a cross-clone (XX16) compared to the original clone (XX06) and ANP are shown in FIG. 13. All cross-clones had similar or even better functional activity compared to their original clones. XX16 even had a maximal cGMP concentration comparable to the natural ligand ANP in an in vitro study analyzing their activity in hNPR1 transformed CHO cells (see FIG. 14).

Cross-cloned and PTM removed clones were tested for their specificity via 3P assay. Both D54K engineered clones XX13 and XX14 showed non-specific binding to several antigens and were deselected, while no cross-clone showed non-specific binding. Results are shown in Table 13.

TABLE 13

In vitro functional data for XX15 and XX16 cGMP Generation for human, rat, cyno NPR1 and human NPR2 expressing CHO cells

| Antibody | hNPR1 EC50 (nM) +/− STDEV | hNPR1 Y max (% of ANP) +/− STDEV | rNPR1 EC50 (nM) +/− STDEV | rNPR1 Y max (% of ANP) +/− STDEV | cNPR1 EC50 (nM) +/− STDEV | cNPR1 Y max (% of ANP) +/− STDEV | hNPR2 EC50 (nM) | hNPR2 Y max (% of ANP) |
|---|---|---|---|---|---|---|---|---|
| XX16 | 3.2 +/− 0.4 | 97 +/− 1 | 8 +/− 2 | 94 +/− 8 | 12 +/− 2 | 86 +/− 2 | >500 | <1 |
| XX15 | 9.4 +/− 0.4 | 98 +/− 7 | 23 +/− 6 | 100 +/− 10 | 30 +/− 2 | 95 +/− 3 | >500 | <1 |
| XX18 | 40 +/− 10 | 110 +/− 10 | 26 +/− 9 | 99 +/− 8 | 50 +/− 10 | 90 +/− 5 | >500 | <1 |

Example 10: Crystal Structure of Anti-NPR1 Antibodies

Crystal structures for several molecules in complex with hNPR1 were created as described below.

For Fab03-WW03, the Fab construct of WW03 was complexed to the extracellular domain of hNPR1 (C264T) with a molar ratio of 2 Fab molecules for every 1 NPR1 molecule. The complex was incubated for 1 hour in the cold room rocking and then loaded onto a Superdex 200 16/60 column in the buffer 20 mM HEPES pH7.4, 100 mM NaCl. The complexed protein was separated from a small aggregate peak and the excess Fab and then concentrated to 19.8 mg/mL. The complex crystallized in space group P212121 and diffracted to a resolution of 2.89 Å. The model was built using molecular replacement with the hNPR1 structure and a Fab molecule, iteratively built in Coot and refined with Buster to an Rfree of 21.7%.

For Fab06-WW06, the Fab construct of WW06 was complexed to the extracellular domain of hNPR1 (C264T) with a molar ratio of 2 Fab molecules for every 1 NPR1 molecule. The complex was incubated for 1 hour in the cold room rocking and then loaded onto a Superdex 200 16/60 column in the buffer 20 mM HEPES pH7.4, 100 mM NaCl. The complexed protein was separated from a small aggregate peak and the excess Fab and then concentrated to approximately 20.0 mg/mL. The complex crystallized in space group P212121 and diffracted to a resolution of 2.17 Å. The model was built using molecular replacement with the hNPR1 structure and a Fab molecule, iteratively built in Coot and refined with Buster to an Rfree of 20.9%.

For Fab16-XX16, the Fab construct of XX16 was complexed to the extracellular domain of hNPR1 (C264T) with a molar ratio of 2 Fab molecules for every 1 NPR1 molecule. The complex was incubated for 1 hour in the cold room rocking and then loaded onto a Superdex 200 16/60 column in the buffer 20 mM HEPES pH7.4, 100 mM NaCl. The complexed protein was separated from a small aggregate peak and the excess Fab and then concentrated to approximately 20.0 mg/mL. The complex crystallized in space group P212121 and diffracted to a resolution of 3.02 Å. The model was built using molecular replacement with the hNPR1 structure and a Fab molecule, iteratively built in Coot and refined with Buster to an Rfree of 24.4%.

Figure 15:
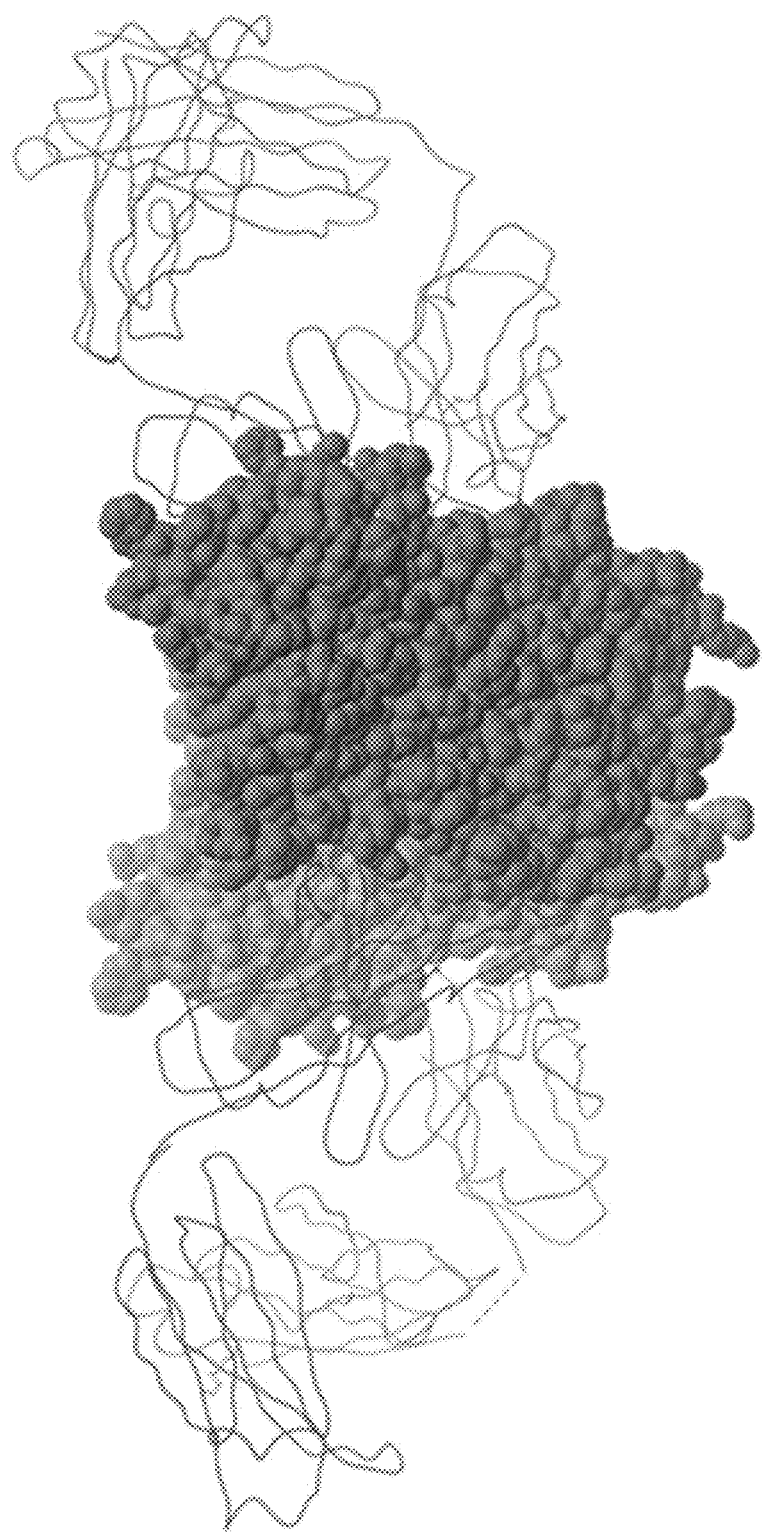
FIG. 15 is a graphical representation of the crystal structure of Fab06 (the WW06 antibody in Fab format) in complex with hNPR1 extracellular domain.
Figure 16:
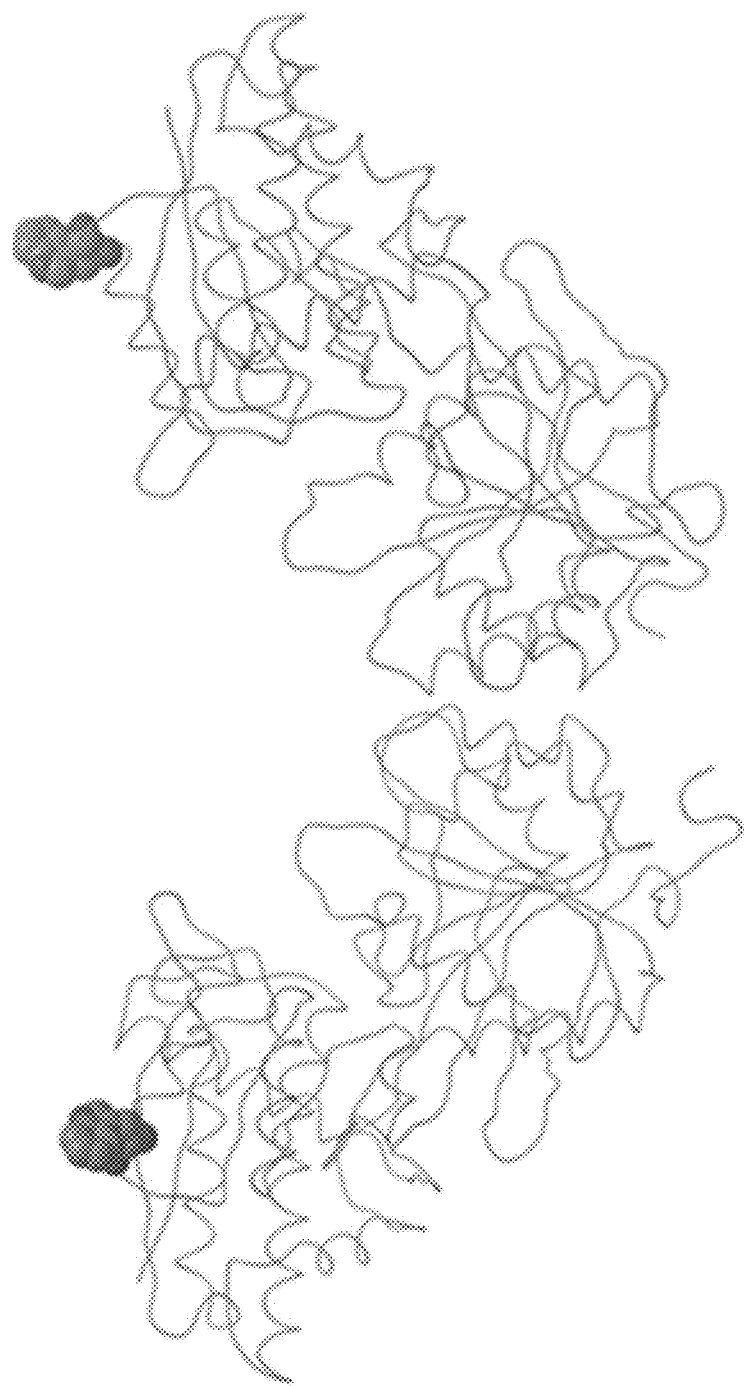
FIG. 16 is a graphical representation of the conformation of the hNPR1 extracellular domain as it would be in complex with Fab06. The Fab06 were removed from this representation to more clearly reveal the conformation of hNPR1 induced by Fab binding. W74R is shown in space filling.
Figure 17:
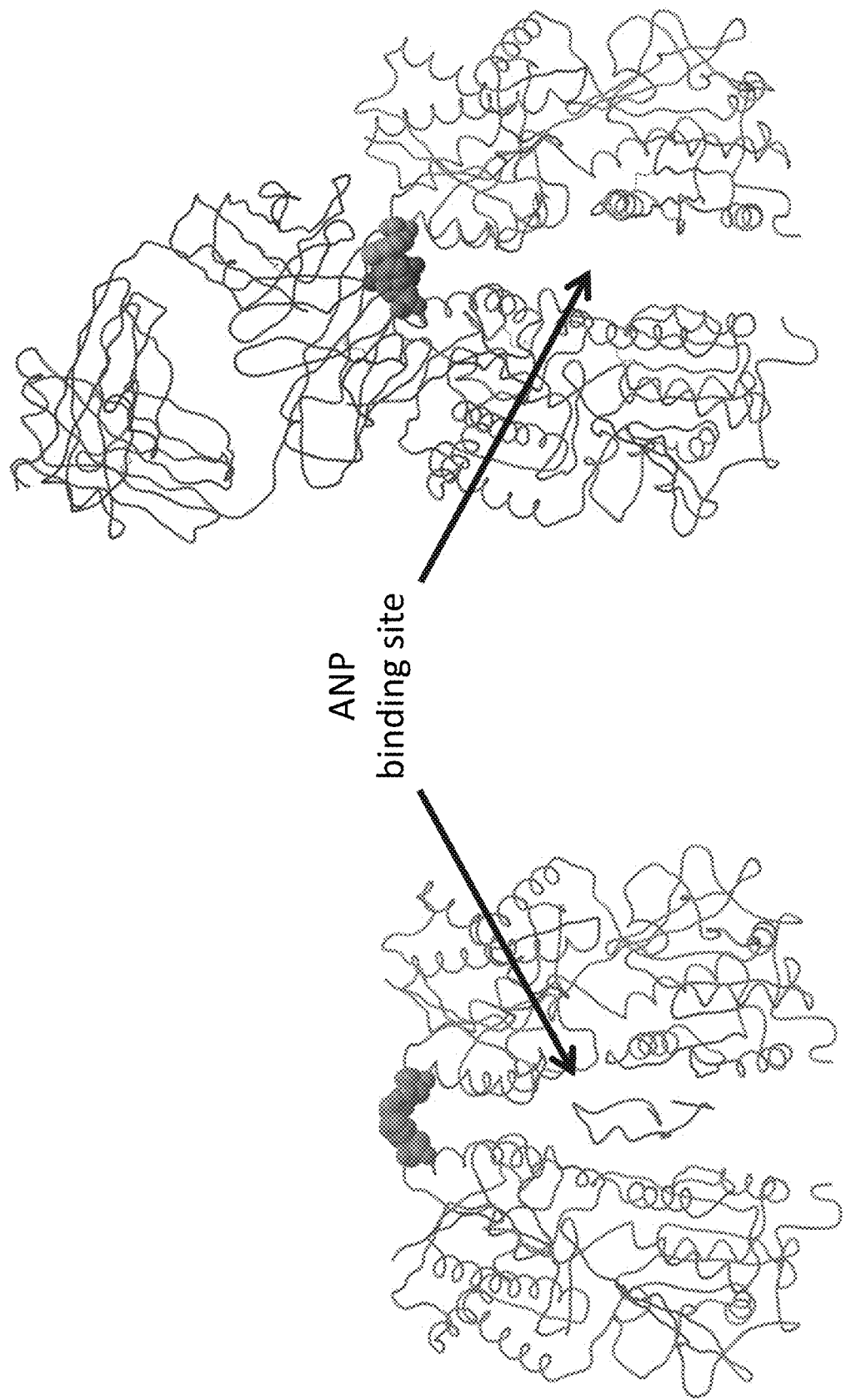
FIG. 17 is a graphical representation of the crystal structure of hNPR1 extracellular domain in complex with ANP (left) and the crystal structure of Fab 16 (the XX16 antibody in Fab format) in complex with hNPR1 extracellular domain (right) with W74 shown in space filling.
Figure 18:
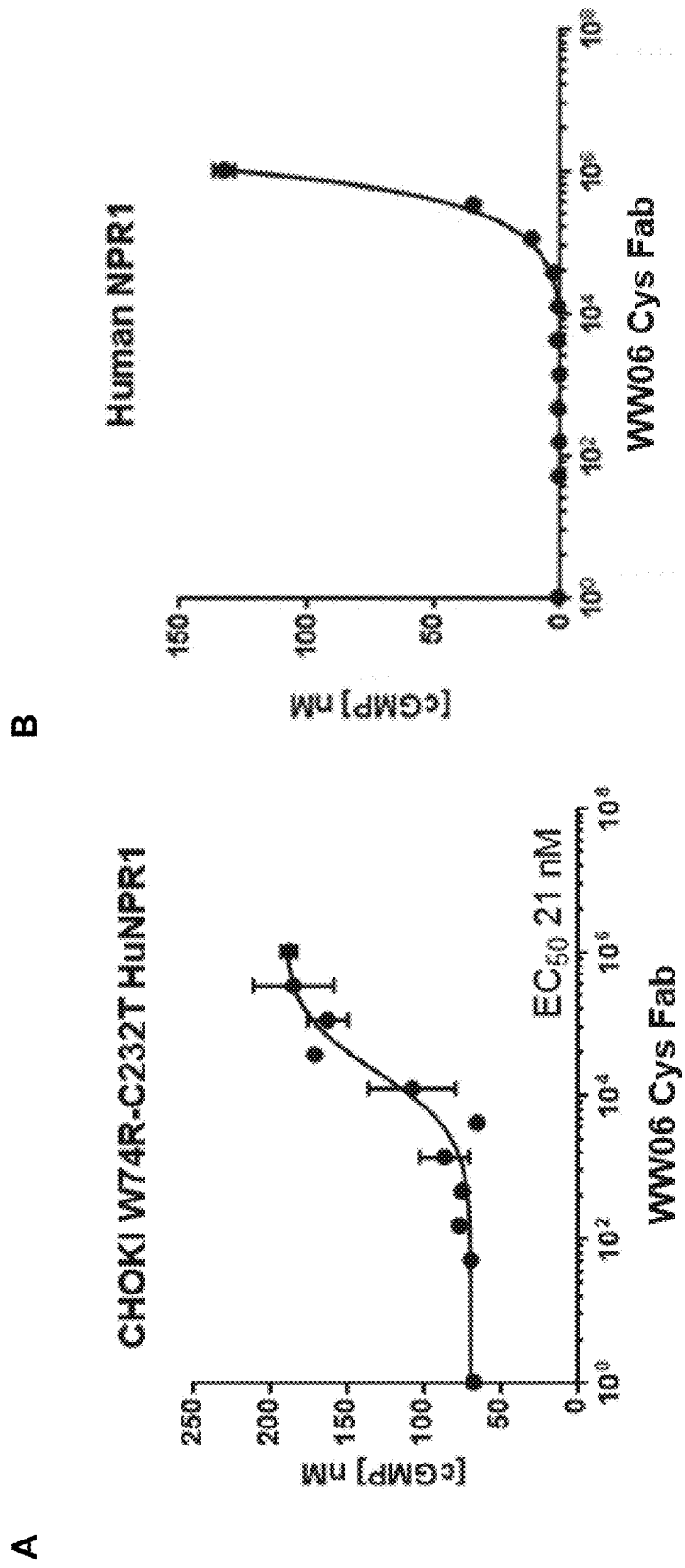
FIG. 18 is a set of graphs depicting the results of functional activity analyses of candidate WW06 in a cellular cGMP production assay using when tested on CHO-K1 cells expressing hNPR1 W74R/C232T (constitutively active mutant; panel A) compared to WT hNPR1 (panel B).
Figure 19A:
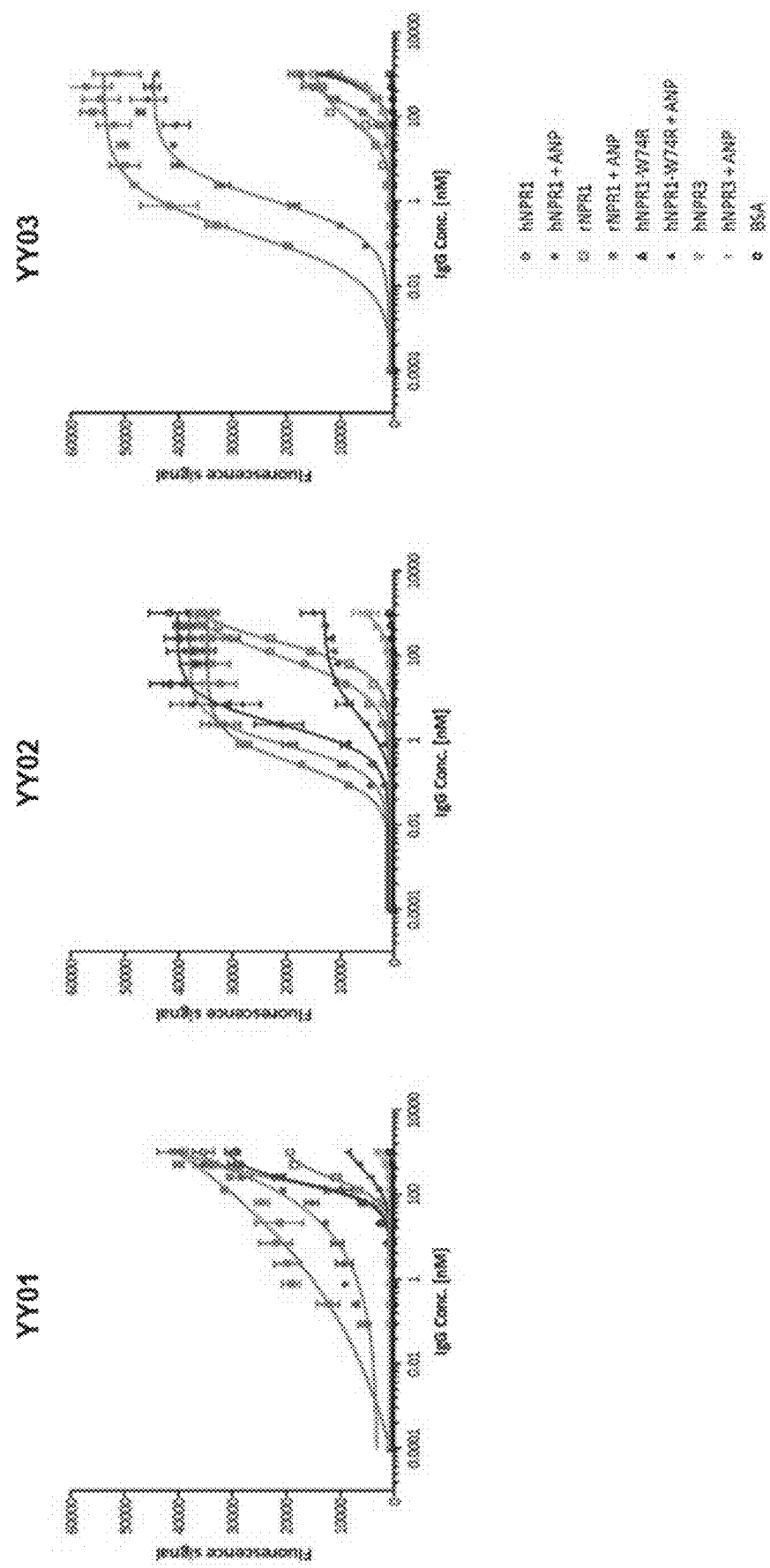
FIGS. 19A and 19B show a set of graphs displaying the results of antibody candidates YY01-YY07 binding to the following antigens (ELISA analysis) human NPR1, constitutively active human NPR1 mutant (W74R), rat NPR1, and human NPR3 (counter target) in the absence of or presence of a 250 fold molar excess of ANP.
Figure 19B:
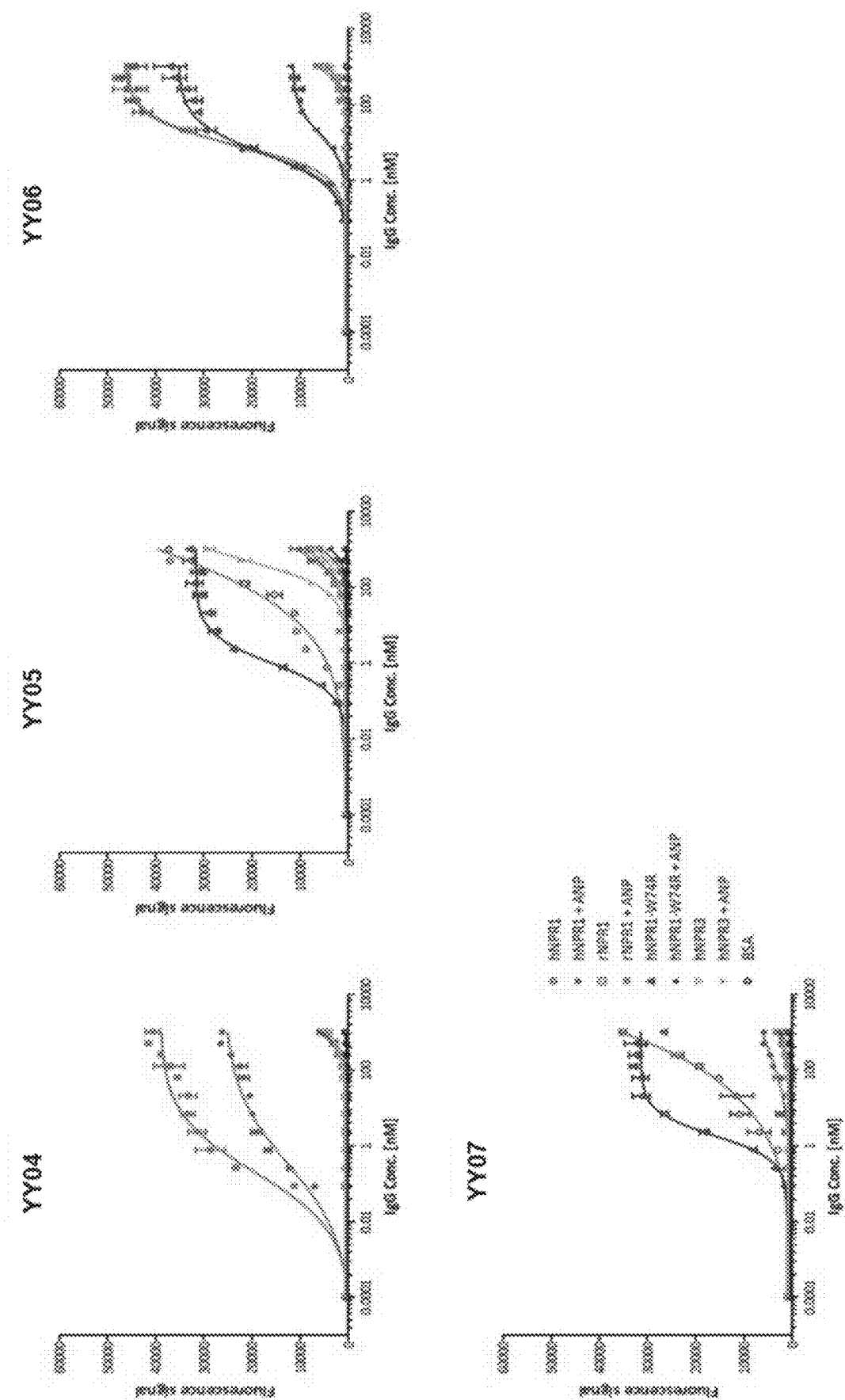
Figure 20A:
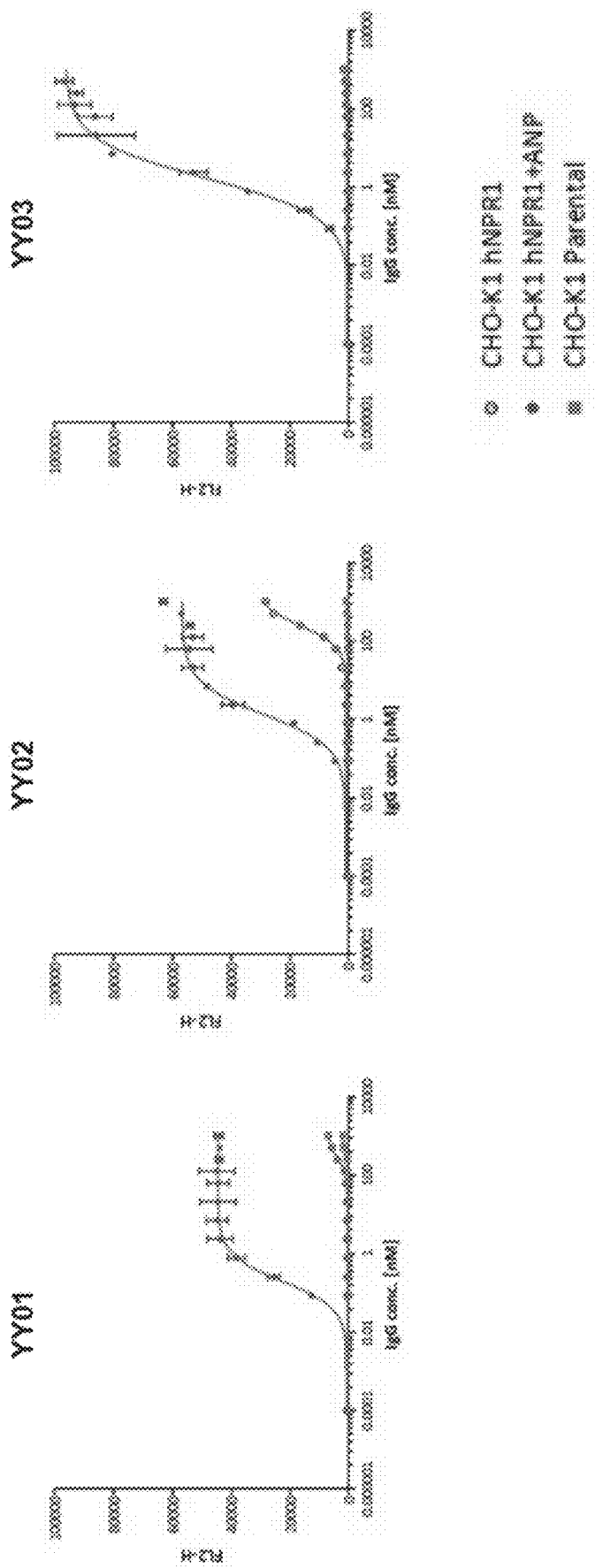
FIGS. 20A and 20B show a set of graphs displaying the results of flow cytometry analysis of antibody candidates YY01-YY07 for binding to human NPR1 expressing CHO-K1 cells in the absence or presence of a saturating concentration of ANP and on parental CHO K1 cells.
Figure 20B:
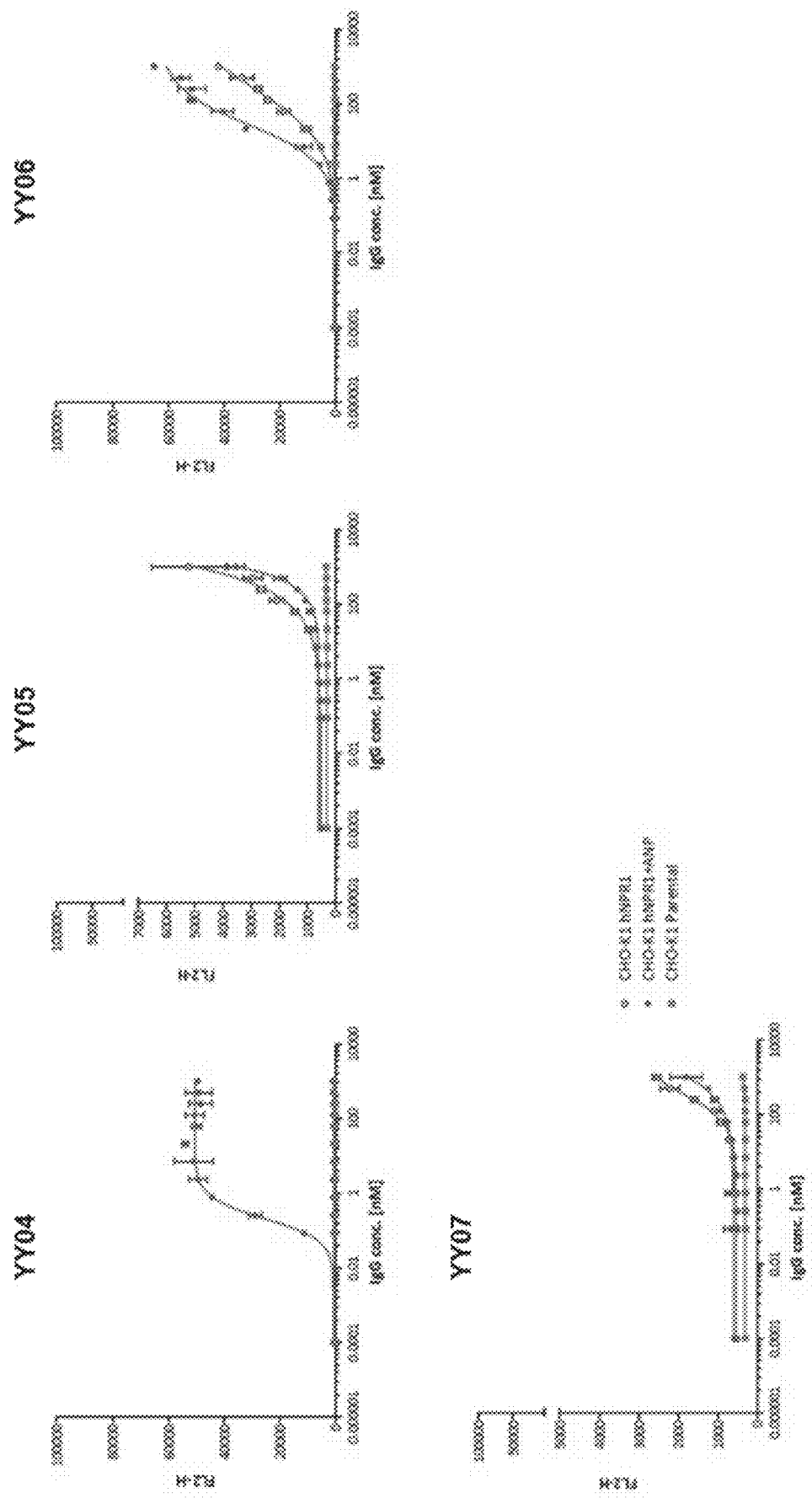

The crystal structure of Fab06 in complex with hNPR1 is shown in FIG. 15. FIG. 16 shows the conformation of the hNPR1 ECD as it would be in complex with Fab06; the Fab06 were removed from the image to more clearly reveal the conformation of hNPR1 induced by Fab binding. The structures shown in FIGS. 15 and 16 explain the discrepancy between Fab and IgG functional data shown in FIG. 6. The Fab C-termini are 180 degrees apart precluding a single IgG spanning a receptor dimer. The structure of hNPR1-ECD in complex with ANP (which was also determined as a part of this work) is shown for comparison in FIG. 17 (left), and the crystal structure of Fab 16 (the XX16 antibody in Fab format) in complex with hNPR1 extracellular domain (right). The WW06 Fab was significantly more potent (cGMP production) when tested on CHO cells expressing hNPR1 W74R/C232T (constitutively active mutant) compared to WT hNPR1 (FIG. 18, panels A and B) suggesting that the mutation destabilizes the head-to-head conformation of NPR1 and facilitates antibody binding/receptor activation.

Example 11: Ylanthia® Phage Library Panning and Screening

Six panning strategies were performed, which reflected the most successful strategies from the initial pannings (HuCAL®) or modifications of these strategies aiming for specific methods of action. The panning strategies are summarized in Table 14 in detail. Strategies #2 and #5 were identical to strategies performed in the initial HuCAL® campaign and were selected because all five initial functional candidates were derived from these panning strategies. Strategies #3 and #4 were variations from initial strategies with focus on hNPR1 alternating with hNPR1 expressing cells. In addition, a constitutively active mutant of NPR1 (W74R) was used as an antigen in strategies #1 and #6. Bacterial lysates (BEL) of the outputs of the 3rd panning rounds in phage display vector pYPDis were directly used for primary and secondary screenings.

TABLE 14

Overview of panning strategies-Ylanthia ®

| Strategy | 1st round | 2nd round | 3rd round | Comments |
|---|---|---|---|---|
| 1 | W74R hNPR1 capture | W74R hNPR1 capture | W74R hNPR1 capture | Fc capture panning with active W74R mutant only |
| 2 | hNPR1-ANP-complex solution | rNPR1-ANP-complex capture | hNPR1-ANP-complex solution | Solution/Fc capture panning aiming for enrichment of NPR1-ANP-complex |
| 3 | CHO-K1 NPR-ANP-complex cell | hNPR1-ANP-complex solution | CHO-K1 NPR-ANP-complex cell | Cell/solution panning aiming for enrichment of NPR1-ANP-complex stabilizers |
| 4 | hNPR1 solution | CHO-K1 NPR1 cell + ANP elution | hNPR1 solution + ANP elution | Solution/cell aiming for enrichment of ANP competitors |
| 5 | pre-adsorption on NPR1-ANP complex, save the unbound phage still in solution, bind to hNPR1 in solution without ANP and capture NPR1/phage complexes | pre-adsorption on NPR1-ANP complex, save the unbound phage still in solution, bind to hNPR1 in solution without ANP and capture NPR1/phage complexes | pre-adsorption on NPR1-ANP complex, save the unbound phage still in solution, bind to hNPR1 in solution without ANP and capture NPR1/phage complexes | Solution panning aiming for enrichment of ANP competitors |
| 6 | CHO-K1 NPR1 cell | W74R hNPR1 capture | CHO-K1 NPR1 cell | Cell/Fc capture panning with human antigen and active W74R mutant |

The outputs of the 3rd panning rounds were analyzed for binding to relevant antigens and cell lines. 368 clones per subcode (in total 4416 clones) were screened in ELISA-based primary screening on human NPR1 in absence and presence of ANP, constitutively active hNPR1 mutant (W74R) and counter-target human hNPR3. The primary screening yielded 810 hits, which were analyzed with respect to binding of relevant cell lines (human NPR1 expressing CHO-K1 cells in absence and presence of ANP, parental CHO-K1 cells) and rat NPR1 in secondary screening In total, 380 clones from primary and secondary screening were selected for sequencing with priority for exclusive binding to NPR1-ANP-complex, good cell binding, and rat cross-reactivity. The VL and VH sequencing resulted in 138 HCDR3 unique clones with different binding properties (Table 15). Of these clones six bound only in presence of ANP.

95 clones were selected for further analysis. 92 of the 95 FabCys passed the production quality control and were analyzed in detail. Afterwards, 30 of the 92 clones with the most promising properties were selected for IgG conversion via AmplyFly®, exploratory scale expression and S-DAS. 24 of the 30 IgGs passed the production quality control and were analyzed in detail.

All 92 FabCys and 24 IgGs were tested for binding to relevant antigens via ELISA and relevant cell lines by flow cytometry. Furthermore, the clones were tested for ANP competition and functional activity in the cellular cGMP production assay. Eight functional candidates were identified and analyzed for specificity in the Protein Panel Profiling assay (3P assay) in IgG format. For comparison, one of the functional candidates from the initial campaign (WW03) was analyzed. YY02 and YY03 showed low non-

TABLE 15

Binding properties of HCDR3 unique hits-Ylanthia ®

| | | | Binding to: | | |
|---|---|---|---|---|---|
| | Number of unique candidates | | hNPR1 | rNPR1 | hNPR1 expressing cells |
| 140 (of which 6 clones bound only in presence of ANP) | 53 human/rat cross-reactive | 2 human/rat cross-reactive cell binders | Yes | Yes | Yes |
| | | 51 human/rat cross-reactive (not binding to cells) | Yes | Yes | No |
| | 79 human specific | 14 human specific cell binders | Yes | No | Yes |
| | | 65 human specific (not binding to cells) | Yes | No | No |

Since candidate WW06 derived from the initial HuCAL® pannings was significantly more active in FabCys format compared to IgG format, the functional screening was performed in FabCys format rather than IgG format.

Figure 21A:
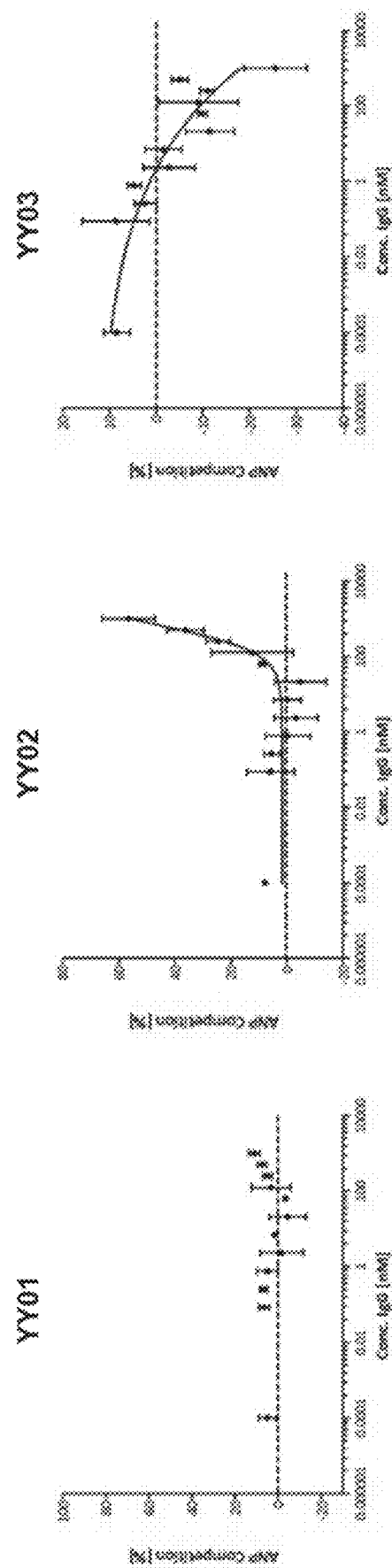
FIGS. 21A and 21B show a set of graphs displaying the results of ANP competition analyses of candidates YY01-YY07 using the FRET-based assay depicted in FIG. 3.
Figure 21B:
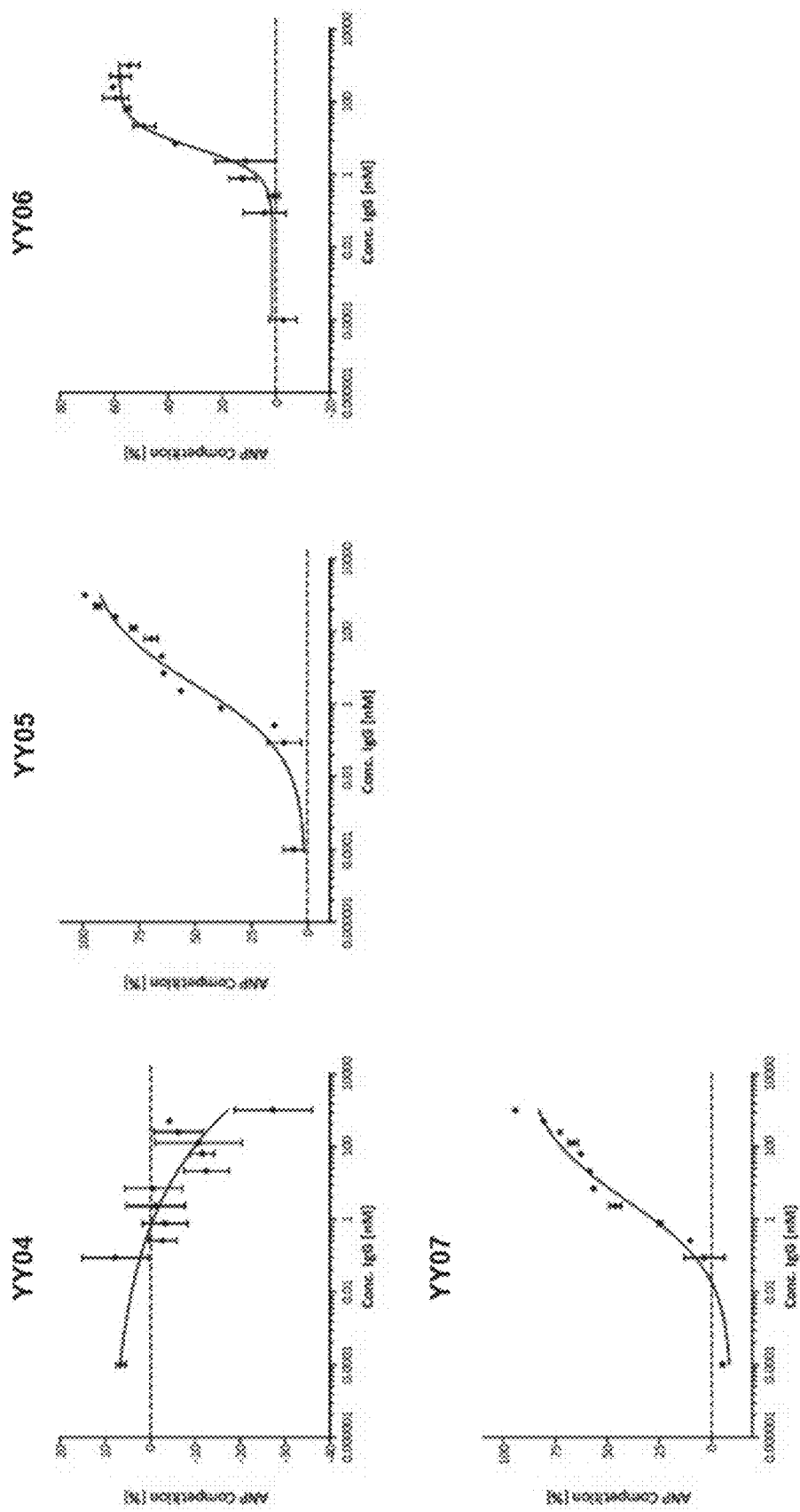

The sub-cloning of 138 HCDR3 unique clones into the FabCys format was performed via YClone®. 111 out of 138 clones were successfully converted into FabCys format and specific binding; and YY01, YY04, YY05, YY06, YY07 and WW03 did not show non-specific binding in this assay. All 92 FabCys and 24 IgGs were tested via ELISA for binding on the following antigens: human NPR1, constitutively active human NPR1 mutant (W74R), rat NPR1, human NPR3 (counter target) in the absence or presence of ANP (100 nM) and irrelevant antigens. The clones were also tested by flow cytometry for binding on human NPR1 expressing CHO K1 cells in the absence and presence of ANP and on parental CHO K1 cells. The binding properties of the seven functional candidates in IgG format are shown in FIGS. 19A, 19B, 20A and 20B. All 92 FabCys and 24 IgGs were tested for ANP competition. 22 out of 92 FabCys and 12 out of 24 IgGs showed a significant ANP competition >70% at a concentration of 1 µM FabCys/IgG. The results of the seven functional candidates in IgG format are shown in FIGS. 21A and 21B. YY02, YY05, YY06, and YY07 showed clear ANP competition. YY03 and YY04 showed a "negative" ANP competition in this assay indicating the stabilization of the NPR1-ANP-complex.

Figure 22A:
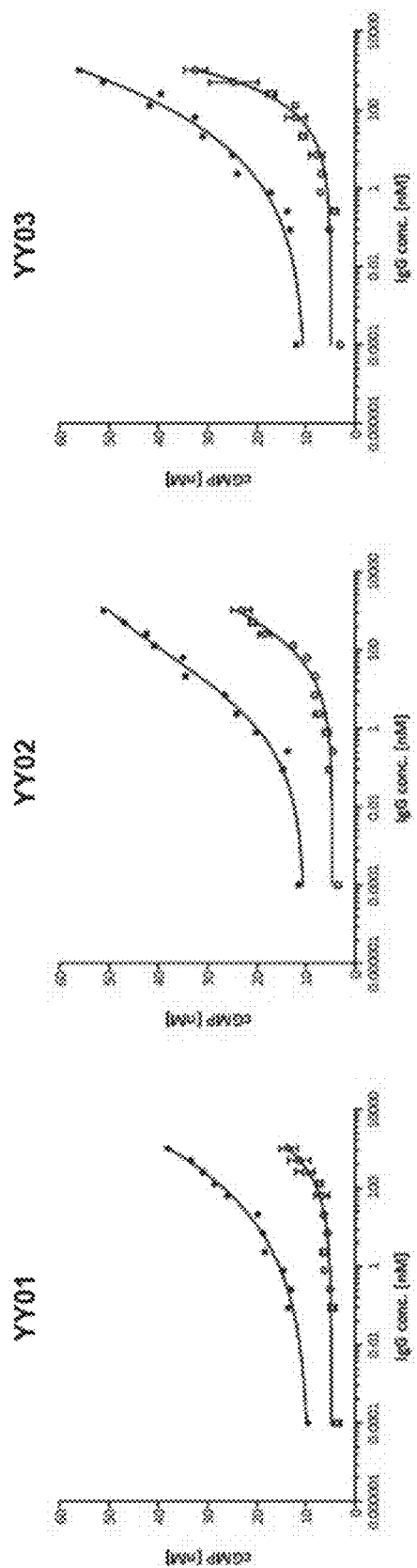
FIGS. 22A and 22B show a set of graphs depicting the results of functional activity analyses of candidates YY01-YY07 in a cellular cGMP production assay using human NPR1 expressing CHO-K1 cells. Results represent the cellular production of cGMP [nM] in the absence or presence of 0.075 nM ANP.
Figure 22B:
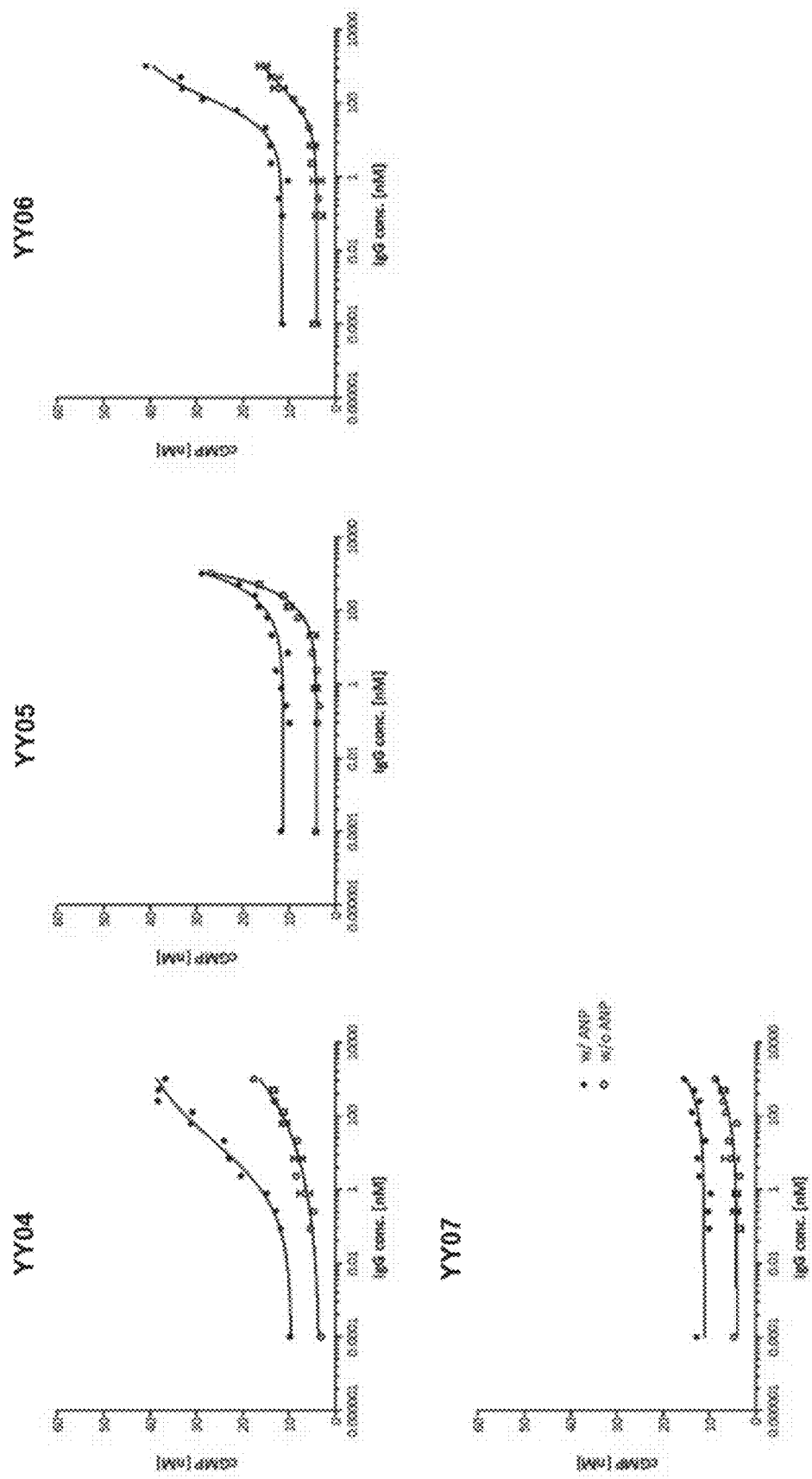
Figure 23:
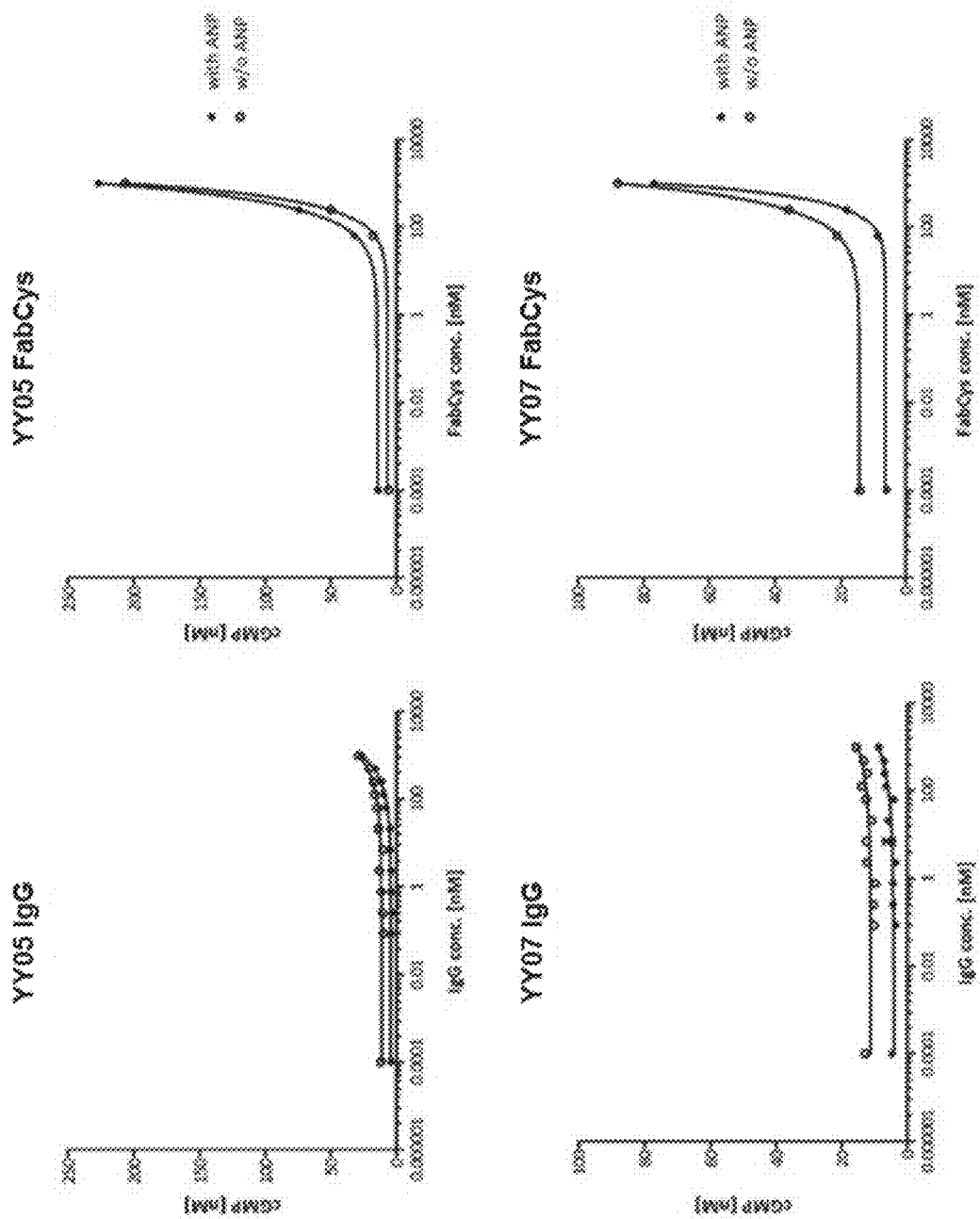
FIG. 23 is a set of graphs depicting the results of functional activity analyses of candidates YY05 and YY07 in IgG or FabCys format in a cellular cGMP production assay using human NPR1 expressing CHO-K1 cells. Results represent the cellular production of cGMP [nM] in the absence or presence of 0.075 nM ANP.

All 92 FabCys and 24 IgGs were tested for their functional activity in the cellular cGMP production assay using human NPR1 expressing CHO-K1 cells in presence and absence of ANP. 8 of the 92 FabCys and the same 8 out of 24 IgGs were functionally active and could be assigned to the different methods of action. Five out of eight clones showed much higher functional activity in presence of ANP, including YY01, YY02, YY03, and YY04. Three other clones behaved ANP independent in the functional assay, namely YY05, YY06, and YY07. All eight clones were derived from the panning strategies #2, #3 and #5, whereby #2 and #5 were exact repetitions of the initial HuCAL® panning strategies #10 and #11, which led to the identification of the five functional clones from the initial HuCAL® campaign. The results of the cGMP assay for seven functional candidates in IgG format are shown in FIGS. 22A and 22B. As seen before for candidate WW06 derived from the initial HuCAL® campaign, the functional activities of candidates YY05 and YY07 significantly increased in monovalent FabCys format compared to the bivalent IgG format (FIG. 23).

The seven functional candidates YY01-YY07 were analyzed with regard to their monovalent affinities for human and rat NPR1 in absence and presence of ANP in monovalent FabCys format. The results of the affinity determination and the epitope binning are summarized in Table 16.

The affinities were in the low nM to low µM range and strongly depended on the presence or absence of ANP. Four of the seven functional candidates showed significantly improved binding in presence of ANP (YY01, YY02, YY03, and YY04). YY05 and YY07 competed with ANP for binding to NPR1 and showed much higher affinities in absence of ANP. The affinities of YY06 were independent from ANP. Some candidates exhibited non-specific binding to the reference flow cell, while others had such high affinities that their $K_D$ values approach the assay limit. YY01, YY02, YY03, and YY04 share one epitope bin, which is the same as for WW03 from the initial HuCAL® campaign. YY05 and YY07 share another epitope bin, which is the same as for WW06 from the initial HuCAL® campaign. YY06 binds to a single epitope bin.

Example 12: Reformatting into IgG—Ylanthia®

Subcloning of the Ylanthia® candidates from the FabCys vector into the IgG1_LALA vector for expression in mammalian cells was performed via amplification of the Fab-encoding insert using two biotinylated primers. The amplified product was bound on streptavidin beads, digested using restriction enzymes, and washed, resulting in the release of the purified insert into the supernatant. The insert was cloned into the acceptor vector, the DNA was transformed and single clones were quality controlled via colony PCR and sequencing.

Five Ylanthia® candidates were selected for affinity maturation. YY01 and YY04 stabilize the NPR1-ANP-complex, YY06 behaves in an ANP-independent manner, and YY05 and YY07 are ANP-competitive. Binding data (ELISA, flow cytometry, ANP competition), functional data (cGMP assay), affinities, and epitope bins are shown in Table 17.

TABLE 16

Characterization in monovalent FabCys format - Ylanthia ®

| | Characterization in monovalent FabCys format | | | | | | |
|---|---|---|---|---|---|---|---|
| | Affinity FabCys $K_D$ [nM] | | | | Epitope | cGMP assay cGMP conc [nM] | |
| Antibody | hNPR1 | hNPR1 + ANP | rNPR1 | rNPR1 + ANP | Bin on hNPR1 (-ANP-complex) | Binning FabCys Without ANP | at 1 µM FabCys +0.075 nm ANP |
| YY01 | — | 16 | — | 14 | B | 15 | 46 |
| YY02 | 45 | 1.1 | 280 | 4.4 | B | — | — |
| YY03 | — | 0.1 | 0.1 | 0.1 | B | — | — |
| YY04 | 4.9 | 1.1 | — | 1 | B | 18 | 67 |
| YY05 | 0.9 | 350 | 700 | 16000 | A | 207 | 227 |
| YY06 | 0.5 | 1 | 1600 | 1400 | C | 20 | 75 |
| YY07 | 1.8 | 590 | — | — | A | 77 | 88 |

TABLE 17

Summary of Affinity, Epitope, and cGMP data for YY01, YY04, YY08, YY06, and YY07 in IgG Format Characterization in bivalent IgG format

| | Elisa +/− 100 nM ANP IgG binding at 1 µM IgG | | | | | | | | Flow Cytometry [S/BG] at 1 µM IgG | | ANP competition assay | cGMP assay cGMP conc [nM] | |
|---|---|---|---|---|---|---|---|---|---|---|---|---|---|
| | | | | | | | | | hNPR1 CHO KI + | | ANP compe- | at 1 µM IgG | |
| Antibody | hNPR1 | hNPR1 + 100 nM ANP | W74R | W74R + 100 nM ANP | rNPR1 | rNPR1 + 100 nM ANP | hNPR3 | hNPR3 + 100 nM ANP | hNPR1 CHO K1 | 100 nM ANP | tition by IgG | Without ANP | +0.075 nm ANP |
| YY01 | 54 | 76 | 33 | 53 | 26 | 50 | 18 | 6 | 35 | 21 | yes | 5 | 14 |
| YY04 | 31 | 60 | 11 | 13 | 8 | 54 | 69 | 18 | 2 | 33 | no | 10 | 15 |
| YY05 | 81 | 32 | 69 | 23 | 11 | 16 | 7 | 4 | 15 | 5 | yes | 13 | 15 |
| YY06 | 91 | 102 | 83 | 86 | 3 | 4 | 6 | 6 | 26 | 18 | yes | 12 | 15 |
| YY07 | 68 | 24 | 53 | 20 | 3 | 3 | 6 | 5 | 8 | 44 | yes | 4 | 9 |

Example 13: Generation of Ylanthia® Maturation Libraries

To increase affinity and biological activity and to reduce non-specificity of selected antibody candidates, LCDR3 and HCDR1/HCDR2 regions were optimized in parallel using diversified Ylanthia® maturation modules (YMM) previously generated with Slonomics® technology (van den Brulle et al. (2008): A novel solid phase technology for high-throughput gene synthesis; *Biotechniques* 45 (3), pp. 340-343, the contents of which are herein incorporated by reference for this purpose).

Cloning of the maturation libraries was performed in vectors encoding the parental Fab fragments. The generation of the maturation libraries was performed for five parental antibodies (YY01, YY04, YY05, YY06, and YY07). For the library generation, all maturation candidates were treated individually. The maturation libraries were successfully cloned and had library sizes between $6.2 \times 10^8$ and $4.5 \times 10^9$ cfu.

In order to monitor the cloning efficiency, the parental HCDR1/2 and LCDR3 were replaced by MBP-stuffers prior to insertion of the diversified YMM. Digested vector fragments were ligated with a 2-fold molar excess of the insert fragments carrying the diversified HCDR1/2 or LCDR3s. Ligation mixtures were electroporated in *E. coli* cells yielding in $>10^8$ independent colonies. Amplification of the library was performed as described in the literature (Tiller et al. (2013): A fully synthetic human Fab antibody library based on fixed VH/VL framework pairings with favorable biophysical properties; mAbs 5 (3), pp. 445-470, the contents of which are herein incorporated by reference for this purpose). For quality control, approx. 10-20 single clones per library were randomly picked and sequenced.

Example 14: Pannings and Screenings—Ylanthia®

The nine maturation libraries were used for four different maturation panning strategies, which aimed for the enrichment of progenies with improved affinities compared to the parental clones. Furthermore, rat material was included where appropriate and the pannings were performed with high stringencies concerning antigen concentration and washing conditions. During the panning process, the libraries of YY01 and YY04 (only LCDR3) as well as YY05 and YY07 were pooled, while the libraries of YY06 were kept separately. The panning strategies are summarized in Table 18 in detail. The bacterial lysates (BEL) of the outputs after the third panning rounds were directly used for an ELISA-based pre-screening and for SET screening.

TABLE 18

Overview of Ylanthia ® Maturation Panning Strategies

| Strategy | Parental antibodies | 1st round | 2nd round | 3rd round | comments |
|---|---|---|---|---|---|
| 1 | YY01/ YY04 | hNPR1-ANP-complex solution | rNPR1-ANP-complex solution | hNPR1-ANP-complex solution | Solution panning aiming for enrichment of NPR1-ANP-complex stabilizers |
| 2 | YY06 | hNPR1-ANP-complex solution | hNPR1-ANP-complex solution | hNPR1-ANP-complex solution | Solution panning aiming for enrichment of NPR1-ANP-complex stabilizers |
| 3 | YY06 YY05/ YY07 | Preadsorption on NPR1-ANP-complex hNPR1 solution | Preadsorption on NPR1-ANP-complex hNPR1 solution | Preadsorption on NPR1-ANP-complex hNPR1 solution | Solution panning aiming for enrichment of ANP competitors |
| 4 | YY05/ YY07 | Preadsorption on NPR1-ANP-complex hNPR1 solution | Preadsorption on NPR1-ANP-complex hNPR1 solution | Preadsorption on NPR1-ANP-complex rNPR1 solution | Solution panning aiming for enrichment of ANP competitors |

The outputs of the third panning rounds were used for an ELISA-based pre-screening to ensure that only clones binding to NPR1 and/or NPR1-ANP-complex were selected for further Solution Equilibrium Titration (SET) screening. 880 clones in total were analyzed in SET screening for improved affinity for hNPR1 and/or hNPR1-ANP-complex compared to the parental clones.

Figure 24:
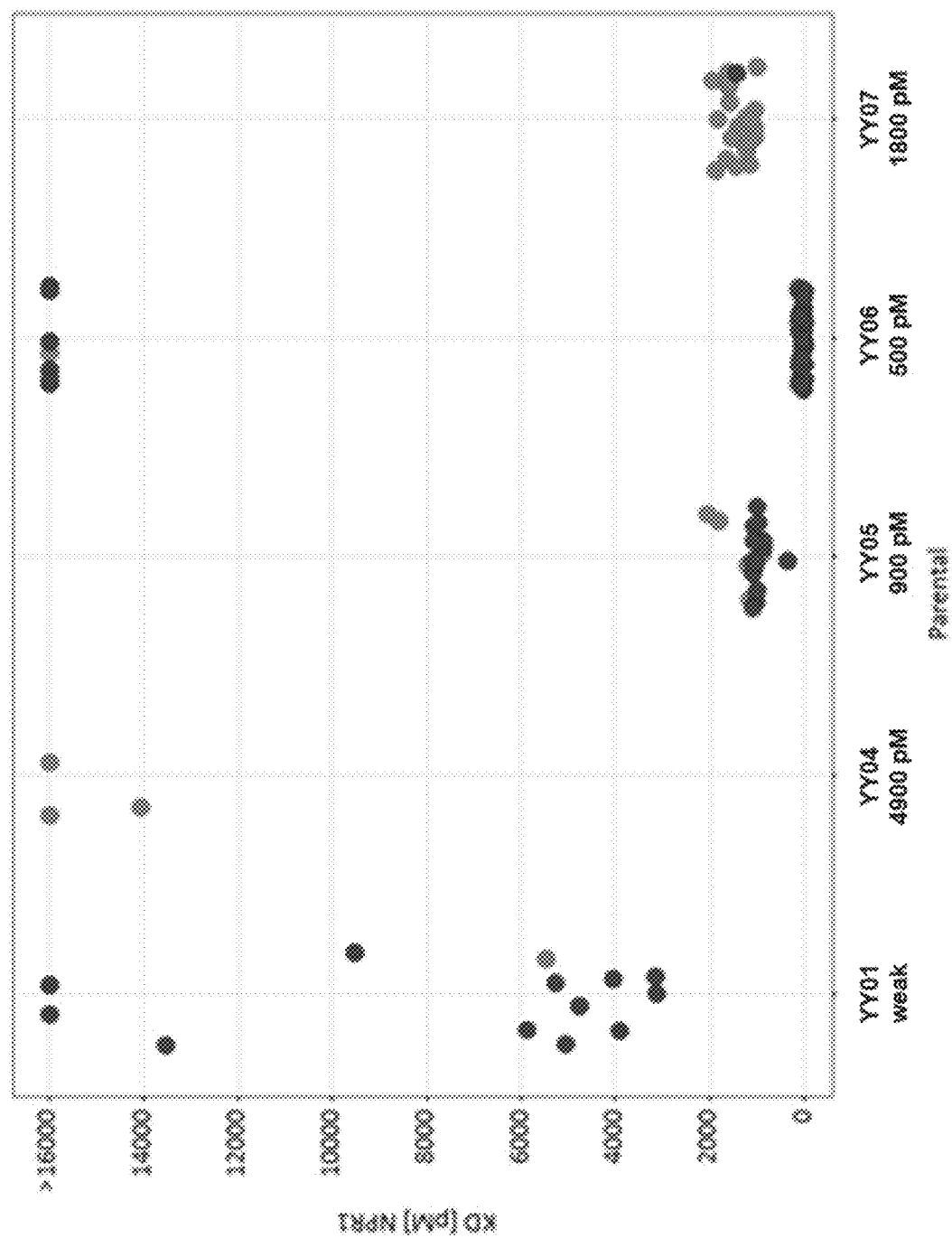
FIG. 24 demonstrates the results of SET screening (hNPR1 affinity) of 112 HCDR1/2 or LCDR3 unique improved Ylanthia® derivatives based on the parental antibody.
Figure 25:
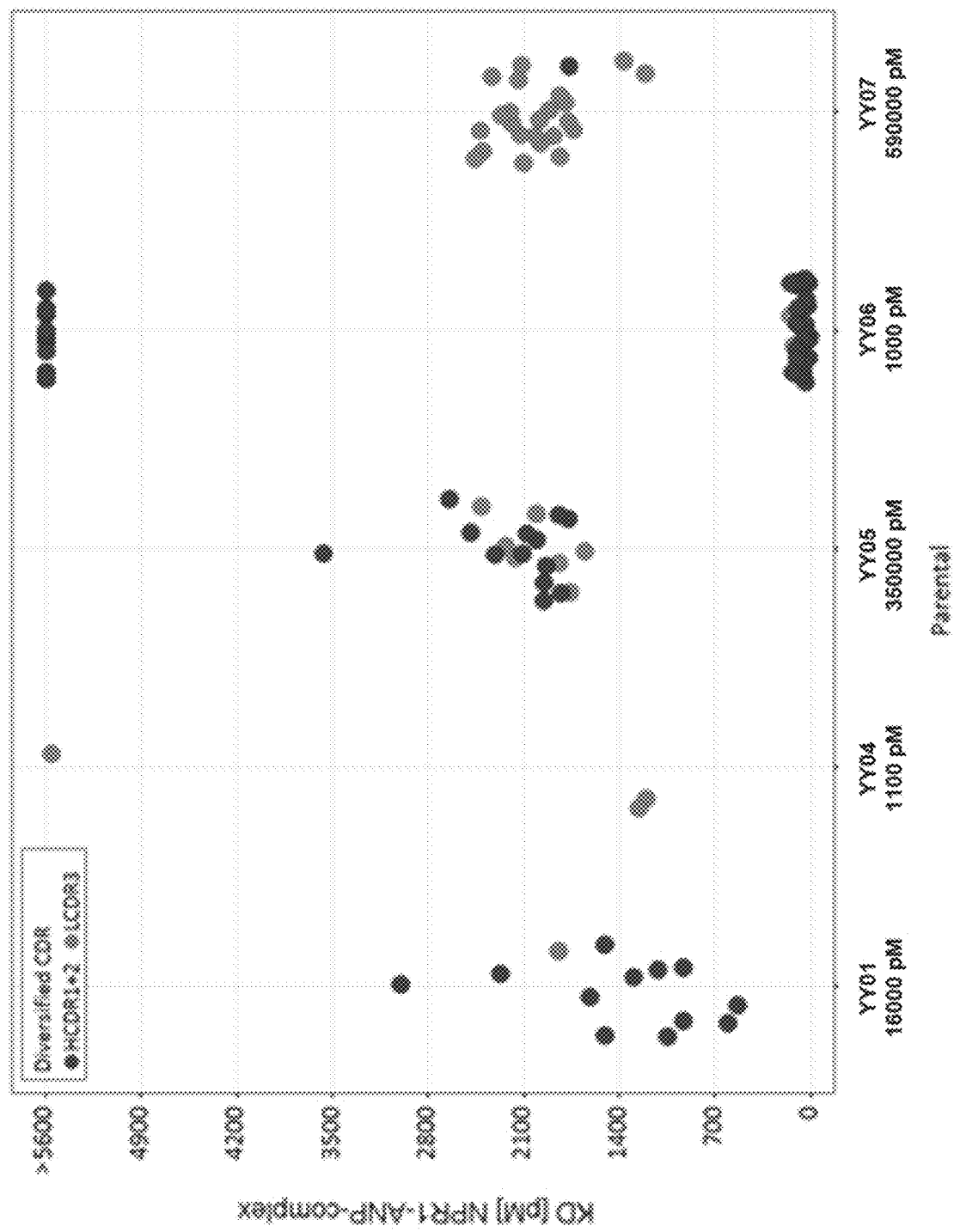
FIG. 25 demonstrates the results of SET screening (hNPR1-ANP complex affinity) of 112 HCDR1/2 or LCDR3 unique improved Ylanthia® derivatives based on the parental antibody.

During SET screening, 263 HCDR1//2 or LCDR3 unique improved derivatives were identified, which resulted in 112 unique clones after sequencing and conversion to IgG1_LALA format. Compared to their parental clones, the affinities of the YY05 and YY07 derivatives were not improved for NPR1 but were improved up to 200-fold for NPR1-ANP-complex. The derivatives of YY01 had similar affinities to the parental clone YY04, whose derivatives had only slightly improved affinities. The affinities of the YY06 derivatives were improved 4- to 40-fold for NPR1 and 7- to 70-fold for NPR1-ANP-complex. See FIG. 24 (which shows affinities for hNPR1) and FIG. 25 (which shows affinities for hNPR1-ANP complex). Affinities ($K_D$ [pM]) are indicated at the x-axis below the parental clone name for both figures.

Example 15: Characterization of Matured Candidates—Ylanthia®

95 of 112 improved candidates were selected for advanced production. 77 of the 95 clones passed the production quality control and were characterized in regard to binding to relevant antigens, binding to relevant cell lines, and functional activity in the cGMP production assay in comparison to their parental clones. After detailed IgG characterization, 17 candidates (detailed in Table 19) were selected, produced in exploratory scale IgG production, and further analyzed via 3P assay. Furthermore, they were converted to FabCys format for their affinity determination on human and rat NPR1 in absence and presence of ANP via SET $K_D$ measurement.

TABLE 19

Overview of Matured Ylanthia ® Candidates

| Matured antibody | Parental antibody | Matured CDR |
|---|---|---|
| ZZ01 | YY07 | LCDR3 |
| ZZ02 | YY05 | LCDR3 |
| ZZ03 | YY07 | LCDR3 |
| ZZ04 | YY07 | LCDR3 |
| ZZ05 | YY07 | LCDR3 |
| ZZ06 | YY07 | LCDR3 |
| ZZ07 | YY07 | LCDR3 |
| ZZ08 | YY07 | LCDR3 |
| ZZ09 | YY05 | HCDR1 + 2 |
| ZZ10 | YY05 | HCDR1 + 2 |
| ZZ11 | YY04 | LCDR3 |
| ZZ12 | YY01 | HCDR1 + 2 |
| ZZ13 | YY01 | HCDR1 + 2 |
| ZZ14 | YY06 | HCDR1 + 2 |
| ZZ15 | YY06 | HCDR1 + 2 |
| ZZ16 | YY06 | HCDR1 + 2 |
| ZZ17 | YY06 | HCDR1 + 2 |

Affinities for 16 of the matured Ylanthia® candidates (in monovalent FabCys format) were determined via SET measurement and/or via Octet. The results are summarized in Tables 20 and 21 below in comparison to the affinities of the parental clones.

TABLE 20

Summary of Affinity data (SET) for YY01, YY06, ZZ12, ZZ13, ZZ15, ZZ16, and ZZ17 in FabCys Format

| Antibody | Affinity (SET measurement) FabCys $K_D$ [nM] | | | | comment |
|---|---|---|---|---|---|
| | hNPR1 | hNPR1 + ANP | rNPR1 | rNPR1 + ANP | |
| YY01 | — | 16.00 | — | 14.00 | $K_D$ determination via Octet |
| ZZ12 | 6.70 | 0.32 | 2.10 | 1.40 | |
| ZZ13 | 9.90 | 1.30 | 2.30 | 1.40 | |
| YY04 | 4.90 | 1.10 | — | 1.00 | $K_D$ determination via Octet |
| ZZ11 | 46.00 | 2.40 | 21.00 | 18.00 | |
| YY05 | 0.90 | 350.00 | 700.00 | 16000.00 | $K_D$ determination via Octet; assay limit reached |
| ZZ02 | 0.37 | 0.58 | — | — | |
| ZZ09 | 0.49 | 0.57 | — | — | |
| ZZ10 | 0.52 | 1.40 | — | — | |
| YY06 | 0.50 | 1.00 | 1600.00 | 1400.00 | $K_D$ determination via Octet |
| ZZ15 | 0.053 | 0.074 | — | — | |
| ZZ16 | 0.040 | 0.034 | 62.00 | 51.00 | |
| ZZ17 | 0.046 | 0.050 | 52.00 | 36.00 | |
| YY07 | 1.80 | 590.0 | — | — | |
| ZZ01 | 0.65 | 0.85 | — | — | |
| ZZ03 | 0.75 | 1.30 | — | — | |
| ZZ04 | 0.30 | 0.38 | — | — | |
| ZZ05 | 0.74 | 1.20 | — | — | |
| ZZ06 | 0.35 | 0.50 | — | — | |
| ZZ07 | 0.62 | 1.50 | — | — | |
| ZZ08 | 0.57 | 1.30 | — | — | |

TABLE 21

Summary of Affinity data (Octet) for YY01, YY06, ZZ12, ZZ13, ZZ15, ZZ16, and ZZ17 in FabCys Format

| Antibody | Affinity (Octet measurement) FabCys $K_D$ [nM] | | | | comment |
|---|---|---|---|---|---|
| | hNPR1 | hNPR1 + ANP | rNPR1 | rNPR1 + ANP | |
| YY01 | — | 26.00 | — | 8.80 | Heterogenous binding |
| ZZ12 | — | 0.04 | — | 0.10 | |
| ZZ13 | — | 0.14 | 66.00 | 0.10 | |
| YY06 | 0.62 | 0.80 | 100.00 | 38.00 | |
| ZZ15 | 0.26 | 0.19 | — | — | |
| ZZ16 | 0.14 | 0.11 | — | — | |
| ZZ17 | 0.16 | 0.09 | — | — | |

Example 16: Epitope Determination for ANP Competitive and ANP Non-Competitive Agonist Antibodies The crystal structure of the hNPR1 and XX16 Fab complex was used to identify the XX16 Fab epitope on hNPR1. The interaction surface on hNPR1 by XX16 Fab was formed by several continuous and discontinuous (i.e., noncontiguous) sequences as detailed in Table 22. These residues form the three-dimensional conformational epitope recognized by XX16 Fab.

Results of the epitope mapping of XX16 Fab (ANP non-competitive) are shown in Table 22. hNPR1 residues are numbered based upon SEQ ID NO: 1 (P16066). Fab residues are numbered based upon their linear amino acid sequence. hNPR1 residues shown have at least one atom within 5 Å of an atom in the XX16 Fab, to account for potential water mediated interactions.

TABLE 22

Epitope Mapping of XX16 Fab

| Antibody XX16 Fab | | | Antigen (NPR1) | | |
|---|---|---|---|---|---|
| Amino acid | Number | Chain | Amino acid | Number | Chain |
| SER | 31 | H | TRP | 106 | A |
| TYR | 32 | H | TRP | 106 | A |
|  |  |  | TRP | 106 | B |
| TRP | 33 | H | ASN | 109 | A |
| GLU | 52 | H | HIS | 108 | A |
|  |  |  | ASN | 109 | A |
| SER | 53 | H | GLU | 107 | A |
|  |  |  | ASN | 109 | A |
| LYS | 54 | H | GLU | 107 | A |
| ASN | 56 | H | GLY | 33 | A |
|  |  |  | ASN | 34 | A |
|  |  |  | THR | 36 | A |
|  |  |  | TRP | 76 | A |
| TYR | 57 | H | ASN | 34 | A |
|  |  |  | TRP | 76 | A |
|  |  |  | ASN | 109 | A |
|  |  |  | PRO | 110 | A |
|  |  |  | ALA | 111 | A |
|  |  |  | VAL | 374 | A |
|  |  |  | THR | 375 | A |
| PHE | 59 | H | THR | 375 | A |
| ARG | 100 | H | TRP | 106 | A |
|  |  |  | ASP | 103 | B |
|  |  |  | GLU | 107 | B |
| TYR | 101 | H | VAL | 102 | A |
|  |  |  | TRP | 106 | A |
|  |  |  | VAL | 102 | B |
|  |  |  | ASP | 103 | B |
|  |  |  | TRP | 106 | B |
|  |  |  | GLU | 107 | B |
| SER | 102 | H | LYS | 105 | A |
|  |  |  | TRP | 106 | A |
| MET | 103 | H | VAL | 102 | A |
|  |  |  | LYS | 105 | A |
|  |  |  | TRP | 106 | A |
|  |  |  | TRP | 132 | A |
|  |  |  | LEU | 99 | B |
|  |  |  | VAL | 102 | B |
|  |  |  | ASP | 103 | B |
| ILE | 104 | H | LYS | 105 | A |
|  |  |  | HIS | 131 | A |
|  |  |  | TRP | 132 | A |
|  |  |  | LEU | 99 | B |
|  |  |  | ALA | 100 | B |
|  |  |  | ASP | 103 | B |
| TYR | 105 | H | LYS | 105 | A |
|  |  |  | TRP | 132 | A |
| SER | 106 | H | LYS | 105 | A |
|  |  |  | HIS | 131 | A |
|  |  |  | TRP | 132 | A |
|  |  |  | ARG | 133 | A |
| TYR | 107 | H | LYS | 105 | A |
|  |  |  | ASN | 109 | A |
|  |  |  | PRO | 110 | A |
|  |  |  | ALA | 111 | A |
|  |  |  | VAL | 134 | A |
| ASP | 113 | H | THR | 375 | A |
|  |  |  | GLU | 107 | B |
| ARG | 18 | L | GLN | 336 | B |
| SER | 30 | L | GLU | 86 | B |
|  |  |  | ASN | 87 | B |
|  |  |  | ALA | 88 | B |
| SER | 31 | L | SER | 84 | B |
|  |  |  | GLU | 86 | B |
| TYR | 32 | L | HIS | 131 | A |
| TYR | 49 | L | ASP | 103 | B |
|  |  |  | LEU | 104 | B |
|  |  |  | GLU | 107 | B |
|  |  |  | HIS | 108 | B |
| SER | 52 | L | LEU | 43 | B |
|  |  |  | LEU | 82 | B |
| THR | 53 | L | VAL | 81 | B |
|  |  |  | LEU | 82 | B |
|  |  |  | GLY | 83 | B |
|  |  |  | LEU | 104 | B |
|  |  |  | HIS | 108 | B |
| LEU | 54 | L | ARG | 79 | B |
|  |  |  | VAL | 81 | B |
|  |  |  | HIS | 108 | B |
| GLN | 55 | L | GLU | 107 | B |
|  |  |  | HIS | 108 | B |
| SER | 56 | L | GLU | 107 | B |
|  |  |  | HIS | 108 | B |
| VAL | 58 | L | ARG | 79 | B |
| PRO | 59 | L | ARG | 79 | B |
| SER | 60 | L | ARG | 79 | B |
| SER | 65 | L | THR | 44 | B |
| GLY | 66 | L | THR | 44 | B |
| SER | 67 | L | THR | 44 | B |
|  |  |  | GLU | 86 | B |
|  |  |  | ASN | 87 | B |
| SER | 76 | L | GLN | 336 | B |
| TRP | 92 | L | HIS | 131 | A |
|  |  |  | ARG | 133 | A |
|  |  |  | ALA | 88 | B |
| ARG | 93 | L | ARG | 133 | A |
|  |  |  | GLU | 378 | A |
| LYS | 94 | L | ASP | 376 | A |

Critical epitope residues for the binding of XX16 Fab and NPR1, which were determined using structural analysis and affinity maturation data, include (first tier) 99-103, 105-111, 131-133, 378; and (second tier): 33-34, 76, 82, 104, 374-375. Amino acids 99-103 of NPR1 (SEQ ID NO: 1) comprise both a E106 backbone that enabled the affinity maturation by D54K in HCDR2, and W106 from both NPR1 protomers that clamp Y101 of HCDR3. Certain critical epitope residues are shown in Table 23 below. Regions of NPR1 encompassing these critical residues include N34, W76, L82, V102-A111, H131-V134, and V374-E378.

TABLE 23

Critical Epitope Residues of XX16 Fab (ANP non-competitive)

| Critical epitope residue (amino acid) | Critical epitope residue (number) | Explanation |
|---|---|---|
| N | 34 | H-bond with N56 (backbone) of VH |
| L | 82 | H-bond (chain B) with T53 (side chain) of VL |
| V | 102 | Packing against M103 (side chain) of VH |
| D | 103 | Salt bridge (chain B) with R100 (side chain) of VH |
| K | 105 | H-bond (backbone) with M103 (backbone) and Y105 (backbone) of VH |
| W | 106 | Packing between Y32 (side chain) and Y101 (side chain) of VH |
| E | 107 | Salt bridge (chain B) with R100 (side chain) of VH |

TABLE 23-continued Critical Epitope Residues of XX16 Fab (ANP non-competitive)

| Critical epitope residue (amino acid) | Critical epitope residue (number) | Explanation |
|---|---|---|
| E | 107 | H-bond (backbone) with K54 (side chain) of VH |
| N | 109 | H-bond with E52 (side chain), S53 (side chain) and W33 (side chain) of VH |
| W | 132 | Packing against M103 (side chain) of VH |
| R | 133 | H-bond with S106 (side chain) of VH |
| T | 375 | Packing against Y57 (side chain) of VH |
| E | 378 | Salt bridge with R93 (side chain) of VL |

The crystal structure of the hNPR1 and WW03 Fab complex was used to identify the WW03 Fab epitope on hNPR1. The interaction surface on hNPR1 by WW03 Fab was formed by several continuous and discontinuous (i.e., noncontiguous) sequences as detailed in Table 24. These residues form the three-dimensional conformational epitope recognized by WW03 Fab.

Results of the epitope mapping of WW03 Fab (ANP non-competitive) are shown in Table 24. hNPR1 residues are numbered based upon SEQ ID NO: 1 (P16066). Fab residues are numbered based upon their linear amino acid sequence. hNPR1 residues shown have at least one atom within 5 Å of an atom in the WW03 Fab, to account for potential water mediated interactions.

TABLE 24

Epitope Mapping of WW03 Fab

| Antibody WW03 Fab | | | Antigen (NPR1) | | |
|---|---|---|---|---|---|
| Amino acid | Number | Chain | Amino acid | Number | Chain |
| SER | 31 | H | TRP | 106 | A |
| TYR | 32 | H | TRP | 106 | A |
|  |  |  | TRP | 106 | B |
| TRP | 33 | H | ASN | 109 | A |
| SER | 52 | H | HIS | 108 | A |
|  |  |  | ASN | 109 | A |
| SER | 53 | H | TRP | 106 | A |
|  |  |  | GLU | 107 | A |
|  |  |  | ASN | 109 | A |
| ASP | 54 | H | THR | 36 | A |
|  |  |  | ARG | 79 | A |
| SER | 56 | H | ASN | 34 | A |
| TYR | 57 | H | ASN | 109 | A |
|  |  |  | PRO | 110 | A |
|  |  |  | ALA | 111 | A |
|  |  |  | VAL | 374 | A |
|  |  |  | THR | 375 | A |
| TYR | 59 | H | THR | 375 | A |
| ARG | 100 | H | ASP | 103 | B |
|  |  |  | TRP | 106 | B |
|  |  |  | GLU | 107 | B |
| TYR | 101 | H | VAL | 102 | A |
|  |  |  | TRP | 106 | A |
|  |  |  | VAL | 102 | B |
|  |  |  | ASP | 103 | B |
|  |  |  | TRP | 106 | B |
|  |  |  | GLU | 107 | B |
| SER | 102 | H | LYS | 105 | A |
|  |  |  | TRP | 106 | A |
|  |  |  | ASN | 109 | A |
| MET | 103 | H | VAL | 102 | A |
|  |  |  | LYS | 105 | A |
|  |  |  | TRP | 106 | A |
|  |  |  | TRP | 132 | A |
|  |  |  | LEU | 99 | B |
|  |  |  | VAL | 102 | B |
|  |  |  | ASP | 103 | B |

TABLE 24-continued

Epitope Mapping of WW03 Fab

| Antibody WW03 Fab | | | Antigen (NPR1) | | |
|---|---|---|---|---|---|
| Amino acid | Number | Chain | Amino acid | Number | Chain |
| ILE | 104 | H | HIS | 131 | A |
|  |  |  | TRP | 132 | A |
|  |  |  | LEU | 99 | B |
|  |  |  | ASP | 103 | B |
| TYR | 105 | H | LYS | 105 | A |
|  |  |  | TRP | 132 | A |
| SER | 106 | H | LYS | 105 | A |
|  |  |  | TRP | 132 | A |
|  |  |  | ARG | 133 | A |
| TYR | 107 | H | LYS | 105 | A |
|  |  |  | ASN | 109 | A |
|  |  |  | PRO | 110 | A |
|  |  |  | ALA | 111 | A |
|  |  |  | VAL | 134 | A |
|  |  |  | THR | 375 | A |
| ASP | 113 | H | GLU | 107 | B |
| ARG | 18 | L | GLN | 336 | B |
| SER | 30 | L | ASN | 87 | B |
|  |  |  | ALA | 88 | B |
| SER | 31 | L | SER | 84 | B |
| TYR | 32 | L | HIS | 131 | A |
| TYR | 49 | L | ASP | 103 | B |
|  |  |  | GLU | 107 | B |
|  |  |  | HIS | 108 | B |
| SER | 52 | L | LEU | 43 | B |
|  |  |  | LEU | 82 | B |
| THR | 53 | L | VAL | 81 | B |
|  |  |  | LEU | 82 | B |
|  |  |  | GLY | 83 | B |
|  |  |  | LEU | 104 | B |
|  |  |  | HIS | 108 | B |
| LEU | 54 | L | ARG | 79 | B |
|  |  |  | VAL | 81 | B |
|  |  |  | HIS | 108 | B |
| GLN | 55 | L | GLU | 107 | B |
|  |  |  | HIS | 108 | B |
| SER | 56 | L | GLU | 107 | B |
|  |  |  | HIS | 108 | B |
| VAL | 58 | L | ARG | 79 | B |
| PRO | 59 | L | ARG | 79 | B |
| SER | 60 | L | ARG | 79 | B |
| GLY | 66 | L | THR | 44 | B |
| SER | 67 | L | THR | 44 | B |
|  |  |  | GLU | 86 | B |
|  |  |  | ASN | 87 | B |
| TYR | 92 | L | ARG | 133 | A |
| GLU | 93 | L | ARG | 133 | A |
| LYS | 94 | L | ASP | 376 | A |

Critical epitope residues for the binding of WW03 Fab and NPR1, which were determined using structural analysis and affinity maturation data, include the residues shown in Table 25. Regions of NPR1 encompassing these critical residues include R79, L82, L99-A111, H131-V134, and V374-T375.

TABLE 25

Critical Epitope Residues of WW03 Fab (ANP non-competitive)

| Critical epitope residue (amino acid) | Critical epitope residue (number) | Explanation |
|---|---|---|
| R | 79 | Salt bridge with D54 (side chain) of VH; H-bond (chain B) with S60 (side chain) of VL |
| L | 82 | H-bond (backbone) with T53 (side chain) of VL |
| L | 99 | Packing against M103 (side chain) and I104 (side chain) of VH |
| V | 102 | Packing against M103 (side chain) of VH |
| D | 103 | Salt bridge with R100 (side chain) of VH |
| K | 105 | H-bond with M103 (backbone) and Y105 (backbone) of VH |
| W | 106 | Packing between Y32 (side chain) and Y101 (side chain) of VH; stacking (chain B) against Y101 (side chain) of VH |
| N | 109 | H-bond with S53 (side chain) of VH |
| H | 131 | H-bond with I104 (backbone) of VH |
| W | 132 | H-bond with M103 (side chain) of VH |
| T | 375 | H-bond with Y59 (side chain) of VH; pack against Y57 (side chain) of VH |

The crystal structure of the hNPR1 and WW06 Fab complex was used to identify the WW06 Fab epitope on hNPR1. The interaction surface on hNPR1 by WW06 Fab was formed by several continuous and discontinuous (i.e., noncontiguous) sequences as detailed in Table 26. These residues form the three-dimensional conformational epitope recognized by WW06 Fab.

Results of the epitope mapping of the WW06 Fab (ANP competitive) are shown in Table 26. hNPR1 residues are numbered based upon SEQ ID NO: 1 (P16066). WW06 Fab residues are numbered based upon their linear amino acid sequence. hNPR1 residues shown have at least one atom within 5 Å of an atom in the WW06 Fab, to account for potential water mediated interactions.

TABLE 26

Epitope Mapping of WW06 Fab (ANP competitive)

| Antibody WW06 Fab | | | Antigen (NPR1) | | |
|---|---|---|---|---|---|
| Amino acid | Number | Chain | Amino acid | Number | Chain |
| Y | 27 | H | R | 294 | B |
|   |    | H | G | 295 | B |
| S | 28 | H | R | 294 | B |
|   |    | H | G | 295 | B |
|   |    | H | D | 296 | B |
| S | 31 | H | R | 230 | A |
|   |    | H | D | 296 | B |
| Y | 32 | H | G | 295 | B |
|   |    | H | D | 296 | B |
|   |    | H | G | 297 | B |
| W | 33 | H | Y | 188 | A |
|   |    | H | E | 219 | A |
| R | 50 | H | F | 197 | A |
|   |    | H | E | 219 | A |
| D | 52 | H | Y | 188 | A |
|   |    | H | A | 221 | A |
|   |    | H | H | 227 | A |
| D | 54 | H | D | 224 | A |
| N | 55 | H | Y | 188 | A |
|   |    | H | P | 190 | A |
|   |    | H | A | 221 | A |
|   |    | H | D | 223 | A |
| Y | 57 | H | Y | 188 | A |
|   |    | H | R | 189 | A |
|   |    | H | P | 190 | A |
|   |    | H | G | 191 | A |
|   |    | H | D | 192 | A |
|   |    | H | E | 193 | A |
|   |    | H | E | 194 | A |
|   |    | H | F | 197 | A |
| T | 58 | H | E | 194 | A |
| R | 59 | H | E | 194 | A |
|   |    | H | F | 197 | A |
|   |    | H | E | 201 | A |
| Q | 65 | H | D | 94  | A |
|   |    | H | E | 194 | A |
| R | 98 | H | G | 295 | B |
| W | 99 | H | E | 219 | A |
| L | 100 | H | R | 230 | A |
| S | 101 | H | H | 217 | A |
| P | 102 | H | K | 238 | A |
| G | 103 | H | D | 216 | A |
|   |     | H | H | 217 | A |
|   |     | H | T | 234 | A |
|   |     | H | K | 238 | A |
| Y | 104 | H | L | 218 | A |
|   |     | H | E | 219 | A |
|   |     | H | F | 220 | A |
|   |     | H | H | 227 | A |
|   |     | H | R | 230 | A |
|   |     | H | L | 231 | A |
|   |     | H | T | 234 | A |
|   |     | H | K | 238 | A |
| A | 105 | H | K | 238 | A |
| L | 106 | H | R | 233 | A |
|   |     | H | T | 234 | A |
|   |     | H | R | 237 | A |
|   |     | H | K | 238 | A |
| G | 107 | H | R | 237 | A |
| Q | 109 | H | G | 297 | B |
|     |     | H | V | 300 | B |
| I | 29 | L | R | 208 | A |
| G | 30 | L | R | 208 | A |
| A | 31 | L | F | 204 | A |
|   |    | L | R | 208 | A |
| G | 32 | L | R | 208 | A |
| Y | 33 | L | Y | 186 | A |
|   |    | L | E | 201 | A |
|   |    | L | F | 204 | A |
|   |    | L | H | 217 | A |
| Y | 93 | L | F | 197 | A |
|   |    | L | E | 201 | A |
| L | 95 | L | L | 144 | A |
|   |    | L | E | 201 | A |
|   |    | L | F | 204 | A |
|   |    | L | M | 205 | A |
| Q | 96 | L | L | 144 | A |
|   |    | L | G | 145 | A |
|   |    | L | V | 148 | A |
|   |    | L | M | 205 | A |

TABLE 26-continued

Epitope Mapping of WW06 Fab (ANP competitive)

| Antibody WW06 Fab | | | Antigen (NPR1) | | |
|---|---|---|---|---|---|
| Amino acid | Number | Chain | Amino acid | Number | Chain |
| S | 98 | L | F | 197 | A |
|   |    | L | F | 198 | A |
|   |    | L | E | 201 | A |
| R | 100 | L | E | 219 | A |

Critical epitope residues for the binding of WW06 and NPR1, which were determined using structural analysis and affinity maturation data, include the residues shown in Table 27. Regions of NPR1 encompassing these critical residues include Y188-F198, E201-R208, V215-K238, and R294-G297.

TABLE 27

Critical Epitope Residues of WW06 (ANP competitive)

| Critical epitope residue (amino acid) | Critical epitope residue (number) | Explanation |
|---|---|---|
| Y | 188 | Packing against W33 (side chain) of VH |
| D | 192 | H-bond with Y57 (side chain) of VH |
| E | 194 | Salt bridge with R59 (side chain) of VH |
| F | 197 | Stacking against R59 (side chain) of VH |
| E | 201 | H-bond with S98 (side chain) of VL |
| R | 208 | H-bond with G30 (backbone) of VL |
| E | 219 | Salt bridge with R50 (side chain) of VH |
| G | 295 | H-bond (backbone, chain B) with S28 (backbone) of VH |

Example 17: Mouse In Vivo Characterization of Effect of WW06 on Plasma cGMP

WW06 FabCys was used in an in vivo study in hNPR1 transgenic mice to determine the effect of this antibody on plasma cGMP levels in vivo.

For analysis of plasma cGMP samples, the LC-MS/MS detection method using $^{15}N_2$, $^{13}C$ cGMP as an internal standard was adopted from Oeckl and Ferger, Journal of Neuroscience Methods 203 (2012) 338-343; and Zhang et al., J. Chromatogr B:Analyt Technol Biomed Life Sci 2009; 877:513-20; the contents of each of which are hereby incorporated by reference for this purpose).

Figure 26:
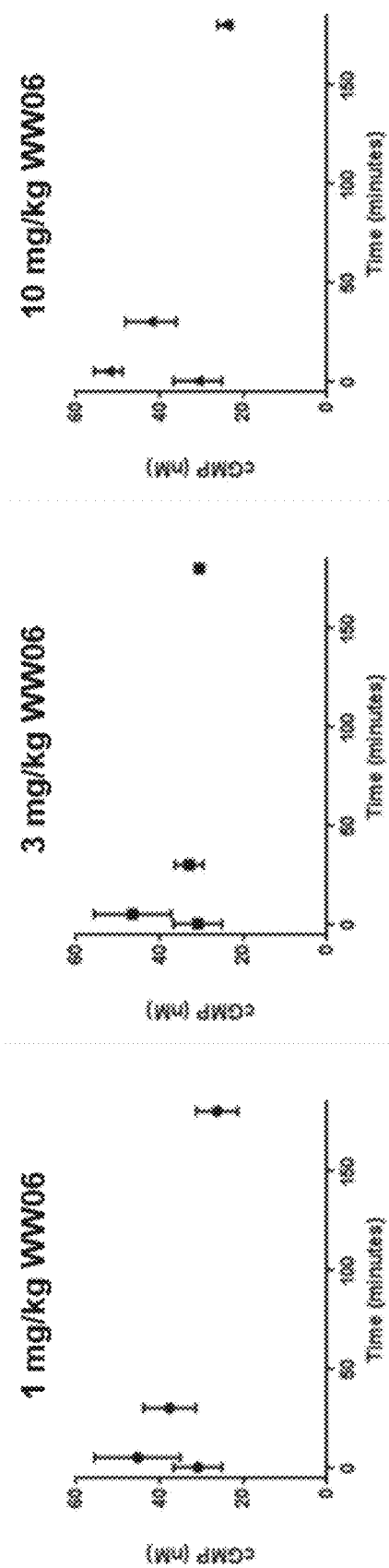
FIG. 26 is a set of graphs representing the plasma cGMP (nM) concentration over time in hNPR1 Tg mice which were intravenously administered 1 mg/kg, 3 mg/kg, or 10 mg/kg of the WW06 Fab.
Figure 27:
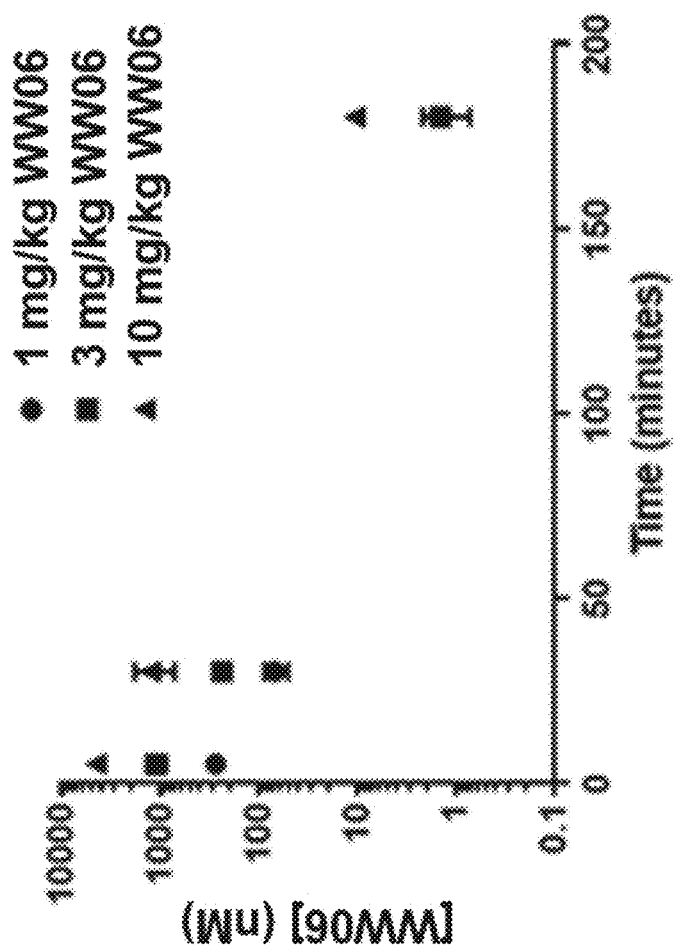
FIG. 27 is a graph representing the concentration of antibody over time in hNPR1 Tg mice which were intravenously administered 1 mg/kg, 3 mg/kg, or 10 mg/kg of the WW06 Fab.

Plasma cGMP concentration in hNPR1 Tg mice which were intravenously administered the WW06 Fab increased at the 5 minute time point and the signal returned to baseline by 3 h. As expected and consistent with the data shown in FIGS. 26 and 27, the $T_{1/2}$ of the FabCys antibody was <30 min. Each value shown is the average of three points collected from three individual animals. Dose response data are shown in FIG. 26, and PK data are shown in FIG. 27.

Example 18: Effect of XX16 on Heart Weight and NT-proBNP in ANP KO and WT Mice XX16 was used in an in vivo study to determine its effect on heart weight and NT-proBNP levels in ANP knockout (KO) and wild-type (WT) mice.

ANP knockout mice are hypertensive and have cardiac hypertrophy (increased HW/BW ratio). NT-proBNP is a biomarker of cardiac dysfunction. XX16 was administered at 0.3 or 3 mg/kg subcutaneously once every two weeks for four weeks in ANP knockout and wild type mice.

Figure 28:
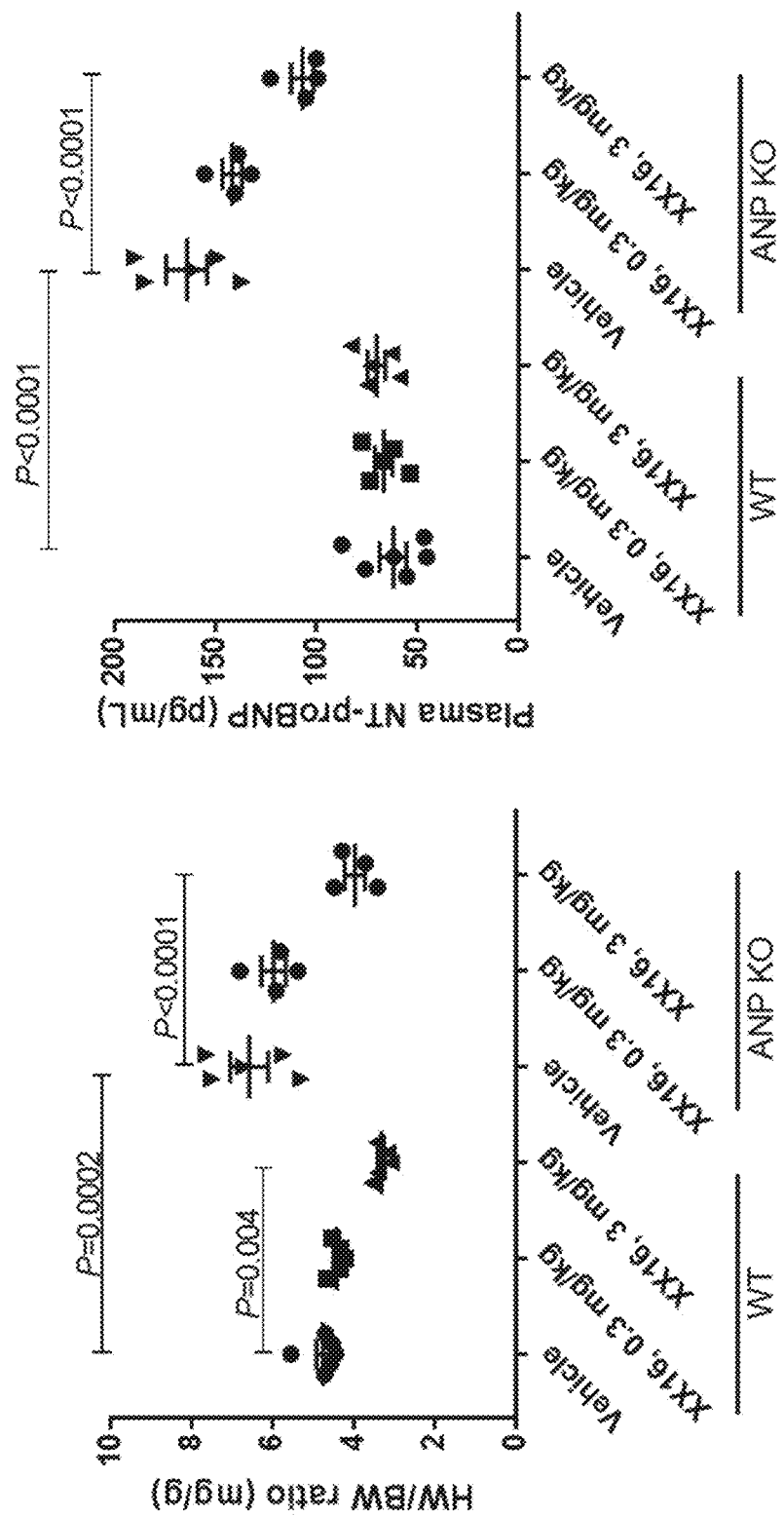
FIG. 28 is a set of graphs demonstrating the results of subcutaneous administration of vehicle, 0.3 mg/kg XX16, or 3 mg/kg XX16 once every two weeks in wild type or ANP knockout (ANP KO) mice on heart weight/body weight ratio (left) and plasma NT-proBNP levels (pg/mL; right). Measurements were taken two weeks after the second administration.

Results are shown in FIG. 28. At two weeks after the second treatment, XX16 dose-dependently reduced heart weight/body weight ratio and NT-proBNP in both wild type and ANP KO mice in comparison to vehicle treated animals.

Figure 29:
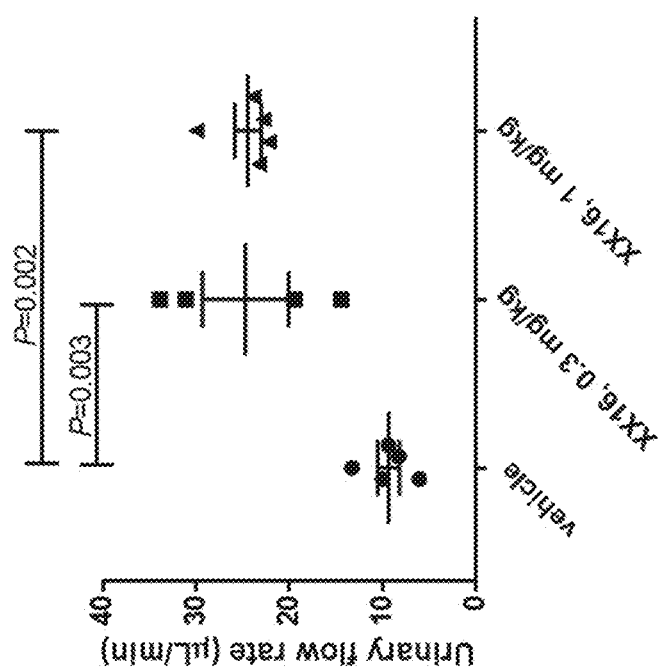
FIG. 29 is a set of graphs demonstrating the results of a single intravenous administration of vehicle, 0.3 mg/kg XX16, or 1 mg/kg XX16 on blood pressure (mean arterial pressure; left) and urinary flow rate (right) in hypertensive rats (spontaneous hypertensive rat stroke prone, SHRsp). Measurements were taken three hours after the intravenous administration.
Figure 29:
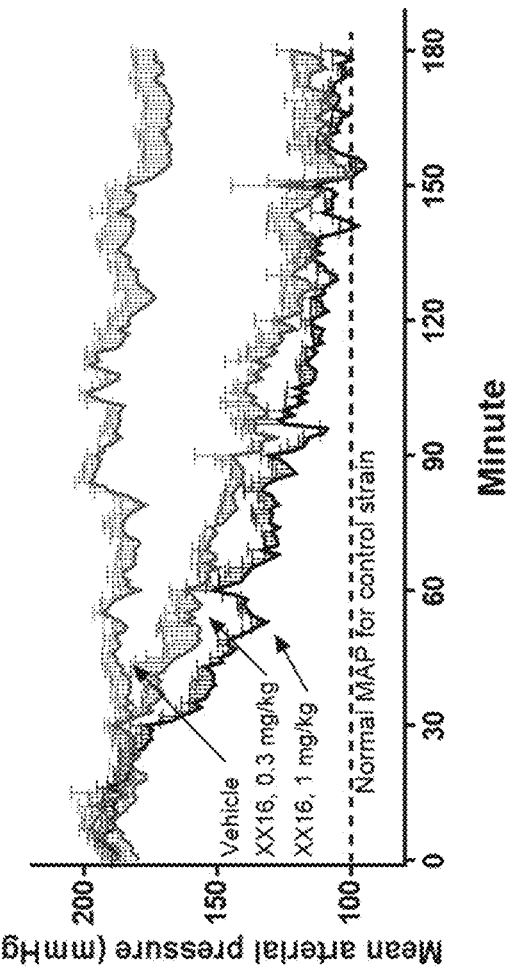

Example 19: Acute Effect of XX16 on Blood Pressure and Urinary Flow Rate in Hypertensive Rats XX16 was used to determine its effect on blood pressure and urinary flow rate in hypertensive rats (spontaneous hypertensive rat stroke prone, SHRsp). Animals were administered 0.3 mg/kg XX16, 1 mg/kg XX16, or a vehicle control intravenously (one time). Blood pressure was measured using a femoral artery catheter. Measurements were taken three hours after the intravenous administration and results are shown in FIG. 29.

Intravenous XX16 treatment normalized mean arterial pressure and increased urinary flow rate acutely in hypertensive rats (SHRsp) in comparison to vehicle treated animals.

Figure 30:
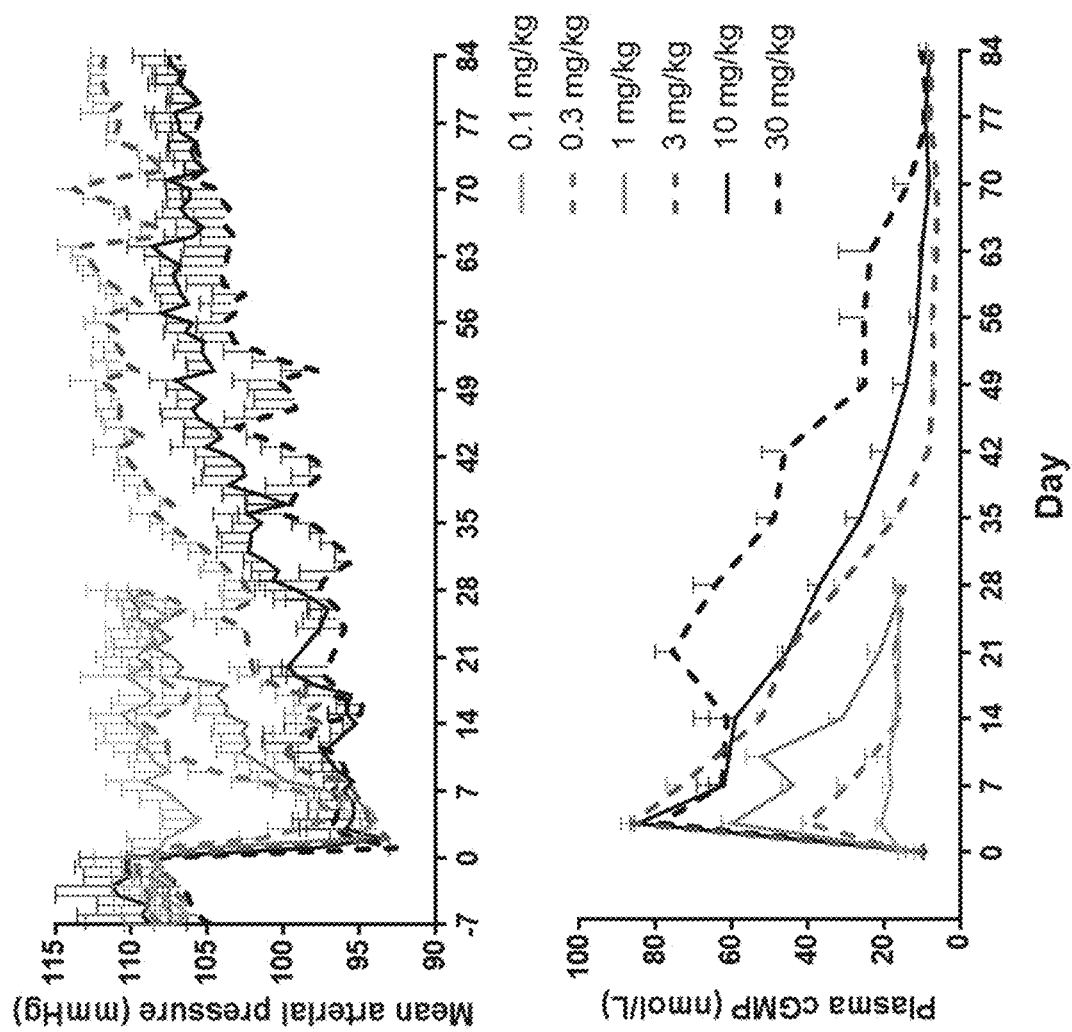
FIG. 30 is a set of graphs demonstrating the results of a single subcutaneous administration of 0.1, 0.3, 1, 3, 10, or 30 mg/kg XX16 in telemetry implanted normal rats on mean arterial pressure (MAP; top) and plasma cGMP (bottom) over time.
Figure 31:
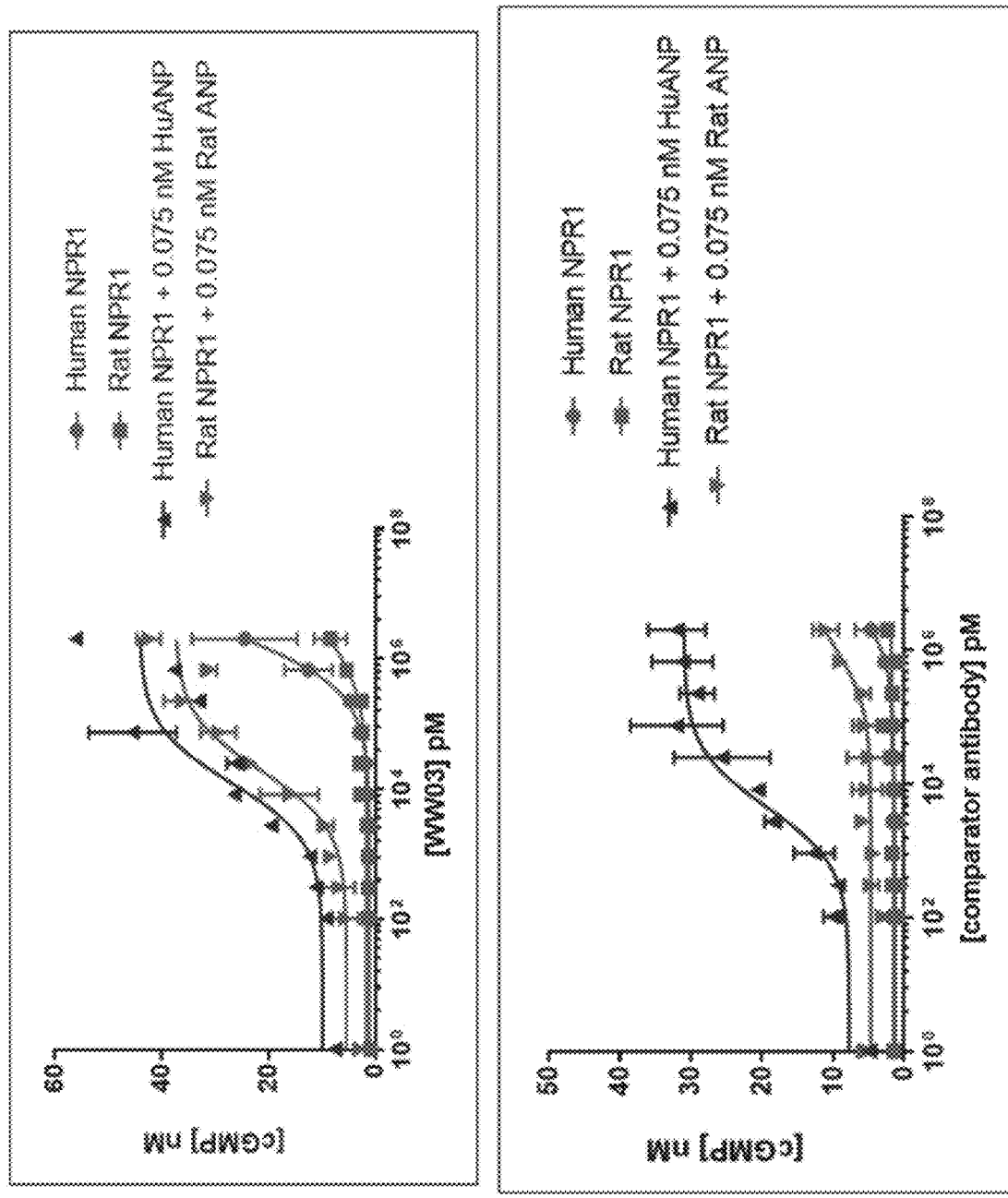
FIG. 31 is a set of graphs depicting the results of functional activity analyses of candidate WW03 and a comparator antibody (antibody 5591-IgG from PCT Application No. WO2010/065293A1) in a cellular cGMP production assay using human NPR1 expressing CHO-K1 cells or rat NPR1 expressing rat cells. Results represent the cellular production of cGMP [nM] in the absence or presence of 0.075 nM ANP (human or rat).

Example 20: Chronic Effects of XX16 on Blood Pressure and Plasma cGMP in Wistar-Han Rats Chronic hemodynamic effects of XX16 in telemetry implanted normal rats were evaluated. XX16 (at doses of 0.1, 0.3, 1, 3, 10, and 30 mg/kg) was administered subcutaneously one time. Results are shown in FIG. 30. Subcutaneous administration of XX16 decreased mean arterial pressure (MAP) in all groups except for the 0.1 mg/kg group. There was a floor (around 95 mmHg) for the MAP reduction. A dose-dependent effect for the time to return baseline MAP was observed; this effect was greater than 70 days for the 30 mg/kg treatment group. Plasma cGMP concentration also had a ceiling around 90 nmol/L, after which the plasma cGMP gradually reduced toward baseline. This effect is very similar to the blood pressure response.

Example 21: Comparison of Extant Anti-NPR1 Antibodies with Antibodies of the Application The WW03 antibody was compared with antibody 5591-IgG of PCT Application No. WO2010/065293A1 in terms of the ability of both antibodies to produce cGMP in human cells expressing hNPR1 or rat cells expressing rNPR1 (both in the presence or absence of 0.075 nM human or rat ANP, respectively). The WW03 antibody displayed superior potentiation in the absence of ANP on both cell lines. Additionally, the WW03 antibody demonstrated superior potentiation on rat cells expressing rNPR1 (both in the presence and absence of ANP).

In summary, previous antibodies (e.g., those of WO2010/065293, including 5591-IgG) demonstrate no activity in vivo (e.g., through analysis of activation using cGMP assays). In contrast, the antibodies of the instant application demonstrated in vivo activity in both mouse and rat. Further, the epitope binding of the antibodies described herein has been demonstrated to be dissimilar to the antibodies of WO2010/065293 using crystal structure data. The activity, cross-reactivity, and crystallographic data described herein demonstrate the differing and superior effects of the antibodies described in this application as compared to previous antibodies.

The invention claimed is:

1. An isolated anti-natriuretic peptide receptor 1 (NPR1) antibody or antigen binding fragment, wherein the antibody or antigen binding fragment comprises three heavy chain complementarity determining regions (HCDR1, HCDR2, and HCDR3) and three light chain complementarity determining regions (LCDR1, LCDR2, and LCDR3) selected from:

(I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3);

(II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3);

(III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 135 (LCDR3); and (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 134 (LCDR3).

2. The antibody or antigen binding fragment of claim 1, wherein the antibody or antigen binding fragment comprises:

(a) a heavy chain variable region comprising an amino acid sequence of SEQ ID NO: 201, and a light chain variable region comprising an amino acid sequence of SEQ ID NO: 136; or (b) a heavy chain variable region comprising an amino acid sequence of SEQ ID NO: 122, and a light chain variable region comprising an amino acid sequence of SEQ ID NO: 136.

3. The antibody or antigen binding fragment of claim 1, wherein the antibody or antigen binding fragment comprises:

(a) a heavy chain comprising an amino acid sequence of SEQ ID NO: 203, and a light chain comprising an amino acid sequence of SEQ ID NO: 138; or (b) a heavy chain comprising an amino acid sequence of SEQ ID NO: 208, and a light chain comprising an amino acid sequence of SEQ ID NO: 138.

4. The antibody or antigen binding fragment of claim 1, which is an antigen binding fragment selected from the group consisting of a Fab, Fab', F(ab')$_2$, Fv, and a single chain variable fragment (scFv).

5. The antibody or antigen binding fragment of claim 1, wherein the antibody or antigen binding fragment is therapeutic.

6. A pharmaceutical composition comprising an antibody or antigen binding fragment of claim 1 and a pharmaceutically acceptable carrier.

7. The pharmaceutical composition of claim 6, wherein the composition further comprises an additional therapeutic agent.

8. The pharmaceutical composition of claim 7, wherein the additional therapeutic agent is selected from an ACE (angiotensin-converting-enzyme) inhibitor, an angiotensin receptor blocker (ARB), a neprily sin inhibitor, a beta blocker, a diuretic, a calcium channel blocker, a cardiac glycoside, a sodium-glucose co-transporter 2 inhibitor (SGLT2i), an angiotensin receptor-neprilysin inhibitor (ARNi), a corticosteroid, a leukotriene modifier, a bronchodilator, a beta-adrenoceptor antagonist, a carbonic anhydrase inhibitor, an alpha 2-adrenoceptor agonist, a parasympathomimetic, a prostaglandin analog, a rho kinase inhibitor, and combinations thereof.

9. The pharmaceutical composition of claim 7, wherein the additional therapeutic agent is selected from enalapril, benazepril, captopril, fosinopril, lisinopril, moexipril, perindopril, quinapril, ramipril, trandolapril, valsartan, azilsartan, candesartan, eprosartan, irbesartan, losartan, olmesartan, telmisartan, sacubitril, bisoprolol, carvedilol, propanolol, metoprolol, metoprolol tartrate, metoprolol succinate, thiazide diuretics, loop diuretics, potassium-sparing diuretics, amlodipine, clevidipine, diltiazem, felodipine, isradipine, nicardipine, nifedipine, nisoldipine, verapamil, a digitalis glycoside, canagliflozin, dapagliflozin, empagliflozin, ertugliflozin, chlorothiazide, chlorthalidone, hydrochlorothiazide, indapamide, metolazone, bumetanide, ethacrynic acid, furosemide, torsemide, amiloride, eplerenone, spironolactonem, triamterene, digoxin, fluticasone, budesonide, mometasone, beclomethasone, ciclesonide, fluticasone furoate, prednisone, methylprednisolone, montelukast, zafirlukast, zileuton, a long-acting beta agonist, a short-acting beta agonist, theophylline, ipratropium, salmeterol, formoterol, albuterol, levalbuterol, timolol, levobunolol, metipranolol, carteolol, betaxolol, acetazolamide, dorzolamide, brinzolamide, methazolamide, brimonidine, apraclonidine, a cholinomimetic, latanoprost, latanoprostene bunod, travoprost, bimatoprost, tafluprost, netarsudil, ripasudil, and combinations thereof.

10. A method of treating a cardiovascular disorder in a subject in need thereof, the method comprising administering to the subject a therapeutically effective amount of the antibody or antigen binding fragment of claim 1.

11. The method of claim 10, wherein the cardiovascular disorder is selected from: hypertension, peripheral vascular disease, heart failure, coronary artery disease (CAD), ischemic heart disease (IHD), mitral stenosis and regurgitation, angina, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, and myocardial infarction (MI).

12. The method of claim 11, wherein the subject has heart failure, and wherein the heart failure is selected from a heart failure with reduced ejection fraction (HFrEF), heart failure with preserved ejection fraction (HFpEF), heart failure after acute myocardial infarct, or acute decompensated heart failure.

13. The method of claim 11, wherein the subject has hypertrophic cardiomyopathy, and wherein the hypertrophic cardiomyopathy is ventricular hypertrophy.

14. The method of claim 11, wherein the subject has hypertension, and wherein the hypertension is selected from resistant hypertension, hypertensive heart disease, pulmonary hypertension, pulmonary arterial hypertension, isolated systolic hypertension, resistant hypertension, and pulmonary arterial hypertension.

15. The method of claim 11, wherein the subject has hypertension, and wherein the hypertension is selected from resistant hypertension or hypertensive heart disease.

16. A method of treating a kidney disorder in a subject in need thereof, the method comprising administering to the subject a therapeutically effective amount of the antibody or antigen binding fragment of claim 1.

17. The method of claim 16, wherein the kidney disorder is selected from: diabetic renal insufficiency, non-diabetic renal insufficiency, renal failure, diabetic nephropathy, non-diabetic nephropathy, acute renal injury, contrast induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, renal fibrosis, and polycystic kidney disease (PKD).

* * * * *